US012673122B2

(12) United States Patent
Liu et al.

(10) Patent No.: US 12,673,122 B2
(45) Date of Patent: *Jul. 7, 2026

(54) CLEAVABLE RADIOLIGANDS FOR TARGETING CELL SURFACE RECEPTORS AND USES THEREOF

(71) Applicant: Full-Life Technologies UK Limited, London (GB)

(72) Inventors: Fa Liu, Watchung, NJ (US); Alla Darwish, Kitchener (CA)

(73) Assignee: FULL-LIFE TECHNOLOGIES UK LIMITED, London (GB)

( * ) Notice: Subject to any disclaimer, the term of this patent is extended or adjusted under 35 U.S.C. 154(b) by 64 days.

This patent is subject to a terminal disclaimer.

(21) Appl. No.: 18/967,265

(22) Filed: Dec. 3, 2024

(65) Prior Publication Data

US 2025/0099632 A1 Mar. 27, 2025

Related U.S. Application Data

(63) Continuation of application No. 18/604,400, filed on Mar. 13, 2024, now Pat. No. 12,214,059, which is a continuation of application No. PCT/US2022/050952, filed on Nov. 23, 2022.

(60) Provisional application No. 63/283,361, filed on Nov. 26, 2021.

(51) Int. Cl.

| | |
|---|---|
| ***A61K 51/04*** | (2006.01) |
| ***A61K 38/05*** | (2006.01) |
| ***A61K 38/26*** | (2006.01) |
| ***A61K 51/02*** | (2006.01) |
| ***A61K 51/06*** | (2006.01) |
| ***A61K 51/08*** | (2006.01) |

(52) U.S. Cl.

CPC .......... *A61K 51/0482* (2013.01); *A61K 38/05* (2013.01); *A61K 38/26* (2013.01); *A61K 51/02* (2013.01); *A61K 51/06* (2013.01); *A61K 51/088* (2013.01); *A61K 51/081* (2013.01)

(58) Field of Classification Search

None

See application file for complete search history.

(56) References Cited

U.S. PATENT DOCUMENTS

| | | | |
|---|---|---|---|
| 5,021,556 | A | 6/1991 | Srinivasan |
| 5,075,099 | A | 12/1991 | Srinivasan |
| 5,364,613 | A | 11/1994 | Sieving |
| 5,367,080 | A | 11/1994 | Toner |
| 5,886,142 | A | 3/1999 | Thakur |
| 12,214,059 | B2 | 2/2025 | Liu et al. |
| 2018/0221494 | A1 | 8/2018 | Manoharan |
| 2020/0078478 | A1 | 3/2020 | Li et al. |
| 2021/0009715 | A1 | 1/2021 | Benesova |
| 2023/0112418 | A1 * | 4/2023 | Maya .................... C07B 59/002 540/465 |
| 2024/0382630 | A1 | 11/2024 | Liu |

FOREIGN PATENT DOCUMENTS

| | | | | |
|---|---|---|---|---|
| AU | 2019243408 | A1 | 10/2020 | |
| WO | 2010108125 | A2 | 9/2010 | |
| WO | 2018031809 | A1 | 2/2018 | |
| WO | 2018187631 | A1 | 10/2018 | |
| WO | 2018215627 | A1 | 11/2018 | |
| WO | 2019075583 | A1 | 4/2019 | |
| WO | 2019165200 | A1 | 8/2019 | |
| WO | 2019246311 | A1 | 12/2019 | |
| WO | WO-2020030663 | A1 * | 2/2020 | ........... C07C 271/22 |
| WO | 2020106886 | A1 | 5/2020 | |
| WO | 2021046233 | A1 | 3/2021 | |
| WO | 2021163498 | A1 | 8/2021 | |
| WO | 2021225760 | A1 | 11/2021 | |
| WO | 2023097038 | A1 | 6/2023 | |

OTHER PUBLICATIONS

Kuo et al., J. Nucl. Med. 62:521-527 (2021) (Year: 2021).*

Tateishi et al., Japanese J. Clin. Oncol. 50:349-356 (2020) (Year: 2020).*

Kelly et al., J. Nucl. Med.:656-663 (2019) (Year: 2019).*

Kelly et al., J. Nucl. Med.: 656-663 (2019), supplemental information (Year: 2019).*

Chigoho et al., Curr. Opin. Chem. Biol. 63:219-228 (Jul. 2021) (Year: 2021).*

Arano, Y. et al. (1996, e-pub. Oct. 15, 1996). "Assessment Of Radiochemical Design Of Antibodies Using An Ester Bond As The Metabolizable Linkage: Evaluation Of Maleimidoethyl 3-(Tri-N-butylstannyl) hippurate As A Radioiodination Reagent Of Antibodies For Diagnostic And Therapeutic Applications," Bioconjug Chem. 7(6):628-637.

(Continued)

*Primary Examiner* — Thea D' Ambrosio

(74) *Attorney, Agent, or Firm* — MORRISON & FOERSTER LLP

(57) ABSTRACT

The present application relates to a compound or a pharmaceutically acceptable salt and/or solvate thereof comprising one or more circulation enhancing groups, one or more target binding groups, one or more chelating groups, at one least cleavable linker and at least one branching group that is at least trivalent. The application further includes a radionuclide complex or a pharmaceutically acceptable salt and/or solvate thereof, comprising a compound of the application or a pharmaceutically acceptable salt and/or solvate thereof, and one or more radionuclides, and to compositions comprising the compound or the complexes. The present application also includes methods of using the compounds, complexes and compositions for targeting and/or killing target cells. For example, the compound includes a compound of Formula I (I)

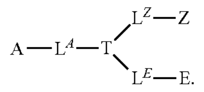

22 Claims, 8 Drawing Sheets

(56) References Cited

OTHER PUBLICATIONS

Banerjee, S.R. et al. (2005). "New Directions In The Coordination Chemistry Of 99mTc: A Reflection On Technetium Core Structures And A Strategy For New Chelate Design," Nuclear Medicine and Biology 32(1):1-20.

Bech, E.M. et al. (2018). "Chemical Strategies for Half-Life Extension of Biopharmaceuticals: Lipidation and its Alternatives," ACS Med Chem Lett 9(7):577-580.

Benesova, M. et al. (Feb. 15, 2016). "Linker Modification Strategies To Control The Prostate-Specific Membrane Antigen (PSMA)-Targeting And Pharmacokinetic Properties Of DOTA-Conjugated PSMA Inhibitors," J. Med. Chem. 59:1761-1775.

Choy, C.J. et al. (Apr. 27, 2017). "Lu-Labeled Phosphoramidate-Based PSMA Inhibitors: The Effect Of An Albumin Binder On Biodistribution And Therapeutic Efficacy In Prostate Tumor-Bearing Mice," Theranostics 7(7):1928-1939.

Deberle, L.M. et al. (Jan. 1, 2020). "Development Of A New Class Of PSMA Radioligands Comprising Ibuprofen As An Albumin-Binding Entity," Theranostics 10(4):1678-1693.

Dorff, T.B. et al. (2019, e-pub. May 17, 2019). "The Evolving Role Of Prostate-Specific Membrane Antigen-Based Diagnostics And Therapeutics In Prostate Cancer," ASCO Educational Book 39:321-330.

Däpp, S. et al. (2011). "PEGylation Of 99mTc-Labeled Bombesin Analogues Improves Their Pharmacokinetic Properties," Nuclear Medicine and Biology 38(7):997-1009.

Fields, G.B. et al. (1990). "Solid Phase Peptide Synthesis Utilizing 9-Fluorenylmethoxycarbonyl Amino Acids," Int. J. Peptide Protein Res. 35(3):161-214.

Geysen, H.M. et al. (1987). "Strategies for Epitope Analysis Using Peptide Synthesis," J. Immunol. Meth. 102:259-274.

International Search Report and Written Opinion from the International Searching Authority mailed Apr. 12, 2023, for International Patent Application No. PCT/US2022/050952 filed on Nov. 23, 2022, 10 pages.

Kalli, K.R. et al. (Mar. 2008). "Folate Receptor Alpha As A Tumor Target In Epithelial Ovarian Cancer," Gynecologio Oncology 108(3):619-626, 16 pages.

Kelly, J.M. et al. (May 2019). "Albumin-Binding PSMA Ligands: Implications For Expanding The Therapeutic Window," J Nucl Med 60(5):656-663.

Korner, M. et al. (Dec. 6, 2012)."Glucagon-Like Peptide-1 Receptor Overexpression In Cancer And Its Impact On Clinical Applications," Frontiers in Endocrinology 3(158):1-7.

Kramer, V. et al. (2021, e-pub. Sep. 19, 2020). "Biodistribution And Dosimetry Of A Single Dose Of Albumin- Binding Ligand [177 Lu] Lu-PSMA-ALB-56 In Patients With mCRPC," European Journal of Nuclear Medicine and Molecular Imaging 48:893-903.

Kuo, H.-T. et al. (2018, e-pub. Sep. 25, 2018). "Enhancing Treatment Efficacy Of 177Lu-PSMA-617 With The Conjugation Of An Albumin-Binding Motif: Preclinical Dosimetry And Endoradiotherapy Studies," Molecular Pharmaceutics 15(11):5183-5191, 25 pages.

Lim, S.I. et al. (Sep. 10, 2013). "Site-Specific Fatty Acid-Conjugation To Prolong Protein Half-Life In Vivo," J Control Release 170(2):219-225, 19 pages.

PubChem. (Jan. 30, 2021). "SCHEMBL22878107" PubChem SID 439920610, 5 pages.

Qian, Z.R. et al. (Nov. 2016). "Association Between Somatostatin Receptor Expression And Clinical Outcomes In Neuroendocrine Tumors," Pancreas 45(10):1386-1393, 21 pages.

Ronnebaum, J.M. et al. (2016). "Synthesis Of 1, 2, 3-Triazole 'Click' Analogues Of Thalidomide," Tetrahedron 72(40):6136-6141, 23 pages.

Ruigrok, E.A. et al. (Oct. 29, 2019). "The Future Of PSMA-Targeted Radionuclide Therapy: An Overview Of Recent Preclinical Research," Pharmaceutics 11(560):21 pages.

Sgouros, G. et al. (Sep. 2020, e-pub. Jul. 29, 2020). "Radiopharmaceutical Therapy In Cancer: Clinical Advances And Challenges," Nature Reviews Drug Discovery 19(9):589-608.

Singh, M.S. et al. (2016). "Advances Of Azide-Alkyne Cycloaddition-Click Chemistry Over The Recent Decade," Tetrahedron 72(35):5257-5283, 30 pages.

Umbricht, C.A. et al. (2018). "Preclinical Development Of Novel PSMA-Targeting Radioligands: Modulation Of Albumin-Binding Properties To Improve Prostate Cancer Therapy," Molecular Pharmaceutics 15(6):2297-2306, 15 pages.

Wadas, T.J. et al. (2010, e-pub. Apr. 23, 2010). "Coordinating Radiometals Of Copper, Gallium, Indium, Yttrium, And Zirconium For PET And SPECT Imaging Of Disease," Chemical Reviews 110(5):2858-2902.

Wang, Z. et al. (Aug. 14, 2018). "Single Low-Dose Injection Of Evans Blue Modified PSMA-617 Radioligand Therapy Eliminates Prostate-Specific Membrane Antigen Positive Tumors," Bioconjugate Chemistry 29(9):3213-3221, 9 pages.

Benešová, M. et al. (2018). "Albumin-Binding PSMA Ligands: Optimization of the Tissue Distribution Profile," Molecular Pharmaceutics 15(3):934-946.

Ke, T. et al. (2007). "RGD Targeted Poly (L-Glutamic Acid)-Cystamine-(Gd-DO3A) Conjugate for Detecting Angiogenesis Biomarker avβ3 Integrin with MR T1 Mapping," International Journal of Nanomedicine 2(2):191-199.

* cited by examiner

CLEAVABLE RADIOLIGANDS FOR TARGETING CELL SURFACE RECEPTORS AND USES THEREOF

RELATED APPLICATIONS

The present application is a continuation of U.S. application Ser. No. 18/604,400, filed on Mar. 13, 2024, which is a continuation of PCT Application No. PCT/US2022/050952, filed on Nov. 23, 2022, which claims the benefit of and priority of U.S. Provisional Patent Application No. 63/283,361, filed on Nov. 26, 2021, the contents of which are incorporated herein by reference in their entirety.

FIELD

The present application relates generally to the field of cleavable radioligands that target cell surface receptors. In particular, it relates to compounds comprising a circulation enhancing group, a target binding group, a radioisotope and a cleavable linker, and compositions thereof. It also relates to methods of using the compounds and compositions for targeting and/or killing target cells.

BACKGROUND

Cancer is a disease in which some of the body's cells grow uncontrollably and spread to other parts of the body. In comparison to normal cells, cancer cells may overexpress specific receptors on the cell membrane (Sgouros G et al., 2020). For examples, prostate cancer cells predominately overexpress Prostate-Specific Membrane Antigen (PSMA) receptor. PSMA is a largely prostate-specific transmembrane protein expressed 100- to 1,000-fold higher in prostatic adenocarcinoma than in the benign prostate (Dorff T B et al., 2019). Glucagon-like peptide 1 (GLP-1) receptor is highly overexpressed in nearly 100% insulinoma tumors (Körner M et al., 2012). Folate receptor-alpha is expressed in majority of ovarian cancer cells with a density of 106 receptor per cell, while its expression in normal cell is significantly lower (Kalli K R et al., 2008). Somatostatin receptor 2 (SSTR2) is highly overexpressed in over 80% of neuroendocrine tumors (Qian Z R et al., 2017).

Such overexpression of receptors has facilitated targeted cancer treatments, where the drug is often constructed as a conjugate or a construct or a complex or a hybrid consisting of a cell-killing moiety and a vector for delivering the payload. Most notable examples include antibody-drug conjugates, peptide-drug conjugates, cell-based therapy CAR-T and others. The therapeutic payloads can be cytotoxic small molecules, proteins, immunostimulants, radionuclides and others. Examples of approved drugs in this class include Adcetris(brentuximab vedotin), Kadcyla (Trastuzumab emtansine), Lutathera (lutetium (177Lu) oxodotreotide), Kymriah (Tisagenlecleucel) etc.

A radioligand typically contains a targeting moiety that seeks overexpressed receptors of interest and directs the radioisotope toward the targeted site. In the case of radiometal-based radioligand therapeutics, a chelate is connected to a targeting moiety via a linker. Once the chelate is complexed with a radionuclide (radiolabeling), the final radioligand complex is formed. The radioligand delivers a radioactive payload to the targeted cell, followed by the on-site emission of alpha, beta, or gamma particles, leading to damage, or the breakdown of DNA strands and eventually killing the cancer cell. Similarly, when a diagnostic radionuclide is used, a radioligand diagnostic agent is produced.

One objective of optimizing a radioligand is to maximize tumor uptake and minimize off-target accumulation in normal organs. When a radioligand binds to the targeted receptor on the cancer cell surface, the resulting receptor-radioligand complex is often internalized, and the radioisotope is concentrated inside the cancer cell. In order to achieve an acceptable therapeutic window, a sufficient amount of the injected radioisotope dose must accumulate in the targeting cell. In addition, the accumulation of the radioisotope in the non-target normal tissue must be reasonably low.

Both small and large molecules have been used as targeting vectors for radioligands, while each resulting in distinct in vivo biodistribution profiles of the radionuclide. Peptide and small molecule-based radioligands, often clear rapidly from systemic circulation, mostly excreted through kidney filtration. Such short half-lives, in some cases, do offer high tumor to normal organ contrast of radioisotope uptake. However, the short blood residence time is often detrimental to tumor uptake. In addition, a considerable amount of peptide scaffolds and small molecule-based radioligand tend to accumulate in the kidney that leads to poor tumor to kidney ratio of radionuclide uptake. On the other side, antibody-based radioligands are distinguished by significantly longer blood circulation half-life and slower kidney clearance, which translates into higher tumor uptake and relatively lower kidney uptake. Despite that, the prolonged blood exposure unavoidably results in high uptake in normal organs including bone marrow, spleen, and liver etc.

Consequently, there is a need for improved radioligands that can deliver a high percentage of dosed radioisotope to the targeted cancer cell, while simultaneously maintaining or ideally reducing uptake by normal organs such as kidney, blood, liver, spleen and bone marrow.

To circumvent the short circulating half-life problem of peptide-based compounds, the attachment of long polyethylene glycol (PEG) and the incorporation of a serum albumin binding moiety, including 4-(p-Iodophenyl) butyric acid (or methyl analogue), Evans blue motif and ibuprofen, have been employed (Däpp S et al., 2011; Wang Z et al., 2018; Choy C J et al., 2017; Kuo H T et al., 2018; Deberle L M et al., 2020; Kramer V et al., 2021). The former extends its plasma half-life through the large hydrodynamic size of PEG while the latter achieves the same by engaging serum albumin protein, which results in the slowdown of the renal clearance of the radioligand. Such modifications have produced mixed results. In the case of PSMA-targeted radioligand therapy, high tumor uptake was achieved; however, significantly increased kidney uptake limited the clinical application of such radioligands. One representative example is HTK01169 (Kuo H T et al., 2018), when compared to PSMA-617. The high uptake of PSMA radioligands in kidneys may be attributed to the high PSMA receptor expression at the kidney, thus any ligand that increases half-life, experiences higher uptake in both the kidneys and tumor. However, it could also be caused by the inherent physicochemical properties of the respectively modified radioligands.

In the case of Mab-based radioligands, cleavable constructs were briefly explored to reduce the accumulation of radioisotope in the liver and other normal organs (Arano Y et al., 1996). This was done by introducing a metabolizable bond between Mab and radioisotope complex. However, only marginal improvement was achieved presumably due to the slow internalization kinetics of the covalently modified Mab that diminished the benefit of having a metabolizable linkage. Separately, these metabolizable linkers could only release a non-targeting radioisotope complex.

Overall, there is still a lack of optimized radioligands that can concurrently achieve high tumor uptake and low normal organ accumulation. Such radioisotope biodistribution profile is expected to result in significantly improved efficacy and safety profiles and increase the therapeutic index.

SUMMARY

Given the aforementioned limitations, new radioligands that target cell surface receptors are described herein. These compounds are designed to optimize cell response, degradation, clearance and other fundamental properties.

Accordingly, the present application includes a compound or a pharmaceutically acceptable salt and/or solvate thereof comprising one or more circulation enhancing groups, one or more target binding groups, one or more chelating groups and at least one branching group that is at least trivalent, wherein the branching group that is at least trivalent is connected to at least one target binding group directly or through a first non-cleavable linker, to at least one circulation enhancing group directly, through a second non-cleavable linker directly or through a first cleavable linker, and to at least one chelating group directly, through a third non-cleavable linker or through a second cleavable linker, provided the branching group that is at least trivalent is connected to the at least one circulation enhancing group through the first cleavable linker, or the branching group that is at least trivalent is connected to the at least one chelating group through the second cleavable linker.

In some embodiments, the compound has an ex vivo half-life in mouse plasma at about 37° C. of about 4 hours to about 360 hours, about 6 hours to about 144 hours, about 12 hours to about 120 hours, about 18 hours to about 108 hours, or about 24 hours to 96 hours.

In some embodiments, the compound is a compound of Formula I and the application also includes compound of Formula I or a pharmaceutically acceptable salt and/or solvate thereof (I)

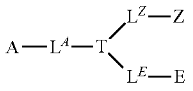

wherein

A is a circulation enhancing group;

Z is a target binding group;

E is a chelating group;

T is a branching group that is at least trivalent;

$L^A$ and $L^E$ are each independently a direct bond, a cleavable linker or a non-cleavable linker; and $L^Z$ is a direct bond or a non-cleavable linker;

provided at least one of $L^A$ and $L^E$ is a cleavable linker.

In some embodiments, $L^A$ is

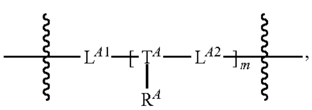

, $L^Z$ is

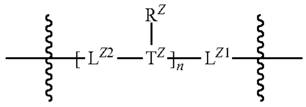

and $L^E$ is

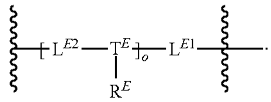

.

Accordingly, the application also includes a compound of Formula I wherein the compound of Formula I is a compound of Formula I-D or a pharmaceutically acceptable salt and/or solvate thereof (I-D)

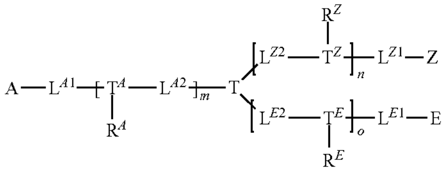

wherein

A, Z, E and T are as defined in Formula I $T^A$, $T^Z$, $T^E$ are each independently T as defined in formula I and $T^A$, $T^Z$, $T^E$ and T are the same or different;

$L^{A1}$ and $L^{A2}$ are each independently $L^A$ as defined in Formula I;

$L^{E1}$ and $L^{E2}$ are each independently $L^E$ as defined in Formula I;

$L^{Z1}$ and $L^{Z2}$ are each independently $L^Z$ as defined in Formula I;

$R^A$ is selected from

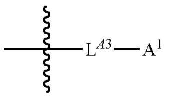

and

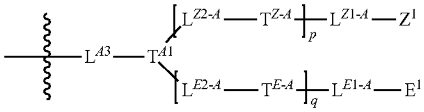

$R^Z$ is selected from

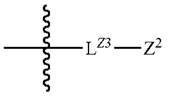

and

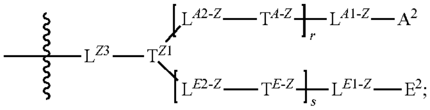

;

$R^E$ is selected from

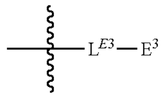

and

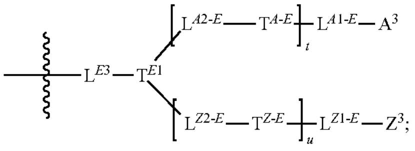

$T^{A1}$, $T^{Z-A}$, $T^{E-A}$, $T^{Z1}$, $T^{A-Z}$, $T^{E-Z}$, $T^{E1}$, $T^{Z-E}$, $T^{A-E}$ are each independently T as defined in Formula I and T, $T^{A1}$, $T^{Z-A}$, $T^{E-A}$, $T^{Z1}$, $T^{A-Z}$, $T^{E-Z}$, $T^{E1}$, $T^{Z-E}$ and $T^{A-E}$ are the same or different;

$L^{A3}$, $L^{A1-Z}$, $L^{A2-Z}$, $L^{A1-E}$ and $L^{A2-E}$ are each independently $L^A$ as defined in Formula I;

$L^{E3}$, $L^{E1-A}$, $L^{E2-A}$, $L^{E1-Z}$ and $L^{E2-Z}$ and are each independently $L^E$ as defined in Formula I;

$L^{Z3}$, $L^{Z1-A}$, $L^{Z2-A}$, $L^{Z1-E}$ and $L^{Z2-E}$ are each independently $L^Z$ as defined in Formula I;

$A^1$, $A^2$ and $A^3$ are each independently A as defined in Formula I and $A^1$, $A^2$, $A^3$ and A are the same or different;

$Z^1$, $Z^2$ and $Z^3$ each independently Z as defined in Formula I and $Z^1$, $Z^2$, $Z^3$ and Z are the same or different;

$E^1$, $E^2$ and $E^3$ each independently E as defined in Formula I and $E^1$, $E^2$, $E^3$ and E are the same or different; and m, n, o, p, q, r, s, t and u are each independently selected from 0 and 1, wherein at least one of $L^{A3}$, $L^{E1-A}$ $L^{E2-A}$, $L^{A1-Z}$, $L^{A2-Z}$, $L^{E1-Z}$, $L^{E2-Z}$, $L^{E3}$, $L^{A1-E}$ and $L^{A2-E}$ is a cleavable linker.

The application further includes a radionuclide complex or a pharmaceutically acceptable salt and/or solvate thereof, comprising a compound as defined above or a pharmaceutically acceptable salt and/or solvate thereof, and one or more radionuclides.

The application includes a composition comprising one or more compounds as described above or a pharmaceutically acceptable salt and/or solvate thereof, or one or more radionuclide complexes as described above or a pharmaceutically acceptable salt and/or solvate thereof and a carrier.

The application includes a composition comprising one or more compounds as described above or a pharmaceutically acceptable salt and/or solvate thereof, or one or more radionuclide complexes as described above or a pharmaceutically acceptable salt and/or solvate thereof and a pharmaceutically acceptable carrier.

The application also includes a kit comprising one or more compounds as described above or a pharmaceutically acceptable salt and/or solvate thereof, and instructions for administration of the one or more compounds of Formula I, or a pharmaceutically acceptable salt and/or solvate thereof, to a subject in need thereof.

The application further includes kit comprising one or more compounds as described above or a pharmaceutically acceptable salt and/or solvate thereof, and one or more radionuclides as defined above, and optionally instructions for administration of the one or more compounds or a pharmaceutically acceptable salt and/or solvate thereof, to a subject in need thereof and the radioisotope to a subject in need thereof.

The application also includes a kit comprising one or more radionuclide complexes as described above or a pharmaceutically acceptable salt and/or solvate thereof, and instructions for administration of the one or more compounds complexes to a subject in need thereof.

Further included is a method of treating a disease or disorder comprising administering a therapeutically effective amount of one or more compounds as described above or one or more radionuclide complexes as described above or a pharmaceutically acceptable salt and/or solvate thereof to a subject in need thereof.

In some embodiments, the disease or disorder is cancer.

The application also includes a method of inhibiting proliferative activity in a cell, comprising administering an effective amount of one or more compounds of as described above or one or more radionuclide complexes as described above or a pharmaceutically acceptable salt and/or solvate thereof to the cell.

The application also includes a method of imaging a tissue in a subject by administering a imaging effective amount of one or more compounds as described above or one or more radionuclide complexes for use in imaging as described above or a pharmaceutically acceptable salt and/or solvate thereof and applying an imaging technique to detect emitted gamma rays.

The application also includes a method of diagnosing cancer in subject by administering a diagnostically effective amount of one or more compounds as described above or one or more radionuclide complexes for use in imaging as described above or a pharmaceutically acceptable salt and/or solvate thereof and applying an imaging technique to detect emitted gamma rays.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Certain embodiments of the application will now be described in greater detail with reference to the attached drawings in which.

DETAILED DESCRIPTION

I. Definitions

Figure 1:
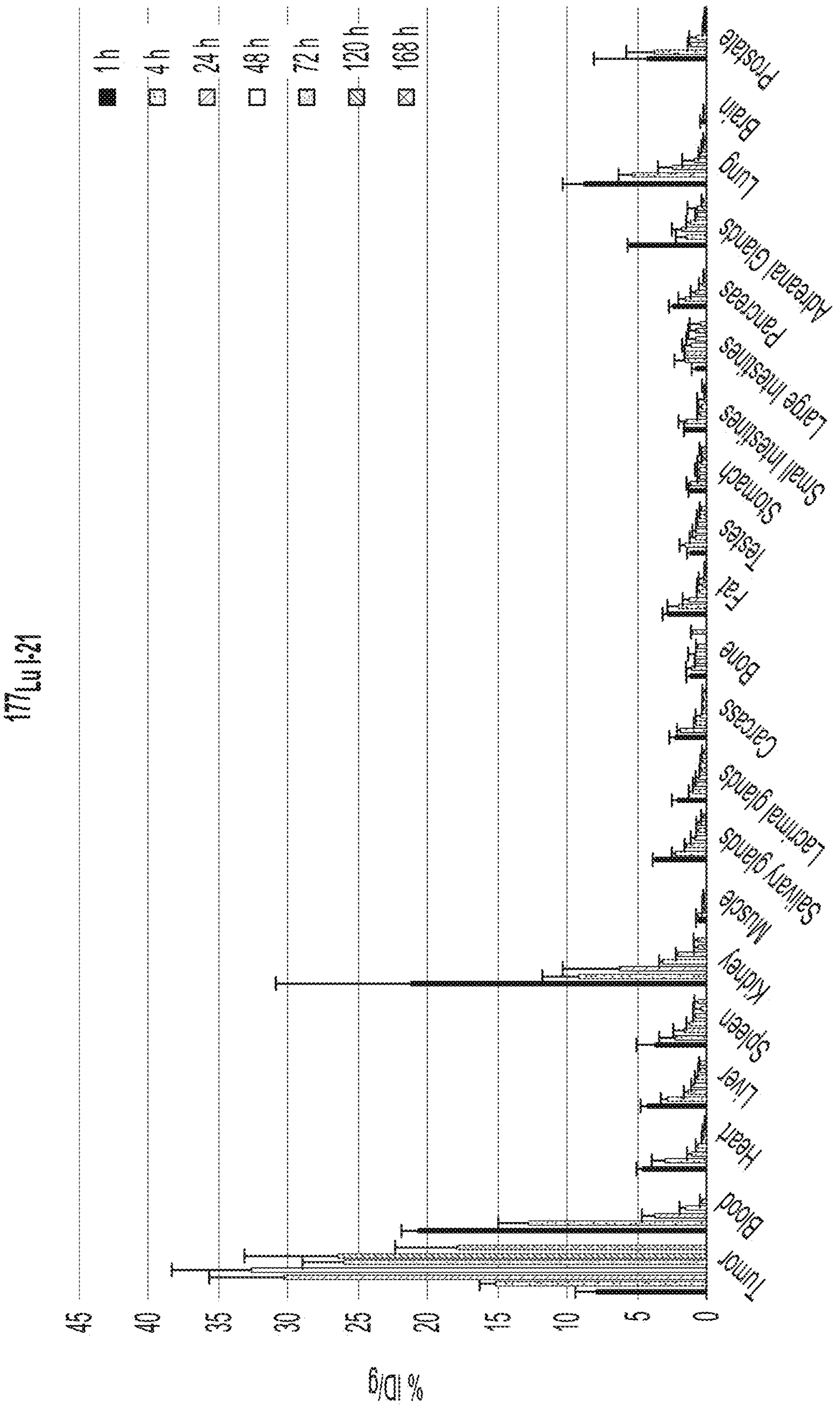
FIG. 1 shows the biodistribution of exemplary complex $^{177}$Lu-I-21 in PC3-PIP tumor bearing mice.

Unless otherwise indicated, the definitions and embodiments described in this and other sections are intended to be applicable to all embodiments and aspects of the present application herein described for which they are suitable as would be understood by a person skilled in the art.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component or effect, such as an additional or second compound, the second compound as used herein is different from the other compounds or first compound. A "third" compound is different from the other, first, and second compounds, and further enumerated or "additional" compounds are similarly different.

The term "and/or" as used herein means that the listed items are present, or used, individually or in combination. In effect, this term means that "at least one of" or "one or more" of the listed items is used or present. The term "and/or" with respect to enantiomers, prodrugs, salts and/or solvates thereof means that the compounds of the application exist as individual enantiomers, prodrugs, salts and hydrates, as well as a combination of, for example, a salt of a solvate of a compound of the application.

The term "compound(s) of the application" or "compound(s) of the present application" and the like as used herein refers to a compound of Formula I, I-A, I-B, I-C, I-D, I-E, I-F, I-G, I-H, I-I, I-J, I-K, I-L, I-A', I-A' (a), I-A' (b), I-A' (c), I-A' (d), I-B', I-C' and I-D' or pharmaceutically acceptable salts and/or solvates thereof.

The term "complex of the application" or "complexes of the application" and the like as used herein refers to a complex comprising one or more compounds of Formula I or pharmaceutically acceptable salts and/or solvates thereof and one or more radionuclides.

The term "composition of the application" or "composition of the present application" and the like as used herein refers to a composition comprising one or more compounds or complexes of the application.

The term "radioligand" as used herein refers to a compound comprising a targeting moiety and a radionuclide. The complexes of the application are examples of radioligands.

The term "radionuclide" as used herein refers to any atom capable of undergoing radioactive decay. The term radionuclide is used synonymously herein with radioactive nuclide, radioisotope, and radioactive isotope.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

The present description refers to a number of chemical terms and abbreviations used by those skilled in the art. Nevertheless, definitions of selected terms are provided for clarity and consistency.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas).

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms. All alkyl groups are optionally fluoro-substituted unless otherwise indicated.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms. All alkylene groups are optionally fluoro-substituted unless otherwise indicated.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond. All alkenyl groups are optionally fluoro-substituted unless otherwise indicated.

The term "alkenylene", whether it is used alone or as part of another group, means straight or branched chain, unsaturated alkyl groups containing at least one double bond that contains substituents on two of its ends. The number of carbon atoms that are possible in the referenced alkylene group are indicated by the prefix "$C_{n1-n2}$". For example, the term $C_{2-6}$alkenylene means an alkenylene group having 2, 3, 4, 5 or 6 carbon atoms. All alkenylene groups are optionally fluoro-substituted unless otherwise indicated.

The term "aryl" as used herein, whether it is used alone or as part of another group, refers to carbocyclic groups containing at least one aromatic ring and contains 6 to 20 carbon atoms.

The term "cycloalkyl," as used herein, whether it is used alone or as part of another group, means a saturated carbocyclic group containing from 3 to 20 carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "heterocycloalkyl" as used herein, whether it is used alone or as part of another group, refers to cyclic groups containing at least one non-aromatic ring containing from 3 to 20 atoms in which one or more of the atoms are a heteroatom selected from O, S and N and the remaining atoms are C. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as selected from O, S and N and the remaining atoms are C. Heterocycloalkyl groups are optionally benzofused.

The term "heteroaryl" as used herein, whether it is used alone or as part of another group, refers to cyclic groups containing at least one heteroaromatic ring containing 5-20 atoms in which one or more of the atoms are a heteroatom selected from O, S and N and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heteroaryl groups are optionally benzofused.

All cyclic groups, including aryl, heteroaryl, heterocycloalkyl and cycloalkyl groups, contain one or more than one ring (i.e. are polycyclic). When a cyclic group contains more than one ring, the rings may be fused, bridged, spirofused or linked by a bond.

The term "benzofused" as used herein refers to a polycyclic group in which a benzene ring is fused with another ring.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "target binding group" are used herein refers to a moiety that is recognized by a target site to which it binds.

The term "target" or "target site" as used herein means a receptor, for example a cell surface receptor, antigen, for example prostate specific membrane antigen (PSMA) or other protein on a cell surface to which a target binding group can bind.

The term "circulation enhancing group" as used herein is a chemical structure that increases the circulation time of the compound of the application in the blood.

The term "chelating group" as used herein is chelator capable of complexing a radionuclide.

The term "branching group that is at least trivalent" as used herein refers to any molecular structure that comprises at least three terminal functional groups and each terminal functional group connects with another molecular structure. The at least three terminal functional groups can be the same or different.

The term "in vivo half-life" as used herein refers to the time required for half the quantity of a compound administered to a subject to be cleared from the circulation (e.g blood) and/or other tissues of the subject.

The term "half-life" as used herein refers to a pharmacokinetic property of a compound and is a measure of the mean survival time of the compound following administration of the compound to a subject. Half-life is the time required for half the quantity of the compound administered in a subject to be cleared from the subject's body or a specific compartment thereof (e.g serum or in other tissues).

The term "ex vivo plasma half-life" as used herein refers to the time required for half the quantity of a compound that has been combined with plasma, for example, mouse plasma, to be degraded within the plasma at about 37° C. and at neutral pH. Ex vivo plasma half-life may be measured for example by incubating a radioligand in mouse plasma at 37° C. At each desired time point, an aliquot of sample may be taken out, worked up and analyzed by HPLC with radiodetection. This measures the remaining % of intact radioligand, which can be plotted to provide a measure of ex vivo plasma half-life.

The term "linker group" as used herein refers to any molecular structure that connects two or more other molecular structures together.

The term "non-cleavable linker group" as used herein refers to any molecular structure that joins two or more other molecular structures together and comprises non-cleavable moieties. The non-cleavable linker group contains functional groups on each of the termini that react with complementary functional groups of the molecules to be linked to form non-cleavable moieties. When a compound of the application comprises more than one non-cleavable linker, each non-cleavable linker is an independent non-cleavable linker and the one or more non-cleavable linkers may be the same or different.

The term "cleavable linker" as used herein refers to any molecular structure that joins two or more other molecular structures together and comprises at least one cleavable moiety. The cleavable linker group contains functional groups on each of the termini that reacts with complementary functional groups of the molecules to be linked to form non-cleavable or cleavable moieties. When a compound of the application comprises more than one cleavable linker, each cleavable linker is an independent cleavable linker and the one or more cleavable linkers may be the same or different.

The term "non-cleavable moiety(ies)" as used herein refers to chemical functional groups that resist degradation by one or more of acids, bases, reducing agents oxidizing agents and enzymes. Non-cleavable moieties are generally stable towards cleavage but can be cleavable, for example, by enzymes or physiological conditions inside a cell, tissue or organ after a period of time and after the compound or the portion of the compound that contains the non-cleavable moiety is delivered or transported to the target site.

The term "cleavable moiety(ies)" as used herein refers to a chemical functional group that is degraded by one or more of acids, bases, reducing agents oxidizing agents and enzymes.

The term "stable towards cleavage", or "resists degradation" as used herein refers to a chemical functional group that less than about 5% of which is degraded in mouse plasma at about 37° C. after at least about 48 hours following combining of a compound comprising the chemical functional group with the mouse plasma.

The term "degraded" or "cleavable" as used herein in relation to the cleavable moiety means that greater than about 5% of the cleavable moiety is degraded in mouse plasma at about 37° C. after at least about 48 hours following combining of a compound comprising the cleavable moiety with the mouse plasma.

The term "amino acid residue" are used herein refers to an amino acid without the "—OH" of its carboxyl group and the "H" portion of an amino group.

The term "amino acid" as used herein is any compound comprising a carboxyl ($—CO_2H$) functional group and an amine ($—NH_2$) functional group.

The term "unnatural amino acid", as used herein, refers to an amino acid that is not a naturally occurring amino acid and is obtained synthetically or by modification of a natural amino acid.

The term "naturally occurring amino acid" as used herein refers amino acids that occur naturally and are encoded by the genetic code, as well as those encoded amino acids that are later modified in vivo.

The term "at least one" when preceding an item refers to a single member of the item or when preceding a list of items refers to a single member of the item and any combination of those items. For example at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. A subject with early cancer can be treated to prevent progression for example, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations.

"Palliating" a disease, disorder or condition means that the extent and/or undesirable clinical manifestations of a disease, disorder or condition are lessened and/or time course of the progression is slowed or lengthened, as compared to not treating the disorder.

The terms "preventing", "prevention" or "prophylaxis", or synonyms thereto, as used herein refers to a reduction in the risk or probability of a patient becoming afflicted with a disease, disorder or condition or manifesting a symptom associated with a disease, disorder or condition.

As used herein, the term "therapeutically effective amount" means an amount of a compound, or one or more compounds, of the application, or complex, or one or more complexes of the application that is effective, at dosages and for periods of time necessary to achieve the desired result.

The term "imaging effective amount" when used in connection with a one or more complexes of the application, is an amount of the complex that is sufficient to produce a visible image when the complex is administered to a subject and the radiation emitted by the complex is detected using positron-emission tomography ("PET") or single photon emission tomography (SPECT) or autoradiography or ex vivo or in vitro binding assays.

As used herein, the term "diagnostic effective amount" means an amount of a compound, or one or more compounds, of the application or complex, or one or more complexes of the application, that is effective, at dosages and for periods of time necessary to achieve the desired diagnostic effect including, for example, diagnosing a particular condition being assessed.

The term "administered" as used herein means administration of an imaging, diagnostic and/or therapeutically effective amount of one or more compounds, complexes or compositions of the application to a cell, tissue, organ or subject.

The term "cancer" as used herein refers to cellular-proliferative disease states.

The term "subject" as used herein includes all members of the animal kingdom including mammals, and suitably refers to humans. Thus, the methods and uses of the present application are applicable to both human therapy and veterinary applications.

The term "cell" as used herein refers to a single cell or a plurality of cells and includes a cell either in a cell culture or in a subject.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate" as used herein means a compound, or a salt and/or prodrug of a compound, wherein molecules of a suitable solvent are incorporated in the crystal lattice. A suitable solvent is physiologically tolerable at the dosage administered.

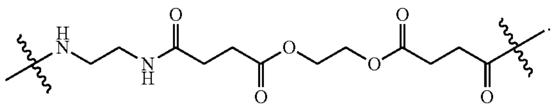

The term “PSMA-617”, ‘Vipivotide tetraxetan”, “DOTA-Trx-2NaI-eKuE”, or “C-1” as used herein refers to a compound having the chemical name: (((S)-1-carboxy-5-((S)-3-(naphthalen-2-yl)-2-((1r,4S)-4-((2-(4,7,10-tris (carboxymethyl)-1,4,7,10-tetraazacyclododecan-1-yl) acetamido)methyl)cyclohexane-1-carboxamido) propanamido) pentyl) carbamoyl)-L-glutamic acid tetra(trifluoroacetic acid), and having the chemical formula:

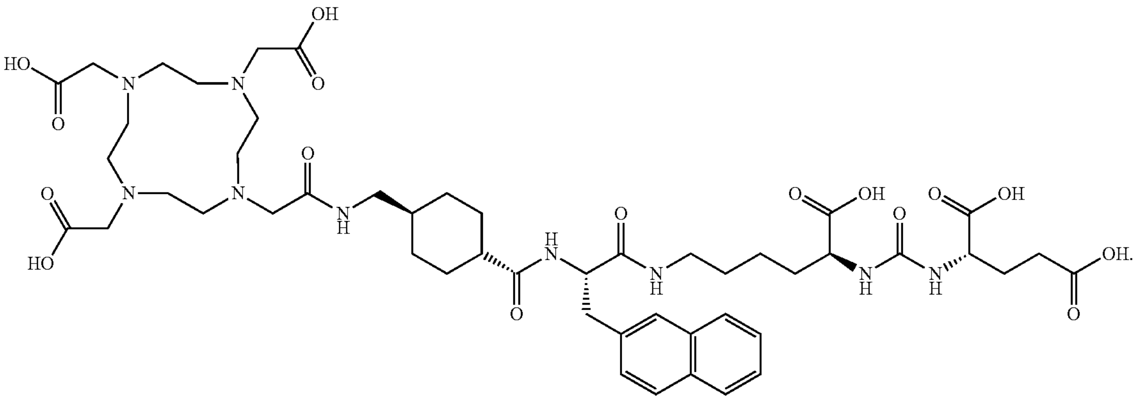

The term “HTK01169” or “4pIBA-Glu-Lys(DOTA)-Trx-2NaI-eKuE” as used herein refers to a compound having the chemical formula:

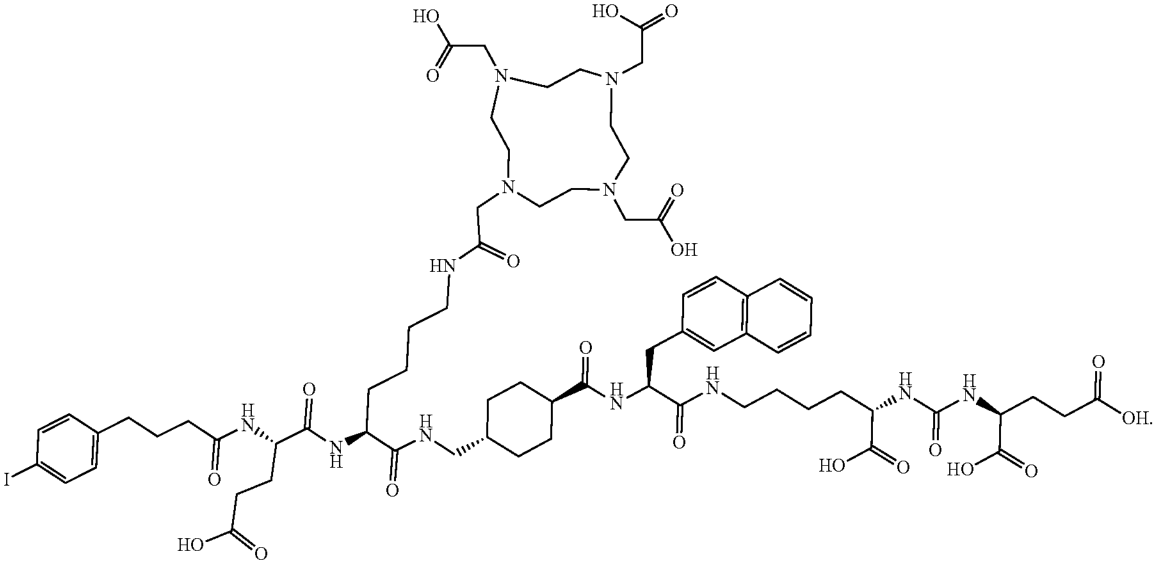 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CN2CCN(CC(=O)O)CCN(CC(=O)O)CCN(CC(=O)O)CC2)NC(=O)[C@H](CCC(=O)O)NC(=O)CCCc2ccc(I)cc2)CC1)C(=O)O)C(=O)O]

The term “ESL1” as used herein refers to a cleavable linker group having the chemical formula:

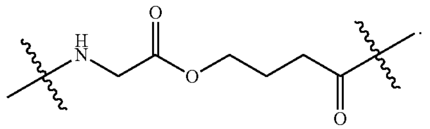 [SMILES: *NCC(=O)OCCCC(*)=O]

The term “ESL2” as used herein refers to a cleavable linker group having the chemical formula:

The term “ESL3” as used herein refers to a cleavable linker group having the chemical formula:

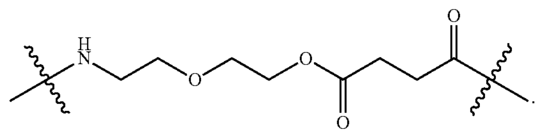 [SMILES: *NCCOCCOC(=O)CCC(*)=O]

The term “SSL1” as used herein refers to a cleavable linker group having the chemical formula:

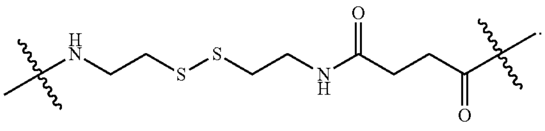 [SMILES: *NCCSSCCNC(=O)CCC(*)=O]

The term "TrX" as used herein refers to a linker group having the chemical formula:

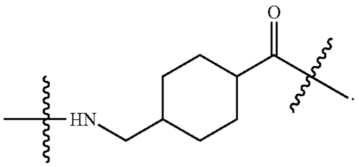 [SMILES: *NCC1CCC(C(*)=O)CC1]

The term "OEG" as used herein refers to a linker group having the chemical formula:

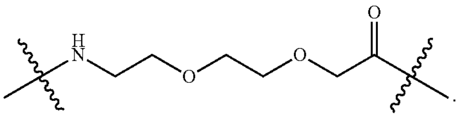 [SMILES: *NCCOCCOCC(*)=O]

The term "2NaI" as used herein refers to a linker group having the chemical formula:

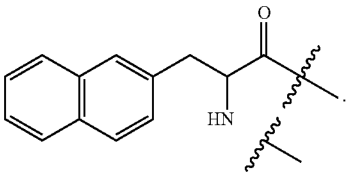

The term "Aoc" as used herein refers to a linker group having the chemical formula:

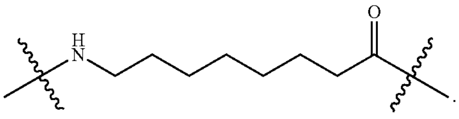 [SMILES: *NCCCCCCCC(*)=O]

The term "Aun" as used herein refers to a linker group having the chemical formula:

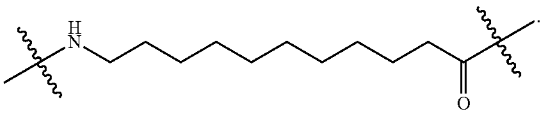 [SMILES: *NCCCCCCCCCCC(*)=O]

The term "Ava" as used herein refers to a linker group having the chemical formula:

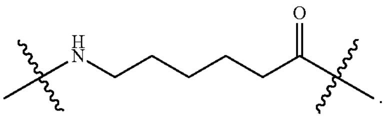 [SMILES: *NCCCCCC(*)=O]

The term "4hBA" as used herein refers to a linker group compound having the chemical name 4-hydroxybutanoic acid and having the chemical formula:

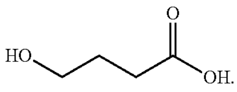

The term "4hPA" as used herein refers to a linker group compound having the chemical name 4-hydroxypentanoic acid and having the chemical formula:

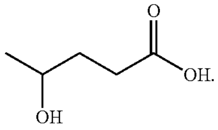

The term "5hPA" as used herein refers to a linker group compound having the chemical name 6-hydroxypentanoic acid and having the chemical formula:

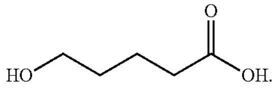

The term "6hPA" as used herein refers to a linker group compound having the chemical name 6-hydroxyhexanoic acid and having the chemical formula:

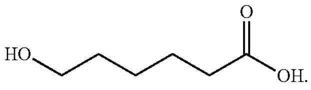

The term "DAB" as used herein refers to a linker group compound having the chemical name 2,4-diaminobutyric acid and having the chemical formula:

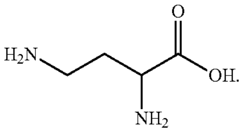

The term "DAP" as used herein refers to a linker group compound having the chemical name 2,3-diaminopropionic acid and having the chemical formula:

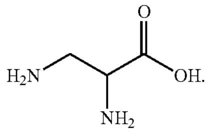

The symbol  when drawn perpendicularly across a bond indicates a point of covalent attachment of a chemical group.

When used, for example, with respect to the methods of treatment, uses, compositions, packages and/or kits of the application, a subject, for example a subject "in need thereof" is a subject that would benefit from administration of one or more compounds or complexes of the application, or a pharmaceutically acceptable salt and/or solvate thereof.

II. Compounds and Complexes of the Application

The present application relates to improved radioligands that target cell surface receptors, methods of preparation of the radioligands and methods of their use for targeting and/or inhibiting target cells. In particular, it relates to radioligands comprising a circulation enhancing group, a targeting moiety, a radionuclide and a cleavable linker and compositions thereof. The inventors have shown that radioligands described herein have greater uptake of the radionuclide in the target cell while maintaining the off-target normal organ accumulation to a minimum. The normal organs include but are not limited to kidney and blood.

When introducing a circulation enhancing group such as an albumin binding motif to a radioligand, the chemical structure of such motif may impact the binding affinity of the resulting radioligand to the target receptor, the in vivo biodistribution for example, the radionuclide uptake by the tumor, and the radionuclide uptake ratio between tumor and kidney. Thus an issue with the albumin binders in the art of radioligand field is that they lead to poor uptake ratio between tumor to kidney. This is seen, for example, between HTK01169 (C-2), PSMA-ABL-56 (C-10) or another known compound C-9 when compared to PSMA-617 (C-1).

To minimize the amount of radionuclide exposure to the normal organs and to purposely degrade the radioligand to metabolites that are less likely accumulate in non-target receptor expressing cells, the present inventors have introduced a cleavable linker to a radioligand compound. Contrary to the drug conjugate concept in the art, the cleavage process of the radioligand compounds of the application is purposely designed to take place preferably in plasma and throughout the body, rather than at the targeted tumor site. Such cleavage processes do not rely on the specific tumor-enriched enzymes or the unique chemical conditions within tumor microenvironment. Accordingly, such design avoids the impact of heterogeneity nature of the tumor that may considerably impact the anticipated cleavage kinetics, and ensures minimal inter-patient variability of drug (radionuclide) distribution profile in the body.

For example, as exemplified by exemplary compounds of the application such as I-2, I-11, I-18, I-21, I-34, I-43 when compared to HTK01169 (C-2) in mice bearing PC3-PIP tumor, and by exemplary compounds of the application such as I-18, I-21, I-67 and I-69 when compared to ABL-56 (C-10) or C-9 in mice bearing LNCap tumor, the present inventors have shown that the introduction of a cleavable linker to radioligand with an albumin binding motif provides an improved uptake ratio between tumor to kidney while maintaining high tumor uptake (see, for example, TABLE 34).

In addition, as exemplified by exemplary compounds of the application such as I-21 vs 1-2, 1-11 or I-18 vs 1-3 in mice bearing PC3-PIP tumor, and by 1-21 vs 1-67, and I-18 vs 1-69 in mice bearing LNCap tumor, the present inventors have shown when compared to the often used albumin binders in the radioligand field such as 4-pIBA in HTK01169 (C-2), the use of a long chain fatty diacid as an albumin binding motif, despite showing a reduced in vitro binding affinity to its receptor, offers an improved biodistribution profiling, for example, enhanced tumor uptake, and improved or equivalent uptake ratio between tumor to kidney (see, for example, TABLE 34).

Furthermore, the present inventors have shown that, for example, the different placement location of the cleavable linker relative to the location of the albumin binding moiety and the chelate, also resulted in different biodistribution profile of the radionuclide in vivo. For example, in the case of a PSMA-targeting radioligand, some compounds comprising cleavable moieties such as ester or esters that specifically release fragments bearing both chelate (radionuclide) and target binding groups, had a better biodistribution profile and tumor uptake, than the ones that contained cleavable moieties such as esters which cleave and release fragments containing only the chelate (radionuclide). Such preference is not dependent on the type of albumin binder. A person of skill in the art might expect that in the presence of normal organs that could specifically take up the radioligand, the release of fragments bearing both chelate (radionuclide) and targeting binding groups should not produce better tumor to non-target ratios versus releasing the non-targeting chelate (radionuclide). However, as exemplified by exemplary compounds I-2 and I-3 in mice bearing PC-3-PIP tumor, and I-21 vs I-18 in mice bearing PC3-PIP or LNCap tumors, the present inventors observed a 2-8-fold increase of tumor to non-tumor ratio at 24 h or 96 h post dosing, while maintaining high tumor uptake (TABLE 34).

Further to the cleavable moieties such as ester moieties mentioned, the cleavage rate and the biodistribution profile can be also influenced by the nature of the circulation enhancing group such as albumin binding moiety, the distance between the circulation enhancing group such as an albumin binding moiety to the cleavable moiety(ies) such as ester, the radionuclide chelating group to the cleavable moiety(ies) such as ester, the residues adjacent to the ester, the ester orientation, and the number of cleavable moieties such as ester (TABLE 3).

Accordingly, the present application includes a compound or a pharmaceutically acceptable salt and/or solvate thereof comprising one or more circulation enhancing groups, one or more target binding groups, one or more chelating groups and at least one branching group that is at least trivalent, wherein the branching group that is at least trivalent is connected to at least one target binding group directly or through a first non-cleavable linker, to at least one circulation enhancing group directly, through a second non-cleavable linker or through a first cleavable linker, and to at least one chelating group directly, through a third non-cleavable linker or through a second cleavable linker, provided the branching group that is at least trivalent is connected to the at least one circulation enhancing group through the first cleavable linker, or the branching group that is at least trivalent is connected to the at least one chelating group through the second cleavable linker.

In some embodiments, the circulation enhancing groups is selected from an albumin binding group and a polyethylene glycol chain. In some embodiments, the circulation enhancing groups is an albumin binding group.

In some embodiments, the target binding group binds to a cell, optionally a cancer cell. Therefore, in some embodiments, the target binding group is a tumor binding group. In some embodiments, the target binding group binds to an antigen or other protein on a cell surface, for example a cell surface receptor. In some embodiments, the target binding group is selected from a prostate specific membrane antigen (PSMA) binding group, a glucagon-like peptide-1 receptor (GLP-1R) binding group, a glucose-dependent insulinotropic polypeptide (gastric inhibitory polypeptide; GIP) receptor (GIP-R) binding group, a folate receptor (FR) binding group, a Cholecystokinin-2 receptor (CCK2R) binding group, a gastrin releasing peptide receptor (GRPR) binding group, a somatostatin receptor 2 (SSTR2) binding group, and a neurotensin receptor 1 (NTR1) binding group, a neuropeptide Y receptor type 1 (Y1R) binding group, a nectin-4 binding group, a Delta-like ligand 3 (DLL3) binding group, an epithelial cell adhesion molecule (EpCAM) binding group, a tumor-associated calcium signal transducer 2 (Trop-2) binding group, an insulin-like growth factor-1 (IGF-1) receptor binding group, a human epidermal growth factor receptor 2 (HER2) binding group. In some embodiments, the target binding group is a PSMA binding group.

In some embodiments, the circulation enhancing groups is an albumin binding group and the target binding group is a PSMA binding group.

In some embodiments, the branching group that is at least trivalent is connected to at least one target binding group directly or through a first non-cleavable linker, to at least one circulation enhancing group through a first cleavable linker, and to at least one chelating group directly or through a third non-cleavable linker. In some embodiments, the branching group that is at least trivalent is connected to at least one target binding group directly or through a first non-cleavable linker, to at least one circulation enhancing group through a first cleavable linker, and directly to at least one chelating group.

In some embodiments, the branching group that is at least trivalent is connected to at least one target binding group directly or through a first non-cleavable linker, to at least one circulation enhancing group directly or through a second non-cleavable linker, and to at least one chelating group through a second cleavable linker.

In some embodiments, the compound has an ex vivo half-life in mouse plasma at about 37° C. of about 4 hours to about 360 hours, about 6 hours to about 144 hours, about 12 hours to about 120 hours, about 18 hours to about 108 hours, or about 24 hours to 96 hours. In some embodiments, the compound has an ex vivo half-life in mouse plasma at about 37° C. of about 24 hours to 96 hours.

In some embodiments, the first, second and third non-cleavable linkers resist degradation and the first, second and third non-cleavable linker are less than 5%, less than 4%, less than 3% or less than 2% degraded in the ex vivo mouse plasma after at least about 4 hours, at least about 8 hours, at least about 12 hours, at least about 16 hours, at least about 32 hours, or at least about 48 hour following administration of the compound to mouse plasma.

In some embodiments, the first, second and third non-cleavable linkers resist degradation and the compound comprising the group is less than 5%, less than 4%, less than 3% or less than 2% degraded in the mouse plasma after at least about 8 hours, at least about 12 hours, at least about 16 hours, at least about 24 hours, or at least about 32 hour following administration of the compound to the mouse plasma.

In some embodiments, the first, second and third non-cleavable linkers resist degradation for at least about 2 to about 8 hours, at least about 4 hours to about 16 hours, at least about 12 hours to about 24 hours, at least about 1 day to about 5 days, or at least about 5 days to about 10 days under physiological conditions.

In some embodiments, the first, second and third non-cleavable linkers each independently comprises one or more non-cleavable moieties. In some embodiments, the first, second and third non-cleavable linkers each comprises one or more non-cleavable moieties that resist degradation by one or more of acids, bases, reducing agents, oxidizing agents and enzymes.

In some embodiments, the first, second and/or third non-cleavable linkers each comprise one or more non-cleavable moieties that resist degradation by one or more of acids and bases. Therefore, in some embodiments, the first, second and/or third non-cleavable linker resists degradation in the plasma. In some embodiments, the first, second and/or third non-cleavable linker comprises one or more non-cleavable moieties that resist degradation in the ex vivo plasma at about 37° C. for at least about 2 to about 8 hours, at least about 4 hours to about 16 hours, at least about 12 hours to about 24 hours, at least about 1 day to about 5 days, at least about 5 days to about 10 days under or at least about 24 hours following administration of a compound comprising the group to the plasma.

In some embodiments, the first, second and third non-cleavable linkers independently comprise one or more non-cleavable moieties that resist degradation by enzymes.

In some embodiments, the first, second and third non-cleavable linkers comprise one or more non-cleavable moieties that resist degradation that are selected from amine bonds, ether bonds, thioether bonds, amide bonds, urea bonds, thiourea groups, thioamide groups or triazole groups. In some embodiments, the triazole group is prepared using click chemistry.

In some embodiments, the first and second cleavable linkers are degraded in ex vivo mouse plasma and have an ex vivo mouse plasma half-life of about 4 hours to about 360 hours, about 6 hours to about 144 hours, about 12 hours to about 120 hours, about 18 hours to about 108 hours, or about 24 hours to 96 at about 37° C. in mouse plasma.

In some embodiments, the first and second cleavable linkers are degraded in ex vivo mouse plasma and greater than about 5%, about 6%, about 7%, about 8%, about 9% or about 10% of the cleavable linker is degraded after about 48 to about 96 hours, or about 60 to 96 hours at about 37° C. in mouse plasma.

In some embodiments, the first and second cleavable linkers each comprise one or more cleavable moieties that are degraded by one or more of acids, bases, reducing agents, oxidizing agents and enzymes.

In some embodiments, the first and second cleavable linkers each comprise one or more cleavable moieties that are degraded by enzymes.

In some embodiments, the one or more cleavable moieties are independently selected from an ester group, a disulfide bond, a thioester group, a carbamate group, a carbonate group, a hydrazone bond, an oxime bond such as a ketoxime or aldoxime bond, and enzymatically cleavable peptide sequences.

In some embodiments, the first and second cleavable linkers comprise one or more cleavable moieties that are degradable by one or more of acids and bases. Therefore, in some embodiments, the first and second cleavable linker are degraded in the circulating blood and ex-vivo plasma such as mouse plasma.

Accordingly, in some embodiments, the first and second cleavable linkers each independently comprises at least one cleavable moiety that is cleavable in the circulating blood and ex vivo plasma. In some embodiments, the first and second cleavable linkers independently comprise one to four cleavable moieties that are cleavable in the circulating blood and ex vivo plasma. In some embodiments, the first and second cleavable linkers independently comprise one to three cleavable moieties that are cleavable in the circulating blood and ex vivo plasma. In some embodiments, the first and second cleavable linkers independently comprise one or two cleavable moieties that are cleavable in the circulating blood and ex vivo plasma. In some embodiments, the first and second cleavable linkers independently comprise one cleavable moiety that is cleavable in the circulating blood and ex vivo plasma. In some embodiments, the first and second cleavable linker each independently comprise at least one cleavable moiety that is cleavable in the ex-vivo mouse plasma and has an ex vivo mouse plasma half-life at about 37° C. of at least about 4 hours to about 360 hours, about 6 hours to about 144 hours, about 12 hours to about 120 hours, about 18 hours to about 108 hours, or about 24 hours to 96 hours following administration of the compound to the mouse plasma.

In some embodiments, the compound or a pharmaceutically acceptable salt and/or solvate thereof (optionally the first and second cleavable linkers) comprises one to four cleavable moieties. In some embodiments, the compound or a pharmaceutically acceptable salt and/or solvate thereof (optionally the first and second cleavable linkers) comprises one to three cleavable moieties. In some embodiments, the compound or a pharmaceutically acceptable salt and/or solvate thereof (optionally the first and second cleavable linkers) comprises three cleavable moieties. In some embodiments, the compound comprises two cleavable moieties. In some embodiments, the compound or a pharmaceutically acceptable salt and/or solvate thereof (optionally the first and second cleavable linkers) comprises one or two cleavable moieties. In some embodiments, the compound or a pharmaceutically acceptable salt and/or solvate thereof (optionally the first and second cleavable linkers) comprises one cleavable moiety.

It would be appreciated by a person skilled in the art that the first, second and third non-cleavable linkers do not comprise a cleavable moiety, while for the cleavable linkers it is an option that they can further comprise non-cleavable moieties. It would be appreciated by a person skilled in the art that the non-cleavable linker group comprises a functional group on each of the termini that reacts with complementary functional groups of the molecules to be linked to form non-cleavable moieties.

It would be further appreciated by a person skilled in the art that the non-cleavable and cleavable linkers join two or more molecular structures together through connections (e.g., functional groups) and that for non-cleavable linkers the connections between the linker and the molecules to be joined are non-cleavable and for cleavable linkers it is an option that the connections between the cleavable linkers and the molecules to be joined can also be cleavable.

Further, it would be appreciated by a person skilled in the art that the branching group that is at least trivalent comprises a functional group on each termini that reacts with a complementary functional group of each of the at least three molecules to be linked. In some embodiments, the branching group that is at least trivalent comprises a functional group on each termini that reacts with a complementary functional group of the circulation enhancing group, the target binding group, and/or the chelating group when bound directly to any one of these groups, or to the first, second and/or third non-cleavable linkers, and/or the first and second cleavable linkers.

It would be further appreciated by a person skilled in the art that the branching group that is at least trivalent comprises a functional group on each termini that connects to the circulation enhancing group, the target binding group, and/or the chelating group, or to the first, second and/or third non-cleavable linkers, and/or to the first and second cleavable linkers through connections (e.g., functional groups) and that, when joining to the first, second and/or third non-cleavable linkers or to the target binding group, the connections between the branching group that is at least trivalent and the first, second and/or third non-cleavable linkers or the target binding group to be joined are non-cleavable, and when joining to the first and/or second cleavable linkers, to the circulation enhancing groups and/or the target binding groups, the connections between the branching group that is at least trivalent and the first and/or second cleavable linkers, the circulation enhancing groups and/or the target binding groups are non-cleavable or cleavable.

In some embodiments, the branching group that is at least trivalent comprises at least a first terminal functionality, a second terminal functionality and a third terminal functionality that connects to the target binding groups directly or through the first non-cleavable linker, to the circulation enhancing groups directly or through the second non-cleavable linker or through the first cleavable linker and to the chelating groups directly or through the third non-cleavable linker or through the second cleavable linker, respectively.

In some embodiments, the non-cleavable linker groups (e.g., the first non-cleavable linker, the second non-cleavable linker and the third non-cleavable groups) and the cleavable linker groups (e.g., the first cleavable linker and the second cleavable linker groups) optionally comprise functional groups, in addition to the functional groups on each of the termini, that react with complementary functional groups of molecules, in addition to the one target binding groups, the one circulation enhancing group or the one chelating group, to be linked. In some embodiments, the molecules in addition to the target binding groups, the circulation enhancing group or the chelating group, are other target binding groups, circulation enhancing groups and/or chelating groups, and/or other cleavable or non-cleavable linkers.

In some embodiments, the first non-cleavable linker further connects a second target binding group to the branching group, the second non-cleavable linker or the first cleavable linker further connects a second circulation enhancing group to the branching group and/or the third non-cleavable linker or the second cleavable linker connects a second chelating group to the branching group. In some embodiments, the first non-cleavable linker further connects a second target binding group to the branching group. In some embodiments, the second non-cleavable linker or the first cleavable linker further connects a second circulation enhancing group to the branching group. In some embodiments, the third non-cleavable linker or the second cleavable linker connects a second chelating group to the branching group.

In some embodiments, the first non-cleavable linker further connects another chelating group and/or circulation enhancing group to the branching group, the second non-cleavable linker or the first cleavable linker further connects another target binding group and/or chelating group to the branching group and/or the third non-cleavable linker or the second cleavable linker connects another circulation enhancing group and/or target binding group to the branching group. In some embodiments, the first non-cleavable linker further connects another chelating group and circulation enhancing group to the branching group, the second non-cleavable linker or the first cleavable linker further connects another target binding group and chelating group to the branching group and/or the third non-cleavable linker or the second cleavable linker connects another circulation enhancing group and target binding group to the branching group. In some embodiments, the first non-cleavable linker further connects a second chelating group and second circulation enhancing group to the branching group. In some embodiments, the second non-cleavable linker or the first cleavable linker further connects a second target binding group and a second chelating group to the branching group. In some embodiments, the third non-cleavable linker or the second cleavable linker connects a second circulation enhancing group and second target binding group to the branching group.

Accordingly, in some embodiments, the compound is a compound of Formula I or a pharmaceutically acceptable salt and/or solvate thereof (I)

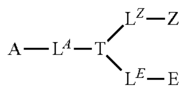

wherein

A is a circulation enhancing group;

Z is a target binding group;

E is a chelating group;

T is a branching group that is at least trivalent;

$L^A$ and $L^E$ are each independently a direct bond, a cleavable linker or a non-cleavable linker; and $L^Z$ is a direct bond or a non-cleavable linker;

provided at least one of $L^A$ and $L^E$ is a cleavable linker.

In some embodiments, A is selected from an albumin binding group, and a polyethylene glycol chain. In some embodiments, A is an albumin binding group. In some embodiments, the albumin binding group is selected from

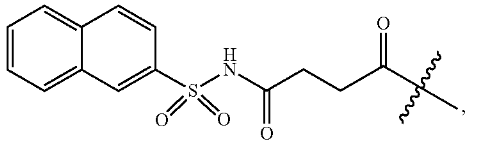

(2-Naph-$SO_2$NH-Suc)

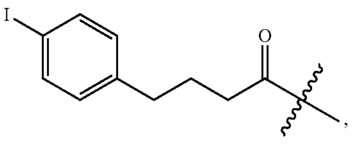

(4-pIBA)

unsubstituted or substituted $C(O)C_{1-26}$alkyleneCO$_2$H, unsubstituted or substituted $C(O)C_{2-26}$alkenyleneCO$_2$H, unsubstituted or substituted $C(O)C_{1-26}$alkyl and unsubstituted or substituted $C(O)C_{2-26}$alkenyl. In some embodiments, the albumin binding group is selected from

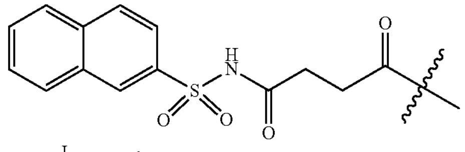

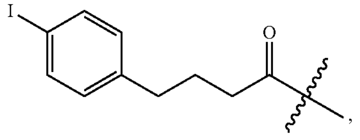

unsubstituted or substituted $C(O)C_{6-20}$alkyleneCO$_2$H, unsubstituted or substituted $C(O)C_{6-20}$alkenyleneCO$_2$H, unsubstituted or substituted $C(O)C_{6-19}$alkyl and unsubstituted or substituted $C(O)C_{2-20}$alkenyl. In some embodiments, the albumin binding group is selected from

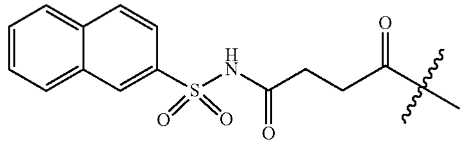

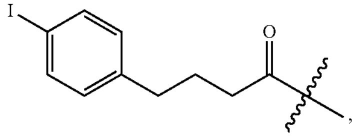

unsubstituted or substituted $C(O)C_{6-20}$alkyleneCO$_2$H, unsubstituted or substituted $C(O)C_{6-20}$alkenyleneCO$_2$H, unsubstituted or substituted $C(O)C_{6-18}$alkyl and unsubstituted or substituted $C(O)C_{2-20}$alkenyl. In some embodiments, the albumin binding group is selected from

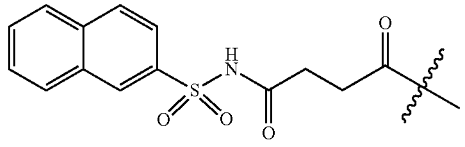

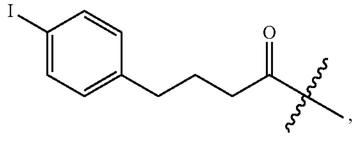

unsubstituted or substituted $C(O)C_{12-18}$alkyleneCO$_2$H and unsubstituted or substituted $C(O)C_{12-18}$alkenyleneCO$_2$H, unsubstituted or substituted $C(O)C_{12-19}$alkyl and unsubstituted or substituted $C(O)C_{12-18}$alkenyl. In some embodiments, the albumin binding group is selected from

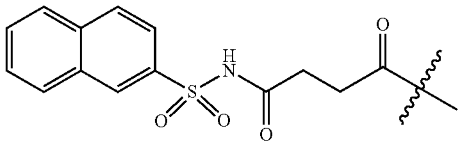

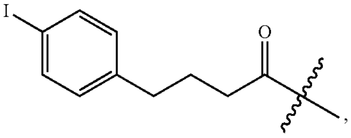

unsubstituted or substituted $C(O)C_{12-18}$alkylene$CO_2H$ and unsubstituted or substituted $C(O)C_{12-18}$alkenylene$CO_2H$, unsubstituted or substituted $C(O)C_{12-18}$alkyl and unsubstituted or substituted $C(O)C_{12-18}$alkenyl. In some embodiments, the albumin binding group is selected from

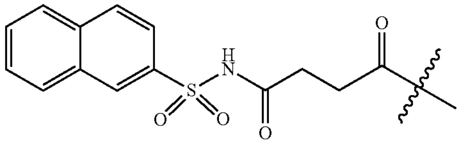

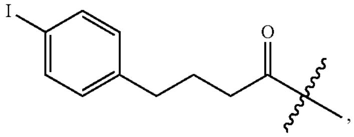

unsubstituted or substituted $C(O)C_{14-18}$alkylene$CO_2H$ and unsubstituted or substituted $C(O)C_{14-18}$alkyl.

In some embodiments, the albumin binding group is selected from

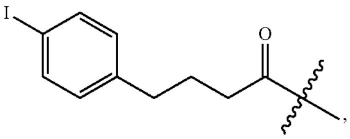

$C(O)C_{15}$alkyl ( 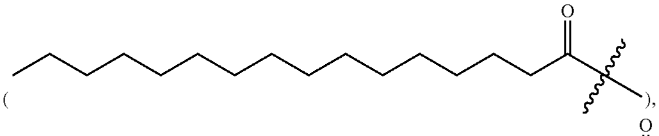 ), $C(O)C_{17}$alkyl ( 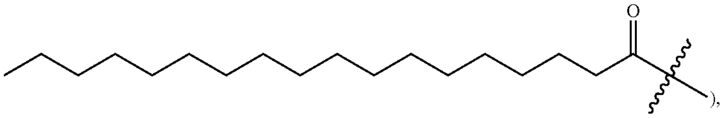 ), $C(O)C_{16}$alkylene$CO_2H$ ( 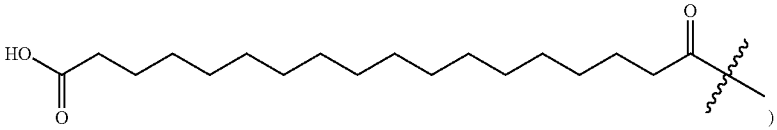 ) and $C(O)C_{18}$alkylene$CO_2H$ 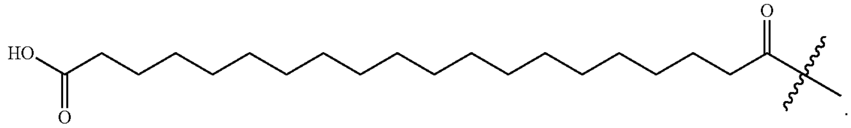 .

In some embodiments, the albumin binding group is selected from

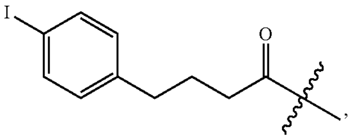,

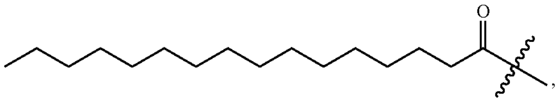,

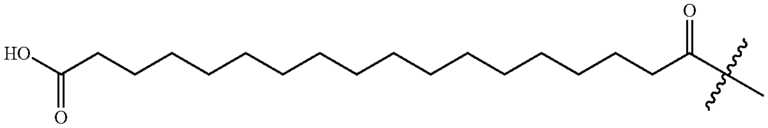 and

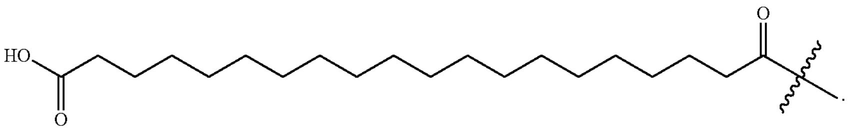.

In some embodiments, the albumin binding group is selected from unsubstituted or substituted $C(O)C_{12-18}$ alkylene$CO_2H$. In some embodiments, the albumin binding group is selected from $C(O)C_{12-18}$alkylene$CO_2H$. In some embodiments, the albumin binding group is selected from $C(O)C_{16}$alkylene$CO_2H$ (

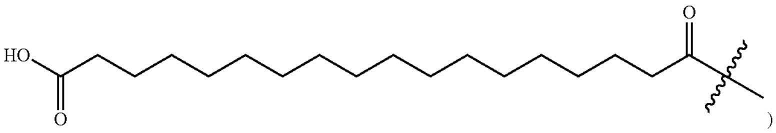

) and $C(O)C_{18}$alkylene$CO_2H$ (

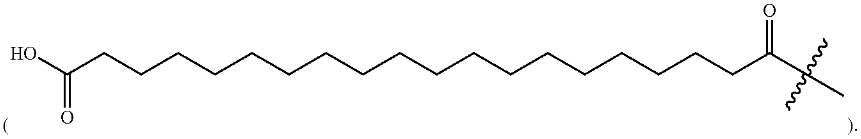

).

In some embodiments, the albumin binding group is selected from $C(O)C_{16}$alkylene$CO_2H$ and $C(O)C_{18}$alkylene$CO_2H$. In some embodiments, the albumin binding group is $C(O)C_{16}$alkylene$CO_2H$.

In some embodiments, when substituted each $C(O)C_{6-20}$ alkylene$CO_2H$, $C(O)C_{6-20}$alkenylene$CO_2H$, $C(O)C_{6-18}$alkyl and $C(O)C_{2-20}$alkenyl is substituted with one or more of halo, $CO_2H$, $CO_2C_1$-$C_4$alkyl, $C(O)NH_2$, $C(O)N(CH_3)_2$, $C(O)NHCH_3$, $SO_2CH_3$, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl, $C_2$-$C_6$fluoroalkynyl, $C_3$-$C_6$cycloalkyl and a 3- to 6-membered heterocyclic ring including 1 to 2 ring members selected from O, S, S(O), $SO_2$, N, NH and $NCH_3$.

In some embodiments, the present inventors have found that compounds of Formula I comprising $C(O)C_{12-18}$alkylene$CO_2H$ as the albumin binding group demonstrate a higher tumor to kidney uptake ratio. Therefore, in an exemplary embodiment, the albumin binding group (A) is selected from unsubstituted or substituted $C(O)C_{12-18}$ alkylene$CO_2H$. Accordingly, in some embodiments, the compound of Formula I is a compound of Formula I-A (I-A)

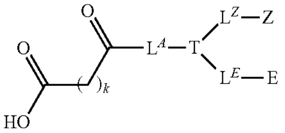

wherein

Z, E, T, $L^A$, $L^E$ and $L^Z$ are as defined in Formula I, and k is an integer from 14 to 20, provided at least one of $L^A$ and $L^E$ is a cleavable linker.

In some embodiments, k is 14 to 18. In some embodiments, k is 16 to 18. In some embodiments, k is 16 or 18.

In some embodiment, E is any chelating group that is capable of binding with and/or complexing a metal ion. In some embodiments, E is any chelating group that is capable of binding with and/or complexing a metal ion to form a heterocyclic ring including the metal ion. In some embodiments, the E is any chelating known in the art, for example, as disclosed in Banerjee et al., Nucl. Med. Biol., 2005, 32, 1-20, Wadas et al., Chem. Rev., 2010, 110, 2858-2902, U.S. Pat. Nos. 5,367,080, 5,364,613, 5,021,556, 5,075,099, and 5,886,142.

In some embodiments, E is a chelating group derived from a chelating agent. In some embodiments, the chelating agent is selected from a cyclic and an acyclic bifunctional chelating agent capable of complexing one or more radionuclides. In some embodiments, the chelating agent is selected from 1,4,7-Triazacyclononane (TACN); 1,4,7-triazacyclononane-triacetic acid (NOTA); 1,4,7-triazacyclononane-N-succinic acid-N',N"-diacetic acid (NOTASA); 1,4,7-triazacyclononane-N-glutamic acid-N',N"-diacetic acid (NODAGA); 1,4,7-triazacyclononane-N,N',N"-tris (methylenephosphonic) acid (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl)diacetic acid (DO2A); 2,2',2"-(1,4,7,10-tetraazacyclododecane-1,4,7-triyl)triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphoriic acid) (DO2P); 1,4,7,10-tetraazacyclododecane-1,4,7-tri(methanephosphonic acid) (DO3P); 1,4,7,10-tetraazacyclo-decane-1-glutamic acid-4,7,10-triacetic acid (DOTAGA); 1,4,7,10-tetraazacyclodecane-1-succinic acid-4,7,10-triacetic acid (DOTASA); 1,4,8,11-tetraazacyclotetradecane ([14]aneN4) (cyclam); 1,4,8,12-tetraazacyclopentadecane ([15]aneN4); 1,5,9,13-tetraazacyclohexadecane ([16]aneN4); 1,4-ethano-1,4,8,11-tetraazacyclo-tetradecane (et-cyclam); 1,4,8,11-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl)diacetic acid (TE2A); 4,11-bis(carboxy methyl)-1,4,8,11-tetraazabicyclo[6.6.2]-hexadecane (CB-TE2A); 3,6,10,13,16,19-hexaazabicyclo[6.6.6]icosane (Sar); 1,4,7,10-tetra-(2-carbamoyl-methyl)-cyclododecane (TCMC); N,N'-bis[(6-carboxy-2-pyridil)methyl]-4,13-diaza-18-crown-6 (macropa), phthalocyanines and derivatives thereof; porphyrins and derivatives thereof. In some embodiments, E is a chelating group derived from a chelating agent selected from DOTA and DOTAGA.

A person skilled in the art would appreciate that "a chelating group derived from a chelating agent" as used herein refers to a chelating agent derivative formed after the chelating agent is connected to the compound of Formula I or a pharmaceutically acceptable salt, solvate and/or prodrug thereof. For example, "a chelating group derived from a chelating agent" may be a chelating agent without the "—OH" (or ester thereof) of an available carboxyl group (or ester thereof) on the chelating agent, without the "H" portion of an available amino group on the chelating agent, without the "NCS" portion of an available isothiocyanate on the chelating agent, without the "H" portion of an available maleimide group on the chelating agent, a chelating agent after an available acetylene group on the chelating agent has been reacted to connect to the compound of Formula I or a pharmaceutically acceptable salt, solvate and/or prodrug thereof, or a chelating agent after an available tetrazole group on the chelating agent has been reacted to connect to the compound of Formula I or a pharmaceutically acceptable salt, solvate and/or prodrug thereof. For example, a person skilled in the art would appreciate that when E is a chelating group derived from a DOTA, one "—OH" from one of the four available carboxyl groups on DOTA is removed to form the connection to $L^A$ (or T when $L^A$ is a direct bond) in the compound of Formula I or a pharmaceutically acceptable salt, solvate and/or prodrug thereof.

In some embodiments, E is connected to $L^A$ or T through any one of the available functional groups. In some embodiments, E is a chelating group comprising two or more carboxyl groups, and E is connected to $L^A$ or T through a carboxyl functional group. In some embodiments, E is a chelating group derived from DOTA or DOTAGA and is connected to $L^A$ or T through any one of the available carboxyl functional groups. In some embodiments, E is a chelating group derived from DOTA and is connected to $L^A$ or T through any one of the available carboxyl functional groups.

In some embodiments, the one or more radionuclides is a radioactive isotope of C, N, F, S, Br, Ru, Pd, Tc, Ga, In, Zn, Gd, Bi, At, Cu, Pb, Fe, Ti, F, I, Y, Sr, Ra, P, Re, Sc, Zr, Rh, Pt, Rb, Au, Sn, Tl, Co, Pm, a lanthanide, or an actinide.

In some embodiments, the lanthanide is Lu, Sm, Pm, Ho, or Tb.

In some embodiments, the actinide is Ac or Th.

In some embodiments, the one or more radionuclides are selected from $^{14}$C, $^{15}$N, $^{18}$F, $^{75}$Br, $^{76}$Br, $^{77}$Br, $^{123}$I, $^{124}$I, $^{125}$I, $^{131}$I, $^{35}$S, $^{99}$Tc, $^{99m}$Tc, $^{18}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{82}$Rb, $^{195m}$Pt, $^{191m}$Pt, $^{193m}$Pt, $^{117m}$Sn, $^{89}$Zr, $^{177}$Lu, $^{18}$F, $^{123}$I, $^{188}$Re, $^{186}$Re, $^{153}$Sm, $^{66}$Ho, $^{86}$Y, $^{87}$Y, $^{90}$Y, $^{89}$Sr, $^{111}$In, $^{153}$Gd, $^{225}$Ac, $^{212}$Bi, $^{213}$Bi, $^{211}$At, $^{198}$Au, $^{199}$Au, $^{193m}$Pt, $^{197}$Pt, $^{103}$Pd, $^{109}$Pd, $^{105}$Rh, $^{103m}$Rh, $^{223}$Ra, $^{224}$Ra, $^{97}$Ru, $^{227}$Th, $^{229}$Th, $^{32}$P, $^{161}$Tb, $^{33}$P, $^{149}$Tb, $^{125}$I, $^{203}$Pb, $^{212}$Pb, $^{201}$Tl, $^{119}$Sb, $^{58m}$Co, $^{55}$Co, $^{47}$Sc, $^{149}$Pm and $^{161}$Ho.

In some embodiments, the one or more radionuclides are for use in imaging or for use in therapy.

In some embodiments, the one or more radionuclides for use in imaging are selected from $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{82}$Rb, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F and $^{123}$I. In some embodiments, the one or more radionuclides for use in imaging is $^{177}$Lu.

In some embodiments, the one or more radionuclides for use in therapy are selected from $^{188}$Re, $^{186}$Re, $^{153}$Sm, $^{66}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{99}$Au, $^{195m}$Pt, $^{193m}$Pt, $^{197}$Pt, $^{117m}$Sn, $^{103}$Pd, $^{105}$Rh, $^{103m}$Rh, $^{177}$Lu, $^{223}$Ra, $^{224}$Ra, $^{227}$Th, $^{229}$Th, $^{149}$Tb, $^{32}$P, $^{161}$Tb, $^{33}$P, $^{125}$I, $^{203}$Pb, $^{212}$Pb, $^{201}$Tl, $^{119}$Sb, $^{58m}$Co, $^{47}$Sc, $^{149}$Pm and $^{161}$Ho.

In some embodiments, the one or more radionuclides for use in therapy are selected from $^{177}$Lu, $^{212}$Pb, and $^{225}$Ac. In some embodiments, the one or more radionuclides for use in therapy is $^{177}$Lu.

In some embodiments, Z binds to a cell, optionally a cancer cell. Therefore, in some embodiments, Z is a tumor binding group. In some embodiments, Z binds to an antigen or other protein on a cell surface, for example a cell surface receptor. In some embodiments, Z is selected from a prostate specific membrane antigen (PSMA) binding group, a glucagon-like peptide-1 receptor (GLP-1R) binding group, a glucose-dependent insulinotropic polypeptide (gastric inhibitory polypeptide; GIP) receptor (GIP-R) binding group, a folate receptor (FR) binding group, a Cholecystokinin-2 receptor (CCK2R) binding group, a gastrin releasing peptide receptor (GRPR) binding group, a somatostatin receptor 2 (SSTR2) binding group, and a neurotensin receptor 1 (NTR1) binding group, a neuropeptide Y receptor type 1 (Y1R) binding group, a nectin-4 binding group, a Delta-like ligand 3 (DLL3) binding group, an epithelial cell adhesion molecule (EpCAM) binding group, a tumor-associated calcium signal transducer 2 (Trop-2) binding group, an insulin-like growth factor-1 (IGF-1) receptor binding group, a human epidermal growth factor receptor 2 (HER2) binding group.

In some embodiments, Z is a PSMA binding group. In some embodiments, the PSMA binding group is a peptide analogue selected from quisqualic acid, aspartate-glutamate (Asp-Glu), Glu-Glu, glycine-glutamate (Gly-Glu), γ-glutamate-glutamate (γ-Glu-Glu) and beta-N-acetyl-L-aspartate-L-glutamate (β-NAAG). In some embodiments, the PSMA binding group comprises a phosphorus, thiol, or urea derivative attached to a glutamate moiety. In some embodiments, the PSMA binding group is

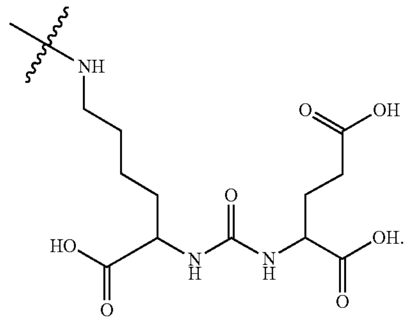

(εKuE or eKuE)

In some embodiments, the PSMA binding group is εKuE and the albumin binding group (A) is selected from unsubstituted or substituted $C(O)C_{12-18}alkyleneCO_2H$. In some embodiments, the PSMA binding group is εKuE and the albumin binding group (A) is selected $C(O)C_{12-18}alkyleneCO_2H$. Accordingly, in some embodiments, when the PSMA binding group is εKuE and the albumin binding group (A) is selected from unsubstituted or substituted $C(O)C_{12-18}alkyleneCO_2H$, the compound of Formula I is a compound of Formula I-A'

(I-A')

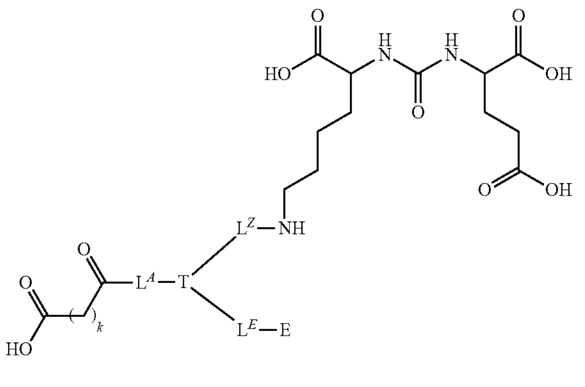

wherein

E, T, $L^A$, $L^E$ and $L^Z$ are as defined in Formula I, and k is an integer from 14 to 20, provided at least one of $L^A$ and $L^E$ is a cleavable linker.

In some embodiments, T is a branching group that is at least trivalent comprising at least a first terminal functionality, a second terminal functionality and a third terminal functionality, which are the same or different and bind to $L^A$ (or alternatively A), $L^Z$ (or alternatively Z) and $L^E$ (or alternatively E), respectively. In some embodiments, T comprises at least a first terminal functionality, a second terminal functionality and a third terminal functionality which are the same or different and when bonded to $L^A$ (or alternatively A), $L^Z$ (or alternatively Z) and $L^E$ (or alternatively E), respectively, independently form an amide group, a urea group, a thiourea groups or a thioamide group. In some embodiments, when bonded to $L^A$ (or alternatively A), and/or $L^E$ (or alternatively E), an ester group, a thioester group, a carbonate group, a carbamate group, a disulfide bond, a hydrazone group, or an oxime group such as a ketoxime or aldoxime is further formed. In some embodiments, when bonded to $L^A$ (or alternatively A), and/or $L^E$ (or alternatively E) an enzymatically cleavable sequence is formed.

In some embodiments, T is a branching group which is trivalent, tetravalent or pentavalent. In some embodiments, T is a branching group which is trivalent. Therefore, in some embodiments, T is a trivalent branching group.

In some embodiments, T comprises at least a first terminal functionality, a second terminal functionality and a third terminal functionality which are the same or different and when bonded to $L^A$ (or alternatively A), $L^Z$ (or alternatively Z) and $L^E$ (or alternatively E), respectively independently form an amide group. In some embodiments, when bonded to $L^A$ (or alternatively A), and/or $L^E$ (or alternatively E), an amide group, an ester group or a disulfide bond group is formed. In some embodiments, when bonded to $L^A$ (or alternatively A), and/or $L^E$ (or alternatively E), an ester group is formed. In some embodiments, T comprises at least a first terminal functionality, a second terminal functionality and a third terminal functionality which are the same or different and when bonded to $L^A$ (or alternatively A), $L^Z$ (or alternatively Z) and $L^E$ (or alternatively E), respectively independently form an amide group.

In some embodiments, T is selected from an amino acid residue derived from lysine, ornithine, homo-lysine, 2,3-diaminopropionic acid (DAP), 2,4-diaminobutyric acid (DAB), cysteine, homo-cysteine, or glutamine. In some embodiments, T is an amino acid residue derived from lysine,

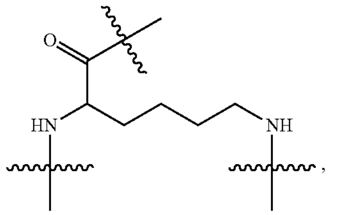 [SMILES: *NCCCCC(N*)C(*)=O]

DAP or DAB. In some embodiments, T is an amino acid residue derived from lysine,

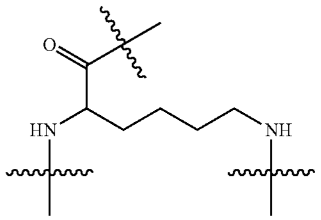 [SMILES: *NCCCCC(N*)C(*)=O]

or DAB. In some embodiments, T is an amino acid residue derived from lysine,

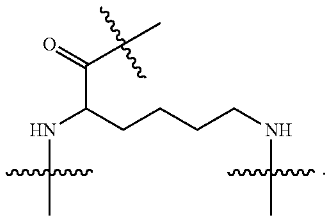 [SMILES: *NCCCCC(N*)C(*)=O]

In some embodiments, T is an amino acid residue derived from DAB.

Therefore, in some embodiments, the compound of Formula I is a compound of Formula I-B or a pharmaceutically acceptable salt and/or solvate thereof, a compound of Formula I-C, or a pharmaceutically acceptable salt and/or solvate thereof, a compound of Formula I-B' or a pharmaceutically acceptable salt and/or solvate thereof, or a compound of Formula I-C', or a pharmaceutically acceptable salt and/or solvate thereof, (I-B)

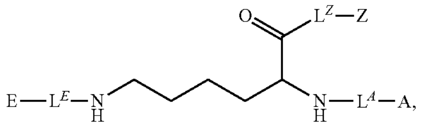

(I-C)

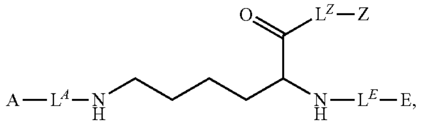

(I-B')

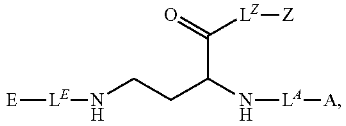

(I-C')

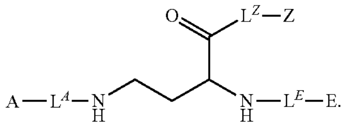

In some embodiments, the compound of Formula I is a compound of Formula I-B or a pharmaceutically acceptable salt and/or solvate thereof or a compound of Formula I-C or a pharmaceutically acceptable salt and/or solvate thereof:

(I-B)

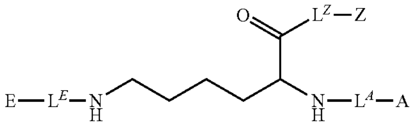

(I-C)

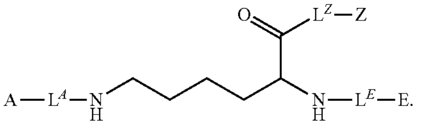

In an exemplary embodiment, the albumin binding group (A) is selected from unsubstituted or substituted $C(O)C_{12-18}alkyleneCO_2H$ and $C(O)C_{14-18}alkyl$. In an exemplary embodiment, the albumin binding group (A) is selected from unsubstituted or substituted $C(O)C_{12-18}alkyleneCO_2H$.

In an exemplary embodiment, the albumin binding group (A) is selected from unsubstituted or substituted $C(O)C_{12-18}alkyleneCO_2H$, the PSMA group is εKuE and T is an amino acid residue derived from lysine,

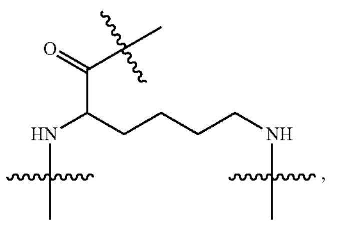 [SMILES: *NCCCCC(N*)C(*)=O]

DAP or DAB. In some embodiments, the albumin binding group (A) is selected from unsubstituted or substituted $C(O)C_{12-18}alkyleneCO_2H$, the PSMA group is εKuE and T is an amino acid residue derived from lysine,

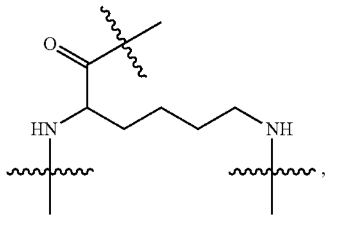 [SMILES: *NCCCCC(N*)C(*)=O]

or DAB. Therefore, in some embodiments, the compound of Formula I is a Formula I is a compound of Formula I-A' (a) or a pharmaceutically acceptable salt and/or solvate thereof, a compound of Formula I-A' (b) or a pharmaceutically acceptable salt and/or solvate thereof, a compound of Formula I-A' (c) or a pharmaceutically acceptable salt and/or solvate thereof, and a compound of Formula I-A' (d) or a pharmaceutically acceptable salt and/or solvate thereof, (I-A'(a))

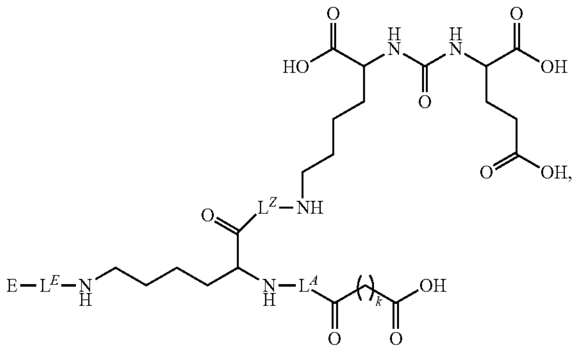

(I-A'(b))

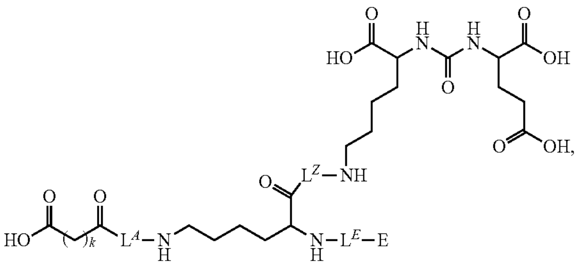

(I-A'(c))

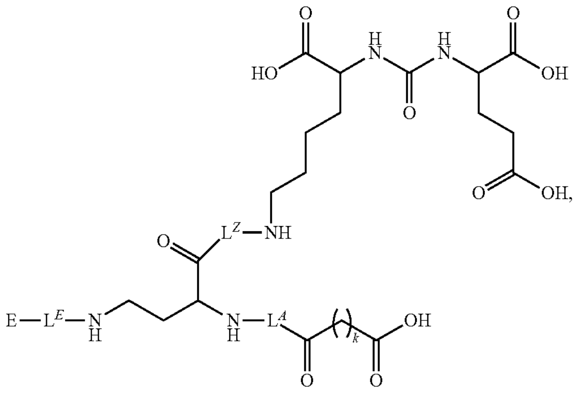

(I-A'(d))

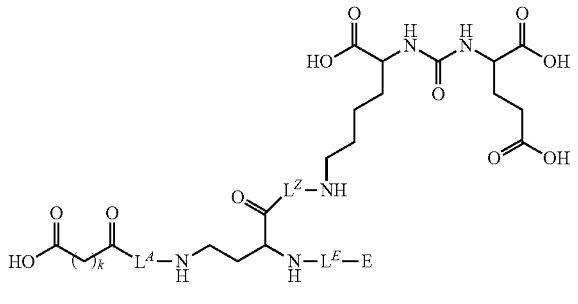

wherein in the Formulae of Formula I-A(a), Formula I-A(b), Formula I-A(c) and Formula I-A(d)

E, T, $L^A$, $L^E$ and $L^Z$ are as defined in Formula I, and k is an integer from 14 to 20, provided at least one of $L^A$ and $L^E$ is a cleavable linker.

In some embodiments, k in the Formulae of Formula I-A(a), Formula I-A(b), Formula I-A(c) and Formula I-A(d) is 14 to 18. In some embodiments, k in the Formulae of Formula I-A(a), Formula I-A(b), Formula I-A(c) and Formula I-A(d) is 16 to 18. In some embodiments, k in the Formulae of Formula I-A(a), Formula I-A(b), Formula I-A (c) and Formula I-A(d) is 16 or 18. In some embodiments, E in the Formulae of Formula I-A(a), Formula I-A(b), Formula I-A(c) and Formula I-A(d) is 14 to 18. In some embodiments, E in the Formulae of Formula I-A(a), Formula I-A(b), Formula I-A(c) and Formula I-A(d) is 16 or 18. In some embodiments, E in the Formulae of Formula I-A(a), Formula I-A(b), Formula I-A(c) and Formula I-A(d) is a chelating group derived from a chelating agent selected from DOTA and DOTAGA.

In some embodiments, $L^Z$ is a direct bond. In some embodiments, $L^Z$ is a non-cleavable linker.

In some embodiments, one of $L^A$ and $L^E$ is a cleavable linker and the other is a direct bond or a non-cleavable linker. In some embodiments, one of $L^A$ and $L^E$ is a direct bond and the other is a cleavable linker. In some embodiments, one of $L^A$ and $L^E$ is a non-cleavable linker and the other is a cleavable linker. In some embodiments, $L^A$ and $L^E$ are both cleavable linkers. In some embodiments, $L^A$ and is a cleavable linker and $L^E$ is a direct bond or a non-cleavable linker. In some embodiments, $L^A$ and is a cleavable linker and $L^E$ is a direct bond. In some embodiments, $L^A$ and is a cleavable linker and $L^E$ is a non-cleavable linker. In some embodiments, $L^A$ and is a cleavable linker and $L^E$ is a direct bond. In some embodiments, $L^A$ and is a cleavable linker and $L^E$ is a non-cleavable linker and $L^Z$ is a non-cleavable linker.

In some embodiments, when $L^Z$ is a non-cleavable linker and/or when one of $L^A$ and $L^E$ is a non-cleavable linker, each non-cleavable linker independently comprises one or more groups each comprising one or more non-cleavable moieties. In some embodiments, when $L^Z$ is a non-cleavable linker and/or when one of $L^A$ and $L^E$ is a non-cleavable linker, each non-cleavable linker independently comprises one or more non-cleavable moieties that resist degradation. In some embodiments, the one or more non-cleavable moieties that resist degradation are selected from amine bonds, ether bonds, thioether bonds, amide bonds, thioamide, urea and thiourea bonds.

In some embodiments, when $L^Z$ is a non-cleavable linker and/or when one of $L^A$ and $L^E$ is a non-cleavable linker, each non-cleavable linker independently comprises one or more groups selected from amino acid residues, $R^1NC_{1-20}$alkyleneNR$^2$, $R^1NC_{1-20}$alkenyleneNR$^2$C(O)$C_{1-20}$alkyleneC(O), C(O)$C_{1-20}$alkenyleneC(O), $R^1NC_{1-20}$alkyleneC(O), $R^1NC_{1-20}$alkenyleneC(O), C(O)$C_{1-20}$alkyleneNHR$^2$, C(O)$C_{1-20}$alkenyleneNR$^2$, C(S)$C_{1-20}$alkyleneC(S), C(S)$C_{1-20}$alkenyleneC(S), C(S)$C_{1-20}$alkyleneC(O), C(S)$C_{1-20}$alkenyleneC(O), C(O)$C_{1-20}$alkyleneC(S), C(O)$C_{1-20}$alkenyleneC(S), C(O)$C_{1-20}$alkyleneO, C(O)$C_{1-20}$alkenyleneO, $R^1NC_{1-20}$alkenyleneC(S), C(S)$C_{1-20}$alkyleneNR$^2$ and C(S)$C_{1-20}$alkenyleneNR$^2$, the latter 19 groups being optionally interrupted by one or more of S, O, NH, N($C_{1-6}$alkyl), C(O), C(O)NH, NHC(O), C(S)NH, NHC(S), NHC(O)NH, NHC(S)NH, NHC(NH), NHC($NC_{1-4}$alkyl), C(NH)NH, C($NC_{1-4}$alkyl)NH, $NC_{4-10}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, NR$^3$R$^4$, $C_{1-4}$alkyleneOH, $C_{1-4}$alkyleneO$C_{1-4}$alkyl and $C_{1-4}$alkyleneNR$^3$R$^4$, wherein each $R^1$, $R^2$, $R^3$ and $R^4$ is independently selected from H and $C_{1-4}$alkyl. In some embodiments, when $L^Z$ is a non-cleavable linker and/or when one of $L^A$ and $L^E$ is a non-cleavable linker, each non-cleavable linker independently comprises one or more groups selected from amino acid residues, $HNC_{1-20}$alkyleneNH, $HNC_{1-20}$alkenyleneNH, C(O)$C_{1-20}$alkyleneC(O), C(O)$C_{1-20}$alkenyleneC(O), $HNC_{1-20}$alkyleneC(O),$HNC_{1-20}$alkenyleneC(O), C(O)$C_{1-20}$alkyleneNH, C(O)$C_{1-20}$alkenyleneNH, C(S)$C_{1-20}$alkyleneC(S), C(S)$C_{1-20}$alkenyleneC(S), C(S)$C_{1-20}$alkyleneC(O), C(S)$C_{1-20}$alkenyleneC(O), C(O)$C_{1-20}$alkyleneC(S), and C(O)$C_{1-20}$alkenyleneC(S), the latter 14 groups being optionally interrupted by one or more of S, O, NH, N($C_{1-6}$alkyl), C(O), C(O)NH, NHC(O), C(S)NH, NHC(S), NHC(O)NH, NHC(S)NH, NHC(NH), NHC($NC_{1-4}$alkyl), C(NH)NH, C($NC_{1-4}$alkyl)NH, $NC_{4-10}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, $NH_2$, $NHC_{1-4}$alkyl and N($C_{1-4}$alkyl)$_2$.

In some embodiments, when $L^Z$ is a non-cleavable linker and/or when one of $L^A$ and $L^E$ is a non-cleavable linker, each non-cleavable linker independently comprises one or more groups selected from amino acid residues, $R^1NC_{1-20}$alkyleneNR$^2$, $R^1NC_{1-20}$alkenyleneNR$^2$, C(O)$C_{1-20}$alkyleneC(O), C(O)$C_{1-20}$alkenyleneC(O), $R^1NC_{1-20}$alkyleneC(O), $R^1NC_{1-20}$alkenyleneC(O), C(O)$C_{1-20}$alkyleneNR$^2$, and C(O)$C_{1-20}$alkenyleneNR$^2$, the latter 8 groups being optionally interrupted by one or more of S, O, NH, N($C_{1-6}$alkyl), C(O), C(O)NH, NHC(O), NHC(O)NH, NHC(S)NH, $NC_{4-6}$cycloalkyl, $C_{4-6}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, NR$^3$R$^4$, $C_{1-4}$alkyleneOH, $C_{1-4}$alkyleneO$C_{1-4}$alkyl and $C_{1-4}$alkyleneNR$^3$R$^4$ wherein each $R^1$, $R^2$, $R^3$ and $R^4$ is independently selected from H and $C_{1-4}$alkyl. In some embodiments, when $L^Z$ is a non-cleavable linker and/or when one of $L^A$ and $L^E$ is a non-cleavable linker, each non-cleavable linker independently comprises one or more groups selected from amino acid residues, $HNC_{1-20}$alkyleneNH, $HNC_{1-20}$alkyleneNH, C(O)$C_{1-20}$alkyleneC(O), C(O)$C_{1-20}$alkyleneC(O), $HNC_{1-20}$alkyleneC(O), $HNC_{1-20}$alkenyleneC(O), C(O)$C_{1-20}$alkyleneNH, and C(O)$C_{1-20}$alkenyleneNH, the latter 8 groups being optionally interrupted by one or more of S, O, NH, N($C_{1-6}$alkyl), C(O), C(O)NH, NHC(O), NHC(O)NH, NHC(S)NH, $NC_{4-6}$cycloalkyl, $C_{4-6}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, $NH_2$, $NHC_{1-4}$alkyl and N($C_{1-4}$alkyl)$_2$.

In some embodiments, when $L^Z$ is a non-cleavable linker and/or when one of $L^A$ and $L^E$ is a non-cleavable linker, each non-cleavable linker independently comprises one or more groups selected from amino acid residues, $R^1NC_{1-20}$alkyleneNR$^2$, C(O)$C_{1-20}$alkyleneC(O), $R^1NC_{1-20}$alkyleneC(O), and C(O)$C_{1-20}$alkyleneNR$^2$, the latter 4 groups being optionally interrupted by one or more of S, O, C(O)NH, NHC(O), $NC_{4-6}$cycloalkyl, $C_{4-6}$heterocycloalkyl, and each alkyl, and alkylene is optionally substituted with one or more substituents selected from halo, $CO_2H$, $C_{1-6}$alkyl, OH, $OC_{1-6}$alkyl, SH, $SC_{1-6}$alkyl, NR$^3$R$^4$, $C_{1-4}$alkyleneOH, $C_{1-4}$alkyleneO$C_{1-4}$alkyl and $C_{1-4}$alkyleneNR$^3$R$^4$ wherein each $R^1$, $R^2$, $R^3$ and $R^4$ is independently selected from H and $C_{1-4}$alkyl. In some embodiments, when $L^Z$ is a non-cleavable linker and/or when one of $L^A$ and $L^E$ is a non-cleavable linker, each non-cleavable linker independently comprises one or more groups selected from amino acid residues, $HNC_{1-20}$alkyleneNH, C(O)$C_{1-20}$alkyleneC(O), $HNC_{1-20}$alkyleneC(O), and C(O)$C_{1-20}$alkyleneNH, the latter 4 groups being optionally interrupted by one or more of S, O, C(O)NH, NHC(O), $NC_{4-6}$cycloalkyl, $C_{4-6}$heterocycloalkyl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, $NH_2$, $NHC_{1-4}$ alkyl and $N(C_{1-4}alkyl)_2$.

In some embodiments, when $L^Z$ is a non-cleavable linker and/or when one of $L^A$ and $L^E$ is a non-cleavable linker, each non-cleavable linker independently comprises one or more groups selected from amino acid residues, $R^1NC_{1-20}$alkyleneNR$^2$, $C(O)C_{1-20}$alkyleneC(O), $R^1NC_{1-20}$alkyleneC(O), and $C(O)C_{1-20}$alkyleneNR$^2$, the latter 4 groups being optionally interrupted by one or more of S, O, C(O)NH, NHC(O), $C_{4-6}$cycloalkyl and $C_{4-6}$heterocycloalkyl and each alkyl and alkylene is optionally substituted with one or more substituents selected from halo, $CO_2H$, $NR^3R^4$ and $C_{1-4}$alkyleneNR$^3$R$^4$ wherein each $R^1$, $R^2$, $R^3$ and $R^4$ is independently selected from H and $C_{1-4}$alkyl.

In some embodiments, when $L^Z$ is a non-cleavable linker and/or when one of $L^A$ and $L^E$ is a non-cleavable linker, each non-cleavable linker independently comprises one or more groups selected from amino acid residues, $R^1NC_{1-20}$alkyleneNR$^2$, $C(O)C_{1-20}$alkyleneC(O), $R^1NC_{1-20}$alkyleneC(O), and $C(O)C_{1-20}$alkyleneNR$^2$, the latter 4 groups being optionally interrupted by one or more of S, O, C(O)NH, NHC(O), $C_{4-6}$cycloalkyl and $C_{4-6}$heterocycloalkyl wherein each $R^1$ and $R^2$ is independently selected from H and $C_{1-4}$alkyl. In some embodiments, when $L^Z$ is a non-cleavable linker and/or when one of $L^A$ and $L^E$ is a non-cleavable linker, each non-cleavable linker independently comprises one or more groups selected from amino acid residues, $HNC_{1-20}$alkyleneNH, $C(O)C_{1-20}$alkyleneC(O), $HNC_{1-20}$alkyleneC(O), and $C(O)C_{1-20}$alkyleneNH, the latter 4 groups being optionally interrupted by one or more of S, O, C(O) NH, NHC(O), $C_{4-6}$cycloalkyl and $C_{4-6}$heterocycloalkyl.

In some embodiments, $R^1$, $R^2$, $R^3$ and $R^4$ are independently selected from H, $CH_3$, $CH_2CH_3$, $CH_2CH_2CH_3$, $CH(CH_3)_2$, and $C(CH_3)_3$. In some embodiments, $R^1$, $R^2$, $R^3$ and $R^4$ are independently selected from H and $C_{1-3}$alkyl. In some embodiments, $R^1$, $R^2$, $R^3$ and $R^4$ are independently selected from H, $CH_3$, $CH_2CH_3$, and $CH(CH_3)_2$. In some embodiments, $R^1$, $R^2$, $R^3$ and $R^4$ are independently selected from H, and $CH_3$.

In some embodiments, one or both of $L^A$ and $L^E$ is a cleavable linker, and each cleavable linker independently comprises at least one group comprising one to four cleavable moieties or at least two groups which connect to form a cleavable moiety. In some embodiments, one or both of $L^A$ and $L^E$ is a cleavable linker, and each cleavable linker independently comprises two to four groups each comprising one or two cleavable moieties and/or which connect to form a cleavable moieties. In some embodiments, one or both of $L^A$ and $L^E$ is a cleavable linker, and each cleavable linker independently comprises two groups which each comprise one or two cleavable moieties and/or which connect to form cleavable moieties. In some embodiments, one or both of $L^A$ and $L^E$ is a cleavable linker, and each cleavable linker independently comprises one group comprising one or two cleavable moieties. In some embodiments, $L^A$ and $L^E$ are both cleavable linkers each comprising one or two groups which each comprise two cleavable moieties and/or which further connect to form a cleavable moiety.

In some embodiments, one or both of $L^A$ and $L^E$ is a cleavable linker and each cleavable linker independently comprises one or more groups selected from one or more amino acid residues, $R^5NC_{1-20}$alkyleneNR$^6$, $R^5NC_{1-20}$alkenyleneNR$^5$, $C(O)C_{1-20}$alkyleneC(O), $C(O)C_{1-20}$alkenyleneC(O), $R^5NC_{1-20}$alkyleneC(O), $R^5NC_{1-20}$alkenyleneC(O), $C(O)C_{1-20}$alkyleneNR$^6$, $C(O)C_{1-20}$alkenyleneNR$^6$, $C(S)C_{1-20}$alkyleneC(S), $C(S)C_{1-20}$alkenyleneC(S), $C(S)C_{1-20}$alkyleneC(O), $C(S)C_{1-20}$alkenyleneC(O), $C(O)C_{1-20}$alkyleneC(S), $C(O)C_{1-20}$alkenyleneC(S), $SC_{1-20}$alkyleneS, $SC_{1-20}$alkenyleneS, $SC_{1-20}$alkyleneNR$^6$, $SC_{1-20}$alkenyleneNR$^6$, $R^5NC_{1-20}$alkyleneS, $R^5NC_{1-20}$alkenyleneS, $R^5NC_{1-20}$alkyleneO, $R^5NC_{1-20}$alkenyleneO, $OC_{1-20}$alkyleneNR$^6$, $OC_{1-20}$alkenyleneNR$^6$, $SC_{1-20}$alkyleneO, $SC_{1-20}$alkenyleneO, $OC_{1-20}$alkyleneS, and $OC_{1-20}$alkenyleneS, $C(O)C_{1-20}$alkyleneO, $C(O)C_{1-20}$alkenyleneO, $OC_{1-20}$alkyleneC(O), $OC_{1-20}$alkenyleneC(O), $C(O)C_{1-20}$alkyleneS, $C(O)C_{1-20}$alkenyleneS, $SC_{1-20}$alkyleneC(O), $SC_{1-20}$alkenyleneC(O), $R^5NC_{1-20}$alkyleneC(S), $R^5NC_{1-20}$alkenyleneC(S), $C(S)C_{1-20}$alkyleneNR$^6$, $C(S)C_{1-20}$alkenyleneNR$^6$, $C(S)C_{1-20}$alkyleneO, $C(S)C_{1-20}$alkenyleneO, $OC_{1-20}$alkyleneC(S), $OC_{1-20}$alkenyleneC(S), $SC_{1-20}$alkyleneC(S), $SC_{1-20}$alkenyleneC(S), $OC_{1-20}$alkyleneO, $OC_{1-20}$alkenyleneCO, $SC_{1-20}$alkyleneS, $SC_{1-20}$alkenyleneS, the latter 50 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), C═NNH, C═$NNH_2$, C═NOH, C═NO, NH—NH, NH—$NC_{1-4}$alkyl, $NC_{1-4}$alkyl-NH, $NC_{1-4}$alkylNC$_{1-4}$alkyl, S, O, NH, $N(C_{1-6}alkyl)$, C(O), C(O)NH, NHC(O), NHC(O) NH, NHC(S)NH, C(S)NH, NHC(S), NHC(NH), NHC ($NC_{1-4}$ alkyl), C(NH)NH, C($NC_{1-4}$alkyl)NH, $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$ alkyl, $NR^7R^7$, $C_{1-4}$alkyleneOH, $C_{1-4}$alkyleneOC$_{1-4}$alkyl and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety, and the cleavable moiety is selected from S—S, C(O)O, OC(O), OC(O)O, OC(O)NH, NHC(O)O, SC(O), C(O) S, C═NNH, C═NO, $NC_{1-4}$alkylC(O)O, NHOC(O)NH, $NC_{1-4}$ alkylOC(O), NH—NH, NH—$NC_{1-4}$alkyl, $NC_{1-4}$alkyl-NH, $NC_{1-4}$alkyl-$NC_{1-4}$alkyl and an enzymatically cleavable peptide sequence. In some embodiments, one or both of $L^A$ and $L^E$ is a cleavable linker and each cleavable linker independently comprises one or more groups selected from amino acid residues, $HNC_{1-20}$alkyleneNH, $HNC_{1-20}$alkenyleneNH, $C(O)C_{1-20}$alkyleneC(O), $C(O)C_{1-20}$alkenyleneC(O), $HNC_{1-20}$alkyleneC(O), $HNC_{1-20}$alkenyleneC(O), $C(O)C_{1-20}$alkyleneNH, $C(O)C_{1-20}$alkenyleneNH, $C(S)C_{1-20}$alkyleneC(S), $C(S)C_{1-20}$alkenyleneC(S), $C(S)C_{1-20}$alkyleneC(O), $C(S)C_{1-20}$alkenyleneC(O), $C(O)C_{1-20}$alkyleneC(S), $C(O)C_{1-20}$alkenyleneC(S), $SC_{1-20}$alkyleneS, $SC_{1-20}$alkenyleneS, $SC_{1-20}$alkyleneNH, $SC_{1-20}$alkenyleneNH, $HNC_{1-20}$alkyleneS, $HNC_{1-20}$alkenyleneS, $HNC_{1-20}$alkyleneO, $HNC_{1-20}$alkenyleneO, $OC_{1-20}$alkyleneNH, $OC_{1-20}$alkenyleneNH, $SC_{1-20}$alkyleneO, $SC_{1-20}$alkenyleneO, $OC_{1-20}$alkyleneS, and $OC_{1-20}$alkenyleneS, the latter 28 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$ alkylOC(O), C═NNH, C═$NNH_2$, C═NOH, C═NO, NH—NH, NH—$NC_{14}$alkyl, $NC_{1-4}$alkyl-NH, $NC_{1-4}$alkylNC$_{1-4}$alkyl, S, O, NH, $N(C_{1-6}alkyl)$, C(O), C(O)NH, NHC(O), NHC(O)NH, NHC(S)NH, C(S)NH, NHC(S), NHC(NH), NHC($NC_{1-4}$alkyl), C(NH)NH, C($NC_{1-4}$alkyl) NH, $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$ alkyl, $NH_2$, $NHC_{1-4}$alkyl and $N(C_{1-4}alkyl)$ 2, provided the one or more groups comprise at least one cleavable moiety selected from S—S, C(O)O, OC(O), OC(O)O, OC(O)NH, NHC(O)O, SC(O), C(O) S, C═NNH, C═NO, $NC_{1-4}$alkylC(O)O, NHOC(O)NH, $NC_{1-4}$alkylOC(O), NH—NH, NH—$NC_{1-4}$alkyl, $NC_{1-4}$alkyl-NH, $NC_{1-4}$alkyl-$NC_{1-4}$alkyl and an enzymatically cleavable peptide sequence.

In some embodiments, one or both of $L^A$ and $L^E$ is a cleavable linker, and each cleavable linker independently comprises one or more groups selected from amino acid residues, $R^5NC_{1-20}$alkyleneNR$^6$, $R^5NC_{1-20}$alkenyleneNR$^6$, C(O)$C_{1-20}$alkyleneC(O), C(O)$C_{1-20}$alkenyleneC(O), $R^5NC_{1-20}$alkyleneC(O), $R^5NC_{1-20}$alkenyleneC(O), C(O)$C_{1-20}$alkyleneNR$^6$, C(O)$C_{1-20}$alkenyleneNR$^6$, C(S)$C_{1-20}$alkyleneC(S), C(S)$C_{1-20}$alkenyleneC(S), C(S)$C_{1-20}$alkyleneC(O), C(S)$C_{1-20}$alkenyleneC(O), C(O)$C_{1-20}$alkyleneC(S), $SC_{1-20}$alkyleneS, $SC_{1-20}$alkyleneNR$^6$, $R^5NC_{1-20}$alkyleneS, $R^5NC_{1-20}$alkyleneO, $R^5NC_{1-20}$alkenyleneO, $OC_{1-20}$alkyleneNR$^6$, $OC_{1-20}$alkenyleneNR$^6$, $SC_{1-20}$alkyleneO, $OC_{1-20}$alkyleneS, C(O)$C_{1-20}$alkyleneO, C(O)$C_{1-20}$alkenyleneO, $OC_{1-20}$alkyleneC(O) and $OC_{1-20}$alkenyleneC(O), the latter 26 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), C═NNH, C═$NNH_2$, C═NOH, C═NO,), NH—NH, S, O, NH, N($C_{1-6}$alkyl), C(O), C(O)NH, NHC(O), NHC(O)NH, NHC(S)NH, C(S)NH, NHC(S), $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, NR$^7$R$^7$, $C_{1-4}$alkyleneOH, $C_{1-4}$alkyleneOC$_{1-4}$alkyl and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety, and the cleavable moiety is selected from S—S, C(O)O, OC(O), OC(O)O, OC(O)NH, NHC(O)O, SC(O), C(O) S, C═NNH, C═NO, $NC_{1-4}$alkylC(O)O, NHOC(O)NH, $NC_{1-4}$ alkylOC(O), NH—NH, NH—$NC_{1-4}$ alkyl, $NC_{1-4}$alkyl-NH, $NC_{1-4}$alkyl-$NC_{1-4}$alkyl and an enzymatically cleavable peptide sequence. In some embodiments, one or both of $L^A$ and $L^E$ is a cleavable linker, and each cleavable linker independently comprises one or more groups selected from amino acid residues, $HNC_{1-20}$alkyleneNH, $HNC_{1-20}$alkenyleneNH, C(O)$C_{1-20}$alkyleneC(O), C(O)$C_{1-20}$alkenyleneC(O), $HNC_{1-20}$alkyleneC(O), $HNC_{1-20}$alkenyleneC(O), C(O)$C_{1-20}$alkyleneNH, C(O)$C_{1-20}$alkenyleneNH, C(S)$C_{1-20}$alkyleneC(S), C(S)$C_{1-20}$alkenyleneC(S), C(S)$C_{1-20}$alkyleneC(O), C(S)$C_{1-20}$alkenyleneC(O), C(O)$C_{1-20}$alkyleneC(S), $SC_{1-20}$alkyleneS, $SC_{1-20}$alkyleneNH, $HNC_{1-20}$alkyleneS, $HNC_{1-20}$alkyleneO, $HNC_{1-20}$alkenyleneO, $OC_{1-20}$alkyleneNH, $OC_{1-20}$alkenyleneNH, $SC_{1-20}$alkyleneO and $OC_{1-20}$alkyleneS, the latter 22 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), C═NNH, C═$NNH_2$, C═NOH, C═NO,), NH—NH, S, O, NH, N($C_{1-6}$alkyl), C(O), C(O)NH, NHC(O), NHC(O)NH, NHC(S)NH, C(S)NH, NHC(S), $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, $NH_2$, $NHC_{1-4}$alkyl and N($C_{1-4}$alkyl) 2, provided the one or more groups comprise at least one cleavable moiety selected from S—S, C(O)O, OC(O), OC(O)O, OC(O)NH, NHC(O)O, C═NNH, C═NO, SC(O), C(O) S, $NC_{1-4}$alkylC(O)O, NHOC(O)NH, $NC_{1-4}$alkylOC(O), NH—NH and an enzymatically cleavable peptide sequence.

In some embodiments, one or both of $L^A$ and $L^E$ is a cleavable linker, and each cleavable linker independently comprises one or more groups selected from amino acid residues, $R^5NC_{1-20}$alkyleneNR$^6$, $R^5NC_{1-20}$alkenyleneNR$^6$, C(O)$C_{1-20}$alkyleneC(O), C(O)$C_{1-20}$alkenyleneC(O), $R^5NC_{1-20}$alkyleneC(O), $R^5NC_{1-20}$alkenyleneC(O), C(O)$C_{1-20}$alkyleneNR$^6$, C(O)$C_{1-20}$alkenyleneNR$^6$, $R^5NC_{1-20}$alkyleneO, $R^5NC_{1-20}$alkenyleneO, $OC_{1-20}$alkyleneNR$^6$, $OC_{1-20}$alkenyleneNR$^6$, $OC_{1-20}$alkyleneS, C(O)$C_{1-20}$alkyleneO, C(O)$C_{1-20}$alkenyleneO, $OC_{1-20}$alkyleneC(O) and $OC_{1-20}$alkenyleneC(O), the latter 16 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), S, O, NH, N($C_{1-6}$alkyl), C(O), C(O)NH, NHC(O), NHC(O)NH, NHC(S)NH, C(S)NH, NHC(S) $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, NR$^7$R$^7$, $C_{1-4}$alkyleneOH, $C_{1-4}$alkyleneOC$_{1-4}$alkyl and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety; and the cleavable moiety is selected from S—S, C(O)O, OC(O), OC(O)O, OC(O)NH, NHC(O)O, SC(O), C(O) S, $NC_{1-4}$alkylC(O)O and an enzymatically cleavable peptide sequence. In some embodiments, one or both of $L^A$ and $L^E$ is a cleavable linker, and each cleavable linker independently comprises one or more groups selected from amino acid residues, $HNC_{1-20}$alkyleneNH, $HNC_{1-20}$alkenyleneNH, C(O)$C_{1-20}$alkyleneC(O), C(O)$C_{1-20}$alkenyleneC(O), $HNC_{1-20}$alkyleneC(O), $HNC_{1-20}$alkenyleneC(O), C(O)$C_{1-20}$alkyleneNH, C(O)$C_{1-20}$alkenyleneNH, $HNC_{1-20}$alkyleneO, $HNC_{1-20}$alkenyleneO, $OC_{1-20}$alkyleneNH, and $OC_{1-20}$alkenyleneNH, the latter 12 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), S, O, NH, N($C_{1-6}$alkyl), C(O), C(O)NH, NHC(O), NHC(O)NH, NHC(S)NH, C(S)NH, NHC(S) $NC_{4-18}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2H$, $C_{1-6}$alkyl, OH, $OC_{1-6}$alkyl, SH, $SC_{1-6}$alkyl, $NH_2$, $NHC_{1-4}$alkyl and N($C_{1-4}$alkyl)$_2$, provided the one or more groups comprise at least one cleavable moiety selected from S—S, C(O)O, OC(O), OC(O)O, OC(O)NH, NHC(O)O, SC(O), C(O) S, $NC_{1-4}$alkylC(O)O and an enzymatically cleavable peptide sequence.

In some embodiments, one or both of $L^A$ and $L^E$ is a cleavable linker, and each cleavable linker independently comprises one or more groups selected from one or more amino acid residues, $R^5NC_{1-20}$alkyleneNR$^6$, C(O)$C_{1-20}$alkyleneC(O), $R^5NC_{1-20}$alkyleneC(O), C(O)$C_{1-20}$alkyleneNR$^6$, $R^5NC_{1-20}$alkyleneO, $OC_{1-20}$alkyleneNR$^6$, C(O)$C_{1-20}$alkyleneO and $OC_{1-20}$alkyleneC(O) the latter 8 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), S, O, NH, N($C_{1-6}$alkyl), C(O), C(O)NH, NHC(O), NHC(O)NH, NHC(S)NH, C(S)NH, NHC(S), $C_{4-18}$cycloalkyl, $C_{4-10}$heterocycloalkyl, $C_{6-10}$aryl and $C_{5-10}$heteroaryl, and each alkyl and alkylene is optionally substituted with one or more substituents selected from halo, $CO_2H$, $C_{1-6}$alkyl, OH, $OC_{1-6}$ alkyl, SH, $SC_{1-6}$alkyl, $NR^7R^7$, $C_{1-4}$alkyleneOH, $C_{1-4}$alkyleneO$C_{1-4}$alkyl and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety; and the cleavable moiety is selected from S—S, C(O)O, OC(O), OC(O)O, OC(O)NH, NHC(O)O, SC(O), C(O) S, $NC_{1-4}$alkylC(O)O and an enzymatically cleavable peptide sequence. In some embodiments, one or both of $L^A$ and $L^E$ is a cleavable linker, and each cleavable linker independently comprises one or more groups selected from amino acid residues, $HNC_{1-20}$alkyleneNH, C(O)$C_{1-20}$alkyleneC(O), $HNC_{1-20}$alkyleneC(O), C(O)$C_{1-20}$alkyleneNH, $HNC_{1-20}$alkyleneO, $OC_{1-20}$alkyleneNH, the latter 6 groups being optionally interrupted by one or more of S—S, C(O)O, OC(O), OC(O)O, OC(O)NH, NHC(O)O, SC(O), C(O) S, $NC_{1-4}$alkylC(O)O, NHOC(O)NH, $NC_{1-4}$alkylOC(O), S, O, NH, N($C_{1-6}$alkyl), C(O), C(O)NH, NHC(O), NHC(O)NH, NHC(S)NH, C(S)NH, NHC(S), $C_{4-18}$cycloalkyl, $C_{4-10}$heterocycloalkyl, $C_{6-10}$aryl and $C_{5-10}$heteroaryl, and each alkyl and alkylene is optionally substituted with one or more substituents selected from halo, $CO_2H$, $C_{1-6}$alkyl, OH, $OC_{1-6}$alkyl, SH, $SC_{1-6}$ alkyl, $NH_2$, $NHC_{1-4}$alkyl and N($C_{1-4}$alkyl)$_2$, provided the one or more groups comprise at least one cleavable moiety selected from S—S, C(O)O, OC(O), OC(O)O, OC(O)NH, NHC(O)O, SC(O), C(O) S, $NC_{1-4}$alkylC(O)O and an enzymatically cleavable peptide sequence.

In some embodiments, one or both of $L^A$ and $L^E$ is a cleavable linker, and each cleavable linker independently comprises one or more groups selected from amino acid residues, $R^5NC_{1-20}$alkyleneNR$^6$, C(O)$C_{1-20}$alkyleneC(O), $R^5NC_{1-20}$alkyleneC(O), C(O)$C_{1-20}$alkyleneNR$^6$, $R^5NC_{1-20}$alkyleneO, $OC_{1-20}$alkyleneNR$^6$, C(O)$C_{1-20}$alkyleneO and $OC_{1-20}$alkyleneC(O) the latter 8 groups being optionally interrupted by one or more of S—S, C(O)O, OC(O), OC(O)O, OC(O)NH, SC(O), C(O) S, S, O, NH, N($C_{1-6}$alkyl), C(O), C(O)NH, NHC(O), NHC(O)NH, NHC(S)NH, C(S)NH, NHC(S), $C_{4-18}$cycloalkyl, and $C_{4-10}$heterocycloalkyl, and each alkyl and alkylene is optionally substituted with one or more substituents selected from halo, $CO_2H$, $C_{1-6}$alkyl, OH, $OC_{1-6}$alkyl, SH, $SC_{1-6}$alkyl, $NR^7R^7$, $C_{1-4}$alkyleneOH, and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety; and the cleavable moiety is selected from S—S, C(O)O, OC(O), OC(O)O, OC(O)NH, NHC(O)O, SC(O), C(O) S and an enzymatically cleavable peptide sequence. In some embodiments, one or both of $L^A$ and $L^E$ is a cleavable linker, and each cleavable linker independently comprises one or more groups selected from amino acid residues, $HNC_{1-20}$alkyleneNH, C(O)$C_{1-20}$alkyleneC(O), $HNC_{1-20}$alkyleneC(O), C(O)$C_{1-20}$alkyleneNH, $HNC_{1-20}$alkyleneO and $OC_{1-20}$alkyleneNH, the latter 6 groups being optionally interrupted by one or more of S—S, C(O)O, OC(O), OC(O)O, OC(O)NH, SC(O), C(O) S, S, O, NH, N($C_{1-6}$alkyl), C(O), C(O)NH, NHC(O), NHC(O)NH, NHC(S)NH, C(S)NH, NHC(S), $C_{4-18}$cycloalkyl, and $C_{4-10}$heterocycloalkyl, and each alkyl and alkylene is optionally substituted with one or more substituents selected from halo, $CO_2H$, $C_{1-6}$alkyl, OH, $OC_{1-6}$alkyl, SH, $SC_{1-6}$ alkyl, $NH_2$, $NHC_{1-4}$alkyl and N($C_{1-4}$alkyl)$_2$, provided the one or more groups comprise at least one cleavable moiety selected from S—S, C(O)O, OC(O), OC(O)O, OC(O)NH, NHC(O)O, SC(O), C(O) S and an enzymatically cleavable peptide sequence.

In some embodiments, one or both of $L^A$ and $L^E$ is a cleavable linker, and each cleavable linker independently comprises one or more groups selected from amino acid residues, $R^5NC_{1-20}$alkyleneNR$^6$, C(O)$C_{1-20}$alkyleneC(O), $R^5NC_{1-20}$alkyleneC(O), C(O)$C_{1-20}$alkyleneNR$^6$, $R^5NC_{1-20}$alkyleneO, $OC_{1-20}$alkyleneNR$^6$, C(O)$C_{1-20}$alkyleneO and $OC_{1-20}$alkyleneC(O) the latter 8 groups being optionally interrupted by one or more of S—S, C(O)O, OC(O), S, O, C(O)NH, NHC(O), $C_{4-18}$cycloalkyl, and $C_{4-10}$heterocycloalkyl, and each alkyl and alkylene is optionally substituted with one or more substituents selected from halo, $CO_2H$, $C_{1-6}$alkyl, OH, $OC_{1-6}$alkyl, SH, $SC_{1-6}$ alkyl, $NR^7R^7$, $C_{1-4}$alkyleneOH, and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety, and the cleavable moiety is selected from S—S, C(O)O, OC(O) and an enzymatically cleavable peptide sequence.

In some embodiments, one or both of $L^A$ and $L^E$ is a cleavable linker, and each cleavable linker independently comprises one or more groups selected from amino acid residues, $HNC_{1-20}$alkyleneNH, C(O)$C_{1-20}$alkyleneC(O), $HNC_{1-20}$alkyleneC(O), C(O)$C_{1-20}$alkyleneNH, $HNC_{1-20}$alkyleneO and $OC_{1-20}$alkyleneNH, the latter 6 groups being optionally interrupted by one or more of S—S, C(O)O, OC(O), S, O, C(O)NH, NHC(O), $C_{4-18}$cycloalkyl, and $C_{4-10}$heterocycloalkyl, and each alkyl, and alkylene is optionally substituted with one or more substituents selected from halo, $CO_2H$, $C_{1-6}$alkyl, OH, $OC_{1-6}$alkyl, SH, $SC_{1-6}$ alkyl, $NH_2$, $NHC_{1-4}$alkyl and N($C_{1-4}$alkyl)$_2$, provided the one or more groups comprise at least one cleavable moiety selected from S—S, C(O)O, OC(O) and an enzymatically cleavable peptide sequence. In some embodiments, one or both of $L^A$ and $L^E$ is a cleavable linker, and each cleavable linker independently comprises one or more groups selected from one or more amino acid residues, $R^5NC_{1-20}$alkyleneNR$^6$, C(O)$C_{1-20}$alkyleneC(O), $R^5NC_{1-20}$alkyleneC(O), C(O)$C_{1-20}$alkyleneNR$^6$, $R^5NC_{1-20}$alkyleneO, $OC_{1-20}$alkyleneNR$^6$, C(O)$C_{1-20}$alkyleneO and $OC_{1-20}$alkyleneC(O), the latter 8 groups being optionally interrupted by one or more of S—S, C(O)O, OC(O), S, O, C(O)NH, NHC(O), $C_{4-18}$cycloalkyl, and $C_{4-10}$heterocycloalkyl, and each alkyl and alkylene is optionally substituted with one or more substituents selected from halo, $CO_2H$, $NR^7R^7$, and $C_{1-4}$alkyleneNR$^7$R$^8$ wherein $R^5$, $R^6$, $R^7$ and $R^8$ are independently selected from H and $C_{1-4}$alkyl, provided at least two groups connect to form a cleavable moiety, or provided the one or more groups comprise at least one cleavable moiety, and the cleavable moiety is selected from S—S, C(O)O, OC(O) and an enzymatically cleavable peptide sequence. In some embodiments, one or both of $L^A$ and $L^E$ is a cleavable linker, and each cleavable linker independently comprises one or more groups selected from amino acid residues, $HNC_{1-20}$alkyleneNH, C(O)$C_{1-20}$alkyleneC(O), $HNC_{1-20}$alkyleneC(O), C(O)$C_{1-20}$alkyleneNH, $HNC_{1-20}$alkyleneO and $OC_{1-20}$alkyleneNH, the latter 6 groups being optionally interrupted by one or more of S—S, C(O)O, OC(O), S, O, C(O)NH, NHC(O), $C_{4-18}$cycloalkyl, and $C_{4-10}$heterocycloalkyl, provided the one or more groups comprise at least one cleavable moiety selected from S—S, C(O)O, OC(O) and an enzymatically cleavable peptide sequence.

In some embodiments, the cleavable moiety is selected from S—S, C(O)O and OC(O). In some embodiments, the cleavable moiety is selected from C(O)O and OC(O).

In some embodiments, at least two groups connect to form a cleavable moiety. In some embodiments, two groups selected from amino acid residue, $R^5NC_{1-20}$alkyleneO, $OC_{1-20}$alkyleneN$R^6$, $C(O)C_{1-20}$alkyleneO and $OC_{1-20}$alkyleneC(O) connect to form a cleavable moiety selected from C(O)O and OC(O). In some embodiments, an amino acid residue and one of $R^5NC_{1-20}$alkyleneO, $OC_{1-20}$alkyleneN$R^6$, $C(O)C_{1-20}$alkyleneO and $OC_{1-20}$alkyleneC(O) connect to form a cleavable moiety selected from C(O)O and OC(O). In some embodiments, an amino acid residue and one of $C(O)C_{1-20}$alkyleneO and $OC_{1-20}$alkyleneC(O) connect to form a cleavable moiety selected from C(O)O and OC(O). In some embodiments, the $OC_{1-20}$alkyleneC(O) is selected from 4-hydroxybutanoic acid (4hBA), 4-hydroxypentanoic acid (4hPA), 5-hydroxypentanoic acid (5HPA) and 6-hydroxyhexanoic acid (6hHA).

In some embodiments, $C_{4-10}$cycloalkyl is selected from cyclopropyl, cyclobutyl, cyclopentyl, cyclohexyl, and cycloheptyl.

In some embodiments, $C_{4-10}$heterocycloalkyl is selected from azetidinyl, oxetanyl, tetrohydrofuranyl, tetrahydrothiophenyl, pyrrolidinyl, dihydropyrrolyl, imidazolidinyl, pyrazolidinyl, thiazolidinyl, isothiazolidinyl, dioxolanyl, dithiolanyl, 3,4,5,6-tetrahydro-1,2,4-triazinyl, dioxidothiomorpholino, tetrahydropyridinyl, dihydropyridinyl, dihydropyranyl, thianyl, piperidinyl, piperazinyl, tetrahydropyranyl, thiomorpholinyl, morpholinyl, dioxanyl, azepanyl, diazepanyl, oxepanyl and thiepanyl.

In some embodiments, the $C_{6-10}$aryl is selected from phenyl, indanyl or naphthyl.

In some embodiments, the $C_{5-11}$heteroaryl is selected from triazolyl, pyrrolyl, imidazolyl, oxazolyl, pyrazolyl, thiazolyl, pyridinyl, pyrazinyl, pyridazinyl and pyrimidinyl.

In some embodiments, the amino acid residue in $L^A$, $L^E$ and/or $L^Z$ is derived from an amino acid. In some embodiments, the amino acid residue in $L^A$, $L^E$ and/or $L^Z$ is derived from a naturally occurring amino acid, a modified amino acid, a β-amino acid, a γ-amino acid, D enantiomer of the naturally occurring amino acids or the modified amino acids, and unnatural amino acids.

In some embodiments, the amino acid residue in $L^A$, $L^E$ and/or $L^Z$ is derived from an amino acid that is a naturally occurring amino acid. In some embodiments, the naturally occurring amino acid is selected from, but are not limited to, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), valine (Val), pyrrolysine (Pyl), selenocycleine (Sec) and pyrroline-carboxy-lysine (PCL).

In some embodiments, the naturally occurring amino acids are further modified in vivo to provide modified amino acids. Therefore, in some embodiments, the amino acid residue is derived from an amino acid selected from, but not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid thioproline.

In some embodiments, the amino acid is derived from modified amino acids selected from ornithine, homo-lysine, 2,3-diaminopropionic acid (DAP), 2,4-diaminobutyric acid (DAB) and homo-cysteine.

In some embodiments, the amino acid residue is derived from the D enantiomer of the naturally occurring amino acids or the modified amino acids.

In some embodiments, the amino acid residue derived from Glu is connected through the α-amino and the α-carboxy or the α-amino and the γ-carboxy terminal. Therefore, in some embodiments, the amino acid residue derived from Glu is

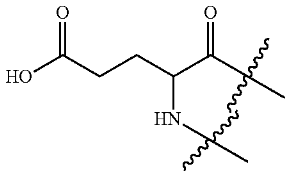

or (γGlu)

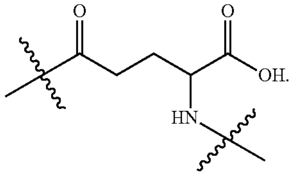

In some embodiments, the amino acid residue derived from Asp is connected through amino and the α-carboxy or is connected through the amino and the β-carboxy terminal. In some embodiments, the amino acid residue derived from Lys is connected through a-amino and the α-carboxy or the α-amino and the ε-amino terminal. Therefore, in some embodiments, the amino acid residue is derived from Lys

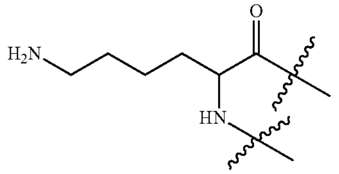

and/or (εLys)

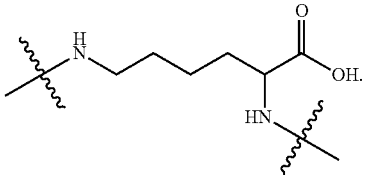

In some embodiments, the amino acid residue in $L^A$, $L^E$ and/or $L^Z$ is derived from a β-amino acid or a γ-amino acid. In some embodiments, the β-amino acid is β-alanine.

In some embodiments, the amino acid residue in $L^A$, $L^E$ and/or $L^Z$ is derived from an unnatural amino acid. In some embodiments, the amino acid residue in $L^A$, $L^E$ and/or $L^Z$ is selected from (2Nal)

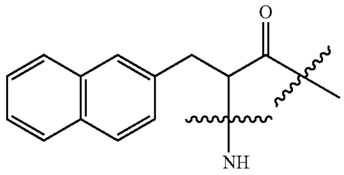

, (Trx)

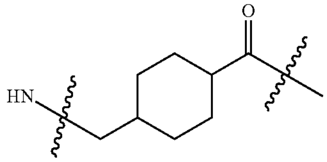

,

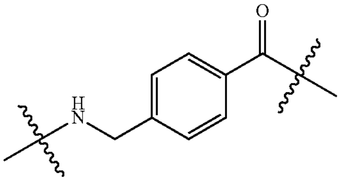

and

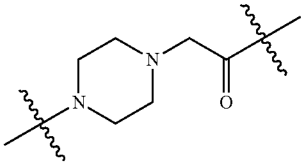

.

Therefore, in some embodiments, when $L^Z$ is a non-cleavable linker and/or one of $L^A$ and $L^E$ is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

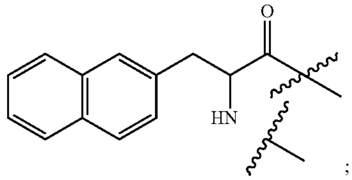

;

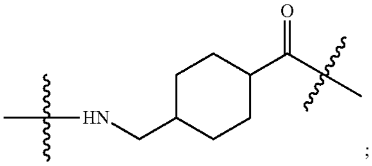

;

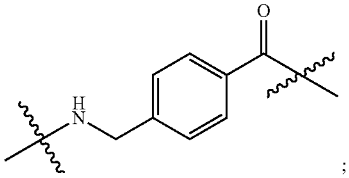

;

-continued

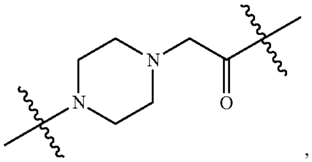

, $R^1NC_{1-20}$alkyleneN$R^2$; C(O)$C_{1-20}$alkyleneC(O); $R^1NC_{1-20}$alkyleneC(O); and C(O)$C_{1-20}$alkyleneN$R^2$, the latter 4 groups being optionally interrupted by one or more of S, O, C(O)NH, NHC(O), $C_{4-6}$cycloalkyl and $C_{4-6}$heterocycloalkyl wherein each $R^1$ and $R^2$ is independently selected from H and $C_{1-2}$alkyl. In some embodiments, when $L^Z$ is a non-cleavable linker and/or one of $L^A$ and $L^E$ is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec of PCL or the D enantiomers thereof; one or more amino acids residues derived from DAB or DAP;

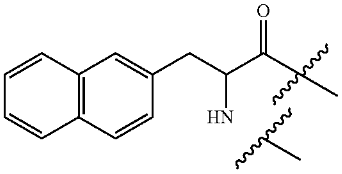

;

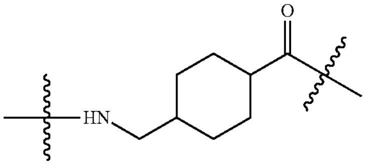

;

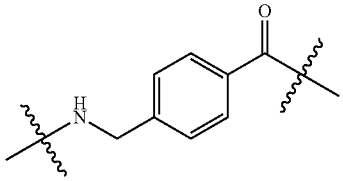

;

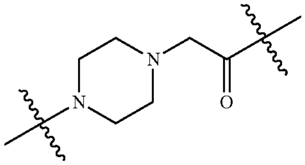

, (OEG)

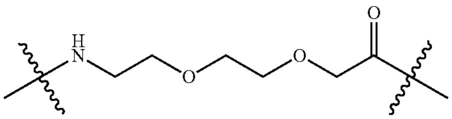

;

$R^1NC_{1-20}$alkyleneN$R^2$, C(O)$C_{1-20}$alkyleneC(O), $R^1NC_{1-20}$alkyleneC(O), and C(O)$C_{1-20}$alkyleneN$R^2$, wherein each $R^1$ and $R^2$ is independently selected from H and $C_{1-2}$alkyl. In some embodiments, when $L^Z$ is a non-cleavable linker and/or one of $L^A$ and $L^E$ is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, and PCL, and the D enantiomers thereof;

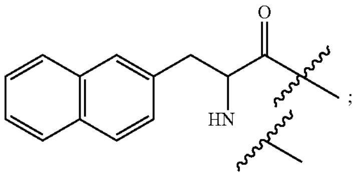

;

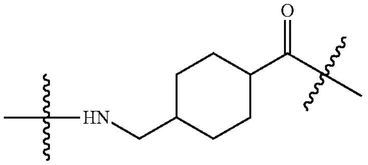

;

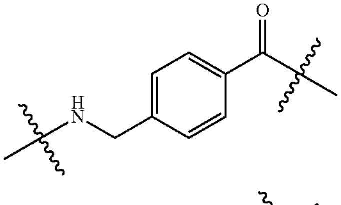

;

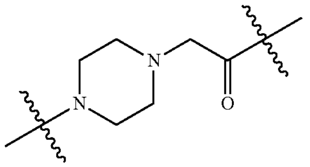

, (OEG)

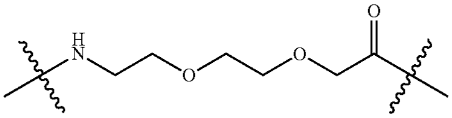

;

(Ava)

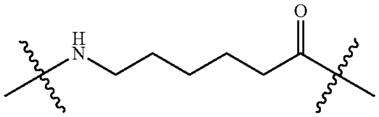

;

(Aoc)

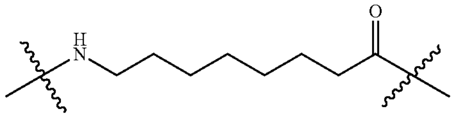

;

(Aun)

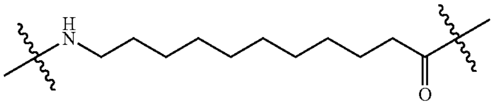

and

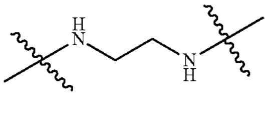

.

In some embodiments, $L^Z$ is a non-cleavable linker comprising one or more groups selected from

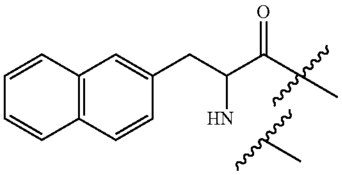

and

-continued

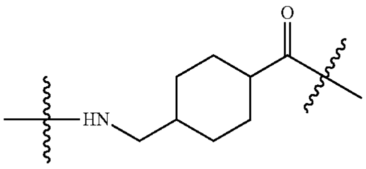

.

In some embodiments, $L^Z$ is a non-cleavable linker and is or comprises

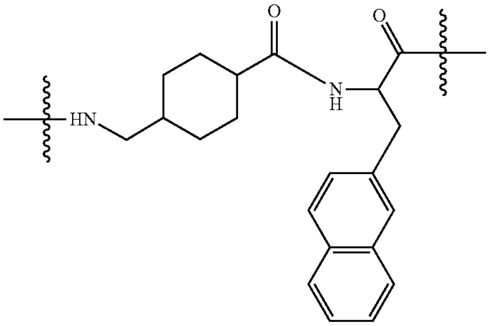

.

In some embodiments, $L^Z$ is a non-cleavable linker connected to Z and the fragment $L^Z$-Z in the compound of Formula I is or comprises

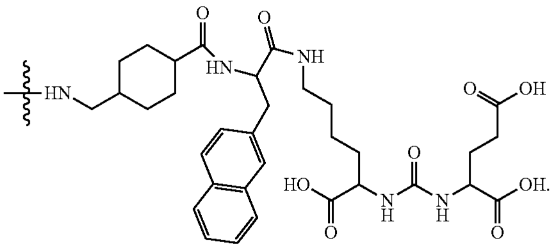

(Trx-2Nal-εKuE)

In some embodiments, $L^Z$ is a non-cleavable linker comprising one or more groups selected from one or more amino acids residues derived from Tyr or Phe. In some embodiments, $L^Z$ is a non-cleavable linker connected to Z and the fragment $L^Z$-Z in the compound of Formula I is or comprises Tyr-Phe-εKuE.

In some embodiments, $L^Z$ further comprises one or more groups selected from OEG; $R^1NC_{1-20}alkyleneNR^2$, $C(O)C_{1-20}alkyleneC(O)$, $R^1NC_{1-20}alkyleneC(O)$, and $C(O)C_{1-20}alkyleneNR^2$, wherein each $R^1$ and $R^2$ is independently selected from H and $C_{1-2}alkyl$. In some embodiments, $L^Z$ further comprises one or more groups selected from (OEG)

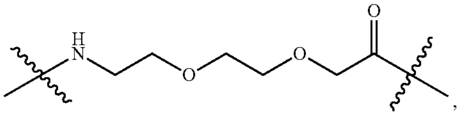

,

-continued

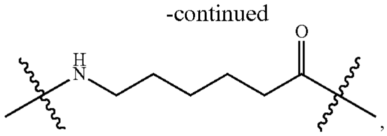

, and

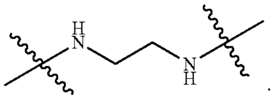

.

In some embodiments, $L^Z$ further comprises one or more groups selected from

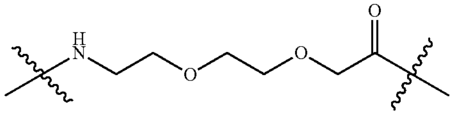

and the fragment $L^Z$-Z in the compound of Formula I is or comprises

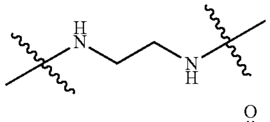

,

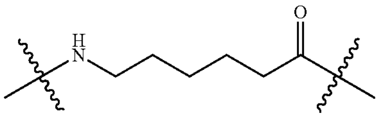

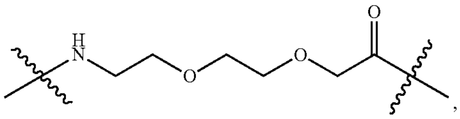

,

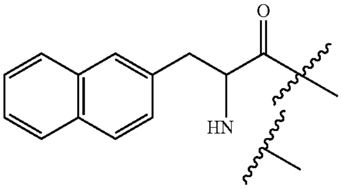

and

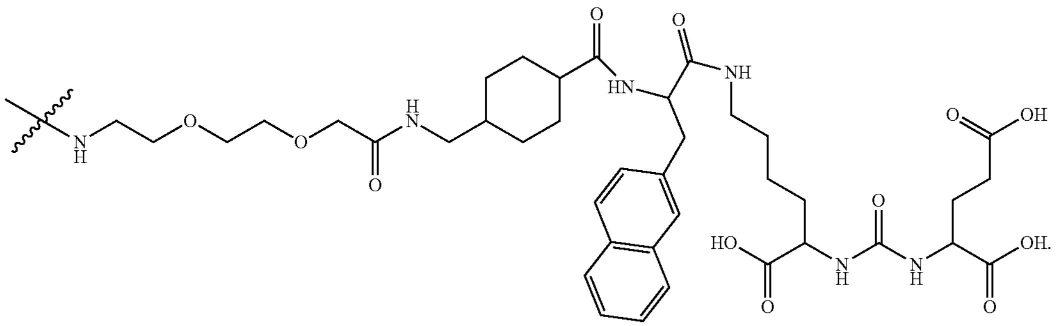 [SMILES: *NCCOCCOCC(=O)NCC1CCC(C(=O)NC(Cc2ccc3ccccc3c2)C(=O)NCCCCC(NC(=O)NC(CCC(=O)O)C(=O)O)C(=O)O)CC1]

Therefore, in some embodiments, $L^Z$ is a non-cleavable linker comprising one or more groups selected from OEG,

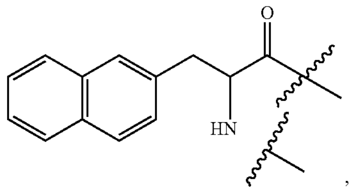

,

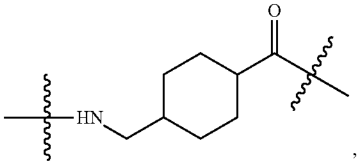

, $R^1NC_{1-20}$alkyleneN$R^2$, $C(O)C_{1-20}$alkyleneC(O), $R^1NC_{1-20}$alkyleneC(O), and $C(O)C_{1-20}$alkyleneN$R^2$, wherein each $R^1$ and $R^2$ is independently selected from H and $C_{1-2}$alkyl. In some embodiments, $L^Z$ is a non-cleavable linker comprising one or more groups selected from -continued

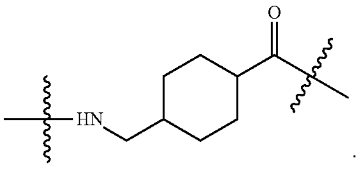

.

In some embodiments, one of $L^A$ and $L^E$ is a non-cleavable linker, and the non-cleavable linker comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP; OEG, $R^1NC_{1-20}$alkyleneN$R^2$, $C(O)C_{1-20}$alkyleneC(O), $R^1NC_{1-20}$alkyleneC(O), and $C(O)C_{1-20}$alkyleneN$R^2$, wherein each $R^1$ and $R^2$ is independently selected from H and $C_{1-2}$alkyl. In some embodiments, one of $L^A$ and $L^E$ is a non-cleavable linker, and the non-cleavable linker comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, and PCL and the D enantiomers thereof;

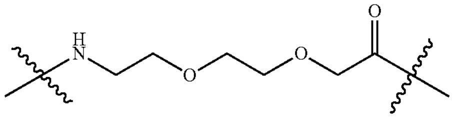
;
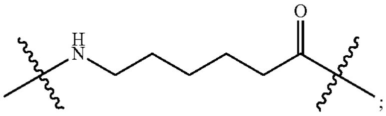
;
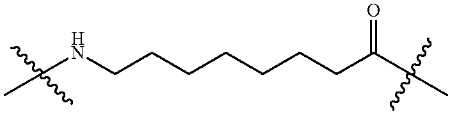
;
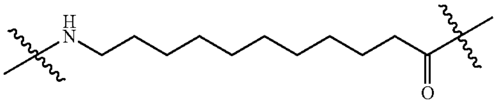
and
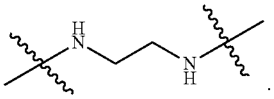
.

In some embodiments, one of $L^A$ and $L^E$ is a non-cleavable linker, and the non-cleavable linker comprises one or more groups selected from one or more amino acids residues derived from Glu, Gly, Lys, Phe, Tyr, and Val, or the D enantiomers thereof; an amino acid residue derived from DAB, $R^1NC_{1-20}$alkyleneN$R^2$, C(O)$C_{1-20}$alkyleneC(O), $R^1NC_{1-20}$alkyleneC(O), and C(O)$C_{1-20}$alkyleneN$R^2$, wherein each $R^1$ and $R^2$ is independently selected from H and $C_{1-2}$alkyl. In some embodiments, one of $L^A$ and $L^E$ is a non-cleavable linker, and the non-cleavable linker comprises one or more groups selected from one or more amino acids residues derived from Glu, Gly, Lys, Phe, Tyr, and Val, and the D enantiomers thereof;

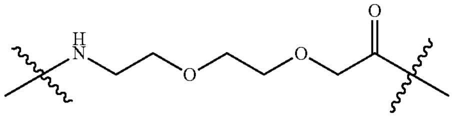
;
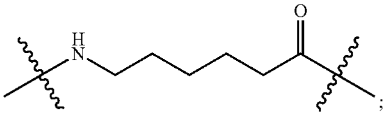
;
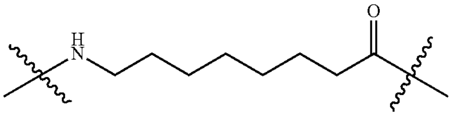
;
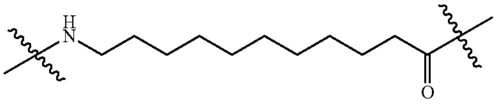
and
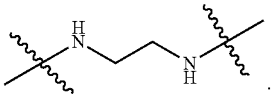
.

In some embodiments, $L^A$ is a non-cleavable linker, and the non-cleavable linker comprises one or more groups selected from amino acids residues derived from Gly, Glu, OEG, $R^1NC_{1-20}$alkyleneN$R^2$, C(O)$C_{1-20}$alkyleneC(O), $R^1NC_{1-20}$alkyleneC(O), and C(O)$C_{1-20}$alkyleneN$R^2$, wherein each $R^1$ and $R^2$ is independently selected from H and $C_{1-2}$alkyl. In some embodiments, $L^A$ is a non-cleavable linker, and the non-cleavable linker comprises one or more groups selected from amino acids residues derived from Glu,

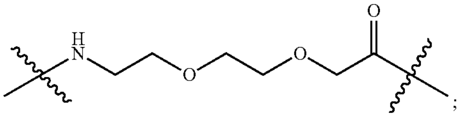
; and
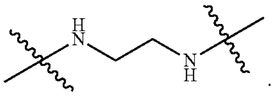
.

In some embodiments, $L^A$ is a non-cleavable linker, and the non-cleavable linker comprises one or more groups selected from amino acids residues derived from Glu and

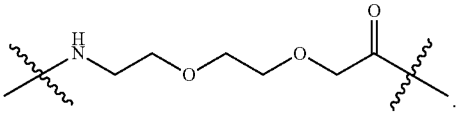 [SMILES: *NCCOCCOCC(*)=O]
.

In some embodiments, the amino acid residue derived from Glu is γGlu ( (
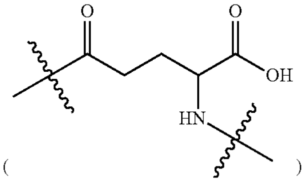 [SMILES: *NC(CCC(*)=O)C(=O)O]
)

and $L^A$ is a non-cleavable linker, and the non-cleavable linker comprises one or more groups selected from γGlu (
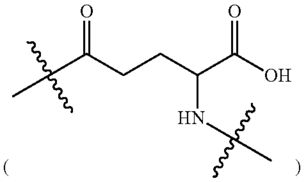
) and (OEG)

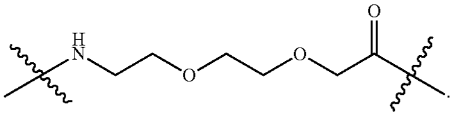
.

In some embodiments, $L^A$ is a non-cleavable linker, and the non-cleavable linker comprises one or more of γGlu

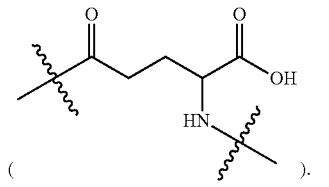 [SMILES: *NC(CCC(*)=O)C(=O)O]

In some embodiments, $L^A$ is a non-cleavable linker, and the non-cleavable linker comprises one or more of (OEG)

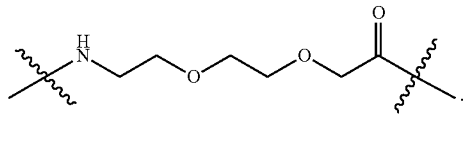

In some embodiments, the non-cleavable linker is or comprises γGlu-$(OEG)_{1-3}$. In some embodiments, the non-cleavable linker is or comprises γGlu-(OEG).

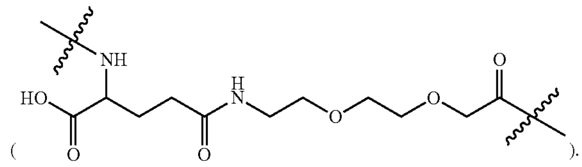 [SMILES: *NC(CCC(=O)NCCOCCOCC(*)=O)C(=O)O]

In some embodiments, $L^A$ comprises two or more of (OEG)

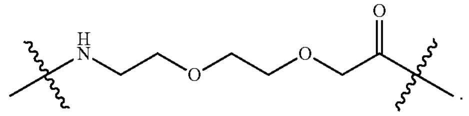

In some embodiments, $L^E$ is a non-cleavable linker, and the non-cleavable linker comprises one or more groups selected from OEG, $R^1NC_{1-20}alkyleneNR^2$, $C(O)C_{1-20}alkyleneC(O)$, $R^1NC_{1-20}alkyleneC(O)$, and $C(O)C_{1-20}alkyleneNR^2$, wherein each $R^1$ and $R^2$ is independently selected from H and $C_{1-2}alkyl$. In some embodiments, $L^E$ is a non-cleavable linker, and the non-cleavable linker comprises one or more groups selected from OEG

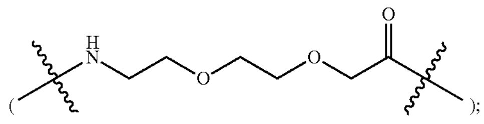

and

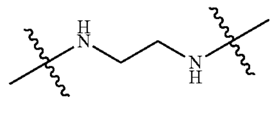

In some embodiments, $L^E$ comprises two or more of OEG

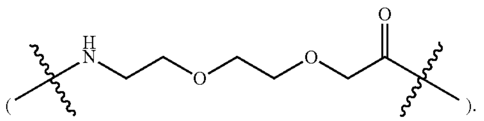 [SMILES: *NCCOCCOCC(*)=O]

In some embodiments, one or both of $L^A$ and $L^E$ is a cleavable linker, and each cleavable linker independently comprises one or more groups selected from one or more amino acid residues; $R^5NC_{1-20}alkyleneC(O)$; $C(O)C_{1-20}alkyleneNR^6$; $C(O)C_{1-20}alkyleneO$ and $OC_{1-20}alkyleneC(O)$, the latter 4 groups being optionally interrupted by one or more of S—S, C(O)O, OC(O), O, C(O)NH and NHC(O), and each alkyl and alkylene is optionally substituted with one or more substituents selected from halo, $CO_2H$, $NR^7R^7$, and $C_{1-4}alkyleneNR^7R^8$; wherein $R^5$, $R^6$, $R^7$ and $R^8$ are independently selected from H and $C_{1-4}alkyl$, provided at least two groups connect to form a cleavable moiety, or provided the one or more groups comprise at least one cleavable moiety, and the cleavable moiety is selected from S—S, C(O)O, OC(O) and an enzymatically cleavable peptide sequence.

In some embodiments, one or both of $L^A$ and $L^E$ is a cleavable linker, and the cleavable linker comprises at least one group selected from $R^5NC_{1-20}alkyleneC(O)$ optionally interrupted by one or more of S—S, C(O)O, OC(O), O, C(O)NH and NHC(O), provided $R^5NC_{1-20}alkyleneC(O)$ is interrupted by at least one of S—S, C(O)O and OC(O); or the cleavable linker comprises at least one group connected to $C(O)C_{1-20}alkyleneO$ or $OC_{1-20}alkyleneC(O)$ to form a cleavable moiety selected from C(O)O and OC(O). In some embodiments, one or both of $L^A$ and $L^E$ is a cleavable linker, and the cleavable linker comprises at least one group selected from $R^5NC_{1-20}alkyleneC(O)$ optionally interrupted by one or more of S—S, C(O)O, OC(O), O, C(O)NH and NHC(O), provided $R^5NC_{1-20}alkyleneC(O)$ is interrupted by at least one of S—S, C(O)O ad OC(O); or the cleavable linker comprises at least one amino acid residue connected to $C(O)C_{1-20}alkyleneO$ or $OC_{1-20}alkyleneC(O)$ to form a cleavable moiety selected from C(O)O and OC(O). In some embodiments, one or both of $L^A$ and $L^E$ is a cleavable linker, and the cleavable linker comprises at least one group selected from $R^5NC_{1-20}alkyleneC(O)$ optionally interrupted by one to five of S—S, C(O)O, OC(O), O, C(O)NH and NHC(O), provided $R^5NC_{1-20}alkyleneC(O)$ is interrupted by at least one of S—S, C(O)O ad OC(O); or the cleavable linker comprises at least one amino acid residue connected to $C(O)C_{1-20}alkyleneO$ or $OC_{1-20}alkyleneC(O)$ to form a cleavable moiety selected from C(O)O and OC(O).

In some embodiments, one or both of $L^A$ and $L^E$ is a cleavable linker, and the cleavable linker comprises at least one group selected from $R^5NC_{1-20}alkyleneC(O)$ optionally interrupted by one to five of S—S, C(O)O, OC(O), O, C(O)NH and NHC(O), provided $R^5NC_{1-20}alkyleneC(O)$ is interrupted by at least one of S—S, C(O)O and OC(O). In some embodiments, $R^5NC_{1-20}alkyleneC(O)$ optionally interrupted by one to five of S—S, C(O)O, OC(O), O, C(O)NH and NHC(O), provided $R^5NC_{1-20}alkyleneC(O)$ is interrupted by at least one of S—S, C(O)O and OC(O) is selected form ESL1, SSL1, ESL2 and ESL3. In some embodiments, one or both of $L^A$ and $L^E$ is a cleavable linker, and the cleavable linker comprises at least one group selected from (ESL1)

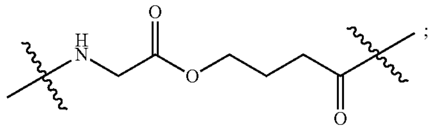

(SSL1)

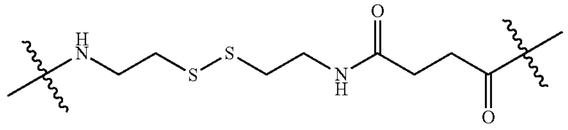

(ESL2)

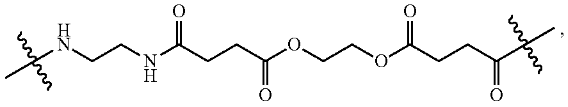

(ESL3)

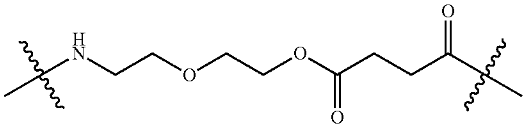

and an enzymatically cleavable peptide sequence.

In some embodiments, one or both of $L^A$ and $L^E$ is a cleavable linker, and the cleavable linker comprises at least one amino acid residue connected to $C(O)C_{1-20}$alkyleneO or $OC_{1-20}$alkyleneC(O) to form a cleavable moiety selected from C(O)O and OC(O). In some embodiments, one or both of $L^A$ and $L^E$ is a cleavable linker, and the cleavable linker comprises at least one amino acid residue connected to $C(O)C_{1-10}$alkyleneO or $OC_{1-10}$alkyleneC(O) to form a cleavable moiety selected from C(O)O and OC(O). In some embodiments, the at least one amino acid residue connected to $C(O)C_{1-10}$alkyleneO or $OC_{1-10}$alkyleneC(O) is derived from an amino acid selected from a naturally occurring amino acid or the D-enantiomer thereof, DAB and DAP. In some embodiments, amino acid is selected from a Gly, Leu, DAB and DAP. Therefore, in some embodiments, one or both of $L^A$ and $L^E$ is a cleavable linker, and the cleavable linker comprises at least one amino acid residue a naturally occurring amino acid or the D-enantiomer thereof, DAB and DAP connected to $C(O)C_{1-10}$alkyleneO or $OC_{1-10}$alkyleneC (O) to form a cleavable moiety selected from C(O)O and OC(O).

In some embodiments, the enzymatically cleavable peptide sequences are peptide sequences cleavable by the kidney brush border enzyme, thermolysin, prolineendopeptidase, fibroblast activation protein (FAP), neprilysin or a general endopeptidase. In some embodiments, the peptide sequences cleavable by the kidney brush border enzyme are selected from Met-Val-Lys. In some embodiments, the peptide sequences cleavable by thermolysin in Ala-Val. In some embodiments, the peptide sequences cleavable by prolineendopeptidase is Ala-Pro and Gly-Pro. In some embodiments, the peptide sequences cleavable by FAP is Gly-Pro. In some embodiments, the peptide sequences cleavable by neprilysin is Ser-Ser, Ser-Gly, Gly-Ala and Ser-Lys. Therefore, in some embodiments, the enzymatically cleavable peptide sequence is selected from Met-Val-Lys, Ala-Val, Ala-Pro, Gly-Pro, Ser-Ser, Ser-Gly, Gly-Ala and Ser-Lys.

In some embodiments, the cleavable linker optionally further comprises one or more groups selected from amino acid residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

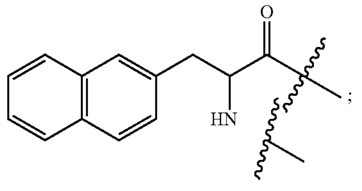

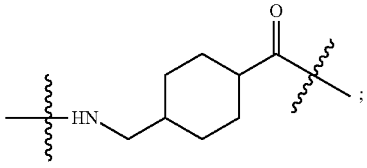

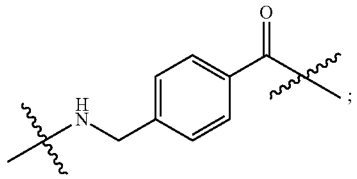

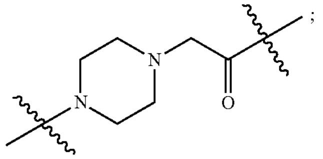

$R^5NC_{1-20}$alkyleneN$R^6$; and $R^5NC_{1-20}$alkyleneC(O) optionally interrupted by one or more of O. In some embodiments, the cleavable linker optionally further comprises one or more groups selected from amino acid residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, and PCL and the D enantiomers thereof,

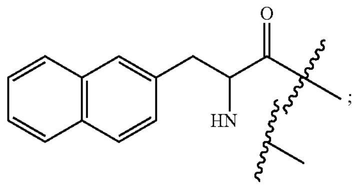

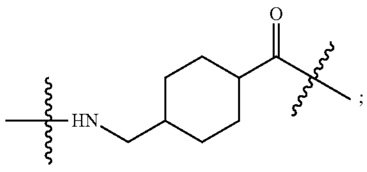

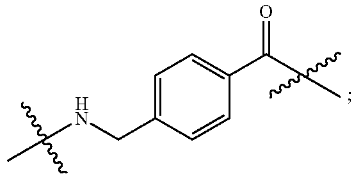

-continued

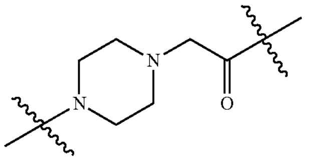

;

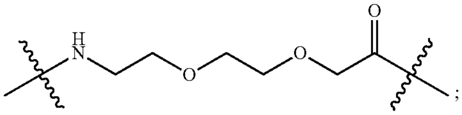 [SMILES: *NCCOCCOCC(*)=O]

;

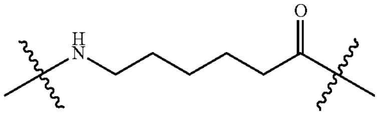

;

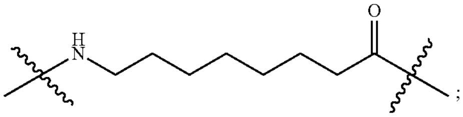

;

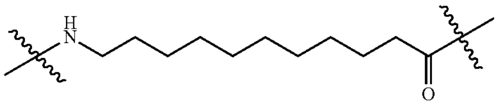

and

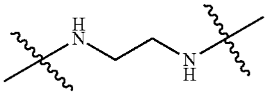

.

In some embodiments, one or both $L^A$ and $L^E$ is a cleavable linker, and each cleavable linker independently comprises one or more groups selected from one or more amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), or at least one amino acid residue connected to C(O)$C_{1-10}$alkyleneO or O$C_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys. In some embodiments, one or both $L^A$ and $L^E$ is a cleavable linker, and each cleavable linker independently comprises one or more groups selected from amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one amino acid residue connected to C(O)$C_{1-10}$alkyleneO or O$C_{1-10}$alkyleneC(O) to form a cleavable moiety selected from C(O)O and OC(O). In some embodiments, one or both $L^A$ and $L^E$ is a cleavable linker, and each cleavable linker independently comprises one or more groups selected from amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one group $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O ad OC(O), or an enzymatically cleavable peptide sequence selected from Met-Val-Lys, Ala-Val, Ala-Pro, Gly-Pro, Ser-Ser, Ser-Gly, Gly-Ala and Ser-Lys. In some embodiments, one or both $L^A$ and $L^E$ is a cleavable linker, and each cleavable linker independently comprises one or more groups selected from amino acid residues derived from Glu, Lys, Phe, Tyr, and the D enantiomers thereof;

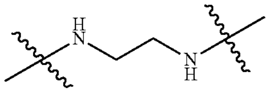

and

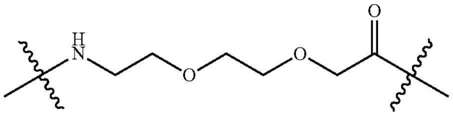

;

and at least one group selected from

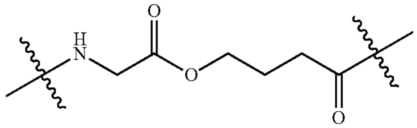

;

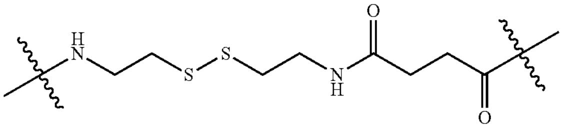

,

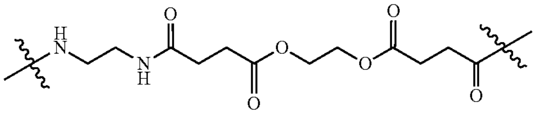

,

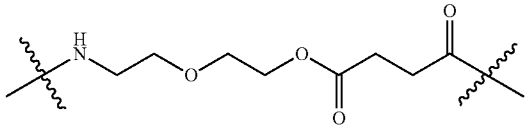

and an enzymatically cleavable peptide sequence selected from Met-Val-Lys, Ala-Val, Ala-Pro, Gly-Pro, Ser-Ser, Ser-Gly, Gly-Ala and Ser-Lys. In some embodiments, one or both $L^A$ and $L^E$ is a cleavable linker, and each cleavable linker independently comprises one or more groups selected from amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one group $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O ad OC(O).

In some embodiments, $L^A$ is a cleavable linker, and the cleavable linker comprises one or more groups selected from amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), at least one amino acid residue connected to C(O)$C_{1-10}$alkyleneO or $OC_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys. In some embodiments, $L^A$ is a cleavable linker, and the cleavable linker comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one amino acid residue connected to C(O)$C_{1-10}$alkyleneO or $OC_{1-10}$alkyleneC(O) to form a cleavable moiety selected from C(O)O and OC(O). In some embodiments, $L^A$ is a cleavable linker, and the cleavable linker comprises one or more groups selected from amino acid residues derived from Glu, Lys, Phe, Tyr, and the D enantiomers thereof;

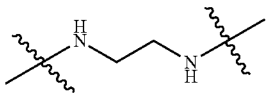

and

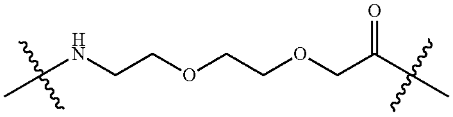

;

and at least one group selected from

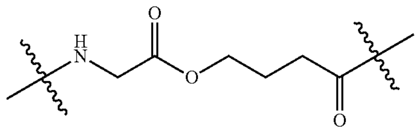

;

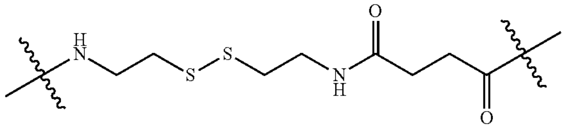

,

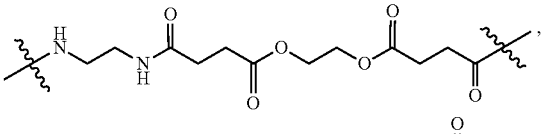

,

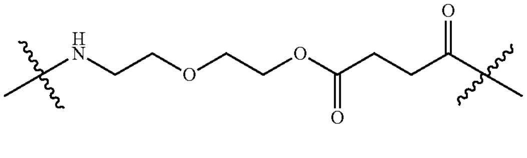

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, $L^E$ is a cleavable linker, and the cleavable linker comprises one or more groups selected from one or more amino acid residues derived from Gly, Glu, Leu, Phe, Tyr, or Lys, or the D enantiomers thereof; one or more amino acid residues derived from DAP or DAB;

$R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O ad OC(O), or at least one amino acid residue connected to C(O)$C_{1-10}$alkyleneO or $OC_{1-10}$alkyleneC(O) to form a cleavable moiety selected from C(O)O and OC(O), or an enzymatically cleavable peptide sequence selected from Met-Val-Ala-Val, Ala-Pro, Gly-Pro, Ser-Ser, Ser-Gly, Gly-Ala and Ser-Lys. In some embodiments, $L^E$ is a cleavable linker, and the cleavable linker comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one amino acid residue connected to C(O)$C_{1-10}$alkyleneO or $OC_{1-10}$alkyleneC(O) to form a cleavable moiety selected from C(O)O and OC(O). In some embodiments, $L^E$ is a cleavable linker, and the cleavable linker comprises one or more

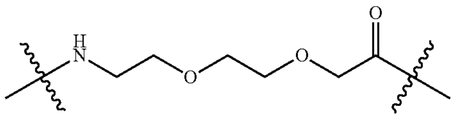

;

and at least one group selected from

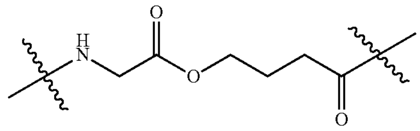

;

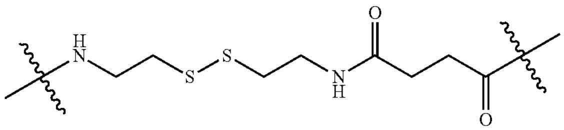

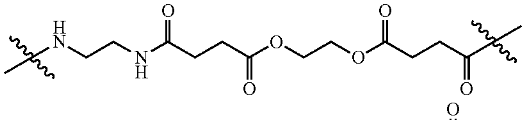

,

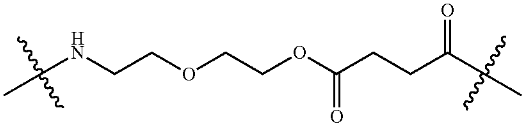

and an enzymatically cleavable peptide sequence selected from Met-Val-Lys, Ala-Val, Ala-Pro, Gly-Pro, Ser-Ser, Ser-Gly, Gly-Ala and Ser-Lys. In an exemplary embodiment, $L^E$ is a cleavable linker, and the cleavable linker is or comprises

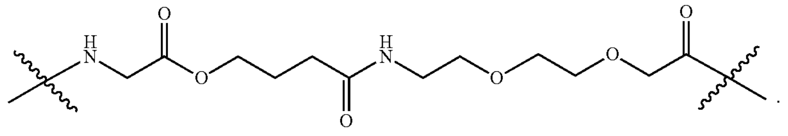 [SMILES: *NCC(=O)OCCCC(=O)NCCOCCOCC(*)=O]

In some embodiments, $R^5$, $R^6$, $R^7$ and $R^8$ are independently selected from H, $CH_3$, $CH_2CH_3$, $CH_2CH_2CH_3$, $CH(CH_3)_2$, and $C(CH_3)_3$. In some embodiments, $R^5$, $R^6$, $R^7$ and $R^8$ are independently selected from H and $C_{1-3}$alkyl. In some embodiments, $R^5$, $R^6$, $R^7$ and $R^8$ are independently selected H, $CH_3$, $CH_2CH_3$, and $CH(CH_3)_2$. In some embodiments, $R^5$, $R^6$, $R^7$ and $R^8$ are independently selected H, and $CH_3$.

In some embodiments, $L^A$, $L^E$, and $L^Z$ each independently comprise 1 to 15 groups, 1 to 12 groups, 1 to 10 groups, 1 to 8 groups, or 1 to 6 groups that are connected together. In some embodiments, $L^A$, $L^E$, and $L^Z$ each independently comprise 1 to 15 groups, 1 to 12 groups or 1 to 10 groups connected together. In some embodiments, $L^A$, $L^E$, and $L^Z$ each independently consist of, 1 to 5 groups, 1 to 4 groups, 1 to 3 groups, or 1 or 2 groups connected together. In some embodiments, $L^A$, $L^E$, and $L^Z$ each independently consist of 1 to 4 groups, 1 to 3 groups, or 1 or 2 groups connected together.

In some embodiments, $L^A$ is

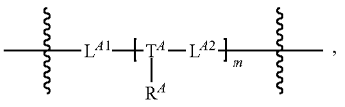

$L^Z$ is

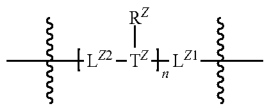

and $L^E$ is

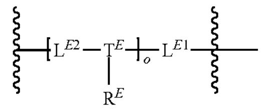

and the compound of Formula I is a compound of Formula I-D or a pharmaceutically acceptable salt and/or solvate thereof (I-D)

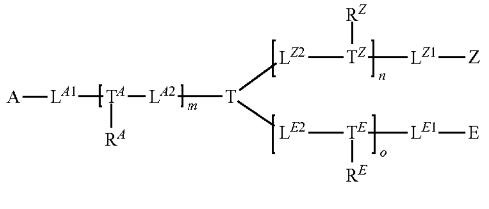

wherein

A, Z, E and T are as defined in Formula I $T^A$, $T^Z$, $T^E$ are each independently T as defined in formula I and $T^A$, $T^Z$, $T^E$ and T are the same or different;

$L^{A1}$ and $L^{A2}$ are each independently $L^A$ as defined in formula I;

$L^{E1}$ and $L^{E2}$ are each independently $L^E$ as defined in formula I;

$L^{Z1}$ and $L^{Z2}$ are each independently $L^Z$ as defined in formula I;

$R^A$ is selected from

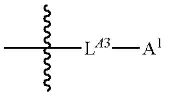

and

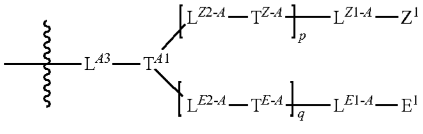

$R^Z$ is selected from

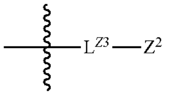

and

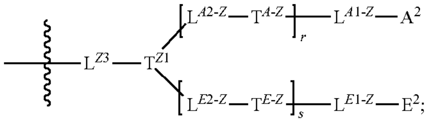

$R^E$ is selected from

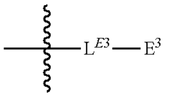

and

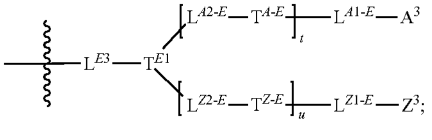

$T^{A1}$, $T^{Z-A}$, $T^{E-A}$, $T^{Z1}$, $T^{A-Z}$, $T^{E-Z}$, $T^{E1}$, $T^{Z-E}$, $T^{A-E}$ are each independently T as defined in Formula I and T, $T^{A1}$, $T^{Z-A}$, $T^{E-A}$, $T^{Z1}$, $T^{A-Z}$, $T^{E-Z}$, $T^{E1}$, $T^{Z-E}$ and $T^{A-E}$ are the same or different;

$L^{A3}$, $L^{A1-Z}$, $L^{A2-Z}$, $L^{A1-E}$ and $L^{A2-E}$ are each independently $L^A$ as defined in Formula I;

$L^{E1-A}$, $L^{E2-A}$, $L^{E1-Z}$, $L^{E2-Z}$ and $L^{E3}$ are each independently $L^E$ as defined in Formula I;

$L^{Z3}$, $L^{Z1-A}$, $L^{Z2-A}$, $L^{Z1-E}$ and $L^{Z2-E}$ are each independently $L^Z$ as defined in Formula I;

$A^1$, $A^2$ and $A^3$ are each independently A as defined in Formula I and $A^1$, $A^2$, $A^3$ and A are the same or different;

$Z^1$, $Z^2$ and $Z^3$ each independently Z as defined in Formula I and $Z^1$, $Z^2$, $Z^3$ and Z are the same or different;

$E^1$, $E^2$ and $E^3$ each independently E as defined in Formula I and $E^1$, $E^2$, $E^3$ and E are the same or different; and m, n, o, p, q, r, s, t and u are each independently selected from 0 and 1, wherein at least one of $L^{A3}$, $L^{E1\text{-}A}$ $L^{E2\text{-}A}$, $L^{A1\text{-}Z}$, $L^{A2\text{-}Z}$, $L^{E1\text{-}Z}$, $L^{E2\text{-}Z}$, $L^{E3}$, $L^{A1\text{-}E}$ and $L^{A2\text{-}E}$ is a cleavable linker.

In some embodiments, T is a branching group that is at least trivalent comprising at least a first terminal functionality, a second terminal functionality and a third terminal functionality, which are the same or different and bind to $L^{A2}$ (or alternatively $T^A$, $L^{A1}$ or A), $L^{Z2}$ (or alternatively $T^Z$, $L^{Z1}$ or Z) and $L^{E2}$ (or alternatively $T^E$, $L^{E1}$ or E), respectively. In an exemplary embodiment, T is lysine or DAB. In an exemplary embodiment, T is lysine. Therefore, in exemplary embodiments, the compound of Formula I-D is a compound of Formula I-E or I-F.

(I-E)

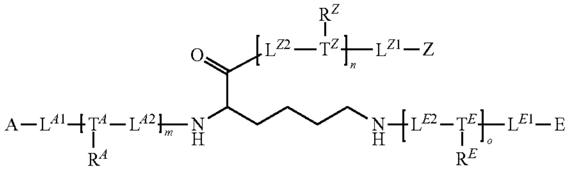

(I-F)

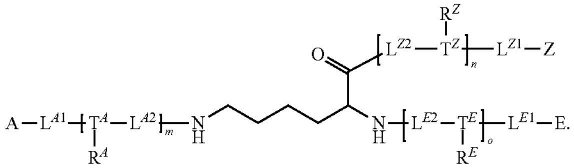

In some embodiments, when p and r are each 0, then $L^{A1}$ is $L^A$ as defined in Formula I, $L^{Z1}$ is $L^Z$ as defined in Formula I, and $L^{E1}$ is $L^E$ as defined in Formula I and the compound of Formula I-D is the same as the compound of Formula I.

In some embodiments, $T^A$, $T^Z$ and $T^E$ are each independently a branching group that is at least trivalent comprising at least a first terminal functionality, a second terminal functionality and a third terminal functionality, which are the same or different and bind to $L^{A1}$, $L^{A2}$ and $R^A$ (or alternatively A and T), to $L^{Z1}$, $L^{Z2}$ and $R^Z$ (or alternatively Z and T), and to $L^{E1}$, $L^{E2}$ and $R^E$ (or alternatively E and T), respectively. In some embodiments, $T^A$, $T^Z$ and $T^E$ are each independently a branching group that is at least trivalent comprising at least a first terminal functionality, a second terminal functionality and a third terminal functionality, which are the same or different and bind to $L^{A1}$, $L^{A2}$ and $R^A$ (or alternatively A or T), to $L^{Z1}$, $L^{Z2}$ and $R^Z$ (or alternatively Z and T), and to $L^{Ed1}$, $L^{E2}$ and $R^E$ (or alternatively E and T), an amide group, a thiourea groups, a urea or a thioamide group. In some embodiments, when bonded to $L^{A1}$, $L^{A2}$ and $R^A$ (or alternatively A or T) and to $L^{Ed1}$, $L^{E2}$ and $R^E$ (or alternatively E and T), an ester group, a thioester group, a carbonate group, a carbamate group, a disulfide bond, a hydrazone group, or a oxime group such as a ketoxime or aldoxime is further formed. In some embodiments, $T^A$, $T^Z$ and $T^E$ are each independently selected from an amino acid residue derived from lysine and/or glutamine and a trimesic acid residue, (TMA)

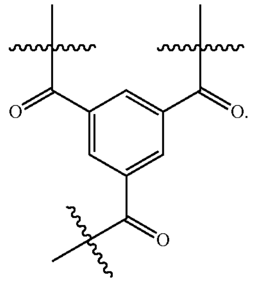

In some embodiments, $T^A$, $T^Z$ and $T^E$ are each independently selected from an amino acid residue derived from lysine and/or glutamine, DAB and TMA. In some embodiments, $T^A$, $T^Z$ and $T^E$ are each independently selected from an amino acid residue derived from lysine and a trimesic acid residue.

In some embodiments, $R^A$ is

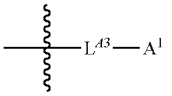

and $L^{A1}$, $L^{A2}$ and $L^{A3}$ are each independently $L^A$ as defined in Formula I. In some embodiments, $A^1$ and A are the same. In some embodiments, $A^1$ and A are different.

In some embodiments, $R^Z$ is

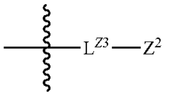

and $L^{Z1}$, $L^{Z2}$ and $L^{Z3}$ are each independently $L^Z$ as defined in Formula I. In some embodiments, $Z^2$ and Z are the same. In some embodiments, $Z^2$ and Z are different.

In some embodiments, $R^E$ is

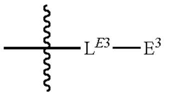

and $L^{E1}$, $L^{E2}$ and $L^{E3}$ are each independently $L^E$ as defined in Formula I. In some embodiments, $E^3$ and E are the same. In some embodiments, $E^3$ and E are different.

In some embodiments, one to three of $L^{A3}$, $L^{E1\text{-}A}$ $L^{E2\text{-}A}$, $L^{A1\text{-}Z}$, $L^{A2\text{-}Z}$, $L^{E1\text{-}Z}$, $L^{E2\text{-}Z}$, $L^{E3}$, $L^{A1\text{-}E}$ and $L^{A2\text{-}E}$ are cleavable linkers. In some embodiments, one or two of $L^{A3}$, $L^{E1\text{-}A}$ $L^{E2\text{-}A}$, $L^{A1\text{-}Z}$, $L^{A2\text{-}Z}$, $L^{E1\text{-}Z}$, $L^{E2\text{-}Z}$, $L^{E3}$, $L^{A1\text{-}E}$ and $L^{A2\text{-}E}$ are cleavable linkers. In some embodiments, each cleavable linker comprises one to three cleavable moieties. In some embodiments, each cleavable linker comprises one or two cleavable moieties.

In some embodiments, m is 1, n and o are both 0, $R^A$ is

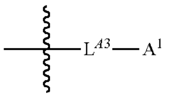

and the compound of Formula I-D is a compound of Formula I-G (I-G)

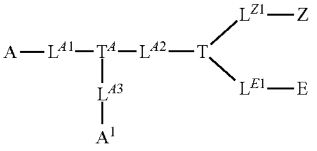

wherein

A, Z, E and T are as defined in Formula I;

$L^{A1}$, $L^{A2}$ and $L^{A3}$ are each independently $L^A$ as defined for in Formula I;

$A^1$ is A as defined in Formula I and $A^1$ and A are the same or different;

$L^{Z1}$ is $L^Z$ as defined for Formula I;

$L^{E1}$ is $L^E$ as defined in Formula I;

provided at least one of $L^{A1}$, $L^{A2}$, $L^{A3}$ and $L^{E1}$ is a cleavable linker In some embodiments, $T^A$ in the compound of Formula I-G is a branching group that is at least trivalent comprising at least a first terminal functionality, a second terminal functionality and a third terminal functionality, which are the same or different and bind to $L^{A1}$, $L^{A2}$ and $R^A$ (or alternatively A and/or T). In exemplary embodiments, $T^A$ in the compound of Formula I-G is amino acid residue derived from lysine or a trimesic acid residue.

In an exemplary embodiment, the $A^1$ and/or A in the compound of Formula I-G are each independently selected from unsubstituted or substituted $C(O)C_{12-18}alkyleneCO_2H$.

In an exemplary embodiment, Z is

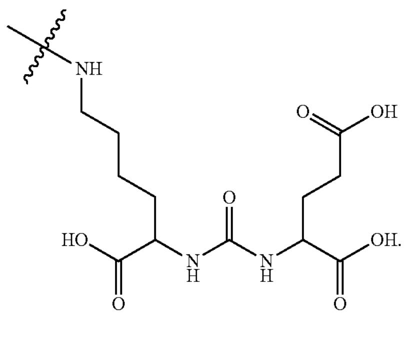 [SMILES: *NCCCCC(NC(=O)NC(CCC(=O)O)C(=O)O)C(=O)O]

In an exemplary embodiment, E is selected from DOTA and DOTAGA.

In some embodiments, when one or more of, $L^{A1}$, $L^{A2}$, $L^{A3}$ and $L^{E1}$ in the compound of Formula I-G is a non-cleavable linker, each of the non-cleavable linkers independently comprises one or more groups selected from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

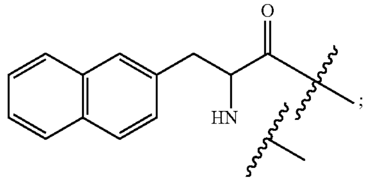

;

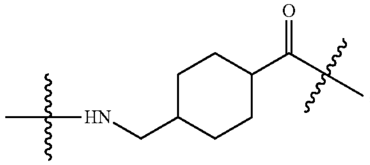

;

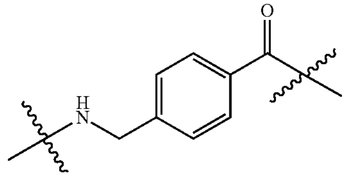

;

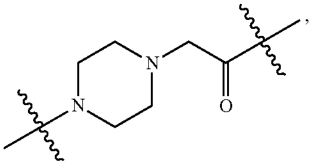

, $R^1NC_{1-20}alkyleneNR^2$; $C(O)C_{1-20}alkyleneC(O)$; $R^1NC_{1-20}alkyleneC(O)$; and $C(O)C_{1-20}alkyleneNR^2$, the latter 4 groups being optionally interrupted by one or more of S, O, C(O)NH, NHC(O), $C_{4-6}$cycloalkyl and $C_{4-6}$heterocycloalkyl wherein each $R^1$ and $R^2$ is independently selected from H and $C_{1-2}$alkyl. In some embodiments, when one or more of $L^{A1}$, $L^{A2}$, $L^{A3}$ and $L^{E1}$ in the compound of Formula I-G is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

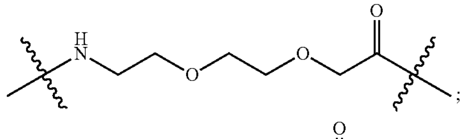

;

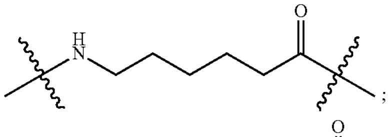

;

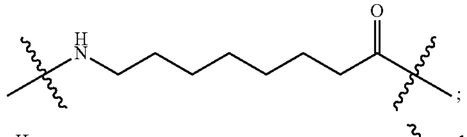

;

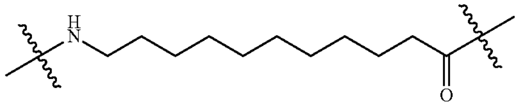

and

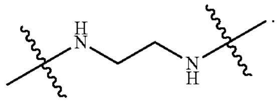

.

In some embodiments, one or more of $L^{A1}$, $L^{A2}$, $L^{A3}$ and $L^{E1}$ in the compound of Formula I-G is independently a cleavable linker and each cleavable linker independently optionally comprises one or more groups selected from one or more amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), or at least one amino acid residue connected to C(O)$C_{1-10}$alkyleneO or O$C_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$ and $L^{E1}$ in the compound of Formula I-G is independently a cleavable linker and each cleavable linker independently optionally comprises one or more groups selected from amino acid residues derived from Glu, Lys, Phe, Tyr, and the D enantiomers thereof;

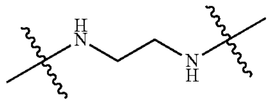

and

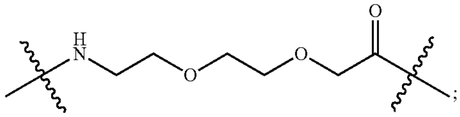

;

and at least one group selected from

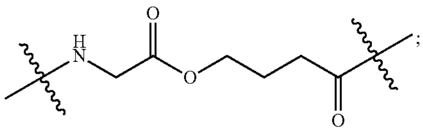

;

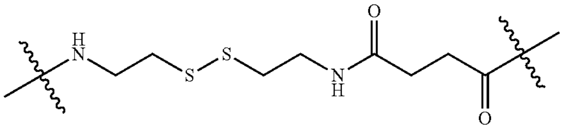

,

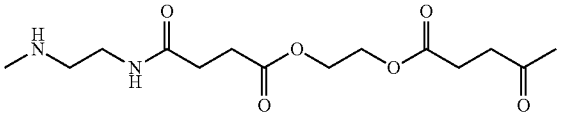

,

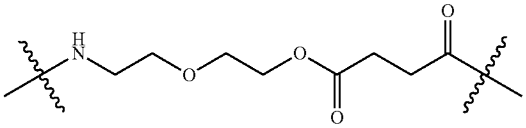

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$ and $L^{E1}$ in the compound of Formula I-G are a cleavable linker each independently comprising at least one group selected from

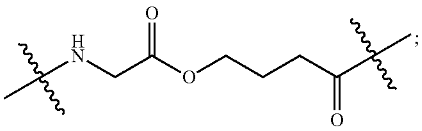

;

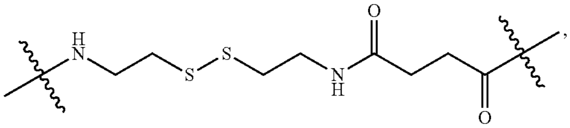

,

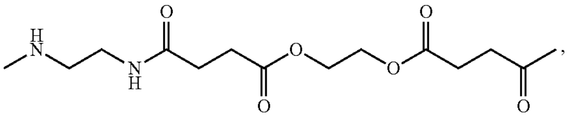

,

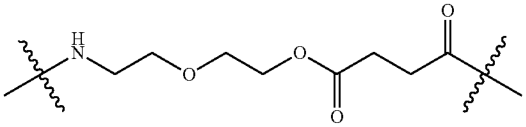

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$ and $L^{E1}$ in the compound of Formula I-G are a cleavable linker each independently comprising one or more

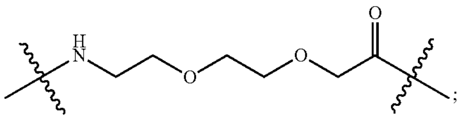 [SMILES: *NCCOCCOCC(*)=O]

;

and at least one group selected from

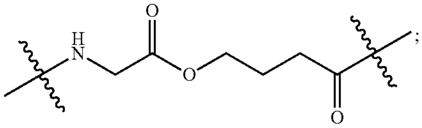

;

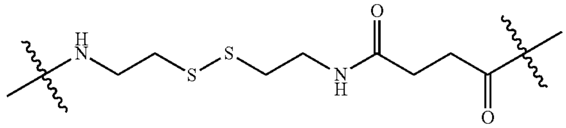

and

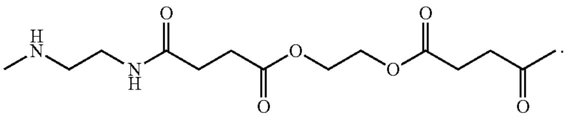

.

In some embodiments, one or more of $L^{A1}$, $L^{A2}$, $L^{A3}$ and $L^{E1}$ in the compound of Formula I-G are an enzymatically cleavable peptide sequence each independently selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$ and $L^{E1}$ in the compound of Formula I-G are a cleavable linker each independently comprising one or more groups selected from one or more amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one amino acid residue connected to $C(O)C_{1-10}$alkyleneO or $OC_{1-10}$alkyleneC(O) to form a cleavable moiety selected from C(O)O and OC(O).

In some embodiments, $L^{Z1}$ in the compound of Formula I-G is a non-cleavable linker comprising one or more groups selected from

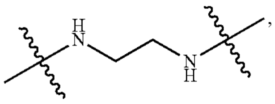

,

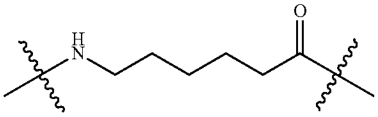

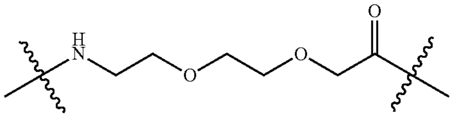

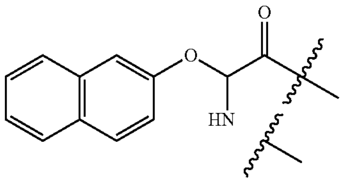

and

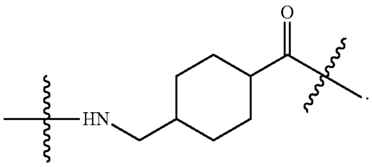

.

In some embodiments, $A^1$ and A in the compound of Formula I-G are both the same. In some embodiments, $L^{A1}$ and $L^{A3}$ in the compound of Formula I-G are the both the same and $A^1$ and A are both the same.

In some embodiments, $L^{A1}$, $L^{A2}$ and $L^{A3}$ in the compound of Formula I-G are each independently a direct bond or a non-cleavable linker and $L^{E1}$ in the compound of Formula I-G is a cleavable linker. In some embodiments, $L^{A1}$ and $L^{A3}$ are each independently a direct bond or a non-cleavable linker, $L^{A2}$ is a cleavable linker and $L^{E1}$ is a direct bond or a non-cleavable linker. In some embodiments, $L^{A1}$ and $L^{A3}$ are each independently a cleavable linker and $L^{A2}$ is a direct bond or a non-cleavable linker and $L^{E1}$ is a direct bond or a non-cleavable linker. In some embodiments, $L^{A1}$ and $L^{A3}$ are both the same.

In some embodiments, n is 1, m and o are both 0, $R^Z$ is

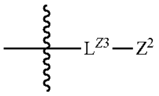

and the compound of Formula I-D is a compound of Formula I-H (I-H)

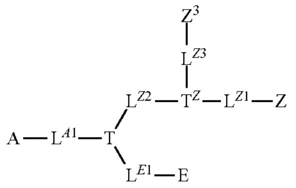

wherein

A, Z, E and T are as defined in Formula I;

$Z^3$ is Z as defined in Formula I and are the same or different;

$L^{A1}$ is $L^A$ as defined in Formula I;

$L^{Z1}$, $L^{Z2}$ and $L^{Z3}$ are each independently $L^Z$ as defined in Formula I;

$L^{E1}$ is $L^E$ as defined in Formula I;

provided at least one of $L^{A1}$ and $L^{E1}$ is a cleavable linker.

In some embodiments, $T^Z$ in the compound of Formula I-H is a branching group that is at least trivalent comprising at least a first terminal functionality, a second terminal functionality and a third terminal functionality, which are the same or different and bind to $L^{Z1}$ (or alternatively Z), $L^{Z2}$ (or alternatively T) and $Z^3$. In exemplary embodiments, $T^Z$ is amino acid residue derived from lysine or an acid residue. In exemplary embodiments, $T^Z$ is a trimesic acid residue In an exemplary embodiment, Z and/or $Z^3$ is

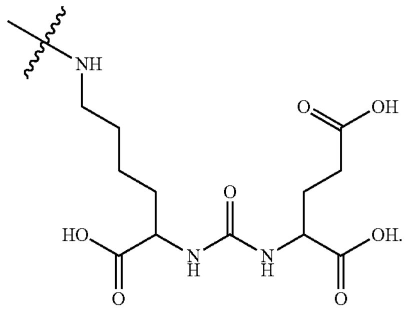 [SMILES: *NCCCCC(NC(=O)NC(CCC(=O)O)C(=O)O)C(=O)O]

.

In an exemplary embodiment, E is selected from DOTA and DOTAGA.

In an exemplary embodiment, A in the compound of Formula I-H is selected from unsubstituted or substituted $C(O)C_{12-18}alkyleneCO_2H$.

In some embodiments, one of $L^{A1}$ and $L^{E1}$ in the compound of Formula I-H is a non-cleavable linker, and the non-cleavable linker comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP; OEG, $R^1NC_{1-20}alkyleneNR^2$, $C(O)C_{1-20}$alkyleneC(O), $R^1NC_{1-20}$alkyleneC(O), and C(O) $C_{1-20}alkyleneNR^2$, wherein each $R^1$ and $R^2$ is independently selected from H and $C_{1-2}$alkyl. In some embodiments, one of $L^{A1}$ and $L^{E1}$ in the compound of Formula I-H is a non-cleavable linker, and the non-cleavable linker comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

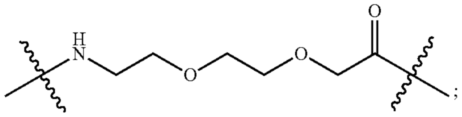

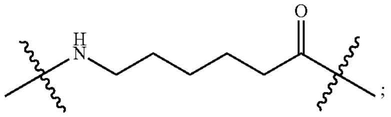

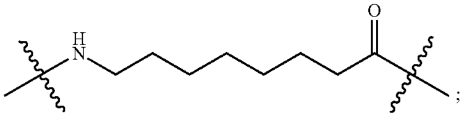

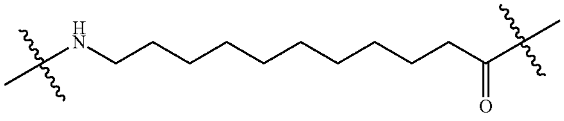

and

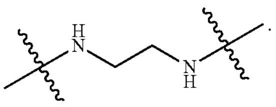

In some embodiments, in the compound of Formula I-H, one of $L^{A1}$ and $L^{E1}$ is a non-cleavable linker, and the non-cleavable linker comprises one or more groups selected from amino acids residues derived from Glu,

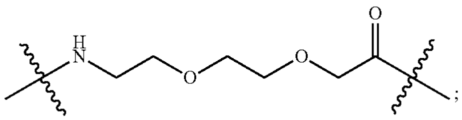 [SMILES: *NCCOCCOCC(*)=O]
and

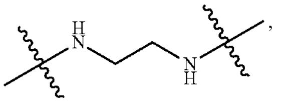

and the other is a direct bond. In some embodiments, $L^{A1}$ and $L^{E1}$ are each independently a non-cleavable linker, and the non-cleavable linker comprises one or more groups selected from amino acids residues derived from Glu and

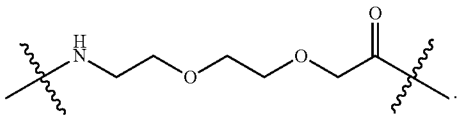 [SMILES: *NCCOCCOCC(*)=O]

In some embodiments, $L^{A1}$ and $L^{E1}$ are the same. In some embodiments, $L^{A1}$ and $L^{E1}$ are comprise two or more of

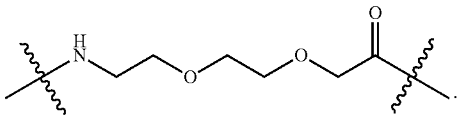

In some embodiments, in the compound of Formula I-H, one or both of $L^{A1}$ and/or $L^{E1}$ is independently a cleavable linker, and each cleavable linker independently optionally comprises one or more groups selected from one or more amino acid residues derived from Gly, Glu, Leu, Phe, Tyr, or Lys, or the D enantiomers thereof; one or more amino acid residues derived from DAP or DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), or at least one amino acid residue connected to C(O)$C_{1-10}$alkyleneO or $OC_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, in the compound of Formula I-H, one or both of $L^{A1}$ and/or $L^{E1}$ is independently a cleavable linker, and each cleavable linker independently optionally comprises one or more groups selected from amino acid residues derived from Glu, Lys, Phe, Tyr, and the D enantiomers thereof;

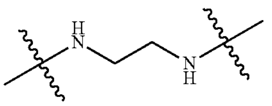
and

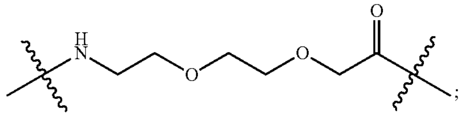

and at least one group selected from

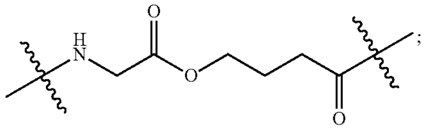

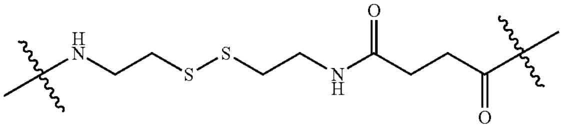

and

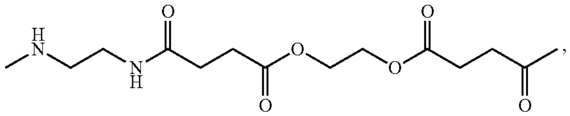

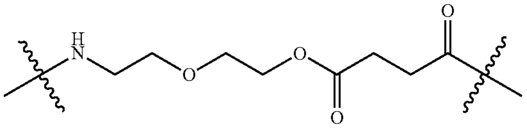

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, $L^{E1}$ in the compound of Formula I-H is a cleavable linker, and the cleavable linker comprises one or more

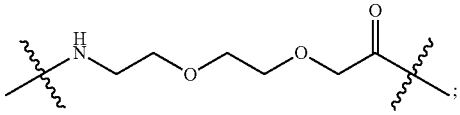 [SMILES: *NCCOCCOCC(*)=O]

and at least one group selected from

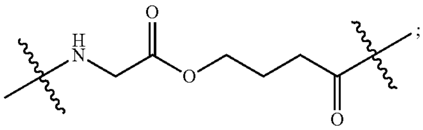

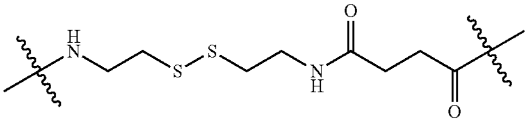

and

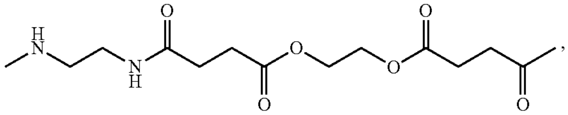

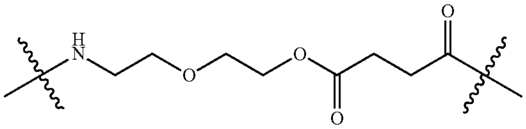

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, $L^{Z1}$ and/or $L^{Z3}$ in the compound of Formula I-H are each independently a non-cleavable linker comprising one or more groups selected from

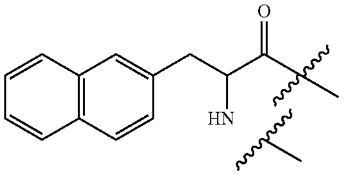

and

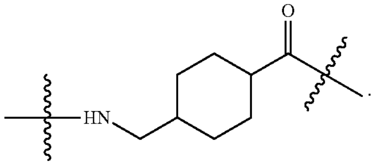

In some embodiments, $L^{Z1}$ and $L^{Z3}$ are both the same. In some embodiments, $L^{Z1}$ and/or $L^{Z3}$ each independently further comprise one or more groups selected from

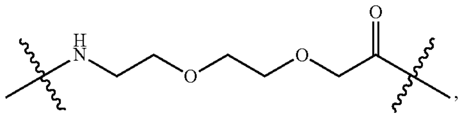

,

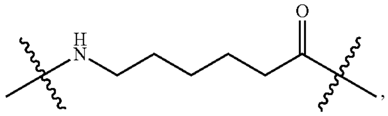

, and

-continued

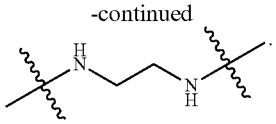

In some embodiments, $L^{Z1}$ and/or $L^{Z3}$ each independently further comprise one or more

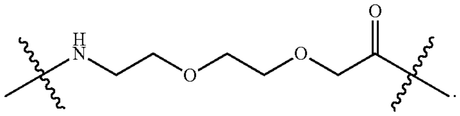 [SMILES: *NCCOCCOCC(*)=O]

in some embodiments, $L^{Z1}$ and $L^{Z3}$ are both the same.

In some embodiments, $L^{Z2}$ in the compound of Formula I-H is a non-cleavable linker comprising one or more groups selected from

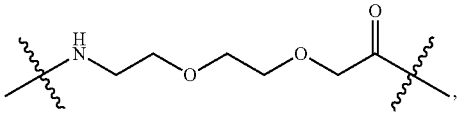

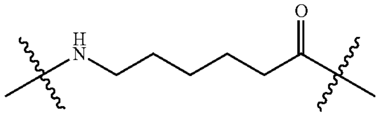

, and

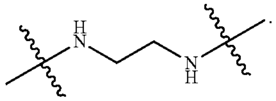

In some embodiments, $L^{A1}$ is a direct bond or a non-cleavable linker and $L^{E1}$ is a cleavable linker. In some embodiments, $L^{A1}$ is a cleavable linker and $L^{E1}$ is a direct bond or a non-cleavable linker. In some embodiments, $L^{Z1}$ and $L^{Z3}$ are both the same non-cleavable linker.

In some embodiments, $Z^2$ and Z in the compound of Formula I-H are both the same. In some embodiments, in the compound of Formula I-H, $L^{Z1}$ and $L^{Z3}$ are the both the same and $Z^1$ and Z are both the same.

In some embodiments, o is 1, m and n are both 0, $R^E$ is

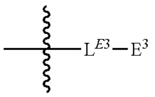

and the compound of Formula I-D is a compound of Formula I-I (I-I)

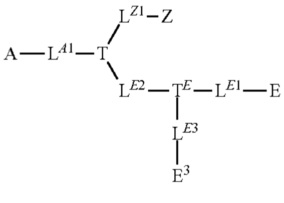

wherein

A, Z, E and T are as defined in Formula I;

$E^3$ is E as defined in Formula I and $E^3$ and E are the same or different;

$L^{A1}$ is $L^A$ as defined in Formula I;

$L^{E1}$, $L^{E2}$ and $L^{E3}$ are each independently $L^E$ as defined in Formula I;

$L^{A1}$ is $L^A$ as defined in Formula I;

$L^{Z1}$ is $L^Z$ as defined in Formula I;

provided at least one of $L^{E1}$, $L^{E2}$ and $L^{E3}$ and $L^{A1}$ is a cleavable linker.

In some embodiments, $T^E$ in the compound of Formula I-I is a branching group that is at least trivalent comprising at least a first terminal functionality, a second terminal functionality and a third terminal functionality, which are the same or different and bind to $L^{E1}$ (or alternatively E), $L^{E2}$ (or alternatively T) and $E^3$. In exemplary embodiments, $T^E$ in the compound of Formula I-I is amino acid residue derived from lysine or a trimesic acid residue.

In an exemplary embodiment, Z is

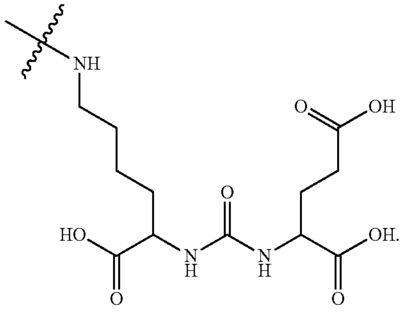 [SMILES: *NCCCCC(NC(=O)NC(CCC(=O)O)C(=O)O)C(=O)O]

In an exemplary embodiment, E and/or $E^3$ is/are each independently selected from DOTA and DOTAGA.

In an exemplary embodiment, A in the compound of Formula I-I is selected from unsubstituted or substituted $C(O)C_{12-18}alkyleneCO_2H$.

In some embodiments, when any one of $L^{E1}$, $L^{E2}$ and $L^{E3}$ in the compound of Formula I-I are a non-cleavable linker, each of the non-cleavable linkers independently comprises one or more groups selected from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

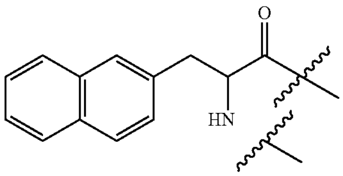

;

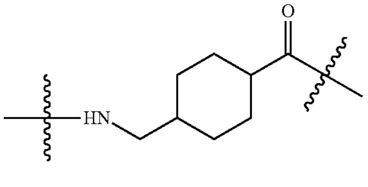

;

-continued

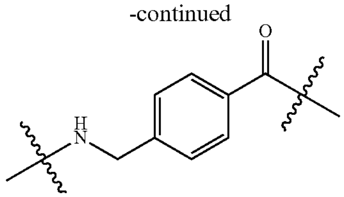

;

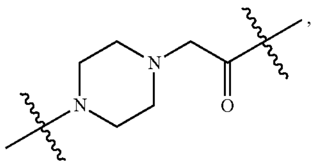

, $R^1NC_{1-20}alkyleneNR^2$; $C(O)C_{1-20}alkyleneC(O)$; $R^1NC_{1-20}alkyleneC(O)$; and $C(O)C_{1-20}alkyleneNR^2$, the latter 4 groups being optionally interrupted by one or more of S, O, C(O)NH, NHC(O), $C_{4-6}cycloalkyl$ and $C_{4-6}heterocycloalkyl$ wherein each $R^1$ and $R^2$ is independently selected from H and $C_{1-2}alkyl$. In some embodiments, when any one of $L^{E1}$, $L^{E2}$ and $L^{E3}$ in the compound of Formula I-I are a non-cleavable linker, each of the non-cleavable linkers independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

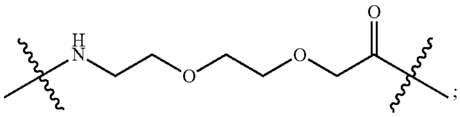 [SMILES: *NCCOCCOCC(*)=O]

;

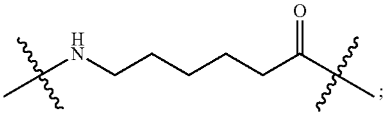

;

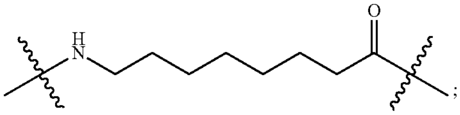

;

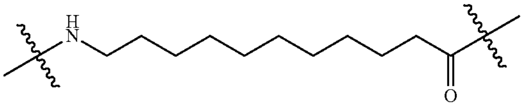

and

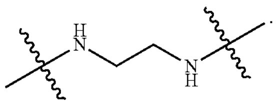

.

In some embodiments, when any one of $L^{E1}$, $L^{E2}$ and $L^{E3}$ are a non-cleavable linker in the compound of Formula I-G, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

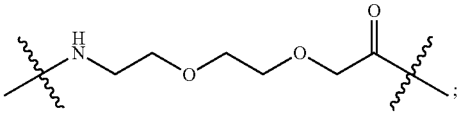 [SMILES: *NCCOCCOCC(*)=O]

;

-continued

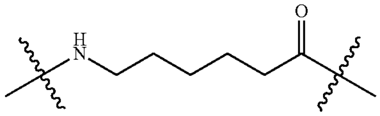

;

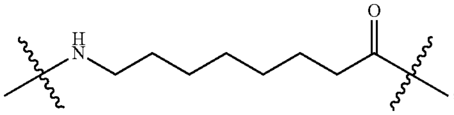

;

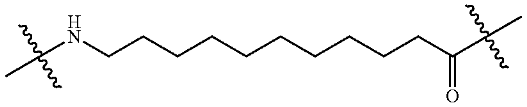

and

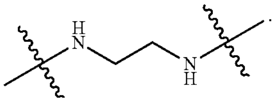

.

In some embodiments, $L^{E1}$ and $L^{E3}$ in the compound of Formula I-G are each independently a non-cleavable linker, and each non-cleavable linker independently comprises one or more groups selected from amino acids residues derived from Glu,

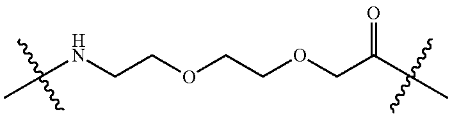

; and

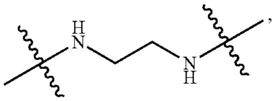

, and $L^{E2}$ is a direct bond. In some embodiments, $L^{E1}$ and $L^{E3}$ are each independently a non-cleavable linker, and each non-cleavable linker independently comprises one or more groups selected from amino acids residues derived from Glu and

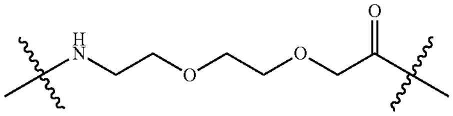

;

and $L^{E3}$ is a direct bond or one or more of

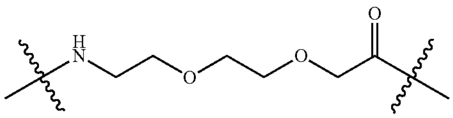

.

In some embodiments, $L^{E1}$ and $L^{E3}$ each independently comprise two or more of

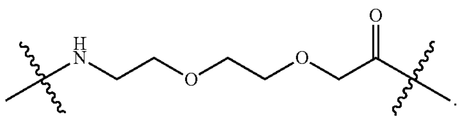 [SMILES: *NCCOCCOCC(*)=O]

.

In some embodiments, one or more of $L^{E1}$, $L^{E2}$, $L^{E3}$ and $L^{A1}$ in the compound of Formula I-I is independently a cleavable linker and each cleavable linker independently optionally comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), or at least one amino acid residue connected to $C(O)C_{1-10}$alkyleneO or $OC_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{E1}$, $L^{E2}$, $L^{E3}$ and $L^{A1}$ in the compound of Formula I-I is independently a cleavable linker and each cleavable linker independently optionally comprises one or more groups selected from amino acid residues derived from

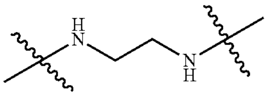

and

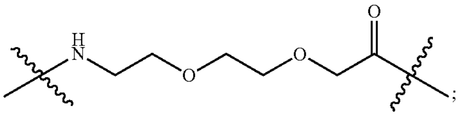

;

Glu, Lys, Phe, Tyr, and the D enantiomers thereof;

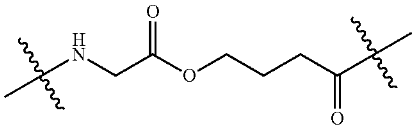

;

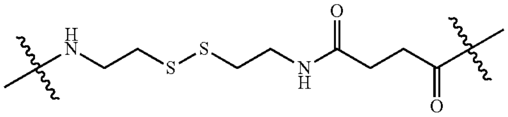

and

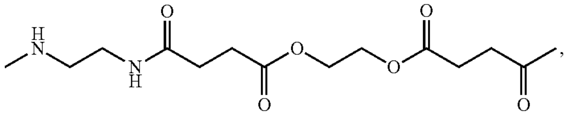

,

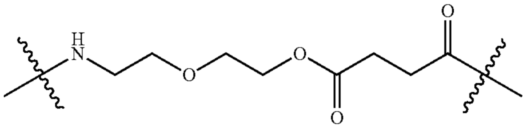

and at least one group selected from and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, when $L^{A1}$ in the compound of Formula I-I is a cleavable linker, and the cleavable linker optionally comprises one or more

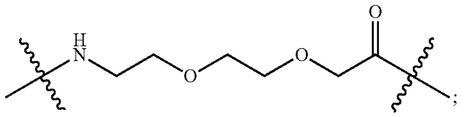 [SMILES: *NCCOCCOCC(*)=O]

and at least one group selected from

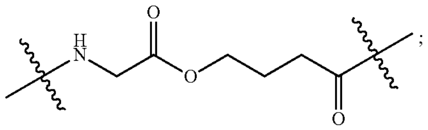

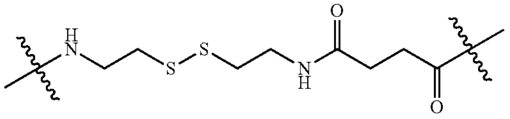

and

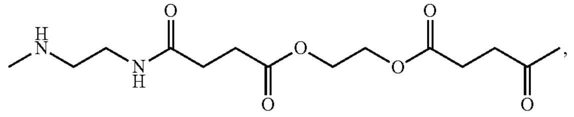

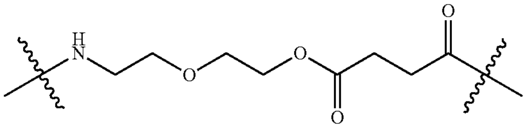

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, $L^{Z1}$ in the compound of Formula I-I is a direct bond or a non-cleavable linker comprising one or more groups selected from

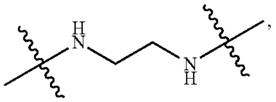

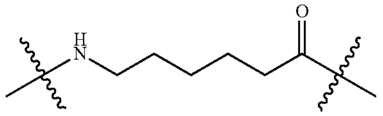

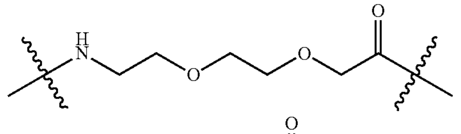

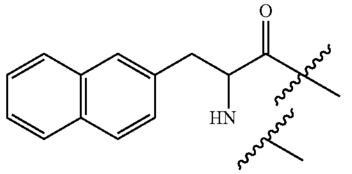

and

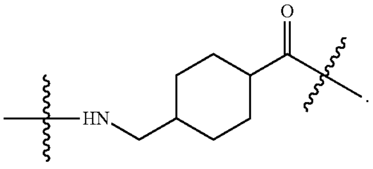

In some embodiments, $L^{E1}$, $L^{E2}$ and $L^{E3}$ in the compound of Formula I-G are each independently a direct bond or a non-cleavable linker and $L^{A1}$ in the compound of Formula I-I is a cleavable linker as defined for $L^{A}$ in Formula I. In some embodiments, $L^{E1}$ and $L^{E3}$ are each independently a direct bond or a non-cleavable linker, $L^{E2}$ is a cleavable linker as defined for $L^{A}$ in Formula I and $L^{A1}$ is a direct bond or a non-cleavable linker. In some embodiments, $L^{E1}$ and $L^{E3}$ are each independently a cleavable linker and $L^{E2}$ is a direct bond or a non-cleavable linker as defined for $L^{A}$ in Formula I and $L^{A1}$ is a direct bond or a non-cleavable liner. In some embodiments, $L^{E1}$ and $L^{E3}$ are both the same.

In some embodiments, $E^3$ and E in the compound of Formula I-I are both the same. In some embodiments, $L^{E1}$ and $L^{E3}$ in the compound of Formula I-I are the both the same and $E^3$ and E are both the same.

In some embodiments, m is 1, n and o are both 0 and $R^A$ is

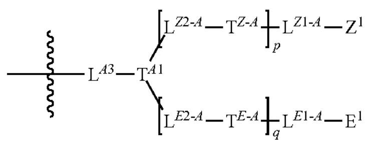

wherein q and p are 0 and the compound of Formula I-D is a compound of Formula I-J:

(I-J)

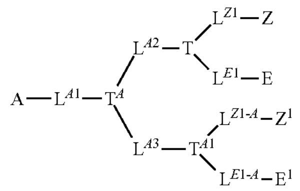

wherein

A, Z, T and E are as defined in Formula I;

$E^1$ is E as defined in Formula I and $E^1$ and E are the same or different;

$Z^1$ is Z as defined in Formula I and $Z^1$ and Z are the same or different;

$L^{A1}$, $L^{A2}$ and $L^{A3}$ are each independently $L^{A}$ as defined for in Formula I;

$T^{A}$ and $T^{A1}$ are each independently T as defined for in Formula I and $T^{A}$, $T^{A1}$ and T are the same or different;

$L^{Z1}$ and $L^{Z1\text{-}A}$ are each independently $L^2$ as defined for Formula I;

$L^{E1}$ and $L^{E1\text{-}A}$ i are each independently $L^{E}$ as defined in Formula I;

provided at least one of $L^{A1}$, $L^{A2}$, $L^{A3}$, $L^{E1}$ and $L^{E1\text{-}A}$ is a cleavable linker.

In some embodiments, each of T, $T^{A}$, and $T^{A1}$ is a branching group that is at least trivalent comprising at least a first terminal functionality, a second terminal functionality and a third terminal functionality, which are the same or different and bind to $L^{A2}$ (or alternatively $T^{A}$), $L^{Z1}$ (or alternatively Z) and $L^{E1}$ (or alternatively E), to $L^{A1}$ (or alternatively A), $L^{A2}$ (or alternatively T) and $L^{A3}$ (or alternatively $T^{A1}$), and to $L^{A3}$ (or alternatively $T^{A}$), $L^{Z1\text{-}A}$ (or alternatively $Z^1$) and $L^{E1\text{-}A}$ (or alternatively $E^1$), respectively. In some embodiments, each of T, $T^{A}$, and $T^{A1}$ are independently selected from an amino acid residue derived from lysine or glutamine and a trimesic acid residue.

In an exemplary embodiment, A in the compound of Formula I-J is selected from unsubstituted or substituted $C(O)C_{12\text{-}18}alkyleneCO_2H$.

In an exemplary embodiment, $Z^1$ and/or Z in the compound of Formula I-J is

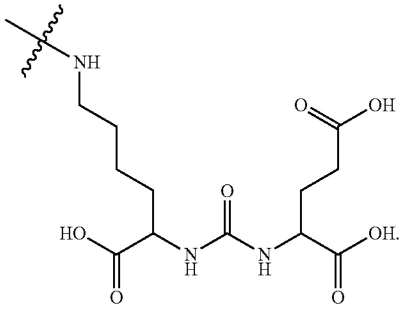 [SMILES: *NCCCCC(NC(=O)NC(CCC(=O)O)C(=O)O)C(=O)O]

In an exemplary embodiment, $E^1$ and/or E the compound of Formula I-J is selected from DOTA and DOTAGA.

In some embodiments, when any of $L^{A1}$, $L^{A2}$, $L^{A3}$, $L^{E1}$ and $L^{E1\text{-}A}$ in the compound of Formula I-J is a non-cleavable linker, each non-cleavable linkers independently comprises one or more groups selected from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

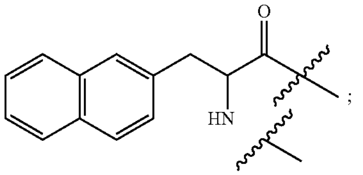

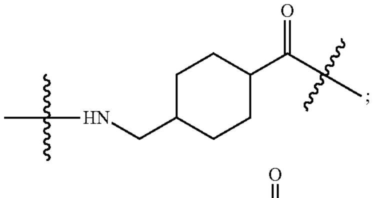

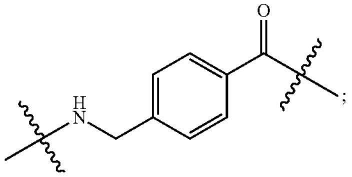

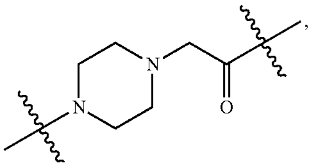

$R^1NC_{1-20}$alkyleneN$R^2$; $C(O)C_{1-20}$alkyleneC(O); $R^1NC_{1-20}$alkyleneC(O); and $C(O)C_{1-20}$alkyleneN$R^2$, the latter 4 groups being optionally interrupted by one or more of S, O, C(O)NH, NHC(O), $C_{4-6}$cycloalkyl and $C_{4-6}$heterocycloalkyl wherein each $R^1$ and $R^2$ is independently selected from H and $C_{1-2}$alkyl. In some embodiments, when any of $L^{A1}$, $L^{A2}$, $L^{A3}$, $L^{E1}$ and $L^{E1\text{-}A}$ in the compound of Formula I-J is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

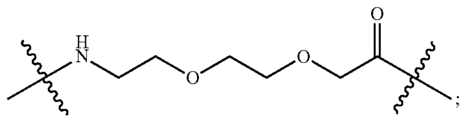 [SMILES: *NCCOCCOCC(*)=O]

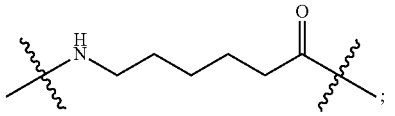

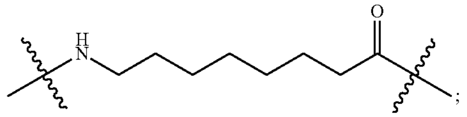

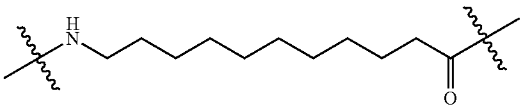

and

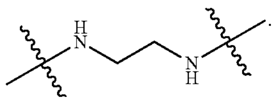

In some embodiments, when any of $L^{A1}$, $L^{A2}$, $L^{A3}$, $L^{E1}$ and $L^{E1\text{-}A}$ in the compound of Formula I-J is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

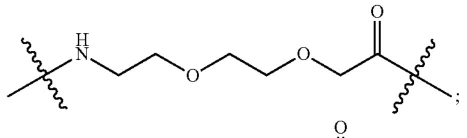

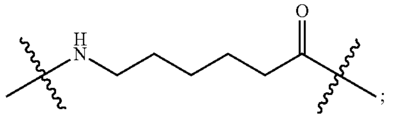

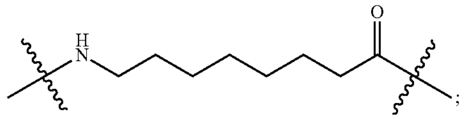

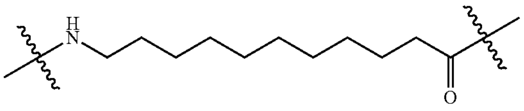

and

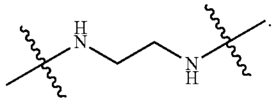

In some embodiments, when any of $L^{A1}$, $L^{A2}$, $L^{A3}$, $L^{E1}$ and $L^{E1\text{-}A}$ in the compound of Formula I-J is a non-cleavable linker, each non-cleavable linker independently comprises one or more groups selected from amino acids residues derived from Glu,

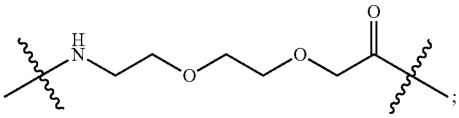 [SMILES: *NCCOCCOCC(*)=O]
; and

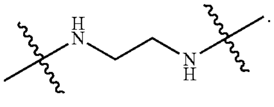
.

In some embodiments, when any of $L^{A1}$, $L^{A2}$, $L^{A3}$, $L^{E1}$ and $L^{E1\text{-}A}$ in the compound of Formula I-J is a non-cleavable linker, each non-cleavable linker independently comprises one or more groups selected from amino acids residues derived from Glu and

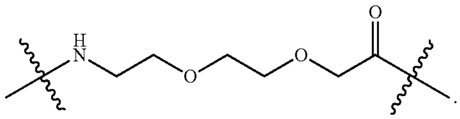
.

In some embodiments, one or more of $L^{A1}$, $L^{A2}$, $L^{A3}$, $L^{E1}$ and $L^{E1\text{-}A}$ in the compound of Formula I-J are independently a cleavable linker, and each cleavable linker independently optionally comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1\text{-}20}alkyleneNR^6$; and $R^5NC_{1\text{-}20}alkyleneC(O)$ optionally interrupted by one or more of O; and at least one $R^5NC_{1\text{-}20}alkyleneC(O)$ optionally interrupted by one or more of S—S, C(O)O, OC(O), O, C(O)NH and NHC(O), provided $R^5NC_{1\text{-}20}alkyleneC(O)$ is interrupted by at least one of S—S, C(O)O and OC(O), or at least one amino acid residue connected to $C(O)C_{1\text{-}10}alkyleneO$ or $OC_{1\text{-}10}alkyleneC(O)$ to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$, $L^{E1}$ and $L^{E1\text{-}A}$ in the compound of Formula I-J are independently a cleavable linker and each cleavable linker independently comprises at least one group selected from

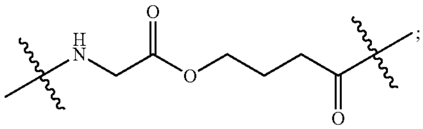
;

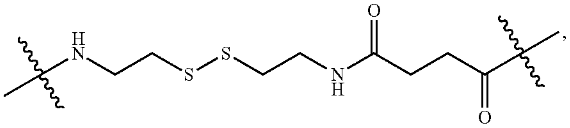
,

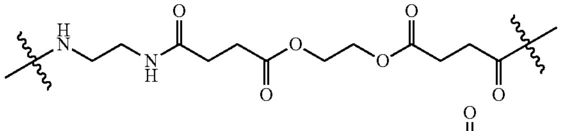
,

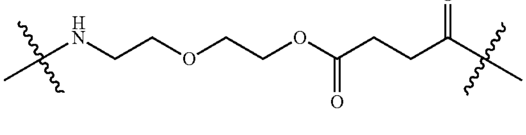

and an enzymatically cleavable peptide sequence selected from Met-Val-Lys, Ala-Val, Ala-Pro, Gly-Pro, Ser-Ser, Ser-Gly, Gly-Ala and Ser-Lys and optionally comprises one or more groups selected from amino acid residues derived from Glu, Lys, Phe, Tyr, and the D enantiomers thereof;

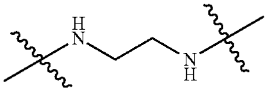
and

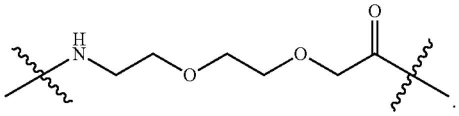 [SMILES: *NCCOCCOCC(*)=O]
.

In some embodiments, one or more of $L^{A1}$, $L^{A2}$, $L^{A3}$, $L^{E1}$ and $L^{E1\text{-}A}$ in the compound of Formula I-J are independently a cleavable linker, and each cleavable linker independently optionally comprises one or more of

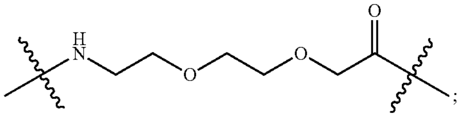
;

and at least one group selected from

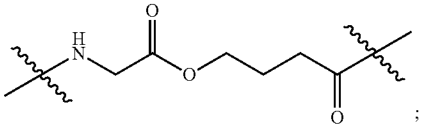
;

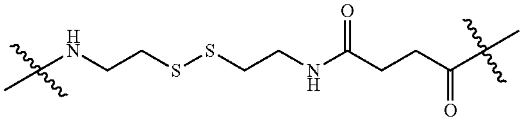
and

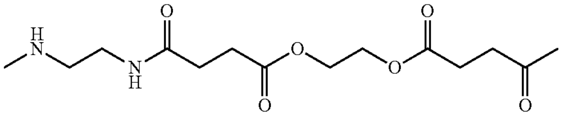
,

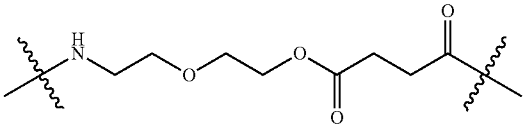

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A2}$, $L^{A3}$, $L^{E1}$ and/$L^{E1\text{-}A}$ in the compound of Formula I-J are independently a cleavable linker, and each cleavable linker independently further comprises one or more of

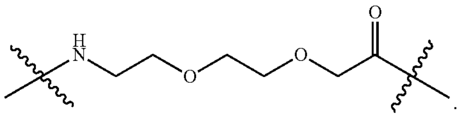
.

In some embodiments, $L^{Z1}$ and $L^{Z1-A}$ in the compound of Formula I-J are each independently a non-cleavable linker comprising one or more groups selected from

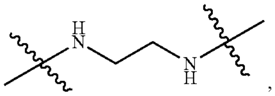

,

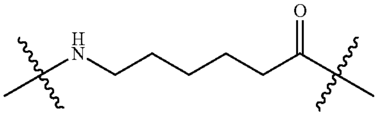

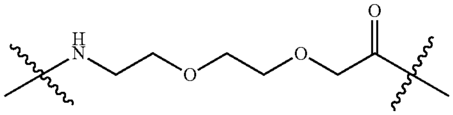

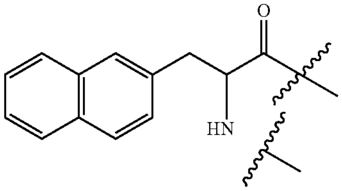

and

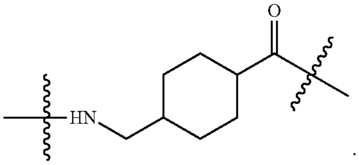

.

In some embodiments, $L^{E1}$, $L^{E1-A}$, $L^{A1}$, $L^{Z1}$ and $L^{Z1-A}$ are each independently a direct bond or a non-cleavable linker, and $L^{A2}$ and $L^{A3}$ are each independently cleavable linkers. In some embodiments, $L^{E1}$, $L^{E1-A}$, $L^{A1}$, $L^{Z1}$ and $L^{Z1-A}$ are each independently a direct bond or a non cleavable linker, and one of $L^{A2}$ and $L^{A3}$ is a non-cleavable linked and the other is a cleavable linkers. In some embodiments, $L^{A1}$, is a cleavable linker and $L^{E1}$, $L^{E1-A}$, $L^{Z1}$, $L^{Z1-A}$ $L^{A2}$ and $L^{A3}$ are each independently a direct bond or a non cleavable linker. In some embodiments, $L^{A2}$ and $L^{A3}$ are both the same. In some embodiments, $L^{Z1}$ and $L^{Z1}$-A are both the same. In some embodiments, $L^{E1}$ and $L^{E1-A}$ are both the same.

In some embodiments, o is 1, n and m are both 0 and $R^E$ is

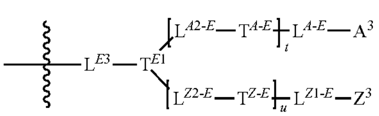

wherein t and u are 0 and the compound of Formula I-D is a compound of Formula I-K:

(I-K)

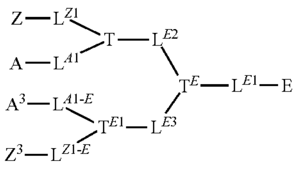

wherein

A, Z, T and E are as defined in Formula I $A^3$ is A as defined in Formula I and $A^3$ and A are the same or different;

$Z^3$ is Z as defined in Formula I and $Z^3$ and Z are the same or different;

$L^{A1}$ and $L^{A1-E}$ are each independently $L^A$ as defined for in Formula I;

$T^E$ and $T^{E1}$ are each independently T as defined for in Formula I and T, $T^E$ and $T^{E1}$ are the same or different;

$L^{Z1}$ and $L^{Z1-E}$ are each independently $L^Z$ as defined for Formula I;

$L^{E1}$, $L^{E2}$, $L^{E3}$ are each independently $L^E$ as defined in Formula I;

provided at least one of $L^{E1}$, $L^{E2}$, $L^{E3}$, $L^{A1}$ and $L^{A1-E}$ is a cleavable linker.

In some embodiments, each of T, $T^E$ and $T^{E1}$ is a branching group that is at least trivalent comprising at least a first terminal functionality, a second terminal functionality and a third terminal functionality, which are the same or different and bind to $L^{A1}$ (or alternatively A), $L^{Z1}$ (or alternatively Z) and $L^{E2}$ (or alternatively $T^E$), $L^{E1}$ (or alternatively E), $L^{E2}$ (or alternatively T) and $L^{A3}$ (or alternatively $T^{E1}$), and to $L^{E3}$ (or alternatively $T^E$), $L^{A1-E}$ (or alternatively $A^3$) and $L^{Z1-2}$ (or alternatively $Z^3$), respectively. In some embodiments, each of T, $T^E$ and $T^{E1}$ are independently selected from an amino acid residue derived from lysine or glutamine and a trimesic acid residue.

In an exemplary embodiment, A and/or $A^3$ in the compound of Formula I-K is selected from unsubstituted or substituted $C(O)C_{12-18}alkyleneCO_2H$.

In an exemplary embodiment, $Z^3$ and/or Z in the compound of Formula I-K is

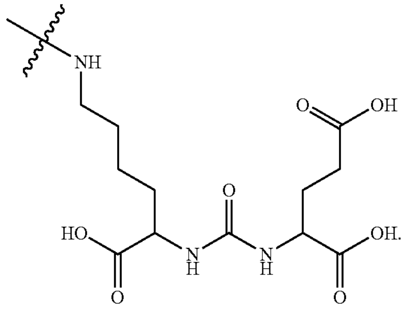 [SMILES: *NCCCCC(NC(=O)NC(CCC(=O)O)C(=O)O)C(=O)O]

In an exemplary embodiment, E the compound of Formula I-K is selected from DOTA and DOTAGA.

In some embodiments, when any one or more of $L^{E1}$, $L^{E2}$, $L^{E3}$, $L^{A1}$ and $L^{A1-E}$ in the compound of Formula I-K is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

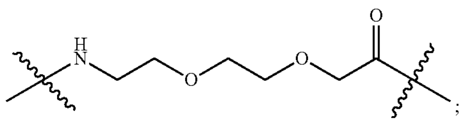

;

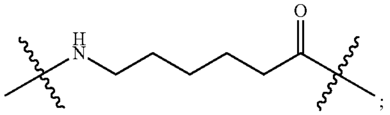

;

-continued

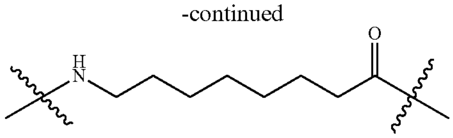

;

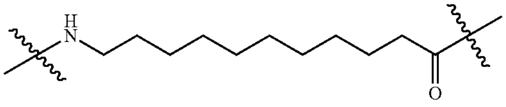

and

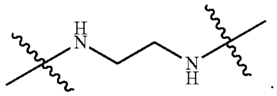

.

In some embodiments, when any of $L^{E1}$, $L^{E2}$, $L^{E3}$, $L^{A1}$ and $L^{A1\text{-}E}$ in the compound of Formula I-K is a non-cleavable linker, each non cleavable linkers independently comprises one or more groups selected from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

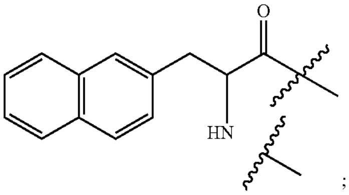

;

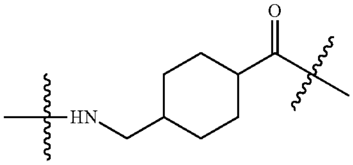

;

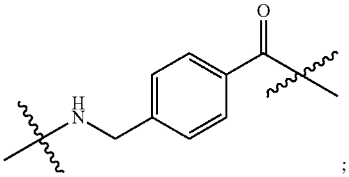

;

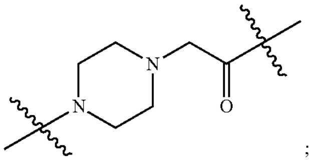

;

$R^1NC_{1\text{-}20}$alkyleneN$R^2$; $C(O)C_{1\text{-}20}$alkyleneC(O); $R^1NC_{1\text{-}20}$alkyleneC(O); and $C(O)C_{1\text{-}20}$alkyleneN$R^2$, the latter 4 groups being optionally interrupted by one or more of S, O, C(O)NH, NHC(O), $C_{4\text{-}6}$cycloalkyl and $C_{4\text{-}6}$heterocycloalkyl wherein each $R^1$ and $R^2$ is independently selected from H and $C_{1\text{-}2}$alkyl. In some embodiments, when any of $L^{E1}$, $L^{E2}$, $L^{E3}$, $L^{A1}$ and $L^{A1\text{-}E}$ in the compound of Formula I-K is a non-cleavable linker, each non-cleavable linker independently one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

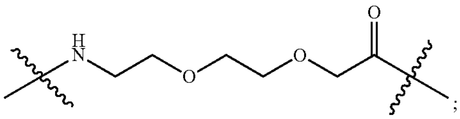

;

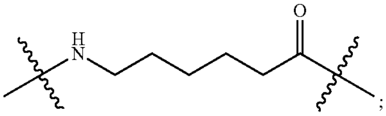

;

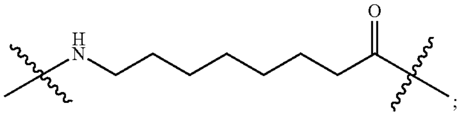

;

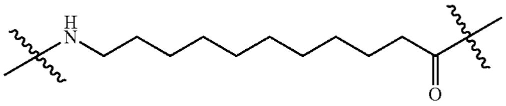

and

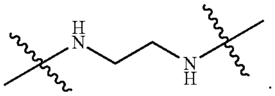

.

In some embodiments, when any one of $L^{E1}$, $L^{E2}$, $L^{E3}$, $L^{A1}$ and $L^{A1\text{-}E}$ in the compound of Formula I-K is a non-cleavable linker, each non-cleavable linker independently one or more groups selected from amino acids residues derived from Glu,

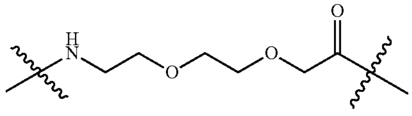

; and

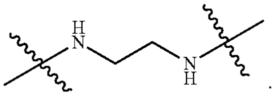

.

In some embodiments, when any of $L^{E1}$, $L^{E2}$, $L^{E3}$, $L^{A1}$ and $L^{A1\text{-}E}$ in the compound of Formula I-K is a non-cleavable linker, each non-cleavable linker independently comprises one or more groups selected from amino acids residues derived from Glu and

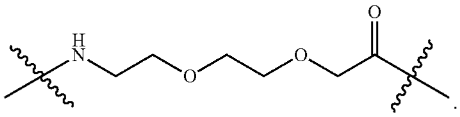

.

In some embodiments, one or more of $L^{E1}$, $L^{E2}$, $L^{E3}$, $L^{A1}$ and $L^{A1\text{-}E}$ in the compound of Formula I-K are independently a cleavable linker and each cleavable linker independently independently comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1\text{-}20}$alkyleneN$R^6$; and $R^5NC_{1\text{-}20}$alkyleneC(O) optionally interrupted by one or more of O; and at least one $R^5NC_{1\text{-}20}$alkyleneC(O) optionally interrupted by one or more of S—S, C(O)O, OC(O), O, C(O)NH and NHC(O), provided $R^5NC_{1\text{-}20}$alkyleneC(O) is interrupted by at least one of S—S, C(O)O and OC(O), or at least one amino acid residue connected to $C(O)C_{1\text{-}10}$alkyleneO or $OC_{1\text{-}10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{E1}$, $L^{E2}$, $L^{E3}$, $L^{A1}$ and $L^{A1\text{-}E}$ in the compound of Formula I-K are independently a cleavable linker and each cleavable linker independently comprises at least one group selected from

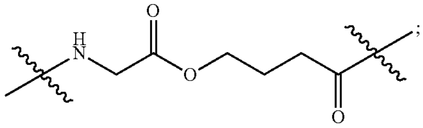
;

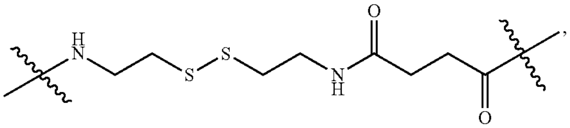
,

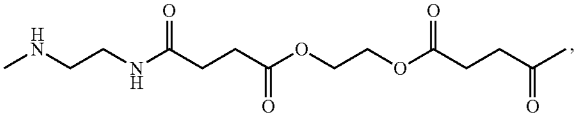
,

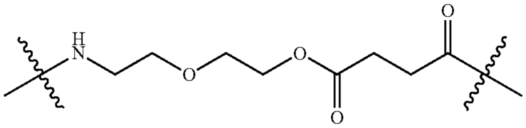

and an enzymatically cleavable peptide sequence selected from Met-Val-Lys, Ala-Val, Ala-Pro, Gly-Pro, Ser-Ser, Ser-Gly, Gly-Ala and Ser-Lys, optionally comprises one or more groups selected from amino acid residues derived from Glu, Lys, Phe, Tyr, and the D enantiomers thereof;

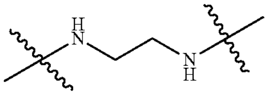
and

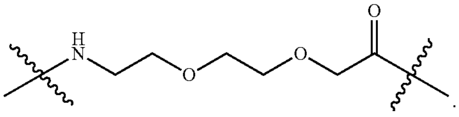 [SMILES: *NCCOCCOCC(*)=O]
.

In some embodiments, one or more of $L^{E1}$, $L^{E2}$, $L^{E3}$, $L^{A1}$ and $L^{A1\text{-}E}$ in the compound of Formula I-K are independently a cleavable linker, and each cleavable linker independently optionally comprises one or more of

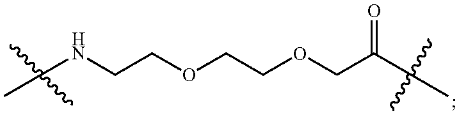 [SMILES: *NCCOCCOCC(*)=O]
;

and at least one group selected from

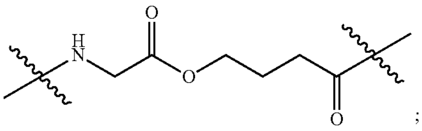
;

-continued

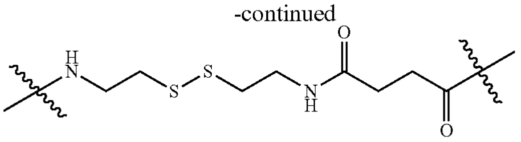
and

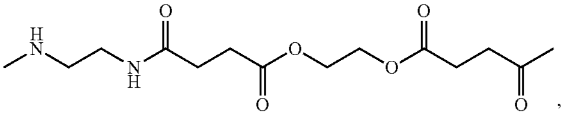
,

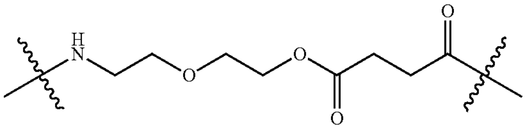

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{E1}$, $L^{E2}$, $L^{E3}$, $L^{A1}$ and $L^{A1\text{-}E}$ in the compound of Formula I-K are a cleavable linker, and each cleavable linker optionally further comprises one or more of

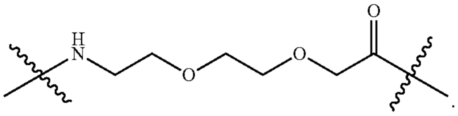 [SMILES: *NCCOCCOCC(*)=O]
.

In some embodiments, $L^{21}$ and $L^{21\text{-}E}$ in the compound of Formula I-K are each independently a non-cleavable linker comprising one or more groups selected from

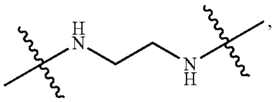
,

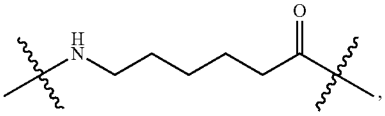
,

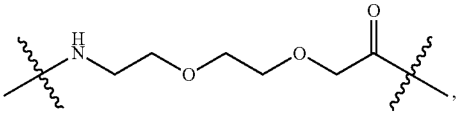
,

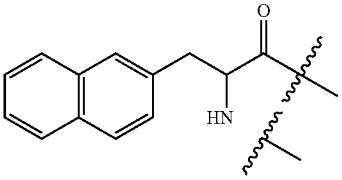
and

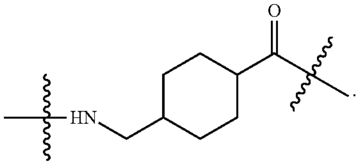
.

In some embodiments, $L^{A1}$, $L^{A1\text{-}E}$, $L^{E1}$, $L^{Z1}$ and $L^{Z1\text{-}E}$ are each independently a direct bond or a non-cleavable linker, and $L^{E2}$ and $L^{E3}$ are each independently cleavable linkers. In some embodiments, $L^{A1}$, $L^{A1\text{-}E}$, $L^{E1}$, $L^{Z1}$ and $L^{Z1\text{-}E}$ are each independently a direct bond or a non cleavable linker, and one of $L^{E2}$ and $L^{E3}$ is a non-cleavable linked and the other is a cleavable linker. In some embodiments, $L^{E1}$ is a cleavable linker and $L^{A1}$, $L^{A1-E}$, $L^{Z1}$, $L^{Z1-E}$, $L^{E2}$ and $L^{E3}$ are each independently a direct bond or a non cleavable linker. In some embodiments, $L^{E2}$ and $L^{E3}$ are both the same. In some embodiments, $L^{Z1}$ and $L^{Z1-E}$ are both the same. In some embodiments, $L^{A1}$ and $L^{A1-E}$ are both the same.

In some embodiments, n is 1, m and o are both 0 and $R^Z$ is

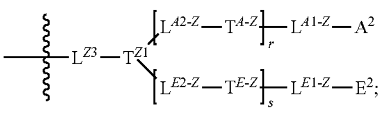

wherein r and s are 0 and the compound of Formula I-D is a compound of Formula I-L:

(I-L)

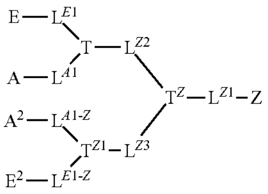

wherein

A, Z, T and E are as defined in Formula I $A^2$ is A as defined in Formula I and $A^2$ and A are the same or different;

$E^2$ is E as defined in Formula I and $E^2$ and E are the same or different;

$L^{A1}$ and $L^{A1-Z}$ are each independently $L^A$ as defined for in Formula I;

$T^Z$ and $T^{Z1}$ are each independently T as defined for in Formula I and T, $T^Z$ and $T^{Z1}$ are the same or different;

$L^{A1}$ and $L^{A1-Z}$ are each independently $L^E$ as defined for Formula I;

$L^{E1}$ and $L^{E1-Z}$ are each independently $L^E$ as defined for Formula I;

$L^{Z1}$, $L^{Z2}$ and $L^{Z3}$ are each independently $L^2$ as defined in Formula I;

provided at least one of $L^{A1}$, $L^{A1-Z}$, $L^{E1}$ and $L^{E1-Z}$ is a cleavable linker.

In some embodiments, each of T, $T^Z$ and $T^{Z1}$ is a branching group that is at least trivalent comprising at least a first terminal functionality, a second terminal functionality and a third terminal functionality, which are the same or different and bind to $L^{A1}$ (or alternatively A), $L^{E1}$ (or alternatively E) and $L^{Z2}$ (or alternatively $T^Z$), $L^{Z1}$ (or alternatively Z), $L^{Z2}$ (or alternatively T) and $L^{Z3}$ (or alternatively $T^{Z1}$), and to $L^{Z3}$ (or alternatively $T^Z$), $L^{A1-Z}$ (or alternatively $A^2$) and $L^{E1-Z}$ (or alternatively $E^2$), respectively. In some embodiments, each of T, $T^Z$ and $T^{Z1}$ are independently selected from an amino acid residue derived from lysine or glutamine and a trimesic acid residue.

In an exemplary embodiment, A and/or $A^2$ in the compound of Formula I-L are independently selected from unsubstituted or substituted $C(O)C_{12-18}alkyleneCO_2H$.

In an exemplary embodiment, Z in the compound of Formula I-L is

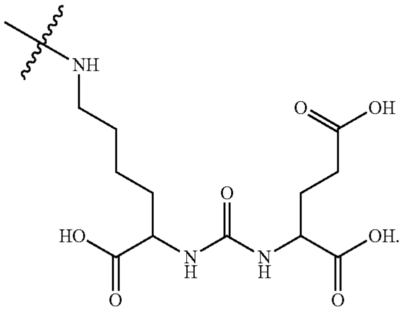 [SMILES: *NCCCCC(NC(=O)NC(CCC(=O)O)C(=O)O)C(=O)O]

In an exemplary embodiment, E and/or $E^2$ the compound of Formula I-L is selected from DOTA and DOTAGA.

In some embodiments, when any of $L^{A1}$, $L^{A1-Z}$, $L^{E1}$ and $L^{E1-Z}$ in the compound of Formula I-L is a non-cleavable linker, each non-cleavable linker independently comprises one or more groups selected from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP;

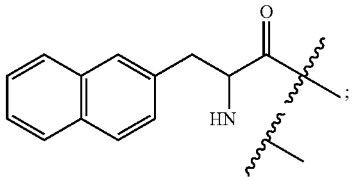
;

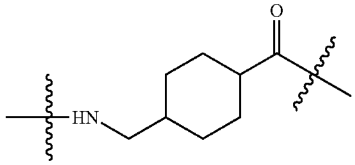
;

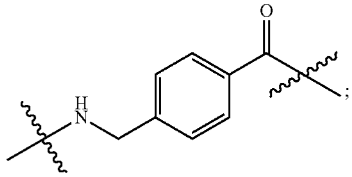
;

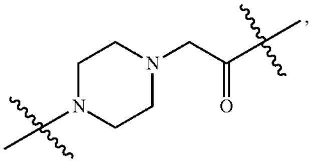
, $R^1NC_{1-20}alkyleneNR^2$; $C(O)C_{1-20}alkyleneC(O)$; $R^1NC_{1-20}alkyleneC(O)$; and $C(O)C_{1-20}alkyleneNR^2$, the latter 4 groups being optionally interrupted by one or more of S, O, C(O)NH, NHC(O), $C_{4-6}$cycloalkyl and $C_{4-6}$heterocycloalkyl wherein each $R^1$ and $R^2$ is independently selected from H and $C_{1-2}$alkyl. In some embodiments, when any of $L^{A1}$, $L^{A1-Z}$, $L^{E1}$ and $L^{E1-Z}$ in the compound of Formula I-L is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

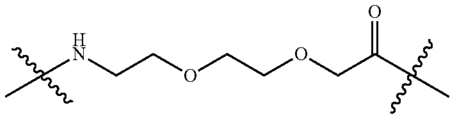
;

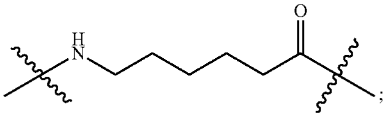
;

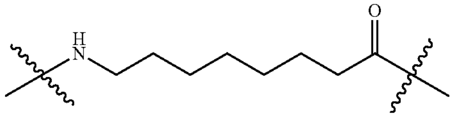
;

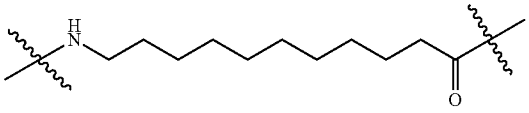
and

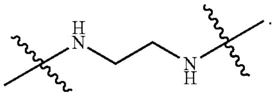
.

In some embodiments, when any of $L^{A1}$, $L^{A1-Z}$, $L^{E1}$ and $L^{E1-Z}$ in the compound of Formula I-L is a non-cleavable linker, each non-cleavable linker independently comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec, PCL and the D enantiomers thereof;

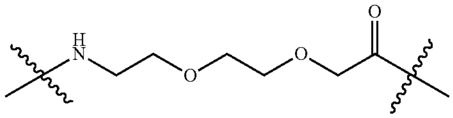
;

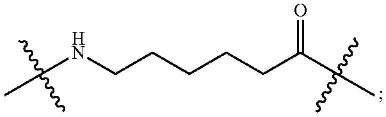
;

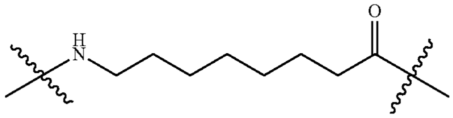
;

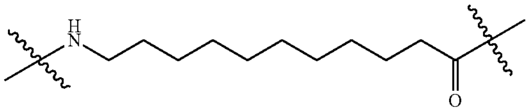
and

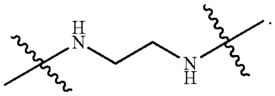
.

In some embodiments, when any of $L^{A1}$, $L^{A1-Z}$, $L^{E1}$ and $L^{E1-Z}$ in the compound of Formula I-L is a non-cleavable linker, each non-cleavable linker independently comprises one or more groups selected from amino acids residues derived from Glu,

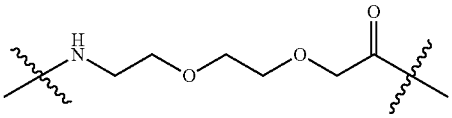
; and

-continued

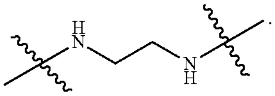
.

In some embodiments, when any of $L^{A1}$, $L^{A1-Z}$, $L^{E1}$ and $L^{E1-Z}$ in the compound of Formula I-L is a non-cleavable linker each non-cleavable linker independently comprises one or more groups selected from amino acids residues derived from Glu and

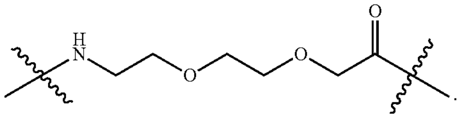
.

In some embodiments, one or more of $L^{A1}$, $L^{A1-Z}$, $L^{E1}$ and $L^{E1-Z}$ in the compound of Formula I-L is independently a cleavable linker and each cleavable linker independently comprises one or more groups selected from one or more amino acid residues derived from Gly, Glu, Leu, Phe, Tyr, or Lys, or the D enantiomers thereof; one or more amino acid residues derived from DAP and DAB; $R^5NC_{1-20}$alkyleneNR$^6$; and $R^5NC_{1-20}$alkyleneC(O) optionally interrupted by one or more of O; and at least one $R^5NC_{1-20}$alkyleneC(O) optionally interrupted by one or more of S—S, C(O)O, OC(O), O, C(O)NH and NHC(O), provided $R^5NC_{1-20}$alkyleneC(O) is interrupted by at least one of S—S, C(O)O and OC(O), or at least one amino acid residue connected to $C(O)C_{1-10}$alkyleneO or $OC_{1-10}$alkyleneC(O) to form a cleavable moiety selected from C(O)O and OC(O), or an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, one or more of $L^{A1}$, $L^{A1-Z}$, $L^{E1}$ and $L^{E1-Z}$ in the compound of Formula I-L is independently a cleavable linker and each cleavable linker independently comprises at least one group selected from

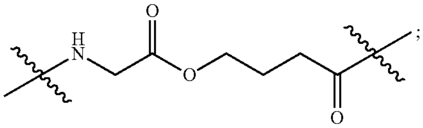
;

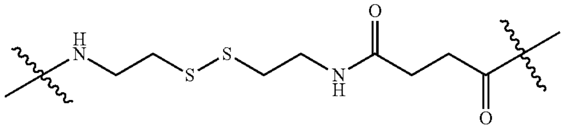

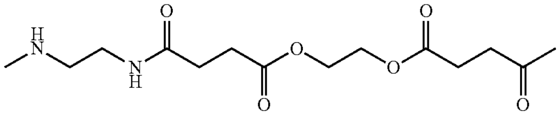
,

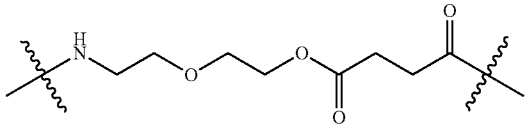

and an enzymatically cleavable peptide sequence selected from Met-Val-Lys, Ala-Val, Ala-Pro, Gly-Pro, Ser-Ser, Ser-Gly, Gly-Ala and Ser-Lys, optionally comprises one or more groups selected from amino acid residues derived from Glu, Lys, Phe, Tyr, and the D enantiomers thereof;

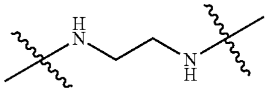
and

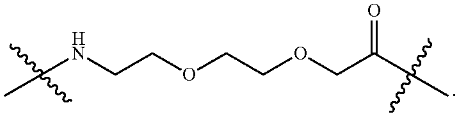 [SMILES: *NCCOCCOCC(*)=O]
.

In some embodiments, one or more of $L^{A1}$, $L^{A1-Z}$, $L^{E1}$ and $L^{E1-Z}$ in the compound of Formula I-L is independently a cleavable linker, and each cleavable linker independently optionally comprises one or more of

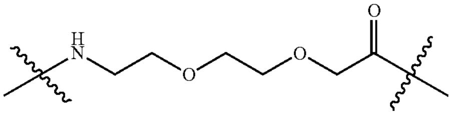
;

and at least one group selected from

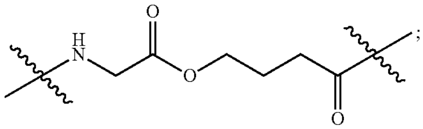
;

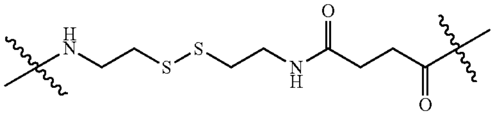
and

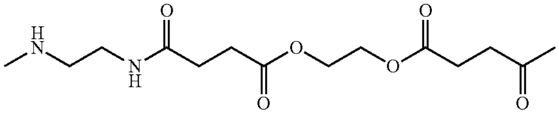
,

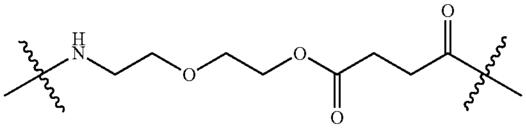

and an enzymatically cleavable peptide sequence selected from Met-Val-Lys, Ala-Val, Ala-Pro, Gly-Pro, Ser-Ser, Ser-Gly, Gly-Ala and Ser-Lys.

In some embodiments, at least one of $L^{A1}$, $L^{A1-Z}$, $L^{E1}$ and $L^{E1-Z}$ in the compound of Formula I-L is a cleavable linker, and each cleavable linker independently further comprises one or more of

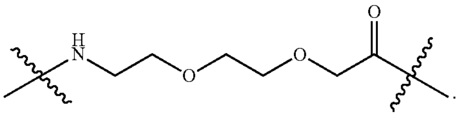 [SMILES: *NCCOCCOCC(*)=O]
.

In some embodiments, $L^{Z1}$, $L^{Z2}$ and $L^{Z3}$ in the compound of Formula I-L are each independently a non-cleavable linker comprising one or more groups selected from

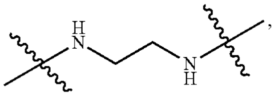
,

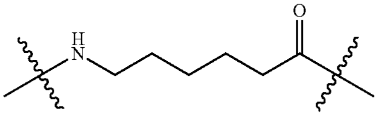

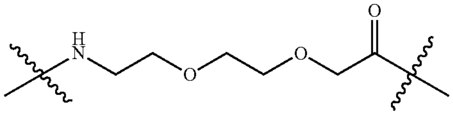

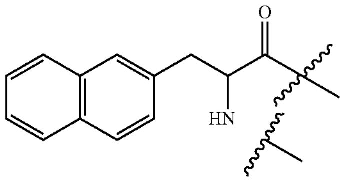
and

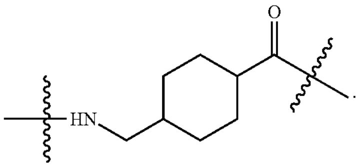
.

In some embodiments, $L^{Z2}$ and $L^{Z3}$ in the compound of Formula I-L are each independently a non-cleavable linker comprising one or more groups selected from

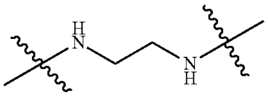
,

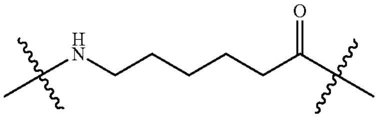
and

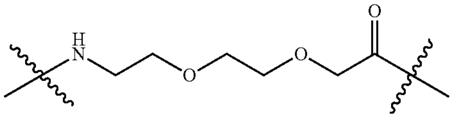
.

In some embodiments, $L^{Z1}$ in the compound of Formula I-L are each independently a non-cleavable linker comprising one or more groups selected from

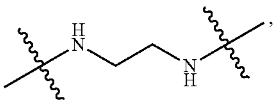
,

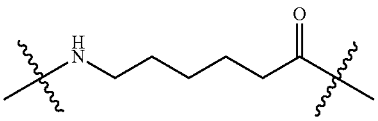

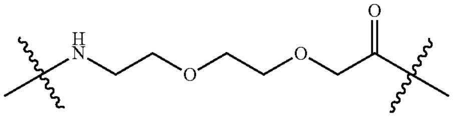

-continued

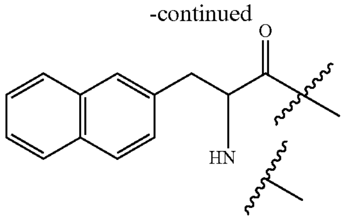

and

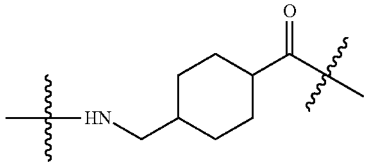

.

In some embodiments, $L^{Z1}$, $L^{Z2}$, $L^{Z3}$, $L^{E1}$ and $L^{E1\text{-}Z}$ are each independently a direct bond or a non-cleavable linker, and $L^{A1}$ and $L^{A1\text{-}Z}$, are each independently cleavable linkers. In some embodiments, $L^{Z1}$, $L^{Z2}$, $L^{Z3}$, $L^{E1}$ and $L^{E1\text{-}Z}$ are each independently a direct bond or a non-cleavable linker, and one of $L^{A1}$ and $L^{A1\text{-}Z}$ is a non-cleavable linked and the other is a cleavable linker. In some embodiments, $L^{Z1}$, $L^{Z2}$, $L^{Z3}$, $L^{A1}$ and $L^{A1\text{-}Z}$ are each independently a direct bond or a non-cleavable linker, and $L^{E1}$ and $L^{E1\text{-}Z}$ are each independently cleavable linkers. In some embodiments, $L^{Z1}$, $L^{Z2}$, $L^{Z3}$, $L^{A1}$ and $L^{A1\text{-}Z}$ are each independently a direct bond or a non-cleavable linker, and one of $L^{E1}$ and $L^{E1\text{-}Z}$ is a non-cleavable linked and the other is a cleavable linker. In In some embodiments, $L^{Z2}$ and $L^{Z3}$ are both the same. In some embodiments, $L^{E1}$ and $L^{E1\text{-}Z}$ are both the same. In some embodiments, $L^{A1}$ and $L^{A1\text{-}Z}$ are both the same.

In some embodiments, the compound of Formula I is selected from the following list of compounds

| I.D | Compound Name | Structure |
|---|---|---|
| I-1 | 4pIBA-Glu-SSL1-Lys(DOTA)-Trx-2Nal-eKuE | 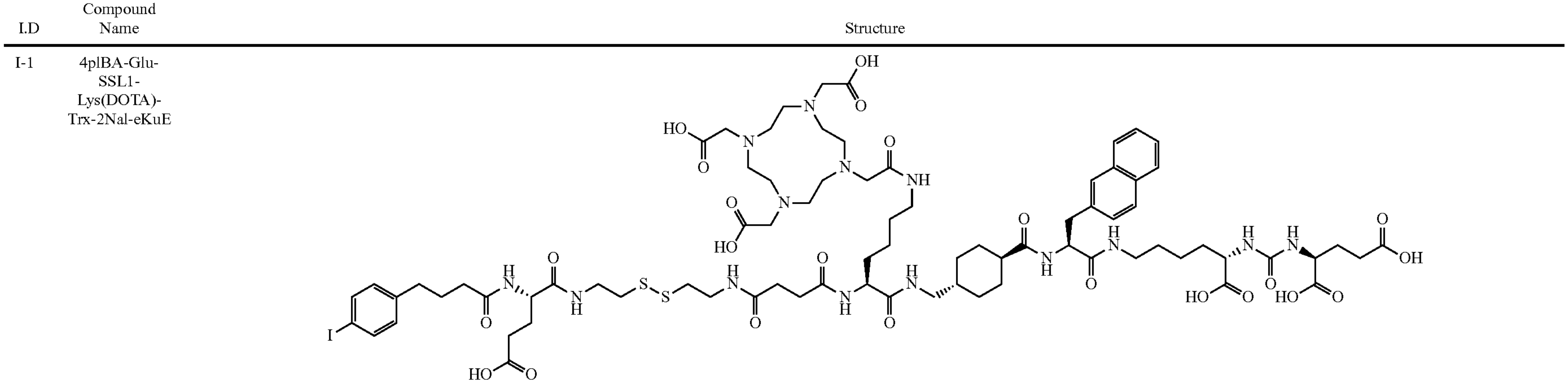 |
| I-2 | 4pIBA-Glu-ESL1-Lys(DOTA)-Trx-2Nal-eKuE | 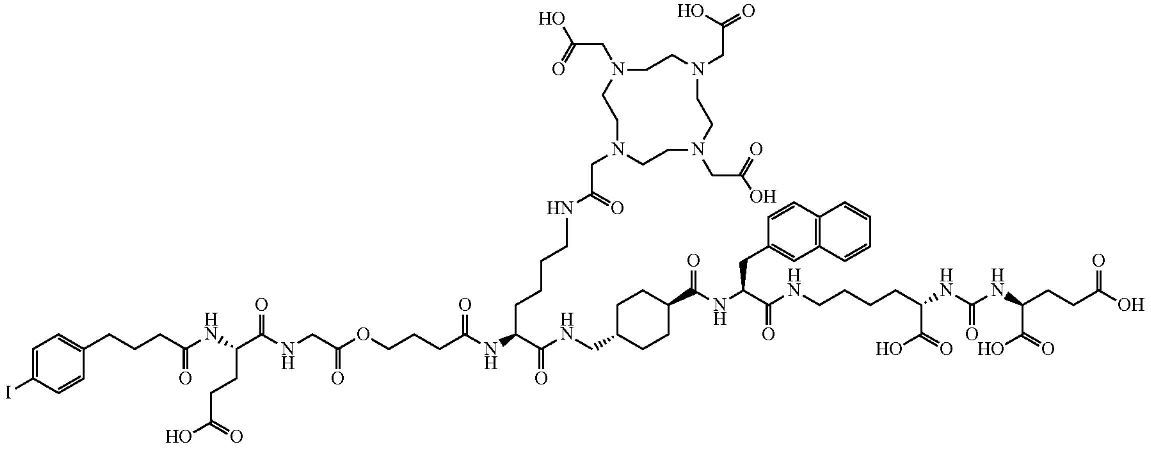 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CN2CCN(CC(=O)O)CCN(CC(=O)O)CCN(CC(=O)O)CC2)NC(=O)CCCOC(=O)CNC(=O)[C@H](CCC(=O)O)NC(=O)CCCc2ccc(I)cc2)CC1)C(=O)O)C(=O)O] |

-continued
| I.D | Compound Name | Structure |
|---|---|---|
| I-3 | 4pIBA-Glu-Lys(-ESL1-DOTA)-Trx-2Nal-eKuE | 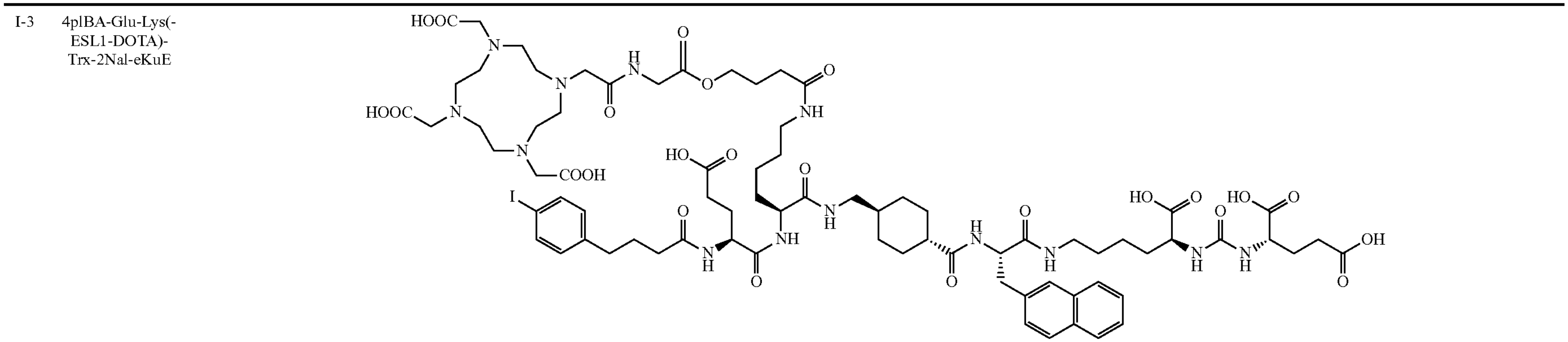 |
| I-4 | 4pIBA-Glu-Lys(-SSL1-DOTA)-Trx-2Nal-eKuE | 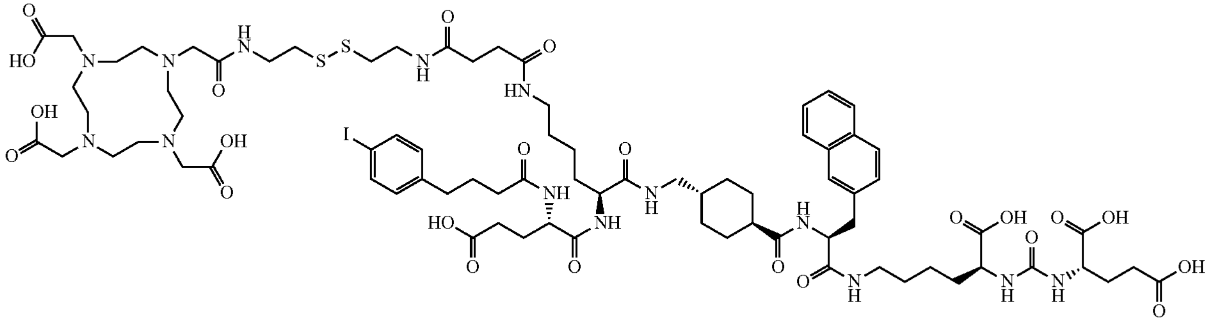 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CCC(=O)NCCSSCCNC(=O)CN2CCN(CC(=O)O)CCN(CC(=O)O)CCN(CC(=O)O)CC2)NC(=O)[C@H](CCC(=O)O)NC(=O)CCCc2ccc(I)cc2)CC1)C(=O)O)C(=O)O] |

-continued
| I.D | Compound Name | Structure |
|---|---|---|
| I-5 | 4pIBA-Glu-Lys(-ESL2-DOTA)-Aun-Trx-2Nal-eKuE | 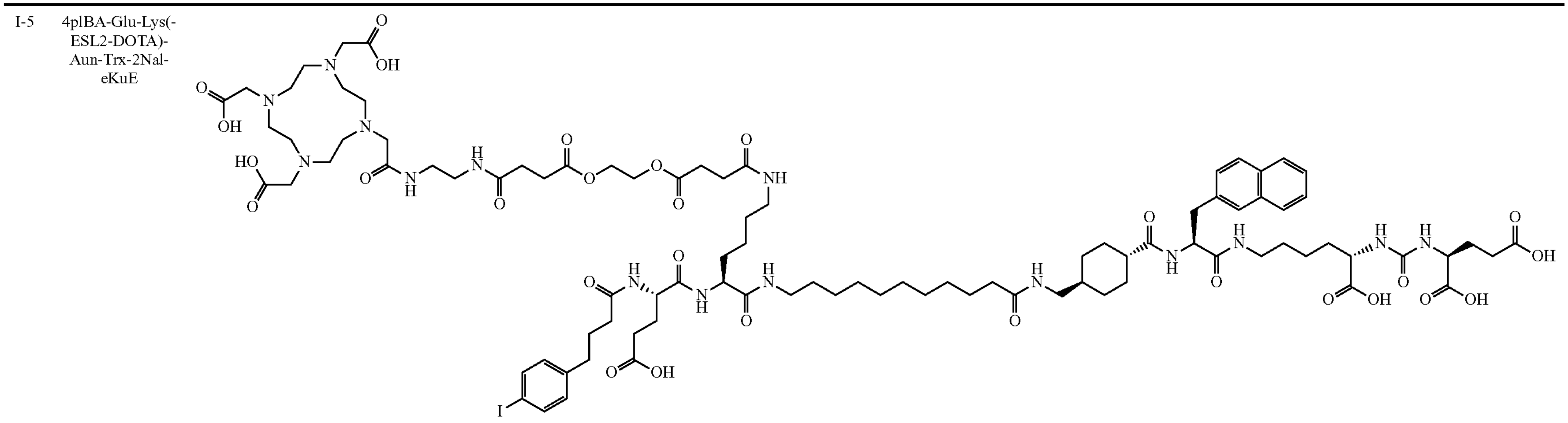 |
| I-6 | DOTA-ESL2-Lys(-Glu-4pIBA)-Trx-2Nal-eKuE | 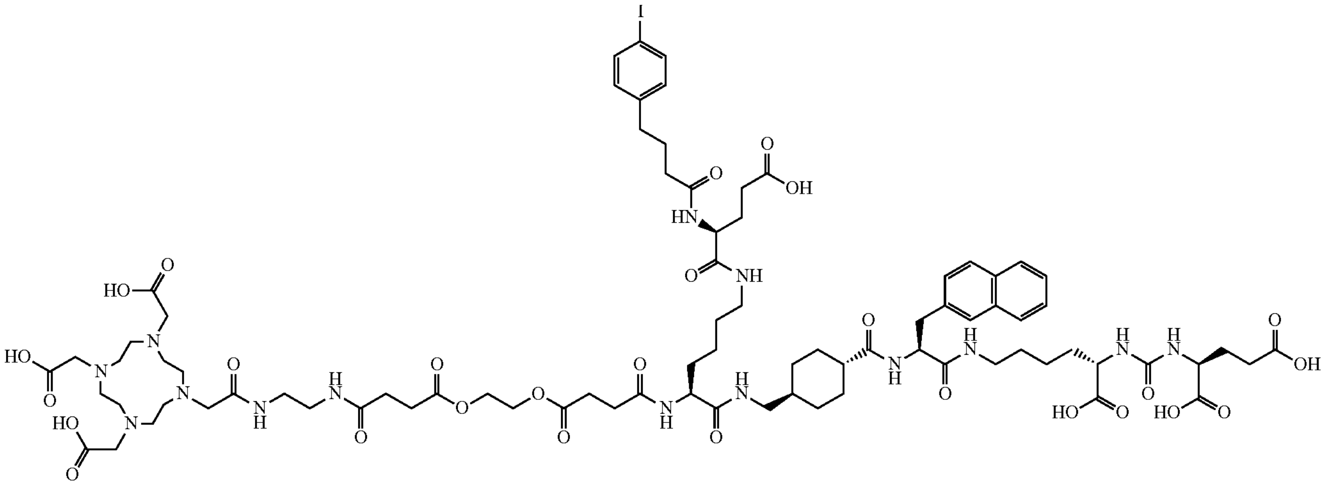 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)[C@H](CCC(=O)O)NC(=O)CCCc2ccc(I)cc2)NC(=O)CCC(=O)OCCOC(=O)CCC(=O)NCCNC(=O)CN2CCN(CC(=O)O)CCN(CC(=O)O)CCN(CC(=O)O)CC2)CC1)C(=O)O)C(=O)O] |

-continued
| I.D | Compound Name | Structure |
|---|---|---|
| I-7 | 4pIBA-Glu-OEG-OEG-Lys(-OEG-OEG-Glu-4pIBA)-Lys(-ESL1-DOTA)-OEG-Trx-2Nal-eKuE | 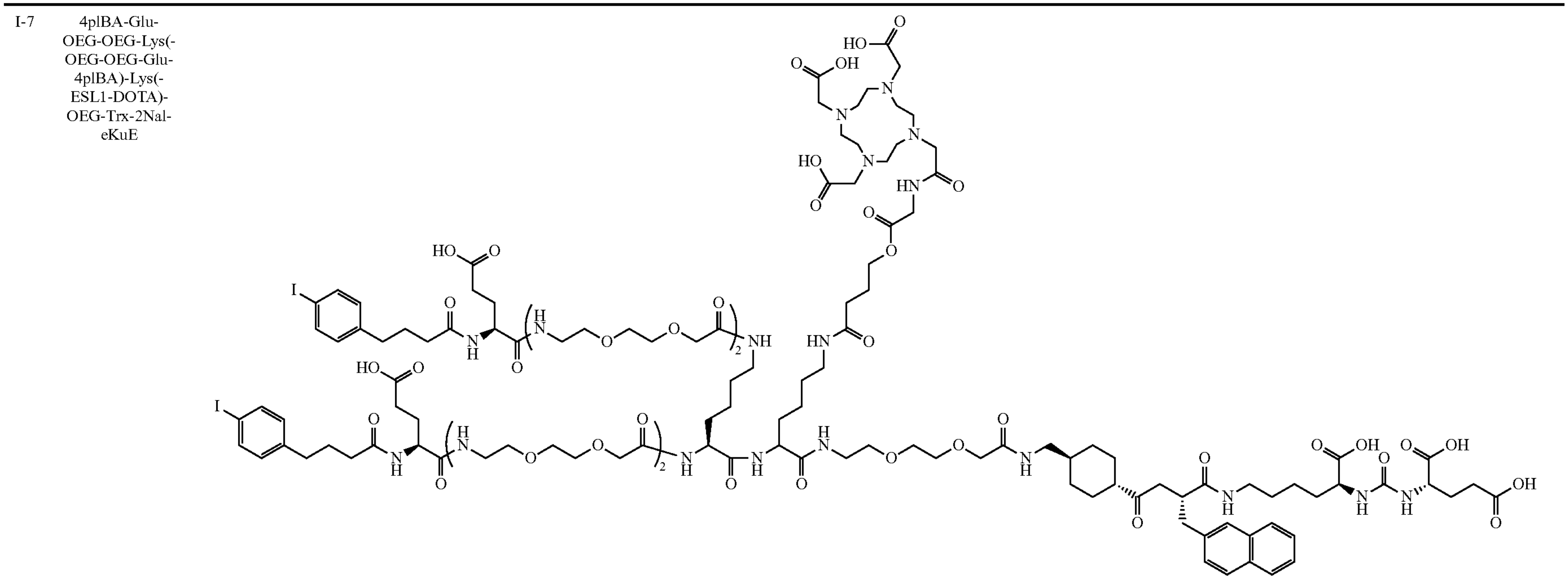 |
| I-8 | 4pIBA-Glu-OEG-OEG-Lys(-OEG-OEG-Glu-4pIBA)-OEG-ESL1-Lys(DOTA)-Trx-2Nal-eKuE | 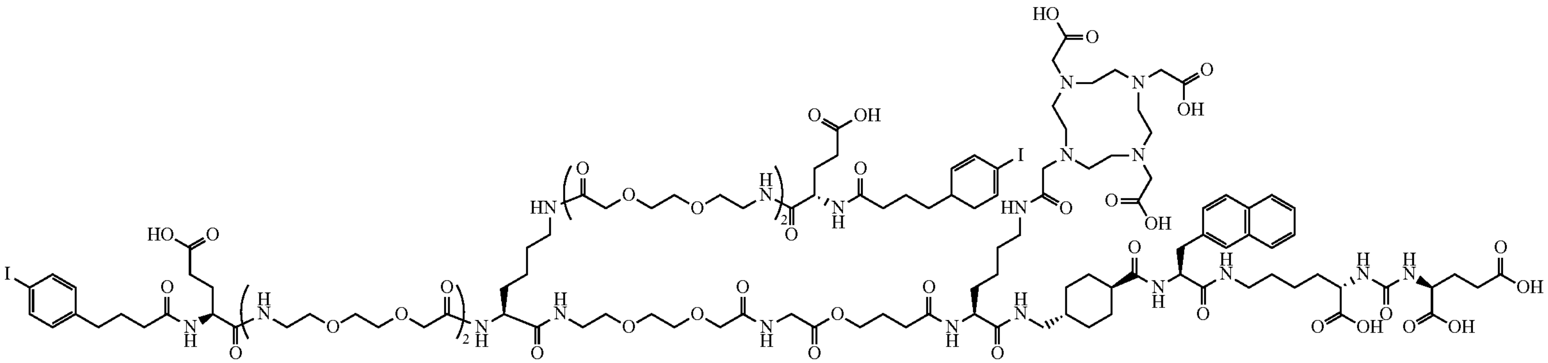 |

-continued
| I.D | Compound Name | Structure |
|---|---|---|
| I-9 | 4pIBA-Glu-Lys[-Suc-eLys-Val-Met-Gly-DOTA]-Trx-2Nal-eKuE | 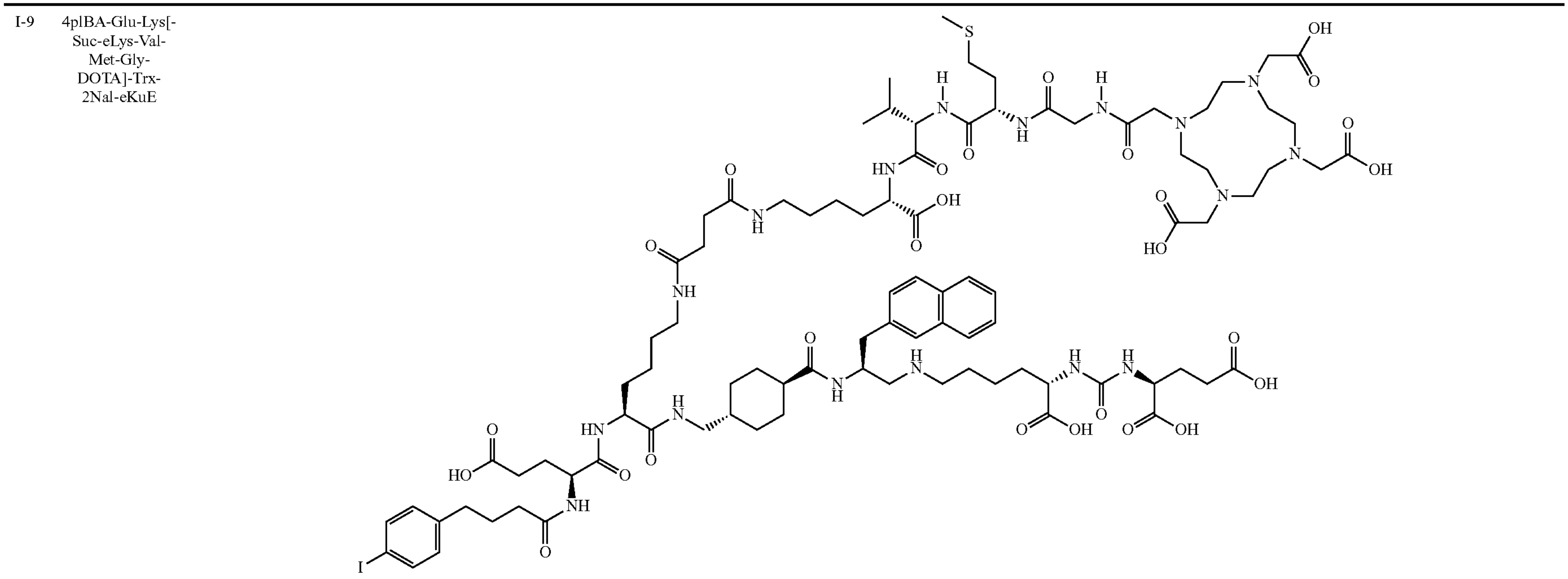 |

-continued
| I.D | Compound Name | Structure |
|---|---|---|
| I-10 | HO-C18-gGlu-Lys(-ESL1-DOTA)-OEG-OEG-OEG-Trx-2Nal-eKuE | 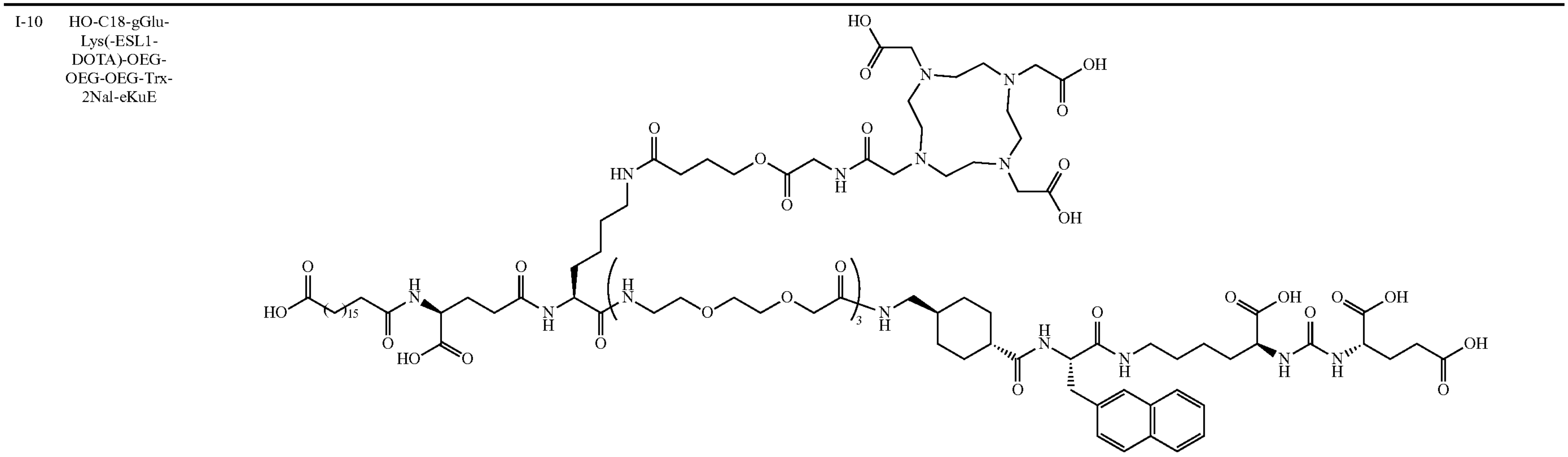 |
| I-11 | HO-C18-gGlu-Lys(-ESL1-DOTA)-OEG-OEG-OEG-OEG-OEG-OEG-Trx-2Nal-eKuE | 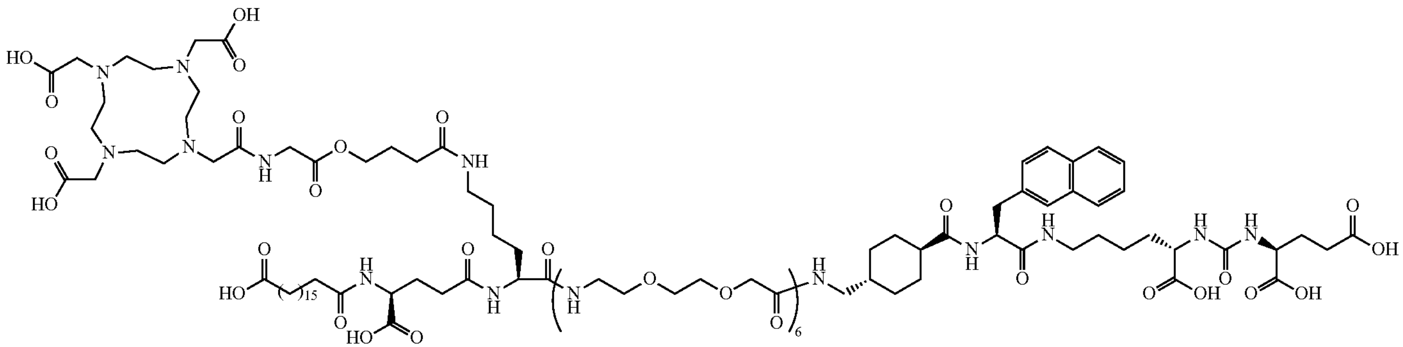 |

-continued
| I.D | Compound Name | Structure |
| --- | --- | --- |
| I-12 | HO-C18-gGlu-Lys(-ESL2-DOTA)-OEG-OEG-Trx-2Nal-eKuE | 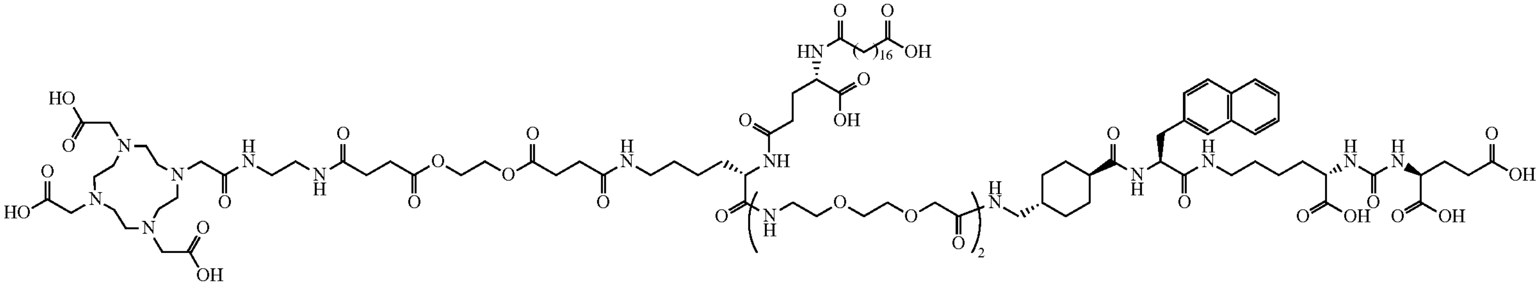 |
| I-13 | HO-C18-gGlu-Lys(-ESL2-DOTA)-OEG-OEG-OEG-Trx-2Nal-eKuE | 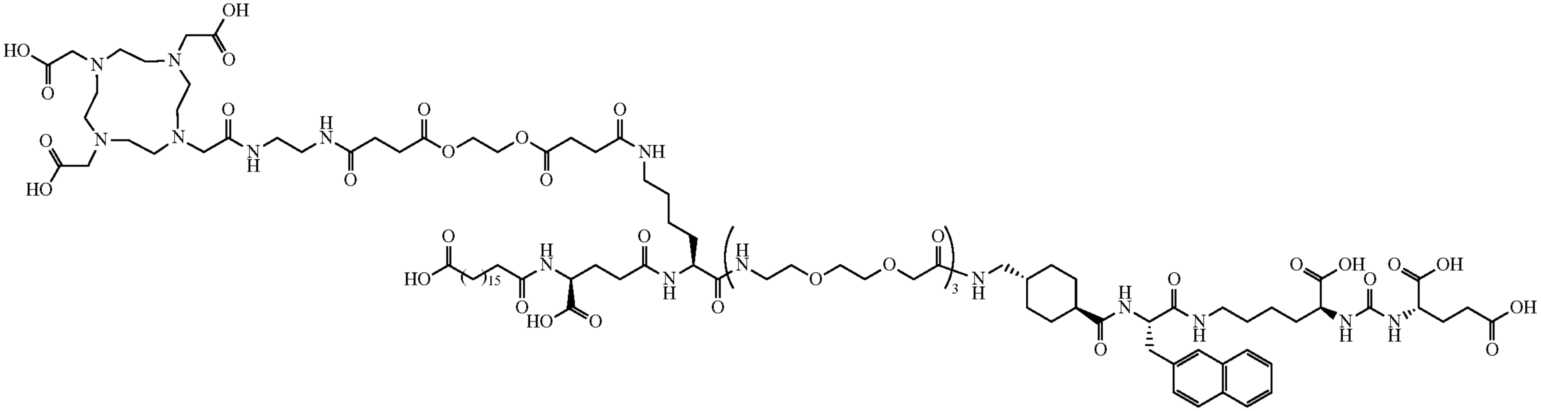 |
| I-14 | HO-C20-gGlu-Lys(-ESL2-DOTA)-OEG-OEG-OEG-Trx-2Nal-eKuE | 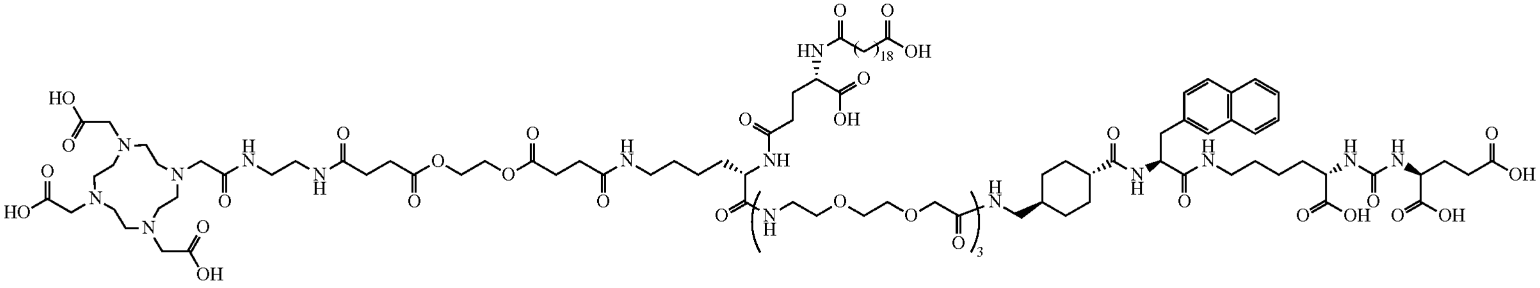 |

-continued
| I.D | Compound Name | Structure |
|---|---|---|
| I-15 | HO-C18-gGlu-Lys(-ESL2-DOTA)-OEG-OEG-OEG-OEG-Trx-2Nal-eKuE | 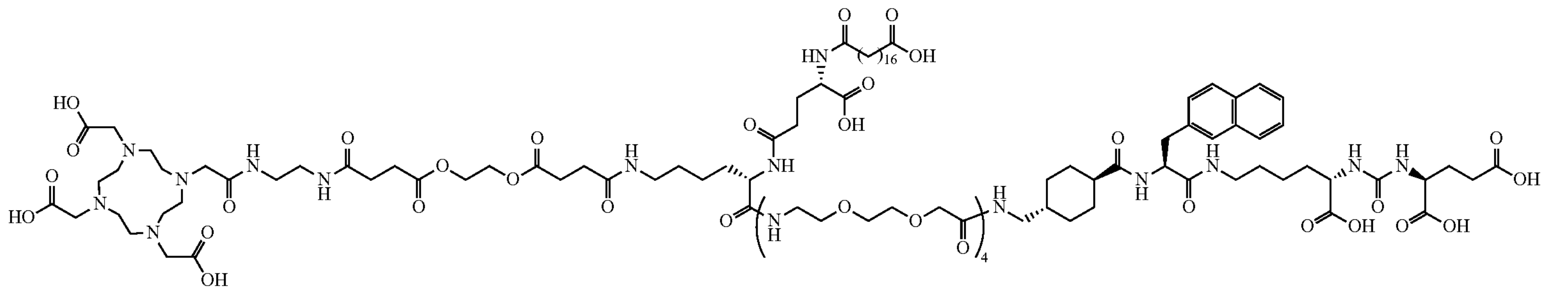 |
| I-16 | HO-C18-gGlu-OEG-OEG-Lys(-ESL2-DOTA)-OEG-Trx-2Nal-eKuE | 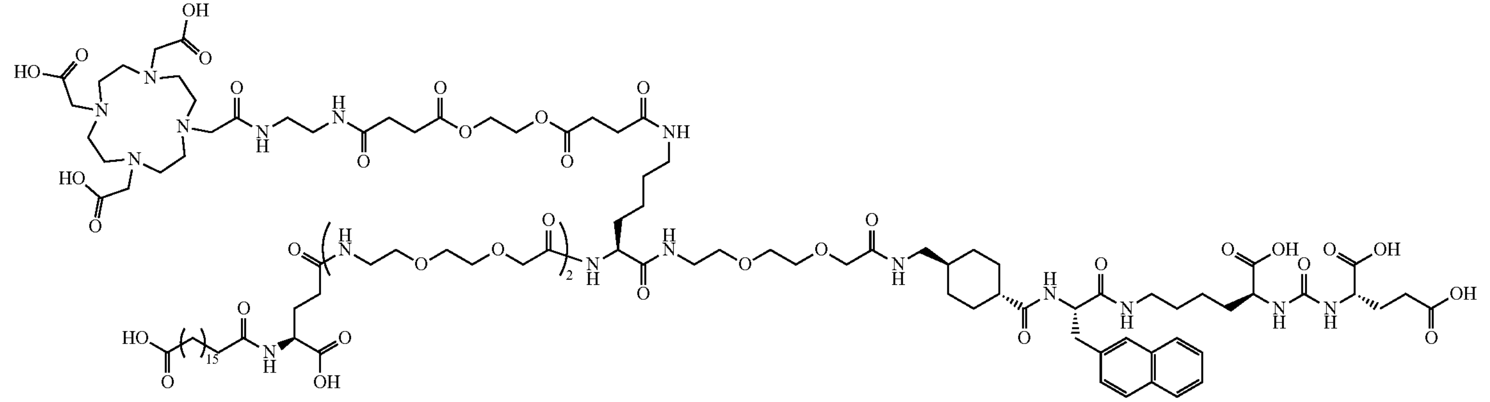 |
| I-17 | HO-C20-gGlu-OEG-Lys(-ESL1-DOTA)-OEG-OEG-Trx-2Nal-eKuE | 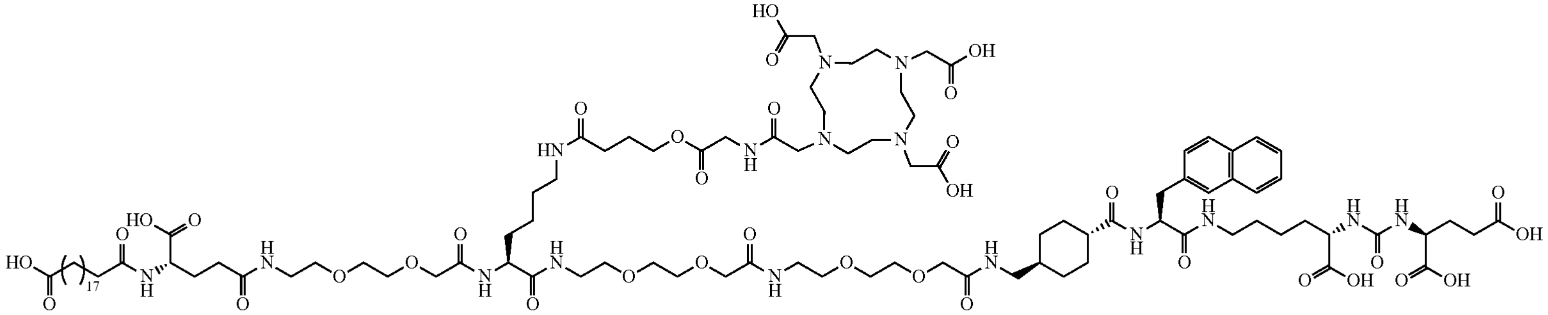 |

-continued
| I.D | Compound Name | Structure |
|---|---|---|
| I-18 | HO-C18-gGlu-OEG-OEG-Lys(-ESL1-DOTA)-OEG-Trx-2Nal-eKuE | 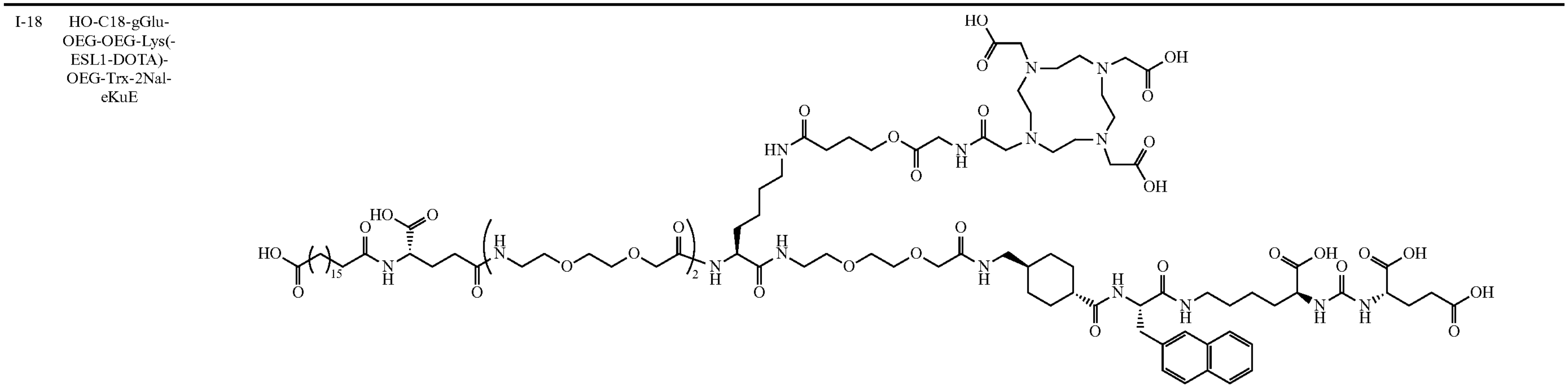 |
| I-19 | HO-C18-gGlu-OEG-OEG-OEG-OEG-OEG-OEG-ESL1-Lys(DOTA)-Trx-2Nal-eKuE | 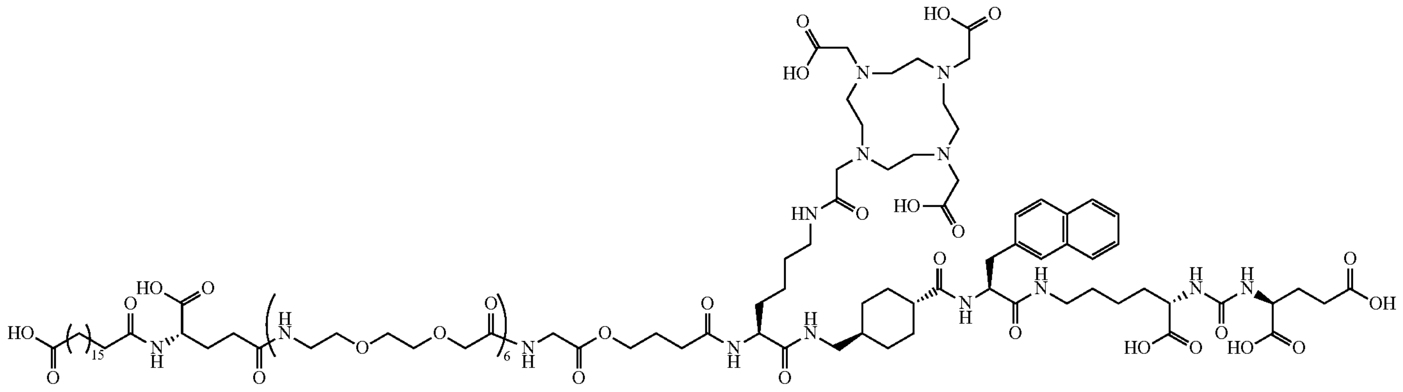 |

-continued
| I.D | Compound Name | Structure |
|---|---|---|
| I-20 | HO-C18-gGlu-OEG-OEG-ESL2-Lys(DOTA)-OEG-Trx-2Nal-eKuE | 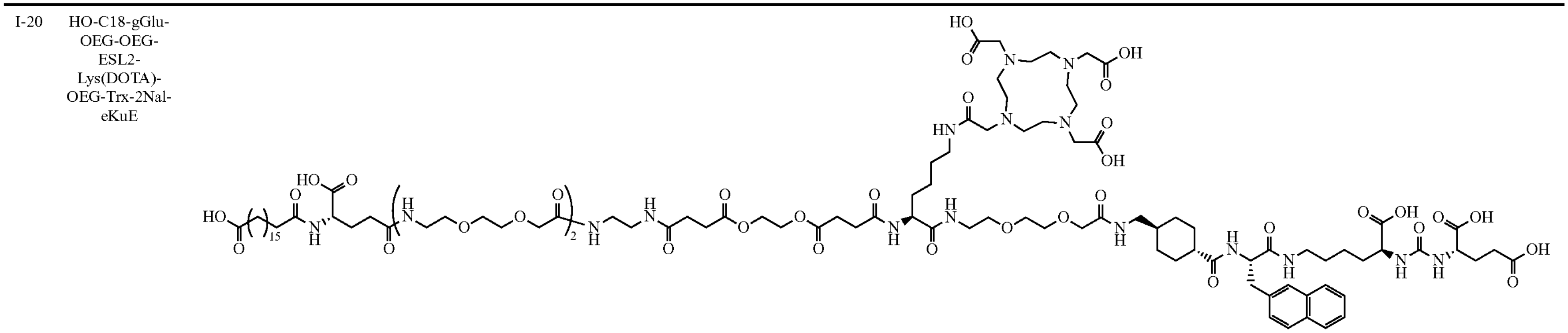 |
| I-21 | HO-C18-gGlu-OEG-OEG-ESL1-Lys(DOTA)-OEG-Trx-2Nal-eKuE | 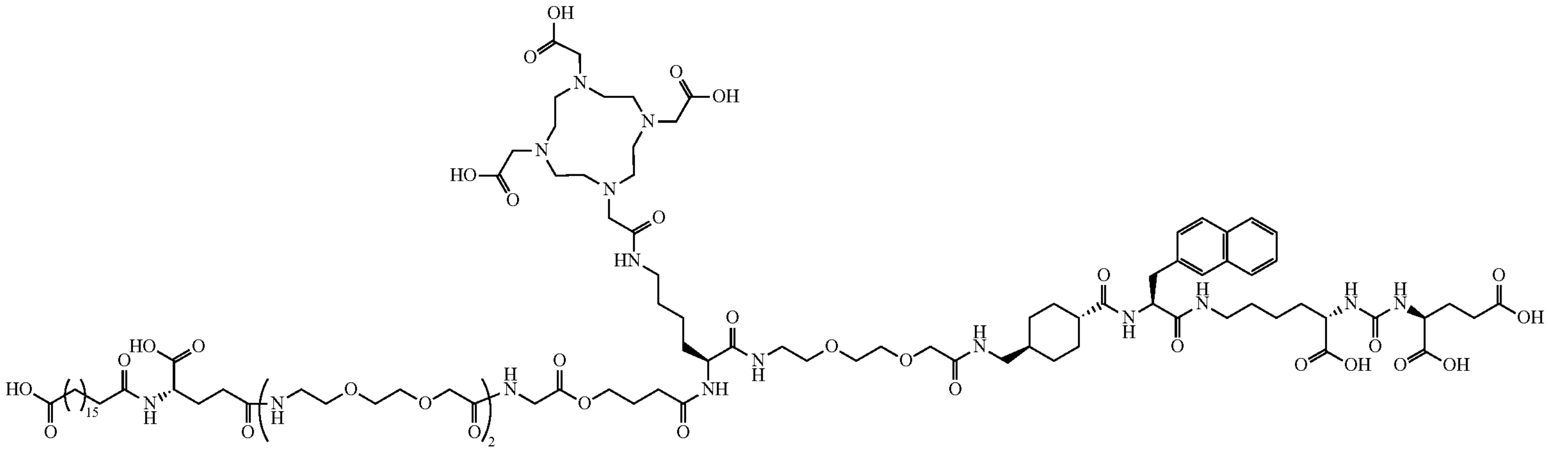 |

-continued
| I.D | Compound Name | Structure |
|---|---|---|
| I-22 | HO-C18-gGlu-OEG-ESL1-ESL1-Lys(DOTA)-OEG-Trx-2Nal-eKuE | 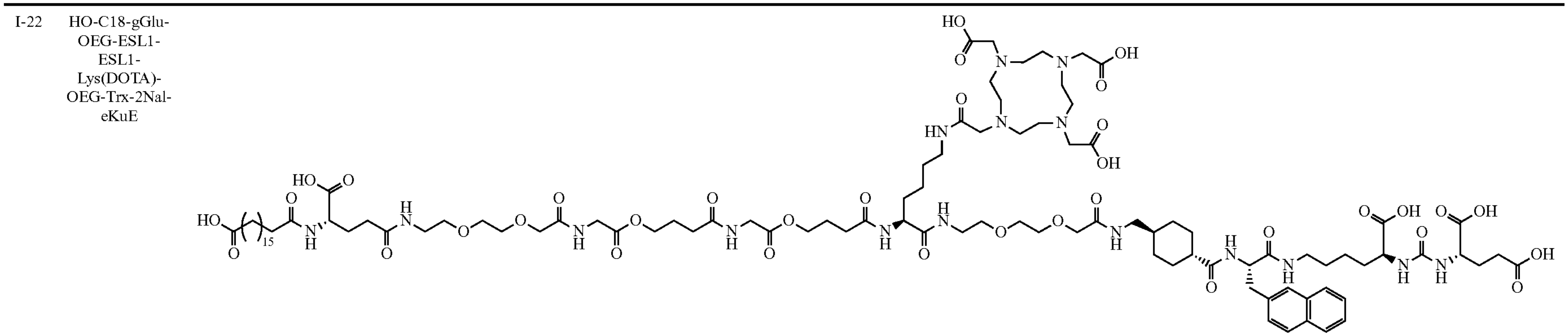 |
| I-23 | HO-C18-gGlu-ESL1-ESL1-ESL1-Lys(DOTA)-OEG-Trx-2Nal-eKuE | 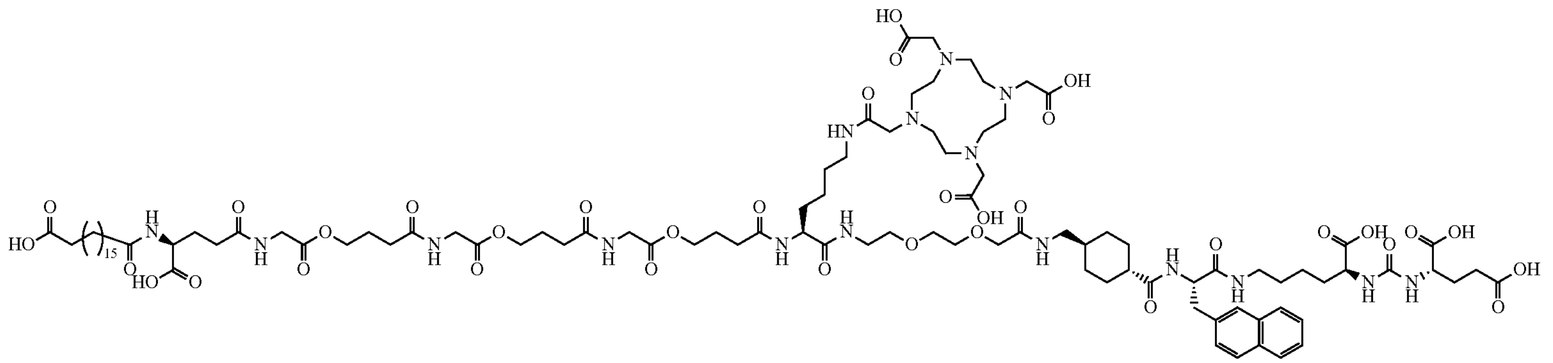 |

-continued
| I.D | Compound Name | Structure |
|---|---|---|
| I-24 | HO-C18-gGlu-OEG-OEG-OEG-OEG-OEG-ESL1-Lys(DOTA)-OEG-Trx-2Nal-eKuE | 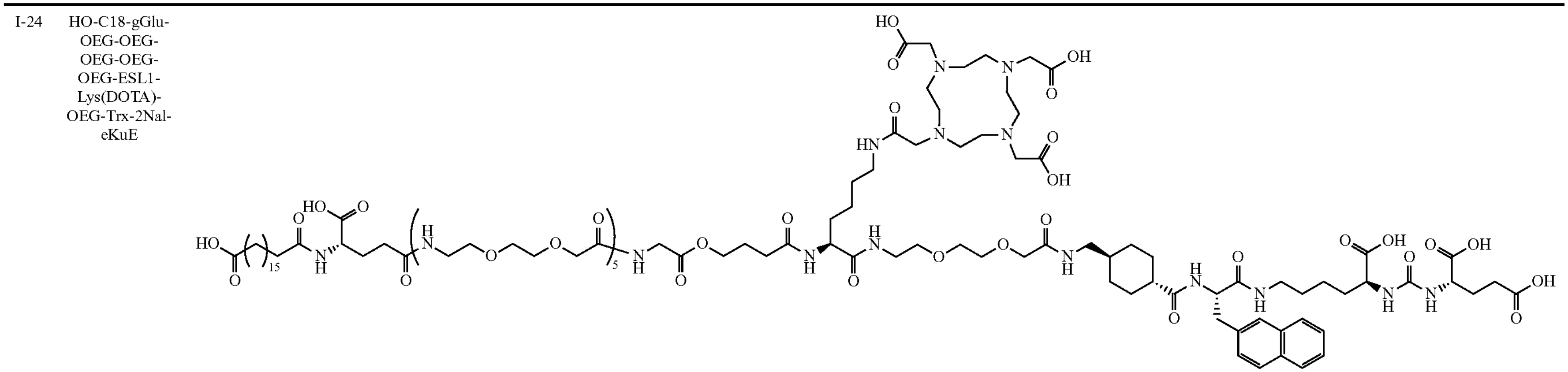 |
| I-25 | HO-C20-gGlu-OEG-OEG-ESL1-Lys(DOTA)-OEG-Trx-2Nal-eKuE | 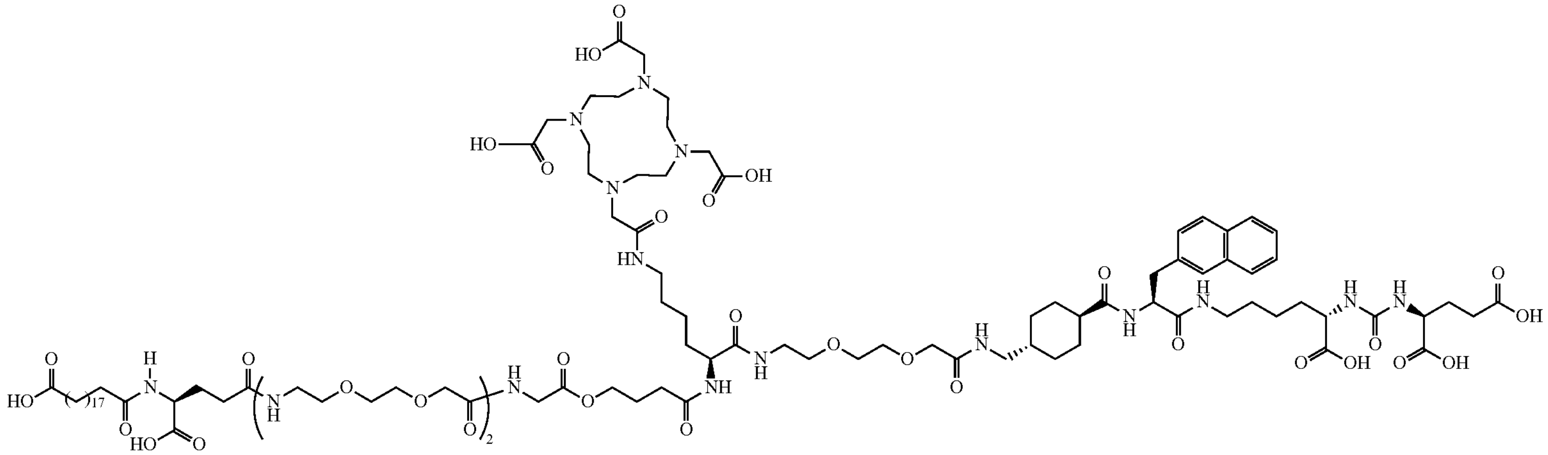 |

-continued
| I.D | Compound Name | Structure |
|---|---|---|
| I-26 | HO-C18-gGlu-OEG-OEG-ESL1-OEG-Lys(DOTA)-Trx-2Nal-eKuE | 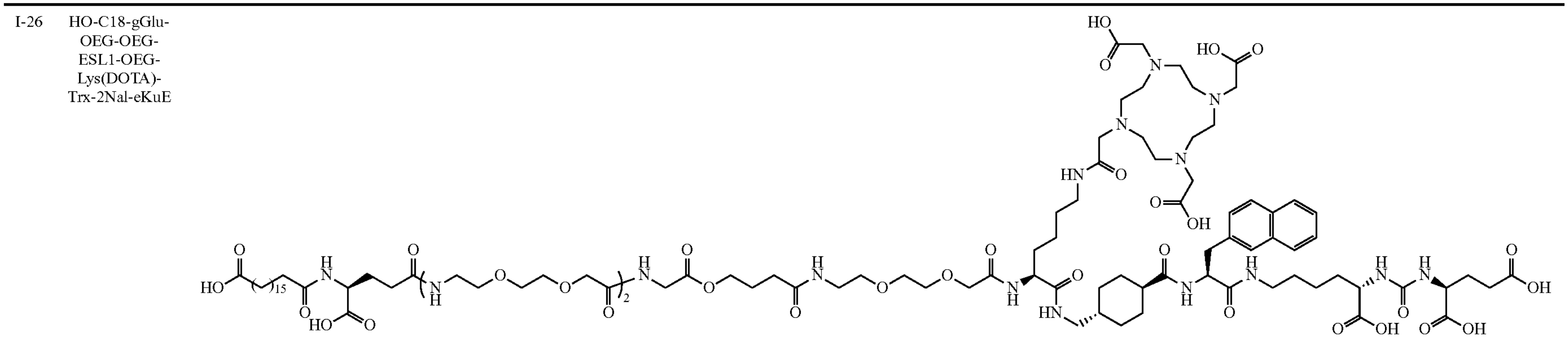 |
| I-27 | HO-C18-gGlu-ESL1-OEG-OEG-Lys(DOTA)-OEG-Trx-2Nal-eKuE | 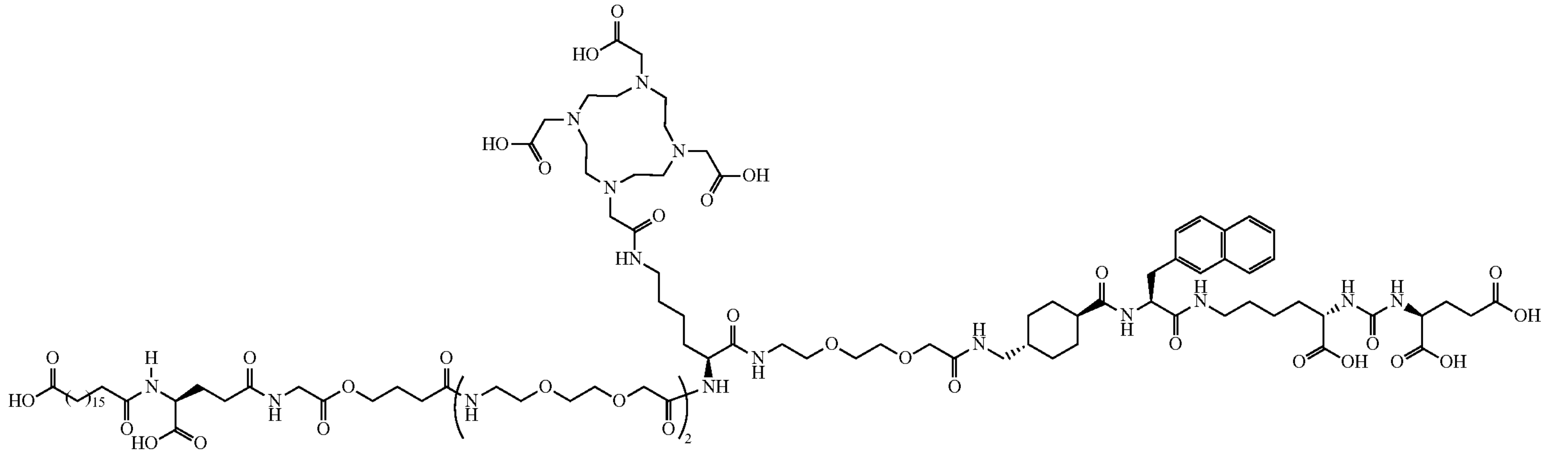 |

-continued
| I.D | Compound Name | Structure |
|---|---|---|
| I-28 | HO-C18-gGlu-gGlu-gGlu-OEG-OEG-ESL1-Lys(DOTA)-OEG-Trx-2Nal-eKuE | 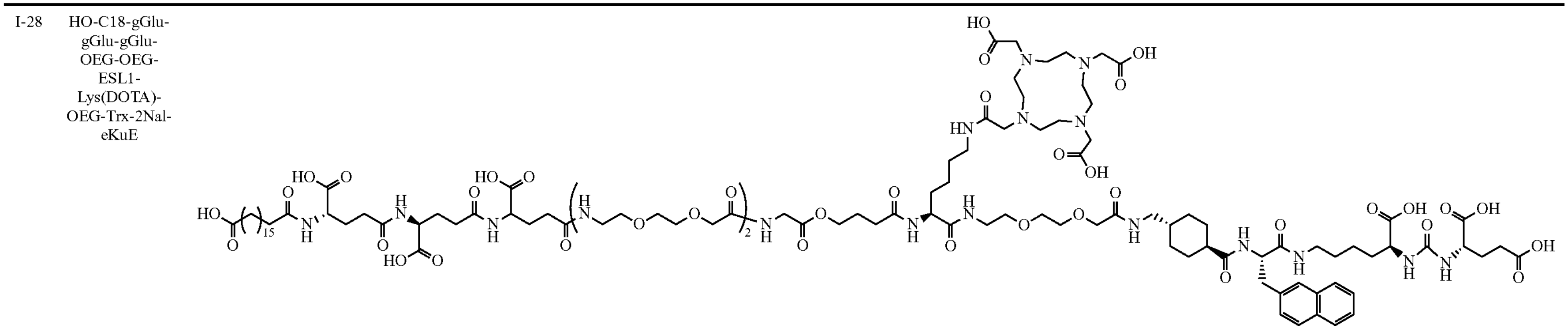 |
| I-29 | HO-C20-gGlu-OEG-ESL1-ESL1-Lys(DOTA)-OEG-Trx-2Nal-eKuE | 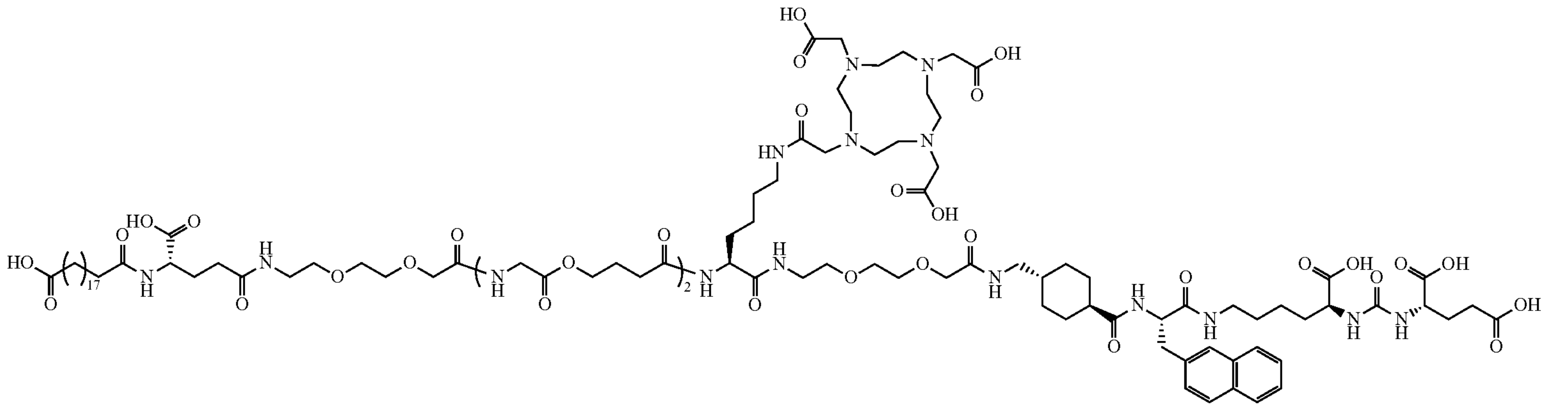 |

-continued
| I.D | Compound Name | Structure |
|---|---|---|
| I-30 | HO-C16-gGlu-OEG-OEG-ESL1-Lys(DOTA)-OEG-Trx-2Nal-eKuE | 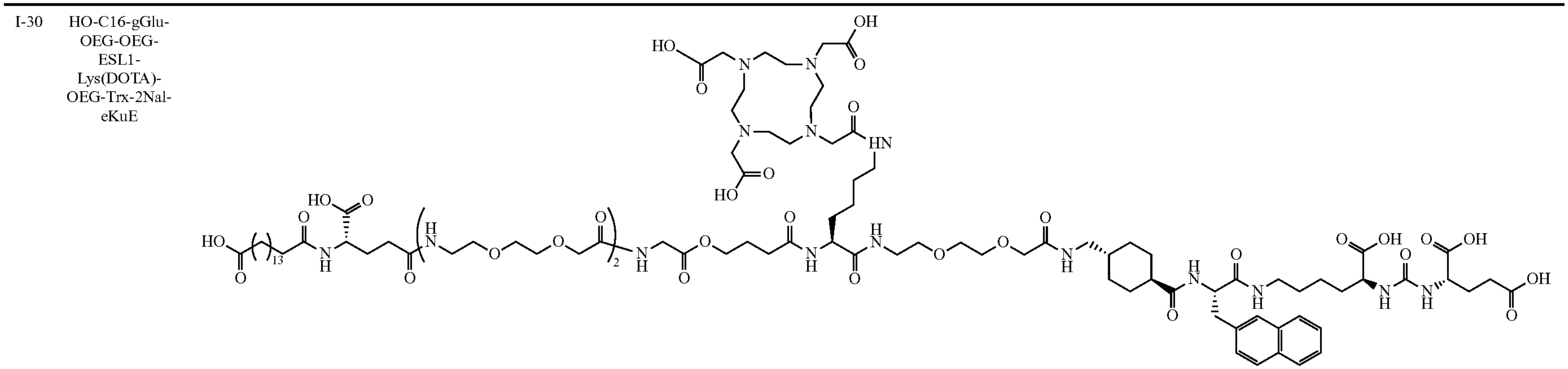 |
| I-31 | HO-C18-gGlu-OEG-OEG-ESL3-Lys(DOTA)-OEG-Trx-2Nal-eKuE | 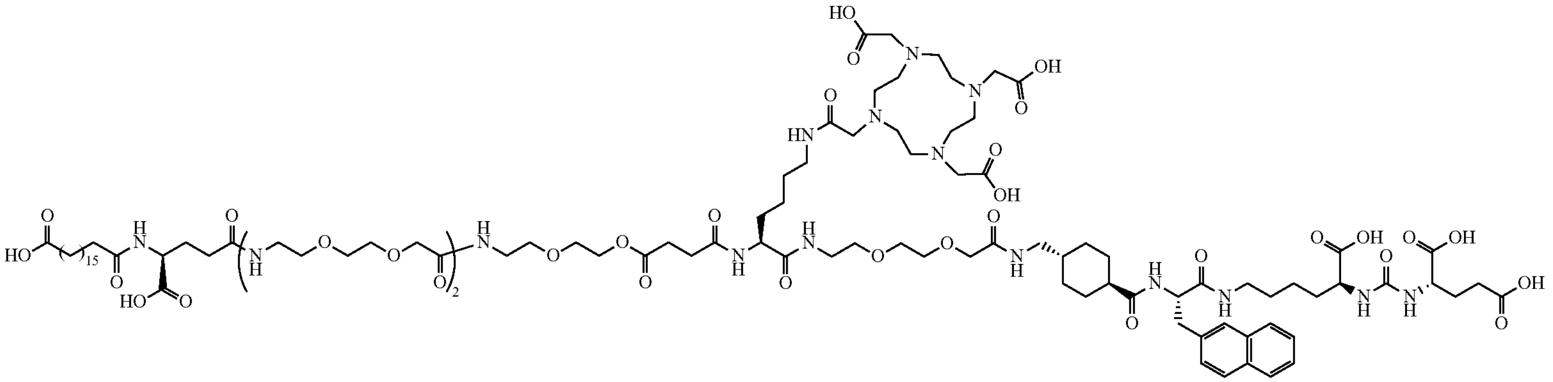 |

-continued
| I.D | Compound Name | Structure |
|---|---|---|
| I-32 | (HO-C18)-gGlu-OEG-OEG-OEG-OEG-OEG-Glu-Arg-Gly-Glu-Thr-Gly-Pro-Ser-Gly-OEG-Lys(-ESL1-DOTA)-Trx-2Nal-eKuE | 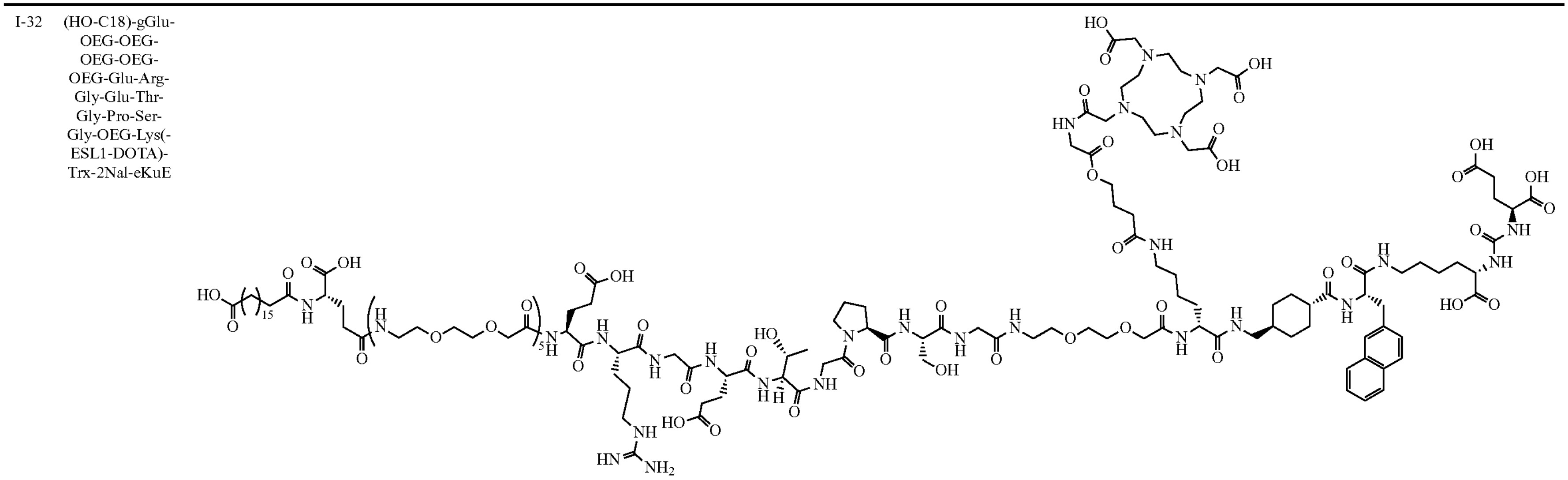 |

-continued
| I.D | Compound Name | Structure |
|---|---|---|
| I-33 | 4pIBA-Glu-OEG-$NH_2CH_2CH_2NH$-TMA[-ESL1-Lys(DOTA)-Trx-2Nal-eKuE]$_2$ | 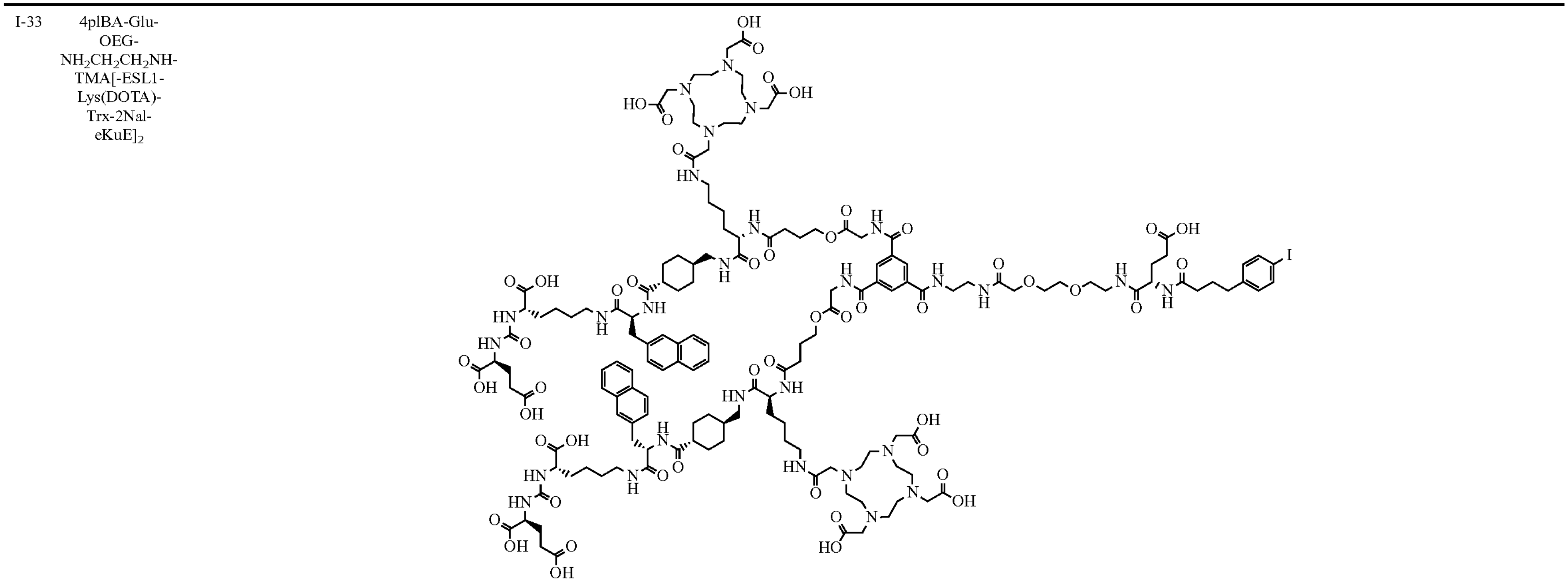 |
| I-34 | HO-C18-gGlu-Lys(-ESL1-DOTA)-OEG-OEG-OEG-$NH_2CH_2CH_2NH$-TMA(-OEG-Trx-2Nal-eKuE)$_2$ | 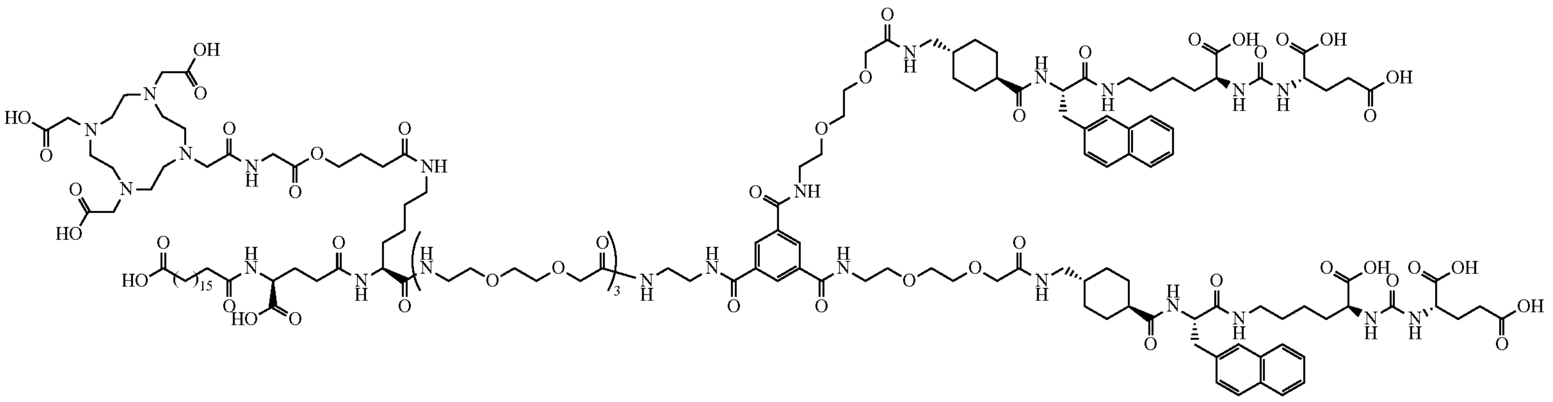 |

-continued
| I.D | Compound Name | Structure |
|---|---|---|
| I-35 | HO-C20-gGlu-OEG-OEG-Lys(-ESL1-DOTA)-OEG-$NH_2CH_2CH_2NH$-TMA(-OEG-Trx-2Nal-eKuE)$_2$ | 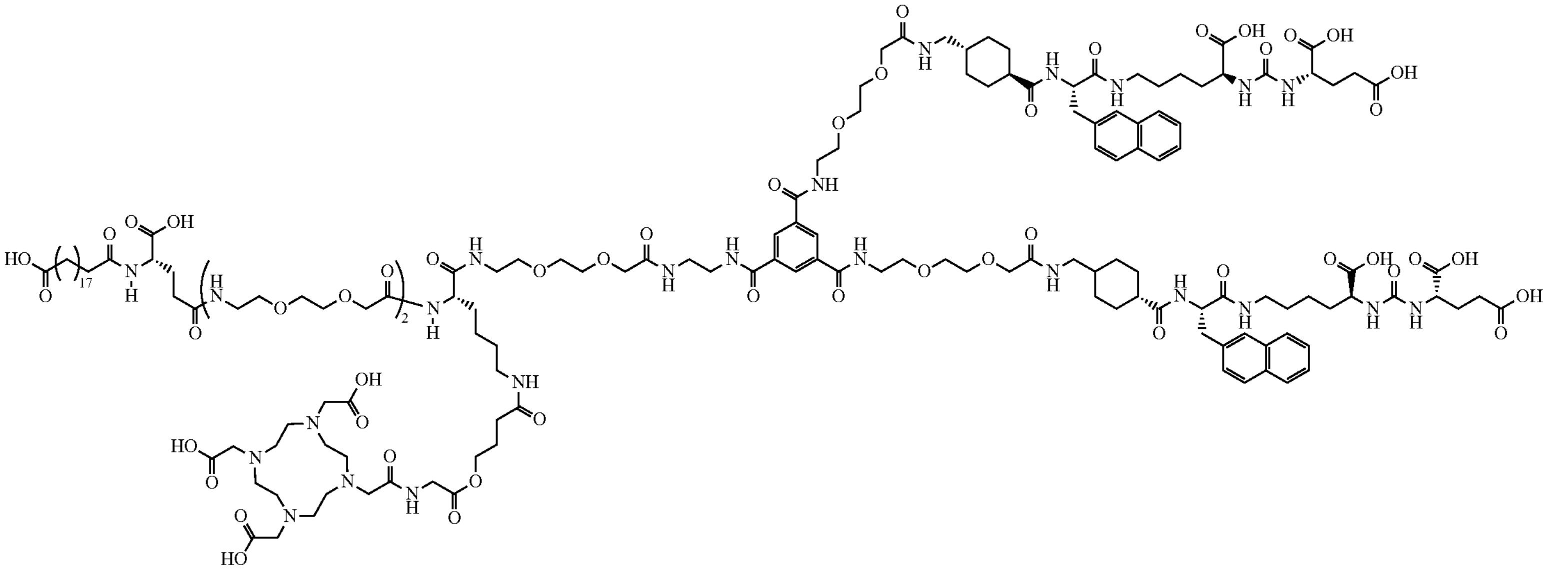 |
| I-36 | HO-C20-gGlu-Lys(-ESL2-DOTA)-OEG-OEG-OEG-$NH_2CH_2CH_2NH$-TMA(-OEG-Trx-2Nal-eKuE)$_2$ | 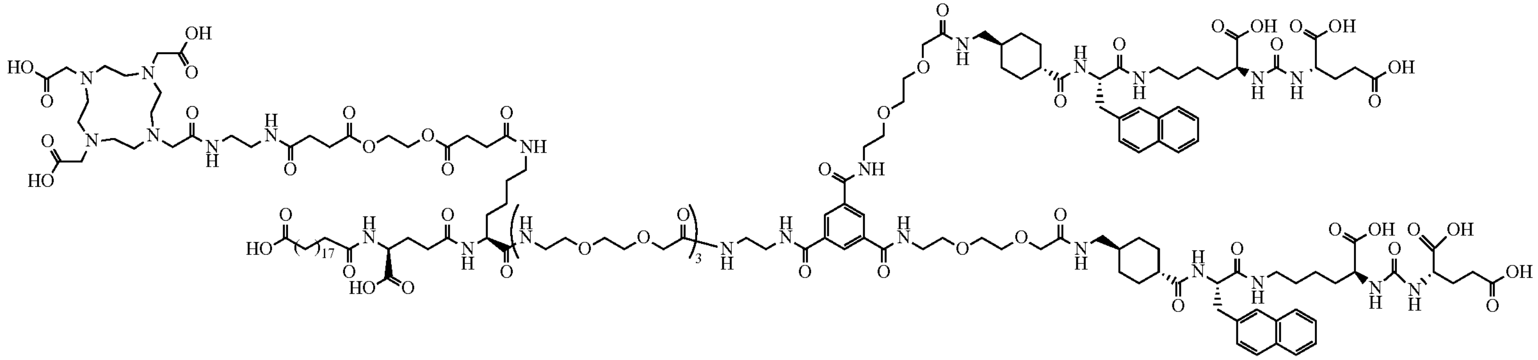 |

-continued
| I.D | Compound Name | Structure |
|---|---|---|
| I-37 | HO-C20-gGlu-Lys(-ESL1-ESL1-DOTA)-OEG-OEG-OEG-$NH_2CH_2CH_2NH$-TMA(-OEG-Trx-2Nal-eKuE)$_2$ | 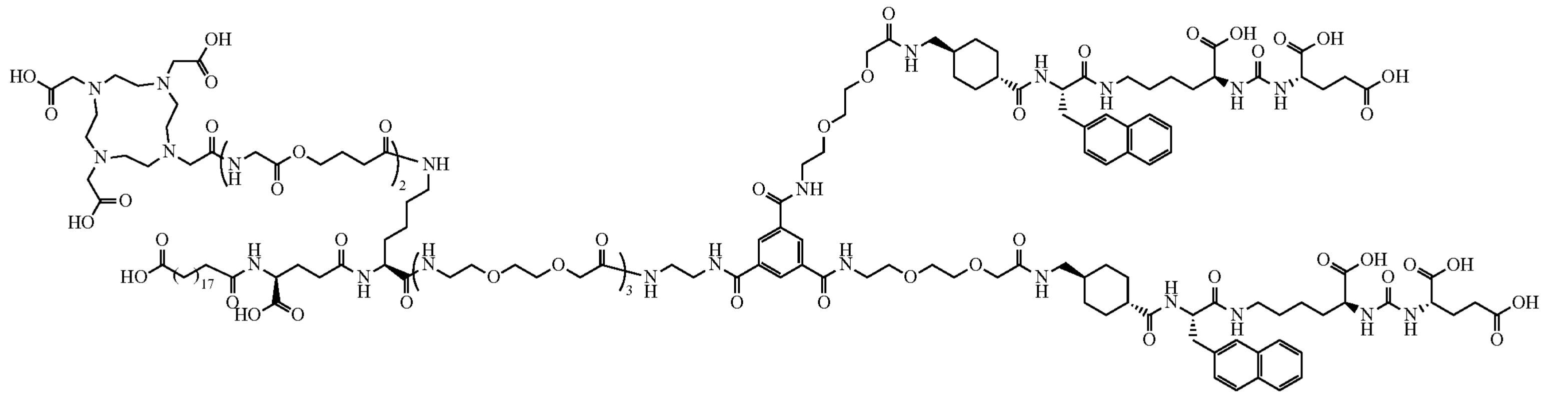 |
| I-38 | HO-C18-gGlu-OEG-OEG-Lys(-ESL1-DOTA)-OEG-$NH_2CH_2CH_2NH$-TMA(-OEG-Trx-2Nal-eKuE)2 | 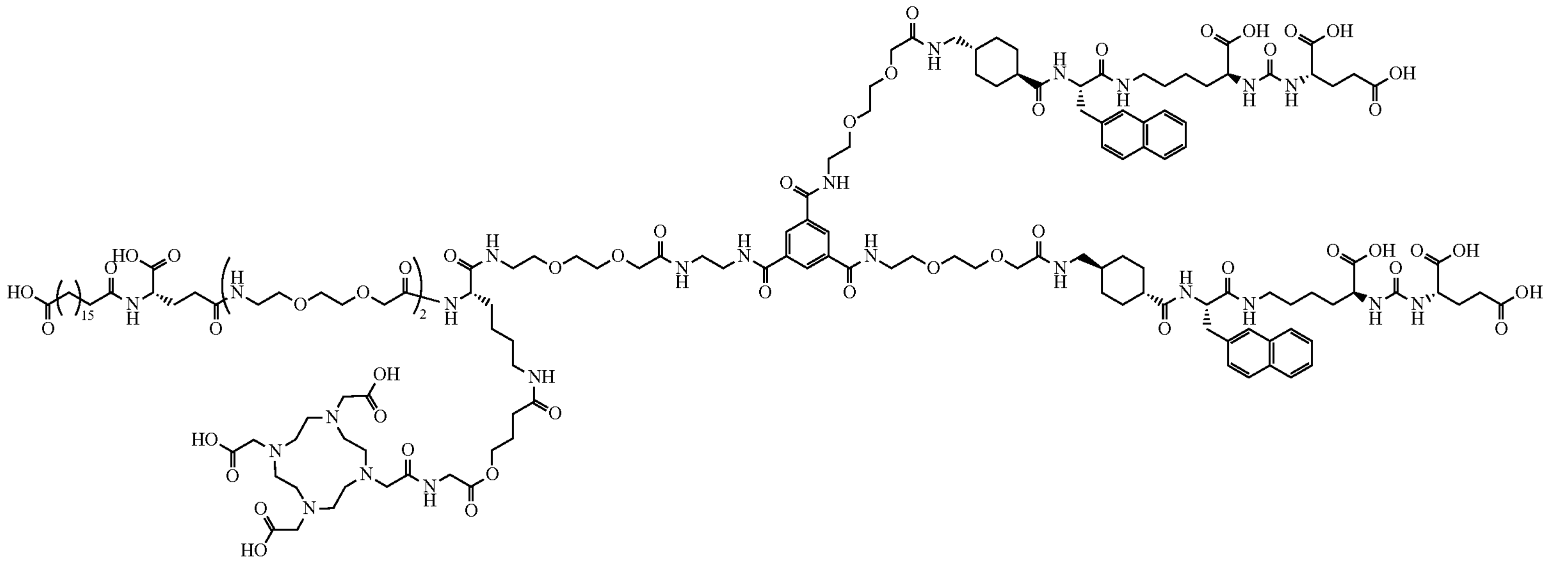 |

-continued
| I.D | Compound Name | Structure |
|---|---|---|
| I-39 | HO-C18-gGlu-Lys(-ESL2-DOTA)-OEG-OEG-OEG-$NH_2CH_2CH_2NH$-TMA(-OEG-Trx-2Nal-eKuE)2 | 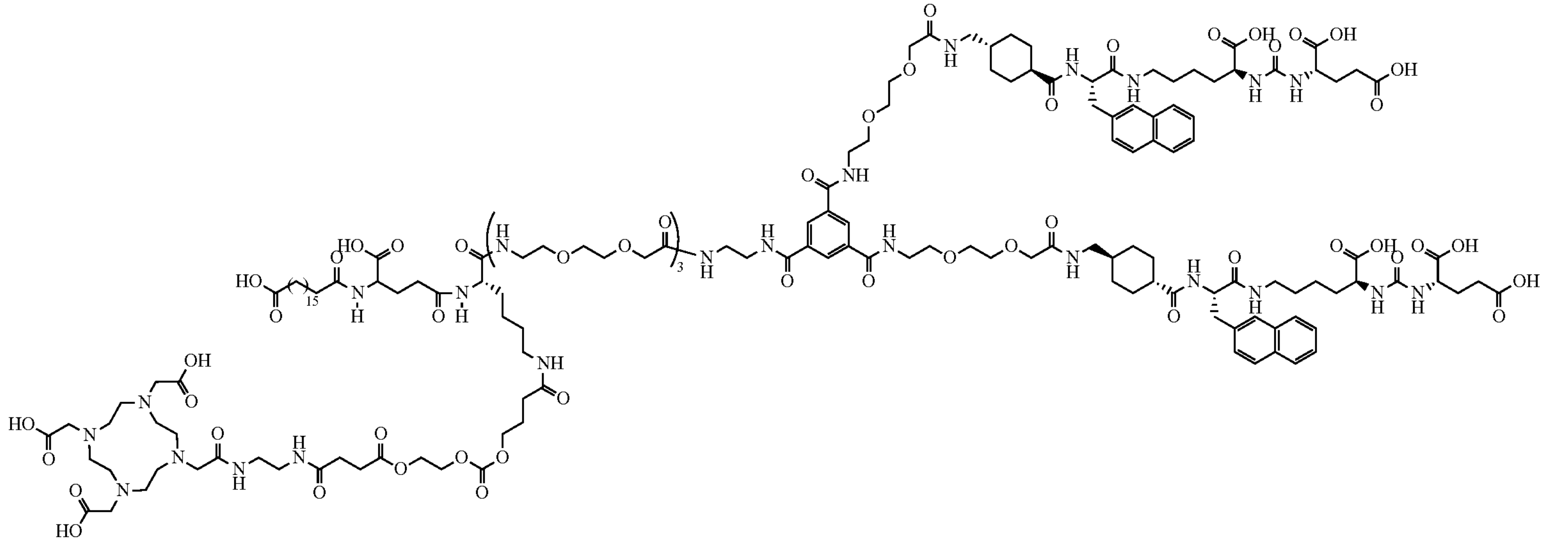 |
| I-40 | HO-C18-gGlu-OEG-Lys(-ESL1-DOTA)-OEG-$NH_2CH_2CH_2NH$-TMA(-OEG-Trx-2Nal-eKuE)2 | 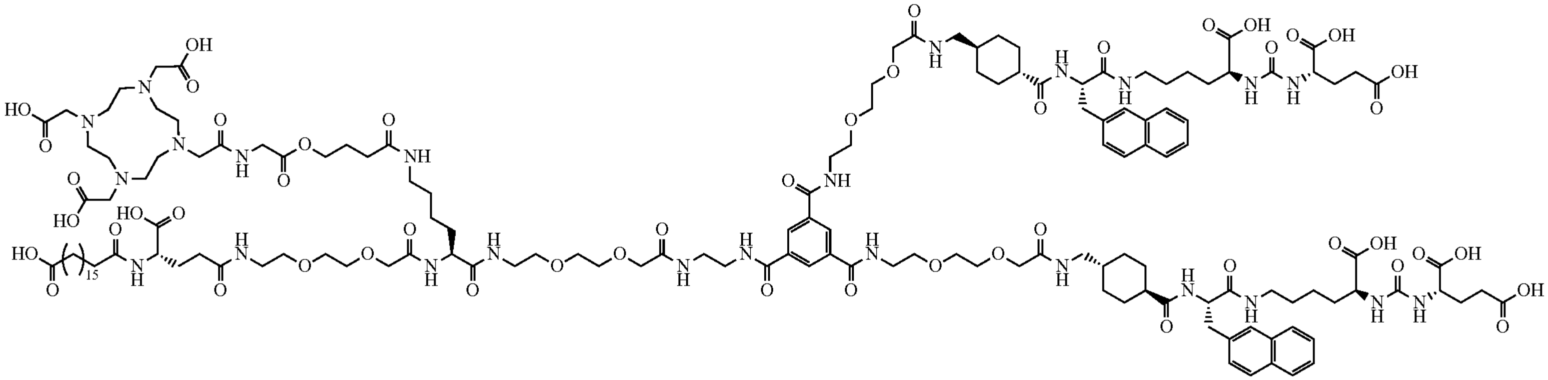 |

-continued
| I.D | Compound Name | Structure |
|---|---|---|
| I-41 | HO-C18-gGlu-OEG-OEG-$NH_2CH_2CH_2NH$-TMA[-ESL1-Lys(DOTA)-Trx-2Nal-eKuE]2 | 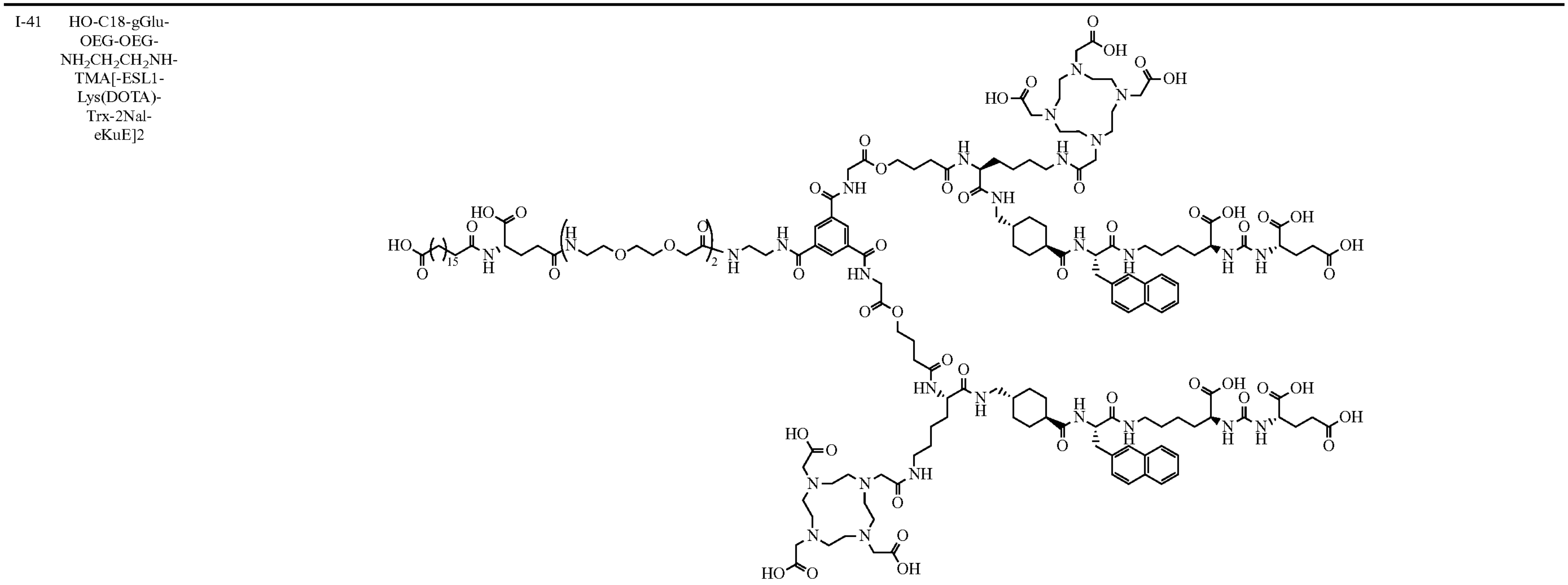 |

-continued
| I.D | Compound Name | Structure |
|---|---|---|
| I-42 | HO-C20-gGlu-OEG-OEG-$NH_2CH_2CH_2NH$-TMAI-ESL1-Lys(DOTA)-Trx-2Nal-eKuE]2 | 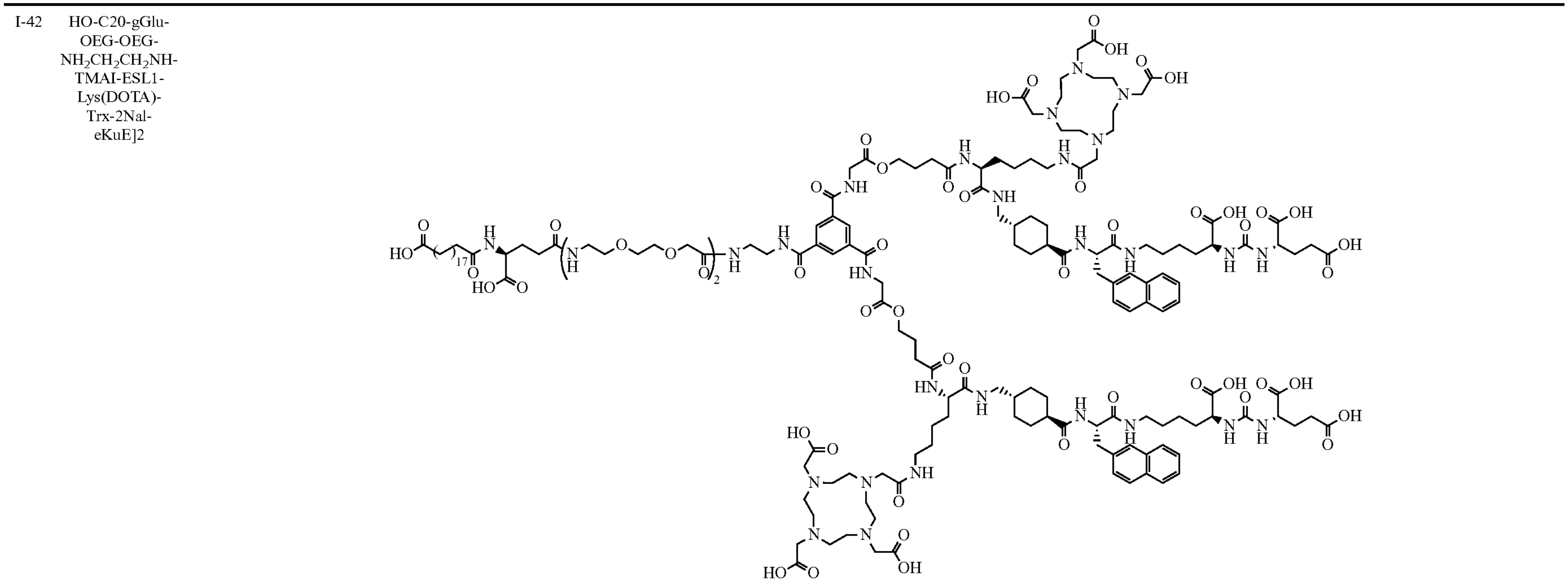 |
| I-43 | [HO-C18-gGlu-OEG-OEG-ESL1-Lys(DOTA)-OEG-$NH_2CH_2CH_2NH$-J-TMA-(-OEG-Trx-2Nal-eKuE)2 | 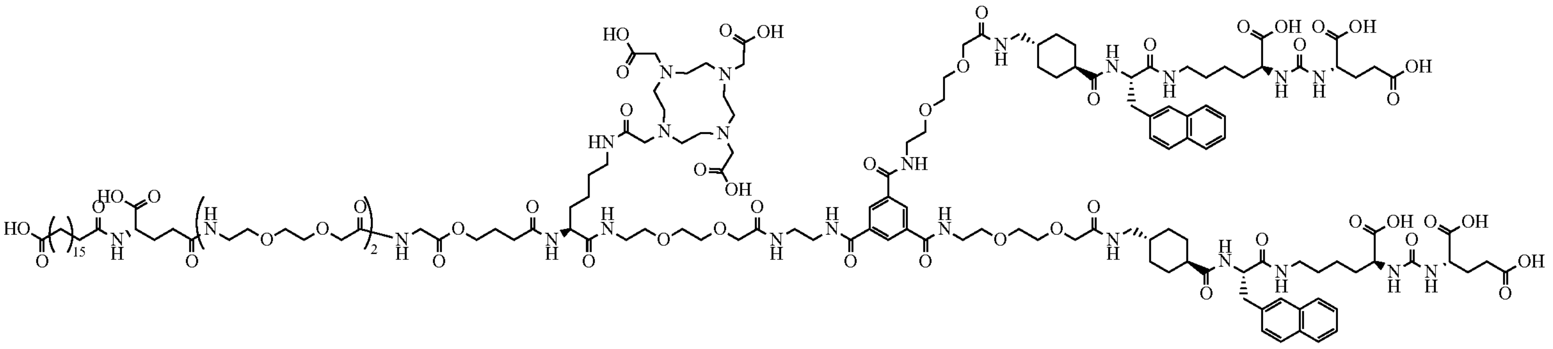 |

-continued
| I.D | Compound Name | Structure |
|---|---|---|
| I-44 | [HO-C20-gGlu-Lys(-ESL1-ESL1-ESL1-DOTA)-OEG-OEG-OEG-$NH_2CH_2CH_2NH$-]-TMA-(-OEG-Trx-2Nal-eKuE)2 | 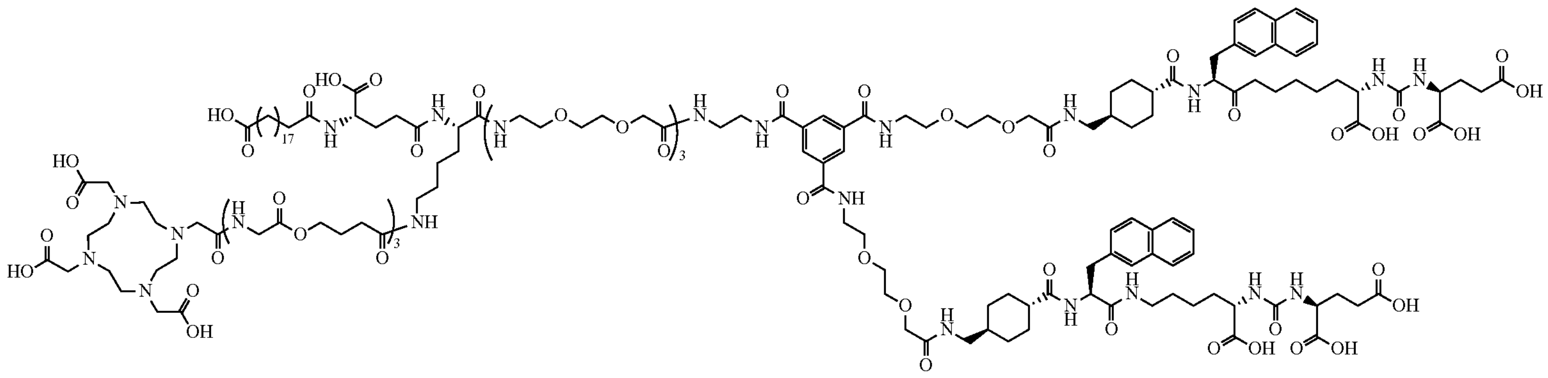 |
| I-45 | HO-C18-gGlu-OEG-OEG-Lys(-ESL1-Gly-Gly-DOTA)-OEG-Trx-2Nal-eKuE | 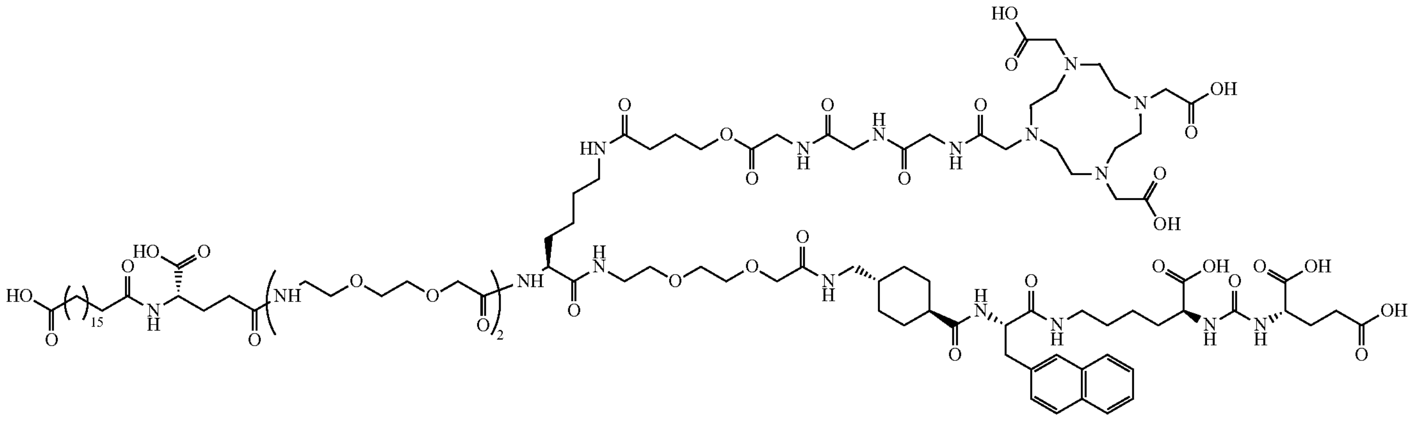 |

-continued
| I.D | Compound Name | Structure |
|---|---|---|
| I-46 | HO-C18-gGlu-OEG-OEG-Lys(-ESL1-Gly-Gly-Gly-DOTA)-OEG-Trx-2Nal-eKuE | 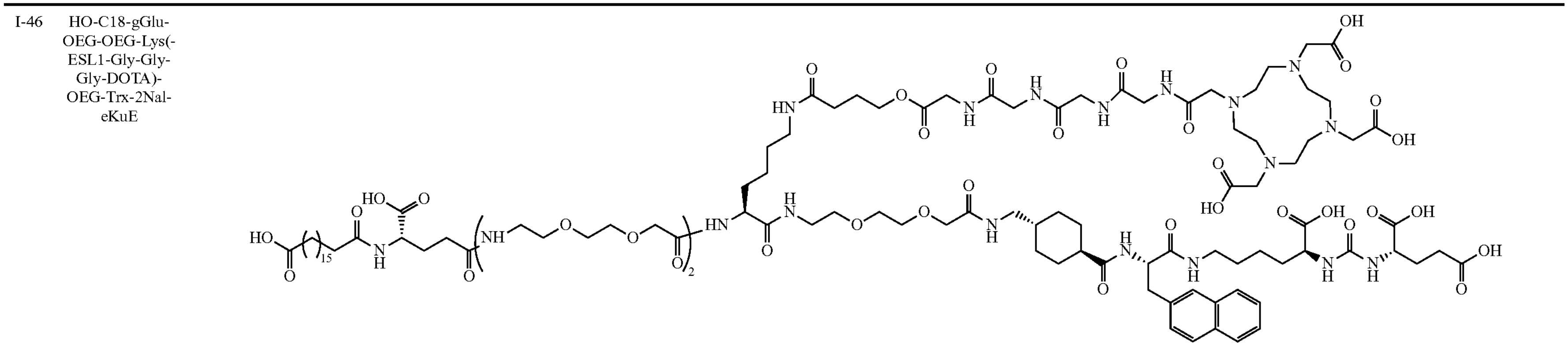 |
| I-47 | HO-C18-gGlu-OEG-OEG-Lys(-ESL1-OEG-DOTA)-OEG-Trx-2Nal-eKuE | 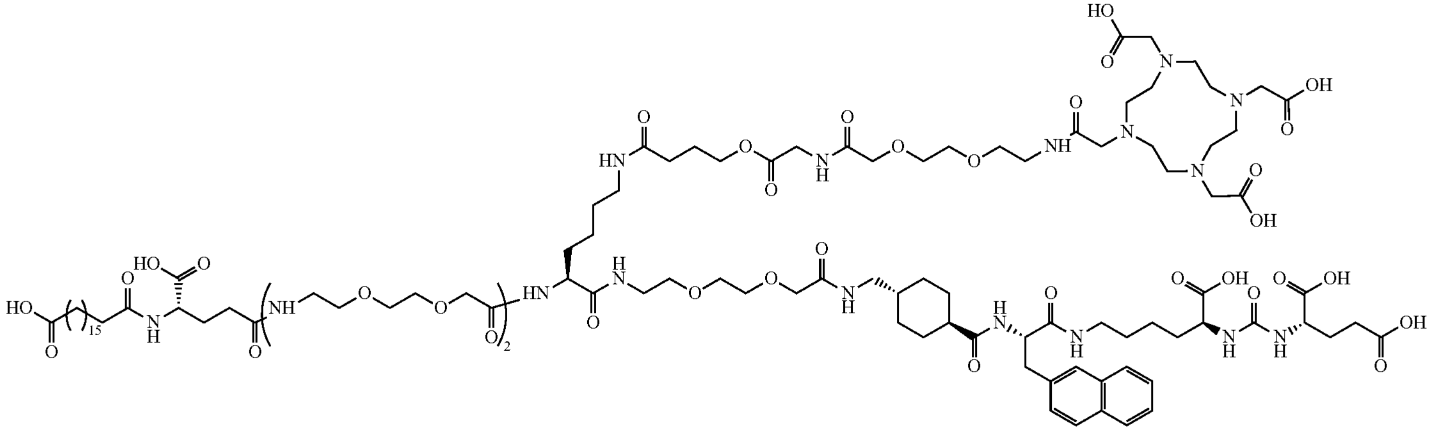 |

-continued
| I.D | Compound Name | Structure |
|---|---|---|
| I-48 | HO-C18-gGlu-OEG-OEG-Lys(-ESL1-Gly-OEG-DOTA)-OEG-Trx-2Nal-eKuE | 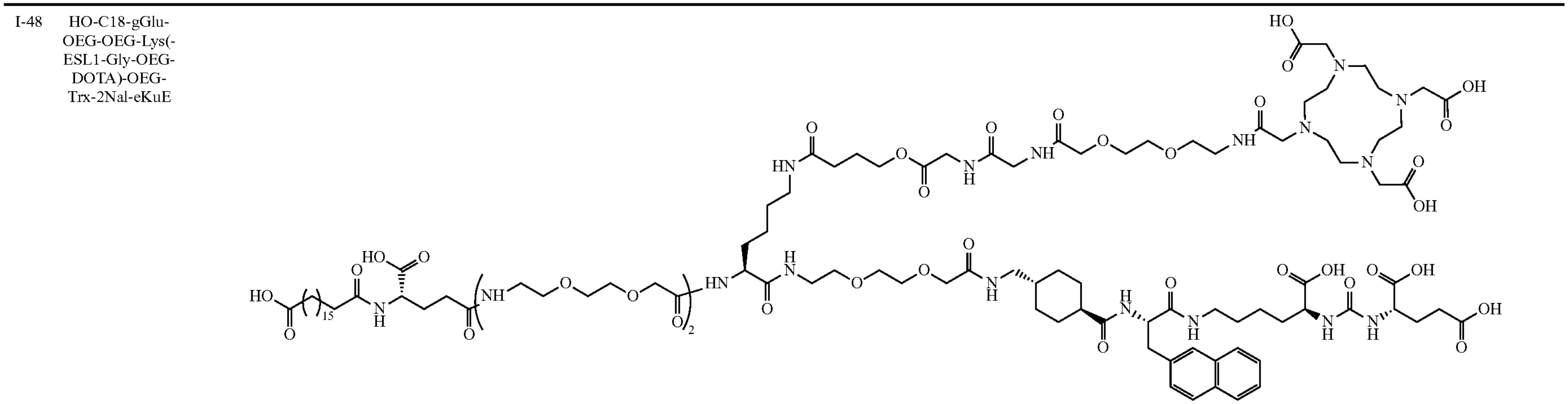 |
| I-49 | HO-C18-gGlu-OEG-OEG-Gly-5hPA-Lys(DOTA)-OEG-Trx-2Nal-eKuE | 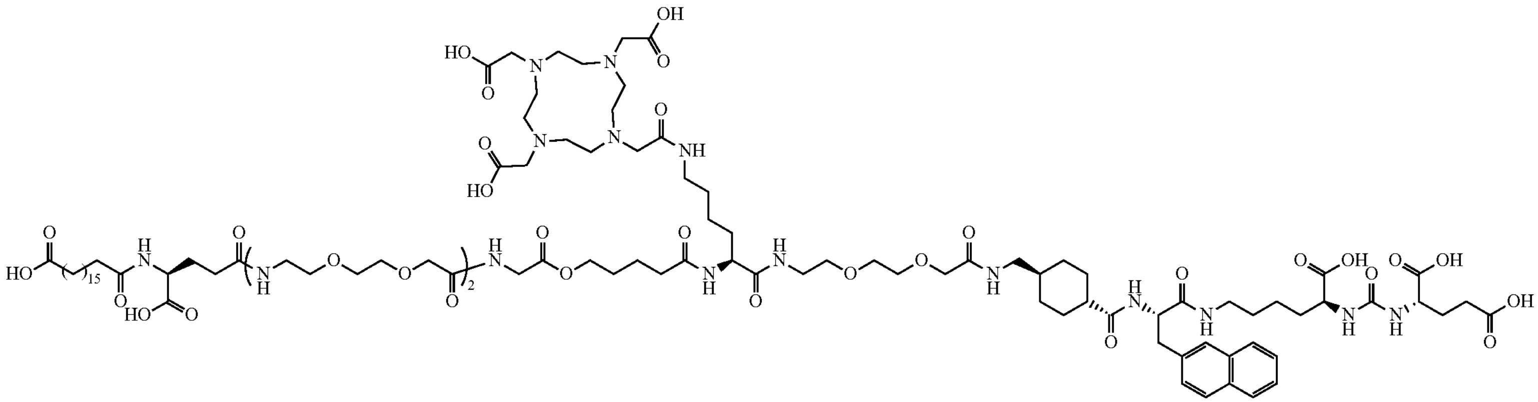 |

-continued
| I.D | Compound Name | Structure |
|---|---|---|
| I-50 | HO-C18-gGlu-OEG-OEG-Gly-6hHA-Lys(DOTA)-OEG-Trx-2Nal-eKuE | 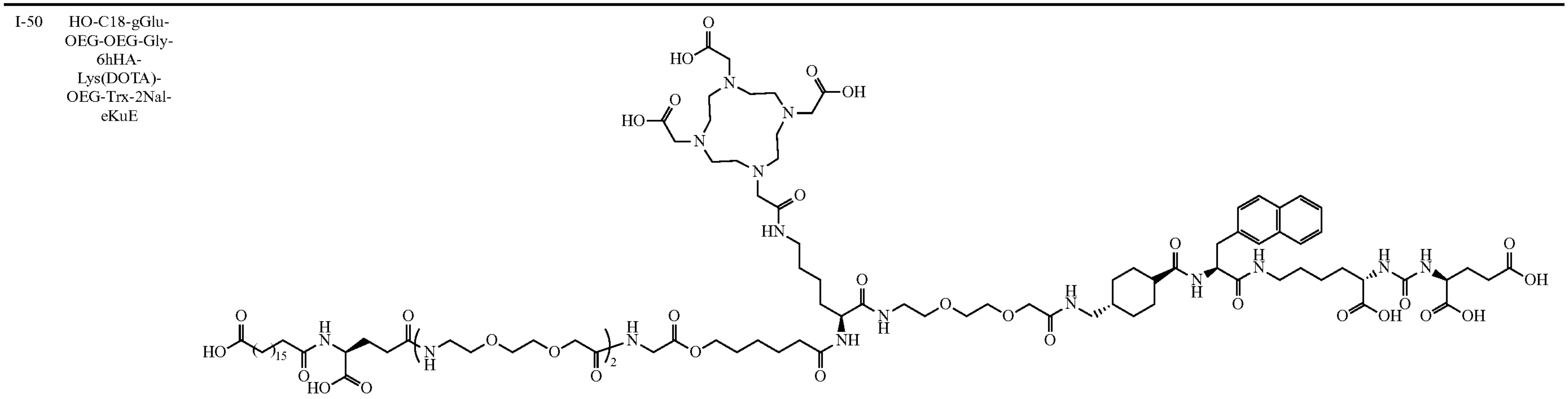 |
| I-51 | HO-C18-gGlu-OEG-OEG-ESL1-Gly-Lys(DOTA)-OEG-Trx-2Nal-eKuE | 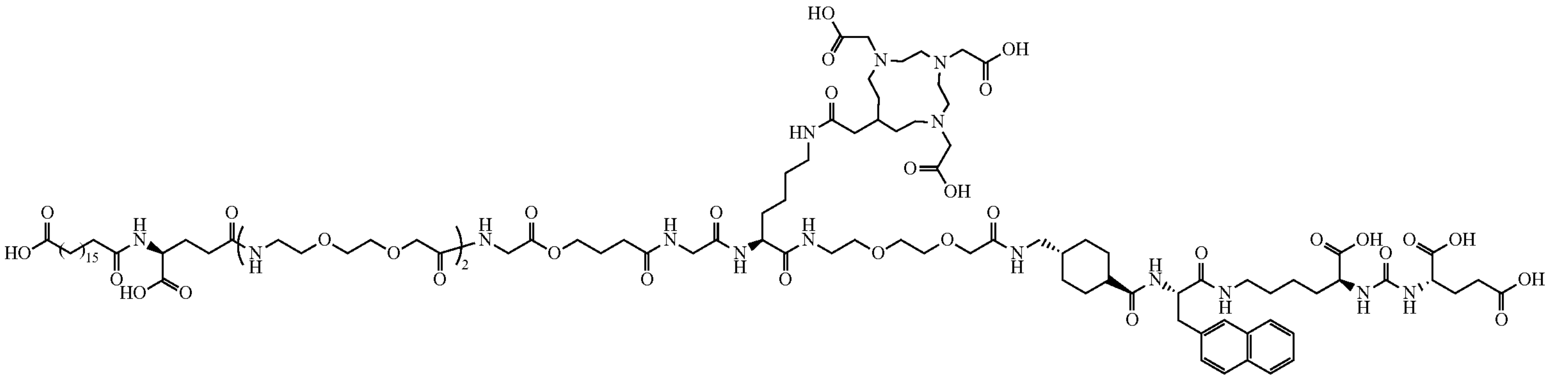 |

-continued
| I.D | Compound Name | Structure |
|---|---|---|
| I-52 | HO-C18-gGlu-OEG-OEG-ESL1-Gly-Gly-Lys(DOTA)-OEG-Trx-2Nal-eKuE | 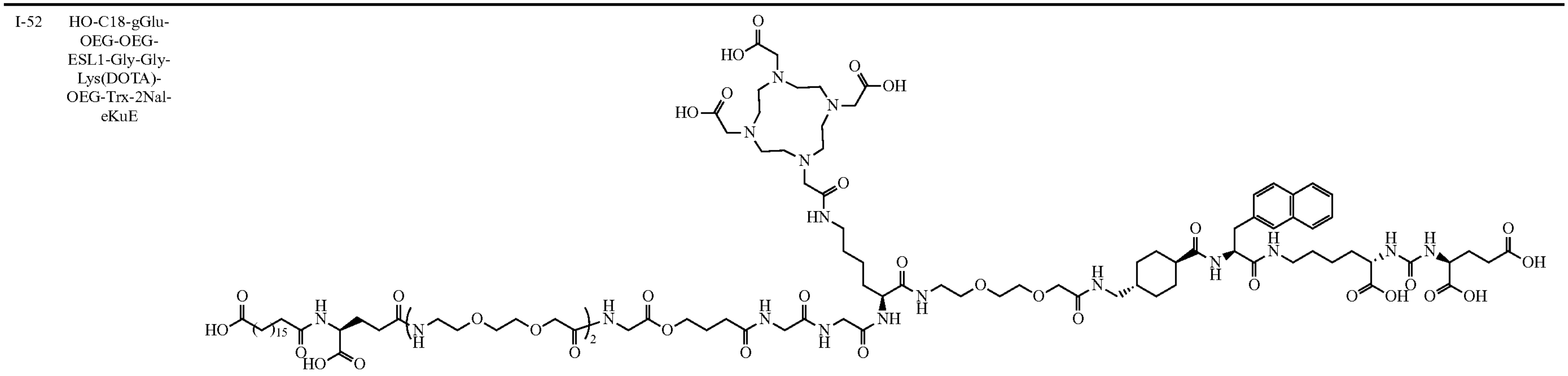 |
| I-53 | HO-C18-gGlu-OEG-OEG-Gly-4hPA-OEG-Lys(DOTA)-Trx-2Nal-eKuE | 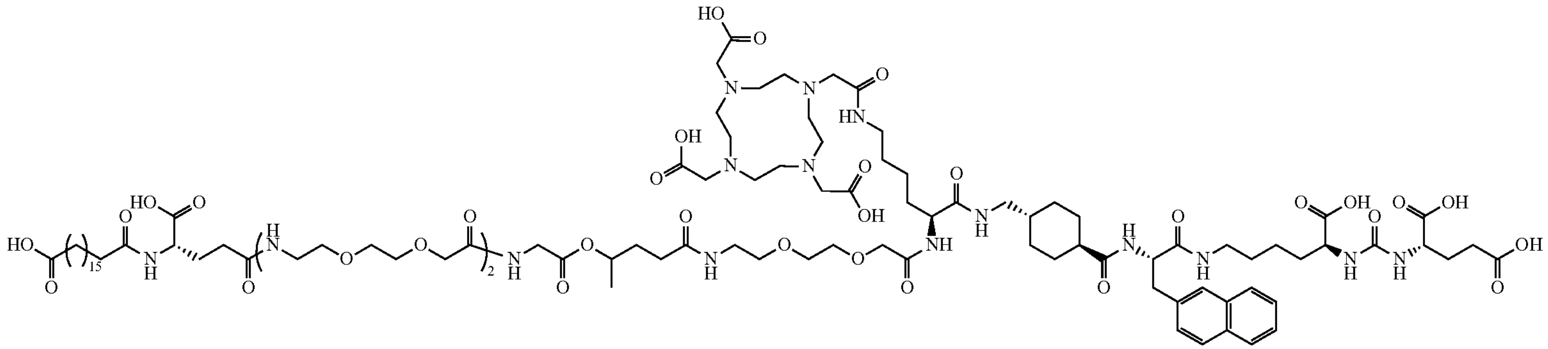 |

-continued
| I.D | Compound Name | Structure |
|---|---|---|
| I-54 | HO-C18-gGlu-OEG-OEG-Leu-4hBA-OEG-Lys(DOTA)-Trx-2Nal-eKuE | 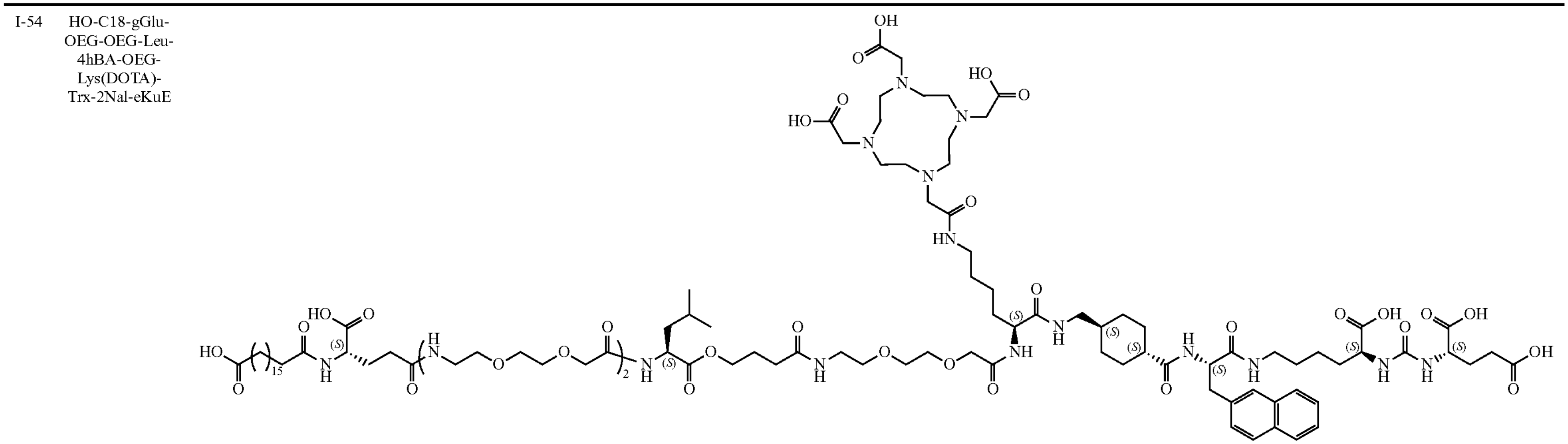 |
| I-55 (a) | (R)-HO-C18-gGlu-OEG-OEG-Leu-4hPA-OEG-Lys(DOTA)-Trx-2Nal-eKuE | 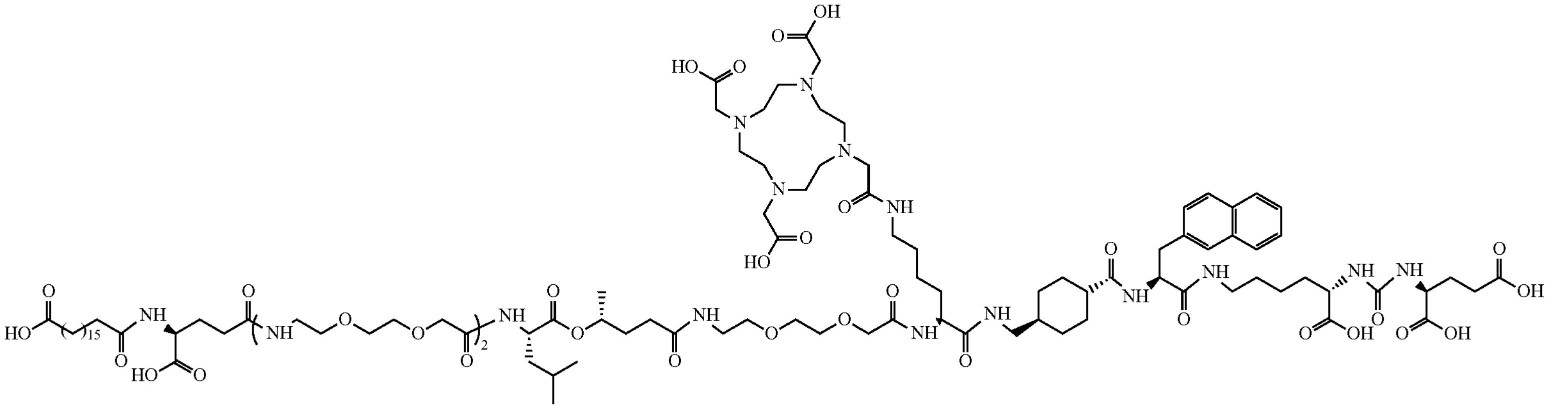 |

-continued
| I.D | Compound Name | Structure |
|---|---|---|
| I-55 (b) | (S)-HO-C18-gGlu-OEG-OEG-Leu-4hPA-OEG-Lys(DOTA)-Trx-2Nal-eKuE | 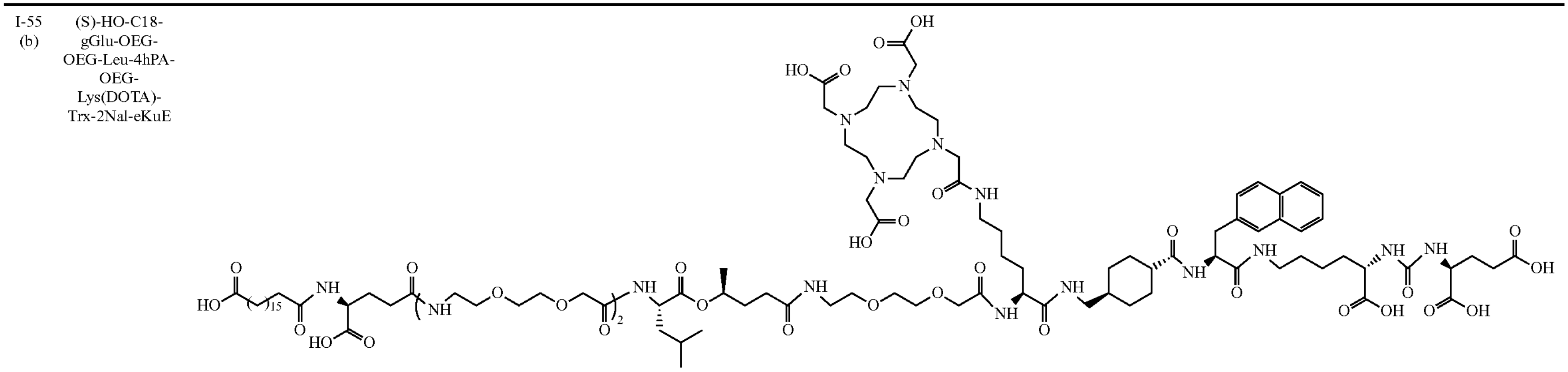 |
| I-56 | HO-C18-gGlu-OEG-OEG-OEG-ESL1-Lys(DOTA)-Trx-2Nal-eKuE | 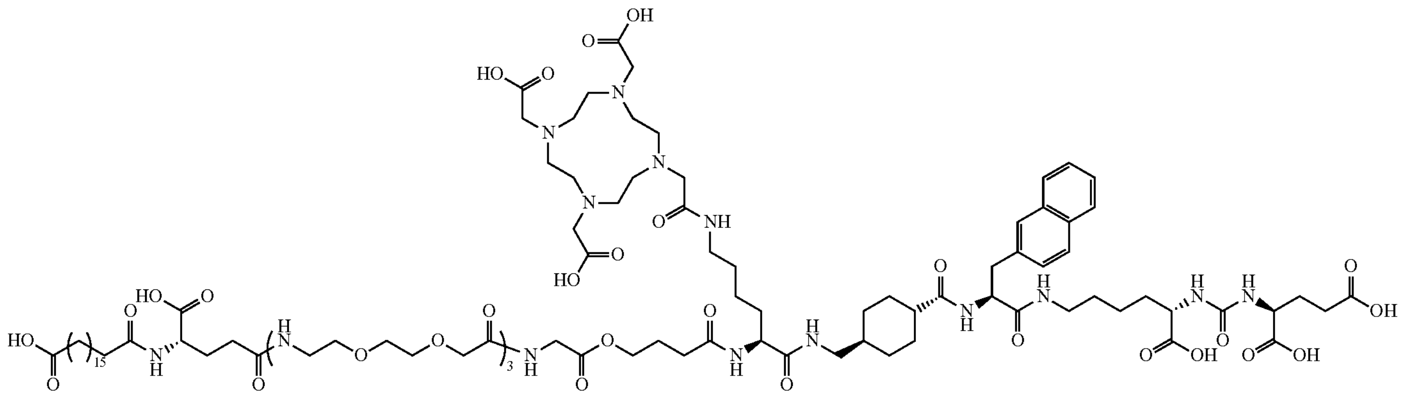 |

-continued
| I.D | Compound Name | Structure |
|---|---|---|
| I-57 | HO-C18-gGlu-OEG-OEG-Gly-OCH2CO-Lys(DOTA)-OEG-Trx-2Nal-eKuE | 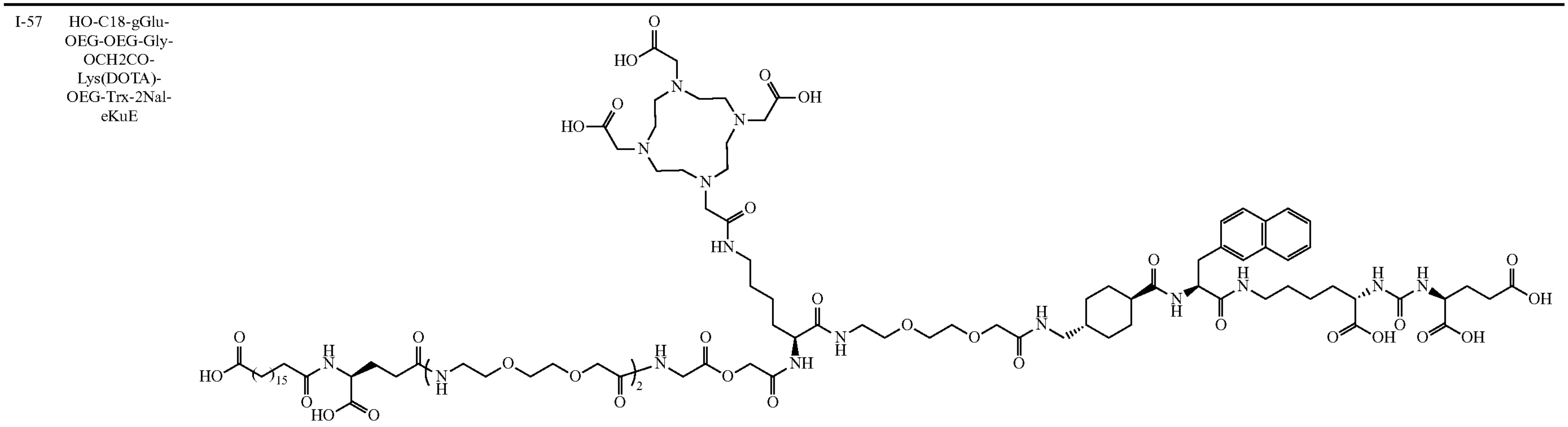 |
| I-58 | HO-C18-gGlu-OEG-OEG-ESL1-Gly-Gly-Gly-Lys(DOTA)-OEG-Trx-2Nal-eKuE | 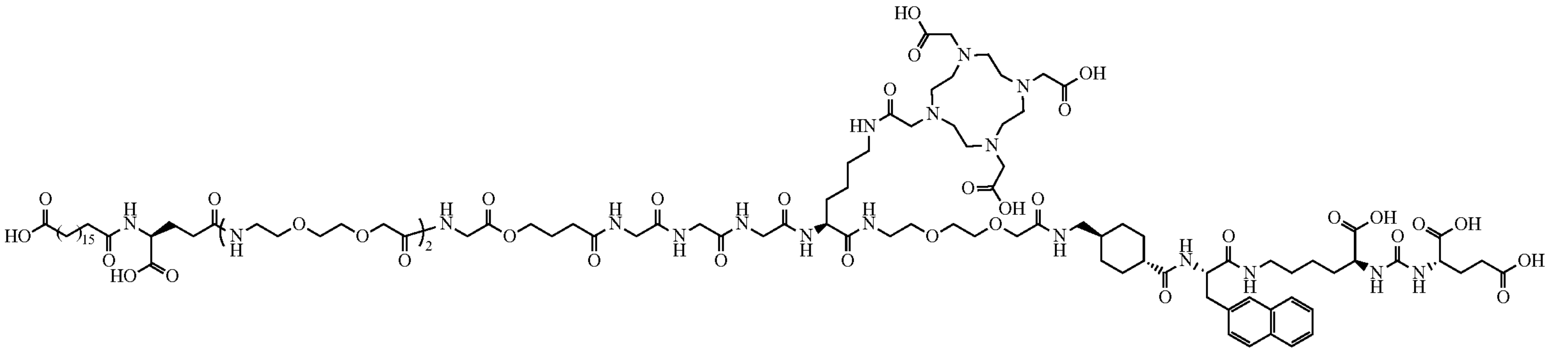 |

-continued
| I.D | Compound Name | Structure |
|---|---|---|
| I-59 | HO-C18-gGlu-OEG-OEG-Dab-4hBA-Lys(DOTA)-OEG-Trx-2Nal-eKuE | 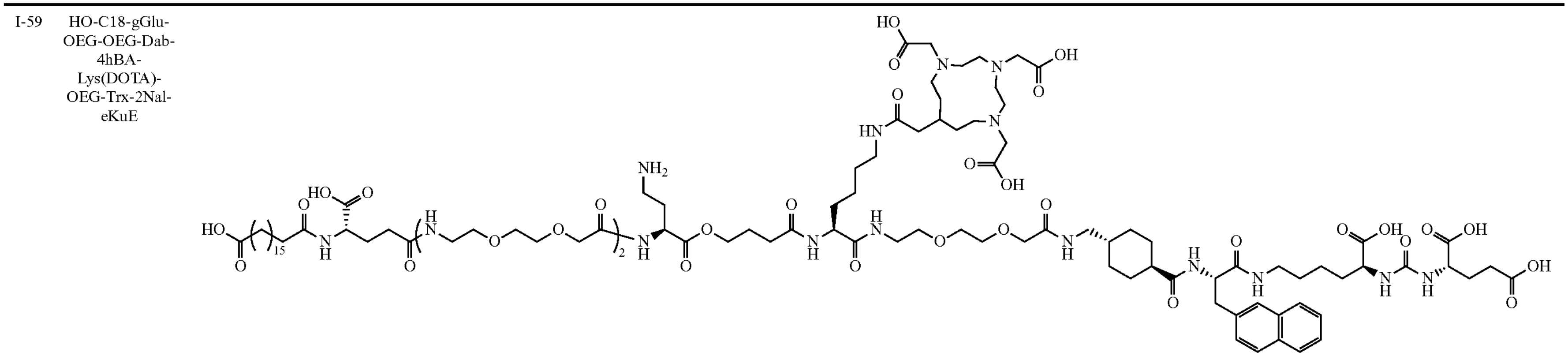 |
| I-60 | HO-C18-gGlu-OEG-OEG-Leu-4hBA-Lys(DOTA)-Trx-2Nal-eKuE | 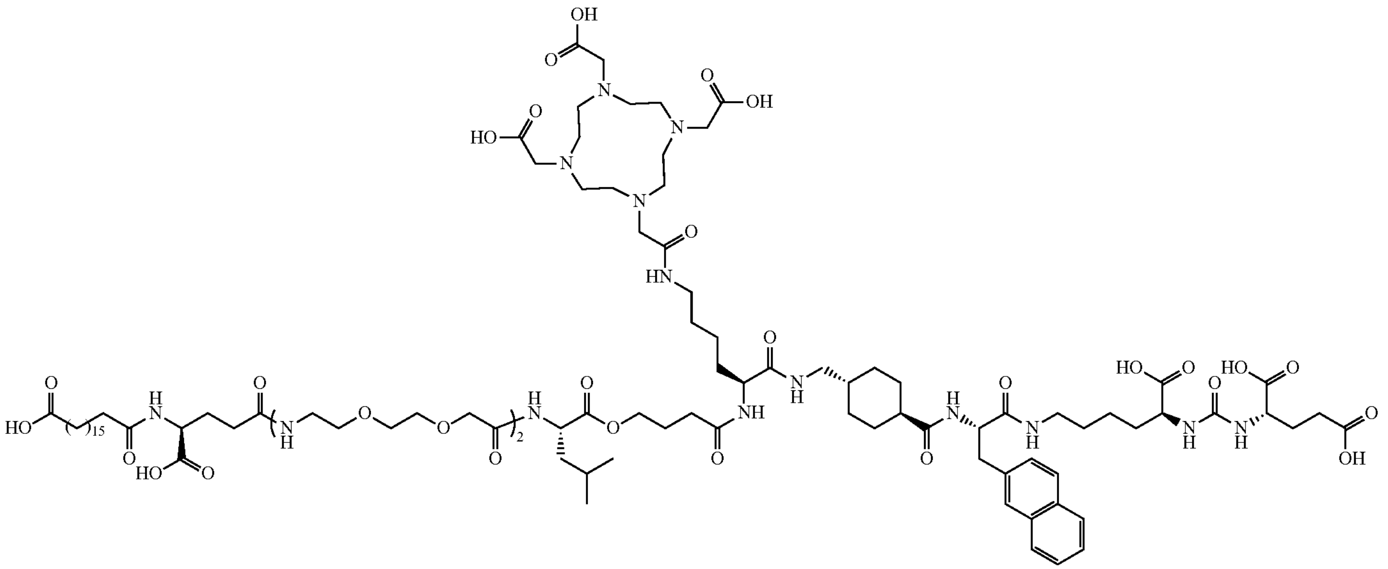 |

-continued
| I.D | Compound Name | Structure |
|---|---|---|
| I-61 | HO-C18-gGlu-OEG-OEG-ESL1-Lys(DOTA)-OEG-Gly-Tyr-Phe-eKuE | 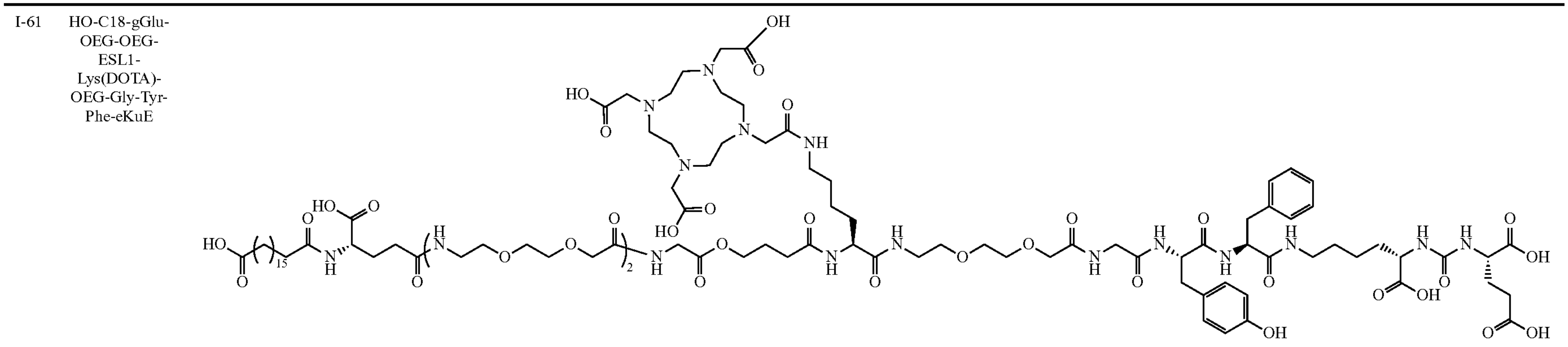 |
| I-62 | HO-C18-gGlu-OEG-OEG-ESL1-k(DOTA)-OEG-Trx-2Nal-eKuE | 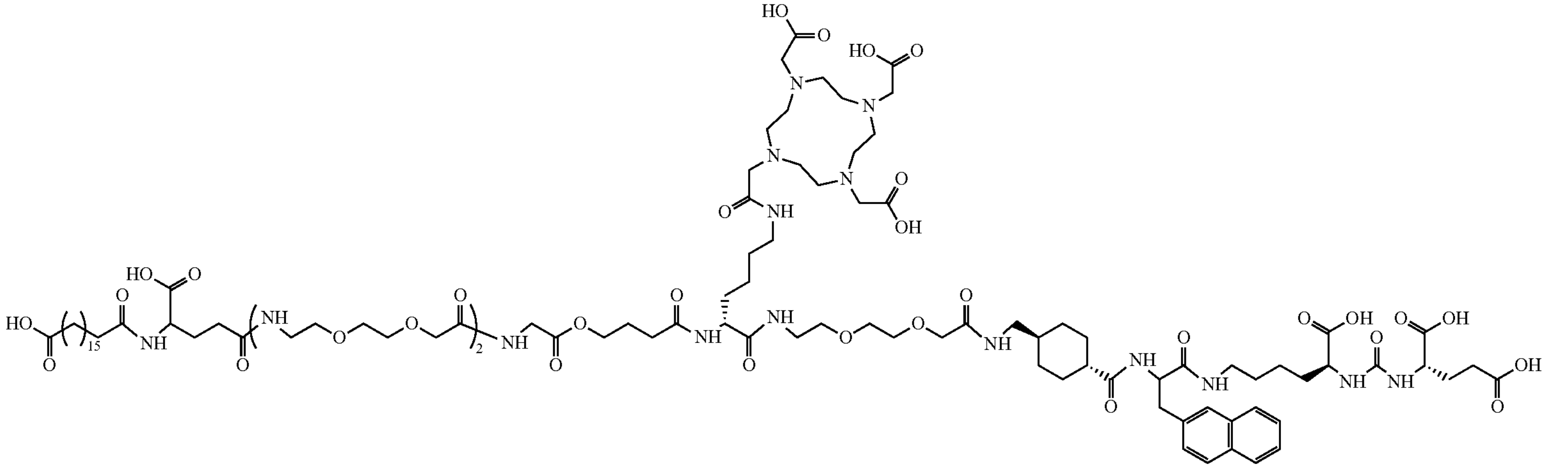 |

-continued
| I.D | Compound Name | Structure |
|---|---|---|
| I-63 | HO-C18-gGlu-OEG-OEG-ESL1-Dab(DOTA)-OEG-Trx-2Nal-eKuE | 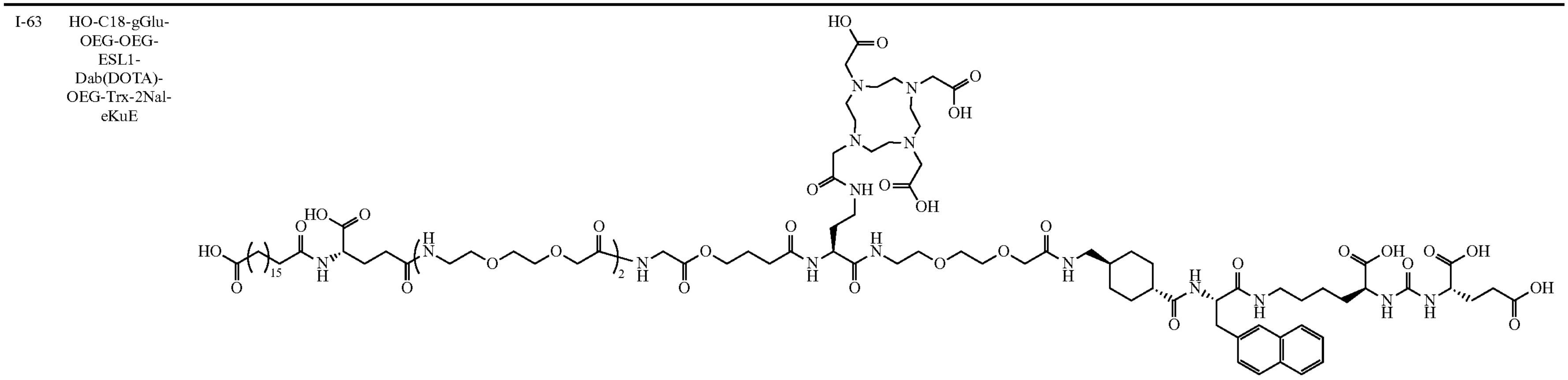 |
| I-64 | HO-C18-gGlu-OEG-OEG-ESL1-Gly-Gly-Lys(DOTA)-OEG-Gly-Tyr-Phe-eKuE | 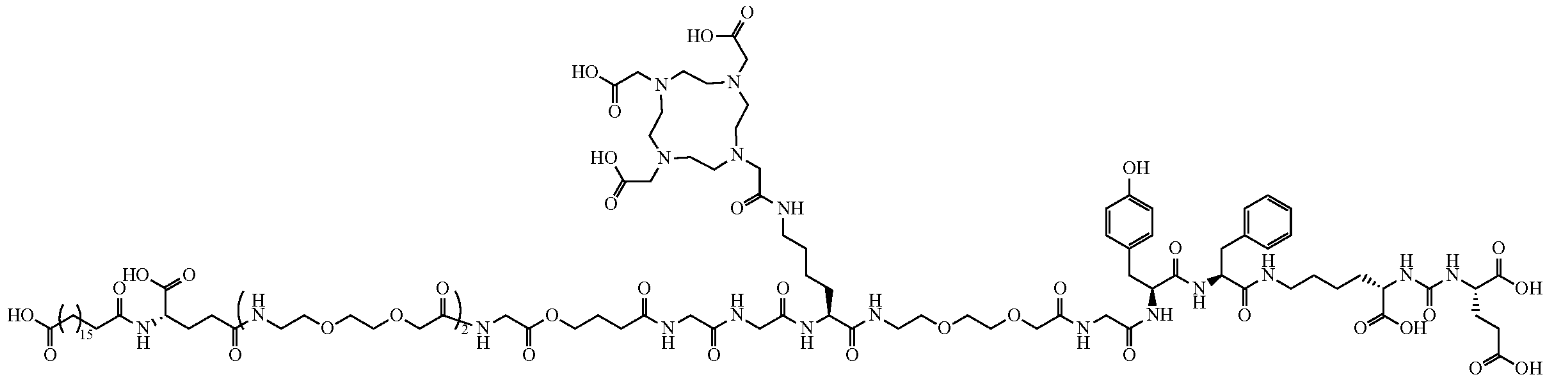 |

-continued
| I.D | Compound Name | Structure |
|---|---|---|
| I-65 | HO-C18-gGlu-OEG-OEG-ESL1-Gly-Gly-Gly-Lys(DOTA)-OEG-Gly-Tyr-Phe-eKuE | 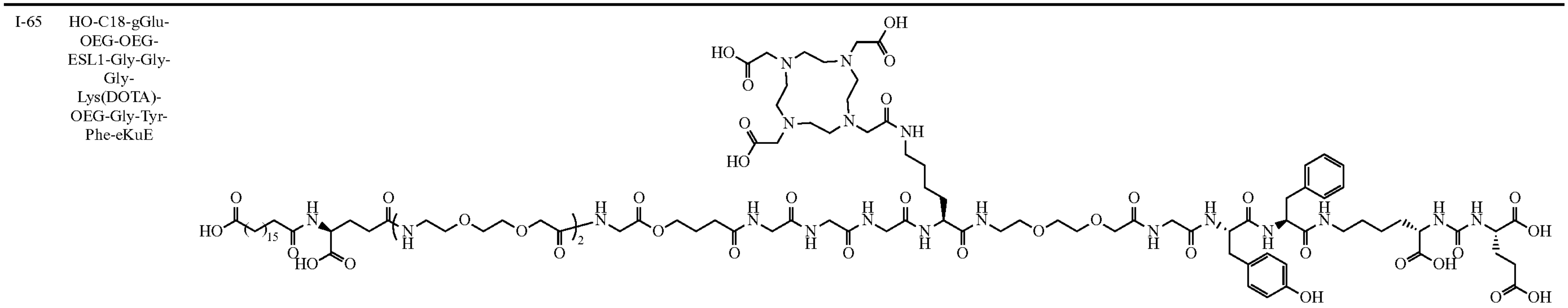 |
| I-66 | HO-C18-gGlu-OEG-OEG-Gly-5hPA-Lys(DOTA)-OEG-Gly-Tyr-Phe-eKuE | 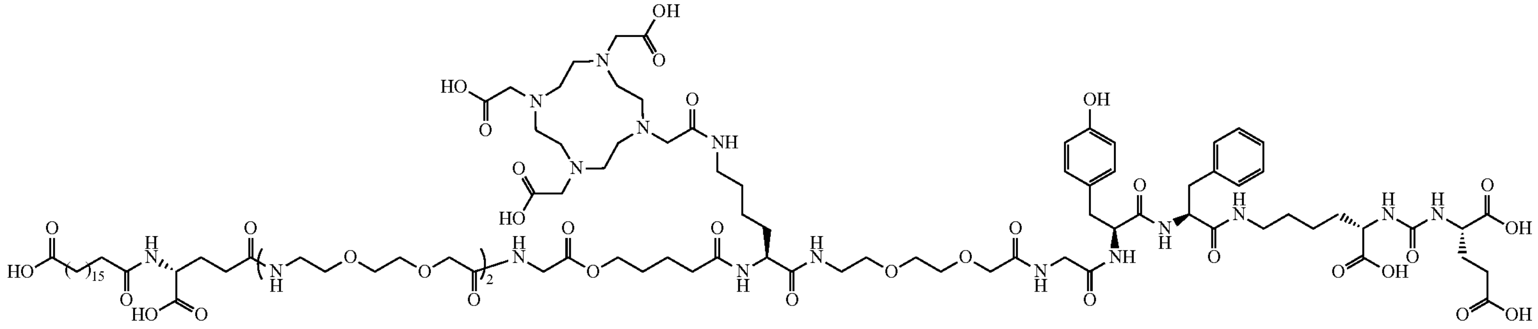 |

-continued
| I.D | Compound Name | Structure |
|---|---|---|
| I-67 | 4pIBA-gGlu-OEG-OEG-ESL1-Lys(DOTA)-OEG-Trx-2Nal-eKuE | 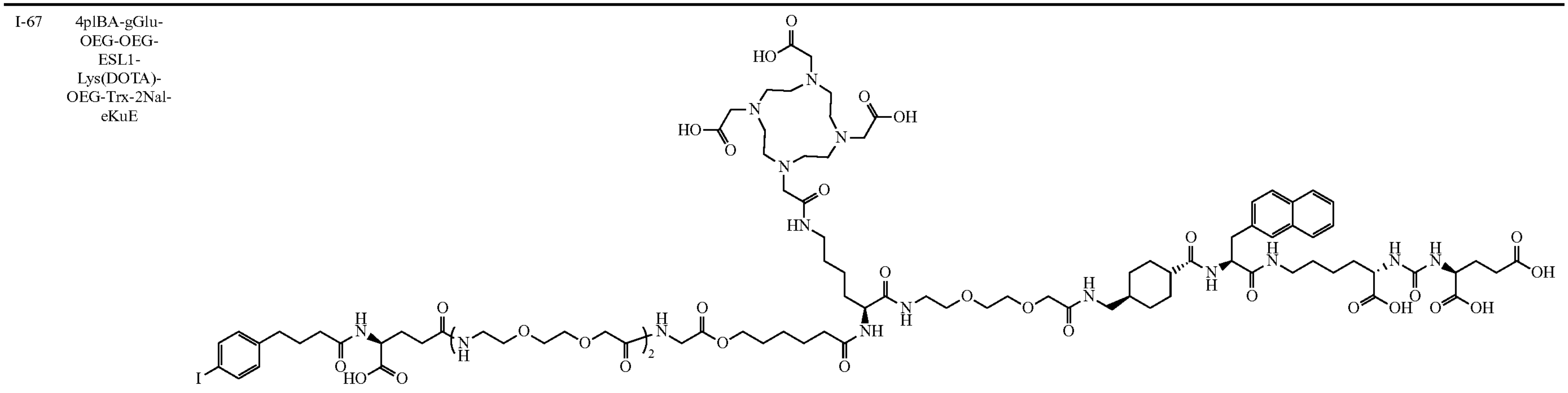 |
| I-68 | C18-gGlu-OEG-OEG-ESL1-Lys(DOTA)-OEG-Trx-2Nal-eKuE | 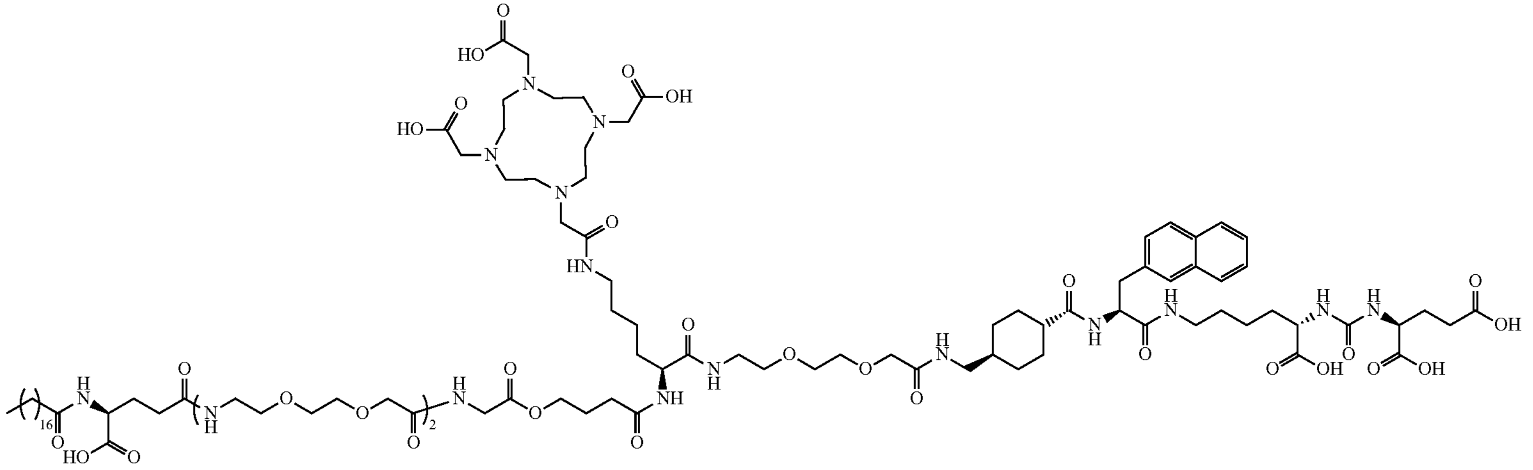 |
and -continued
| I.D | Compound Name | Structure |
|---|---|---|
| I-69 | 4pIBA-gGlu-OEG-OEG-Lys(-ESL1-DOTA)-OEG-Trx-2Nal-eKuE | 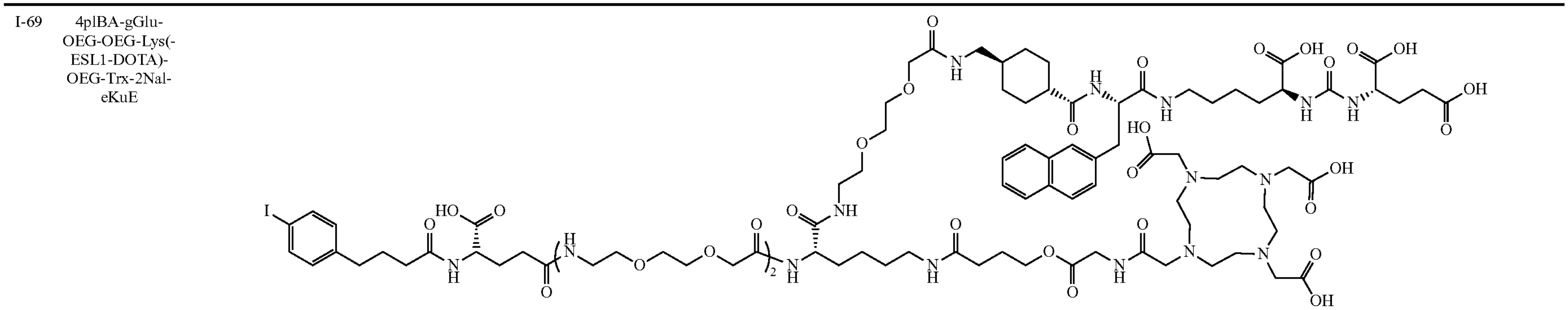 |

or a pharmaceutically acceptable salt and/or solvate thereof.

The chelating binding group is capable of complexing a radionuclide. Therefore, in some embodiments, the compound of Formula I further comprises a radioisotope complexed to the chelating binding group.

Accordingly, the present application also includes a radionuclide complex or a pharmaceutically acceptable salt and/or solvate thereof, comprising a compound of the application or a pharmaceutically acceptable salt and/or solvate thereof, and one or more radionuclides.

In some embodiments, the one or more radionuclides is a radioactive isotope of C, N, F, S, Br, Ru, Tc, Ga, In, Zn, Gd, Bi, At, Cu, Pb, Fe, Ti, F, I, Y, Sr, Ra, P, Re, Sc, Zr, Rh, Pt, Rb, Au, Sn, Tl, Co, Pm, a lanthanide, or an actinide.

In some embodiments, the lanthanide Lu, Sm, Ho, or Tb.

In some embodiments, the actinide is Ac or Th.

In some embodiments, the one or more radionuclides are selected from $^{14}$C, $^{15}$N, $^{18}$F, $^{75}$Br, $^{76}$Br, $^{77}$Br, $^{123}$I, $^{124}$I, $^{125}$I, $^{131}$I, $^{35}$S, $^{99}$Tc, $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{82}$Rb, $^{195m}$Pt, $^{191m}$Pt, $^{193m}$Pt, $^{117m}$Sn, $^{89}$Zr, $^{177}$Lu, $^{18}$F, $^{123}$I, $^{188}$Re, $^{186}$Re, $^{153}$Sm, $^{66}$Ho, $^{86}$Y, $^{87}$Y, $^{90}$Y, $^{89}$Sr, $^{111}$In, $^{153}$Gd, $^{225}$Ac, $^{212}$Bi, $^{213}$Bi, $^{211}$At, $^{198}$Au, $^{199}$Au, $^{193m}$Pt, $^{197}$Pt, $^{103}$Pd, $^{109}$Pd, $^{105}$Rh, $^{103m}$Rh, $^{223}$Ra, $^{224}$Ra, $^{97}$Ru, $^{227}$Th, $^{229}$Th, $^{32}$P, $^{161}$Tb, $^{33}$P, $^{149}$Tb, $^{125}$I, $^{203}$Pb, $^{212}$Pb, $^{201}$Tl, $^{119}$Sb, $^{58m}$Co, $^{55}$Co, $^{47}$Sc, $^{149}$Pm and $^{161}$Ho.

In some embodiments, the one or more radionuclide are for use in imaging or for use in therapy.

In some embodiments, the one or more radionuclide for use in imaging is selected from $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{82}$Rb, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, $^{203}$Pb and $^{123}$I. In some embodiments, the one or more radionuclides for use in imaging is $^{111}$In. In some embodiments, the one or more radionuclides for use in imaging is $^{177}$Lu In some embodiments, one or more radionuclides for use in therapy are selected from $^{188}$Re, $^{186}$Re, $^{153}$Sm, $^{66}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{99}$Au, $^{195m}$Pt, $^{193m}$Pt, $^{197}$Pt, $^{117m}$Sn, $^{103}$Pd, $^{105}$Rh, $^{103m}$Rh, $^{177}$Lu, $^{223}$Ra, $^{224}$Ra, $^{227}$Th, $^{229}$Th, $^{149}$Tb, $^{32}$P, $^{161}$Tb, $^{33}$P, $^{125}$I, $^{203}$Pb, $^{212}$Pb, $^{201}$Tl, $^{119}$Sb, $^{58m}$Co, $^{47}$Sc, $^{149}$Pm and $^{161}$Ho.

In some embodiments, the radionuclides for use in therapy are selected from $^{177}$Lu, $^{212}$Pb and $^{225}$Ac. In some embodiments, the one or more radionuclides for use in imaging is $^{177}$Lu.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art.

Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

III. Compositions and Kits of the Application

The compounds and complexes of the present application are suitably formulated in a conventional manner into compositions using one or more carriers. Accordingly, the present application also includes a composition comprising one or more compounds or complexes of the application and a carrier. The compounds or complexes of the application are suitably formulated into pharmaceutical compositions for administration to subjects in a biologically compatible form suitable for administration in vivo. Accordingly, the present application further includes a pharmaceutical composition comprising one or more compounds or complexes of the application and a pharmaceutically acceptable carrier. In embodiments of the application the pharmaceutical compositions are used in the treatment of any of the diseases, disorders or conditions described herein.

The present application also includes a kit comprising
- one or more compounds of Formula I as defined above, or a pharmaceutically acceptable salt and/or solvate thereof, and
- instructions for administration of the one or more compounds of Formula I, or a pharmaceutically acceptable salt and/or solvate thereof, to a subject in need thereof.

The present application also includes a kit comprising
- one or more compounds of Formula I as defined above, or a pharmaceutically acceptable salt and/or solvate thereof, and
- one or more radioisotope as defined above, and
- optionally instructions for administration of the one or more compounds of Formula I, or a pharmaceutically acceptable salt and/or solvate thereof, to a subject in need thereof and the radioisotope to a subject in need thereof.

The present application also includes a kit comprising
- one or more complexes of the application as defined above, or a pharmaceutically acceptable salt and/or solvate thereof, and
- instructions for administration of the one or more compounds complexes to a subject in need thereof.

In some embodiments, the one or more compounds of Formula I or a pharmaceutically acceptable salt and/or solvate thereof as defined above, the one or more complexes or a pharmaceutically acceptable salt and/or solvate thereof as defined above, or the one or more radioisotope as defined above and are each present in the kits in one or more pharmaceutical compositions.

In some embodiments, the pharmaceutical compositions comprising the one or more compounds of Formula I or a pharmaceutically acceptable salt and/or solvate thereof as defined above, the one or more complexes or a pharmaceutically acceptable salt and/or solvate thereof as defined above, or the one or more radioisotope as defined above are formulated for parenteral administration as described below. In some embodiments, the parenteral administration is by injection.

In some embodiments, the kit further comprises a pharmaceutically acceptable buffer such as bacteriostatic water for injection (BWFI), phosphate-buffered saline, Ringer's solution or dextrose solution. In some embodiments, the pharmaceutically acceptable buffer is present in the kits in one or more containers such as vial or ampoule.

In some embodiments, the kits are for use in imaging. In some embodiments, the kits are for use in therapy. In some embodiments, the kits are for use in treating cancer. In some embodiments, the kits are adapted and/or arranged to carry out any method of the present application. Therefore, the present application also includes pharmaceutical packages or kits adapted and arranged to carry out any method of the present application.

The compounds or complexes of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, minipump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound or complex of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound or complex of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiments, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound or complex of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds or complexes of the application are suitably in a sterile powder form for reconstitution with a suitable vehicle, e.g., sterile pyrogen-free water, before use.

In some embodiments, compositions for nasal administration are conveniently formulated as aerosols, drops, solutions, gels and powders.

Compositions suitable for buccal or sublingual administration include tablets, lozenges, and pastilles, wherein a compound or complex of the application is formulated with a carrier such as sugar, acacia, tragacanth, or gelatin and glycerine.

Suppository forms of the compounds or complexes of the application are useful for vaginal, urethral and rectal administrations.

In some embodiments a compound or complex of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound or complex of the application including pharmaceutically acceptable salts and/or solvates thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

III. Methods and Uses of the Application

Accordingly, the present application also includes a method of treating a disease or disorder comprising administering a therapeutically effective amount of one or more compounds or complexes of the application or a pharmaceutically acceptable salt and/or solvate thereof to a subject in need thereof. The present application also includes a use of one or more compounds or complexes of the application or a pharmaceutically acceptable salt and/or solvate thereof for treatment of a disease or disorder as well as a use of one or more compounds or complexes of the application or a pharmaceutically acceptable salt and/or solvate thereof for the preparation of a medicament for treatment of a disease or disorder. The application further includes one or more compounds or complexes of the application or a pharmaceutically acceptable salt and/or solvate thereof for use in treating a disease or disorder.

In one embodiment, a target of the target binding group of the compound or complex is present on disease cells. Indeed, the presence and/or overexpression of receptors on the cell surface is a hallmark of many disease associated cells including cancer cells. According, in another embodiment, a target of the target binding group (for example a cell surface receptor) is present on cancer cells and disease or disorder is cancer. For example, in one embodiment, the target of the target binding group is PSMA and the disease or disorder is prostate cancer. In another embodiment, the target of the target binding group is Somatostatin receptor 2 and the disease or disorder is a neuroendocrine tumor.

In one embodiment, the disease or disorder is cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; Wilms' Tumor and a neuroendocrine tumor. Metastases of the aforementioned cancers can also be treated in accordance with the methods described herein.

In an embodiment, the cancer is prostate cancer or a neuroendocrine tumor.

In an embodiment, the cancer is a PSMA positive cancer. In an embodiment, the PSMA positive cancer is prostate cancer.

Efficaciousness of treatment is determined in association with any known method for diagnosing or treating the particular cancer. Alleviation of one or more symptoms of the cancer indicates that the compound or complex confers a clinical benefit.

The compound or complex may be administered in combination with at least one additional cancer therapy, including chemotherapy, radiation and/or immuno-oncology therapy. The other cancer therapy may be administered in any order with the at least one additional cancer therapy, for example simultaneously, sequentially or separately.

As used herein, "treating a cancer" includes, but is not limited to, reversing, alleviating or inhibiting the progression of the cancer or symptoms or conditions associated with the cancer. "Treating the cancer" also includes extending survival in a subject. Survival is optionally extended by at least 1, 2, 3, 6 or 12 months, or at least 2, 3, 4, 5 or 10 years over the survival that would be expected without treatment with a cytotoxic agent or composition as described herein. "Treating the cancer" also includes reducing tumour mass and/or reducing tumour. Optionally, tumour mass and/or tumour burden is reduced by at least 5, 10, 25, 50, 75 or 100% following treatment with a cytotoxic agent or composition as described herein. "Treating the cancer" also includes reducing the aggressiveness, grade and/or invasiveness of a tumour.

The application also includes a method of inhibiting proliferative activity in a cell, comprising administering an effective amount of one or more compounds or complexes of the application or a pharmaceutically acceptable salt and/or solvate thereof to the cell. The present application also includes a use of one or more compounds or complexes of the application or a pharmaceutically acceptable salt and/or solvate thereof for inhibition of proliferative activity in a cell as well as a use of one or more compounds one or more compounds or complexes of the application or a pharmaceutically acceptable salt and/or solvate thereof for the preparation of a medicament for inhibition of proliferative activity in a cell. The application further includes one or more compounds one or more compounds or complexes of the application or a pharmaceutically acceptable salt and/or solvate thereof for use in inhibiting proliferative activity in a cell. In one embodiment, the one or more compounds or complexes comprises a radionuclide for use in therapy, optionally $^{188}$Re, $^{186}$Re, $^{153}$Sm, $^{66}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{99}$Au, $^{195m}$Pt, $^{193m}$Pt, $^{197}$Pt, $^{117m}$Sn, $^{103}$Pd, $^{103m}$Rh, $^{177}$Lu, $^{223}$Ra, $^{224}$Ra, $^{227}$Th, $^{32}$P, $^{161}$Tb, $^{33}$P, $^{125}$I, $^{203}$Pb, $^{212}$Pb, $^{201}$Tl, $^{119}$Sb, $^{58m}$Co or $^{161}$Ho. In some embodiments, the one or more radionuclides is $^{111}$In. In some embodiments, the one or more radionuclides is $^{177}$Lu The present application also includes a method of imaging a tissue in a subject by administering an imaging effective amount of one or more compounds or complexes of the application or a pharmaceutically acceptable salt and/or solvate thereof for use in imaging to a subject in need thereof and applying an imaging technique to detect emitted gamma rays.

The present application also includes a use of one or more compounds or complexes of the application or a pharmaceutically acceptable salt and/or solvate thereof for use in imaging for imaging a tissue well as a use of one or more compounds or complexes of the application or a pharmaceutically acceptable salt and/or solvate thereof comprising a radionuclide for use in imaging for the preparation of a medicament for imaging a tissue. The application further includes one or more compounds or complexes of the application or a pharmaceutically acceptable salt and/or solvate thereof comprising a radionuclide for use in imaging for use in imaging a tissue. In some embodiments, the use further includes applying an imaging technique to detect emitted gamma rays. In one embodiment, the one or more compounds or complexes comprises a radionuclide for use in imaging, optionally $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, $^{203}$Pb or $^{123}$I. In some embodiments, the one or more radionuclides is $^{111}$In. In some embodiments, the one or more radionuclides is $^{177}$Lu The present application also includes a method of diagnosing cancer in subject by administering a diagnostic effective amount of one or more compounds or complexes of the application or a pharmaceutically acceptable salt and/or solvate thereof to a subject in need thereof and applying an imaging technique to detect emitted gamma rays. The present application also includes a use of one or more compounds or complexes of the application or a pharmaceutically acceptable salt and/or solvate thereof for diagnosing cancer in well as a use of one or more compounds or complexes of the application or a pharmaceutically acceptable salt and/or solvate thereof for diagnosing cancer. The application further includes one or more compounds or complexes of the application or a pharmaceutically acceptable salt and/or solvate thereof comprising a radionuclide for use in imaging for use in diagnosing cancer. In some embodiments, the use further includes applying an imaging technique to detect emitted gamma rays. In one embodiment, the one or more compounds or complexes of the application or a pharmaceutically acceptable salt and/or solvate thereof comprises a radionuclide for use in imaging, optionally $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F or $^{123}$I. In some embodiments, the one or more radionuclides is $^{111}$In. In some embodiments, the one or more radionuclides is $^{177}$Lu.

In some embodiments, the treating disease or disorder such as cancer, or imaging a tissue or diagnosing cancer having a greater uptake of the compounds or complex of the application or a pharmaceutically acceptable salt and/or solvate thereof in a target cells, tissues and/or organs compared to off-target cells, tissues and/or organs. In some embodiments, the treating disease or disorder such as cancer, or imaging a tissue or diagnosing cancer having a greater uptake of the compounds or complex of the application or a pharmaceutically acceptable salt and/or solvate thereof in a target cells, tissues and/or organs compared to off-target cells, tissues and/or organs, and compared to otherwise identical compounds or complexes except for the presence of the cleavable moiety(ies) in the compounds or complexes of the application.

To minimize the amount of radionuclide exposure to the normal organs and to purposely degrade the radioligand to metabolites that are less likely accumulate in non-target receptor expressing cells, the present inventors have introduced a cleavable linker to a radioligand compound.

In an embodiment, effective amounts vary according to factors such as the disease state, age, sex and/or weight of the subject. In a further embodiment, the amount of a given compound or complex that will correspond to an effective amount will vary depending upon factors, such as the given compound or complex, the pharmaceutical formulation, the route of administration, the type of condition, disease or disorder, the identity of the subject being treated, and the like, but can nevertheless be routinely determined by one skilled in the art. In an embodiment, the effective amount is one that following treatment therewith manifests as an improvement in or reduction of any disease symptom.

In an embodiment, the compound or complex is administered at least once a week. However, in another embodiment, the compound or complex is administered to the subject from about one time per two weeks, three weeks or one month. In another embodiment, the compound or complex is administered about one time per week to about once daily. In another embodiment, the compound or complex is administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound or complex is used for the treatment may increase or decrease over the course of a particular treatment regime. Changes in dosage may result and become apparent by standard diagnostic assays known in the art. In some instances, chronic administration is required. For example, the compound or complex is administered to the subject in an amount and for duration sufficient to treat the subject.

In an embodiment, the subject is a mammal. In another embodiment, the subject is human. In an embodiment, the subject is a non-human animal. In an embodiment, the subject is canine. In an embodiment, the subject is feline. Accordingly, the compounds, methods and uses of the present application are directed to both human and veterinary diseases, disorders and conditions.

The dosage of a compound or complex of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound or complex of the application is administered initially in a suitable dosage that is adjusted as required, depending on the clinical response. Dosages will generally be selected to maintain a serum level of the compound of the application from about 0.01 μg/cc to about 1000 μg/cc, or about 0.1 μg/cc to about 100 μg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg.

IV. Methods of Preparing the Compounds of the Application

Compounds and/or complexes of the present application or comparator compounds can be prepared by various synthetic processes. The choice of particular structural features and/or substituents may influence the selection of one process over another. The selection of a particular process to prepare a given compound and/or complexes of the present application or comparator compounds I is within the purview of the person of skill in the art. Some starting materials for preparing compounds of the present application are available from commercial chemical sources. Other starting materials, for example as described below, are readily prepared from available precursors using straightforward transformations that are well known in the art.

In some embodiments, the compound of Formula I or comparator compound is prepared all or in part using solid phase peptide synthesis (SPPS) or solution phase coupling techniques known in the art, for example, using the synthetic procedures found in Stewart and Young, 1984, Solid Phase Synthesis, Second Edition, Pierce Chemical Co., Rockford, Ill.; Fields and Noble, 1990, "Solid phase peptide synthesis utilizing 9-fluorenylmethyloxycarbonyl amino acids," Int. J. Pept. Protein Res. 35:161-214; Geysen et al., 1987, J. Immunol. Methods 102:259-274.

Accordingly, in some embodiments, in SPPS, an Na-protected linker group, such as a tert-butoxycarbonyl (Boc) or 9-fluorenylmethyloxycarbonyl (Fmoc) amino acid linker group, is activated at the α-carbonyl and coupled with the deprotected Nα functionality of the solid phase support. The newly added Na-protected linker group is then deprotected and coupled to the next Na-protected linker group if necessary until the final cleavage step. It would be appreciated by the person skilled in the art the chemistry of the coupling, deprotection, and final cleavage step of the linker from the solid phase support depends on choice of a N-protecting group. In some embodiments, the cleavage is accomplished by treatment with acid, for example trifluoro acetic acid (TFA) optionally in the presence of scavenger reagents such as triisopropylsilane. In some embodiments, when the α N-protecting group is Fmoc, cleavage in acid will also result in deprotection of the side chains.

Therefore, in an exemplary embodiment, the compounds of Formula I or comparator compounds are prepared using fluorenylmethyloxycarbonyl (Fmoc) solid-phase peptide synthesis chemistry known in the art. Accordingly, in some embodiments, the compounds of Formula I or fragments therefore are prepared, manually or by using automated multiple solid-phase peptide synthesizer, using a Wang resin, Rink Amide-MBHA or equivalent resin and Fmoc-protected linker group derivatives with suitable side-chain protections such as Fmoc-Ala-OH, Fmoc-Arg (Pbf)-OH, Fmoc-Asn (Trt)-OH, Fmoc-Asp (OtBu)-OH, Fmoc-Cys (Trt)-OH, Fmoc-Gln (Trt)-OH, Fmoc-Glu (OtBu)-OH, Fmoc-Gly-OH, Fmoc-His (Trt)-OH, Fmoc-Ile-OH, Fmoc-Leu-OH, Fmoc-Lys (Boc)-OH, Fmoc-Met-OH, Fmoc-Phe-OH, Fmoc-Pro-OH, Fmoc-Ser (tBu)-OH, Fmoc-Thr (tBu)-OH, Fmoc-Trp (Boc)-OH, Fmoc-Tyr (tBu)-OH, Fmoc-Val-OH, Fmoc-Lys(Mtt)-OH, Fmoc-Aib-OH, Fmoc-Nle-OH, Fmoc-8-amino-3,6-dioxaoctanoic acid (Fmoc-OEG-OH), Fmoc-tranexamic acid (Fmoc-Trx-OH), Fmoc-Glu-OtBu, octadecanedioic acid mono-tert-butyl ester, nonadecanedioic acid mono-tert-butyl ester, eicosanedioic acid mono-tert-butyl ester and tetradecanedioic acid mono-tert-butyl ester. The resin is swelled using a suitable solvent such as combination of dichloromethane (DCM) and (DMF). Prior to each coupling step the base-labile Na-protecting group Fmoc is cleaved off from the Fmoc protected linker groups using a suitable base such as piperidine in a suitable solvent such as DMF for time to cleave to cleave the Fmoc protecting group, for example, about 10-15 min. The resin is then subsequently washed with a suitable solvent such as the DMF to, for example, remove piperidine. An excess amount of the Fmoc-linker group (e.g., 4 to 8 molar equivalent) is then coupled using coupling agents known in the art, for example, N,N'-diisopropylcarbodiimide (DIC) and ethyl cyanohydroxyiminoacetate (Oxyma, e.g Oxyma Pure®) or (Benzotriazol-1-yloxy)tripyrrolidinophosphonium hexafluorophosphate (PyBOP) and (1-Hydroxybenzotriazole (HOBt), in a suitable solvent such as DMF for about 1 to about 2 hours and then further washed with a suitable solvent, such as DMF. The coupling step is repeated once for each linker group.

When necessary, the methyltrityl (Mtt) group of the Fmoc-Lys(Mtt)-OH (i.e., N-α-Fmoc-N-ε-4-methyltrityl-L-lysine) linker group or the deprotected Lys(Mtt)-residue in the linker fragment is removed by treating the group or residue with hexafluoroisopropanol (HFIP) in a suitable solvent such as dichloromethane (DCM) (e.g. about 30% v/v) for suitable amount of time, for example, about 1 hour, followed by washing the resin with the suitable solvent and repeating the treatment with HFIP in DCM with a final washing with DCM after treatment.

After coupling, the compound of Formula I, comparator compound or fragment thereof is cleaved from the solid phase by treatment with a suitable acid for example, trifluoroacetic acid (TFA) and optionally in the presence of a trialkylsilane such as triisopropylsilane (TIP) and water and then precipitated with a suitable solvent such as diethyl ether. The product is dissolved in a suitable solvent such as water and acetonitrile and purified using high-performance liquid chromatography (HPLC) such as reversed phase HPLC using a suitable solvent or solvent mixture such as water with acetonitrile and TFA with an increasing gradient of acetonitrile. Relevant fractions are checked by analytical UPLC. Fractions containing the pure target compounds are pooled and freeze-dried.

The chelating group such as DOTA is conjugated to the linker fragment, for example, ε-amine of a lysine residue of the linker fragment or the linker fragment attached to the tumour binding group and/or circulation enhancing group using active ester chemistry known in the art. For example, DOTA is combined with the linker fragment in the presence of a base such as an amine The tumour binding group or derivative thereof can be synthesized through methods known in the art or are commercially available. For example, the tumor binding group εKuE,

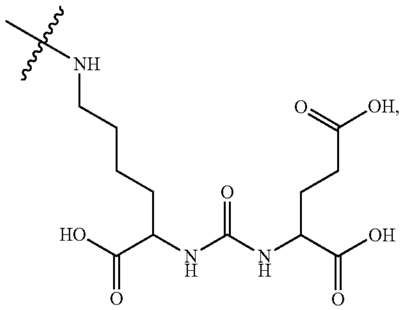 [SMILES: *NCCCCC(NC(=O)NC(CCC(=O)O)C(=O)O)C(=O)O]

can be synthesized by combining a Wang resin loaded with suitably protected lysine and a suitably protected glutamate pre-activated with 4-nitrophenyl chloroformate in a suitable solvent such as $CH_2Cl_2$ at low temperatures such as about 0° C. in the presence of a suitable base such as N,N-Diisopropylethylamine (DIEA).

The chelating groups can be synthesized through methods known in the art or are commercially available. For example, DOTA is available from Sigma-Aldrich (St. Louis, Missouri, United States).

In some embodiments, when the linker comprises a triazole (i.e., $X^3$ is triazole), the triazole ring is incorporated in the linker group by reacting a suitable azide precursor compound with a suitable acetylene precursor compound using click reaction conditions (e.g., *Tetrahedron* 2016, 72, 5257-5283; *Tetrahedron* 2016, 72, 6136-6141).

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations-A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

The following non-limiting examples are illustrative of the present application.

EXAMPLES

A. Synthesis of Exemplary Compounds of Formula I

General Methods

I) Synthesis of Exemplary Linker Groups Moieties

The Synthesis of Protected Linker Group ESL1

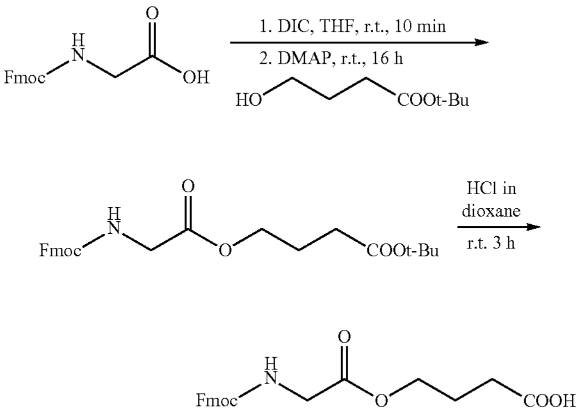

A mixture of Fmoc-Gly-OH (2.45 g, 8.25 mmol) and DIC (1.04 g, 8.25 mmol) in THF (15 mL) was stirred at room temperature (r.t.) for 10 min before the addition of DMAP (67 mg, 0.55 mmol) and tert-Butyl 4-hydroxybutanoate (880 mg, 5.5 mmol). The resulting mixture was stirred at r.t. overnight. The solvent was removed by rotatory evaporator, and the crude product was extracted with ethyl acetate (EA) (50 mL×3). The combined organic layers was washed by brine and dried over $Na_2SO_4$, concentrated and purified by the flash chromatography to afford the ester intermediate (1.6 g, 75% yield) as a white solid. The ester intermediate (1.6 g, 3.65 mmol) was dissolved in HCl/dioxane (2.5 M, 5 mL) and stirred at r.t. for 3 h. The resulting crude product was purified by preparative reverse phase HPLC to afford Fmoc protected ESL1 carboxylic acid (800 mg) as a white solid.

The Synthesis of Protected ESL2 Linker Group Moiety

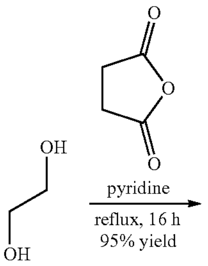

-continued

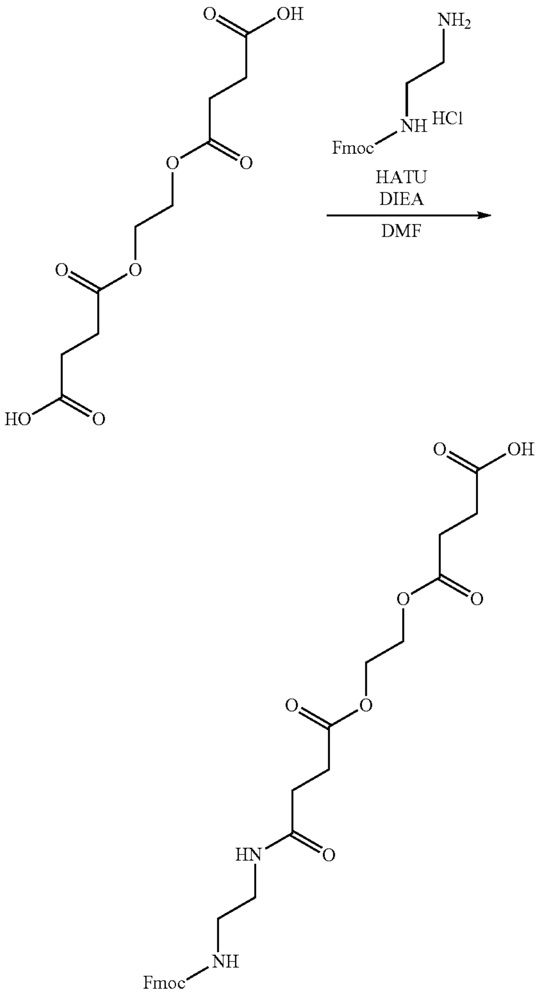

A mixture of succinic anhydride (2.0 g, 20 mmol) and ethylene glycol (0.5 mL, 10 mmol) in pyridine (1.6 mL) was stirred at 120° C. overnight. The reaction mixture was concentrated to afford crude diacid intermediate as an oil (2.9 g, purity: 50%, 61% yield). A mixture of such intermediate (975 mg, 3.72 mmol), mono-Fmoc ethylene diamine hydrochloride (1 g, 3.1 mmol), HBTU (1.78 g, 5.58 mmol) and DIEA (2.6 mL, 15.5 mmol) in DMF (5 mL) was stirred at r.t. for 2 h. The crude product was purified by preparative reverse phase HPLC to afford protected ESL2 carboxylic acid (320 mg) as a white solid.

The Synthesis of Protected ESL3 Linker Group Moiety

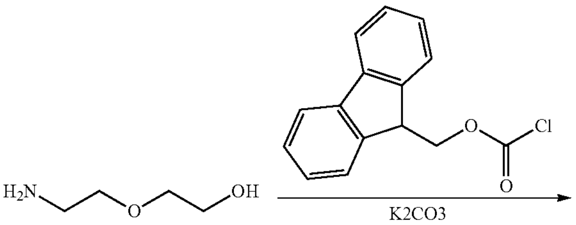

-continued

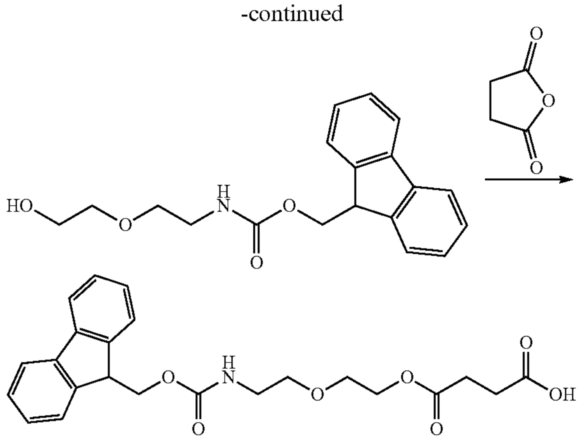

A solution of Fmoc-Cl (630 mg, 6 mmol) and 2-(2-aminoethoxy) ethanol (1.3 g, 5 mmol) in DCM (10 mL) was added dropwisely to a $K_2CO_3$ (1.4 g, 10 mmol) solution in $H_2O$ (10 mL) at 0° C. The resulting mixture was stirred at r.t. for 4 h. The organic phase was separated and washed with $H_2O$ (20 mL) 3 times, then concentrated. The resulting residue was dissolved in methyl t-butyl ether (20 mL) and re-concentrated. The crude product was mixed with n-Hexane (20 mL), and cooled to −20° C., centrifuged. The pellet was washed with n-hexane and dried under vacuum at 35° C. to afford 2-(Fmoc-2-aminoethoxy) ethanol intermediate (1.1 g) as a white solid which was used directly without further purification. To a solution of such intermediate (1.1 g, 3.4 mmol) and DMAP (83 mg, 0.68 mmol) in DCM (20 mL) was dropwisely added a solution of succinic anhydride (680 mg, 6.8 mmol) in DCM (10 mL). The resulting reaction solution was stirred at r.t. for 24 h. The solvent was removed under and the residue was purified by preparative reverse phase HPLC to afford protected ESL3 carboxylic acid (800 mg) as a white solid.

The Synthesis of Protected Linker SSL1 Linker Group Moiety

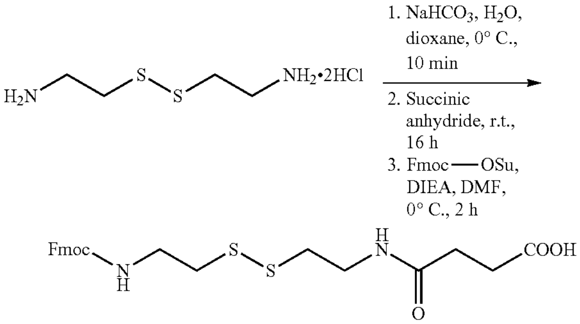

To a solution of 2,2'-Dithiobis(ethylamine)dihydrochloride (2.25 g, 10 mmol) in H2O (10 mL) at 0° C. was added $NaHCO_3$ (2.52 g, 30 mmol). The resulting solution was stirred for 10 min before the addition of dioxane (100 mL) and succinic anhydride (1 g, 10 mmol). The reaction mixture was stirred at r.t. for 16 h before a solution of Fmoc-OSu (3.4 g, 10 mmol) and DIEA (3.3 mL) in DMF (10 mL) was dropwise added at 0° C. The final reaction mixture was stirred at r.t for 2 h, then diluted by ethyl acetate. The organic phase was washed with $H_2O$ (100 mL) 3 times and dried over $Na_2SO_4$, then concentrated and purified by the flash chromatography to afford SSL1 (1.5 g) as a white solid.

The synthesis of exemplary linker Fmoc-Lys(-CO—$CH_2CH_2CO_2H$)-OtBu fragment

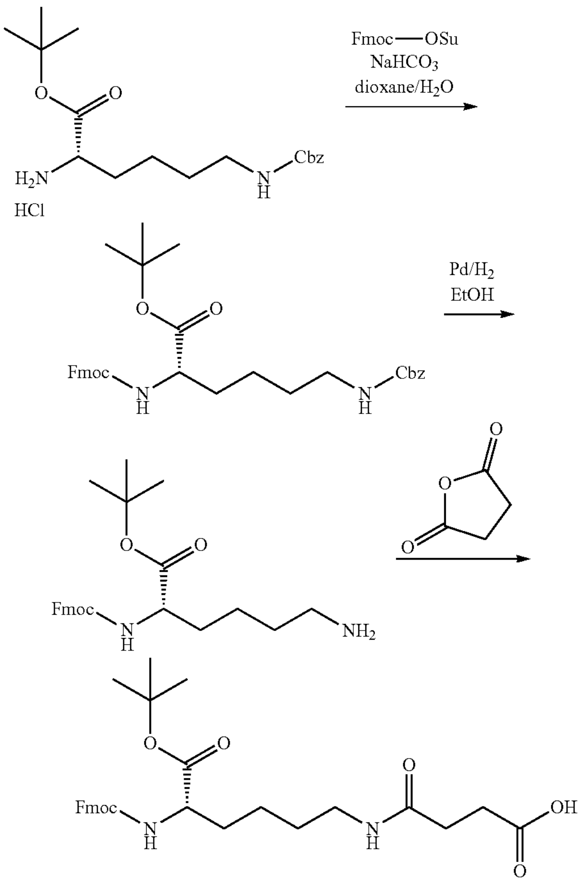

Fmoc-Lys(—CO—CH2CH2CO2H)—OtBu

A solution of H-Lys(Cbz)-OtBu·HCl (5 g, 13.5 mmol), Fmoc-OSu (3.8 g, 11.25 mmol) and $NaHCO_3$ (3.4 g, 40.5 mmol) in dioxane (45 mL) and $H_2O$ (15 mL), was stirred at r.t. for 2 h. The mixture was extracted with EA (50 mL) 3 times, the combined organic layers was washed by brine and dried over $Na_2SO_4$, concentrated and purified by the flash chromatography to afford Fmoc-Lys (Cbz)-OtBu (6.5 g, 95% yield) as a white solid. To a solution of Fmoc-Lys (Cbz)-OtBu (3.0 g, 5.4 mmol) in EtOH (20 mL) and AcOH (2 mL), was added Pb/C (150 mg) under hydrogen atmosphere. The mixture was stirred at 40° C. for 1 h and filtered, the filtrate was concentrated to afford Fmoc-Lys-OtBu (2.0 g) as a solid. To a solution of Fmoc-Lys-OtBu (2.7 g, 4.8 mmol) and succinic anhydride (0.48 g, 4.8 mmol) in DCM (20 mL), was added DIEA (1.24 g, 9.6 mmol). The resulting mixture was stirred at r.t. for 2 h, then concentrated and purified by preparative reverse phase HPLC to afford Fmoc-Lys(-CO—$CH_2CH_2CO_2H$)-OtBu (800 mg) as a white solid.

The synthesis of exemplary linker Fmoc-$NH_2$—$CH_2CH_2$—NH-TMA fragment

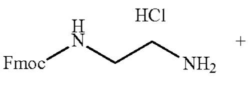

-continued

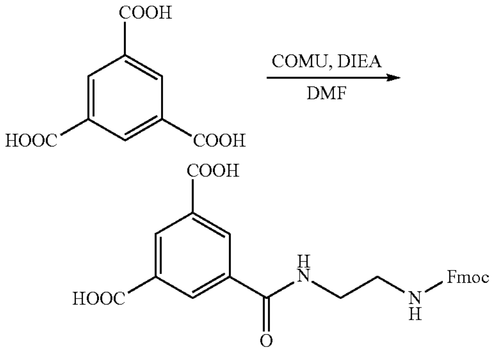

Fmoc—$NH_2$—$CH_2CH_2$—NH—TMA

To a solution of mono-Fmoc ethylene diamine hydrochloride (2.0 g, 6.2 mmol) in DMSO (30 mL) were added trimesic acid (TMA) (1.36 g, 6.6 mmol), COMU (3.2 g, 7.4 mmol) and DIEA (3.2 g, 24.8 mmol). The reaction mixture was stirred at r.t for 4 h, then diluted by ethyl acetate (100 mL) and extracted with $H_2O$ (100 mL) by 3 times. The combined H2O phase was added HCl (aq.) to adjust the pH to 6 to precipitate the product. The solid was collected by filtration and washed with $H_2O$ (100 mL) by 3 times to afford Fmoc-$NH_2$—$CH_2CH_2$—NH-TMA (1.0 g) as a white solid.

ii) Peptide Synthesis and Characterization

Solid-Phase Peptide Synthesis Protocol

The resin employed was Wang resin (loading 1.1 mmol/g). The Fmoc-protected amino acid derivatives used, unless specifically stated otherwise, were the standard recommended: Fmoc-Ala-OH, Fmoc-Arg (Pbf)-OH, Fmoc-Asn (Trt)-OH, Fmoc-Asp (OtBu)-OH, Fmoc-Cys (Trt)-OH, Fmoc-Gln (Trt)-OH, Fmoc-Glu (OtBu)-OH, Fmoc-Gly-OH, Fmoc-His (Trt)-OH, Fmoc-Ile-OH, Fmoc-Leu-OH, Fmoc-Lys (Boc)-OH, Fmoc-Met-OH, Fmoc-Phe-OH, Fmoc-Pro-OH, Fmoc-Ser (tBu)-OH, Fmoc-Thr (tBu)-OH, Fmoc-Trp (Boc)-OH, Fmoc-Tyr (tBu)-OH, Fmoc-Val-OH, Fmoc-Lys (Mtt)-OH, Fmoc-8-amino-3,6-dioxaoctanoic acid (Fmoc-OEG-OH), Fmoc-tranexamic acid (Fmoc-Trx-OH), Fmoc-Glu-OtBu, Fmoc-3-(2-naphthyl)-L-alanine (Fmoc-2-Nal-OH) etc. Other reagents used included DOTA-tris(tert-butyl ester), palmitic acid, octadecanedioic acid mono-tert-butyl ester, eicosanedioic acid mono-tert-butyl ester etc.

Preparation of [Glu (tBu)-OtBu]-Urea-Lys-Wang Resin

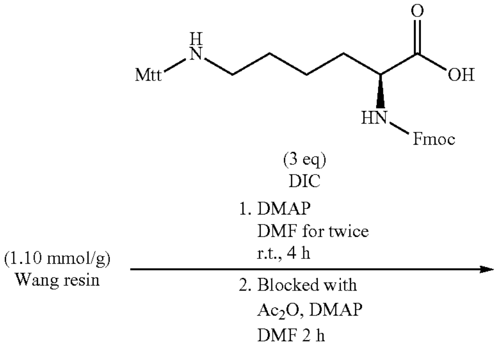

-continued

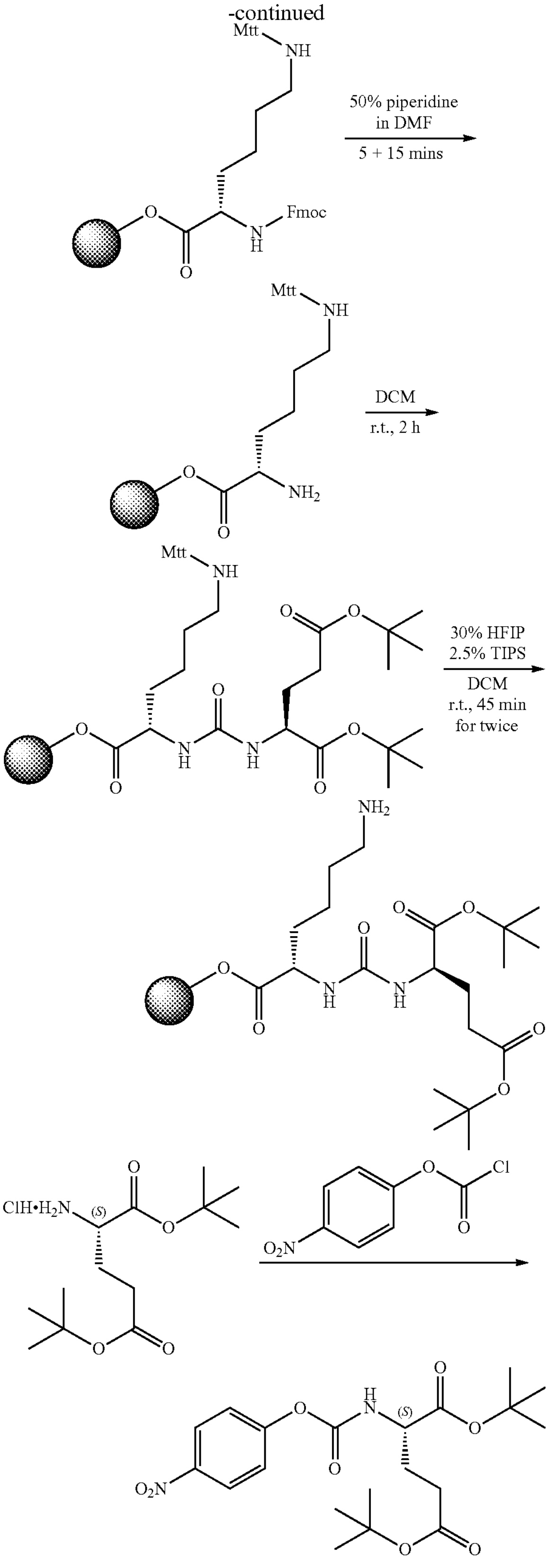

Wang resin (Loading 1.1 mmol/g, 5.0 mmol) was swelled with DCM (50 mL) in a SPPS reaction vessel with $N_2$ bubbling for 30 min. The resin was drained and washed with DMF (50 mL) for 3 times. In a separate flask, a mixture of Fmoc-Lys(Mtt)-OH (15 mmol), DIC (15 mmol) and DMAP (0.5 mmol) in DMF (60 mL) was stirred for 15 min at room temperature before being transferred to the above reaction vessel. The resulting mixture was bubbled with $N_2$ for 4 h, then drained and washed with DMF (50 mL) for 6 times, followed by the addition of DMF (60 mL), acetic anhydride (50 mmol) and DMAP (0.50 mmol). The resulting mixture was bubbled with $N_2$ for 2 h, then drained and the resin was washed with DMF (50 mL) for 6 times. To remove the Fmoc, the resulting resin was treated with 20% piperidine in DMF (60 mL) for 10 min, and this step was repeated once. The resulting resin was washed with DMF (50 mL) for 6 times. In a separate flask, to a solution of L-Glutamic acid di-tert-butyl ester hydrochloride salt (3.1 g, 10.5 mmol) and 4-nitrophenyl chloroformate (2 g, 10 mmol) in DCM (80 mL) at 0° C., DIEA (3.65 mL, 21 mmol) was added dropwisely. The reaction mixture was stirred at 0° C. for 30 min, then warmed to room temperature and stirred for another 30 min before being transferred to the above SPPS reaction vessel. The reaction mixture was mixed with $N_2$ bubbling for 1 h, then the resin was drained and washed with DMF (50 mL) for 6 times. To remove the Mtt group, the resin was treated with a solution of 30% HFIP/2.5% TIPS in DCM (60 mL) with $N_2$ bubbling for 45 min. This step was repeated once and the final resin was washed with DMF (50 mL) for 6 times and used as the starting resin to assemble the PSMA binding peptides.

Standard Solid-Phase Peptide Synthesis:

Assembly Protocol

The synthesis was performed using Fmoc-based chemistry manually. The stepwise assembly was conducted following the below steps:

1) Pre-swell the resin with DCM and DMF
2) Remove the Fmoc group by 20% piperidine; 2 treatments, 10 min each
3) Washes the resin with DMF to remove piperidine
4) add Fmoc-amino acid (1 mmol), PyBOP (1 mmol), HOBt (0.2 mmol) and DMF (5 mL) to a reaction vessel containing 0.20 mmol resin followed by addition of DIEA (2 mmol), the resulting mixture was mixed by bubbling nitrogen for 1-2 h
5) Drain the resin, and wash the resin with DMF
6) When needed, the N-epsilon-lysine Mtt protective group can be removed by treating the resin with 30% (v/v) HFIP in DCM for 1 h twice; drain the resin and wash it by DCM and DMF
7) When needed, linker Fmoc-$NHCH_2CH_2$—NH-TMA was preactivated by mixed with DIC and HOSu in DMF at 1:2:2 molar ratio to a final concentration of 0.20 M and stirred at room temperature for 4 h. The activated linker (0.25 eq. to the resin substitution) was transfer to the peptidyl resin, and the mixture was mixed with $N_2$ bubbling for 1 h. This step was repeated twice, each with 0.125 eq. (to the resin substitution) of the activated linker.
8) The final wash was done with DMF (3 times), DCM (3 times) and MeOH (3 times), respectively Resin Cleavage Condition and Purification After solid-phase peptide assembly was completed, the resin was washed with DCM, then subject to a 1.5-3 h treatment of TFA/TIS/H2O (95:2.5:2.5, v/v/v). The resin was filtered off and washed one time with TFA, the combined filtrate was treated with methyl tert-butyl ether (MTBE) to precipitate the crude peptide out of the solution. The precipitate was collected by centrifugation and washed 3 times with diethylether, and then dissolved in a minimal amount of DMF to achieve a clear solution. The crude peptide DMF solution was purified by a reverse phase preparative HPLC (Waters Delta Prep 4000) using a C18-reverse phase column. Mobile phases: A: 0.1% TFA H2O; B: 0.1% TFA acetonitrile (ACN). Relevant fractions were analyzed by analytical UPLC. The pure fractions were pooled and freeze-dried.

Post-Solid Phase Dimerization of Peptides in Solution

Isophthalic acid was preactivated by mixed with DIC and HOSu in DMF at 1:2:2 molar ratio to a final concentration of 0.20 M and stirred at room temperature for 4 h. Activated isophthalic acid (1.0 eq.) was transferred to a peptide (2.2 eq.) solution in DMSO with DIEA (5 eq.), and the resulting mixture was stirred at room temperature for 16 h. 1-2 drops of concentrated $NH_4OH$ solution was added to the reaction mixture before it was submitted for reverse-phase HPLC purification.

LC-MS Condition

Instrument: Agilent prime-6125B_2LCMS

Column: Boltimate EXT C18CoreShell 4.6×50 mm, 2.7 μm

Detection: UV (254 nm 214 nm 280 nm) and MS (ESI, 100 to 1000 amu)

Mobile Phase: A: $H_2O$ (0.05% formic acid); B: ACN (0.05% formic acid)

Flow Rate: 2.0 mL/min

Column Temperature: 45° C.

Gradient: 10% to 95% B within 1.5 min, followed by 95% B for 1.0 min

Analytical HPLC Condition

Instrument: WATERS ARC UPLC

Column: XBridge BEH peptide BEH C18, 3.5 μm, 2.1 mm×150 mm

Detection: UV 254 nm, 214 nm, 280 nm

Mobile Phase: A: $H_2O$ (0.1% TFA); B: ACN (0.1% TFA)

Column Temperature: 40° C.

Flow Rate: 0.6 mL/min

Gradient:

| Time (min) | 0 | 1 | 11 | 13 | 13.5 | 15 |
|---|---|---|---|---|---|---|
| A % | 90 | 90 | 5 | 5 | 90 | 90 |
| B % | 10 | 10 | 95 | 95 | 10 | 10 |

iii) Radiochemistry Methods $^{125}$I-Complex Synthesis

To a 38 μL of exemplary or comparator compound in solution (20 μM in 100 mM pH 7.5 sodium phosphate), was added $Na^{125}I$ solution (2.0 mCi, Perkin Elmer), then added 14 μL of a Chloramine-T solution (fresh 500 UM in 100 mM pH 7.5 sodium phosphate). The resulting solution was mixed well then left at room temperature for 5 min before the addition of 2 μL of the sodium ascorbate solution (fresh 50 mM in $H_2O$). The resulting crude product was mixed at room temperature for 2 min before loaded to Oasis HLB cartridge (10 mg) for purification. The cartridge was first washed with 0.80 mL×3 $H_2O$, then the product was eluted by 0.40 mL×3 80% aqueous ethanol. The fractions were analyzed by radio-TLC on a polyamide film using methanol and 1M ammonium acetate as the mobile phase (v/v:4:1) and detected by Mini Scan (Eckert & Ziegler Radiopharma Inc.). The selected fractions were pooled and diluted by 1% BSA and 5 mg/mL sodium ascorbate-containing pH 7.5 100 mM sodium phosphate buffer to a final activity of ~50-100

μCi/mL. The aliquoted products were stored at −80° C. until being used for the radioligand binding assay and expired at 4 weeks after synthesis.

$^{125}$I-C-8 complex was prepared using the above protocol $^{177}$Lu complex synthesis To a 0.5 M NaOAc buffer (20-50 μL, pH=4.5) was added 4 μL of exemplary or comparator compound in DMSO stock solution (2000 μM) and 2 mCi $^{177}$Lu (ITM Isotope Technologies Munich), the resulting mixture was heated to 95° C. for 15 min. The resulting product was analyzed by radio-TLC and radio-HPLC (column: Shim-pack GIST 5 μm 4.6*150 mm; buffer A: 0.2% formic acid H2O; buffer B: 0.1% formic acid acetonitrile; flow rate: 1 mL/min; gradient: 0-5 min: 10% B to 95% B; then 5-8 min: 95% B).

$^{177}$Lu complexes of the application were prepared using similar protocols as described above.

Synthesis of Exemplary Compounds of Formula I

The following exemplary compounds of Formula I were prepared using the above methods:

Example 1: 4pIBA-Glu-SSL1-Lys(DOTA)-Trx-2Nal-eKuE (I-1)

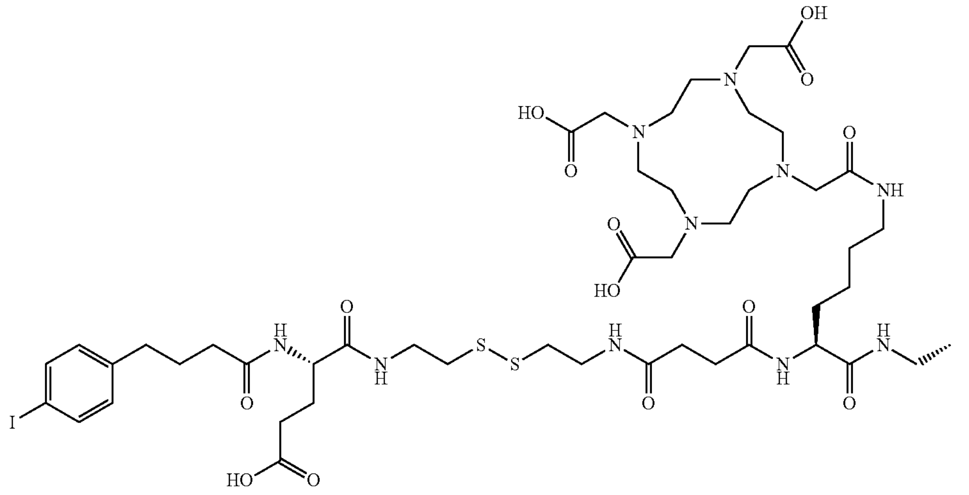

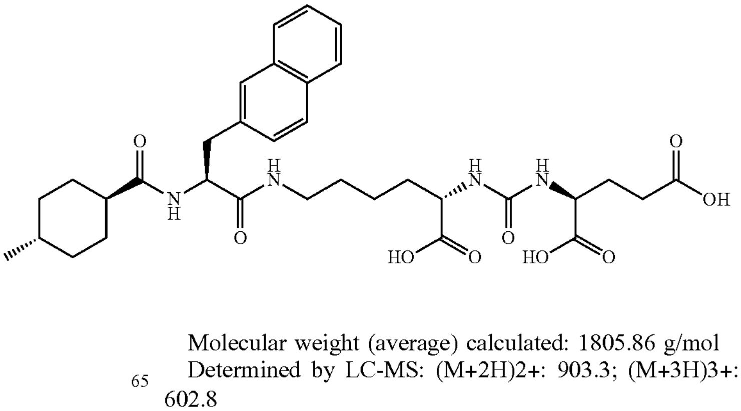

Molecular weight (average) calculated: 1805.86 g/mol

Determined by LC-MS: (M+2H)2+: 903.3; (M+3H)3+: 602.8

Purity by UPLC (214 nm): 98.8%

Example 2: 4pIBA-Glu-ESL1-Lys(DOTA)-Trx-2NaI-eKuE (I-2)
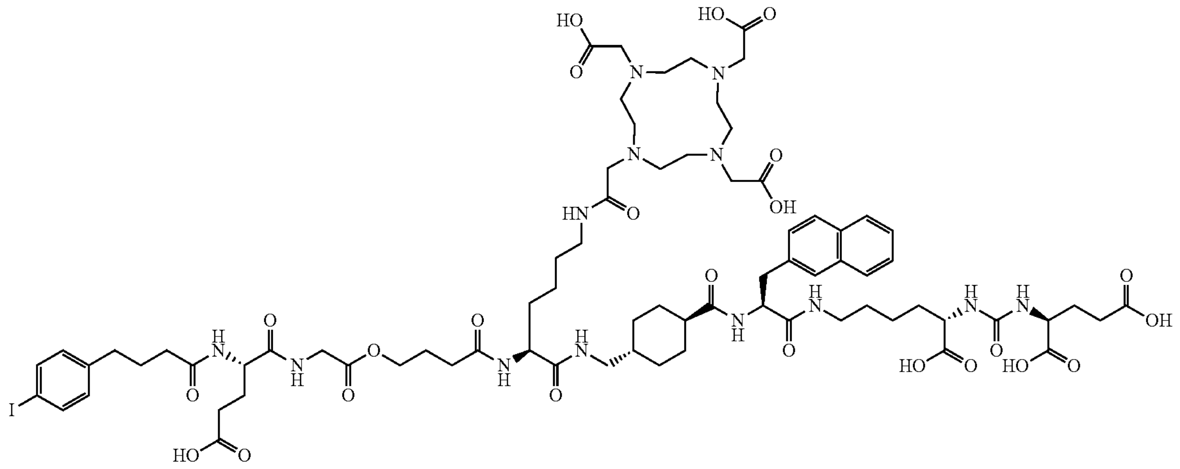 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CN2CCN(CC(=O)O)CCN(CC(=O)O)CCN(CC(=O)O)CC2)NC(=O)CCCOC(=O)CNC(=O)[C@H](CCC(=O)O)NC(=O)CCCc2ccc(I)cc2)CC1)C(=O)O)C(=O)O]
Molecular weight (average) calculated: 1714.67 g/mol
Determined by LC-MS: (M+2H)2+: 858.3; (M+3H)3+: 572.5
Purity by UPLC (214 nm): 97.4%
Example 3: 4pIBA-Glu-Lys(-ESL1-DOTA)-Trx-2NaI-eKuE (I-3)
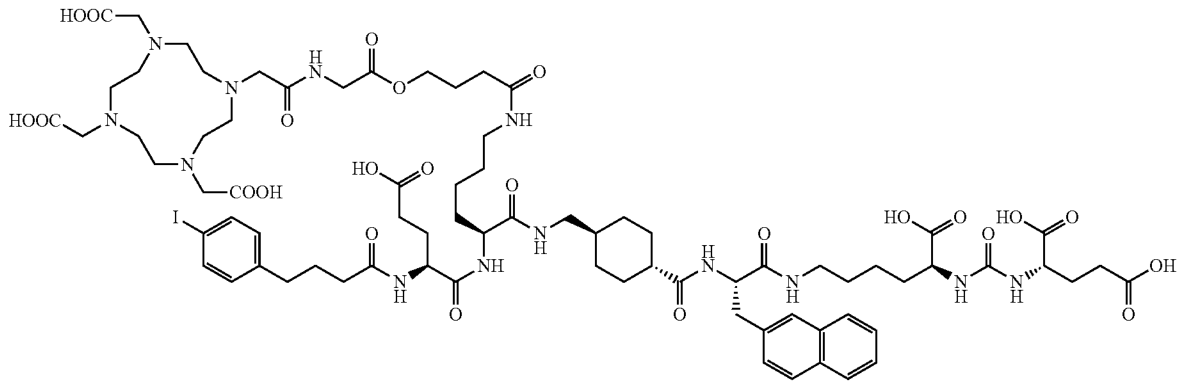 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CCCOC(=O)CNC(=O)CN2CCN(CC(=O)O)CCN(CC(=O)O)CCN(CC(=O)O)CC2)NC(=O)[C@H](CCC(=O)O)NC(=O)CCCc2ccc(I)cc2)CC1)C(=O)O)C(=O)O]
Molecular weight (average) calculated: 1714.67 g/mol
Determined by LC-MS: (M+2H)2+: 858.4; (M+3H)3+: 572.4
Purity by UPLC (214 nm): 95.5%
Example 4: 4pIBA-Glu-Lys(-SSL1-DOTA)-Trx-2NaI-eKuE, (I-4)
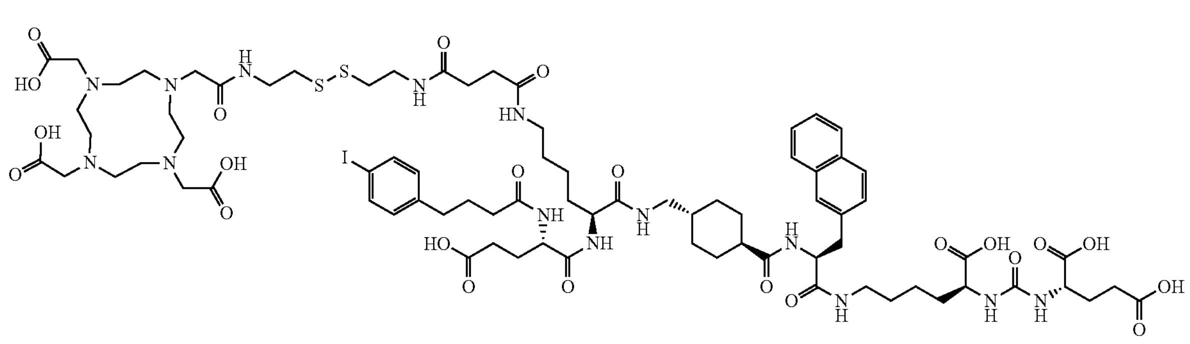 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CCC(=O)NCCSSCCNC(=O)CN2CCN(CC(=O)O)CCN(CC(=O)O)CCN(CC(=O)O)CC2)NC(=O)[C@H](CCC(=O)O)NC(=O)CCCc2ccc(I)cc2)CC1)C(=O)O)C(=O)O]

Molecular weight (average) calculated: 1805.86 g/mol
Determined by LC-MS: (M+2H)2+: 903.8; (M+3H)3+: 602.8
Purity by UPLC (214 nm): 96.8%
Example 5: 4pIBA-Glu-Lys(-ESL2-DOTA)-Aun-Trx-2NaI-eKuE (I-5)
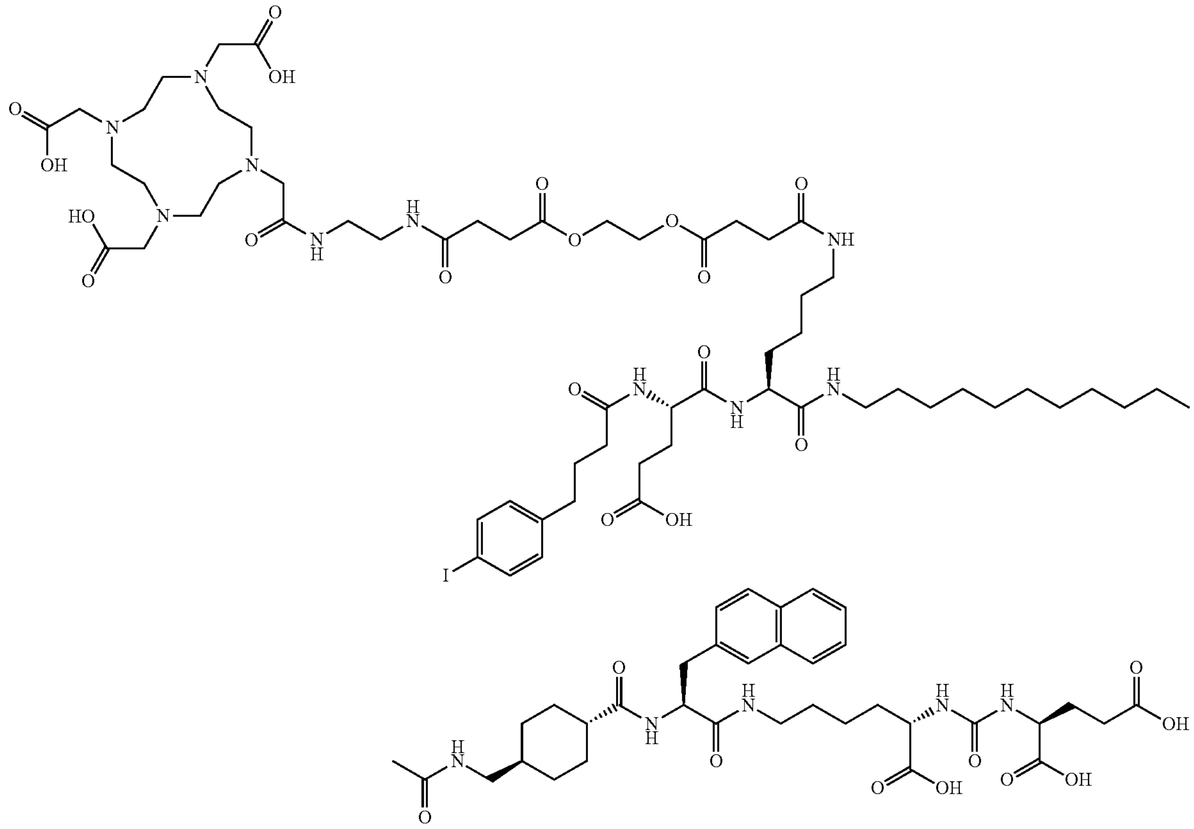
Molecular weight (average) calculated: 2041.1 g/mol
Determined by LC-MS: (M+3H)3+: 681.2
Purity by UPLC (214 nm): 98.3%
Example 6: DOTA-ESL2-Lys(-Glu-4pIBA)-Trx-2NaI-eKuE (I-6)
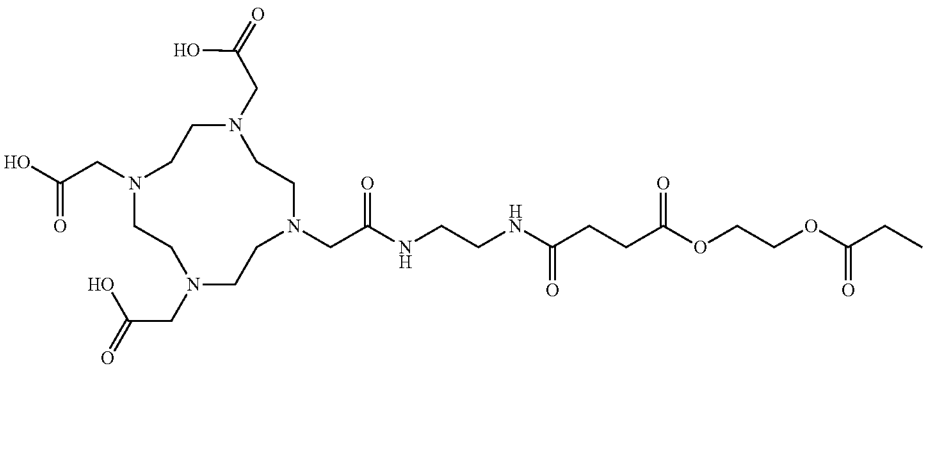

-continued
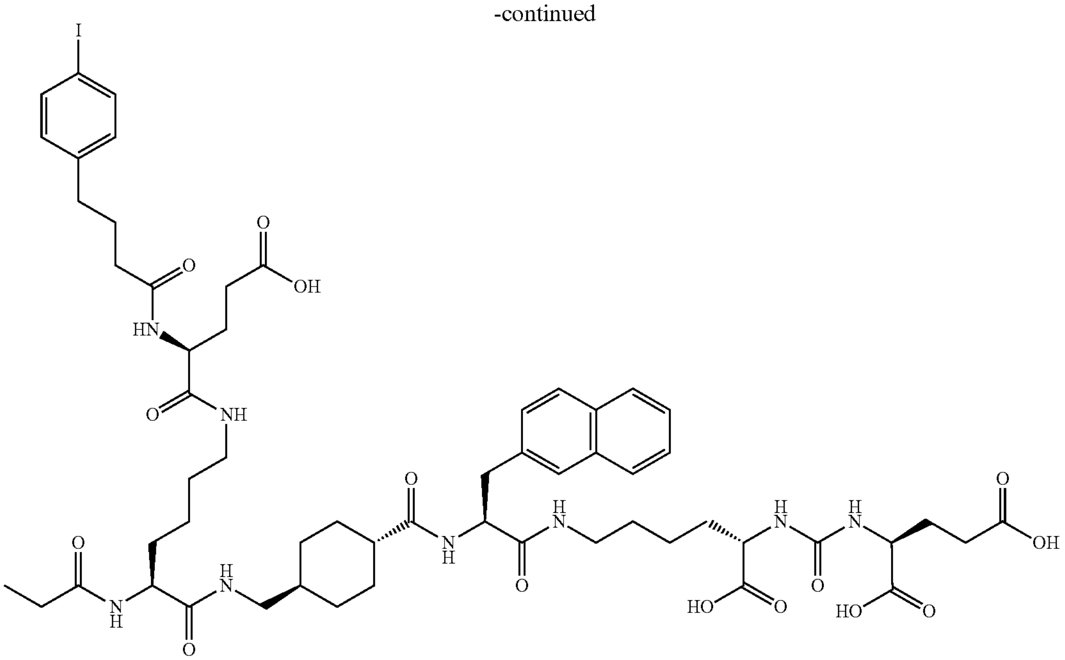
Molecular weight (average) calculated: 1857.81 g/mol
Determined by LC-MS: (M+2H)2+: 929.8; (M+3H)3+: 620.3
Purity by UPLC (214 nm): 97.13%
Example 7: 4pIBA-Glu-OEG-OEG-Lys(-OEG-OEG-Glu-4pIBA)-Lys(-ESL1-DOTA)-OEG-Trx-2NaI-eKuE (I-7)
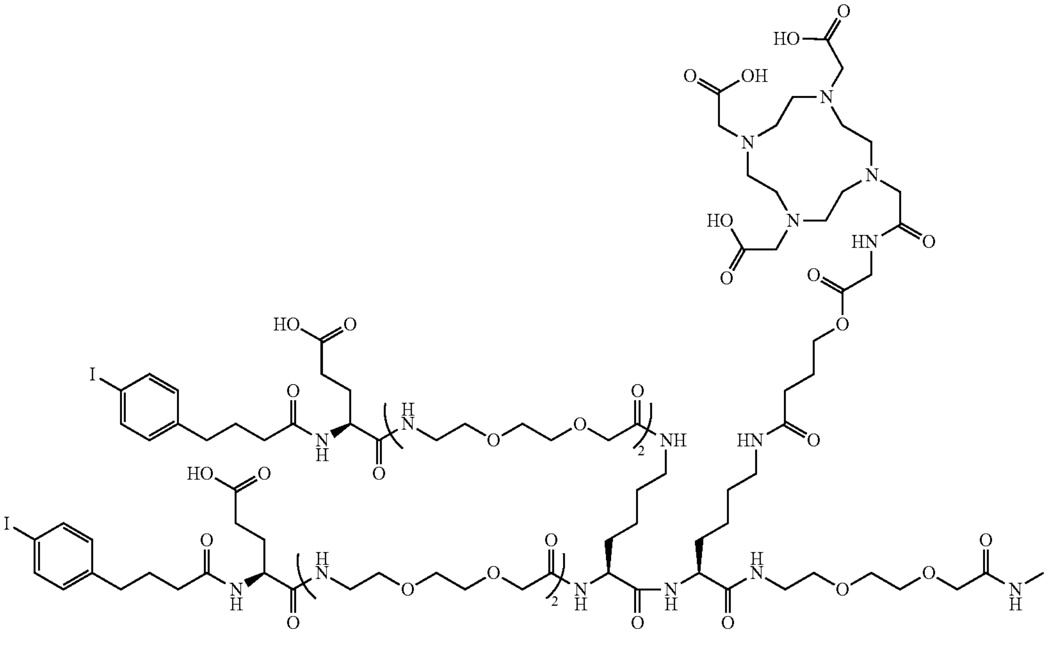

-continued
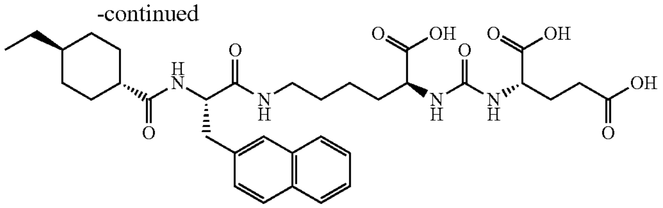
Molecular weight (average) calculated: 2969.84 g/mol
Determined by LC-MS: (M+2H)2+: 1486.4; (M+3H)3+: 991.6
Purity by UPLC (214 nm): 98.7%
Example 8: 4pIBA-Glu-OEG-OEG-Lys(-OEG-OEG-Glu-4pIBA)-OEG-ESL1-Lys(DOTA)-Trx-2NaI-eKuE (I-8)
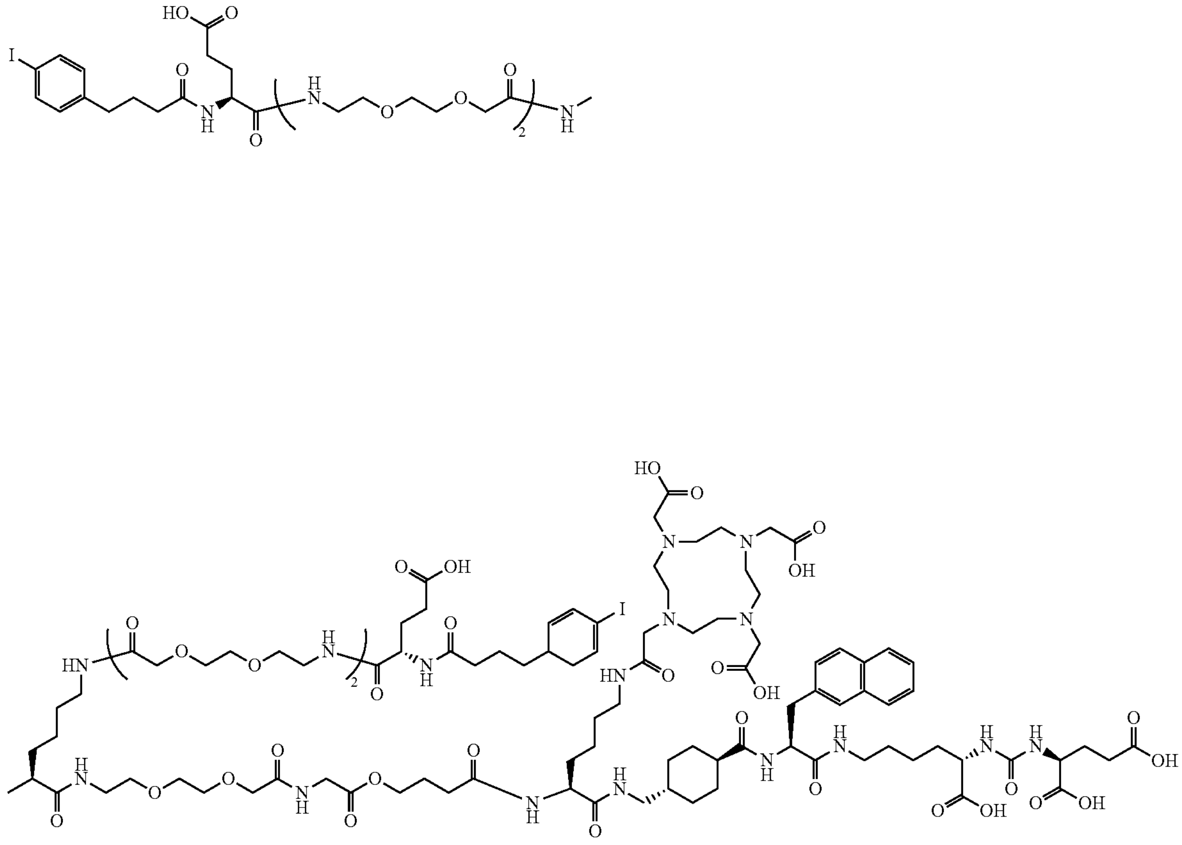
Molecular weight (average) calculated: 2969.84 g/mol
Determined by LC-MS: (M+2H)2+: 1485.5; (M+3H)3+: 990.5
Purity by UPLC (214 nm): 98.9%

Example 9: 4pIBA-Glu-Lys[-Suc-eLys-Val-Met-Gly-DOTA]-Trx-2NaI-eKuE (I-9)
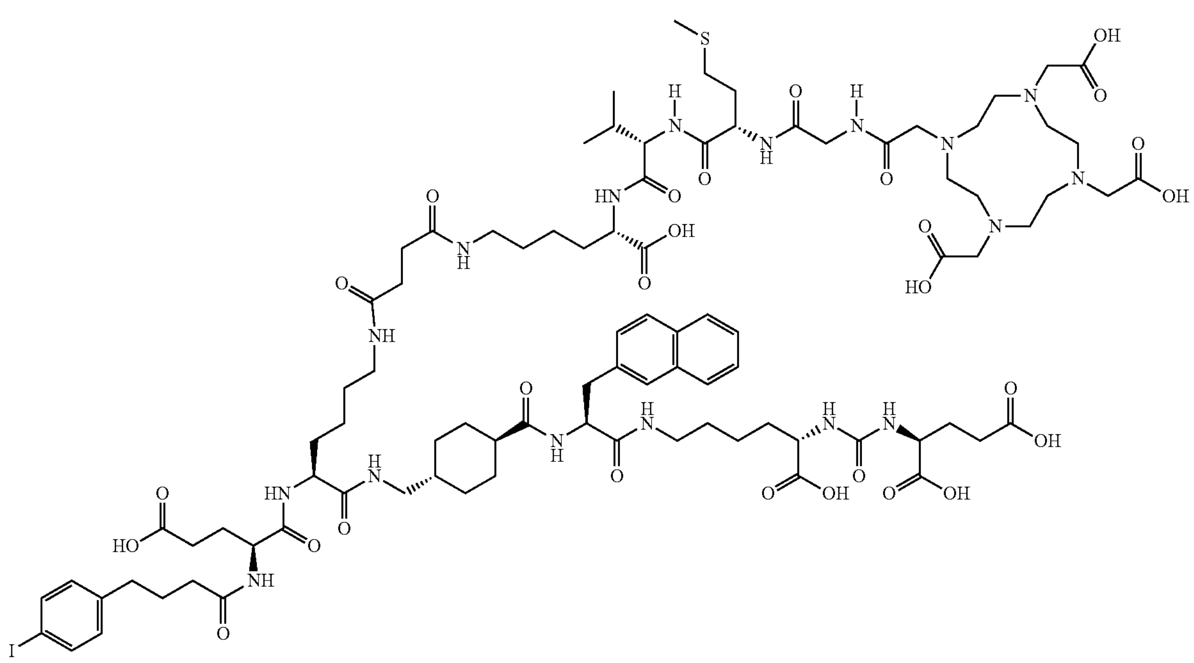 [SMILES: CSCC[C@H](NC(=O)CNC(=O)CN1CCN(CC(=O)O)CCN(CC(=O)O)CCN(CC(=O)O)CC1)C(=O)N[C@H](C(=O)N[C@@H](CCCCNC(=O)CCC(=O)NCCCC[C@H](NC(=O)[C@H](CCC(=O)O)NC(=O)CCCc1ccc(I)cc1)C(=O)NC[C@H]1CC[C@H](C(=O)N[C@@H](Cc2ccc3ccccc3c2)C(=O)NCCCC[C@H](NC(=O)N[C@@H](CCC(=O)O)C(=O)O)C(=O)O)CC1)C(=O)O)C(C)C]
Molecular weight (average) calculated: 2087.16 g/mol
Determined by LC-MS: (M+2H)2+: 1044.4; (M+3H)3+: 696.5
Purity by UPLC (214 nm): 96.5%
Example 10: HO-C18-gGlu-Lys(-ESL1-DOTA)-OEG-OEG-OEG-Trx-2NaI-eKuE (I-10)
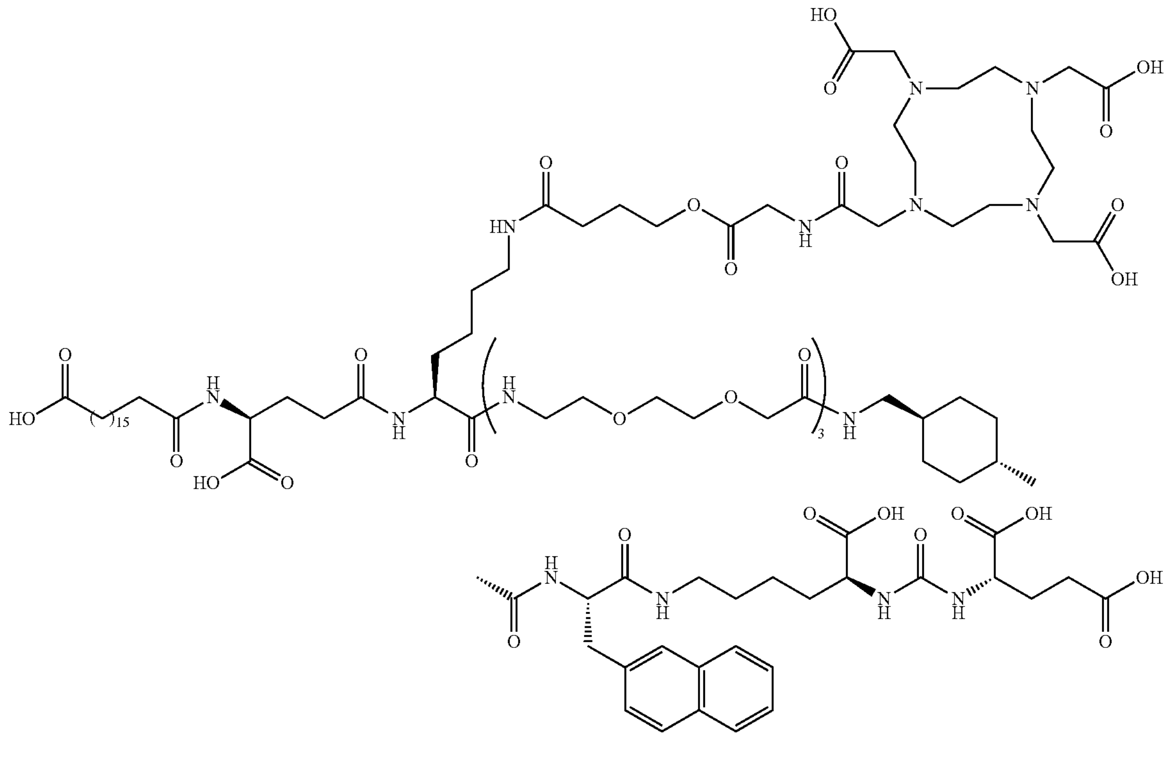

Molecular weight (average) calculated: 2174.51 g/mol
Determined by LC-MS: (M+3H)3+: 725.7; (M+4H)4+: 544.6
Purity by UPLC (214 nm): 97.1%
Example 11: HO-C18-gGlu-Lys(-ESL1-DOTA)-OEG-OEG-OEG-OEG-OEG-OEG-Trx-2NaI-eKuE (I-11)
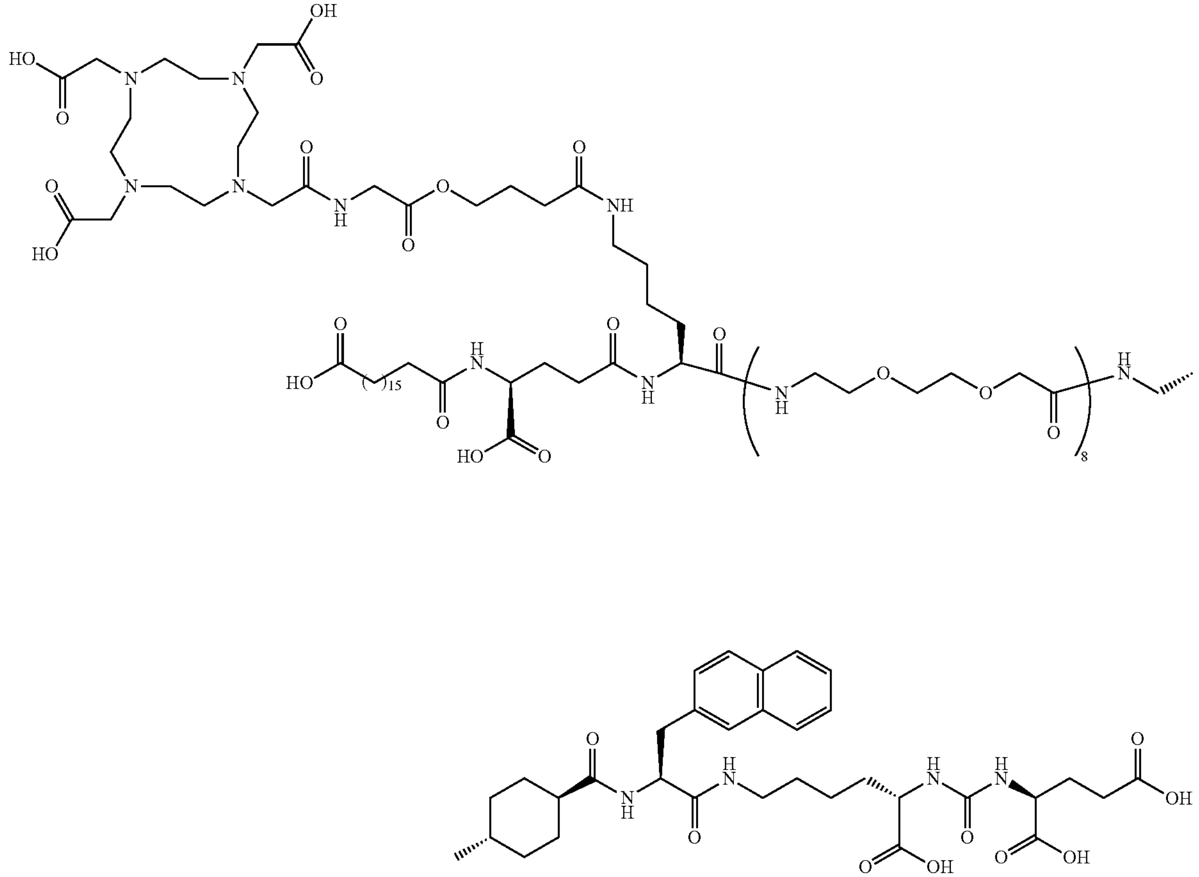
Molecular weight (average) calculated: 2610.00 g/mol
Determined by LC-MS: (M+3H)3+: 870.7; (M+4H)4+: 653.4; (M+5H)5+: 523.0
Purity by UPLC (214 nm): 100%
Example 12: HO-C18-gGlu-Lys(-ESL2-DOTA)-OEG-OEG-Trx-2NaI-eKuE (I-12)
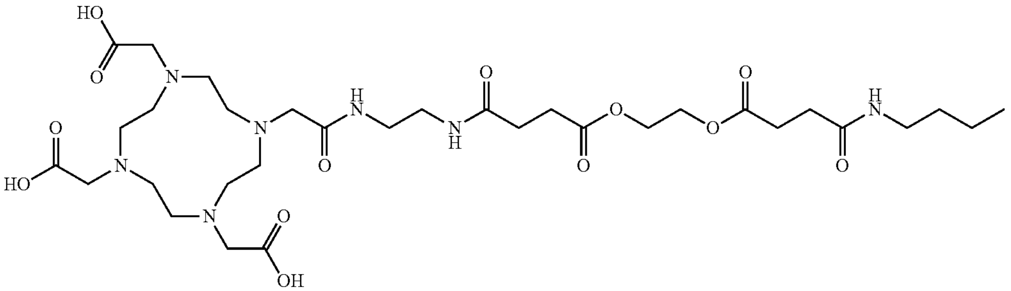

-continued
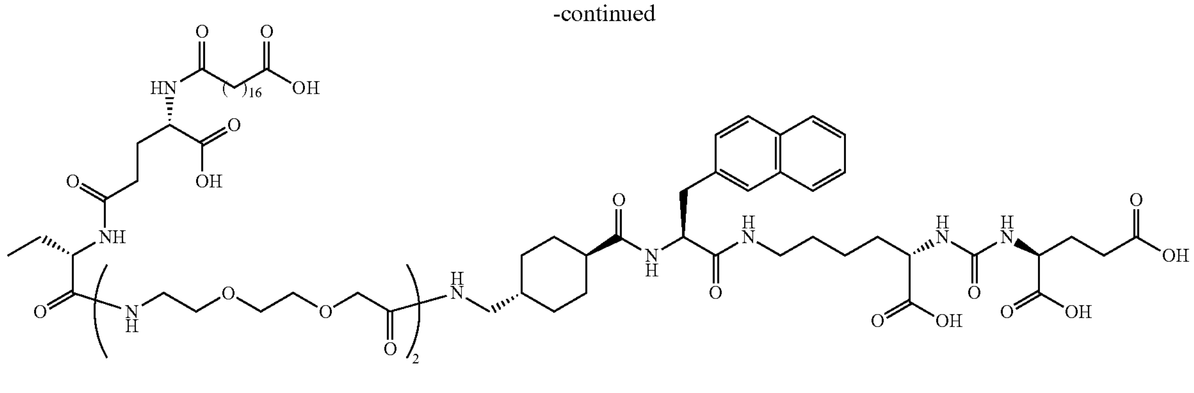
Molecular weight (average) calculated: 2172.50 g/mol
Determined by LC-MS: (M+3H)3+: 724.9; (M+4H)4+: 544.0
Purity by UPLC (214 nm): 95.3%
Example 13: HO-C18-gGlu-Lys(-ESL2-DOTA)-OEG-OEG-OEG-Trx-2NaI-eKuE (I-13)
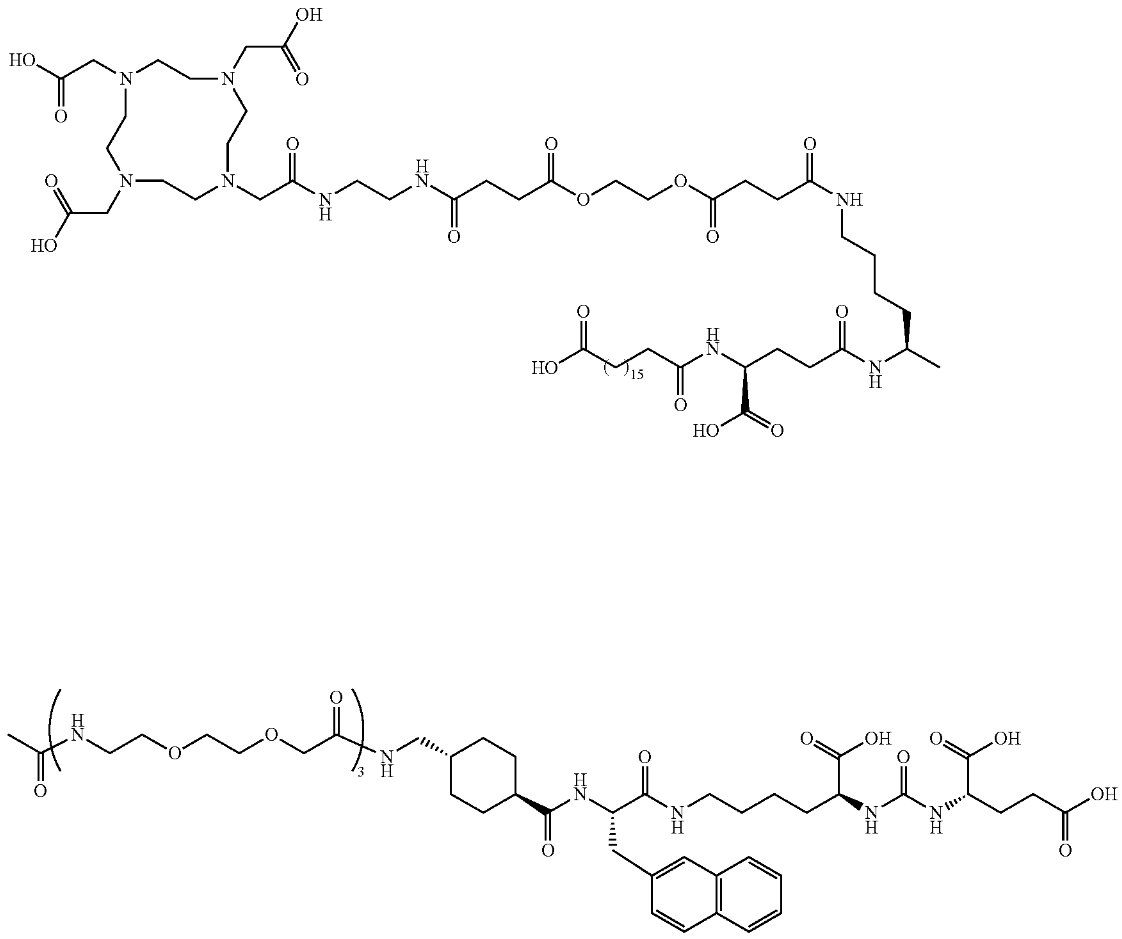
Molecular weight (average) calculated: 2317.55 g/mol
Determined by LC-MS: (M+2H)2+: 1159.3; (M+3H)3+: 773.3; (M+4H)4+: 580.4
Purity by UPLC (214 nm): 96.6%

Example 14: HO-C20-gGlu-Lys(-ESL2-DOTA)-OEG-OEG-OEG-Trx-2NaI-eKuE (I-14)
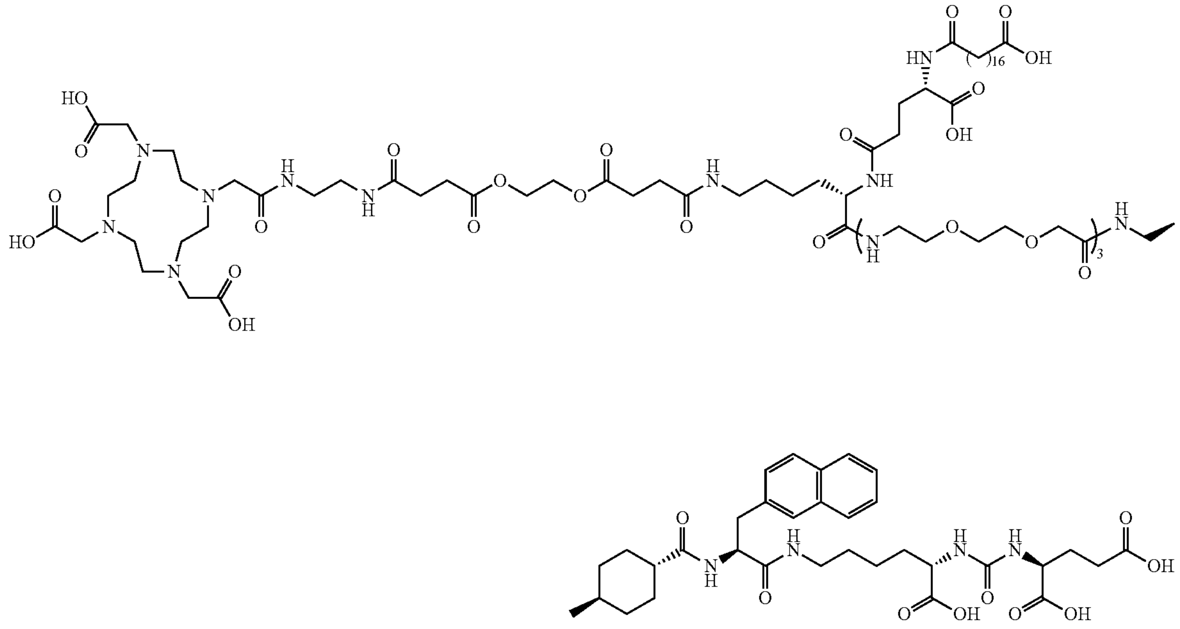
Molecular weight (average) calculated: 2345.71 g/mol
Determined by LC-MS: (M+2H)2+: 1173.6; (M+3H)3+: 782.6; (M+4H)4+: 587.3
Purity by UPLC (214 nm): 99.2%
Example 15: HO-C18-gGlu-Lys(-ESL2-DOTA)-OEG-OEG-OEG-OEG-Trx-2NaI-eKuE (I-15)
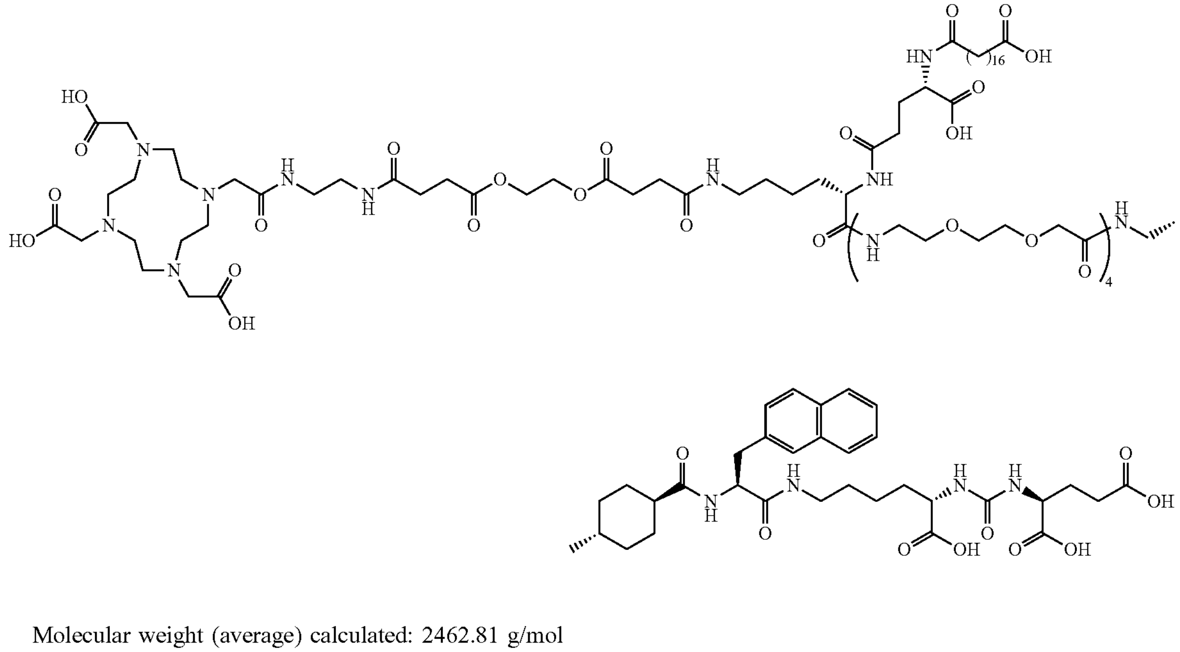
Molecular weight (average) calculated: 2462.81 g/mol
Determined by LC-MS: (M+2H)2+: 1232.0; (M+3H)3+: 821.7; (M+4H)4+: 616.6
Purity by UPLC (214 nm): 99.6%

Example 16: HO-C18-gGlu-OEG-OEG-Lys(-ESL2-DOTA)-OEG-Trx-2NaI-eKuE (I-16)
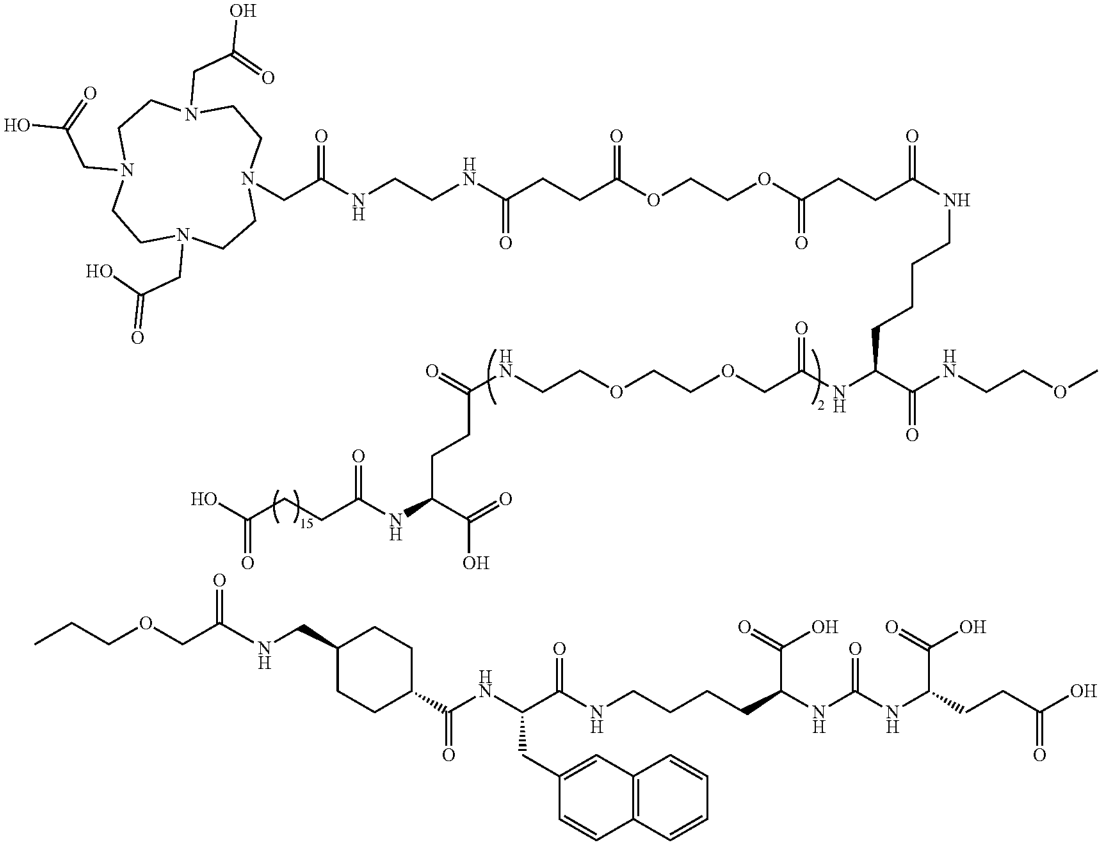
Molecular weight (average) calculated: 2317.65 g/mol 580.4
Determined by LC-MS: (M+2H)2+: 1159.3; (M+3H)3+: 773.3; (M+4H)4+:
Purity by UPLC (214 nm): 96.6%
Example 17: HO-C20-gGlu-OEG-Lys(-ESL1-DOTA)-OEG-OEG-Trx-2NaI-eKuE (I-17)
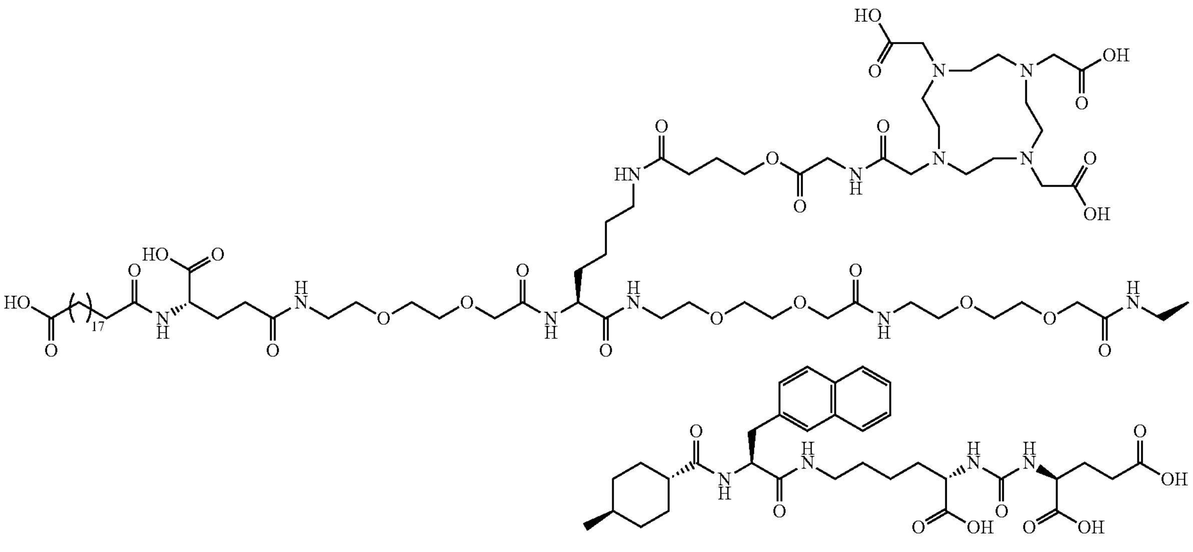

Molecular weight (average) calculated: 2202.57 g/mol
Determined by LC-MS: (M+2H)2+: 1101.8; (M+3H)3+: 735.0; (M+4H)4+: 551.7
Purity by UPLC (214 nm):
Example 18: HO-C18-gGlu-OEG-OEG-Lys(-ESL1-DOTA)-OEG-Trx-2NaI-eKuE (I-18)
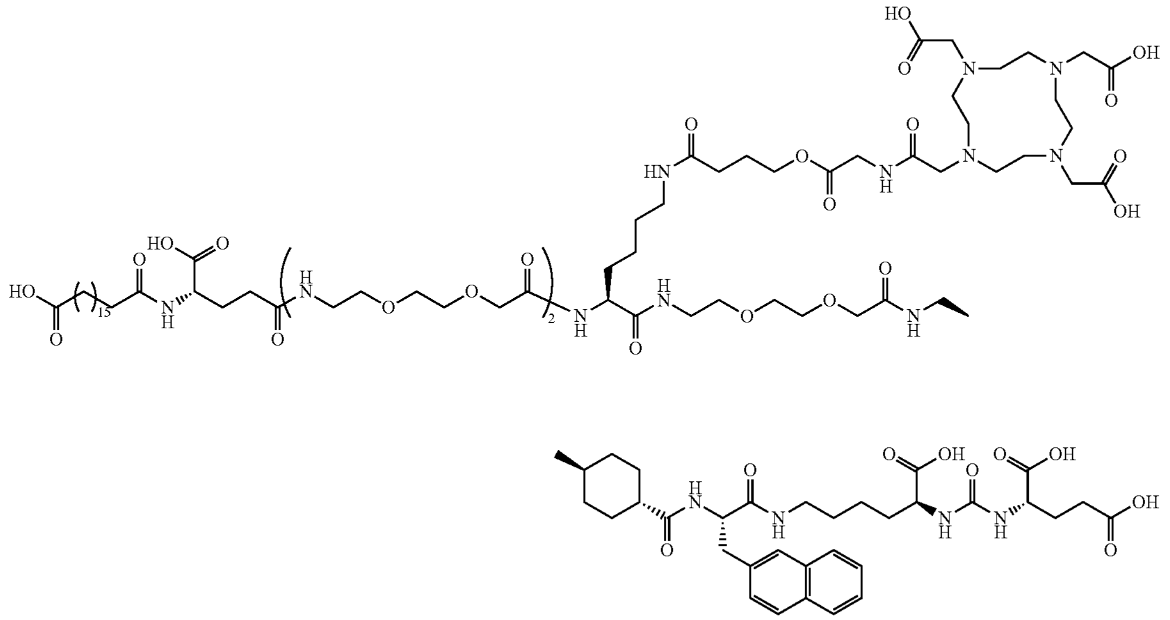
Molecular weight (average) calculated: 2173.51 g/mol
Determined by LC-MS: (M+2H)2+: 1087.8; (M+3H)3+: 725.7; (M+4H)4+: 544.6
Purity by UPLC (214 nm): 96.6%
Example 19: HO-C18-gGlu-OEG-OEG-OEG-OEG-OEG-OEG-ESL1-Lys(DOTA)-Trx-2NaI-eKuE (I-19)
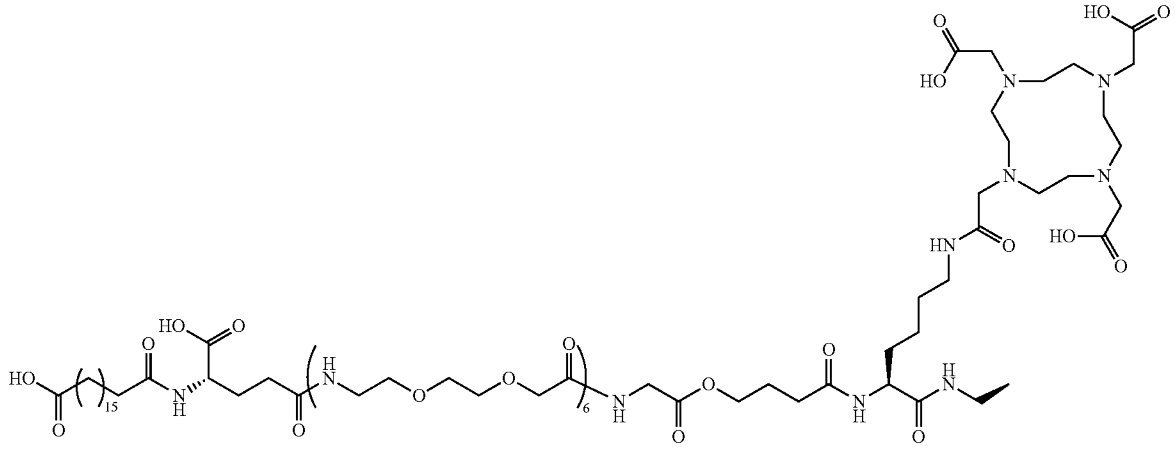

-continued
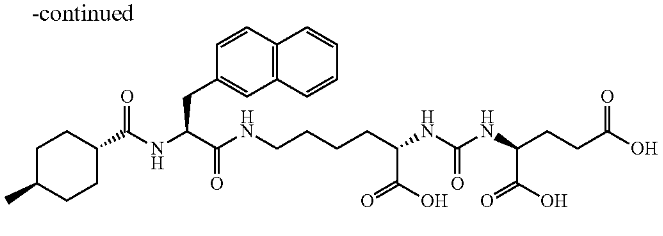
Molecular weight (average) calculated: 2610.00 g/mol
Determined by LC-MS: (M+2H)2+: 1306.0; (M+3H)3+: 870.7; (M+4H)4+: 653.3
Purity by UPLC (214 nm): 99.3%
Example 20: HO-C18-gGlu-OEG-OEG-ESL2-Lys (DOTA)-OEG-Trx-2NaI-eKuE (I-20)
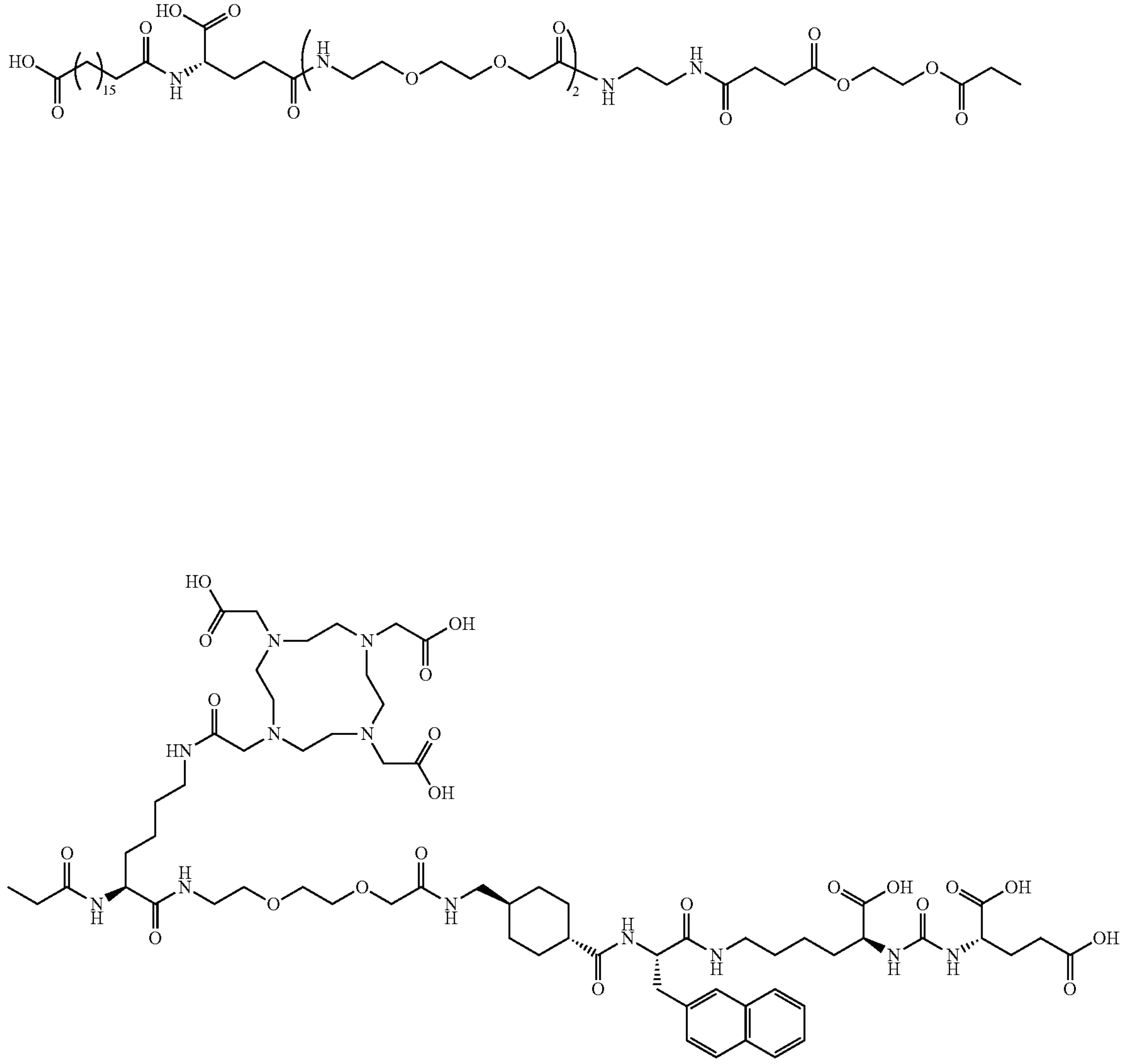
Molecular weight (average) calculated: 2317.65 g/mol
Determined by LC-MS: (M+2H)2+: 1159.4; (M+3H)3+: 773.4
Purity by UPLC (214 nm): 97.1%

Example 21: HO-C18-gGlu-OEG-OEG-ESL1-Lys (DOTA)-OEG-Trx-2NaI-eKuE (I-21)
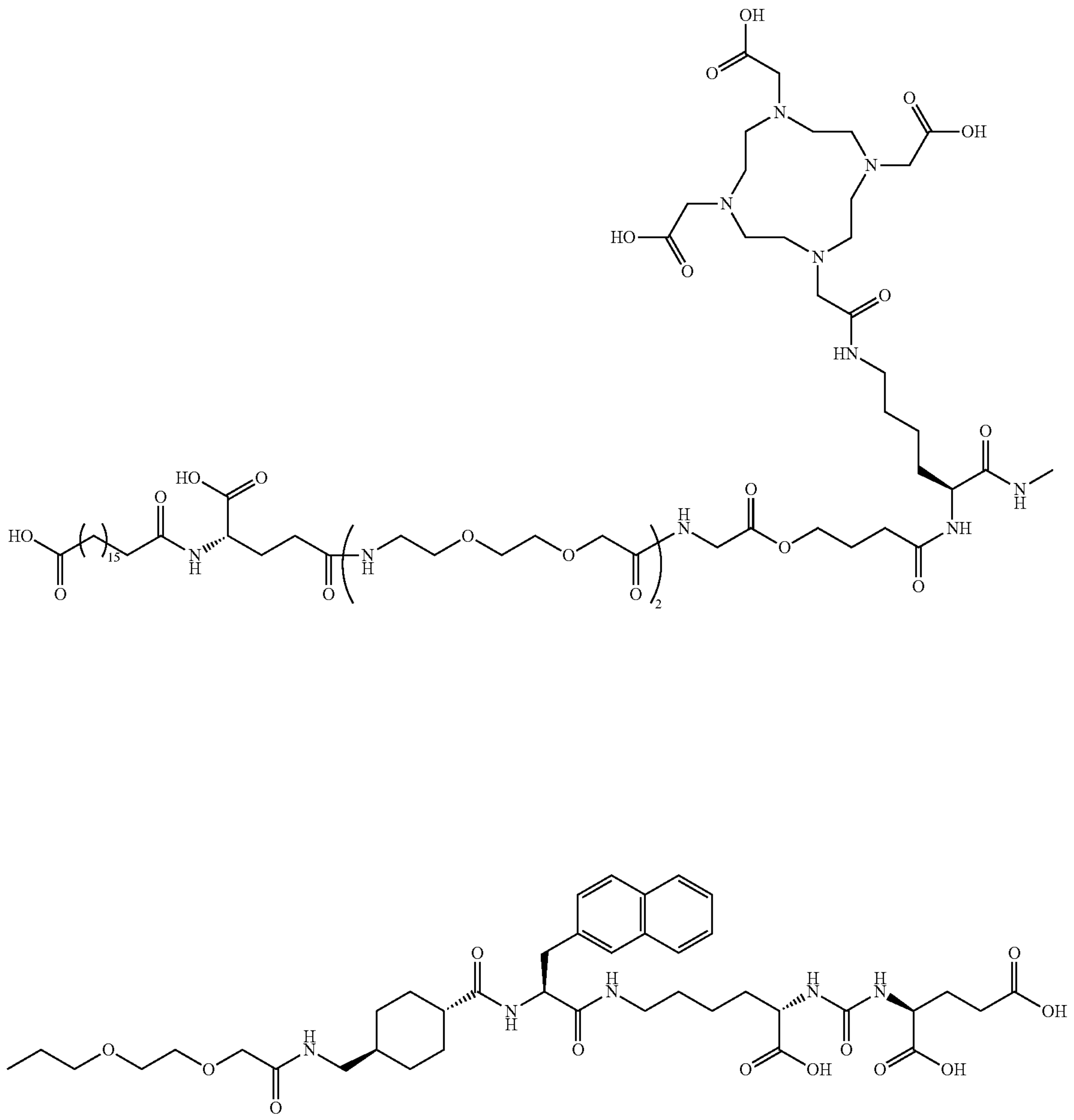
Molecular weight (average) calculated: 2174.51 g/mol
Determined by LC-MS: (M+2H)2+: 1087.8; (M+3H)3+: 725.7
Purity by UPLC (214 nm): 98.4%
Example 22: HO-C18-gGlu-OEG-ESL1-ESL1-Lys (DOTA)-OEG-Trx-2NaI-eKuE (I-22)
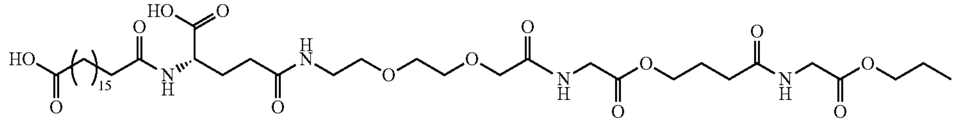

-continued
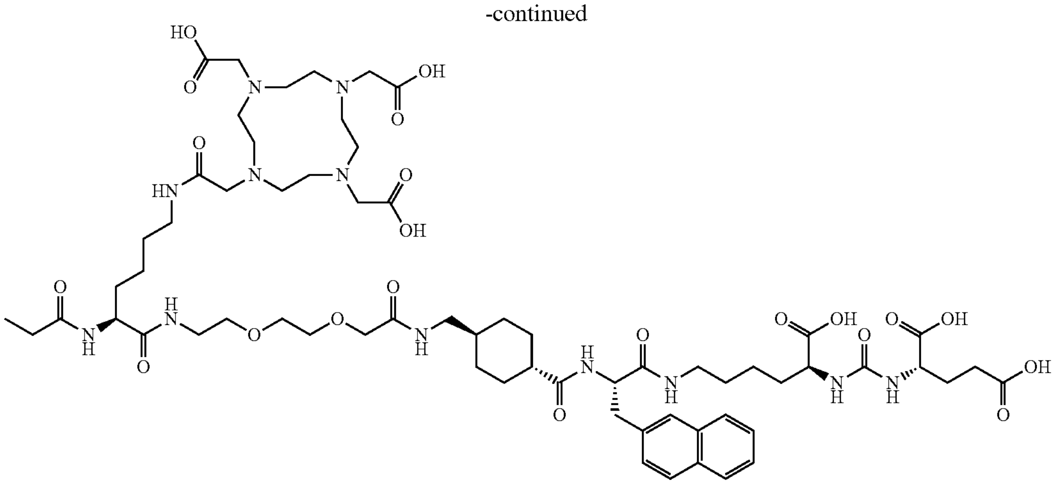
Molecular weight (average) calculated: 2172.50 g/mol
Determined by LC-MS: (M+2H)2+: 1087.1; (M+3H)3+: 725.0
Purity by UPLC (214 nm): >99.0%
Example 23: HO-C18-gGlu-ESL1-ESL1-ESL1-Lys (DOTA)-OEG-Trx-2NaI-eKuE (I-23)
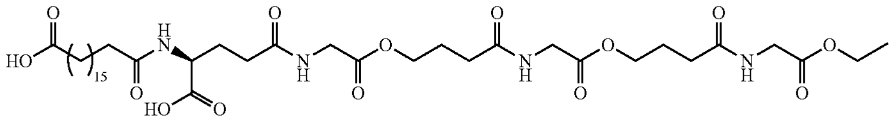
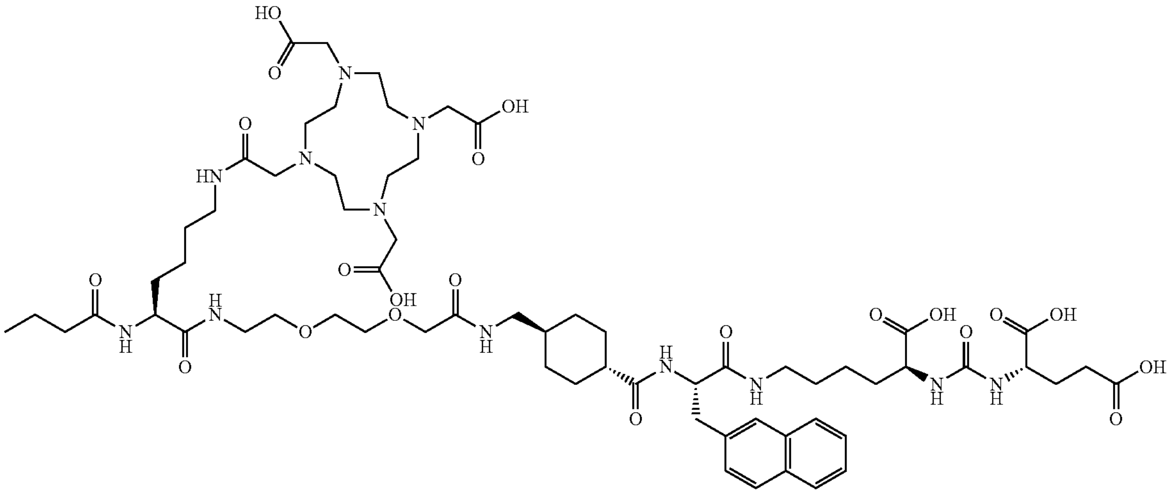
Molecular weight (average) calculated: 2170.48 g/mol
Determined by LC-MS: (M+2H)2+: 1086.0; (M+3H)3+: 724.4
Purity by UPLC (214 nm): 97.7%

Example 24: HO-C18-gGlu-OEG-OEG-OEG-OEG-OEG-ESL1-Lys(DOTA)-OEG-Trx-2Nal-eKuE (I-24)
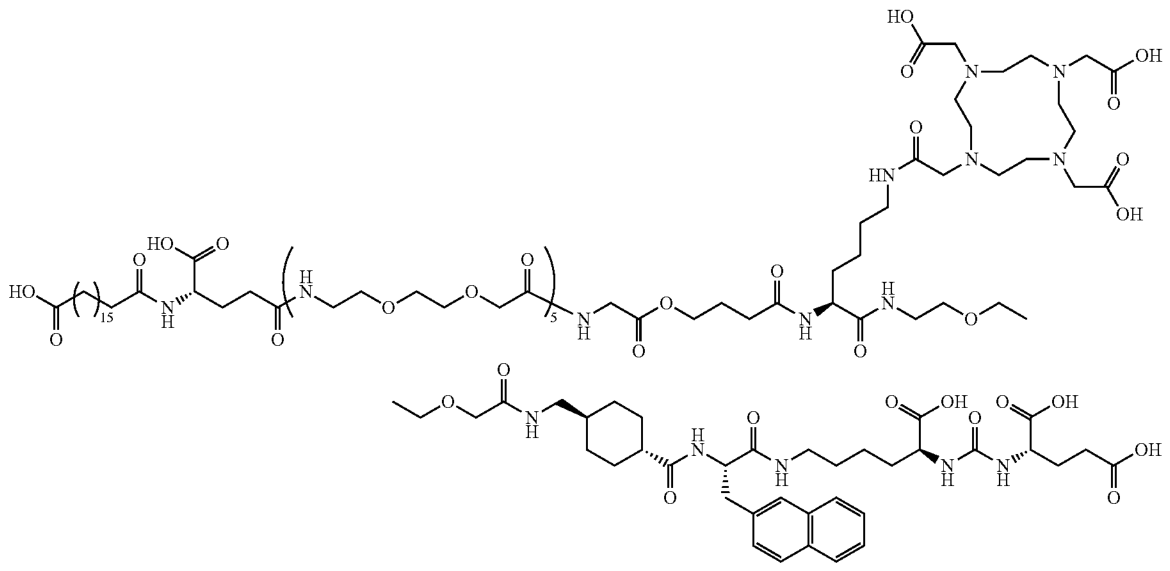
Molecular weight (average) calculated: 2609.99 g/mol
Determined by LC-MS: (M+2H)2+: 1305.3; (M+3H)3+: 870.8; (M+4H)4+: 653.4
Purity by UPLC (214 nm): >99.0%
Example 25: HO-C20-gGlu-OEG-OEG-ESL1-Lys(DOTA)-OEG-Trx-2Nal-eKuE (I-25)
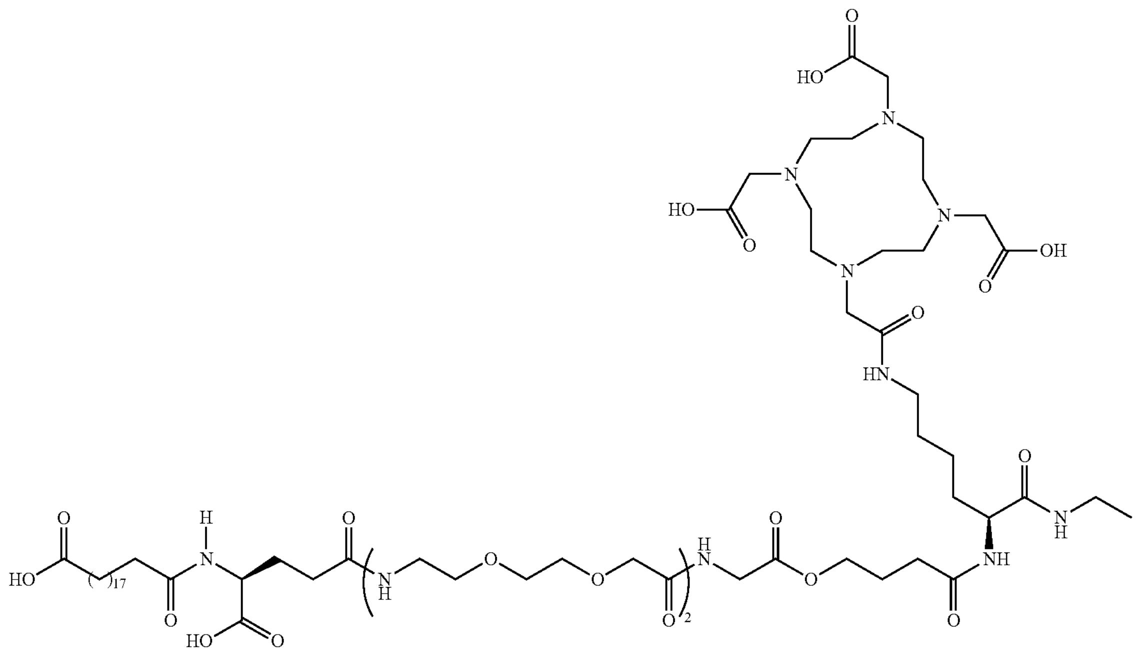

-continued
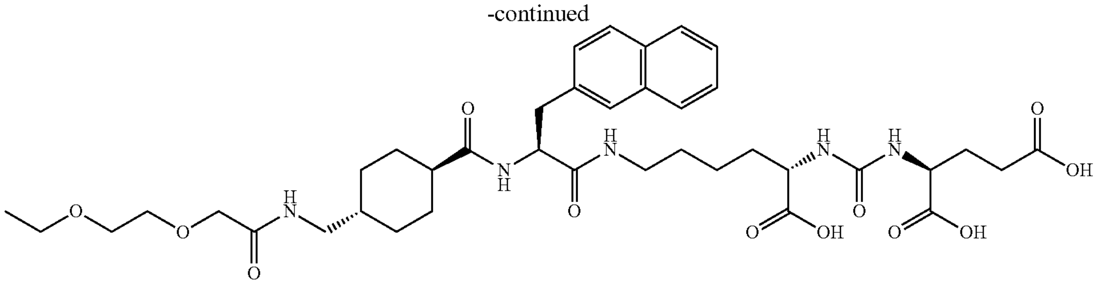
Molecular weight (average) calculated: 2202.57 g/mol
Determined by LC-MS: (M+2H)2+: 1101.8; (M+3H)3+: 735.0
Purity by UPLC (214 nm): 98.8%
Example 26: HO-C18-gGlu-OEG-OEG-ESL1-OEG-Lys(DOTA)-Trx-2NaI-eKuE (I-26)
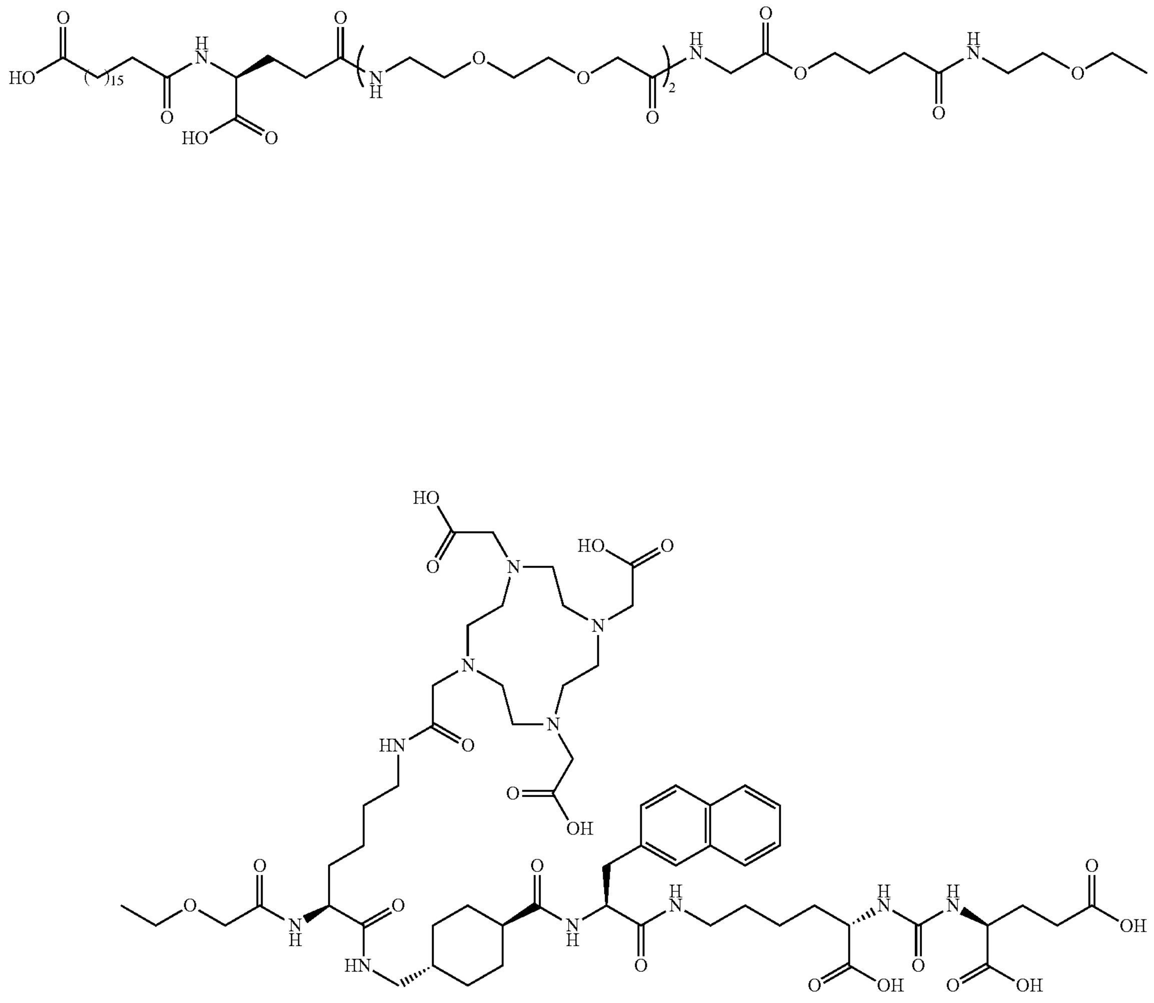
Molecular weight (average) calculated: 2174.51 g/mol
Determined by LC-MS: (M+2H)2+: 1087.8; (M+3H)3+: 725.6
Purity by UPLC (214 nm): 94.0%

Example 27: HO-C18-gGlu-ESL1-OEG-OEG-Lys(DOTA)-OEG-Trx-2NaI-eKuE (I-27)
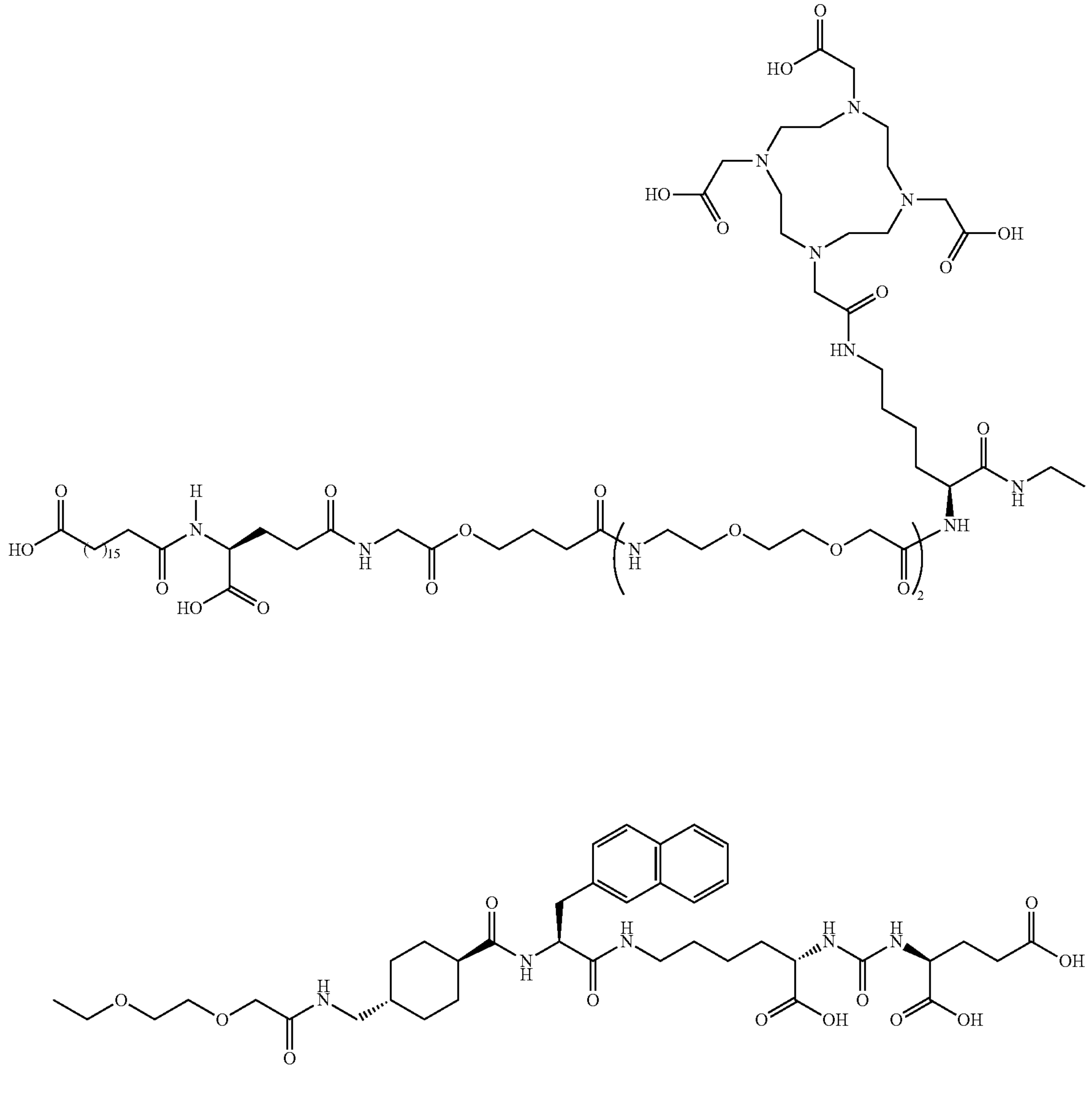
Molecular weight (average) calculated: 2174.51 g/mol
Determined by LC-MS: (M+2H)2+: 1087.6; (M+3H)3+: 725.7
Purity by UPLC (214 nm): 95.6%
Example 28: HO-C18-gGlu-gGlu-gGlu-OEG-OEG-ESL1-Lys(DOTA)-OEG-Trx-2NaI-eKuE (I-28)
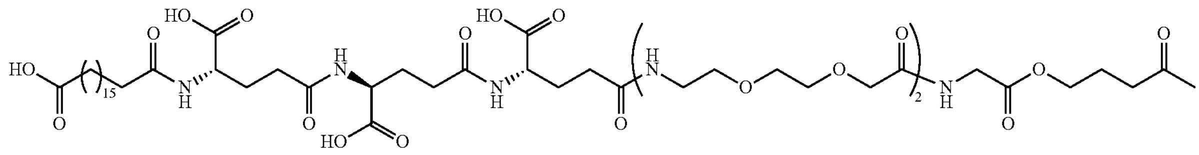

-continued
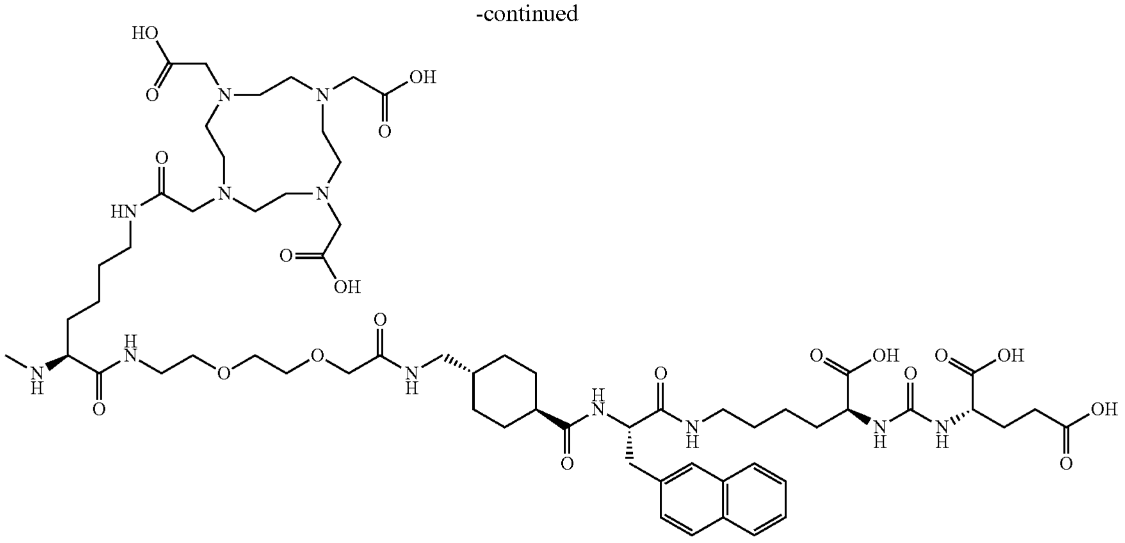
Molecular weight (average) calculated: 2432.74 g/mol
Determined by LC-MS: (M+2H)2+: 1217.2; (M+3H)3+: 811.8
Purity by UPLC (214 nm): >99.0%
Example 29: HO-C20-gGlu-OEG-ESL1-ESL1-Lys (DOTA)-OEG-Trx-2NaI-eKuE (I-29)
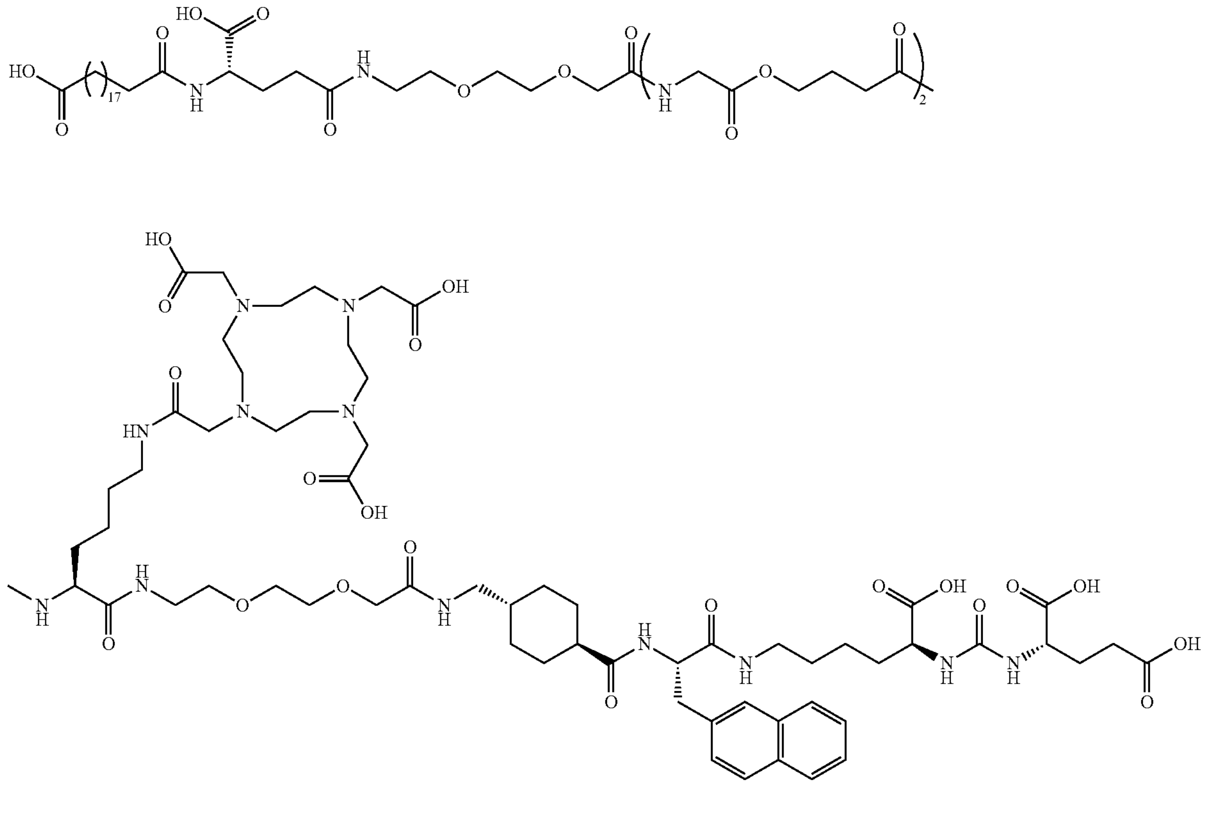
Molecular weight (average) calculated: 2200.55 g/mol
Determined by LC-MS: (M+2H)2+: 1101.0; (M+3H)3+: 734.3
Purity by UPLC (214 nm): >99.0%

11Example 30: HO-C16-gGlu-OEG-OEG-ESL1-Lys(DOTA)-OEG-Trx-2NaI-eKuE (I-30)
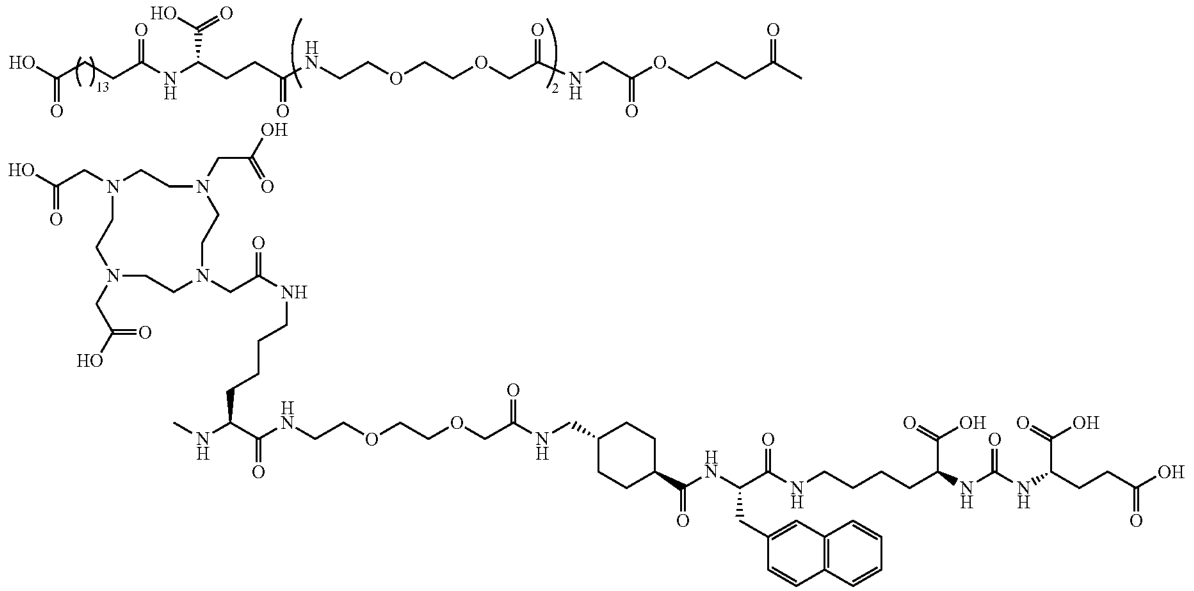
Molecular weight (average) calculated: 2146.46 g/mol
Determined by LC-MS: (M+2H)2+: 1074.0; (M+3H)3+: 716.6
Purity by UPLC (214 nm): 95.4%
Example 31: HO-C18-gGlu-OEG-OEG-ESL3-Lys(DOTA)-OEG-Trx-2NaI-eKuE (I-31)
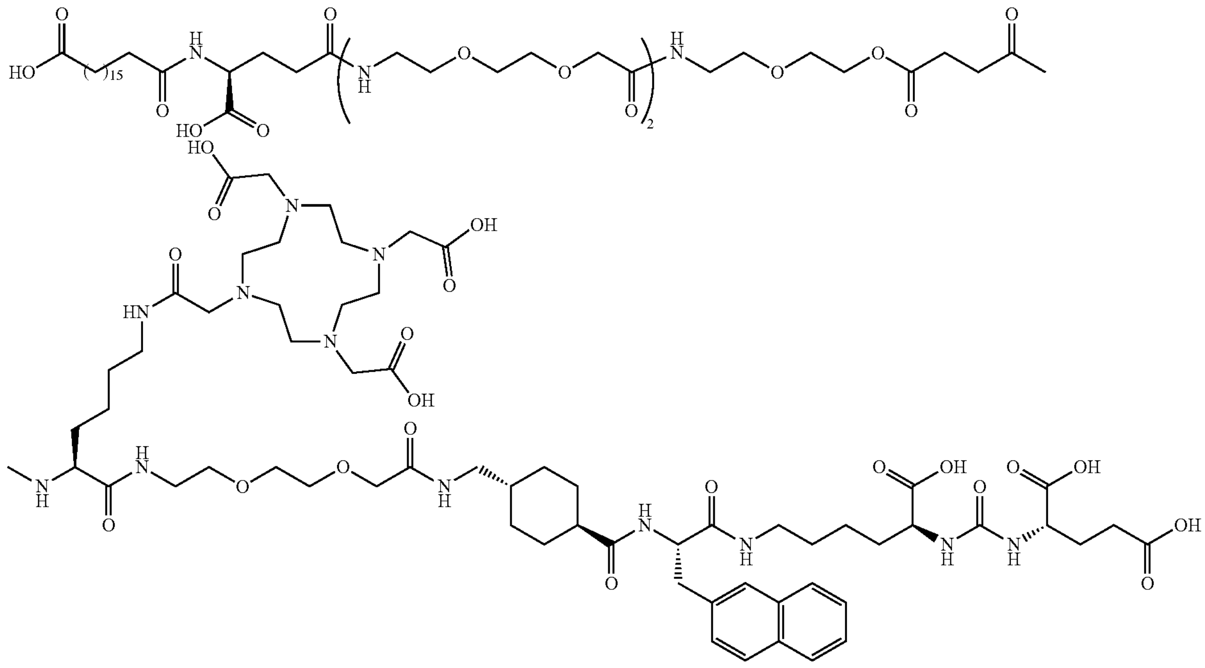
Molecular weight (average) calculated: 2218.56 g/mol
Determined by LC-MS: (M+2H)2+: 1109.8; (M+3H)3+: 740.3
Purity by UPLC (214 nm): >99.0%

Example 32: (HO-C18)-gGlu-OEG-OEG-OEG-OEG-OEG-Glu-Arg-Gly-Glu-Thr-Gly-Pro-Ser-Gly-OEG-Lys(-ESL1-DOTA)-Trx-2NaI-eKuE (I-32)
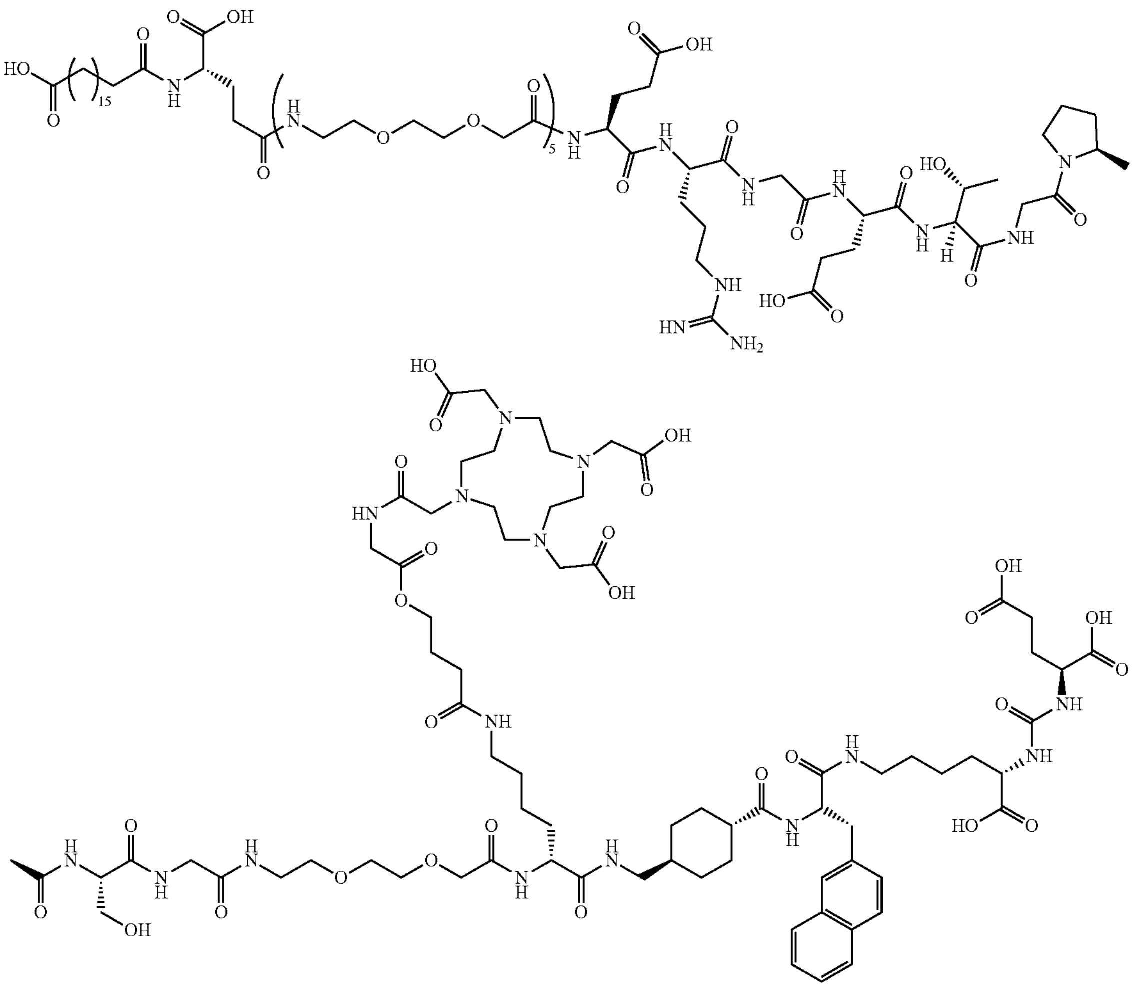
Molecular weight (average) calculated: 3480.86 g/mol
Determined by LC-MS: (M+2H)2+: 1741.2; (M+3H)3+: 1160.8; (M+4H)4+: 871.0
Purity by UPLC (214 nm): 99.7%
Example 33: 4pIBA-Glu-OEG-$NH_2CH_2CH_2NH$-TMA[-ESL1-Lys(DOTA)-Trx-2NaI-eKuE]$_2$ (I-33)
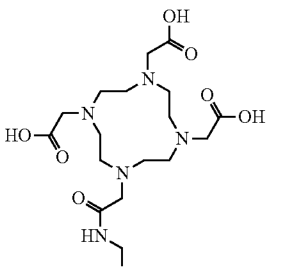

-continued
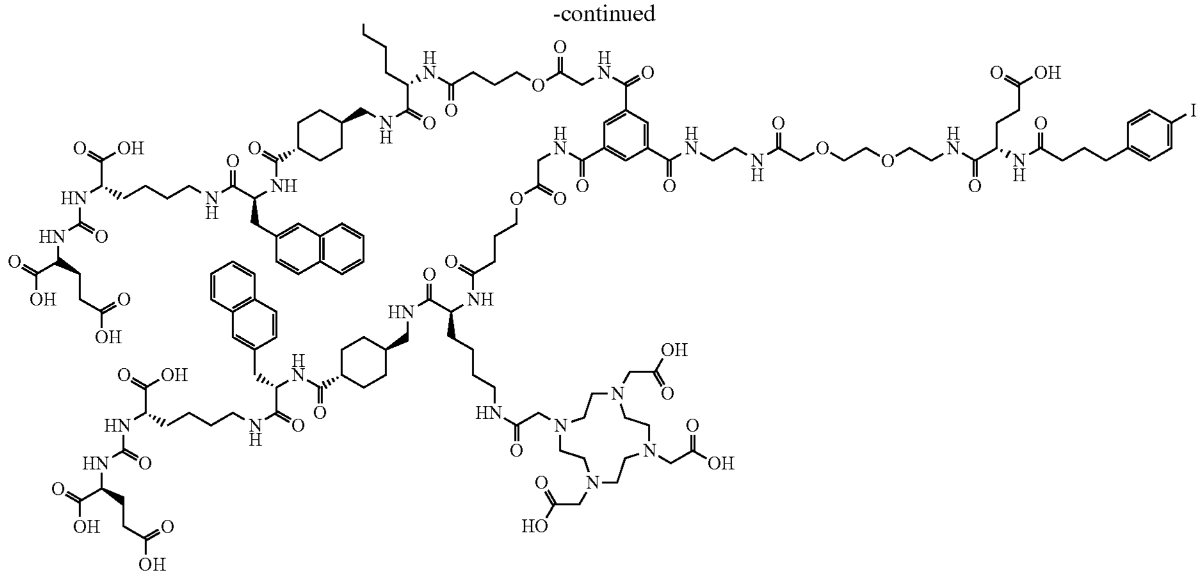
Molecular weight (average) calculated: 3389.50 g/mol
Determined by LC-MS: (M+2H)2+: 1694.9; (M+3H)3+: 1130.3; (M+4H)4+: 848.0
Purity by UPLC (214 nm): 99.2%
Example 34: HO-C18-gGlu-Lys(-ESL1-DOTA)-OEG-OEG-OEG-$NH_2CH_2CH_2NH$-TMA(-OEG-Trx-2NaI-eKuE)2 (I-34)
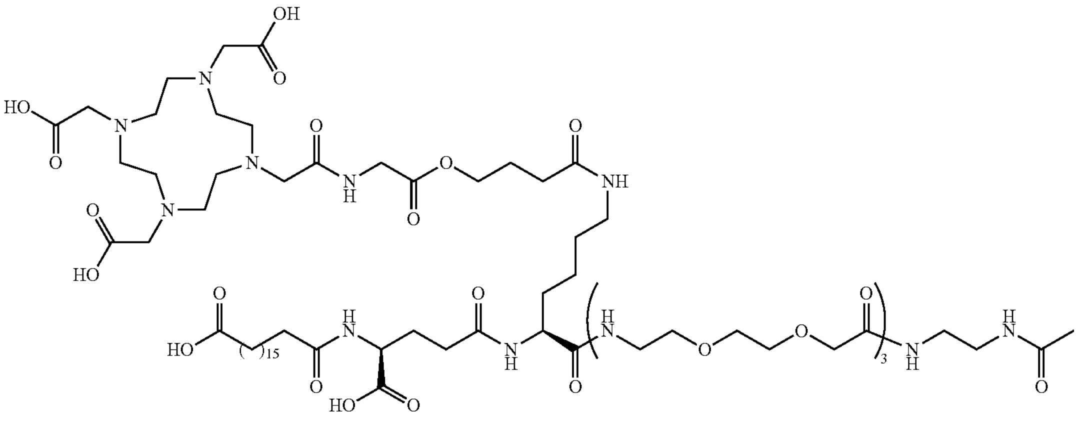

-continued
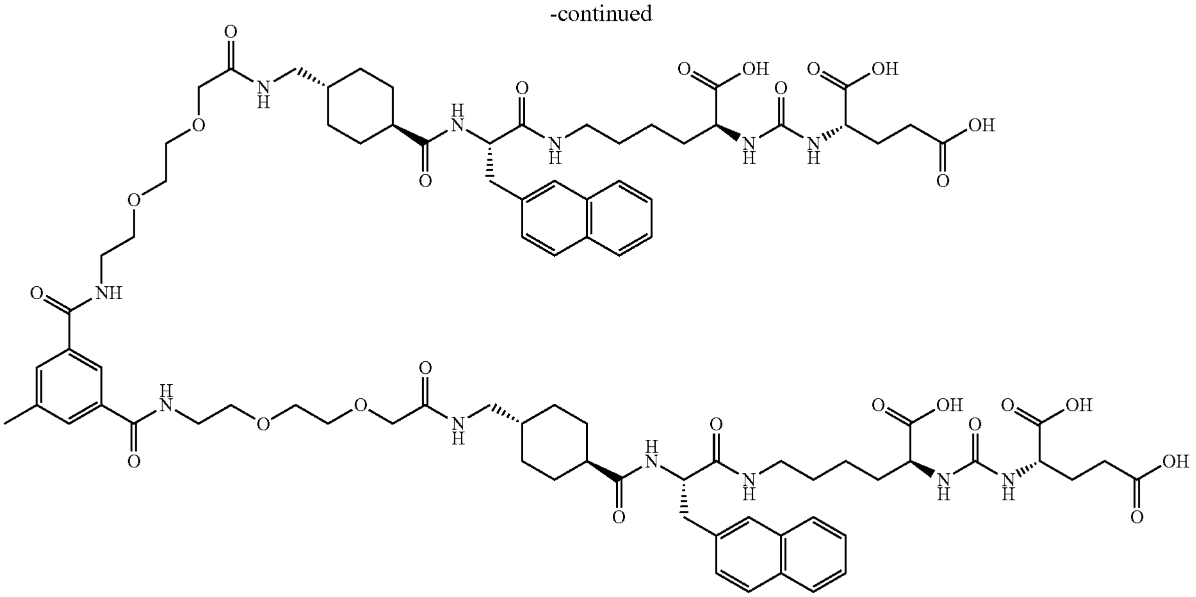
Molecular weight (average) calculated: 3336.77 g/mol
Determined by LC-MS: (M+2H)2+: 1670.4; (M+3H)3+: 1114.0; 835.7
Purity by UPLC (214 nm): 97.1%
Example 35: HO-C20-gGlu-OEG-OEG-Lys(-ESL1-DOTA)-OEG-$NH_2CH_2CH_2NH$-TMA(-OEG-Trx-2NaI-eKuE)2 (I-35)
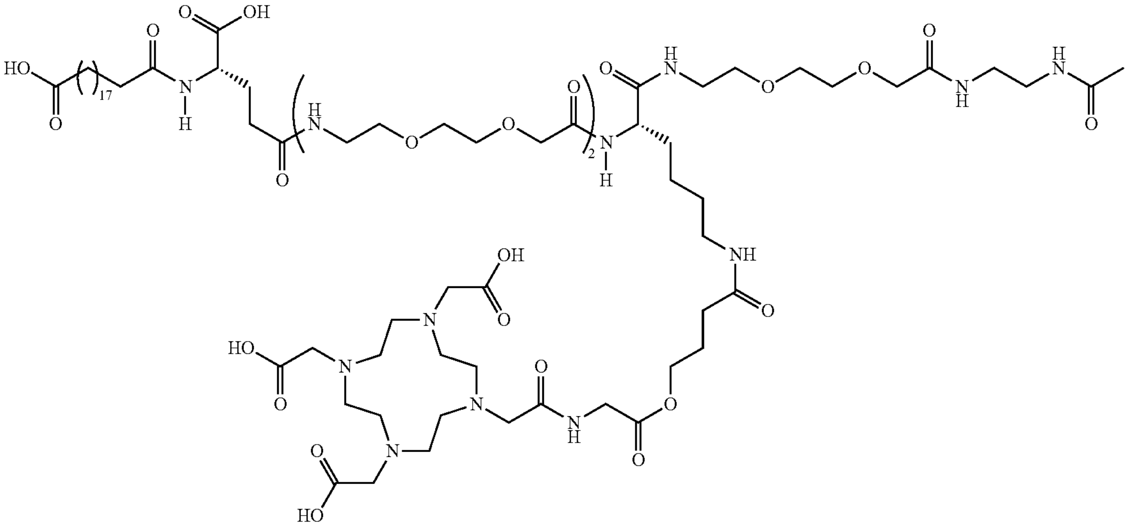

-continued
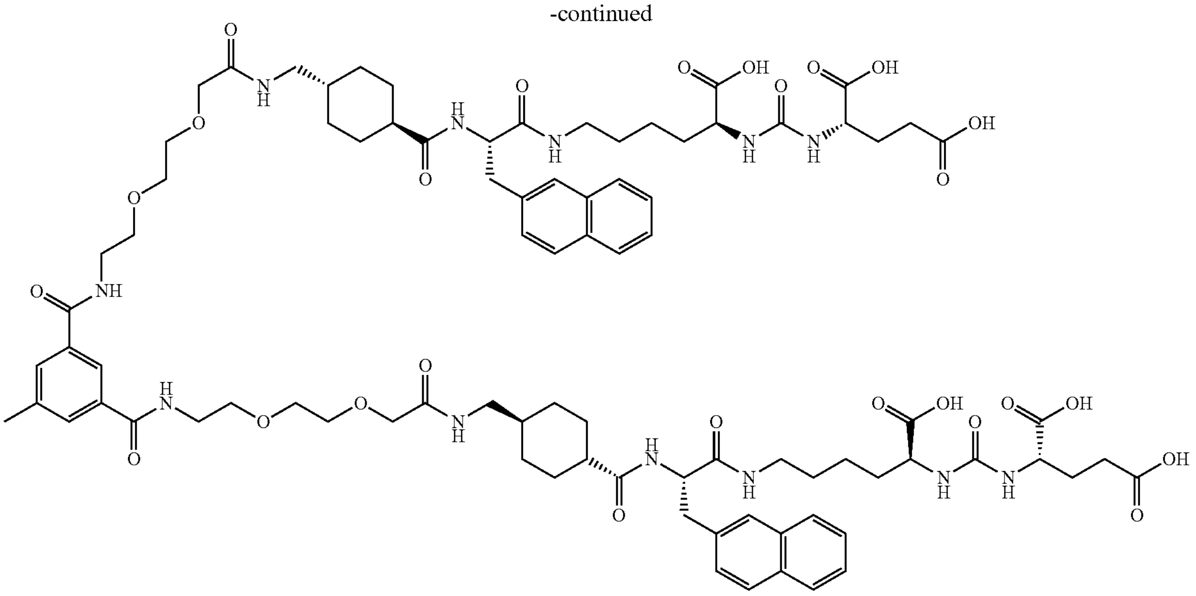
Molecular weight (average) calculated: 3364.83 g/mol
Determined by LC-MS: (M+2H)2+: 1682.6; (M+3H)3+: 1122.3; (M+4H)4+: 842.0; (M+5H)5+: 673.9
Purity by UPLC (214 nm): 99.6%
Example 36: HO-C20-gGlu-Lys(-ESL2-DOTA)-OEG-OEG-OEG-$NH_2CH_2CH_2NH$-TMA(-OEG-Trx-2NaI-eKuE)2 (I-36)
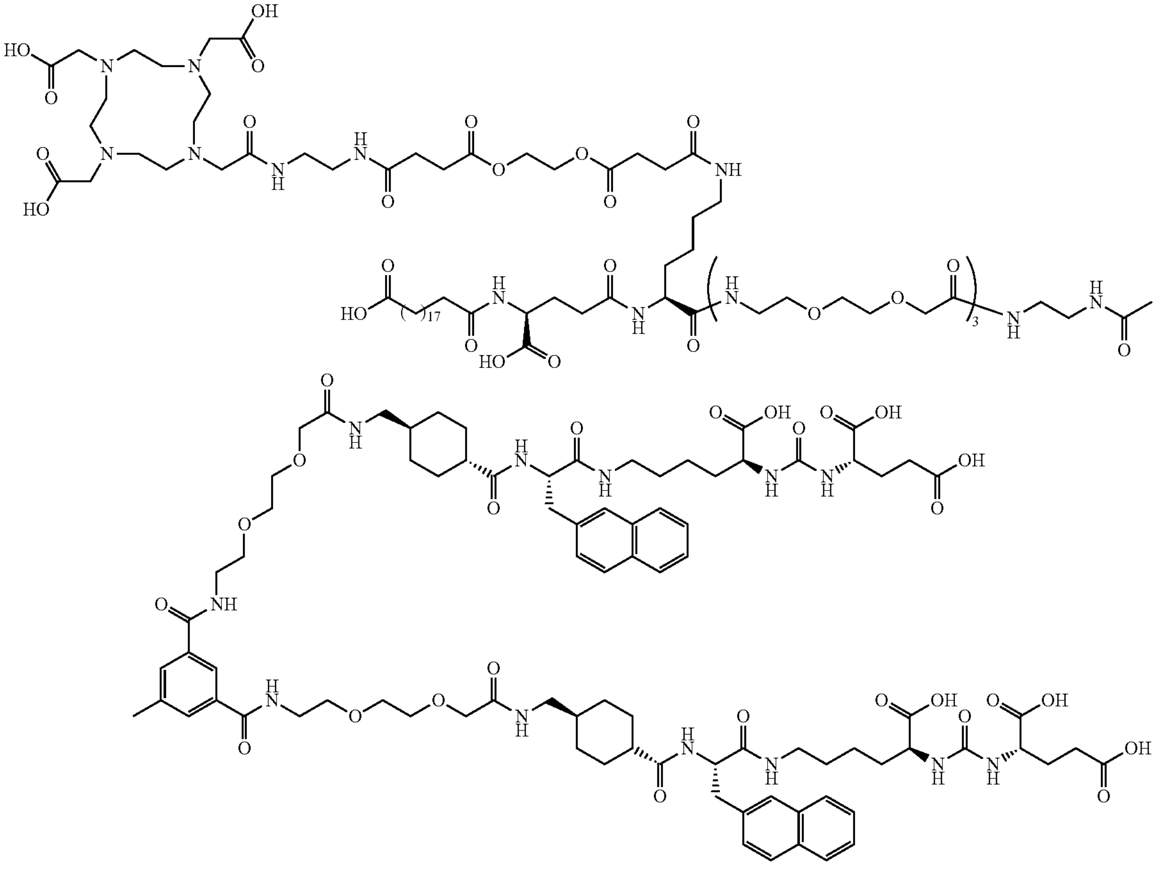

Molecular weight (average) calculated: 3507.97 g/mol
Determined by LC-MS: (M+3H)3+: 1169.9; (M+4H)4+: 877.8; (M+5H)5+: 702.5
Purity by UPLC (214 nm): 99.6%
Example 37: HO-C20-gGlu-Lys(-ESL1-ESL1-DOTA)-OEG-OEG-OEG-$NH_2CH_2CH_2NH$-TMA(-OEG-Trx-2Nal-eKuE)$_2$ (I-37)
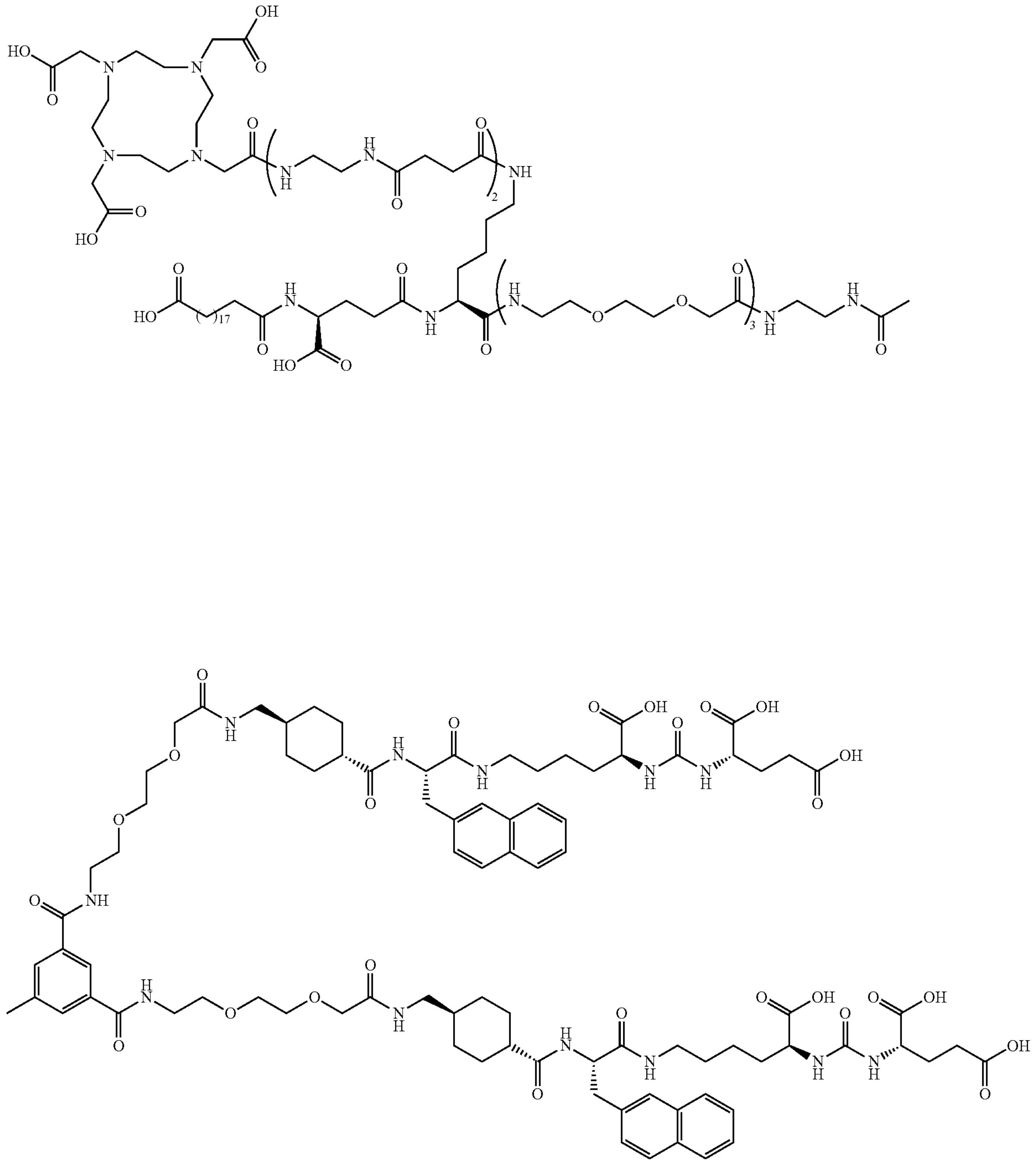
Molecular weight (average) calculated: 3507.97 g/mol
Determined by LC-MS: (M+3H)3+: 1169.9; (M+4H)4+: 877.8; (M+5H)5+: 702.4
Purity by UPLC (214 nm): 99.6%

Example 38: HO-C18-gGlu-OEG-OEG-Lys(-ESL1-DOTA)-OEG-$NH_2CH_2CH_2NH$-TMA(-OEG-Trx-2Nal-eKuE)$_2$ (I-38)
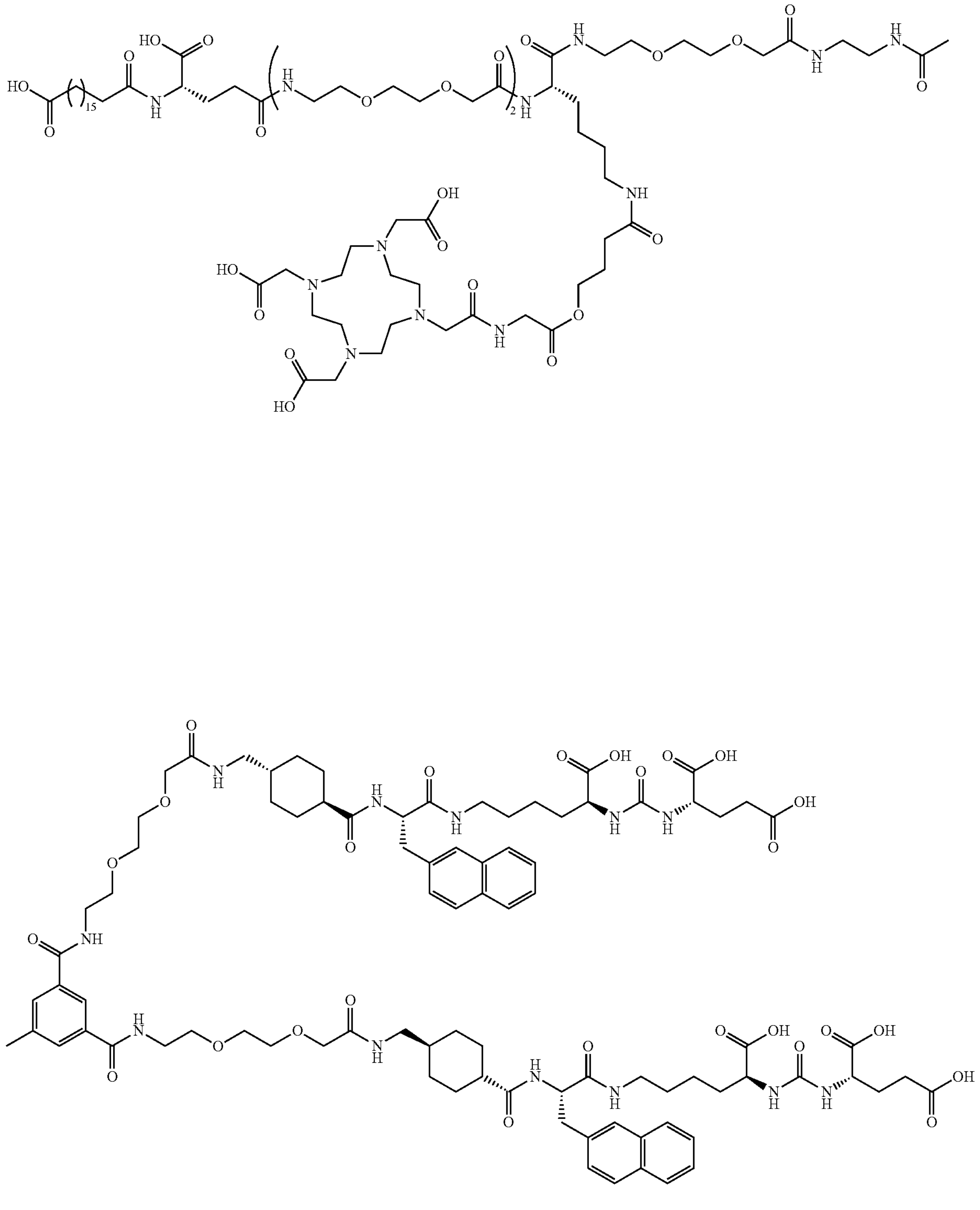
Molecular weight (average) calculated: 3336.77 g/mol
Determined by LC-MS: (M+2H)2+: 1668.6; (M+3H)3+: 1112.9; (M+4H)4+: 835.0; (M+5H)5+: 668.4
Purity by UPLC (214 nm): 98.9%

Example 39: HO-C18-gGlu-Lys(-ESL2-DOTA)-OEG-OEG-OEG-$NH_2CH_2CH_2NH$-TMA(-OEG-Trx-2Nal-eKuE)$_2$ (I-39)
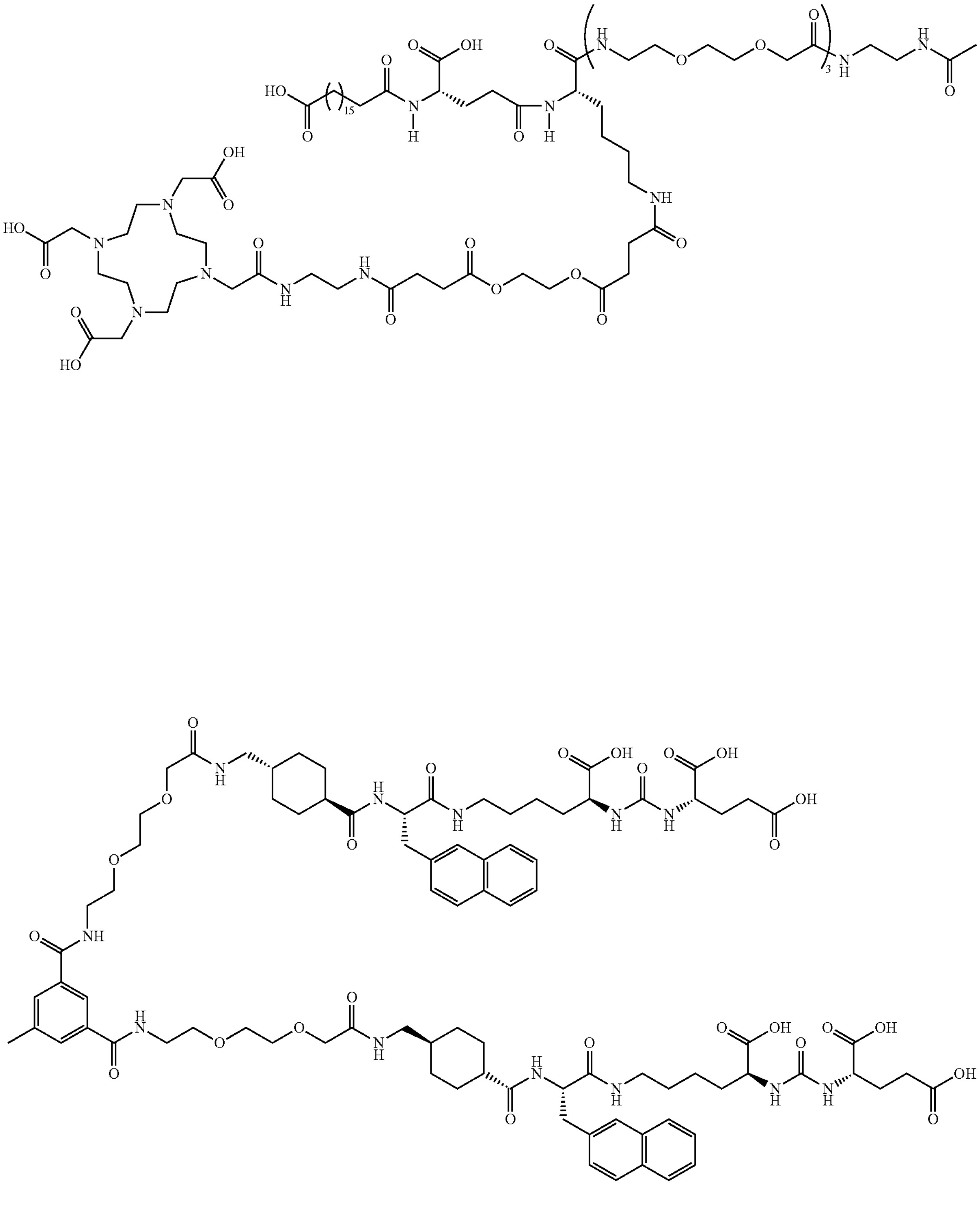
Molecular weight (average) calculated: 3479.91 g/mol
Determined by LC-MS: (M+2H)2+: (M+3H)3+: 1160.6; (M+4H)4+: 870.8; (M+5H)5+: 696.8
Purity by UPLC (214 nm): 96.8%

Example 40: HO-C18-gGlu-OEG-Lys(-ESL1-DOTA)-OEG-$NH_2CH_2CH_2NH$-TMA(-OEG-Trx-2NaI-eKuE)$_2$ (I-40)
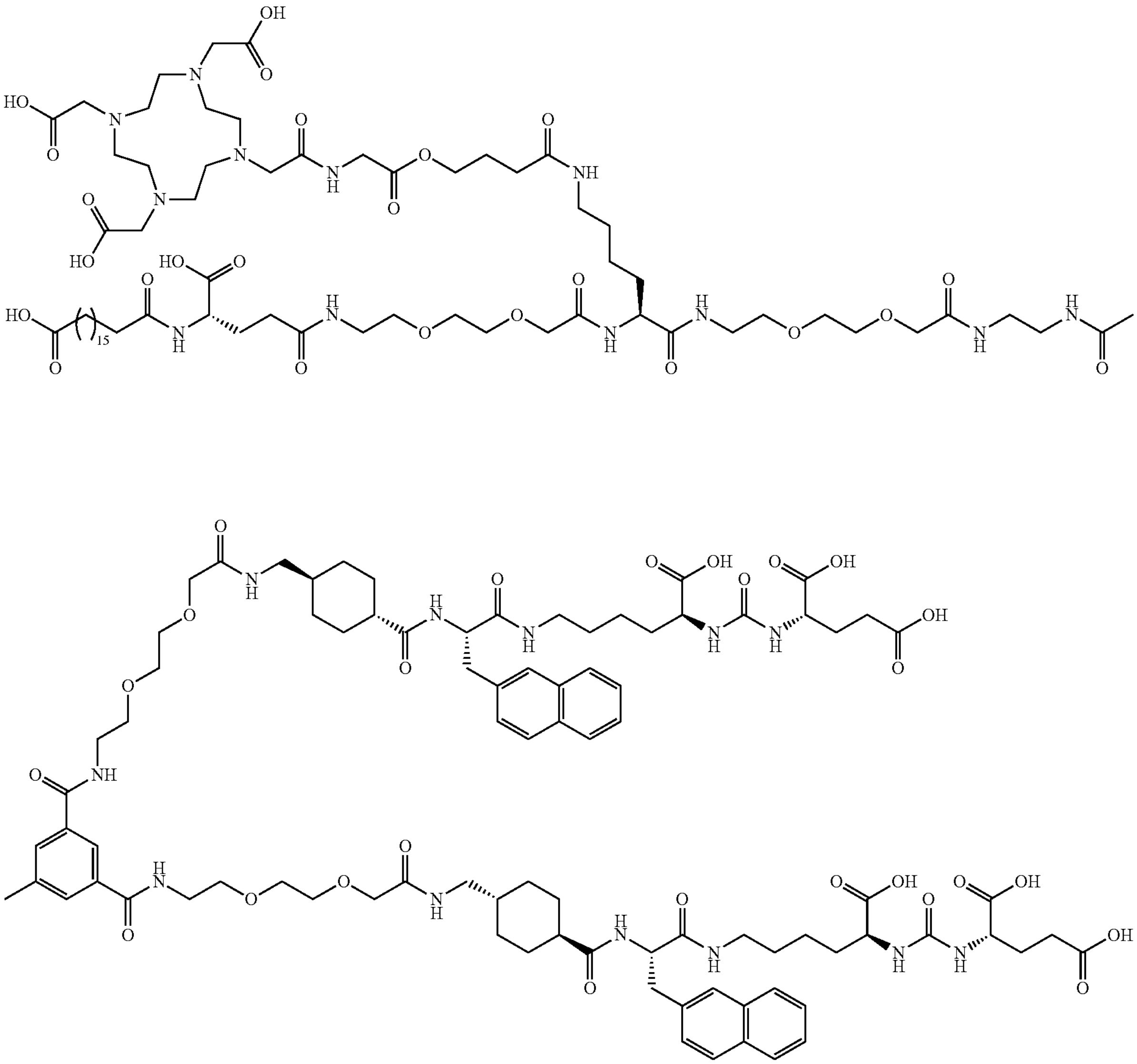
Molecular weight (average) calculated: 3191.61 g/mol
Determined by LC-MS: (M+2H)2+: 1596.5; (M+3H)3+: 1064.6; (M+4H)4+: 798.8
Purity by UPLC (214 nm): >99.0%
Example 41: HO-C18-gGlu-OEG-OEG-$NH_2CH_2CH_2NH$-TMA[-ESL1-Lys(DOTA)-Trx-2NaI-eKuE]$_2$ (I-41)
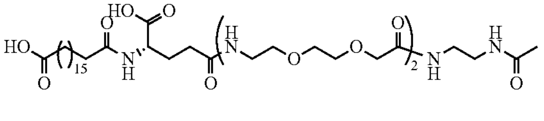

-continued
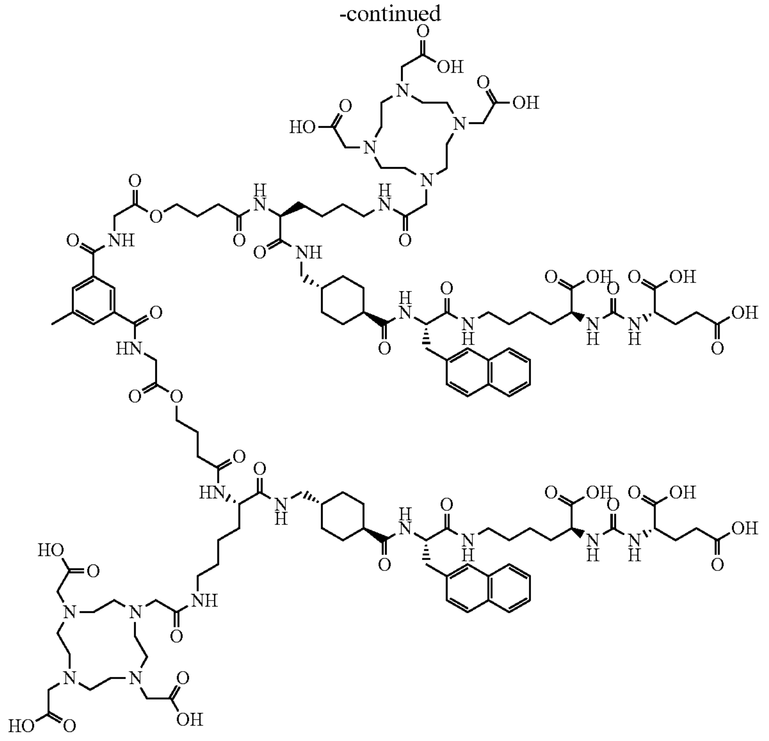
Molecular weight (average) calculated: 3559.02 g/mol
Determined by LC-MS: (M+2H)2+: (M+3H)3+: 1186.9; (M+4H)4+: 890.4; (M+5H)5+: 712.7
Purity by UPLC (214 nm): 98.2%
Example 42: HO-C20-gGlu-OEG-OEG-$NH_2CH_2CH_2NH$-TMA[-ESL1-Lys(DOTA)-Trx-2NaI-eKuE]$_2$ (I-42)
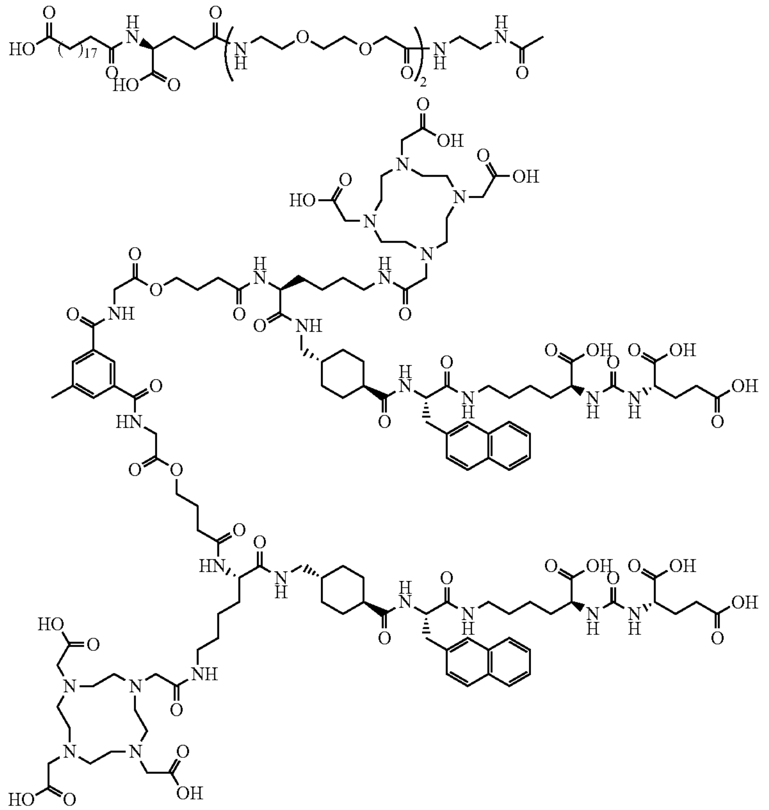

Molecular weight (average) calculated: 3587.07 g/mol
Determined by LC-MS: (M+3H)3+: 1196.4; (M+4H)4+: 897.5; (M+5H)5+: 718.4
Purity by UPLC (214 nm): 99.2%
Example 43: [HO-C18-gGlu-OEG-OEG-ESL1-Lys(DOTA)-OEG-$NH_2CH_2CH_2NH$-]-TMA-(-OEG-Trx-2NaI-eKuE)$_2$ (I-43)
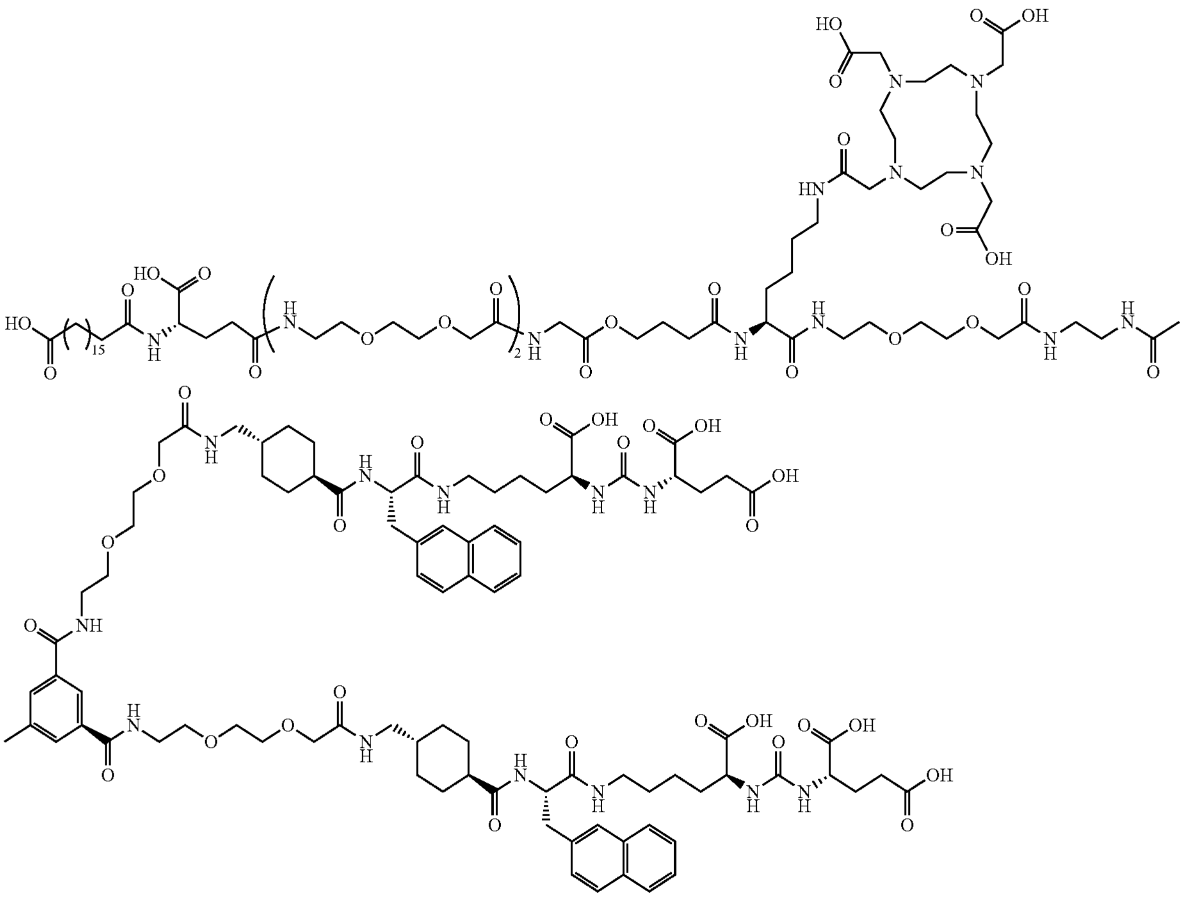
Molecular weight (average) calculated: 3336.77 g/mol
Determined by LC-MS: (M+2H)2+: 1669.0; (M+3H)3+: 1112.9; (M+4H)4+: 835.
Purity by UPLC (214 nm): >99.0%
Example 44: [HO-C20-gGlu-Lys(-ESL1-ESL1-ESL1-DOTA)-OEG-OEG-OEG-$NH_2CH_2CH_2NH$-]-TMA-(-OEG-Trx-2NaI-eKuE)$_2$ (I-44)
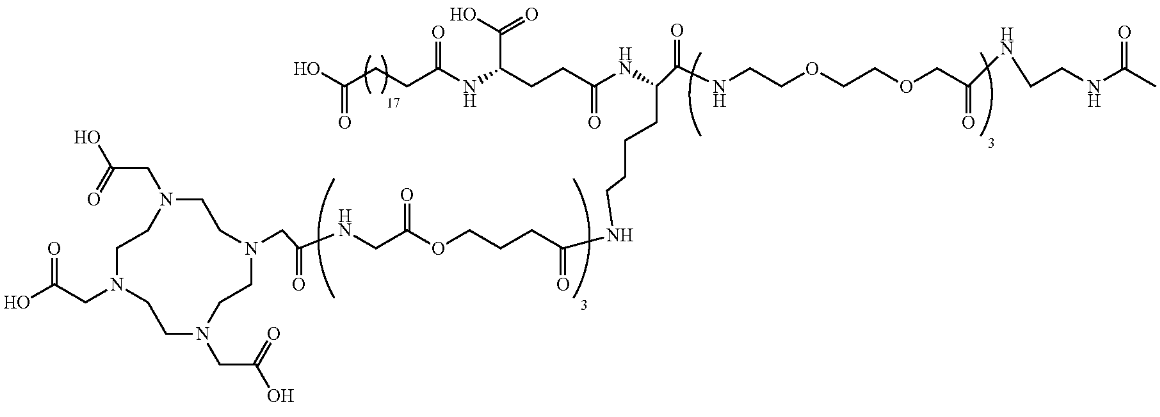

-continued
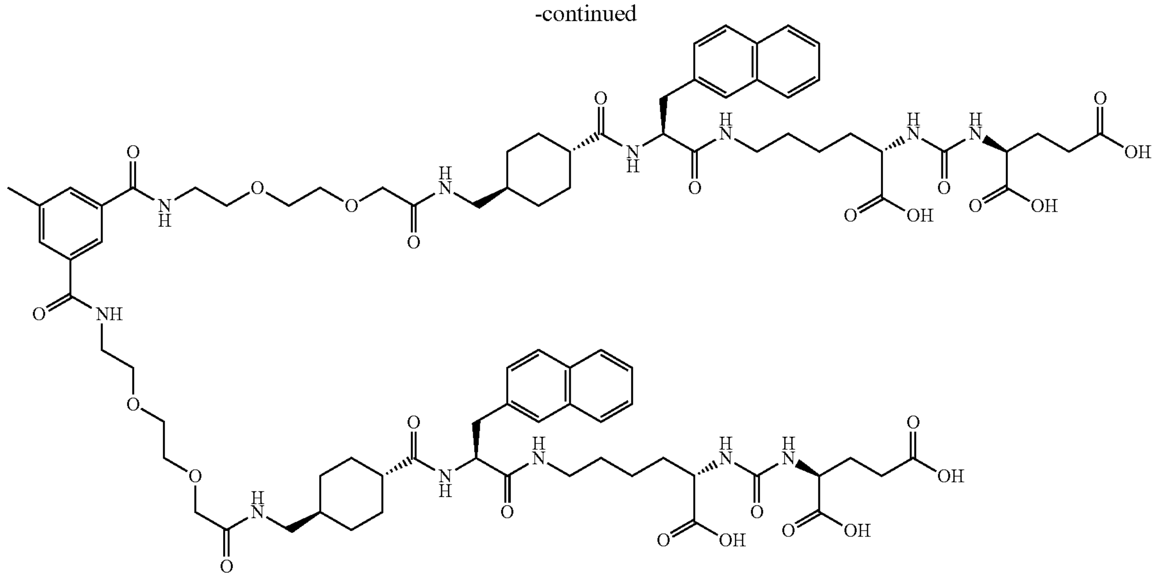
Molecular weight (average) calculated: 3651.11 g/mol
Determined by LC-MS: (M+3H)3+: 1217.7; (M+4H)4+: 913.5; (M+5H)5+: 731.2
Purity by UPLC (214 nm): >99.0%
Example 45: HO-C18-gGlu-OEG-OEG-Lys(-ESL1-Gly-Gly-DOTA)-OEG-Trx-2NaI-eKuE (I-45)
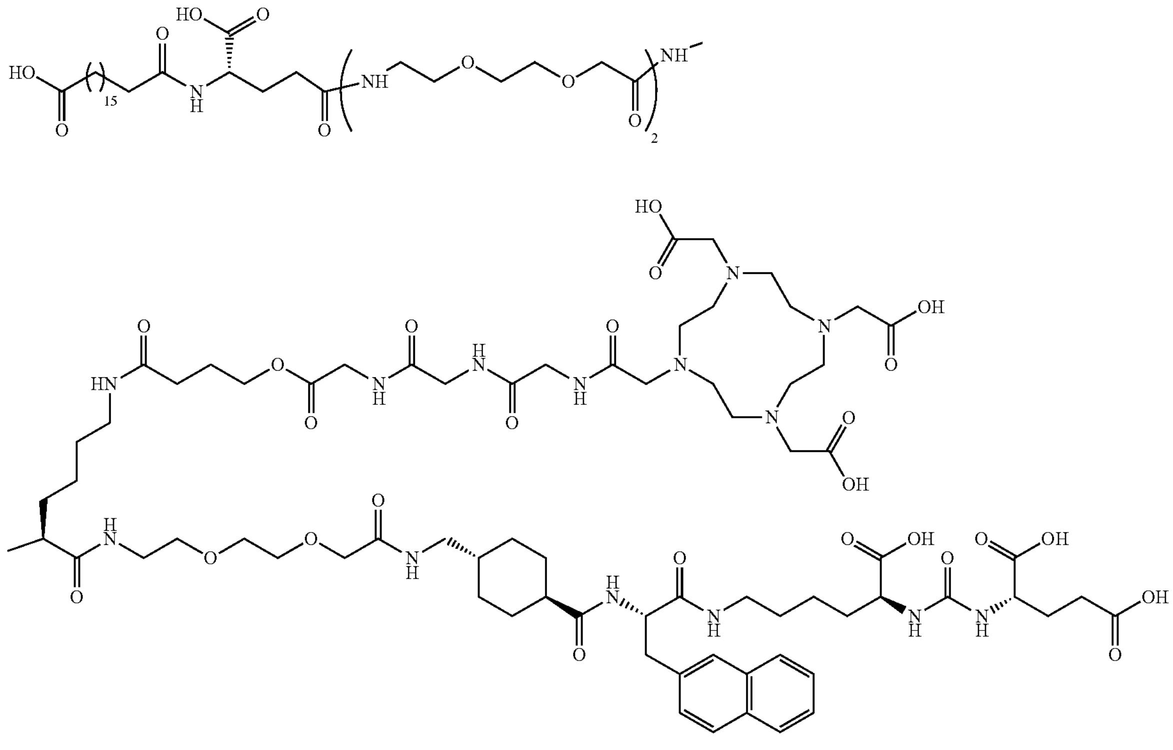
Molecular weight (average) calculated: 2288.6 g/mol
Determined by LC-MS: (M+2H)2+: 1145.0; (M+3H)3+: 763.6; (M+4H)4+: 573.0
Purity by UPLC (214 nm): >99.0%

Example 46: HO-C18-gGlu-OEG-OEG-Lys(-ESL1-Gly-Gly-Gly-DOTA)-OEG-Trx-2NaI-eKuE (I-46)
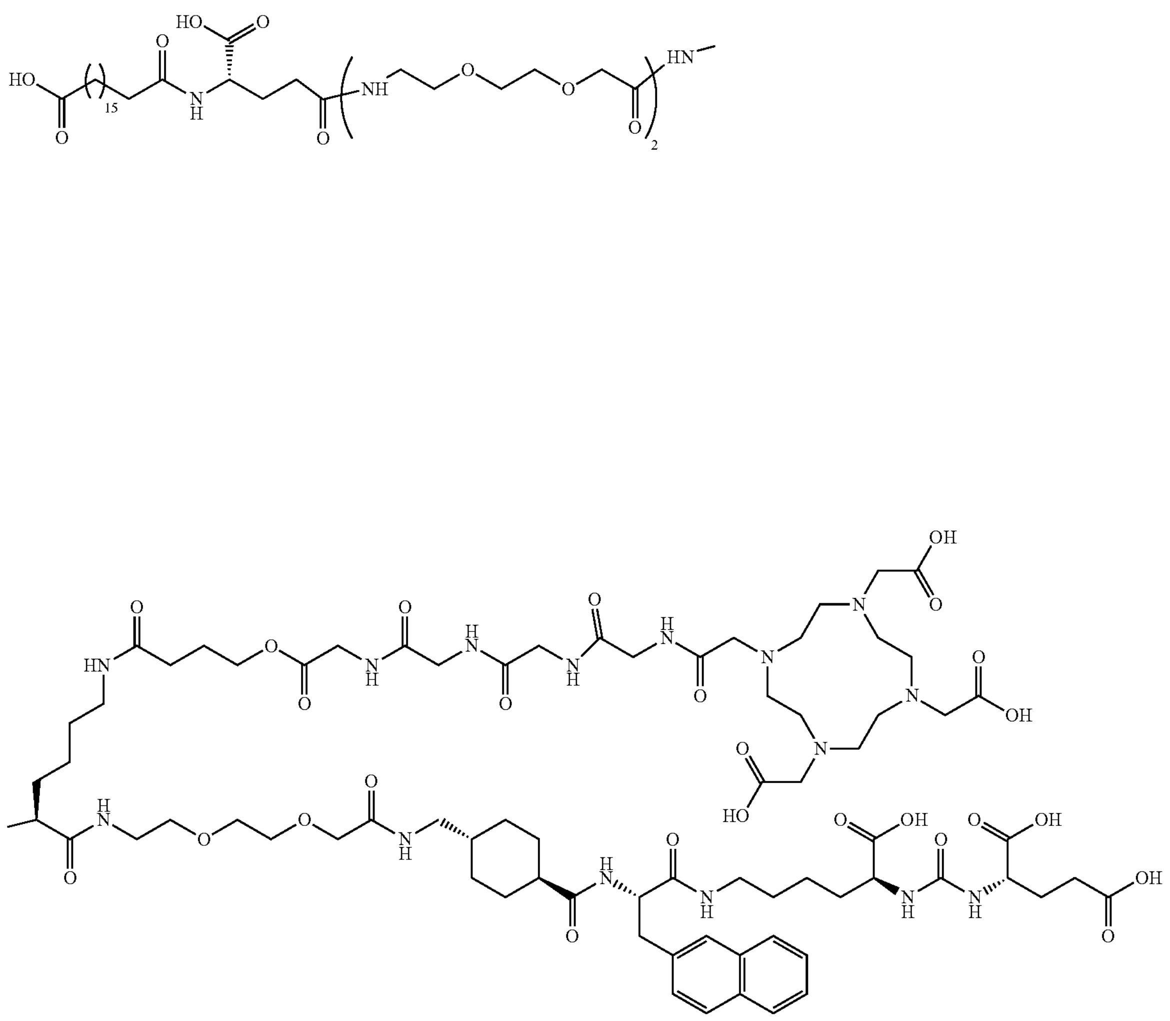
Molecular weight (average) calculated: 2345.7 g/mol
Determined by LC-MS: (M+2H)2+: 1173.4; (M+3H)3+: 782.6; (M+4H)4+: 587.3
Purity by UPLC (214 nm): >99.0%
Example 47: HO-C18-gGlu-OEG-OEG-Lys(-ESL1-OEG-DOTA)-OEG-Trx-2NaI-eKuE (I-47)
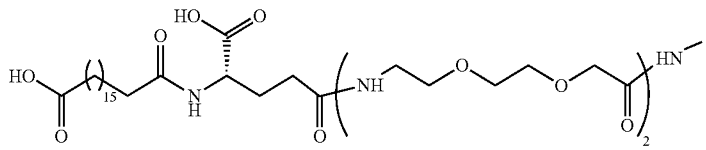

-continued
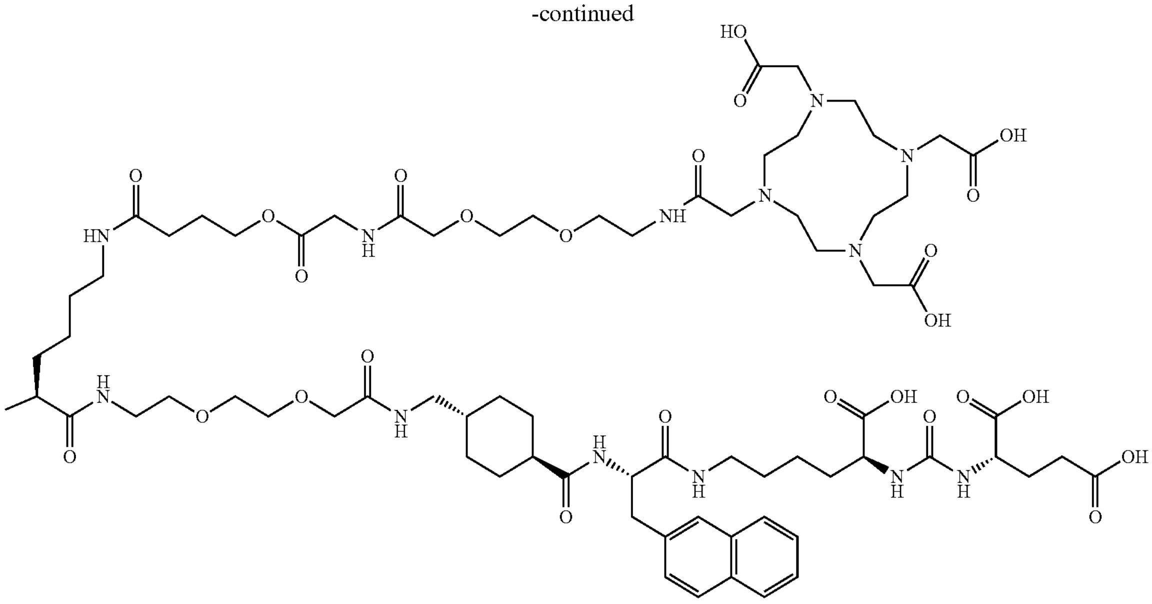
Molecular weight (average) calculated: 2319.7 g/mol
Determined by LC-MS: (M+2H)2+: 1160.5; (M+3H)3+: 774.0; (M+4H)4+: 580.8
Purity by UPLC (214 nm): 95.4%
Example 48: HO-C18-gGlu-OEG-OEG-Lys(-ESL1-Gly-OEG-DOTA)-OEG-Trx-2NaI-eKuE
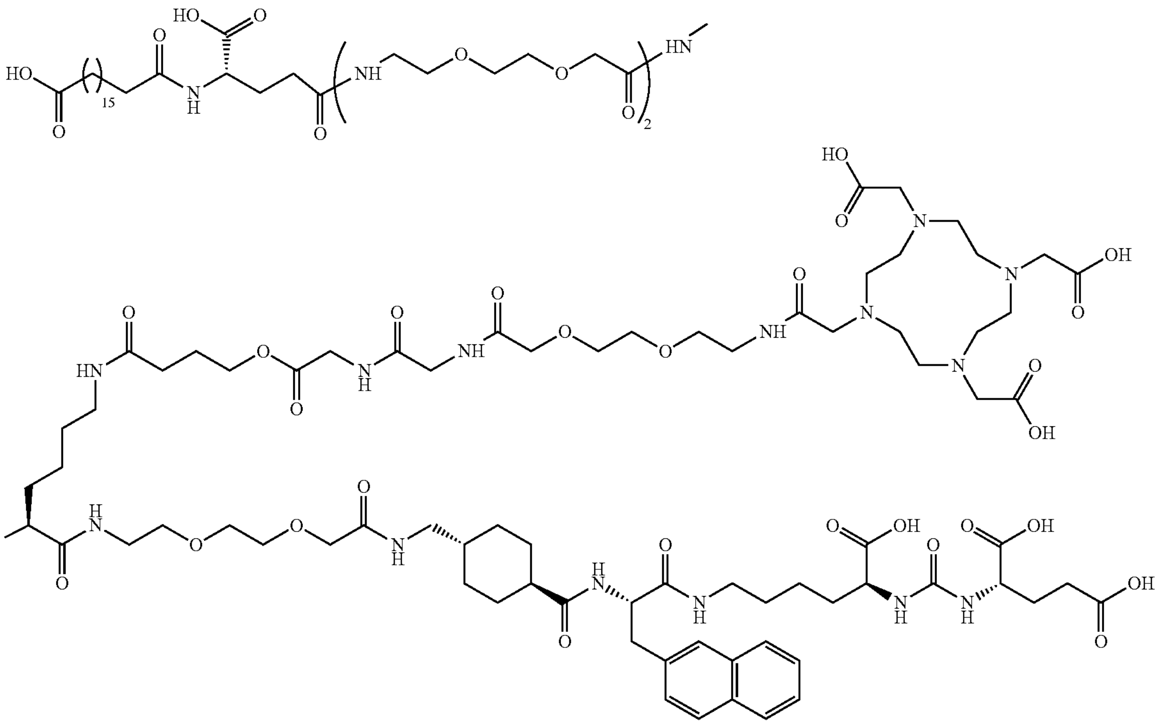
Molecular weight (average) calculated: 2376.7 g/mol
Determined by LC-MS: (M+2H)2+: 1188.9; (M+3H)3+: 793.1; (M+4H)4+: 595.2
Purity by UPLC (214 nm): 98.1%

Example 49: HO-C18-gGlu-OEG-OEG-Gly-5hPA-Lys(DOTA)-OEG-Trx-2NaI-eKuE (I-49)
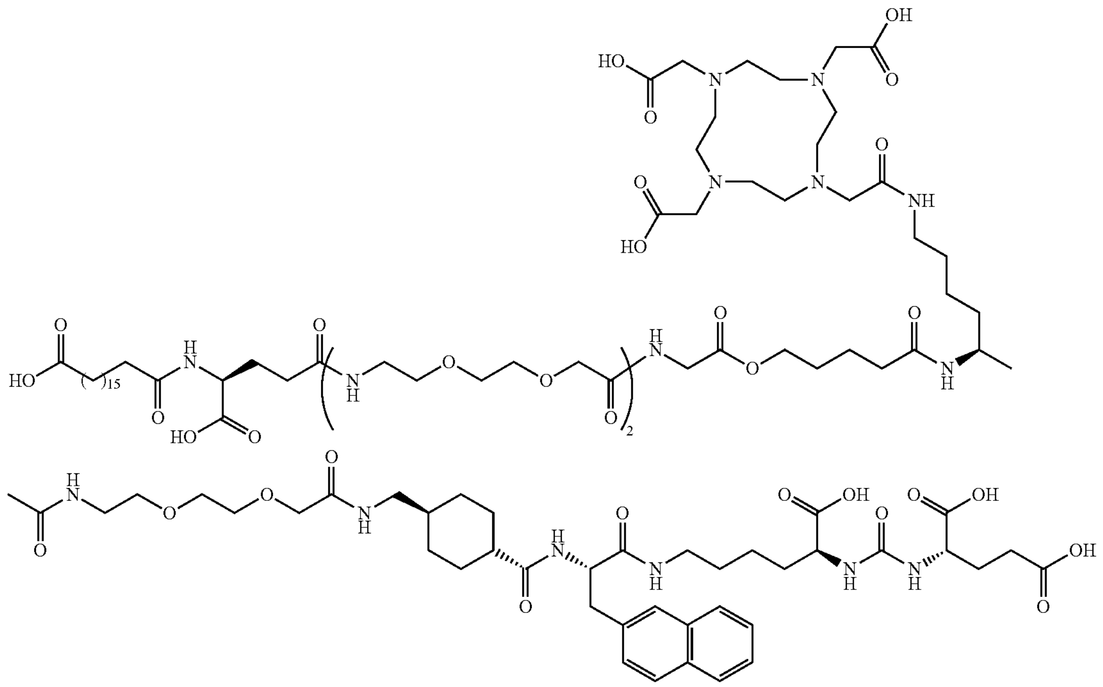
Molecular weight (average) calculated: 2188.5 g/mol
Determined by LC-MS: (M+2H)2+: 1094.8; (M+3H)3+: 730.3
Purity by UPLC (214 nm): >94.8%
Example 50: HO-C18-gGlu-OEG-OEG-Gly-6hHA-Lys(DOTA)-OEG-Trx-2NaI-eKuE (I-50)
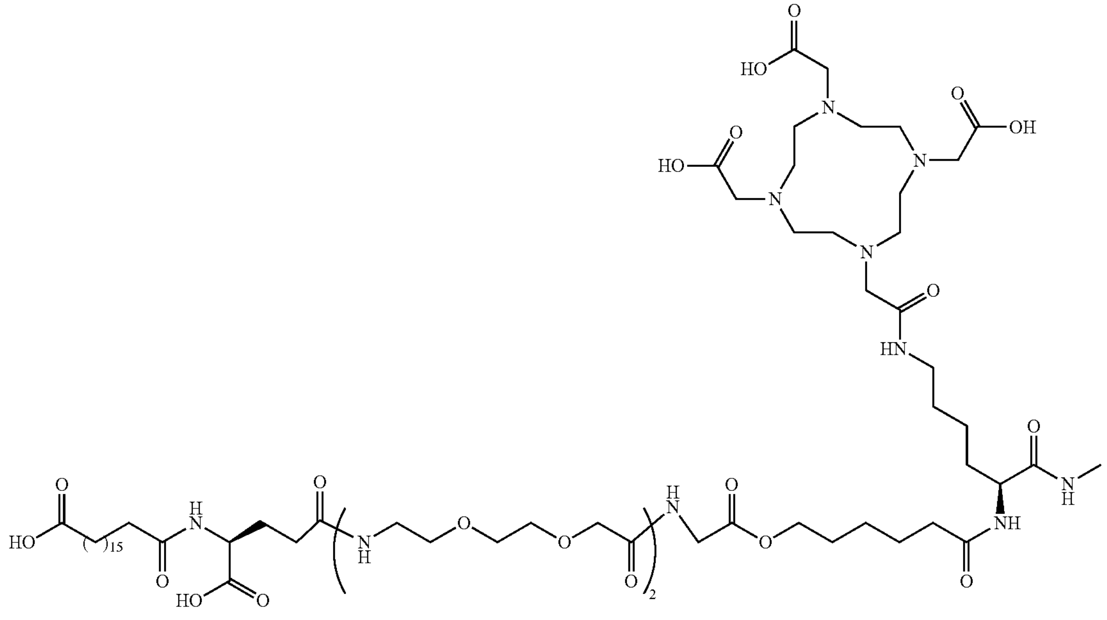

-continued
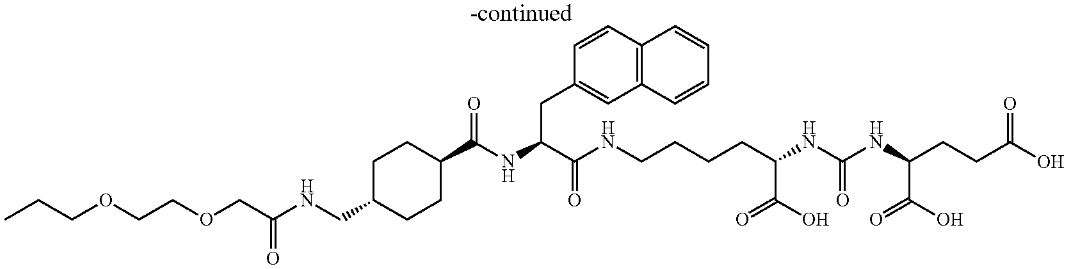
Molecular weight (average) calculated: 2202.6 g/mol
Determined by LC-MS: (M+2H)2+: 1101.8; (M+3H)3+: 735.0
Purity by UPLC (214 nm): 95.3%
Example 51: HO-C18-gGlu-OEG-OEG-ESL1-Gly-Lys(DOTA)-OEG-Trx-2NaI-eKuE (I-51)
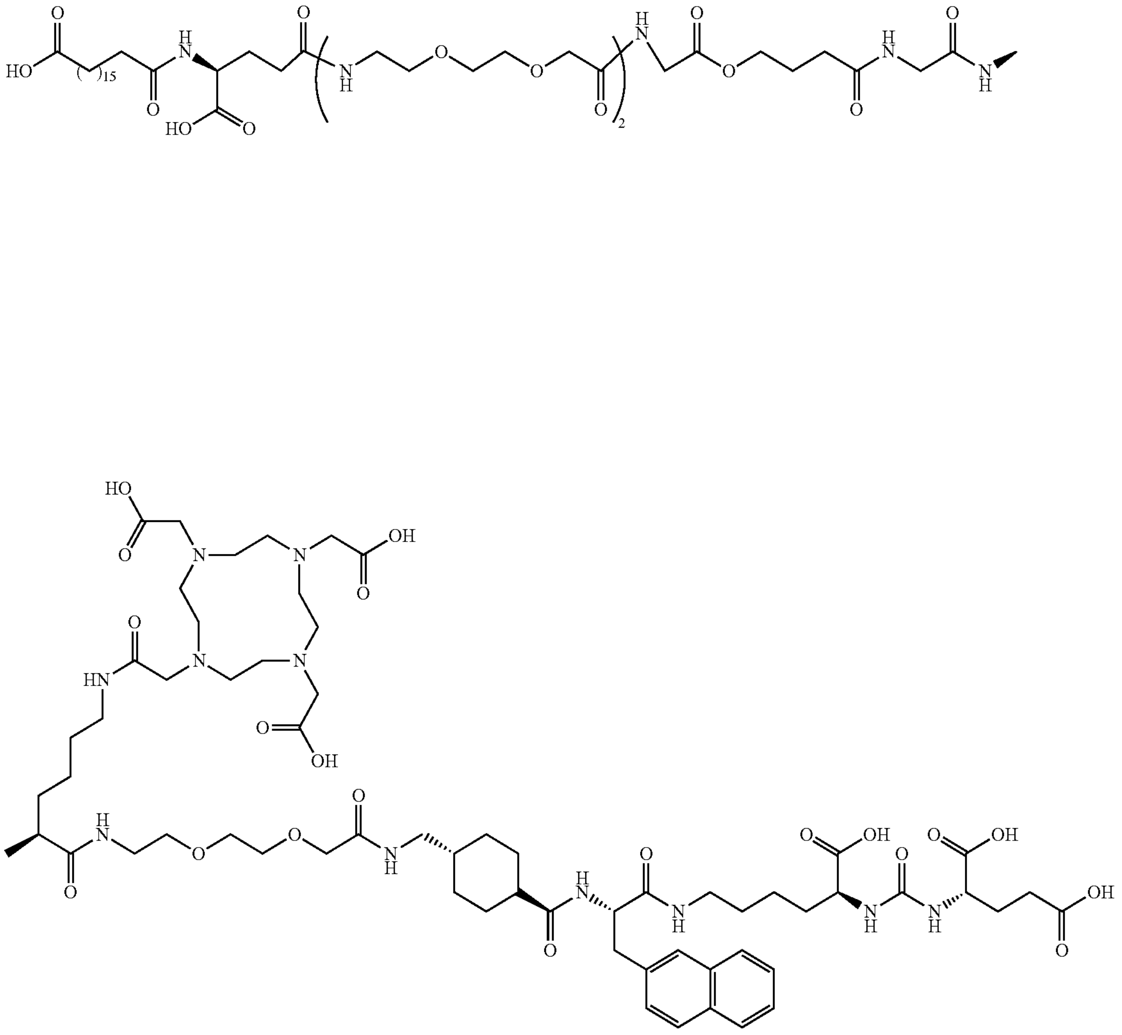
Molecular weight (average) calculated: 2231.6 g/mol
Determined by LC-MS: (M+2H)2+: 1116.3; (M+3H)3+: 744.7
Purity by UPLC (214 nm): >99.0%

Example 52: HO-C18-gGlu-OEG-OEG-ESL1-Gly-Gly-Lys(DOTA)-OEG-Trx-2NaI-eKuE (I-52)
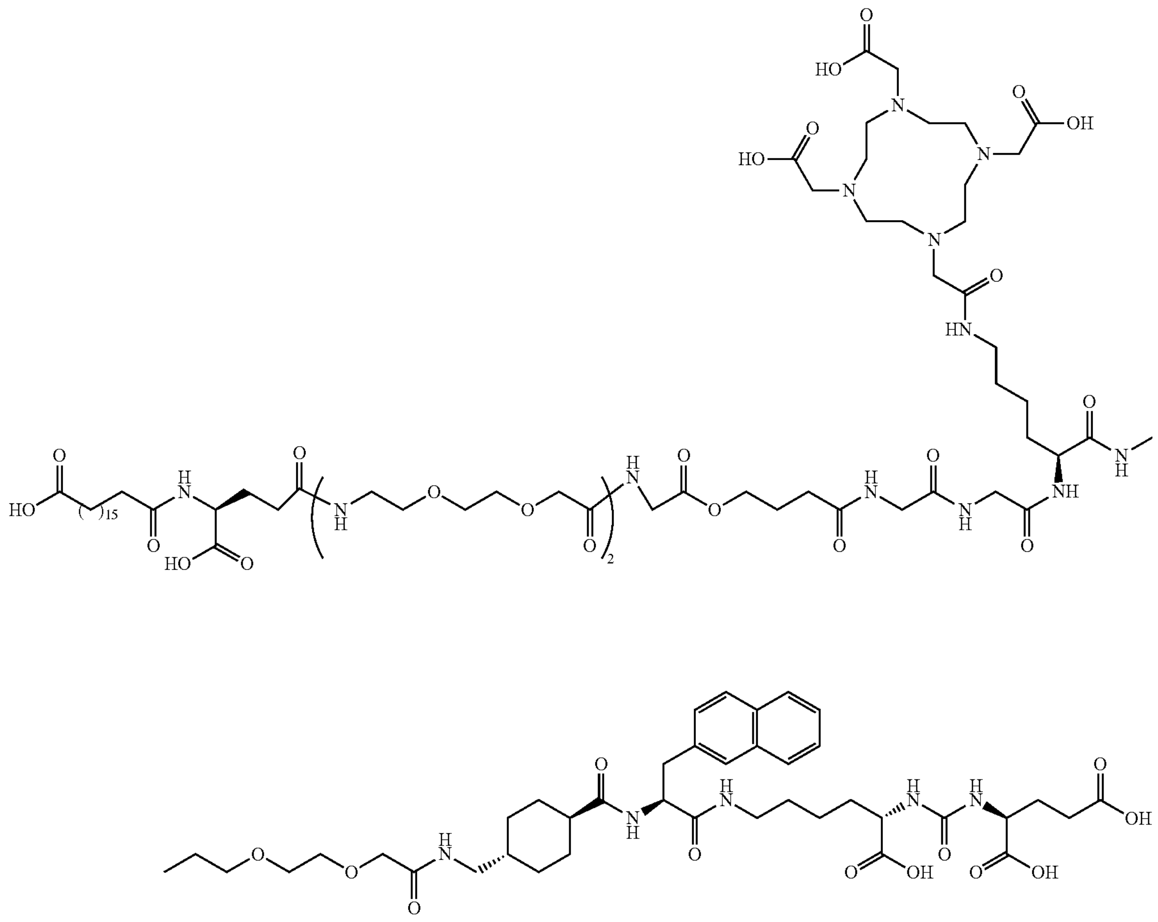
Molecular weight (average) calculated: 2288.6 g/mol
Determined by LC-MS: (M+2H)2+: 1144.7; (M+3H)3+: 763.7
Purity by UPLC (214 nm): 96.7%
Example 53: HO-C18-gGlu-OEG-OEG-Gly-4hPA-OEG-Lys(DOTA)-Trx-2NaI-eKuE (I-53)
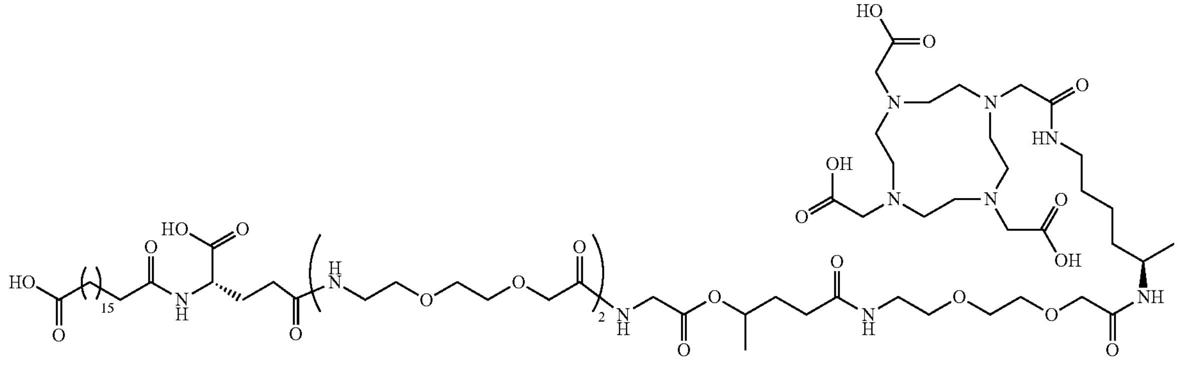

-continued
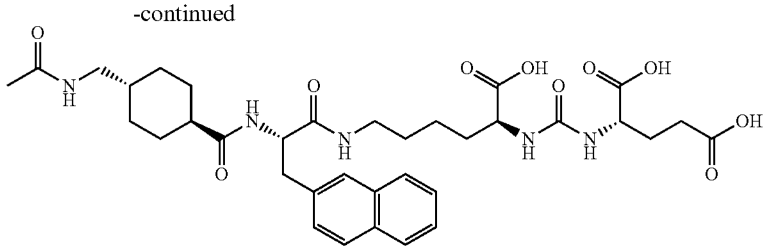
Molecular weight (average) calculated: 2188.5 g/mol
Determined by LC-MS: (M+2H)2+: 1095.1; (M+3H)3+: 730.3
Purity by UPLC (214 nm): >99.0%
Example 54: HO-C18-gGlu-OEG-OEG-Leu-4hBA-OEG-Lys(DOTA)-Trx-2NaI-eKuE (I-54)
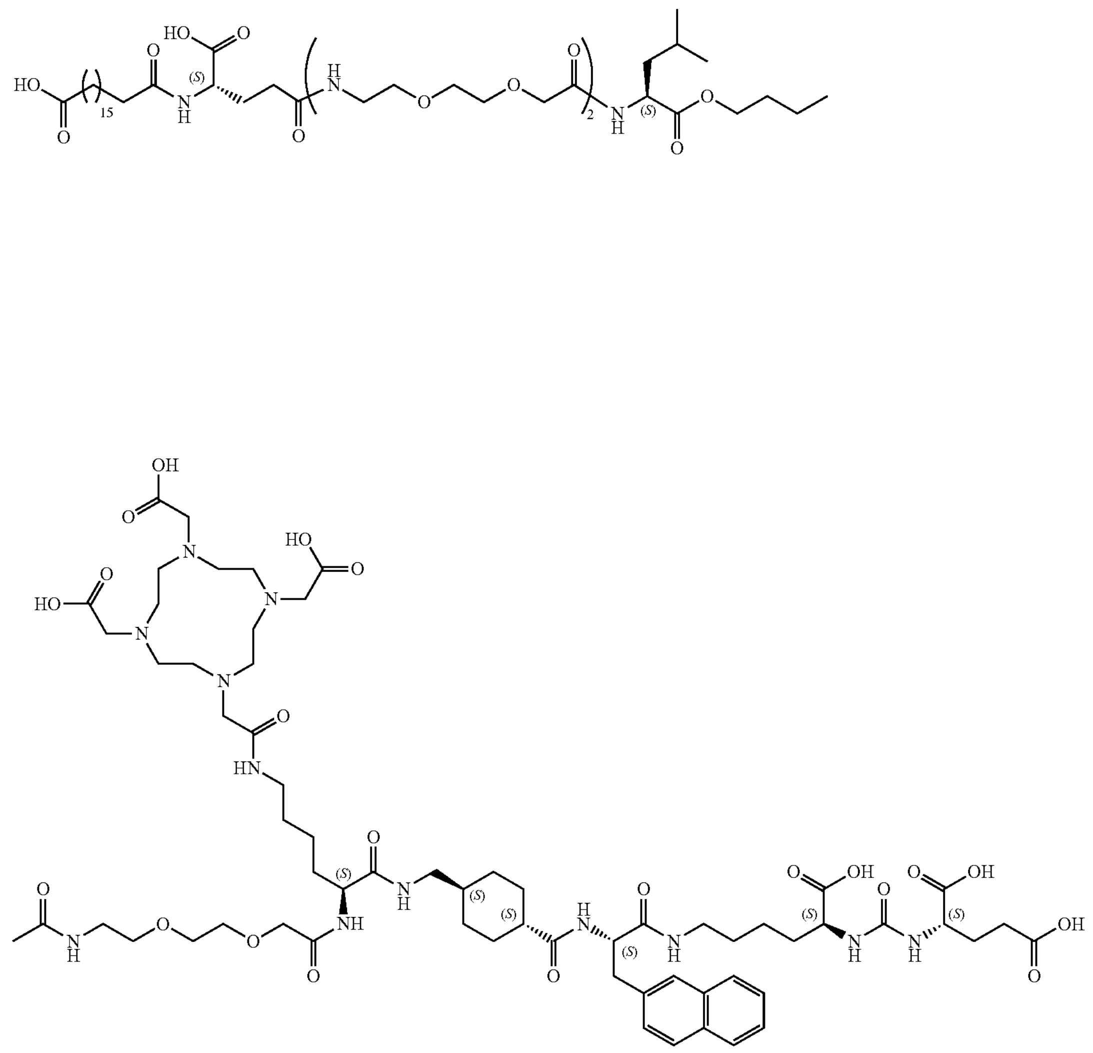
Molecular weight (average) calculated: 2230.6 g/mol
Determined by LC-MS: (M+2H)2+: 1115.9; (M+3H)3+: 744.3
Purity by UPLC (214 nm): >99.0%

Example 55(a): HO-C18-gGlu-OEG-OEG-Leu-4hPA-OEG-Lys(DOTA)-Trx-2NaI-eKuE (I-55(a))
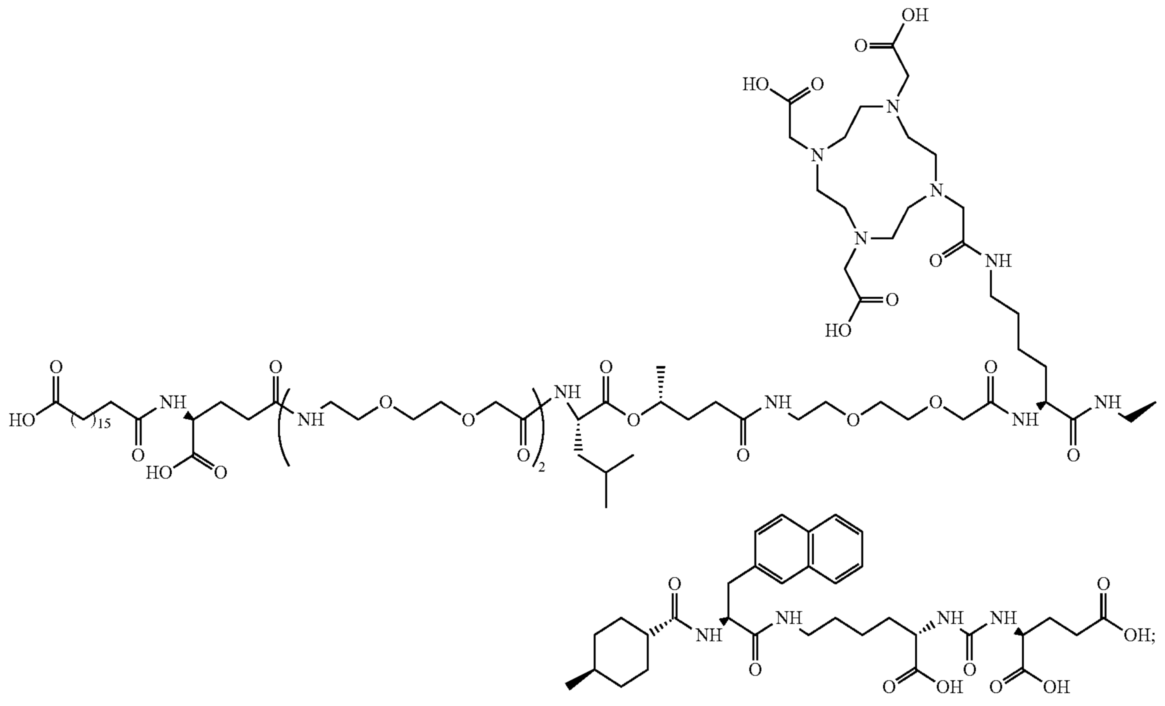
and
Example 55(b): HO-C18-gGlu-OEG-OEG-Leu-4hPA-OEG-Lys(DOTA)-Trx-2NaI-eKuE (I-55(b))
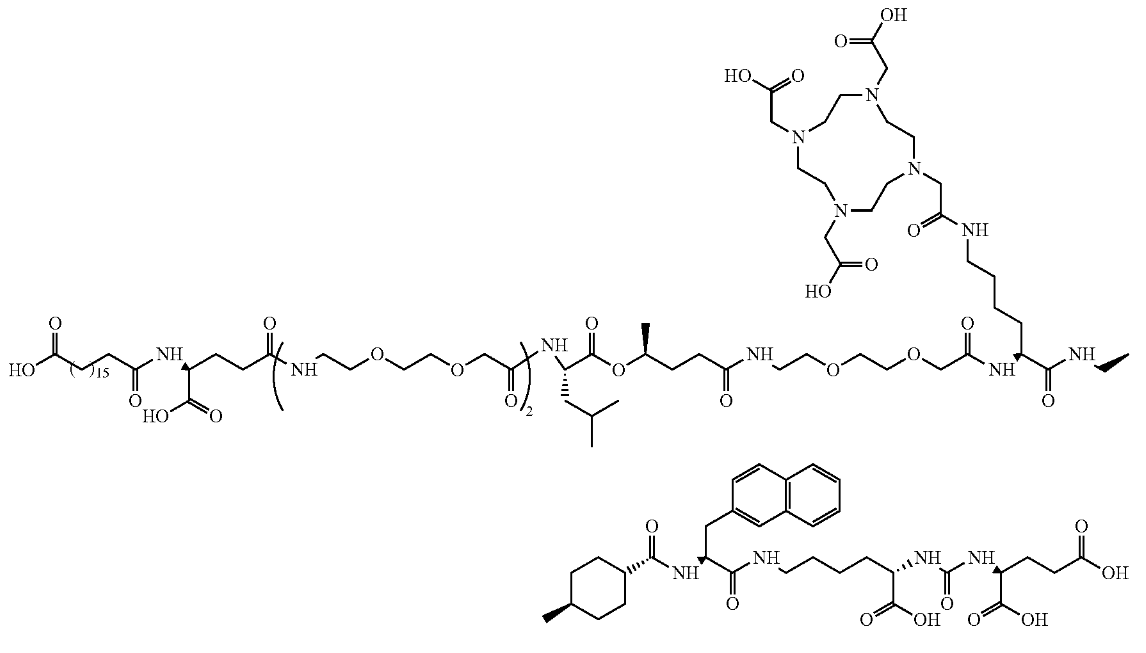

I-55 was prepared as a mixture of two diastereomers using racemic 4hPA. Each diastereomer was separated and isolated using HPLC. The characterization of each isomer by UPLC is provided below. It was not determined which of the two compounds had the (R) configuration at 4hPA and which had the(S) configuration at 4hPA. The data in (i) relates to one of I-55(a) and I-55(b), and the data in (ii) relates to the other of I-55(a) or I-55(b).

(i) Molecular weight (average) calculated: 2244.7 g/mol

Determined by LC-MS: (M+2H)2+: 1122.9; (M+3H)3+: 749.0

Purity by UPLC (214 nm): >99.0%

Retention time: 7.58 min; and (ii) Molecular weight (average) calculated: 2244.7 g/mol Determined by LC-MS: (M+2H)2+: 1122.8; (M+3H)3+: 749.0

Purity by UPLC (214 nm): 97.6%

Retention time: 7.66 min

Example 56: HO-C18-gGlu-OEG-OEG-OEG-ESL1-Lys(DOTA)-Trx-2NaI-eKuE (I-56)

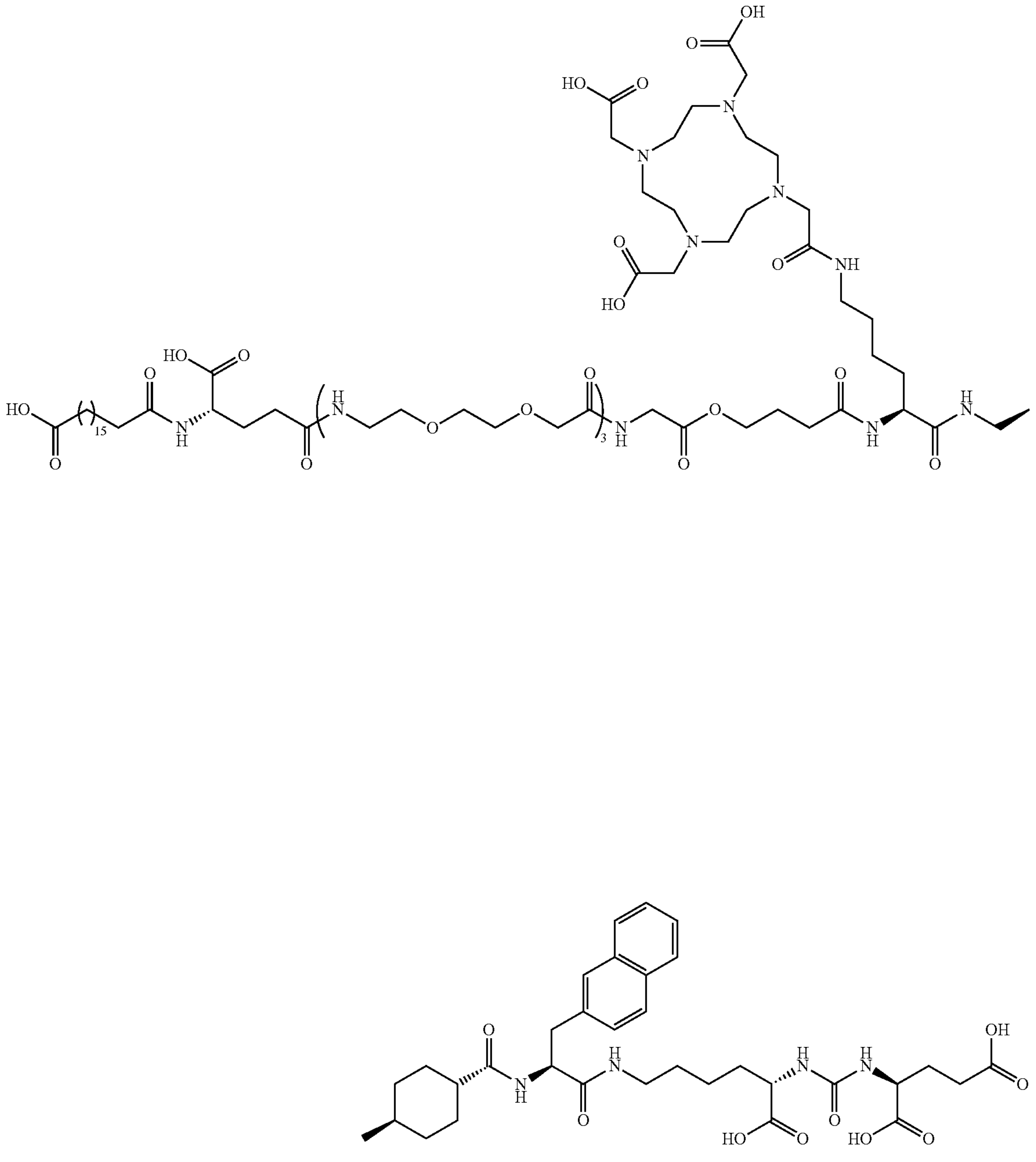

Molecular weight (average) calculated: 2174.5 g/mol

Determined by LC-MS: (M+2H)2+: 1087.7; (M+3H)3+: 725.6

Purity by UPLC (214 nm): >99.0%

Example 57: HO-C18-gGlu-OEG-OEG-Gly-OCH2CO-Lys(DOTA)-OEG-Trx-2NaI-eKuE (I-57)
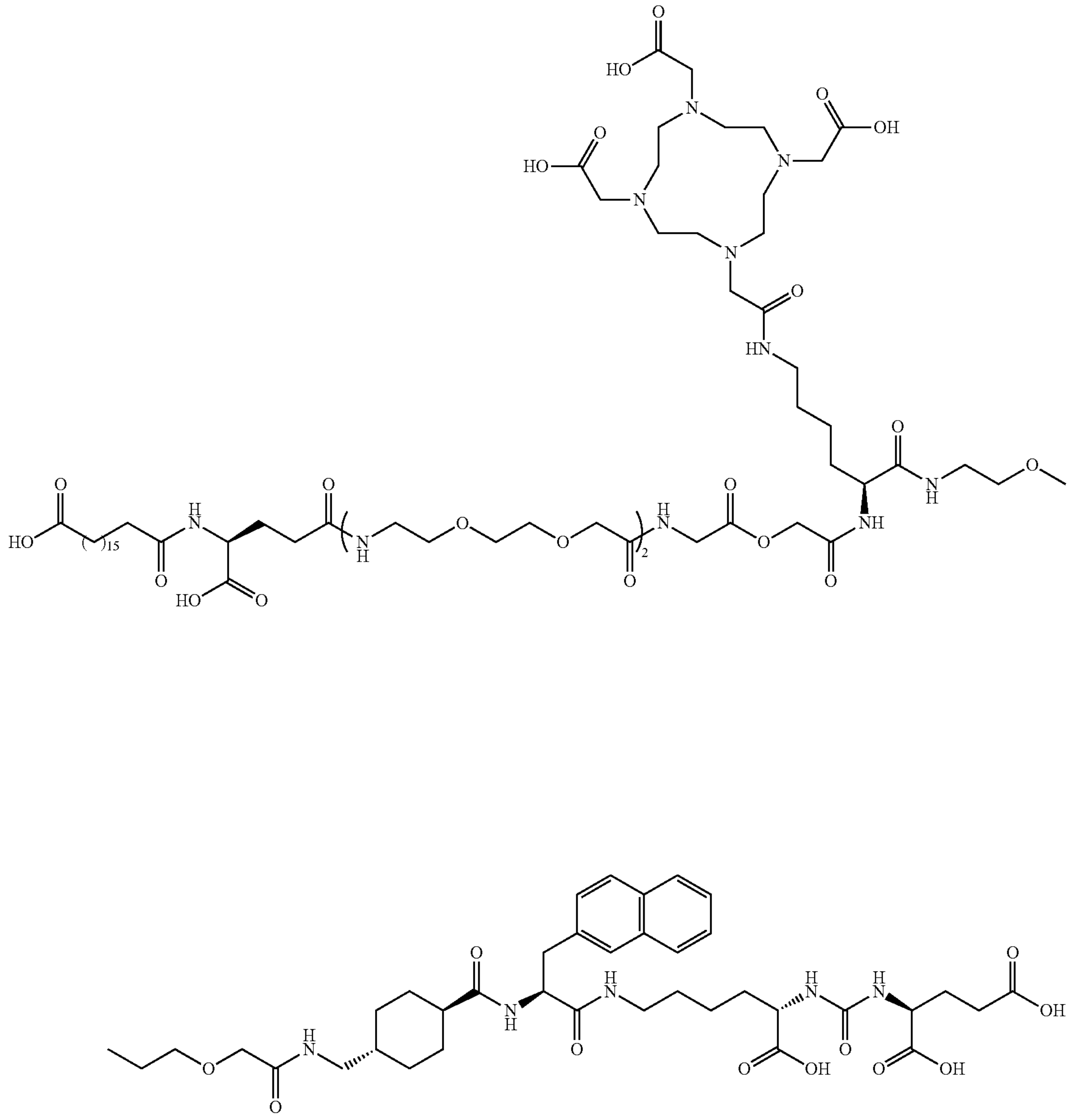
Molecular weight (average) calculated: 2146.5 g/mol
Determined by LC-MS: (M+2H)2+: 1073.6; (M+3H)3+: 716.3
Purity by UPLC (214 nm): 86.8%
Example 58: HO-C18-gGlu-OEG-OEG-ESL1-Gly-Gly-Gly-Lys(DOTA)-OEG-Trx-2NaI-eKuE (I-58)
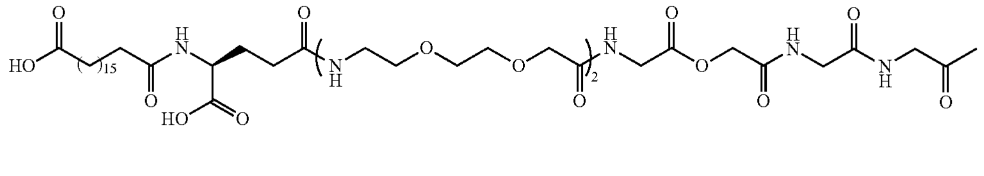

-continued
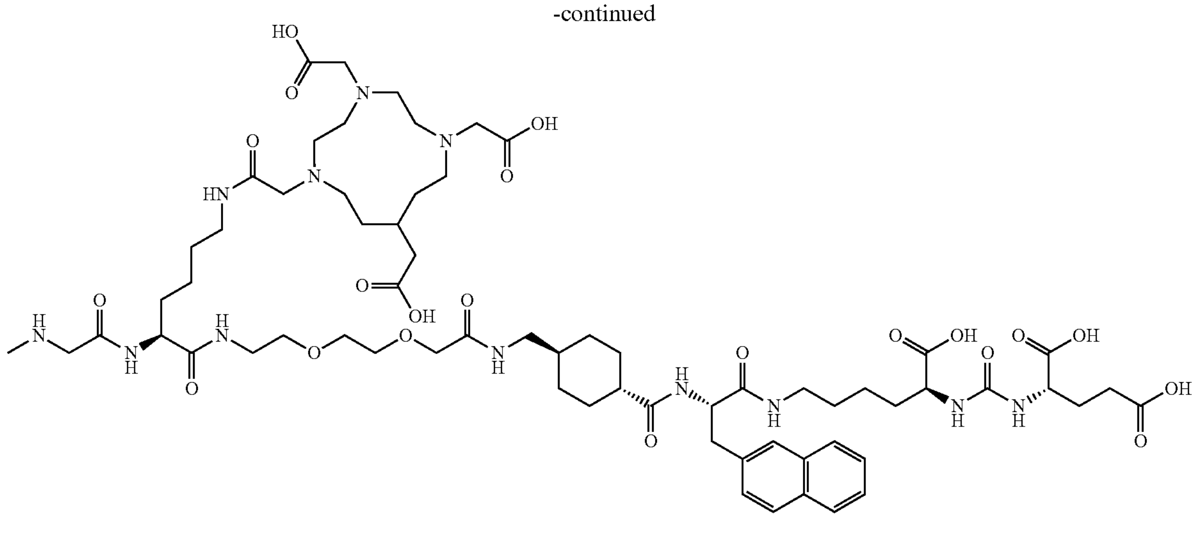
Molecular weight (average) calculated: 2345.7 g/mol
Determined by LC-MS: (M+2H)2+: 1173.4; (M+3H)3+: 782.8 Purity by UPLC (214 nm): 99.2%
Example 59: HO-C18-gGlu-OEG-OEG-Dab-4hBA-Lys(DOTA)-OEG-Trx-2NaI-eKuE (I-59)
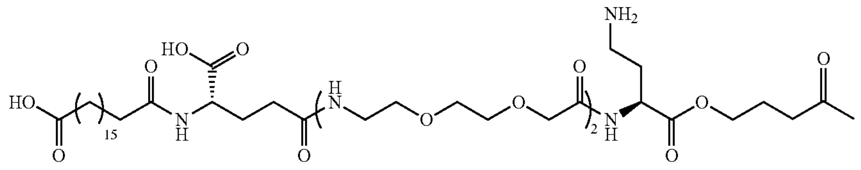
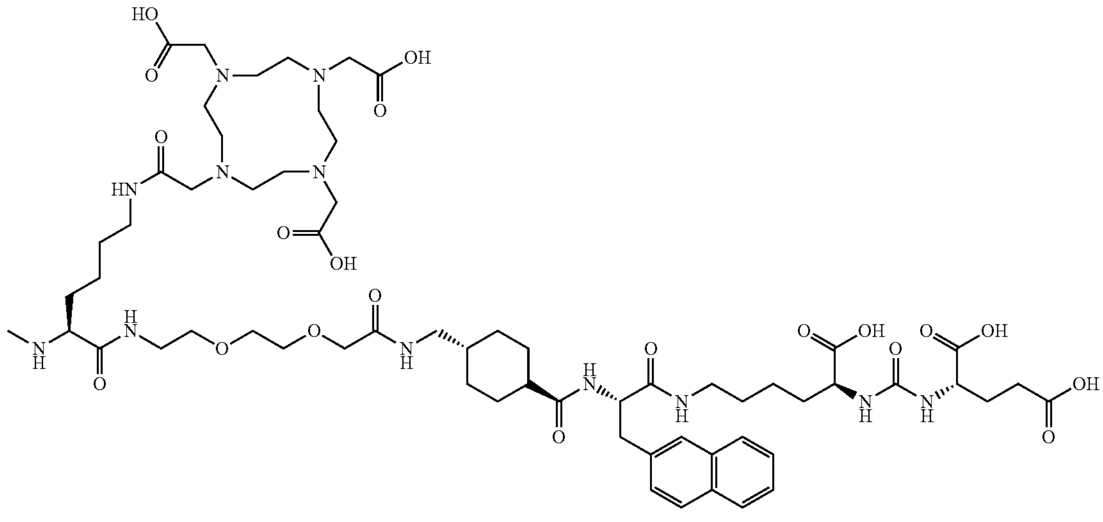
Molecular weight (average) calculated: 2217.6 g/mol
Determined by LC-MS: (M+2H)2+: 1109.7; (M+3H)3+: 740.0
Purity by UPLC (214 nm): 88.1%

Example 60: HO-C18-gGlu-OEG-OEG-Leu-4hBA-Lys(DOTA)-Trx-2NaI-eKuE (I-60)
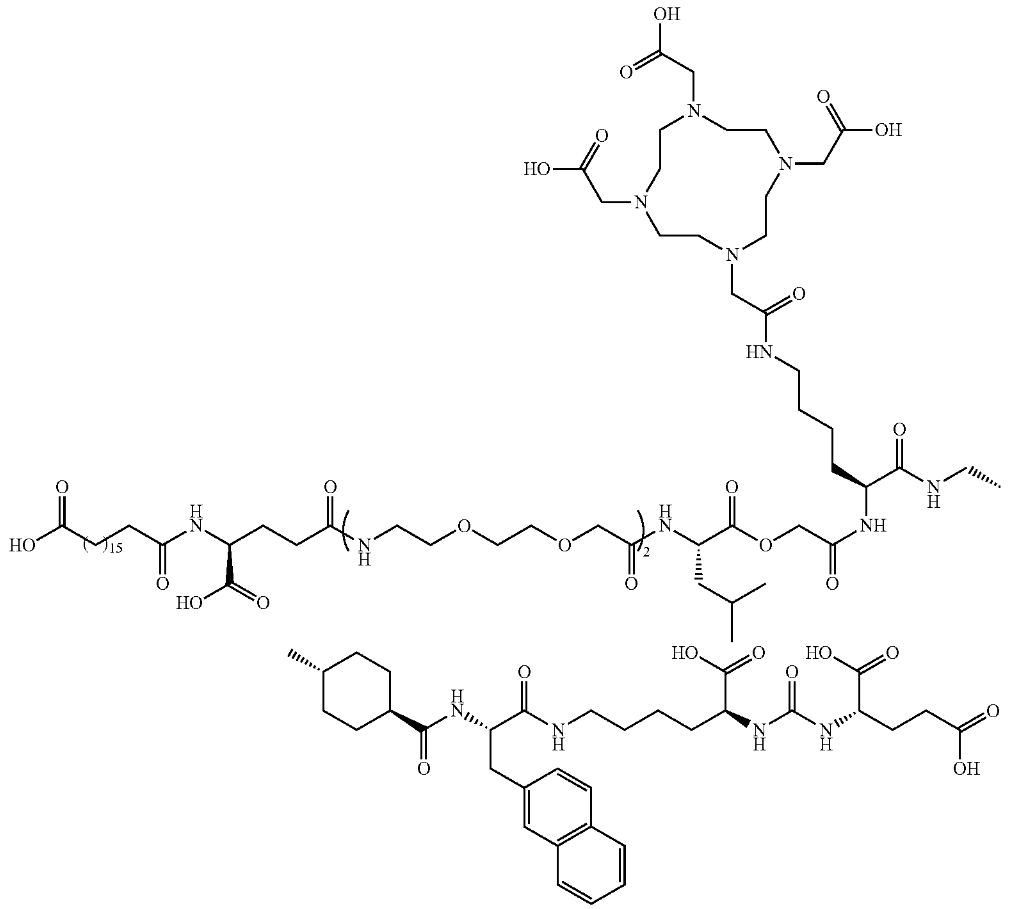
Molecular weight (average) calculated: 2085.5 g/mol
Determined by LC-MS: (M+2H)2+: 1043.5; (M+3H)3+: 696.0
Purity by UPLC (214 nm): 94.1%
Example 61: HO-C18-gGlu-OEG-OEG-ESL1-Lys (DOTA)-OEG-Gly-Tyr-Phe-eKuE (I-61)
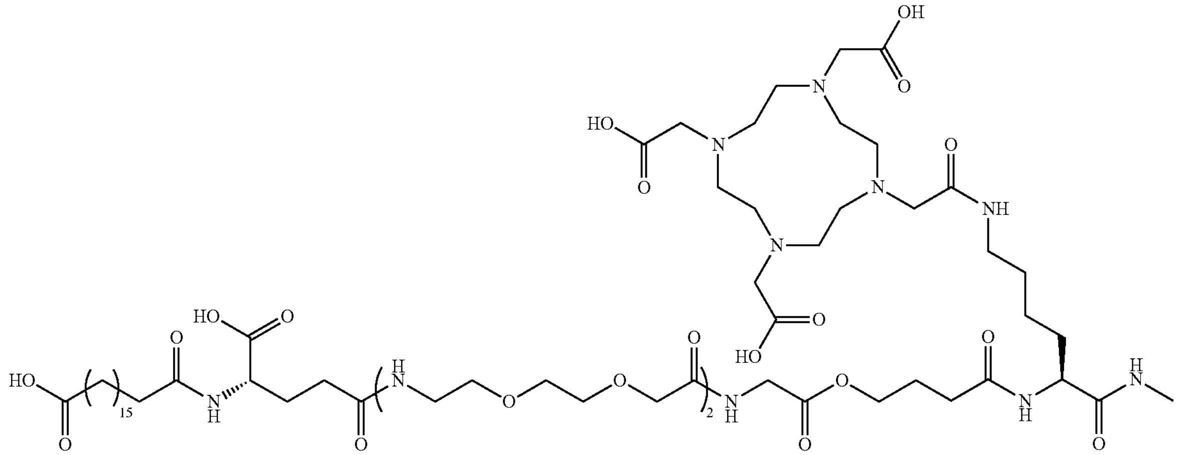

-continued
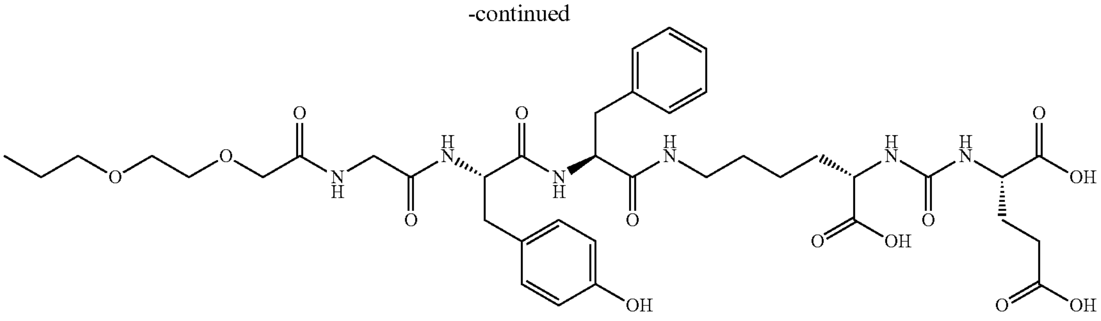
Molecular weight (average) calculated: 2205.5 g/mol
Determined by LC-MS: (M+2H)2+: 1103.5; (M+3H)3+: 736.0
Purity by UPLC (214 nm): >99.0%
Example 62: HO-C18-gGlu-OEG-OEG-ESL1-k(DOTA)-OEG-Trx-2NaI-eKuE (I-62)
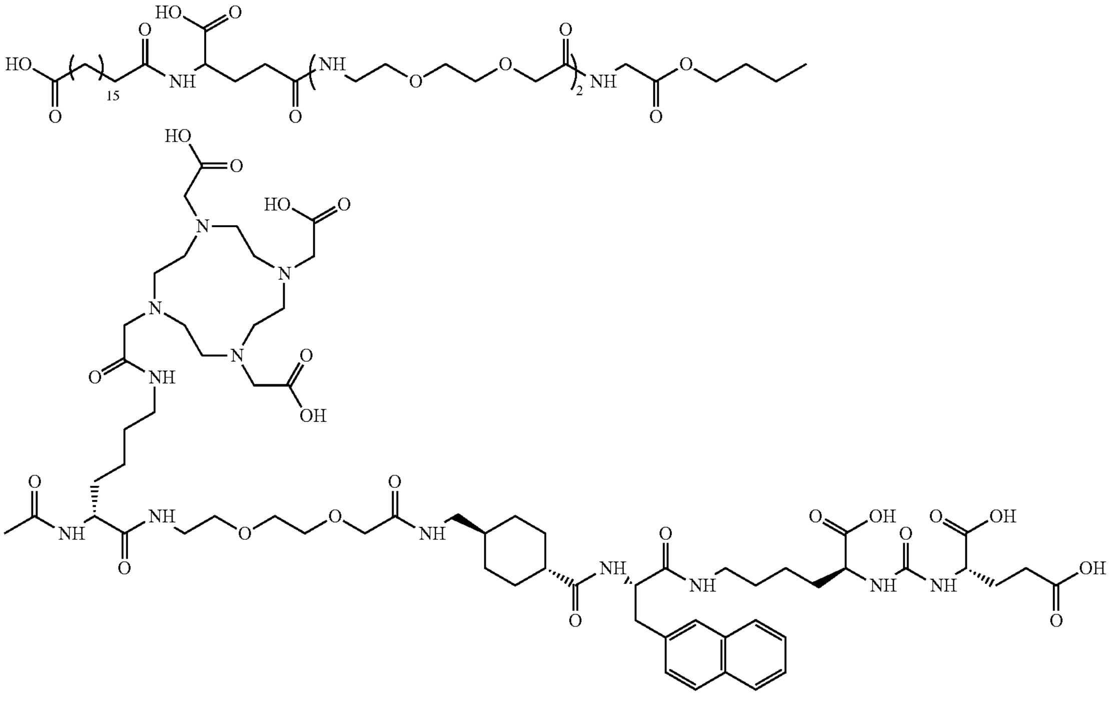
Molecular weight (average) calculated: 2174.5 g/mol
Determined by LC-MS: (M+2H)2+: 1087.8; (M+3H)3+: 725.6
Purity by UPLC (214 nm): 95.8%
Example 63: HO-C18-gGlu-OEG-OEG-ESL1-Dab(DOTA)-OEG-Trx-2NaI-eKuE (I-63)
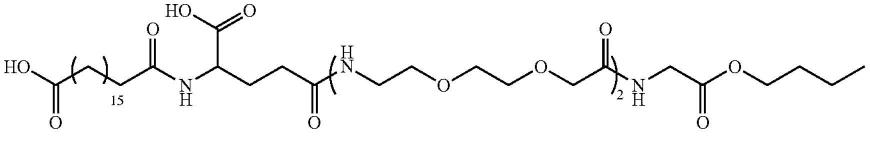

-continued
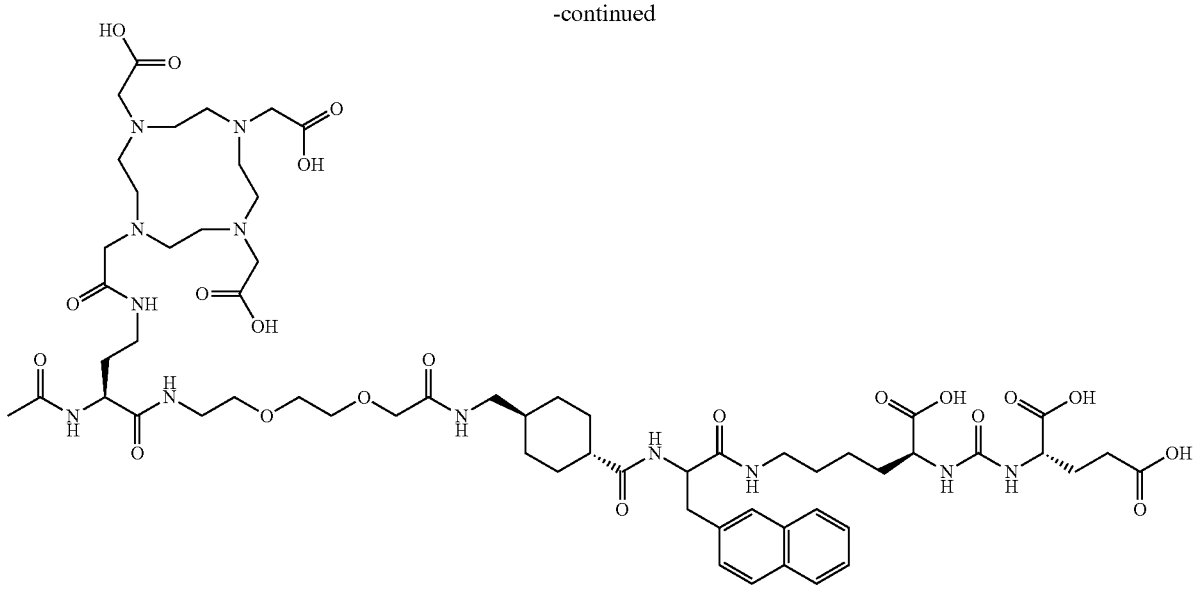
Molecular weight (average) calculated: 2146.5 g/mol Determined by LC-MS: (M+2H)2+: 1074.1; (M+3H)3+: 716.4 Purity by UPLC (214 nm): >99.0%
Example 64: HO-C18-gGlu-OEG-OEG-ESL1-Gly-Gly-Lys(DOTA)-OEG-Gly-Tyr-Phe-eKuE (I-64)
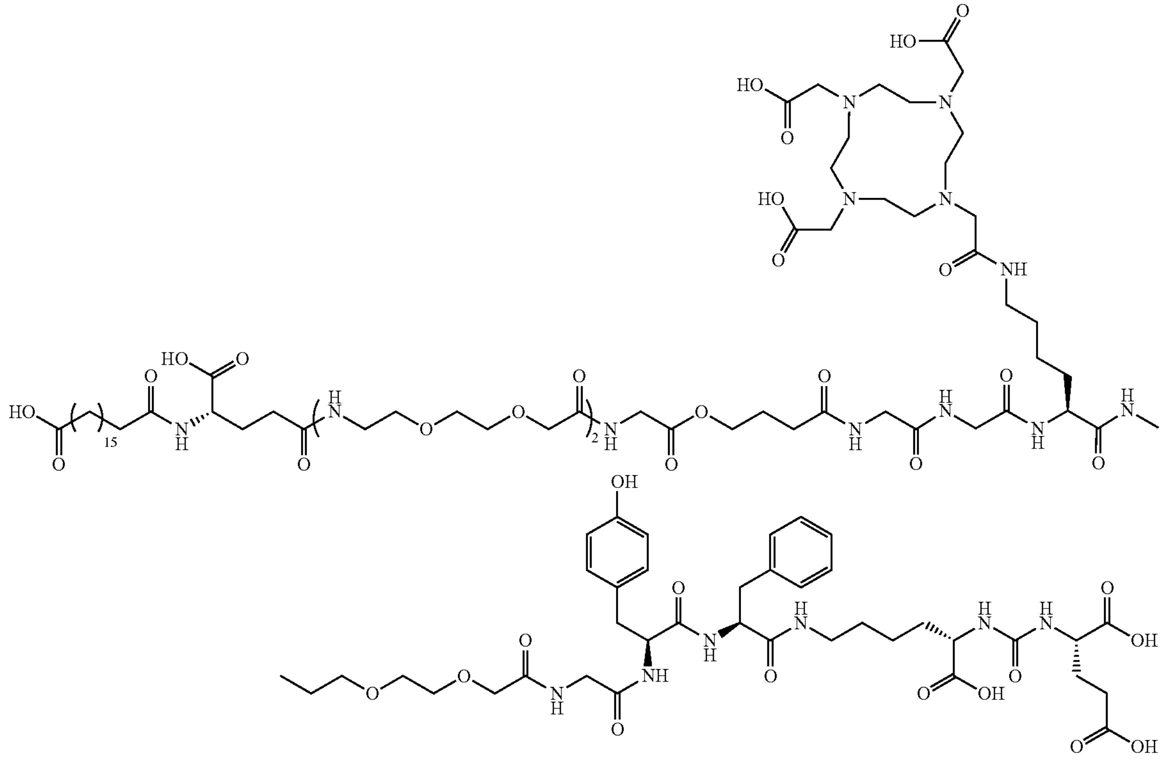
Molecular weight (average) calculated: 2319.6 g/mol
Determined by LC-MS: (M+2H)2+: 1160.4; (M+3H)3+: 774.0
Purity by UPLC (214 nm): >99.0%

Example 65: HO-C18-gGlu-OEG-OEG-ESL1-Gly-Gly-Gly-Lys(DOTA)-OEG-Gly-Tyr-Phe-eKuE (I-65)
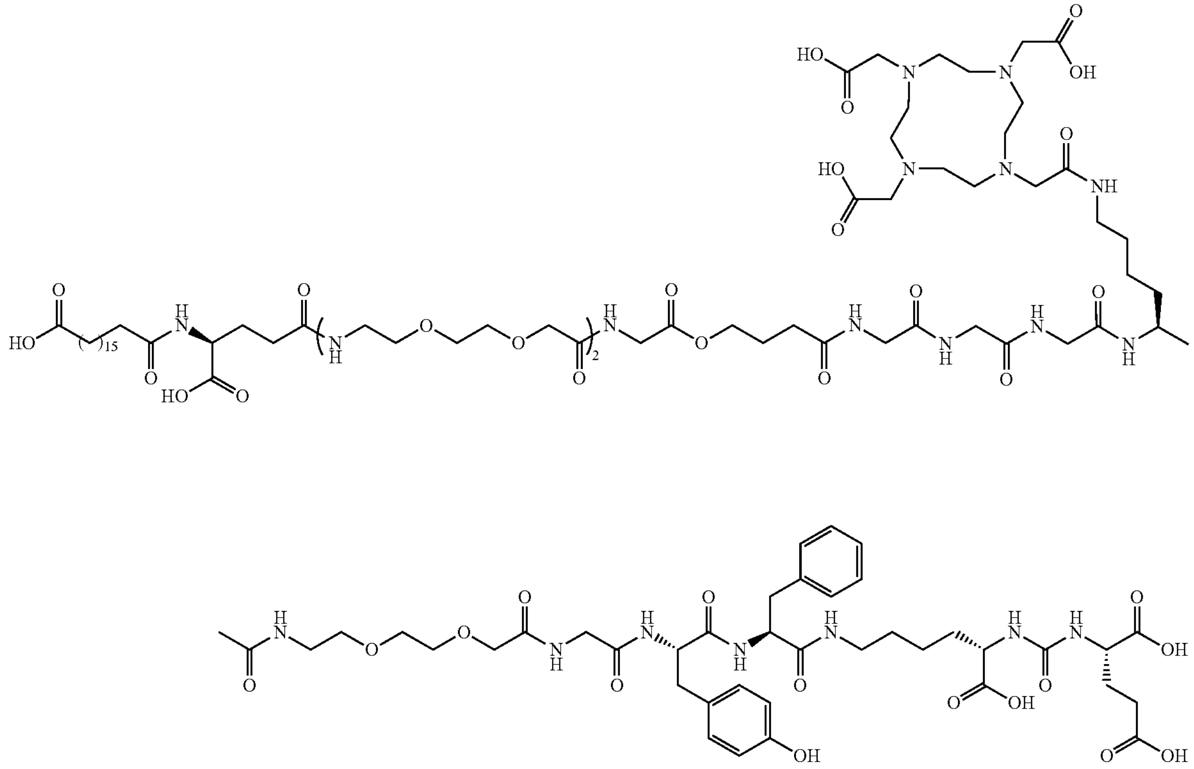
Molecular weight (average) calculated: 2376.6 g/mol
Determined by LC-MS: (M+2H)2+: 1189.0; (M+3H)3+: 793.0
Purity by UPLC (214 nm): 97.9%
Example 66: HO-C18-gGlu-OEG-OEG-Gly-5hPA-Lys(DOTA)-OEG-Gly-Tyr-Phe-eKuE (I-66)
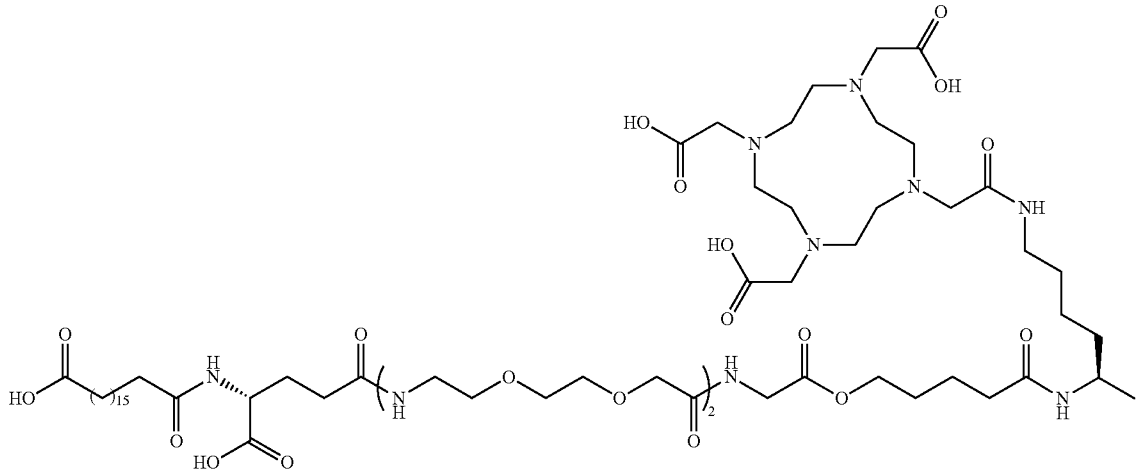

-continued
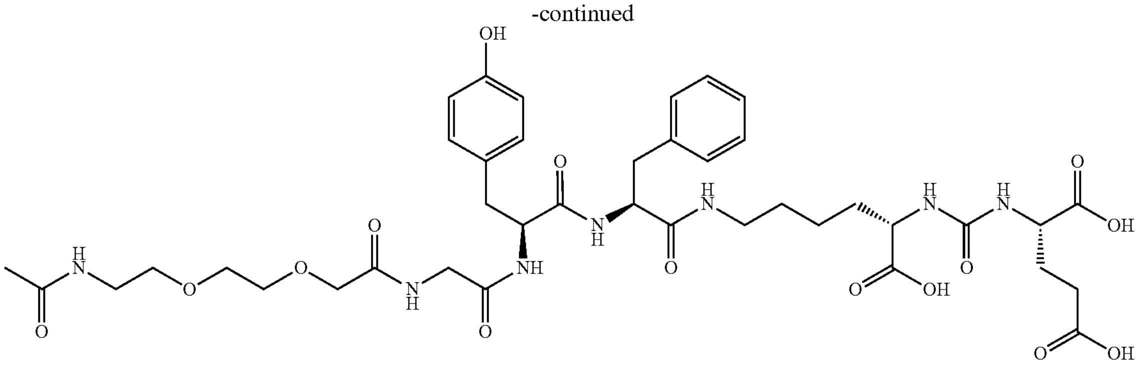
Molecular weight (average) calculated: 2219.5 g/mol
Determined by LC-MS: (M+2H)2+: 1110.3; (M+3H)3+: 740.7
Purity by UPLC (214 nm): >99.0%
Example 67: 4pIBA-gGlu-OEG-OEG-ESL1-Lys (DOTA)-OEG-Trx-2NaI-eKuE (I-67)
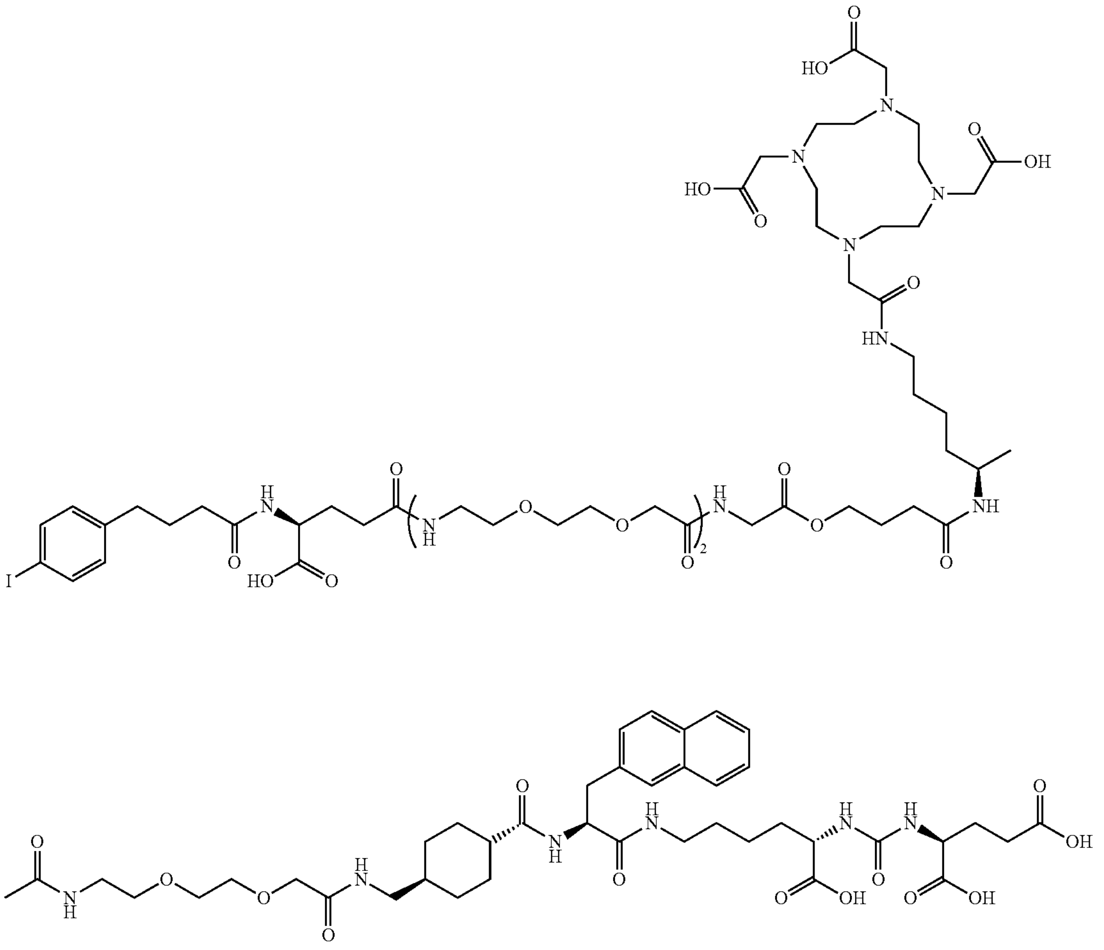
Molecular weight (average) calculated: 2150.2 g/mol
Determined by LC-MS: (M+2H)2+: 1075.7; (M+3H)3+: 717.5
Purity by UPLC (214 nm): 94.9%

Example 68: C18-gGlu-OEG-OEG-ESL1-Lys (DOTA)-OEG-Trx-2NaI-eKuE (I-68)
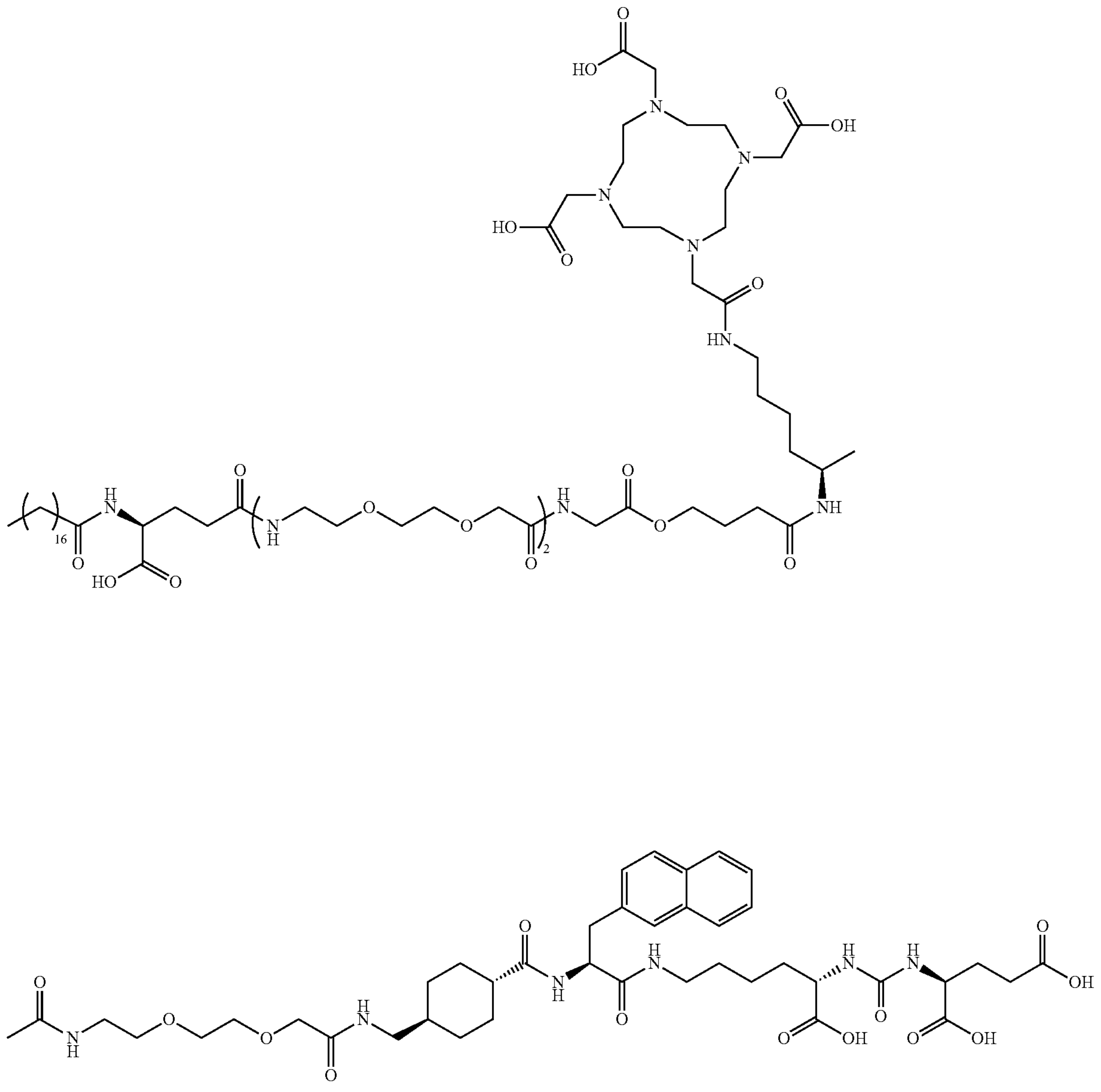
Molecular weight (average) calculated: 2144.5 g/mol
Determined by LC-MS: (M+2H)2+: 1072.7; (M+3H)3+: 715.7
Purity by UPLC (214 nm): 97.8%
Example 69: 4pIBA-gGlu-OEG-OEG-Lys(-ESL1-DOTA)-OEG-Trx-2NaI-eKuE (I-69)
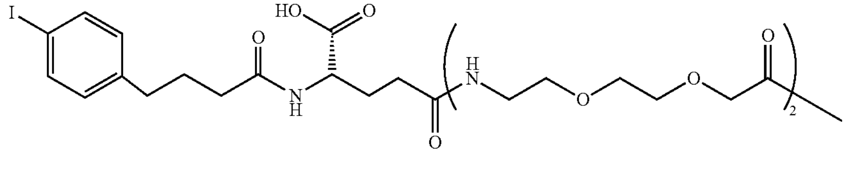

-continued

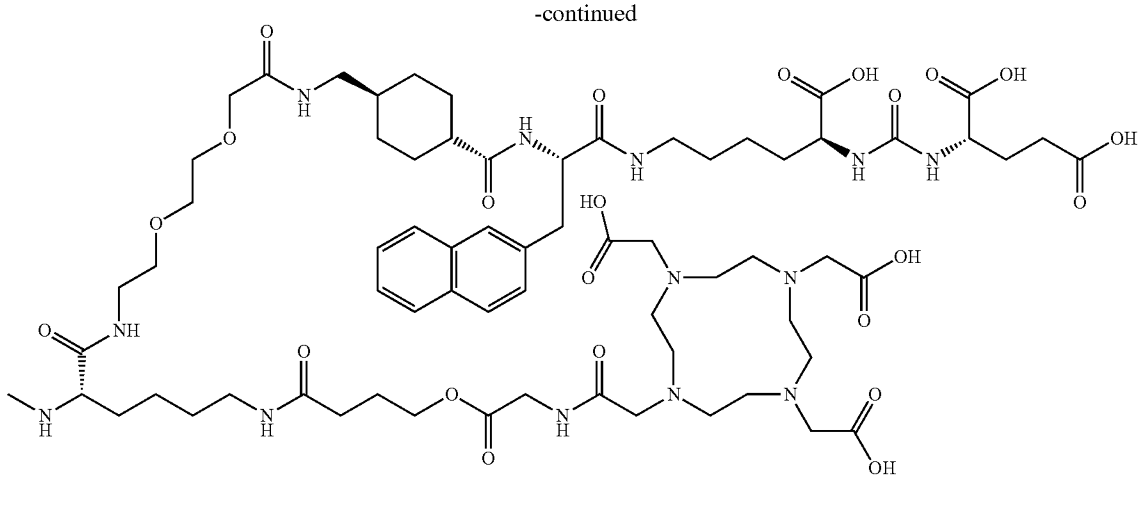

Molecular weight (average) calculated: 2150.2 g/mol

Determined by LC-MS: (M+2H)2+: 1075.6; (M+3H)3+: 717.4

Purity by UPLC (214 nm): 97.8%

Synthesis of Comparative Compounds

The following comparative compounds were synthesized using the above methods.

Comparator 1: PSMA-617, DOTA-Trx-2NaI-eKuE (C-1)

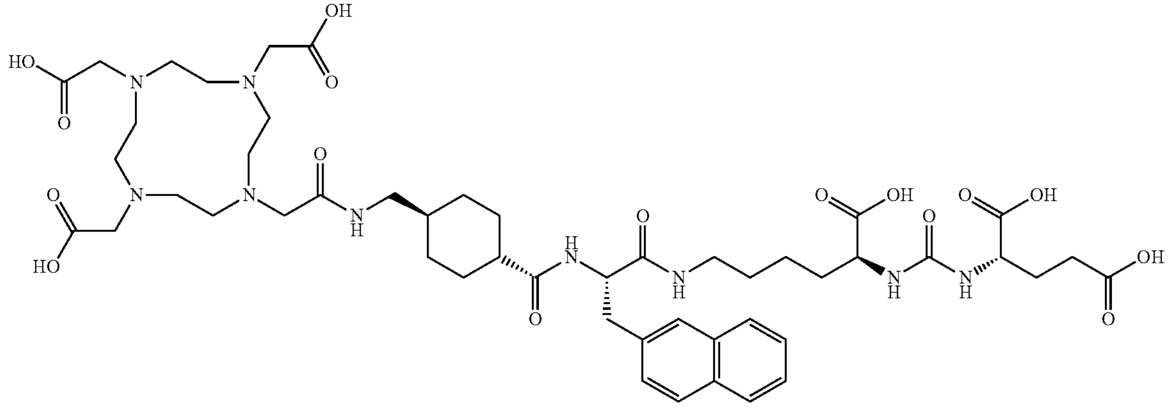

Molecular weight (average) calculated: 1042.14 g/mol

Determined by LC-MS: (M+2H)2+: 521.8

Purity by UPLC (214 nm): >99.0%

Comparator 2: HTK01169, 4pIBA-Glu-Lys(DOTA)-Trx-2NaI-eKuE (C-2)

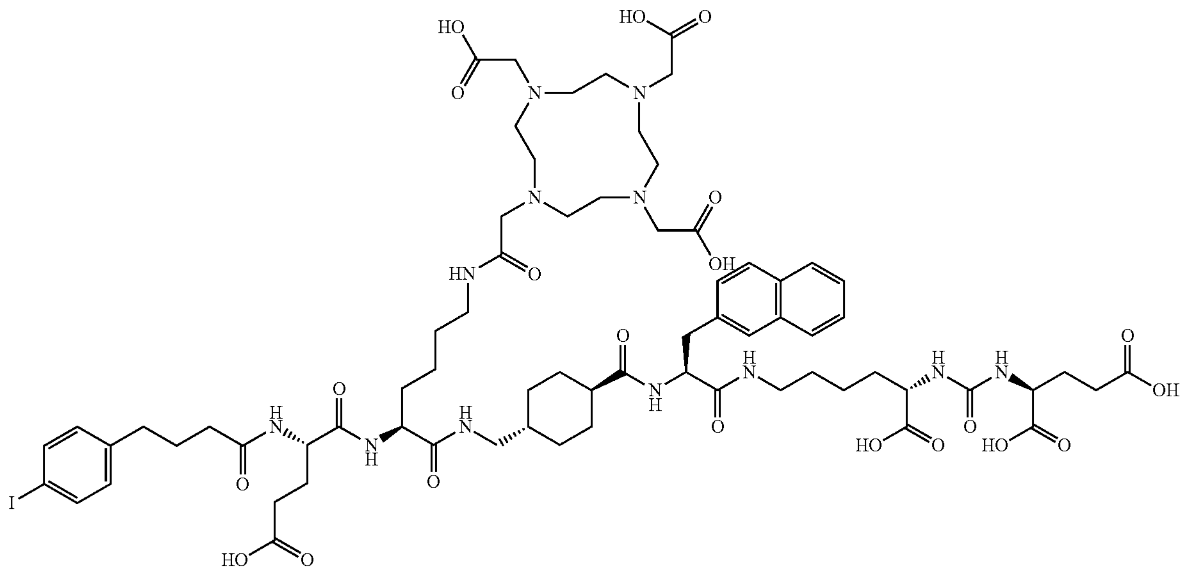 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)[C@H](CCCCNC(=O)CN2CCN(CC(=O)O)CCN(CC(=O)O)CCN(CC(=O)O)CC2)NC(=O)[C@H](CCC(=O)O)NC(=O)CCCc2ccc(I)cc2)CC1)C(=O)O)C(=O)O]
Molecular weight (average) calculated: 1571.53 g/mol
Determined by LC-MS: (M+2H)2+: 786.4; (M+3H)3+: 524.7
Purity by UPLC (214 nm): 96.8%
Comparator 3: C16-gGlu-OEG-OEG-OEG-K (DOTA)-Trx-2NaI-eKuE (C-3)
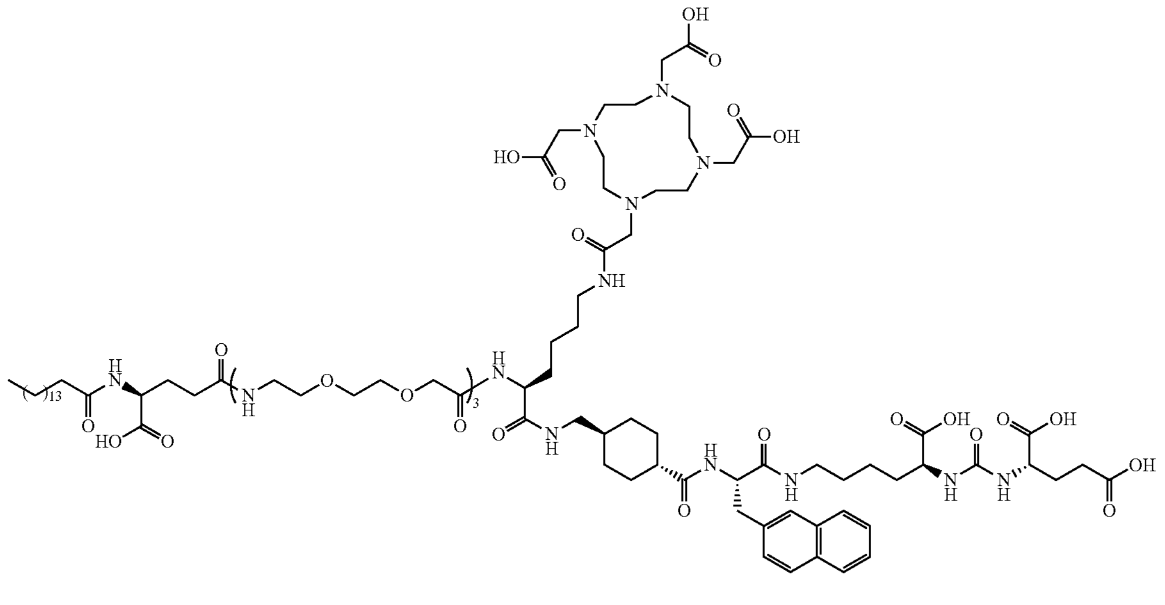
Molecular weight (average) calculated: 1973.33 g/mol
Determined by LC-MS: (M+2H)2+: 987.5; (M+3H)3+: 658.7
Purity by UPLC (214 nm): 99.8%
Comparator 4: HO-C18-gGlu-K (DOTA)-Trx-2NaI-eKuE (C-4)

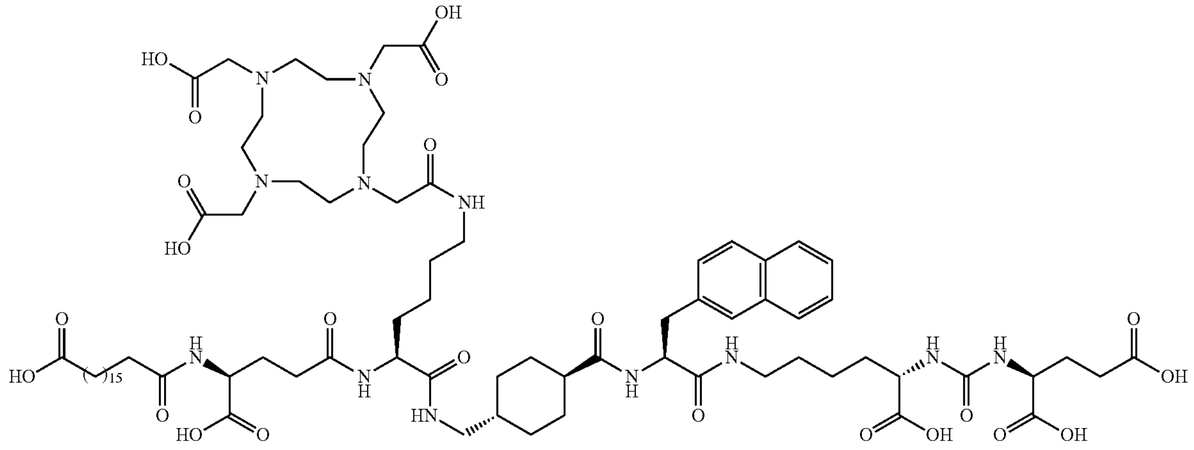
Molecular weight (average) calculated: 1595.50 g/mol
Determined by LC-MS: (M+2H)2+: 799.0; (M+3H)3+: 532.9
Purity by UPLC (214 nm): 97.0%
Comparator 5: C16-gGlu-K (DOTA)-Trx-2NaI-eKuE (C-5)
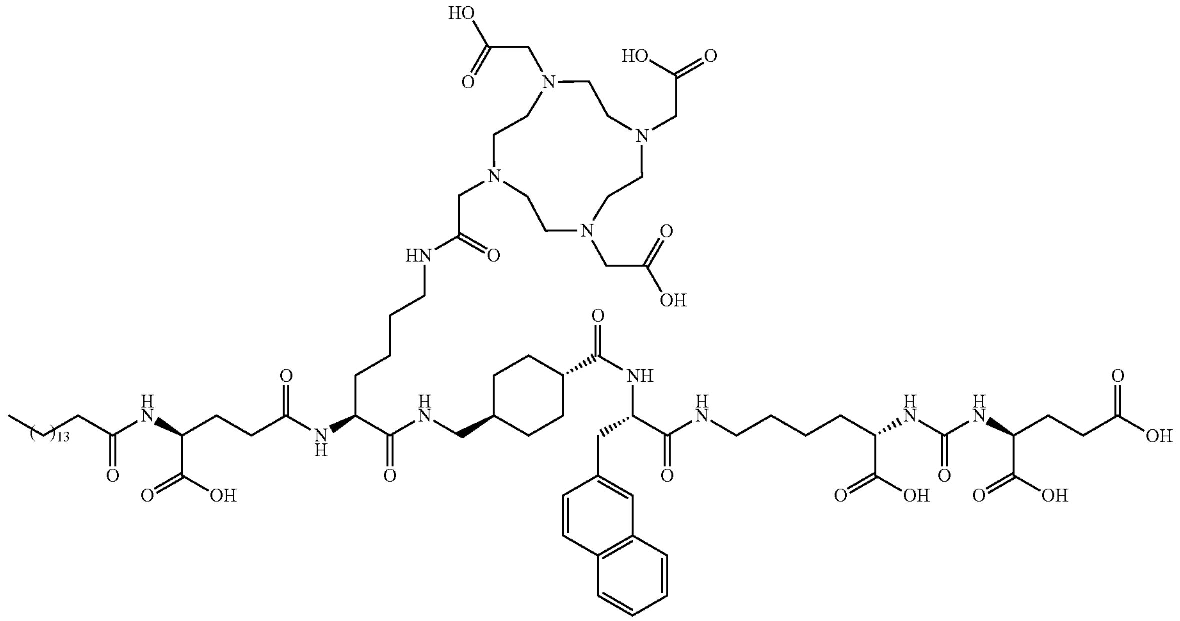
Molecular weight (average) calculated: 1537.86 g/mol
Determined by LC-MS: (M+2H)2+: 770.0; (M+3H)3+: 513.4
Purity by UPLC (214 nm): 98.6%
Comparator 6: HO-C18-gGlu-OEG-OEG-OEG-Lys (DOTA)-OEG-Trx-2NaI-eKuE (C-6)

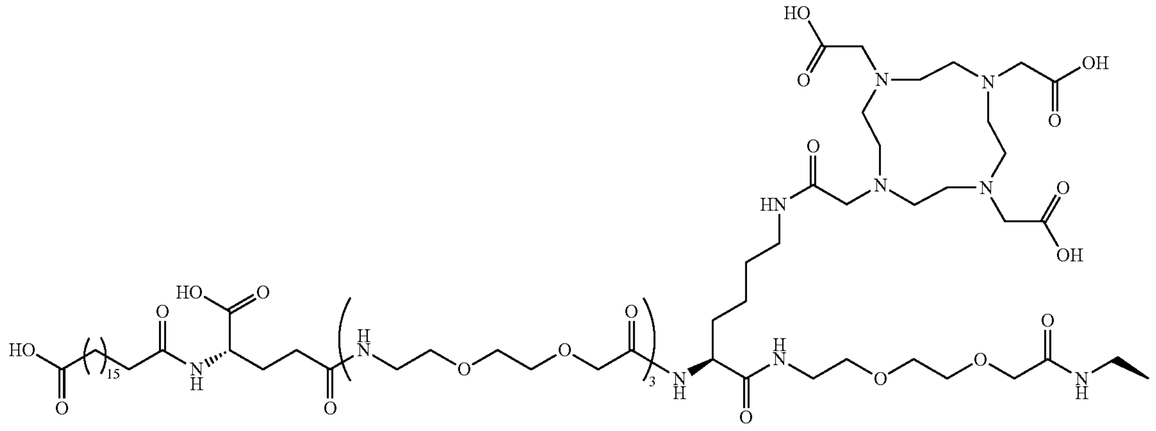
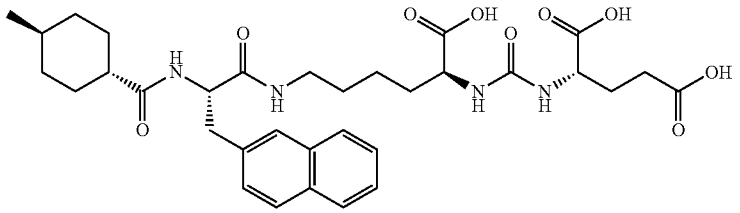
Molecular weight (average) calculated: 2176.53 g/mol
Determined by LC-MS: (M+2H)2+: 1089.2; (M+3H)3+: 726.3
Purity by UPLC (214 nm): >99.0%
Comparator 7: (HO-C18-gGlu-Lys(-OEG-DOTA)-OEG-OEG-OEG-NH2CH2CH2NH-TMA(-OEG-Trx-2NaI-eKuE)$_2$ (C-7)
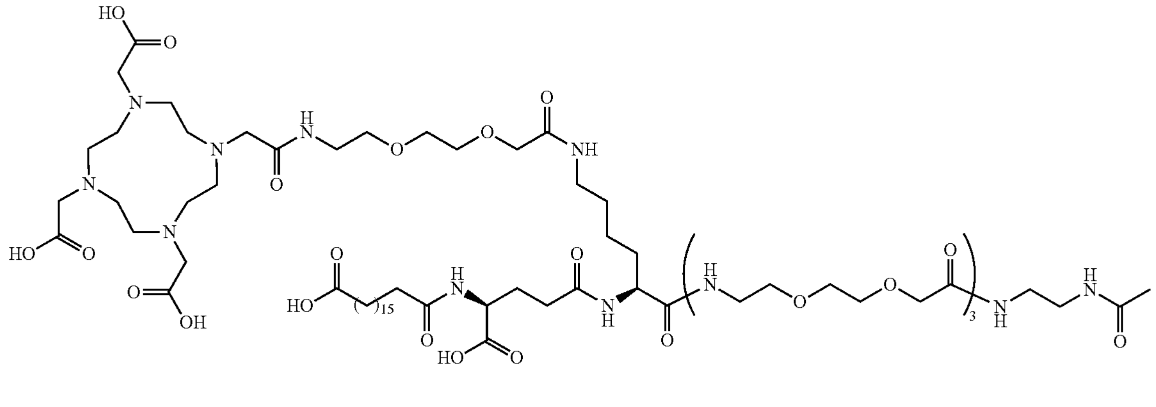

-continued
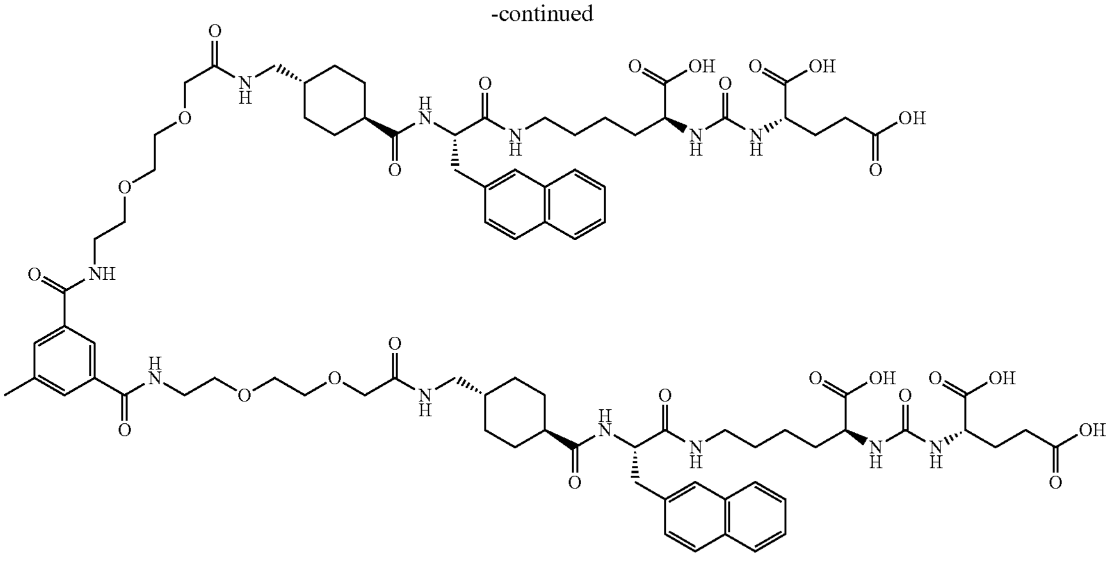
Molecular weight (average) calculated: 3338.79 g/mol
Determined by LC-MS: (M+2H)2+: 1669.6; (M+3H)3+: 1113.5; (M+4H)4+: 835.5; (M+5H)5+: 668.7
Purity by UPLC (214 nm): 97.5%
Comparator 8 (C-8)
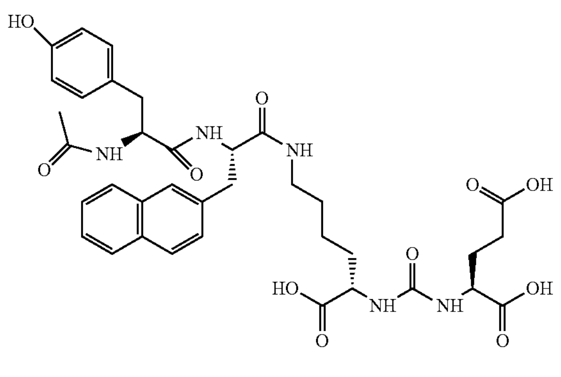 [SMILES: CC(=O)N[C@@H](Cc1ccc(O)cc1)C(=O)N[C@@H](Cc1ccc2ccccc2c1)C(=O)NCCCC[C@H](NC(=O)N[C@@H](CCC(=O)O)C(=O)O)C(=O)O]
Comparator 9: DOTA-gGlu(-eLys-4pIBA)-Trx-2NaI-eKuE (C-9)

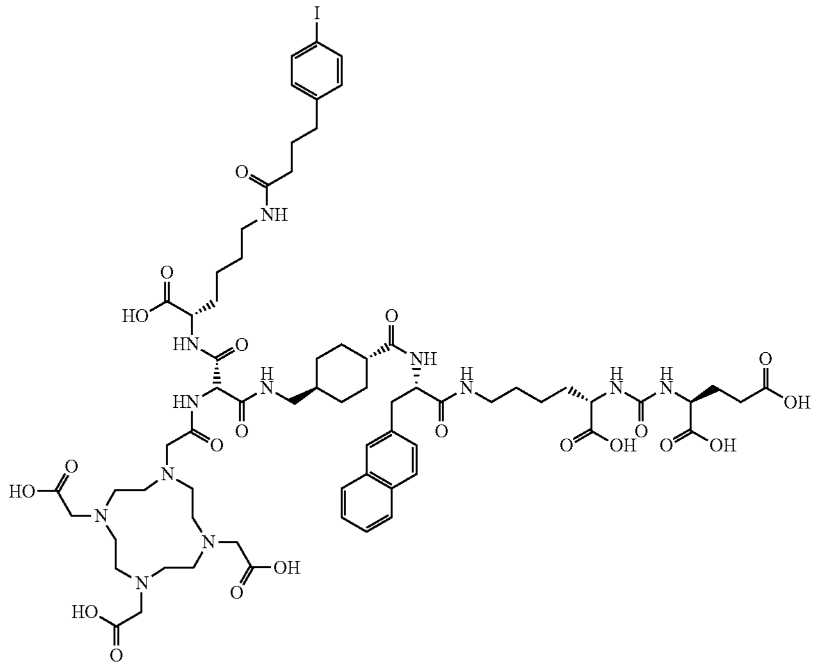
Molecular weight (average) calculated: 1571.5 g/mol
Determined by LC-MS: (M+2H)2+: 786.4; (M+3H)3+: 524.8
Purity by UPLC (214 nm): 99.3%
Comparator 9 (DOTA-gGlu(-eLys-4pIBA)-Trx-2NaI-eKuE) is disclosed in U.S. Pat. No. 11,147,889
Comparator 10: DOTA-Lys(pTBA)-Trx-2NaI-eKuE (PSMA-ALB-56) (C-10)
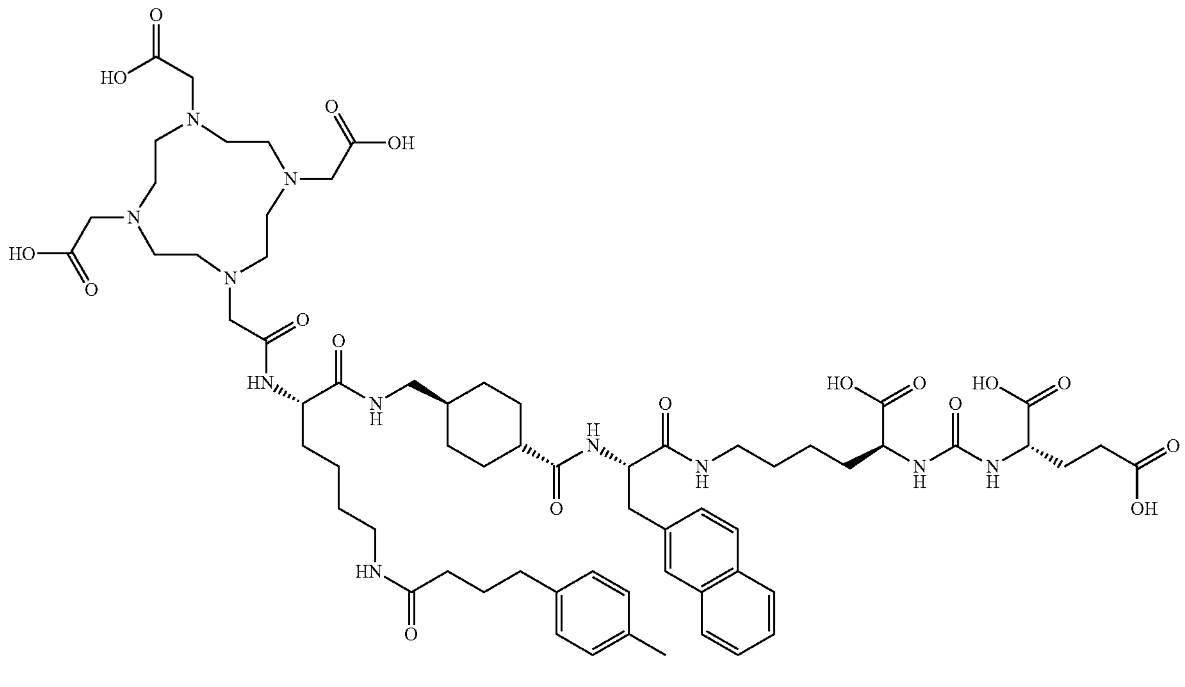

Molecular weight (average) calculated: 1330.6 g/mol

Determined by LC-MS: (M+2H)2+: 666.1

Purity by UPLC (214 nm): >99.0%

Comparator 9 (DOTA-Lys(pTBA)-Trx-2NaI-eKuE) is also known as PSMA-ALB-56 (Muller et al Mol. Pharmaceutics, 2018, 15, 2297-2306).

B: Biological Data

Cell-Based Binding Assay

Cell Culture

LNCaP cells (ATCC) were maintained in RPMI-1640 medium (Gibco) supplemented with 15% fetal bovine serum (Gibco) and 1% penicillin-streptomycin (BI) at 37° C. in a humidified incubator with 5% CO2. The culture medium was replaced with fresh medium every 2-3 days. Experiments were performed with cells at 70-80% confluence.

Binding Assay Protocol

The binding affinities of test compounds were determined by a competitive cell-binding assay using $^{125}$I-C8 as the radio-ligand. The suspended LNCaP cells at a density of 1~3×10$^6$ cells/mL in binding buffer (RPMI-1640 medium supplemented with 0.25% bovine serum albumin) were transferred to a MultiScreen-DV Filter Plate (Millipore) with 100 μL per well except the blank group where the binding buffer was used instead. The cells were then incubated with $^{125}$I-C-8 (0.02 μCi/well) in the presence of increasing concentrations (0-10000 nM) of test compounds at 37° C. for 1 h (n=3). The final volume in each well was maintained at 200 μL and insufficient volume was adjusted by the binding buffer. After the 1 h incubation, unbound $^{125}$I-C-8 was removed by filtration using a Multiscreen vacuum manifold (Millipore) followed by rinses with the binding buffer (3 times). The filters were collected, and their radioactivity were individually measured by γ counter (2480 WIZARD2, PerkinElmer). The best-fit $IC_{50}$ value (inhibitory concentration when 50% of the bound 125I-C-8 on cells were displaced) of test compounds were calculated by fitting the data with nonlinear regression using GraphPad Prism 8.0.1.

Stability Studies

Plasma Stability Study (Mouse and Human)

Mouse blood was collected via cardiac puncture of the left ventricle. Blood was placed into heparin-coated microfuge tubes and then centrifuged at 3500 rpm for 10 min to separate plasma for stability studies. Human plasma was purchased directly.

Figure 2:
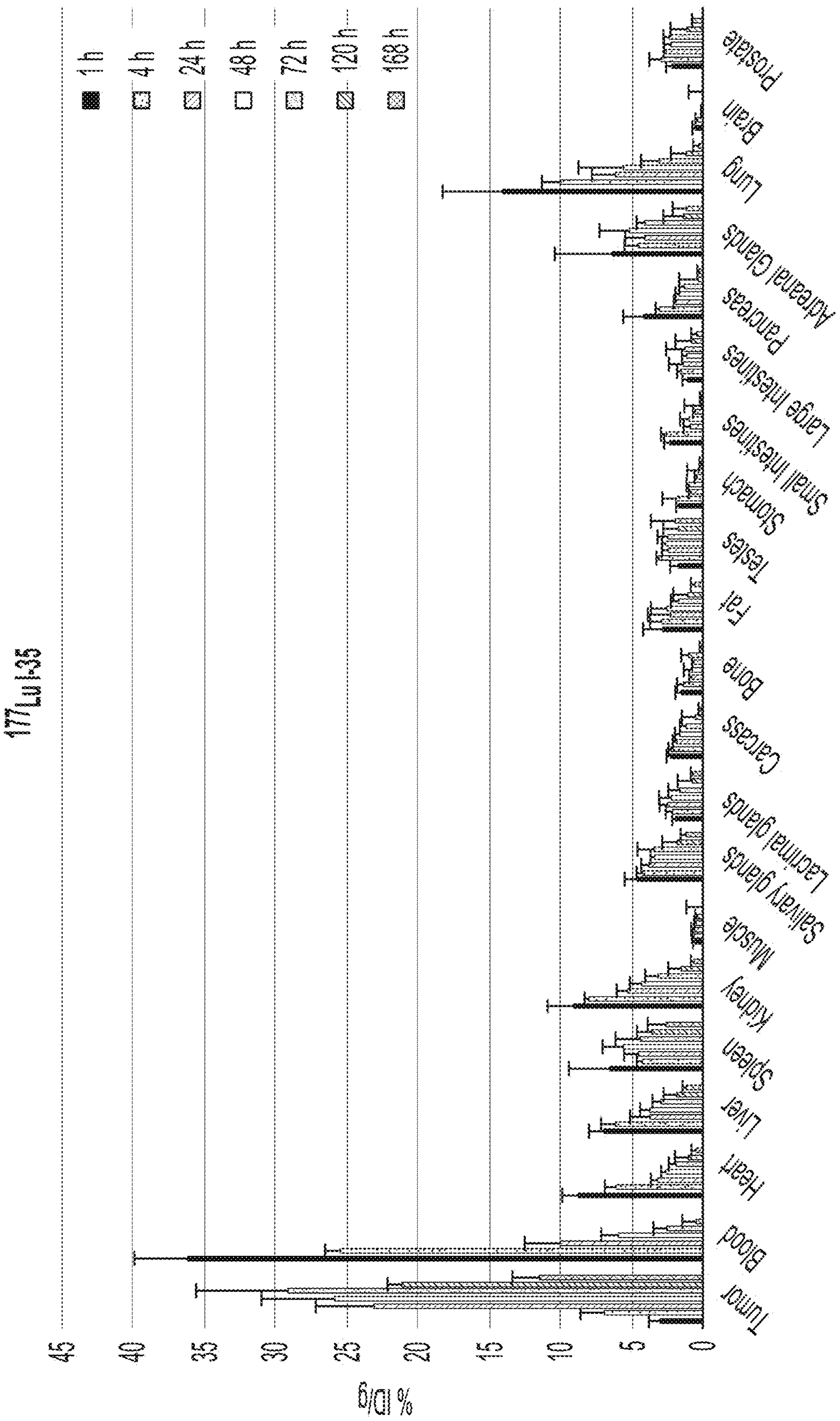
FIG. 2 shows the biodistribution of exemplary complex $^{177}$Lu-I-35 in PC3-PIP tumor bearing mice

2.0 mCi $^{177}$Lu labelled peptide in 50 μL labeling buffer was mixed 0.20 mL mouse serum and 50 μL 0.8 M sodium phosphate buffer (pH 7.4) and incubated at 37° C. At each time point (0, 1, 2, 4, 24, 48 72 h), an aliquot of 25 μL sample was taken and mixed with 100 μL methanol containing 1% formic acid, vertex for 30-60 sec, then centrifuged at 20000 rpm for 10 min. 100 μL supernatant was collected and diluted with 40 μL H2O. 100 μL of the resulting mixture was injected to radio-HPLC for stability assessment, as shown examples FIG. 2 and FIG. 3. The best-fit T1/2 value of test compounds were calculated by fitting the data with linear or non-linear regression using GraphPad Prism 8.0.1.

Buffer stability study (pH 4.5 and pH 7.4)

$^{177}$Lu-labeled peptide was diluted by 25 mM NaOAc buffer (pH 4.5), 25 mM NaOAc buffer and 3 mg/mL ascorbic acid, PBS, PBS with 3 mg/mL ascorbic acid to ~1.5 mCi/0.30 mL. The samples were incubated at room temperature. At each time point, 0, 1, 4, 24, 48, 72 h, an aliquot of 25 μL was taken and injected to radio-HPLC for stability assessment. The best-fit T1/2 value of test compounds were calculated by fitting the data with linear or non-linear regression using GraphPad Prism 8.0.1.

Biodistribution Study

Biodistribution Study in SCID Mice Bearing PC3-PIP Tumor

Severe combined immunodeficient (ICR-SCID) mice from the Institute of Cancer Research (Taconic Farms, Germantown, NY) were utilized for these studies. Mice were housed four per cage in sterile, microisolator cages under temperature- and humidity-controlled conditions with a 12 h light/12 h dark schedule and fed autoclaved rodent chow (Ralston Purina 300Company, St. Louis, MO) and acidified water ad libitum. In preparation for tumor cell inoculations, SCID mice were anesthetized with isoflurane (Baxter Healthcare Corp., Deerfield, IL) at an induction rate of 4% and maintained at a rate of 2.5% with 0.4 L oxygen delivered via precision vaporizer and a non-rebreathing apparatus. These mice received bilateral subcutaneous rear flank injections of approximately 10×10$^6$ PC-3 PIP cells (prostate cancer cell PC-3 stably expressing human PSMA) suspended in 100 μL of 0.9% NaCl. Xenografted tumors were allowed to grow for ~3-5 weeks post-inoculation and ranged in mass from 0.05 to 2.26 g (average tumor size, 0.39 g). Biodistribution studies in SCID mice (average weight, 28.4 g) were performed by the tail vein injection of each exemplary test compound, ~5.0-30 μCi (~0.185-1.11 MBq) with specific activity 83-300 μCi/nmol, delivered in 100 μL of 0.9% NaCl. The mice were euthanized, and the tissues and organs were excised from the animals at 1, 4, 24, 48, 72, 96, 120 and 168 h post-injection. The tissues and organs were weighed, counted in a PerkinElmer Wizard 3 automatic γ counter, and the percent injected dose (% ID) and % ID/g of each organ or tissue were calculated, as shown in Tables 5-24 and FIG. 1 and FIG. 2. The % ID in whole blood was estimated assuming a whole blood volume of 6.5% of the total body weight.

Biodistribution Study in CB-17 SCID Mice Bearing LNCap Tumor

All animal care and experimental procedure were performed by following the animal protocols approved by the ethics committee of China Institute of Radiation Protection. The CB-17 SCID mice (Charles River, Beijing) were utilized for these studies. Mice were below 5 per cage in sterile, microisolator cages under temperature- and humidity-controlled conditions with a 12 h light/12 h dark schedule and fed irradiated rodent chow and reverse osmosis (RO) sterile water ad libitum. In preparation for tumor cell inoculations, mice were anesthetized with isoflurane (RWD Life Science Inc.) at an induction rate of 4% and maintained at a rate of 2.5% with 0.4 L oxygen delivered via precision vaporizer and a non-rebreathing apparatus. These mice received subcutaneous rear flank injections of approximately 4×10$^6$ LNCap cells suspended in 200 μL of phosphate-buffered saline (PBS) and Matrigel (Corning) (1/1). Xenografted tumors were allowed to grow for ~2-4 weeks post-inoculation and ranged in mass from 0.05 to 0.50 g (average tumor size, 0.20 g). Biodistribution studies in nude mice were performed by the tail vein injection of each exemplary test compound, ~10-50 μCi (~0.37-1.85 MBq) with specific activity 50-250 μCi/nmol, delivered in 100 μL of 0.9% NaCl. The mice were euthanized, and the tissues and organs were excised from the animals at 1, 4, 24, 48, 72, 96, 120 and 168 h post-injection. The tissues and organs were weighed, counted in a PerkinElmer 2480 WIZARD2 γ counter, and the percent injected dose (% ID) and % ID/g of each organ or tissue were calculated, as shown in Tables 25-33.

Human Imaging Data

Whole-body PET/CT acquisitions were performed with a United Imaging, uMI780 scanner ~60 min after the dosing of 0.05 mCi per kilogram body weight of $^{68}$Ga-PSMA11 (gozetotide). Whole-body scintigraphy and SPECT/CT imaging were performed with a Siemens symbia T16 scanner at 4, 24, 48 and 96 hours post dosing of exemplary compound $^{111}$IN-FXN001 (3.3-4.4 mCi per patient).

Results and Discussion

Radioligand Binding Assay

The $IC_{50}$ of selected exemplary compounds of the application in a radioligand competitive binding assay was determined as described above. The results are shown in Table 1. The relative binding affinity of selected exemplary compounds of the application based on the mean value of the $IC_{50}$ number is shown in Table 2.

The compounds of the present application all displayed binding ability to PSMA with a $IC_{50}$ value in the range of about 1 nM to about 1 μM in the above described radioligand competitive binding assay. It was observed that the modification of groups on the radioligand, such as the PSMA binding motif, for example, as long-chain fatty acid (e.g. palmitic acid) and long-chain fatty diacid (e.g. octadecanedioic acid), can have an impact on the binding affinity.

TABLE 1

$IC_{50}$ of selected compounds in radioligand competitive binding assay.

| Nonlin fit | $LogIC_{50}$ | | | $IC_{50}$ | | |
|---|---|---|---|---|---|---|
| Summary table | Mean | +Error | −Error | Mean | +Error | −Error |
| C-1 | −8.544 | 0.138 | 0.138 | 2.86E−09 | 1.07E−09 | 7.80E−10 |
| C-7 | −7.766 | 0.152 | 0.150 | 1.716E−08 | 7.213E−09 | 5.009E−09 |
| I-12 | −6.906 | 0.156 | 0.157 | 1.24E−07 | 5.38E−08 | 3.77E−08 |
| I-13 | −6.647 | 0.302 | 0.299 | 2.25E−07 | 2.26E−07 | 1.12E−07 |
| I-15 | −6.502 | 0.205 | 0.201 | 3.15E−07 | 1.90E−07 | 1.17E−07 |
| I-16 | −6.579 | 0.222 | 0.213 | 2.637E−07 | 1.755E−07 | 1.023E−07 |
| I-17 | −6.274 | 0.218 | 0.211 | 5.32E−07 | 3.47E−07 | 2.05E−07 |
| I-21 | −7.202 | 0.164 | 0.161 | 6.279E−08 | 2.883E−08 | 1.949E−08 |
| I-34 | −7.361 | 0.301 | 0.283 | 4.360E−08 | 4.367E−08 | 2.089E−08 |
| I-35 | −7.233 | 0.165 | 0.161 | 5.84E−08 | 2.70E−08 | 1.81E−08 |
| I-36 | −6.965 | 0.213 | 0.203 | 1.083E−07 | 6.851E−08 | 4.049E−08 |
| I-38 | −7.627 | 0.084 | 0.083 | 2.36E−08 | 5.01E−09 | 4.13E−09 |
| I-39 | −7.064 | 0.262 | 0.246 | 8.63E−08 | 7.16E−08 | 3.74E−08 |
| I-40 | −7.677 | 0.198 | 0.190 | 2.104E−08 | 1.213E−08 | 7.461E−09 |
| I-41 | −7.437 | 0.313 | 0.291 | 3.652E−08 | 3.852E−08 | 1.785E−08 |
| I-42 | −7.757 | 0.138 | 0.137 | 1.749E−08 | 6.543E−09 | 4.739E−09 |

TABLE 2

Relative Binding Affinity of selected compounds based on the mean value of the $IC_{50}$ number

| Compound | Relative Binding Affinity |
|---|---|
| C-1 | 1.00 |
| C-2 | 1.78 |
| C-3 | 0.02 |
| C-4 | 0.03 |
| C-5 | 0.04 |
| C-6 | 0.05 |
| C-7 | 0.14 |
| C-9 | 0.92 |
| I-1 | 1.84 |
| I-2 | 1.59 |
| I-3 | 1.30 |
| I-4 | 0.95 |
| I-5 | 1.08 |
| I-6 | 0.62 |
| I-7 | 0.56 |
| I-8 | 0.58 |
| I-9 | 1.80 |
| I-10 | 0.11 |
| I-11 | 0.04 |

TABLE 2-continued

Relative Binding Affinity of selected compounds based on the mean value of the $IC_{50}$ number

| Compound | Relative Binding Affinity |
|---|---|
| I-12 | 0.02 |
| I-13 | 0.01 |
| I-14 | 0.03 |
| I-15 | 0.01 |
| I-16 | 0.01 |
| I-17 | 0.01 |
| I-18 | 0.07 |
| I-19 | 0.07 |
| I-20 | 0.09 |
| I-21 | 0.09 |
| I-22 | 0.03 |
| I-23 | 0.04 |
| I-24 | 0.12 |
| I-25 | 0.20 |
| I-26 | 0.06 |

TABLE 2-continued

Relative Binding Affinity of selected compounds based on the mean value of the $IC_{50}$ number

| Compound | Relative Binding Affinity |
|---|---|
| I-27 | 0.09 |
| I-28 | 0.23 |
| I-29 | 0.07 |
| I-30 | 0.26 |
| I-31 | 0.13 |
| I-32 | 0.04 |
| I-33 | 0.81 |
| I-34 | 0.12 |
| I-35 | 0.05 |
| I-36 | 0.02 |
| I-37 | 0.29 |
| I-38 | 0.12 |
| I-39 | 0.03 |
| I-40 | 0.11 |
| I-41 | 0.06 |
| I-42 | 0.13 |
| I-43 | 0.28 |
| I-44 | 0.13 |
| I-49 | 0.09 |

TABLE 2-continued

| Relative Binding Affinity of selected compounds based on the mean value of the $IC_{50}$ number | |
|---|---|
| Compound | Relative Binding Affinity |
| I-51 | 0.08 |
| I-52 | 0.05 |
| I-56 | 0.02 |
| I-61 | 0.01 |
| I-65 | 0.06 |
| I-67 | 0.33 |
| I-68 | 0.08 |

Stability Studies

Stability studies were performed as described above.

Figure 3:
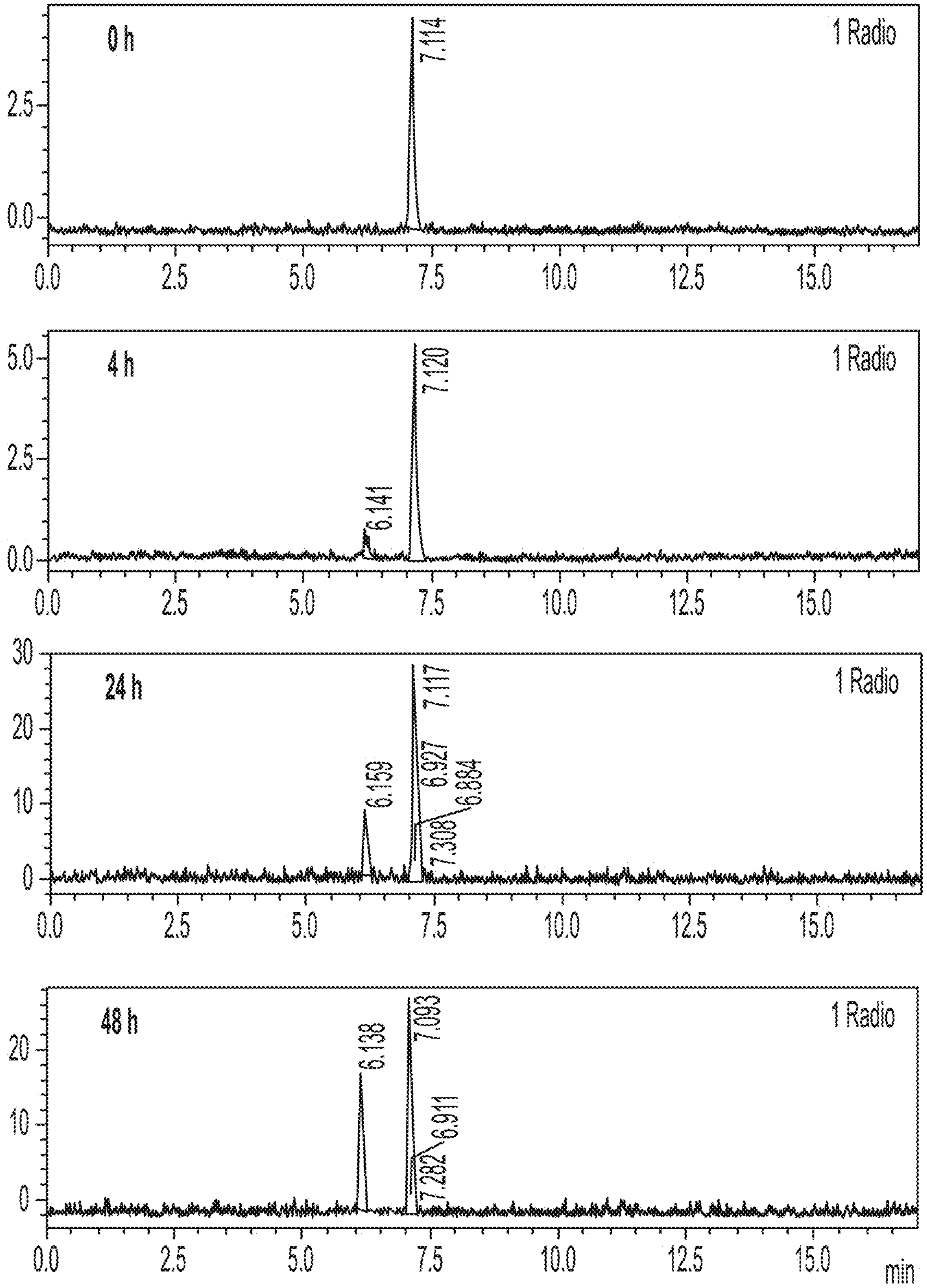
FIG. 3 shows radio-HPLC traces of ex-vivo mouse plasma stability samples of exemplary compound 177Lu-I-21.
Figure 4:
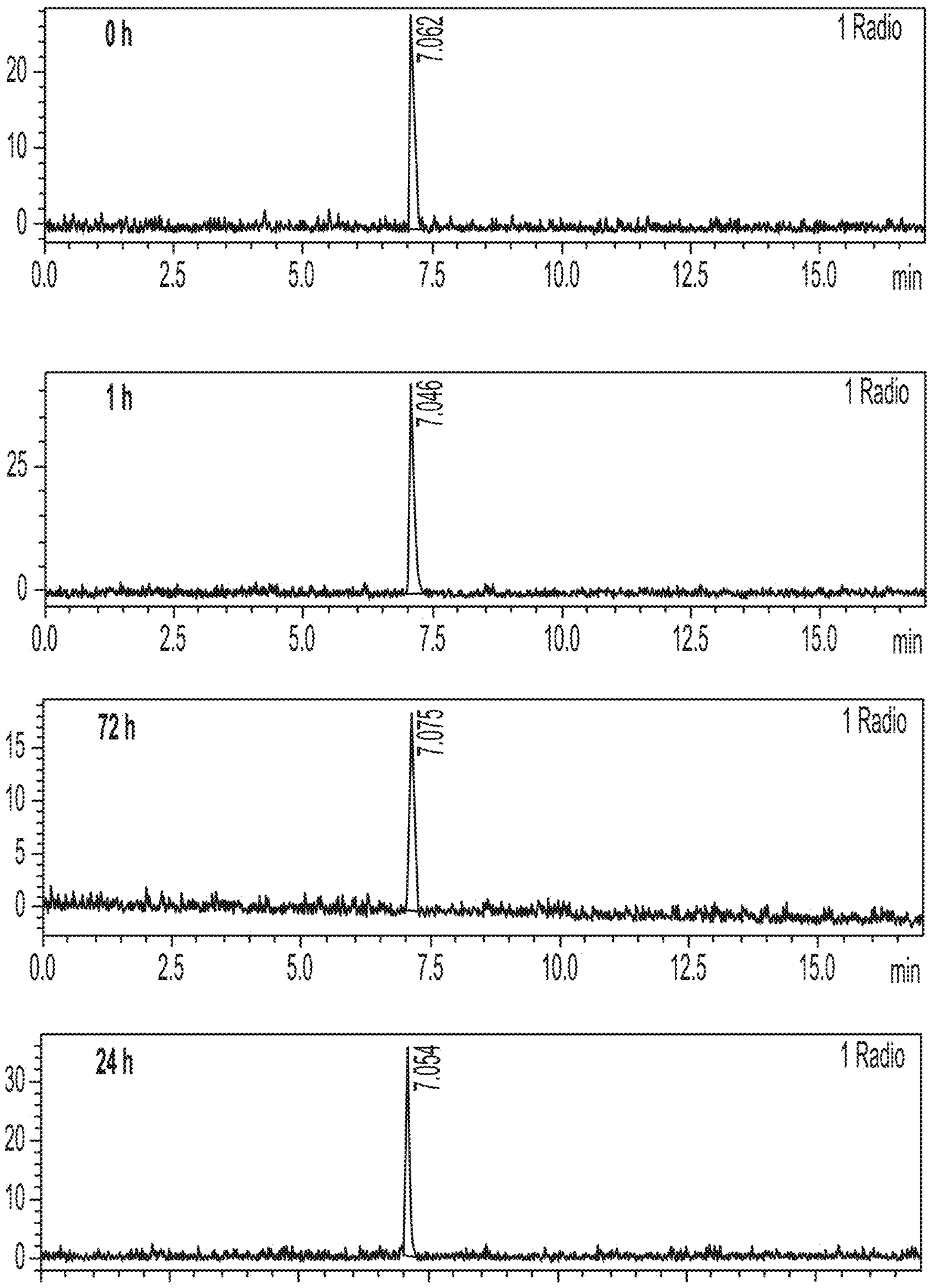
FIG. 4 shows radio-HPLC traces of ex-vivo mouse plasma stability samples of $^{177}$Lu-C-6.
Figure 5A:
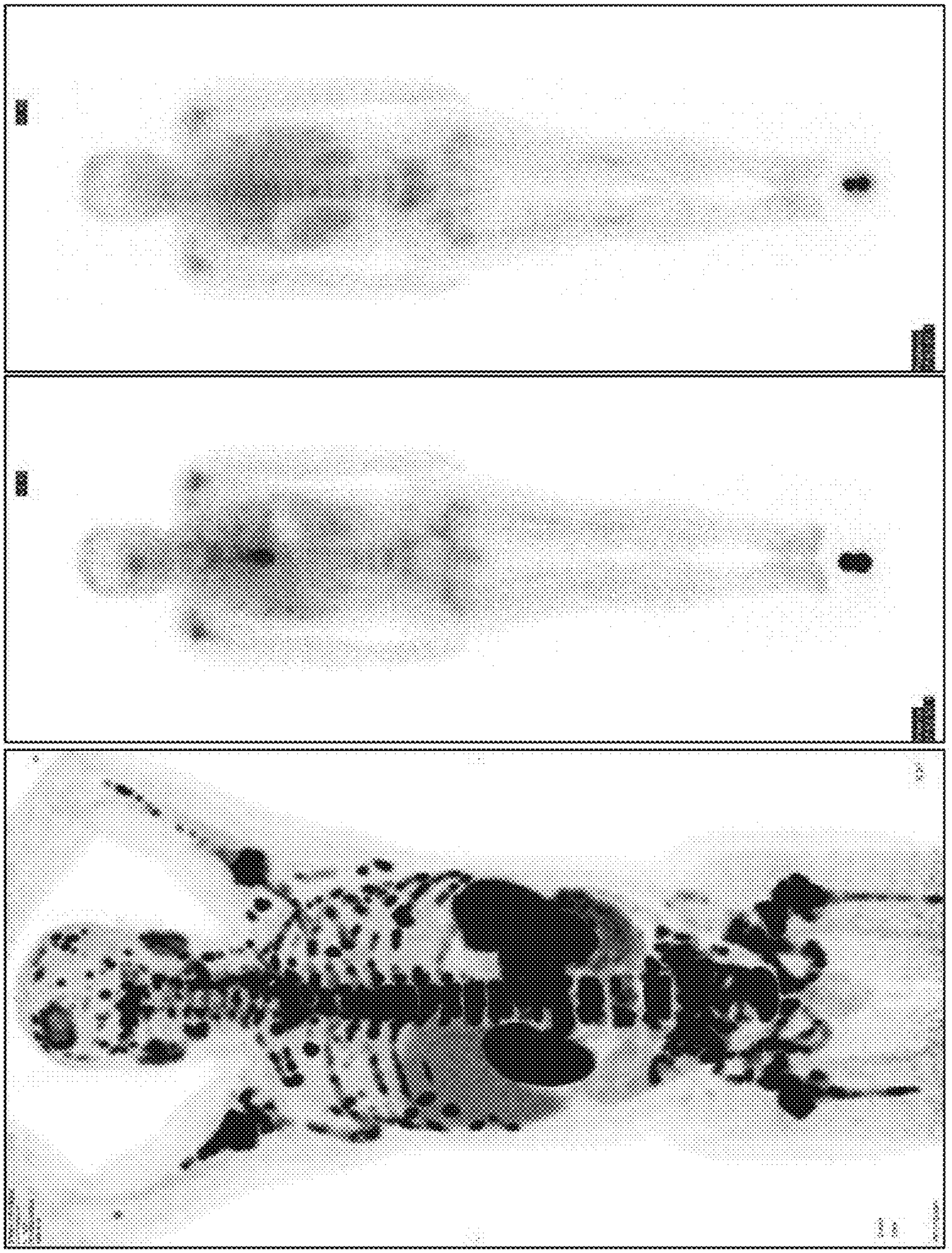
FIGS. 5A to 5D show $^{68}$Ga-PSMA11 (gozetotide) PET/CT imaging (Left panel) and $^{111}$In-I-21 SPECT/CT imaging (48 hours after dosing) (Middle panel: Anterior; Right panel: Posterior) of 4 (FIG. 5A, FIG. 5B, FIG. 5C, FIG. 5D) metastatic castration-resistant prostate cancer (mCRPC) patients.
Figure 5B:
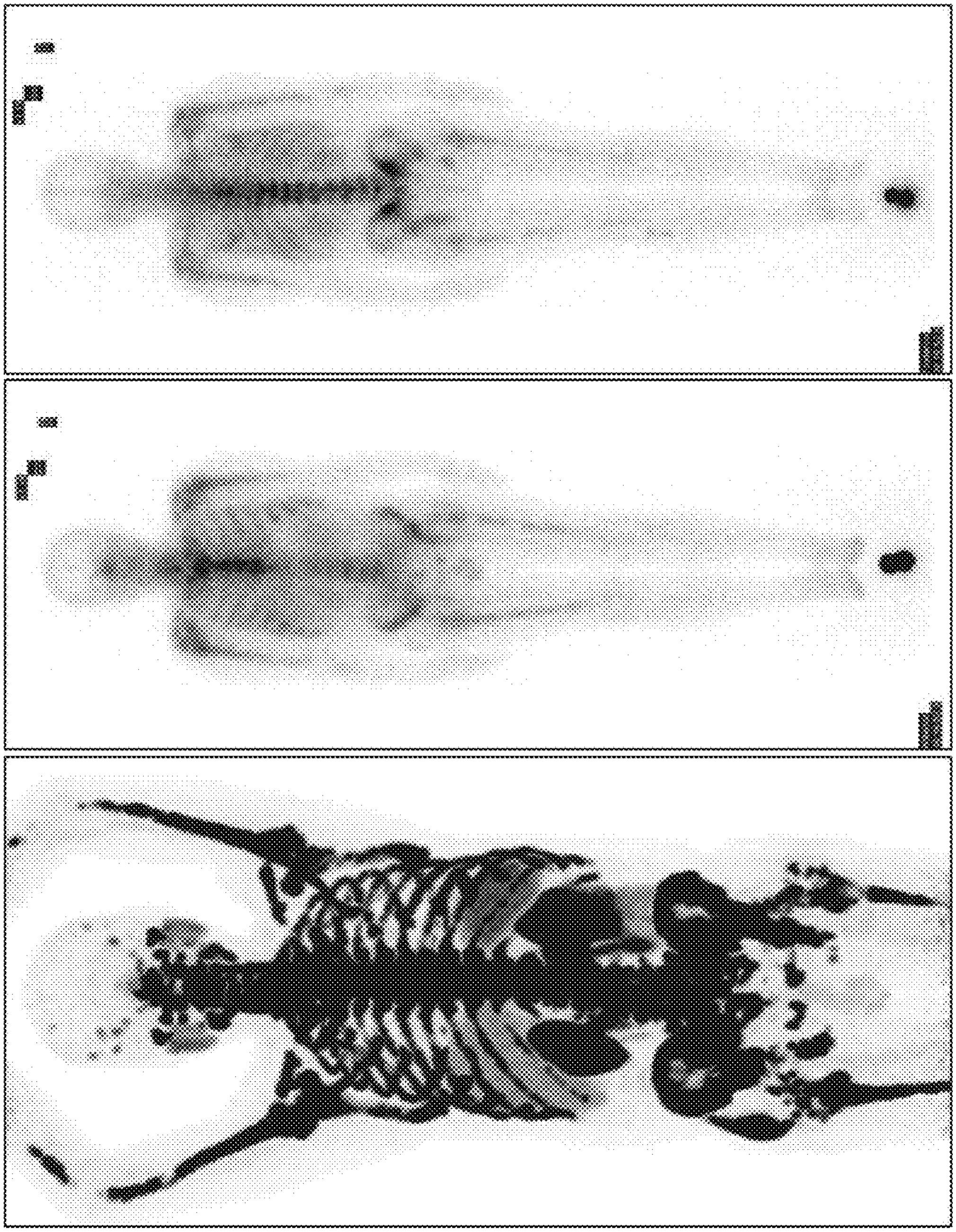
Figure 5C:
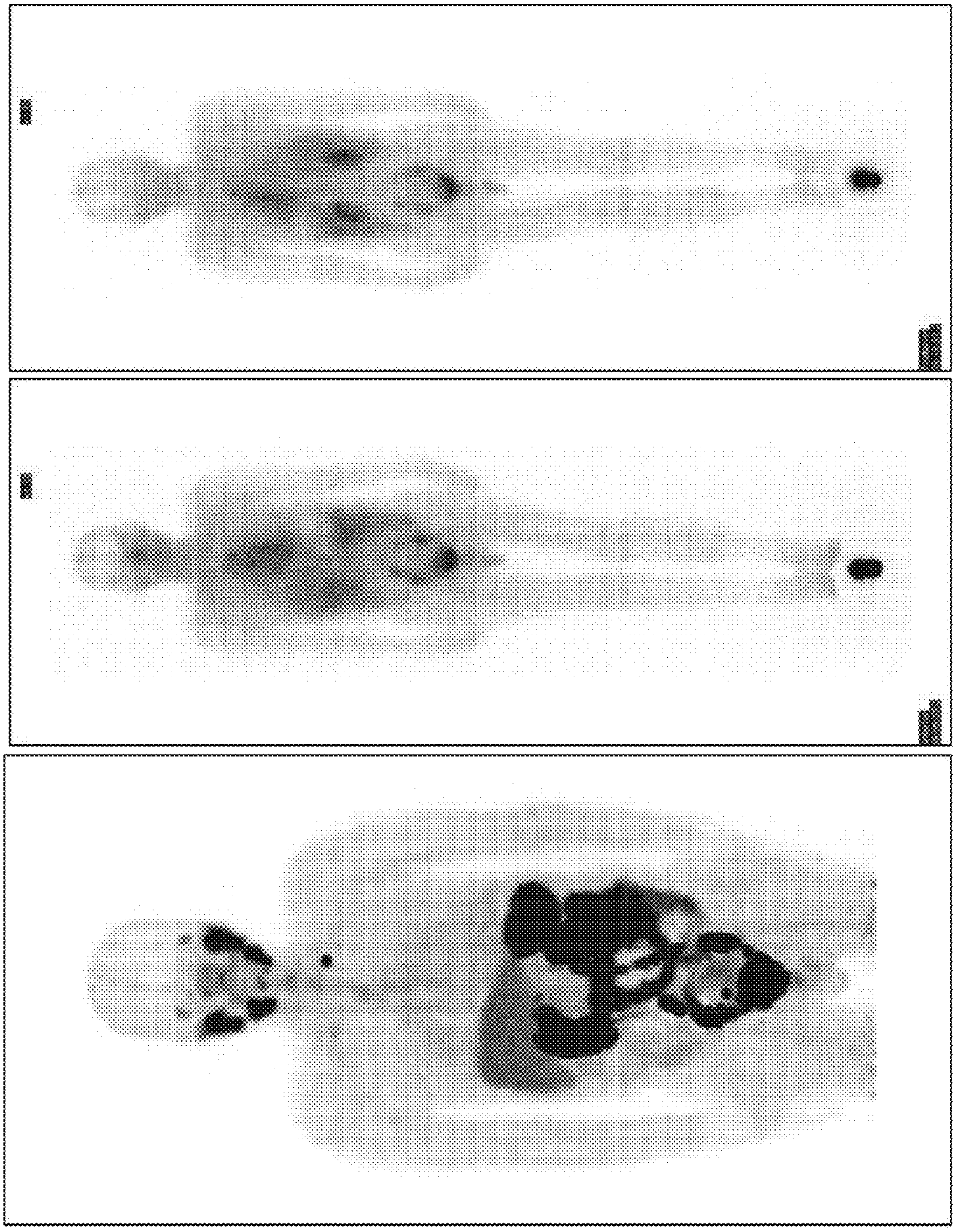
Figure 5D:
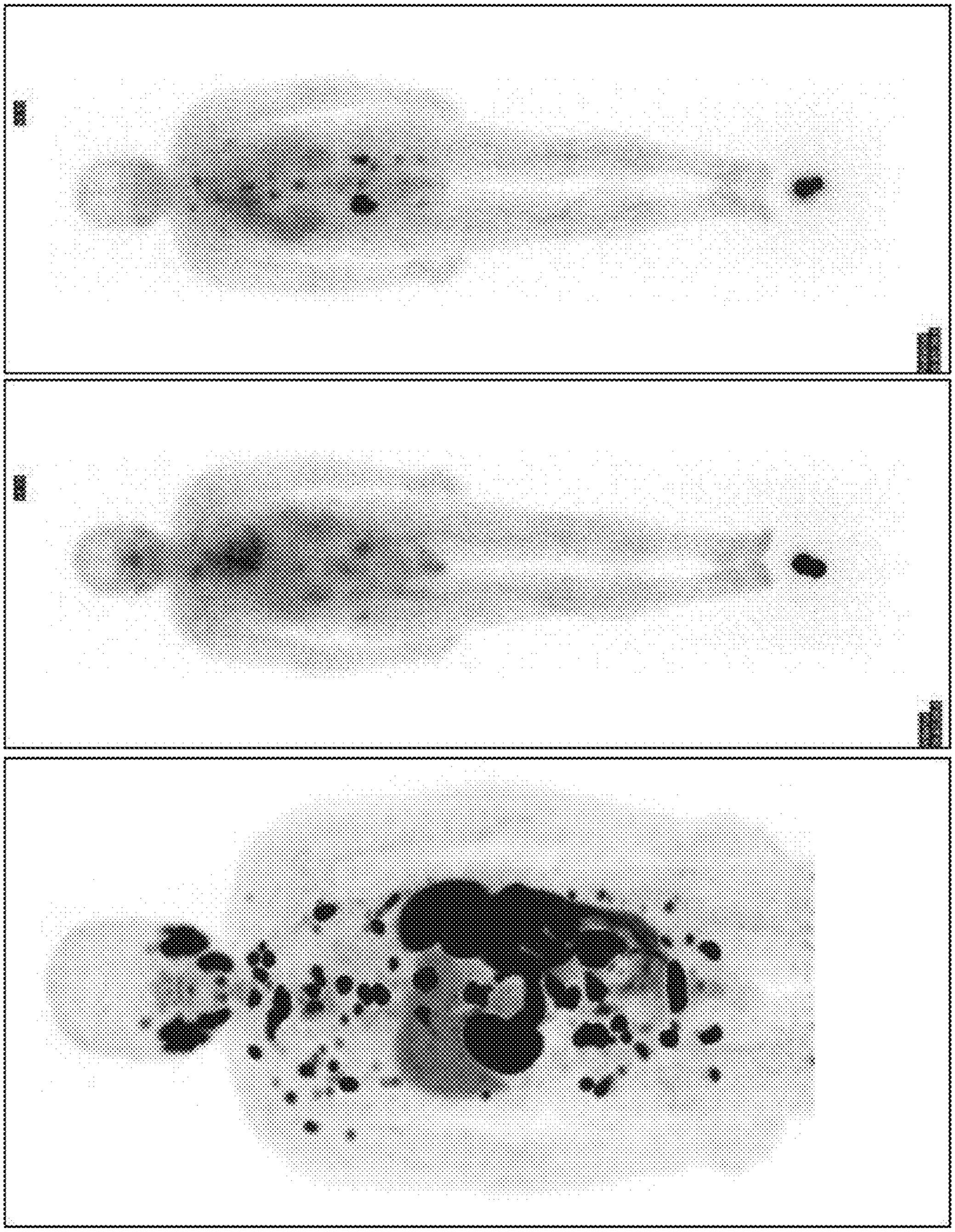

The exemplary compounds with cleavable linkers tested in the mouse plasma stability study all demonstrated significant degradation over time with a T1/2 in the range of around a few hours to about 100 hours, as shown in FIG. 3. In comparison, the non-cleavable compounds, such as $^{177}$Lu-C-2, $^{177}$Lu-C-7 and $^{177}$Lu-C-6 were completely stable in the study, non-degradation was observed over 72 hours, as shown in FIG. 4. Separately, the cleavable compounds, such as exemplary compound $^{177}$Lu-I-21 were completely stable in the tested buffer conditions.

TABLE 3

Data summary of ex-vivo mouse plasma stability study of $^{177}$Lu-labeled compounds (*value obtained using nonlinear regression)

| % Remaining | 0 min | 30 min | 1 h | 2 h | 4 h | 24 h | 48 h | 72 h | T½ (h) |
|---|---|---|---|---|---|---|---|---|---|
| C-1 | 100 | — | 100 | — | 100 | 100 | 100 | 100 | Stable |
| C-2 | 100 | — | 100 | — | 100 | 100 | 100 | 100 | Stable |
| C-6 | 100 | — | 100 | — | 100 | 100 | 100 | 100 | Stable |
| C-7 | 100 | — | 100 | — | 100 | 100 | 100 | 100 | Stable |
| I-2 | 100 | — | 95.6 | — | 93.2 | 76.5 | 67.5 | 57.3 | 80.4 |
| I-3 | 100 | — | 88.6 | — | 54.8 | 13.0 | 9.30 | 3.99 | 4.9* |
| I-11 | 100 | — | 100 | — | 100 | 76.64 | 69.48 | 56.04 | 56.0* |
| I-18 | 100 | — | 100 | — | 89.5 | 79.5 | 59.8 | 51.8 | 78.8* |
| I-20 | 89.90 | — | 88.52 | — | — | 34.55 | 15.66 | 0 | 11.0* |
| I-21 | 100 | 100 | 100 | 100 | 89.7 | 81.1 | 65.1 | — | 70.5 |
| I-22 | 100 | — | 82.3 | — | 48.9 | 17.1 | 7.2 | 0 | 4.1* |
| I-23 | 100 | — | 65.5 | — | 18.2 | 12.1 | — | 2.41 | 1.5* |
| I-24 | 100 | — | 100 | — | 100 | 95.92 | 83.83 | 75.28 | 139.3* |
| I-26 | 100 | — | 56.78 | — | 7.97 | 0 | 0 | 0 | 1.2* |
| I-27 | 100 | — | 76.41 | — | 67.57 | 7.59 | 0 | 0 | 5.3* |
| I-30 | 100 | — | 100 | — | 90.22 | 82.22 | 68.73 | 62.49 | 143* |
| I-31 | 100 | — | 100 | — | 93.02 | 83.94 | 63.55 | 52.78 | 78.5* |
| I-35 | 100 | — | 100 | — | 100 | 83.05 | 71.49 | 54.27 | 84.8* |
| I-38 | 100 | 100 | 100 | 100 | 100 | 85.3 | 72.6 | — | 83.7 |
| I-37 | 100 | — | 95.73 | — | 90.7 | 75.7 | 57.9 | 46.3 | 62.9 |
| I-39 | 92.5 | — | 87.5 | — | 79.3 | 35.3 | 20.3 | 2.96 | 12.3* |
| I-41 | 100 | — | 100 | — | 100 | 100 | 88.8 | 87.1 | 234* |
| I-43 | 100 | — | 100 | — | 100 | 89.04 | 84.93 | 79.08 | 320* |
| I-46 | 100 | — | 95.1 | — | 93.5 | 81.9 | 70.6 | 55.9 | 102* |
| I-47 | 100 | — | 100 | — | 94.7 | 81.5 | 76.1 | 59.6 | 121* |
| I-49 | 100 | — | 100 | — | 83.1 | 54.2 | 46.5 | 32.4 | 33.0* |
| I-50 | 100 | — | 100 | — | 58.4 | 13.7 | 8.87 | 0 | 5.7* |
| I-51 | 100 | — | 100 | — | 87.5 | 70.7 | 59.2 | 37.6 | 55.0* |
| I-52 | 100 | — | 94.7 | — | 91.8 | 69.1 | 56.4 | 45.4 | 61.4* |
| I-53 | 100 | — | 82.1 | — | 53.0 | 25.2 | 17.4 | 0 | 5.2* |
| I-54 | 100 | — | 90.7 | — | 11.2 | 0 | 0 | 0 | 2.1* |
| **I-55(a) or (b) | 100 | — | 100 | — | 81.4 | 47.9 | 29.8 | 20.4 | 20.7* |
| **I-55 (a) or (b) | 100 | — | 88.1 | — | 73.8 | 23.6 | 10.3 | 0 | 8.5* |
| I-58 | 100 | — | 100 | — | 87.4 | — | 52.2 | 37.2 | 45.8 |

**I-55 was prepared as a mixture of two diastereomers and each diastereomer was separated and isolated using HPLC. Stereochemistry of each was not assigned. The stability of each of the two isomers was measured and entered above.

TABLE 4

Data summary of stability study of $^{177}$Lu—I-21 in various buffer conditions

| % Remaining | 0 h | 1 h | 4 h | 24 h | 48 h | 72 h |
|---|---|---|---|---|---|---|
| pH 4.5 25 mM NaOAc | 100 | 100 | 100 | 100 | 100 | 100 |
| pH 4.5 25 mM NaOAc + 3 mg/mL ascorbate | 100 | 100 | 100 | 100 | 100 | 100 |
| pH 7.4 PBS | 100 | 100 | 100 | 100 | 100 | 100 |
| pH 7.4 PBS + 3 mg/mL ascorbate | 100 | 100 | 100 | 100 | 100 | 100 |

Biodistribution Studies

Biodistribution studies of selected compounds were performed as described above

All tested exemplary compounds demonstrated good to excellent tumor uptake of the radionuclide regardless of their binding affinity to PSMA. The uptake of radionuclide in normal organs including blood, kidney and liver were found to be dependent on the modification groups introduced to extend the circulation time in blood, and the cleavable and non-cleavable linkers placed between chelator, albumin binding domain and PSMA binding domain. In addition, it was also found that these modification and linkers play roles in determining the tumor residence time of radionuclide and the wash-out kinetics of the radionuclide in normal organs such as blood, kidney, liver etc.

Tables 5-24 show the biodistribution of various compounds in PC3-PIP tumor-bearing mice, Tables 25-33 show the biodistribution of various compounds in LNCap tumor-bearing mice. Table 34 contains a comparison of tumor and kidney uptake of selected $^{177}$Lu-labeled compounds in PC3-PIP or LNCap tumor-bearing mice.

TABLE 5

Biodistribution of $^{177}$Lu—C-1 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | 14.01 | 12.78 | 10.43 | 8.39 | 7.25 | 6.03 | 5.64 | 2.85 | 1.65 | 0.97 |
| Blood | 0.38 | 0.02 | 0.00 | 0.00 | 0.00 | 0.18 | 0.01 | 0.00 | 0.00 | 0.00 |
| Heart | 0.18 | 0.01 | 0.00 | 0.00 | 0.00 | 0.08 | 0.01 | 0.00 | 0.00 | 0.00 |
| Liver | 0.23 | 0.06 | 0.02 | 0.02 | 0.01 | 0.10 | 0.02 | 0.00 | 0.00 | 0.00 |
| Spleen | 1.12 | 0.14 | 0.01 | 0.01 | 0.01 | 0.35 | 0.03 | 0.01 | 0.00 | 0.01 |
| Kidney | 10.89 | 1.82 | 0.18 | 0.10 | 0.04 | 3.67 | 1.00 | 0.05 | 0.03 | 0.01 |
| Muscle | 0.11 | 0.01 | 0.00 | 0.00 | 0.00 | 0.03 | 0.00 | 0.00 | 0.00 | 0.00 |
| Salivary glands | 0.23 | 0.04 | 0.01 | 0.01 | 0.00 | 0.08 | 0.01 | 0.01 | 0.00 | 0.00 |
| Lacrimal glands | 0.36 | 0.03 | 0.00 | 0.01 | 0.00 | 0.09 | 0.03 | 0.00 | 0.01 | 0.01 |
| Carcass | 0.72 | 0.07 | 0.03 | 0.09 | 0.02 | 0.57 | 0.03 | 0.02 | 0.10 | 0.01 |
| Bone | 0.11 | 0.01 | 0.12 | 0.00 | 0.00 | 0.04 | 0.01 | 0.22 | 0.00 | 0.01 |

TABLE 6

Biodistribution of $^{177}$Lu—C-2 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | n/d | 29.98 | 41.11 | 30.71 | 19.78 | n/d | 6.01 | 8.30 | 0.89 | 7.46 |
| Blood | n/d | 7.07 | 0.53 | 0.09 | 0.02 | n/d | 0.65 | 0.12 | 0.03 | 0.01 |
| Heart | n/d | 2.09 | 0.31 | 0.18 | 0.12 | n/d | 0.32 | 0.05 | 0.03 | 0.01 |
| Liver | n/d | 1.45 | 0.49 | 0.36 | 0.18 | n/d | 0.20 | 0.07 | 0.08 | 0.02 |
| Spleen | n/d | 6.36 | 2.21 | 0.73 | 0.40 | n/d | 2.04 | 0.54 | 0.13 | 0.09 |
| Kidney | n/d | 85.51 | 42.16 | 10.67 | 5.32 | n/d | 25.98 | 16.39 | 1.56 | 1.78 |
| Muscle | n/d | 0.52 | 0.08 | 0.05 | 0.03 | n/d | 0.06 | 0.02 | 0.01 | 0.00 |
| Salivary glands | n/d | 1.85 | 0.56 | 0.33 | 0.19 | n/d | 0.18 | 0.14 | 0.04 | 0.01 |
| Lacrimal glands | n/d | 3.17 | 0.98 | 0.33 | 0.24 | n/d | 0.62 | 0.47 | 0.05 | 0.05 |
| Carcass | n/d | 1.23 | 0.30 | 0.16 | 0.12 | n/d | 0.11 | 0.02 | 0.01 | 0.05 |
| Bone | n/d | 0.54 | 0.11 | 0.07 | 0.04 | n/d | 0.12 | 0.04 | 0.02 | 0.01 |

TABLE 7

Biodistribution of $^{177}$Lu—I-2 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | n/d | 15.15 | 32.41 | 19.55 | 9.76 | n/d | 4.38 | 9.87 | 3.13 | 3.11 |
| Blood | n/d | 6.87 | 0.65 | 0.10 | 0.01 | n/d | 0.96 | 0.19 | 0.03 | 0.01 |
| Heart | n/d | 1.78 | 0.28 | 0.09 | 0.06 | n/d | 0.26 | 0.07 | 0.02 | 0.03 |
| Liver | n/d | 1.61 | 0.36 | 0.27 | 0.15 | n/d | 0.32 | 0.11 | 0.07 | 0.09 |
| Spleen | n/d | 2.97 | 0.60 | 0.36 | 0.14 | n/d | 1.07 | 0.29 | 0.19 | 0.08 |
| Kidney | n/d | 27.61 | 6.39 | 3.04 | 0.96 | n/d | 10.75 | 3.20 | 1.59 | 0.89 |
| Muscle | n/d | 0.45 | 0.07 | 0.02 | 0.01 | n/d | 0.04 | 0.01 | 0.01 | 0.01 |
| Salivary glands | n/d | 1.59 | 0.36 | 0.16 | 0.10 | n/d | 0.18 | 0.09 | 0.03 | 0.03 |
| Lacrimal glands | n/d | 1.41 | 0.28 | 0.13 | 0.08 | n/d | 0.23 | 0.04 | 0.04 | 0.05 |
| Carcass | n/d | 1.19 | 0.28 | 0.12 | 0.07 | n/d | 0.12 | 0.12 | 0.03 | 0.03 |
| Bone | n/d | 0.56 | 0.23 | 0.18 | 0.05 | n/d | 0.03 | 0.18 | 0.06 | 0.01 |

TABLE 8

Biodistribution of $^{177}$Lu—I-3 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | n/d | 21.64 | 13.88 | 14.31 | 6.29 | n/d | 2.48 | 3.36 | 3.70 | 1.34 |
| Blood | n/d | 5.70 | 0.18 | 0.03 | 0.00 | n/d | 1.52 | 0.08 | 0.01 | 0.00 |
| Heart | n/d | 1.55 | 0.17 | 0.09 | 0.07 | n/d | 0.39 | 0.03 | 0.01 | 0.02 |
| Liver | n/d | 1.45 | 0.28 | 0.33 | 0.09 | n/d | 0.36 | 0.09 | 0.07 | 0.02 |
| Spleen | n/d | 4.44 | 0.83 | 0.43 | 0.23 | n/d | 1.27 | 0.46 | 0.05 | 0.10 |
| Kidney | n/d | 66.57 | 18.02 | 6.36 | 1.58 | n/d | 14.24 | 12.66 | 1.97 | 0.64 |
| Muscle | n/d | 0.39 | 0.05 | 0.03 | 0.02 | n/d | 0.10 | 0.02 | 0.01 | 0.01 |
| Salivary glands | n/d | 1.78 | 0.34 | 0.22 | 0.13 | n/d | 0.41 | 0.07 | 0.04 | 0.03 |
| Lacrimal glands | n/d | 2.35 | 0.38 | 0.19 | 0.13 | n/d | 0.52 | 0.14 | 0.04 | 0.04 |
| Carcass | n/d | 1.17 | 0.17 | 0.20 | 0.08 | n/d | 0.34 | 0.03 | 0.12 | 0.04 |
| Bone | n/d | 0.50 | 0.08 | 0.24 | 0.05 | n/d | 0.09 | 0.01 | 0.04 | 0.01 |

TABLE 9

Biodistribution of $^{177}$Lu—I-4 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | n/d | 1.97 | 0.79 | 0.56 | 0.31 | n/d | 0.36 | 0.07 | 0.10 | 0.10 |
| Blood | n/d | 0.33 | 0.02 | 0.01 | 0.01 | n/d | 0.07 | 0.00 | 0.00 | 0.01 |
| Heart | n/d | 0.14 | 0.04 | 0.02 | 0.01 | n/d | 0.02 | 0.01 | 0.00 | 0.00 |
| Liver | n/d | 0.33 | 0.16 | 0.12 | 0.06 | n/d | 0.04 | 0.02 | 0.03 | 0.01 |
| Spleen | n/d | 0.56 | 0.16 | 0.12 | 0.06 | n/d | 0.19 | 0.03 | 0.04 | 0.02 |
| Kidney | n/d | 19.91 | 4.05 | 1.37 | 0.26 | n/d | 5.91 | 1.10 | 0.33 | 0.10 |
| Muscle | n/d | 0.05 | 0.02 | 0.01 | 0.00 | n/d | 0.01 | 0.02 | 0.01 | 0.00 |
| Salivary glands | n/d | 0.19 | 0.08 | 0.06 | 0.02 | n/d | 0.04 | 0.01 | 0.02 | 0.00 |
| Lacrimal glands | n/d | 0.25 | 0.06 | 0.03 | −0.01 | n/d | 0.06 | 0.03 | 0.01 | 0.00 |
| Carcass | n/d | 0.22 | 0.10 | 0.06 | 0.03 | n/d | 0.06 | 0.10 | 0.03 | 0.01 |
| Bone | n/d | 0.09 | 0.04 | 0.03 | 0.00 | n/d | 0.01 | 0.01 | 0.01 | 0.01 |

TABLE 10

Biodistribution of $^{177}$Lu—I-11 in PC-3 PIP tumor-bearing mice (n = 4)

| % ID/g | 1 h | 4 h | 24 h | 48 h | 72 h | 1 h STDEV | 4 h STDEV | 24 h STDEV | 48 h STDEV | 72 h STDEV |
|---|---|---|---|---|---|---|---|---|---|---|
| Tumor | 8.11 | 16.03 | 36.26 | 31.62 | 18.93 | 0.59 | 2.68 | 1.83 | 11.43 | 8.27 |
| Blood | 23.54 | 17.47 | 4.27 | 1.29 | 0.21 | 2.81 | 2.33 | 0.94 | 0.68 | 0.10 |
| Heart | 6.08 | 4.91 | 1.72 | 0.90 | 0.49 | 0.47 | 0.58 | 0.15 | 0.34 | 0.08 |
| Liver | 4.61 | 3.74 | 1.74 | 1.13 | 0.54 | 0.29 | 0.72 | 0.32 | 0.44 | 0.10 |
| Spleen | 4.45 | 3.62 | 2.69 | 1.81 | 0.94 | 1.33 | 0.94 | 0.88 | 0.63 | 0.33 |
| Kidney | 14.54 | 11.82 | 7.82 | 5.23 | 2.07 | 3.69 | 2.86 | 2.06 | 2.64 | 0.82 |
| Muscle | 1.16 | 1.25 | 0.43 | 0.25 | 0.17 | 0.09 | 0.13 | 0.06 | 0.07 | 0.03 |
| Salivary glands | 5.18 | 3.79 | 2.13 | 1.52 | 0.94 | 0.82 | 0.57 | 0.30 | 0.49 | 0.20 |
| Lacrimal glands | 3.79 | 2.68 | 1.37 | 0.87 | 0.65 | 0.72 | 0.39 | 0.07 | 0.21 | 0.06 |
| Carcass | 2.63 | 2.71 | 0.95 | 0.59 | 0.33 | 0.20 | 0.27 | 0.16 | 0.16 | 0.06 |
| Bone | 1.36 | 1.43 | 0.48 | 0.34 | 0.19 | 0.39 | 0.43 | 0.29 | 0.17 | 0.06 |

TABLE 11

Biodistribution of $^{177}$Lu—I-7 in PC-3 PIP tumor-bearing mice (n = 4)

| % ID/g | 1 h | 4 h | 24 h | 48 h | 96 h | 1 h STDEV | 4 h STDEV | 24 h STDEV | 48 h STDEV | 96 h STDEV |
|---|---|---|---|---|---|---|---|---|---|---|
| Tumor | 8.61 | 17.21 | 16.70 | 8.13 | 2.61 | 1.59 | 8.61 | 5.75 | 1.46 | 2.61 |
| Blood | 17.77 | 10.37 | 0.86 | 0.07 | 0.01 | 1.41 | 17.77 | 0.38 | 0.03 | 0.01 |
| Heart | 4.22 | 3.12 | 0.48 | 0.21 | 0.15 | 0.43 | 4.22 | 0.13 | 0.05 | 0.15 |
| Liver | 3.51 | 2.48 | 0.62 | 0.27 | 0.19 | 0.30 | 3.51 | 0.15 | 0.05 | 0.19 |
| Spleen | 3.89 | 2.45 | 1.13 | 0.56 | 0.38 | 0.43 | 3.89 | 0.45 | 0.07 | 0.38 |
| Kidney | 32.70 | 24.75 | 18.01 | 4.45 | 1.92 | 4.79 | 32.70 | 9.09 | 1.06 | 1.92 |
| Muscle | 1.11 | 0.77 | 0.11 | 0.06 | 0.03 | 0.13 | 1.11 | 0.03 | 0.00 | 0.03 |
| Salivary glands | 3.91 | 2.51 | 0.71 | 0.40 | 0.27 | 0.32 | 3.91 | 0.18 | 0.07 | 0.27 |
| Lacrimal glands | 2.93 | 2.36 | 0.41 | 0.25 | 0.17 | 0.31 | 2.93 | 0.08 | 0.07 | 0.17 |
| Carcass | 2.58 | 1.88 | 0.33 | 0.17 | 0.11 | 0.28 | 2.58 | 0.08 | 0.04 | 0.11 |
| Bone | 1.34 | 0.59 | 0.18 | 0.10 | 0.07 | 0.39 | 1.34 | 0.08 | 0.02 | 0.07 |

TABLE 12

Biodistribution of $^{177}$Lu—I-34 and $^{177}$Lu—I-41in PC-3 PIP tumor-bearing mice (n = 4)

| | $^{177}$Lu—I-34 | | | | $^{177}$Lu—I-41 | | | |
|---|---|---|---|---|---|---|---|---|
| % ID/g | 24 h | 24 h STDEV | 96 h | 96 h STDEV | 24 h | 24 h STDEV | 96 h | 96 h STDEV |
| Tumor | 30.69 | 5.03 | 30.41 | 8.40 | 37.99 | 5.31 | 48.84 | 8.77 |
| Blood | 8.28 | 1.33 | 0.59 | 0.07 | 9.56 | 2.08 | 0.65 | 0.14 |
| Heart | 2.99 | 0.37 | 1.15 | 0.16 | 2.68 | 0.55 | 0.52 | 0.07 |
| Liver | 3.99 | 0.67 | 2.55 | 0.33 | 3.28 | 0.76 | 1.27 | 0.50 |
| Spleen | 4.79 | 0.98 | 4.32 | 1.42 | 5.12 | 1.85 | 1.56 | 0.34 |
| Kidney | 16.99 | 2.87 | 5.34 | 1.03 | 39.21 | 5.16 | 16.07 | 4.16 |
| Muscle | 0.84 | 0.13 | 0.36 | 0.04 | 0.73 | 0.05 | 0.14 | 0.04 |
| Salivary glands | 3.53 | 0.54 | 2.69 | 0.34 | 6.67 | 6.74 | 0.92 | 0.21 |
| Lacrimal glands | 2.70 | 1.69 | 1.19 | 0.23 | 2.10 | 1.55 | 0.74 | 0.32 |
| Carcass | 1.85 | 0.34 | 0.79 | 0.10 | 1.97 | 0.41 | 0.42 | 0.10 |
| Bone | 1.10 | 0.15 | 0.70 | 0.20 | 0.91 | 0.23 | 0.49 | 0.06 |

TABLE 13

Biodistribution of $^{177}$Lu—I-35, $^{177}$Lu—I-36, $^{177}$Lu—I-39, $^{177}$Lu—I-42 and $^{177}$Lu—I-21 in PC-3 PIP tumor-bearing mice (n = 4)

| | $^{177}$Lu—I-35 | | $^{177}$Lu—I-36 | | $^{177}$Lu—I-39 | | $^{177}$Lu—I-42 | | $^{177}$Lu—I-21 | |
|---|---|---|---|---|---|---|---|---|---|---|
| % ID/g | 24 h | 24 h STDEV | 24 h | 24 h STDEV | 24 h | 24 h STDEV | 24 h | 24 h STDEV | 24 h | 24 h STDEV |
| Tumor | 21.63 | 1.60 | 2.84 | 0.32 | 5.41 | 0.66 | 28.67 | 5.66 | 44.94 | 4.98 |
| Blood | 11.10 | 2.14 | 0.50 | 0.07 | 0.31 | 0.16 | 13.76 | 1.69 | 6.55 | 0.45 |
| Heart | 3.43 | 0.34 | 0.37 | 0.02 | 0.37 | 0.10 | 3.92 | 0.26 | 2.01 | 0.31 |
| Liver | 4.83 | 0.69 | 0.90 | 0.07 | 0.91 | 0.18 | 4.74 | 0.58 | 2.15 | 0.12 |
| Spleen | 5.24 | 1.39 | 1.31 | 0.22 | 1.23 | 0.22 | 6.18 | 0.85 | 2.64 | 0.33 |
| Kidney | 6.23 | 0.98 | 1.88 | 0.26 | 4.18 | 1.71 | 11.60 | 1.92 | 8.10 | 1.48 |
| Muscle | 0.91 | 0.08 | 0.12 | 0.04 | 0.09 | 0.02 | 0.95 | 0.16 | 0.49 | 0.04 |
| Salivary glands | 4.00 | 0.91 | 0.64 | 0.10 | 0.64 | 0.16 | 3.77 | 0.49 | 2.26 | 0.24 |
| Lacrimal glands | 3.05 | 0.47 | 0.45 | 0.11 | 0.42 | 0.07 | 3.09 | 1.00 | 1.34 | 0.26 |
| Carcass | 2.15 | 0.43 | 0.26 | 0.03 | 0.33 | 0.14 | 2.29 | 0.23 | 1.32 | 0.15 |

TABLE 14

Biodistribution of $^{177}$Lu—I-21 in PC-3 PIP tumor-bearing mice (n = 4)

| % ID/g | 1 h | 4 h | 24 h | 48 h | 72 h | 120 h | 168 h | 1 h STDEV | 4 h STDEV | 24 h STDEV | 48 h STDEV | 72 h STDEV | 120 h STDEV | 168 h STDEV |
|---|---|---|---|---|---|---|---|---|---|---|---|---|---|---|
| Tumor | 8.00 | 15.15 | 30.21 | 32.65 | 25.97 | 26.46 | 18.00 | 1.41 | 1.12 | 5.34 | 5.56 | 2.87 | 6.60 | 4.23 |
| Blood | 20.63 | 12.77 | 3.84 | 1.75 | 0.51 | 0.11 | 0.05 | 1.15 | 2.22 | 0.94 | 0.24 | 0.01 | 0.04 | 0.02 |
| Heart | 4.64 | 3.18 | 1.28 | 0.81 | 0.46 | 0.34 | 0.20 | 0.53 | 0.92 | 0.22 | 0.08 | 0.03 | 0.06 | 0.02 |
| Liver | 4.25 | 2.95 | 1.31 | 1.07 | 0.80 | 0.55 | 0.49 | 0.63 | 0.48 | 0.36 | 0.15 | 0.11 | 0.18 | 0.08 |
| Spleen | 3.98 | 2.40 | 1.66 | 1.27 | 0.84 | 0.72 | 0.76 | 1.09 | 1.05 | 0.79 | 0.34 | 0.20 | 0.23 | 0.21 |
| Kidney | 21.14 | 9.33 | 6.36 | 3.32 | 2.12 | 0.78 | 0.76 | 9.51 | 2.51 | 4.02 | 0.10 | 0.13 | 0.26 | 0.25 |
| Muscle | 0.83 | 0.74 | 0.33 | 0.22 | 0.10 | 0.06 | 0.05 | 0.04 | 0.05 | 0.02 | 0.02 | 0.03 | 0.00 | 0.02 |
| Salivary glands | 3.85 | 2.33 | 1.33 | 1.07 | 0.57 | 0.56 | 0.36 | 0.12 | 0.26 | 0.33 | 0.15 | 0.17 | 0.17 | 0.10 |
| Lacrimal glands | 2.31 | 1.30 | 0.88 | 0.86 | 0.44 | 0.29 | 0.22 | 0.31 | 0.14 | 0.14 | 0.07 | 0.16 | 0.12 | 0.08 |
| Carcass | 2.42 | 1.94 | 0.91 | 0.72 | 0.45 | 0.28 | 0.35 | 0.32 | 0.27 | 0.11 | 0.15 | 0.04 | 0.11 | 0.05 |
| Bone | 1.33 | 1.37 | 0.80 | 1.28 | 0.84 | 0.06 | 1.08 | 0.24 | 0.22 | 0.08 | 0.17 | 0.11 | 0.01 | 0.22 |
| Fat | 2.89 | 2.11 | 1.25 | 0.72 | 0.37 | 0.44 | 0.22 | 0.43 | 0.82 | 0.58 | 0.08 | 0.08 | 0.19 | 0.02 |
| Testes | 1.31 | 1.71 | 1.03 | 0.92 | 0.63 | 0.75 | 0.49 | 0.28 | 0.37 | 0.23 | 0.11 | 0.04 | 0.11 | 0.10 |
| Stomach | 1.13 | 1.21 | 0.51 | 0.74 | 0.43 | 0.20 | 0.27 | 0.22 | 0.36 | 0.31 | 0.31 | 0.33 | 0.16 | 0.32 |
| Small Intestine | 1.65 | 1.62 | 0.56 | 0.63 | 0.45 | 0.19 | 0.24 | 0.18 | 0.51 | 0.27 | 0.10 | 0.35 | 0.08 | 0.26 |
| Large Intestine | 0.98 | 1.58 | 0.91 | 1.29 | 0.96 | 0.77 | 0.59 | 0.21 | 0.78 | 0.66 | 0.63 | 0.59 | 0.62 | 0.74 |
| Pancreas | 2.58 | 1.62 | 0.95 | 0.56 | 0.24 | 0.07 | 0.12 | 0.23 | 0.52 | 0.28 | 0.17 | 0.05 | 0.08 | 0.02 |
| Adrenal Glands | 4.58 | 1.75 | 1.87 | 1.40 | 0.83 | 0.83 | 0.41 | 1.12 | 0.55 | 0.72 | 0.22 | 0.09 | 0.63 | 0.08 |
| Lung | 9.00 | 5.51 | 2.56 | 1.50 | 0.70 | 0.36 | 0.29 | 1.30 | 0.78 | 1.05 | 0.25 | 0.10 | 0.07 | 0.06 |
| Brain | 0.45 | 0.25 | 0.12 | 0.07 | 0.03 | 0.02 | 0.02 | 0.08 | 0.08 | 0.01 | 0.01 | 0.01 | 0.01 | 0.00 |
| Prostate | 6.02 | 3.87 | 1.26 | 1.04 | 0.41 | 0.33 | 0.25 | 2.16 | 2.06 | 0.19 | 0.34 | 0.06 | 0.05 | 0.06 |

TABLE 15

Biodistribution of $^{177}$Lu—I-35 in PC-3 PIP tumor-bearing mice (n = 4)

| % ID/g | 1 h | 4 h | 24 h | 48 h | 72 h | 120 h | 168 h | 1 h STDEV | 4 h STDEV | 24 h STDEV | 48 h STDEV | 72 h STDEV | 120 h STDEV | 168 h STDEV |
|---|---|---|---|---|---|---|---|---|---|---|---|---|---|---|
| Tumor | 3.06 | 7.00 | 23.26 | 25.79 | 29.25 | 21.16 | 11.67 | 0.92 | 1.62 | 3.88 | 5.24 | 6.26 | 2.45 | 1.81 |
| Blood | 36.31 | 25.53 | 10.18 | 6.02 | 2.68 | 0.58 | 0.14 | 3.47 | 0.99 | 2.30 | 1.26 | 0.75 | 0.12 | 0.05 |
| Heart | 8.81 | 6.29 | 3.40 | 2.79 | 2.15 | 1.12 | 0.78 | 0.79 | 0.65 | 0.46 | 0.23 | 0.46 | 0.20 | 0.14 |
| Liver | 6.98 | 6.31 | 3.95 | 3.86 | 3.16 | 1.92 | 1.31 | 1.04 | 0.94 | 1.30 | 0.70 | 0.54 | 0.67 | 0.33 |
| Spleen | 6.70 | 4.32 | 4.66 | 5.78 | 4.54 | 3.68 | 2.74 | 2.85 | 0.42 | 1.04 | 1.34 | 1.62 | 1.14 | 1.16 |
| Kidney | 9.12 | 8.09 | 5.40 | 4.49 | 3.21 | 1.61 | 0.88 | 1.95 | 0.35 | 0.73 | 0.67 | 0.93 | 0.29 | 0.14 |
| Muscle | 0.66 | 0.76 | 0.84 | 0.71 | 0.54 | 0.27 | 0.14 | 0.14 | 0.08 | 0.08 | 0.07 | 0.10 | 0.07 | 0.05 |
| Salivary glands | 4.85 | 4.50 | 4.03 | 3.58 | 3.54 | 1.95 | 1.43 | 0.74 | 0.23 | 0.42 | 0.21 | 1.26 | 0.42 | 0.27 |
| Lacrimal glands | 1.83 | 2.26 | 2.62 | 2.47 | 1.78 | 0.89 | 0.81 | 0.42 | 0.37 | 0.56 | 0.71 | 0.69 | 0.15 | 0.19 |
| Carcass | 2.28 | 2.40 | 1.97 | 1.76 | 1.31 | 0.65 | 0.37 | 0.41 | 0.15 | 0.27 | 0.23 | 0.41 | 0.05 | 0.06 |
| Bone | 1.73 | 1.53 | 0.97 | 1.13 | 0.75 | 0.56 | 0.33 | 0.38 | 0.45 | 0.11 | 0.29 | 0.15 | 0.14 | 0.05 |
| Fat | 3.00 | 3.13 | 2.46 | 2.78 | 1.79 | 1.15 | 0.72 | 1.30 | 0.60 | 1.55 | 0.97 | 0.59 | 0.39 | 0.23 |
| Testes | 1.88 | 3.22 | 2.60 | 2.79 | 2.66 | 1.88 | 2.14 | 0.52 | 0.14 | 0.40 | 0.27 | 0.75 | 0.44 | 1.72 |
| Stomach | 1.82 | 2.13 | 0.81 | 0.91 | 0.55 | 0.32 | 0.16 | 0.29 | 0.78 | 0.36 | 0.39 | 0.14 | 0.13 | 0.11 |
| Small Intestine | 2.48 | 2.70 | 1.10 | 1.22 | 0.77 | 0.45 | 0.23 | 0.35 | 0.30 | 0.38 | 0.46 | 0.10 | 0.20 | 0.12 |
| Large Intestine | 1.35 | 1.76 | 1.47 | 1.31 | 1.48 | 1.07 | 0.60 | 0.24 | 0.14 | 1.12 | 0.27 | 1.14 | 0.51 | 0.32 |
| Pancreas | 4.35 | 3.18 | 2.16 | 1.77 | 1.39 | 0.68 | 0.34 | 1.32 | 0.36 | 0.14 | 0.28 | 0.31 | 0.12 | 0.07 |
| Adreanal Glands | 6.52 | 4.66 | 4.20 | 5.37 | 4.22 | 1.82 | 1.41 | 3.87 | 0.68 | 1.35 | 2.00 | 0.58 | 0.73 | 0.86 |
| Lung | 14.30 | 10.24 | 6.29 | 5.76 | 3.17 | 1.32 | 0.62 | 3.95 | 1.09 | 1.58 | 3.17 | 1.25 | 0.22 | 0.12 |
| Brain | 0.73 | 0.59 | 0.25 | 0.20 | 0.12 | 0.05 | 0.03 | 0.07 | 0.05 | 0.03 | 0.03 | 0.03 | 0.00 | 0.00 |
| Prostate | 2.39 | 3.07 | 2.65 | 2.52 | 2.27 | 1.30 | 0.83 | 0.36 | 0.66 | 0.22 | 0.19 | 0.64 | 0.31 | 0.13 |

TABLE 16

Biodistribution of $^{177}$Lu—C-6 in PC-3 PIP tumor-bearing mice (n = 4)

| % ID/g | 24 h | 96 h | 24 h STDEV | 96 h STDEV |
|---|---|---|---|---|
| Tumor | 49.74 | 42.79 | 5.58 | 4.02 |
| Blood | 8.57 | 0.73 | 1.01 | 0.10 |
| Heart | 3.26 | 0.88 | 0.43 | 0.09 |
| Liver | 3.41 | 1.41 | 0.71 | 0.19 |
| Spleen | 4.89 | 4.10 | 0.21 | 0.50 |
| Kidney | 19.55 | 6.58 | 1.54 | 0.17 |
| Muscle | 0.70 | 0.22 | 0.09 | 0.04 |
| Salivary glands | 2.67 | 1.36 | 0.38 | 0.29 |
| Lacrimal glands | 1.30 | 0.88 | 0.64 | 0.32 |
| Carcass | 1.95 | 0.82 | 0.15 | 0.18 |
| Bone | 0.74 | 0.26 | 0.13 | 0.07 |

TABLE 17

Biodistribution of $^{177}$Lu—C-7 in PC-3 PIP tumor-bearing mice (n = 4)

| % ID/g | 24 h | 96 h | 24 h STDEV | 96 h STDEV |
|---|---|---|---|---|
| Tumor | 31.41 | 48.72 | 6.36 | 5.13 |
| Blood | 9.82 | 1.23 | 2.63 | 0.39 |
| Heart | 4.07 | 1.93 | 1.20 | 0.29 |
| Liver | 4.46 | 3.72 | 1.04 | 0.69 |
| Spleen | 6.91 | 8.26 | 1.01 | 2.65 |
| Kidney | 27.59 | 16.32 | 3.53 | 5.86 |
| Muscle | 0.83 | 0.45 | 0.08 | 0.11 |
| Salivary glands | 3.33 | 3.38 | 0.85 | 0.55 |
| Lacrimal glands | 2.59 | 2.50 | 1.44 | 0.68 |
| Carcass | 2.53 | 1.34 | 0.27 | 0.16 |
| Bone | 0.95 | 0.84 | 0.24 | 0.08 |

TABLE 18

Biodistribution of $^{177}$LuI-18 in PC-3 PIP tumor-bearing mice (n = 4)

| % ID/g | 24 h | 96 h | 24 h STDEV | 96 h STDEV |
|---|---|---|---|---|
| Tumor | 27.55 | 15.98 | 1.25 | 0.71 |
| Blood | 5.16 | 0.22 | 0.49 | 0.02 |
| Heart | 1.92 | 0.58 | 0.15 | 0.08 |
| Liver | 2.32 | 0.87 | 0.60 | 0.08 |
| Spleen | 2.47 | 2.59 | 0.87 | 0.70 |
| Kidney | 17.29 | 4.91 | 1.44 | 0.46 |
| Muscle | 0.35 | 0.11 | 0.07 | 0.02 |
| Salivary glands | 1.87 | 0.88 | 0.30 | 0.20 |
| Lacrimal glands | 0.88 | 0.58 | 0.07 | 0.20 |
| Carcass | 1.34 | 0.42 | 0.04 | 0.06 |
| Bone | 0.42 | 0.34 | 0.16 | 0.03 |

TABLE 19

Biodistribution of $^{177}$Lu—I-26 in PC-3 PIP tumor-bearing mice (n = 4)

| % ID/g | 24 h | 96 h | 24 h STDEV | 96 h STDEV |
|---|---|---|---|---|
| Tumor | 16.38 | 9.80 | 2.01 | 1.12 |
| Blood | 0.18 | 0.05 | 0.03 | 0.01 |
| Heart | 0.09 | 0.06 | 0.01 | 0.01 |
| Liver | 0.26 | 0.20 | 0.05 | 0.04 |
| Spleen | 0.24 | 0.22 | 0.10 | 0.11 |
| Kidney | 1.82 | 1.15 | 0.48 | 0.71 |
| Muscle | 0.02 | 0.03 | 0.01 | 0.03 |

TABLE 19-continued

Biodistribution of $^{177}$Lu—I-26 in PC-3 PIP tumor-bearing mice (n = 4)

| % ID/g | 24 h | 96 h | 24 h STDEV | 96 h STDEV |
|---|---|---|---|---|
| Salivary glands | 0.11 | 0.10 | 0.02 | 0.02 |
| Lacrimal glands | 0.05 | 0.04 | 0.03 | 0.04 |
| Carcass | 0.12 | 0.07 | 0.02 | 0.01 |
| Bone | 0.03 | 0.02 | 0.07 | 0.03 |

TABLE 20

Biodistribution of $^{177}$Lu—I-43 in PC-3 PIP tumor-bearing mice (n = 4)

| % ID/g | 24 h | 96 h | 24 h STDEV | 96 h STDEV |
|---|---|---|---|---|
| Tumor | 35.66 | 44.73 | 6.52 | 3.17 |
| Blood | 8.56 | 0.67 | 2.37 | 0.10 |
| Heart | 3.09 | 1.20 | 0.75 | 0.17 |
| Liver | 4.83 | 2.73 | 0.75 | 0.32 |
| Spleen | 4.34 | 3.75 | 0.47 | 1.31 |
| Kidney | 20.77 | 8.72 | 4.71 | 1.53 |
| Muscle | 0.74 | 0.22 | 0.24 | 0.04 |
| Salivary glands | 3.06 | 1.60 | 0.83 | 0.43 |
| Lacrimal glands | 2.39 | 0.94 | 1.01 | 0.14 |
| Carcass | 2.02 | 0.90 | 0.43 | 0.12 |
| Bone | 1.32 | 0.59 | 0.41 | 0.16 |

TABLE 21

Biodistribution of $^{177}$Lu—I-30 in PC-3 PIP tumor-bearing mice (n = 4)

| % ID/g | 24 h | 96 h | 24 h STDEV | 96 h STDEV |
|---|---|---|---|---|
| Tumor | 24.14 | 19.07 | 3.51 | 2.82 |
| Blood | 0.21 | 0.02 | 0.04 | 0.01 |
| Heart | 0.15 | 0.07 | 0.03 | 0.01 |
| Liver | 0.32 | 0.21 | 0.05 | 0.06 |
| Spleen | 0.30 | 0.25 | 0.10 | 0.11 |
| Kidney | 7.51 | 1.99 | 0.69 | 0.55 |
| Muscle | 0.04 | 0.01 | 0.01 | 0.00 |
| Salivary glands | 0.19 | 0.12 | 0.03 | 0.04 |
| Lacrimal glands | 0.18 | 0.06 | 0.12 | 0.01 |
| Carcass | 0.22 | 0.12 | 0.14 | 0.05 |
| Bone | 0.07 | 0.20 | 0.04 | 0.06 |

TABLE 22

Biodistribution of $^{177}$Lu—I-49 in PC-3 PIP tumor-bearing mice (n = 4)

| % ID/g | 24 h | 96 h | 24 h STDEV | 96 h STDEV |
|---|---|---|---|---|
| Tumor | 35.08 | 26.00 | 3.07 | 4.59 |
| Blood | 2.74 | 0.09 | 0.19 | 0.02 |
| Heart | 1.09 | 0.30 | 0.13 | 0.02 |
| Liver | 1.45 | 0.67 | 0.07 | 0.18 |
| Spleen | 1.19 | 0.99 | 0.43 | 0.14 |
| Kidney | 10.05 | 1.94 | 1.73 | 0.23 |
| Muscle | 0.23 | 0.06 | 0.04 | 0.01 |
| Salivary glands | 1.05 | 0.56 | 0.18 | 0.08 |
| Lacrimal glands | 0.57 | 0.36 | 0.21 | 0.11 |
| Carcass | 0.78 | 0.24 | 0.05 | 0.04 |
| Bone | 0.23 | 0.14 | 0.03 | 0.03 |

TABLE 23

| Biodistribution of $^{177}$Lu—I-52 in PC-3 PIP tumor-bearing mice (n = 4) | | | | |
|---|---|---|---|---|
| % ID/g | 24 h | 96 h | 24 h STDEV | 96 h STDEV |
| Tumor | 38.45 | 35.33 | 10.45 | 2.22 |
| Blood | 3.82 | 0.17 | 0.98 | 0.03 |
| Heart | 1.44 | 0.52 | 0.43 | 0.09 |
| Liver | 2.06 | 1.02 | 0.44 | 0.31 |
| Spleen | 2.70 | 1.73 | 0.87 | 0.59 |
| Kidney | 11.98 | 3.67 | 2.50 | 0.97 |
| Muscle | 0.30 | 0.11 | 0.07 | 0.05 |
| Salivary glands | 1.60 | 1.03 | 0.56 | 0.25 |
| Lacrimal glands | 0.93 | 0.44 | 0.54 | 0.10 |
| Carcass | 1.12 | 0.41 | 0.14 | 0.09 |
| Bone | 0.32 | 0.32 | 0.15 | 0.11 |

TABLE 24

| Biodistribution of $^{177}$Lu—I-56 in PC-3 PIP tumor-bearing mice (n = 4) | | | | |
|---|---|---|---|---|
| % ID/g | 24 h | 96 h | 24 h STDEV | 96 h STDEV |
| Tumor | 30.33 | 22.89 | 7.75 | 1.85 |
| Blood | 2.24 | 1.87 | 0.34 | 3.27 |
| Heart | 0.95 | 0.17 | 0.14 | 0.03 |
| Liver | 1.15 | 0.47 | 0.10 | 0.03 |
| Spleen | 1.55 | 1.00 | 0.41 | 0.25 |
| Kidney | 9.53 | 2.03 | 2.20 | 0.44 |
| Muscle | 0.19 | 0.04 | 0.05 | 0.00 |
| Salivary glands | 0.67 | 0.31 | 0.19 | 0.07 |
| Lacrimal glands | 1.08 | 0.29 | 0.11 | 0.09 |
| Carcass | 0.70 | 0.20 | 0.03 | 0.04 |
| Bone | 0.26 | 0.07 | 0.05 | 0.03 |

TABLE 25

| Biodistribution of $^{177}$Lu—C-1 in LNCap tumor-bearing mice (n = 3) | | | | | | | | | | |
|---|---|---|---|---|---|---|---|---|---|---|
| % ID/g | 1 h | 4 h | 24 h | 72 h | 168 h | 1 h STDEV | 4 h STDEV | 24 h STDEV | 72 h STDEV | 168 h STDEV |
| Kidney | 14.54 | 7.76 | 1.42 | 0.65 | 0.13 | 9.76 | 3.77 | 0.67 | 0.41 | 0.11 |
| Blood | 0.41 | 0.06 | 0.01 | 0.03 | 0.01 | 0.22 | 0.01 | 0.00 | 0.04 | 0.01 |
| Tumor | 30.19 | 19.59 | 10.00 | 10.09 | 5.67 | 9.08 | 9.07 | 2.73 | 5.93 | 4.57 |
| Intestine | 0.63 | 0.66 | 0.08 | 0.12 | 0.05 | 0.32 | 0.47 | 0.04 | 0.10 | 0.02 |
| Heart | 0.28 | 0.33 | 0.20 | 0.07 | 0.04 | 0.11 | 0.20 | 0.22 | 0.05 | 0.04 |
| Liver | 0.26 | 0.09 | 0.09 | 0.02 | 0.02 | 0.17 | 0.01 | 0.07 | 0.01 | 0.00 |
| Spleen | 3.08 | 1.99 | 0.41 | 0.19 | 0.38 | 0.28 | 1.06 | 0.19 | 0.06 | 0.47 |
| Lung | 0.29 | 0.08 | 0.10 | 0.03 | 0.01 | 0.15 | 0.01 | 0.13 | 0.01 | 0.00 |
| Stomach | 0.75 | 0.25 | 0.09 | 0.06 | 0.06 | 0.23 | 0.15 | 0.03 | 0.02 | 0.02 |
| Femur | 0.28 | 0.06 | 0.05 | 0.04 | 0.02 | 0.22 | 0.01 | 0.04 | 0.04 | 0.01 |
| Muscle | 0.58 | 0.14 | 0.04 | 0.02 | 0.02 | 0.61 | 0.11 | 0.04 | 0.00 | 0.01 |
| Pancreas | 0.36 | 0.12 | 0.02 | 0.02 | 0.00 | 0.43 | 0.12 | 0.01 | 0.02 | 0.00 |

TABLE 26

| Biodistribution of $^{177}$Lu—C-9 in LNCap tumor-bearing mice (n = 3) | | | | |
|---|---|---|---|---|
| % ID/g | 24 h | 96 h | 24 h STDEV | 96 h STDEV |
| Kidney | 35.98 | 58.68 | 4.98 | 19.14 |
| Blood | 19.26 | 9.41 | 3.89 | 1.63 |
| Tumor | 45.66 | 52.50 | 15.69 | 19.24 |
| Intestine | 2.31 | 1.03 | 0.76 | 0.18 |
| Heart | 7.55 | 4.34 | 1.96 | 0.84 |
| Liver | 1.21 | 0.97 | 0.07 | 0.26 |
| Spleen | 12.17 | 14.68 | 10.38 | 3.48 |
| Lung | 5.84 | 5.93 | 3.96 | 2.33 |
| Stomach | 1.51 | 1.58 | 0.43 | 0.79 |
| Femur | 2.65 | 2.44 | 0.34 | 0.57 |
| Muscle | 1.25 | 0.67 | 0.29 | 0.25 |
| Pancreas | 1.02 | 1.59 | 0.36 | 1.02 |

TABLE 27

| Biodistribution of $^{177}$Lu—C-10 in LNCap tumor-bearing mice (n = 3) | | | | |
|---|---|---|---|---|
| % ID/g | 24 h | 96 h | 24 h STDEV | 96 h STDEV |
| Kidney | 52.18 | 11.03 | 11.67 | 3.97 |
| Blood | 5.08 | 0.42 | 1.31 | 0.14 |
| Tumor | 46.51 | 34.92 | 7.10 | 7.30 |
| Intestine | 0.53 | 0.10 | 0.38 | 0.08 |
| Heart | 1.31 | 0.12 | 0.67 | 0.07 |
| Liver | 0.83 | 0.17 | 0.70 | 0.09 |
| Spleen | 3.23 | 0.60 | 2.12 | 0.85 |
| Lung | 1.87 | 0.55 | 0.56 | 0.15 |
| Stomach | 1.25 | 0.07 | 1.00 | 0.05 |
| Femur | 1.04 | 0.07 | 0.81 | 0.01 |
| Muscle | 0.39 | 0.00 | 0.24 | 0.00 |
| Pancreas | 0.42 | 0.04 | 0.10 | 0.03 |

TABLE 28

Biodistribution of $^{177}$Lu—I-21 in LNCap tumor-bearing mice (n = 3)

| % ID/g | 1 h | 4 h | 24 h | 72 h | 96 h | 168 h | 1 h STDEV | 4 h STDEV | 24 h STDEV | 72 h STDEV | 96 h STDEV | 168 h STDEV |
|---|---|---|---|---|---|---|---|---|---|---|---|---|
| Kidney | 19.37 | 19.94 | 18.76 | 3.58 | 2.54 | 1.59 | 16.16 | 6.25 | 6.43 | 1.38 | 1.15 | 0.29 |
| Blood | 31.08 | 17.21 | 7.72 | 1.60 | 0.49 | 0.05 | 2.66 | 0.83 | 0.70 | 0.31 | 0.14 | 0.01 |
| Tumor | 6.61 | 44.23 | 73.78 | 51.37 | 47.95 | 40.08 | 1.24 | 24.13 | 5.39 | 25.44 | 15.38 | 20.18 |
| Intestine | 1.37 | 1.28 | 1.98 | 0.36 | 0.28 | 0.09 | 0.57 | 0.13 | 0.06 | 0.07 | 0.08 | 0.03 |
| Heart | 6.90 | 4.61 | 2.86 | 1.35 | 0.67 | 0.31 | 4.05 | 1.89 | 1.16 | 0.18 | 0.24 | 0.08 |
| Liver | 2.70 | 1.57 | 1.97 | 1.03 | 1.05 | 1.40 | 2.54 | 0.28 | 1.21 | 0.05 | 0.39 | 0.22 |
| Spleen | 19.58 | 15.72 | 5.42 | 3.54 | 1.31 | 1.17 | 11.00 | 5.90 | 2.74 | 1.78 | 0.49 | 0.37 |
| Lung | 5.56 | 2.98 | 2.66 | 1.11 | 0.56 | 0.16 | 2.03 | 1.32 | 0.78 | 0.18 | 0.05 | 0.05 |
| Stomach | 1.95 | 1.61 | 0.96 | 0.49 | 0.36 | 0.17 | 0.92 | 0.80 | 0.24 | 0.19 | 0.05 | 0.01 |
| Femur | 3.03 | 1.93 | 0.98 | 0.41 | 0.31 | 0.17 | 1.43 | 0.75 | 0.30 | 0.24 | 0.17 | 0.08 |
| Muscle | 1.67 | 1.62 | 0.73 | 0.20 | 0.29 | 0.15 | 0.42 | 0.72 | 0.30 | 0.07 | 0.25 | 0.15 |
| Pancreas | 2.58 | 1.53 | 1.10 | 0.53 | 0.33 | 0.11 | 0.91 | 1.40 | 0.40 | 0.34 | 0.06 | 0.03 |

TABLE 29

Biodistribution of $^{177}$Lu—I-52 in LNCap tumor-bearing mice (n = 3)

| % ID/g | 4 h | 24 h | 72 h | 24 h STDEV | 48 h STDEV | 72 h STDEV |
|---|---|---|---|---|---|---|
| Kidney | 8.30 | 8.79 | 6.94 | 0.93 | 6.33 | 1.64 |
| Blood | 18.49 | 5.05 | 0.83 | 4.16 | 1.22 | 0.50 |
| Tumor | 28.18 | 48.30 | 38.54 | 9.09 | 26.64 | 27.21 |
| Intestine | 1.11 | 0.93 | 0.35 | 0.39 | 0.41 | 0.10 |
| Heart | 5.35 | 2.78 | 1.24 | 1.11 | 0.37 | 1.23 |
| Liver | 1.63 | 1.80 | 0.66 | 0.52 | 0.98 | 0.22 |
| Spleen | 11.06 | 6.89 | 5.47 | 4.84 | 5.65 | 3.16 |
| Lung | 3.77 | 2.86 | 0.88 | 2.54 | 1.58 | 0.24 |
| Stomach | 1.12 | 0.90 | 0.36 | 0.39 | 0.56 | 0.14 |
| Femur | 1.92 | 1.30 | 0.73 | 0.81 | 0.45 | 0.49 |
| Muscle | 0.69 | 0.69 | 0.32 | 0.40 | 0.51 | 0.09 |
| Pancreas | 1.25 | 0.80 | 0.48 | 0.56 | 0.30 | 0.21 |

TABLE 30

Biodistribution of $^{177}$Lu—I-61 in LNCap tumor-bearing mice (n = 3)

| % ID/g | 24 h | 96 h | 24 h STDEV | 96 h STDEV |
|---|---|---|---|---|
| Kidney | 7.31 | 8.58 | 2.14 | 1.95 |
| Blood | 11.38 | — | 1.06 | — |
| Tumor | 55.64 | 32.10 | 34.38 | 6.49 |
| Intestine | 1.22 | 1.82 | 0.35 | 0.43 |
| Heart | 4.35 | 1.15 | 0.14 | 0.36 |
| Liver | 2.17 | 2.01 | 0.86 | 0.48 |
| Spleen | 3.36 | 2.01 | 0.32 | 0.52 |
| Lung | 4.93 | 1.82 | 2.60 | 0.76 |
| Stomach | 1.20 | 0.38 | 1.13 | 0.04 |
| Femur | 0.88 | 0.51 | 0.35 | 0.10 |
| Muscle | 0.56 | 0.25 | 0.14 | 0.05 |
| Pancreas | 0.717 | 0.35 | 0.32 | 0.08 |

TABLE 31

Biodistribution of $^{177}$Lu—I-18 in LNCap tumor-bearing mice (n = 3)

| % ID/g | 24 h | 96 h | 24 h STDEV | 96 h STDEV |
|---|---|---|---|---|
| Kidney | 27.75 | 13.98 | 15.82 | 1.90 |
| Blood | 10.51 | 0.40 | 2.88 | 0.11 |
| Tumor | 54.68 | 32.93 | 32.71 | 9.32 |
| Intestine | 1.19 | 0.35 | 0.06 | 0.10 |
| Heart | 5.16 | 0.73 | 1.27 | 0.23 |

TABLE 31-continued

Biodistribution of $^{177}$Lu—I-18 in LNCap tumor-bearing mice (n = 3)

| % ID/g | 24 h | 96 h | 24 h STDEV | 96 h STDEV |
|---|---|---|---|---|
| Liver | 1.53 | 0.99 | 0.22 | 0.23 |
| Spleen | 7.42 | 11.53 | 4.00 | 1.19 |
| Lung | 4.41 | 0.82 | 1.23 | 0.66 |
| Stomach | 1.90 | 0.52 | 0.18 | 0.07 |
| Femur | 2.60 | 0.60 | 0.48 | 0.11 |
| Muscle | 1.47 | 0.32 | 0.52 | 0.11 |
| Pancreas | 1.12 | 0.41 | 0.35 | 0.38 |

TABLE 32

Biodistribution of $^{177}$Lu—I-67 in LNCap tumor-bearing mice (n = 3)

| % ID/g | 4 h | 24 h | 96 h | 24 h STDEV | 48 h STDEV | 96 h STDEV |
|---|---|---|---|---|---|---|
| Kidney | 33.10 | 9.49 | 0.90 | 16.79 | 3.14 | 0.29 |
| Blood | 11.80 | 1.54 | 0.04 | 1.94 | 0.30 | 0.02 |
| Tumor | 47.99 | 33.87 | 11.49 | 4.37 | 9.80 | 6.22 |
| Intestine | 1.58 | 0.25 | 0.10 | 0.41 | 0.02 | 0.06 |
| Heart | 3.76 | 0.81 | 0.19 | 0.76 | 0.14 | 0.03 |
| Liver | 1.37 | 0.26 | 0.15 | 0.33 | 0.05 | 0.04 |
| Spleen | 10.96 | 1.73 | 0.73 | 6.04 | 0.59 | 1.00 |
| Lung | 3.55 | 1.16 | 0.62 | 1.93 | 0.37 | 0.65 |
| Stomach | 1.85 | 0.48 | 0.12 | 0.40 | 0.13 | 0.04 |
| Femur | 2.14 | 0.38 | 0.13 | 0.68 | 0.23 | 0.04 |
| Muscle | 1.12 | 0.39 | 0.14 | 0.59 | 0.15 | 0.03 |
| Pancreas | 1.09 | 0.26 | 0.15 | 0.30 | 0.08 | 0.02 |

TABLE 33

Biodistribution of $^{177}$Lu—I-69 in LNCap tumor-bearing mice (n = 3)

| % ID/g | 24 h | 96 h | 24 h STDEV | 96 h STDEV |
|---|---|---|---|---|
| Kidney | 20.58 | 11.36 | 5.19 | 0.11 |
| Blood | 1.20 | 0.00 | 0.14 | 0.00 |
| Tumor | 37.85 | 26.67 | 5.92 | 2.87 |
| Intestine | 0.29 | 0.16 | 0.02 | 0.10 |
| Heart | 0.55 | 0.19 | 0.20 | 0.01 |
| Liver | 0.29 | 0.37 | 0.09 | 0.00 |
| Spleen | 2.84 | 1.41 | 1.24 | 0.83 |
| Lung | 0.82 | 0.42 | 0.39 | 0.04 |
| Stomach | 0.20 | 0.17 | 0.04 | 0.07 |
| Femur | 0.29 | 0.07 | 0.22 | 0.06 |

TABLE 33-continued

| Biodistribution of $^{177}$Lu—I-69 in LNCap tumor-bearing mice (n = 3) | | | | |
|---|---|---|---|---|
| % ID/g | 24 h | 96 h | 24 h STDEV | 96 h STDEV |
| Muscle | 0.19 | 0.11 | 0.10 | 0.14 |
| Pancreas | 0.16 | 0.10 | 0.08 | 0.01 |

TABLE 34

Comparation of tumor and kidney uptake of selected $^{177}$Lu-labeled compounds in PC3-PIP or LNCap tumor-bearing mice.

| Compound | Relative Binding Affinity | T/K at 4 h | T/K at 24 h | T/K at 96 h | T at 24 h | T at 96 h | AUC T (0-96 h) | AUC K (0-96 h) | AUC T/ AUC K (0-96 h) |
|---|---|---|---|---|---|---|---|---|---|
| C-1 (PC3 PIP) | 1.00 | 7.0 | 57 | 182 | 10.4 | 7.3 | 880 | 51 | 17.3 |
| C-2 (PC3 PIP) | 1.78 | 0.3 | 1.0 | 3.7 | 41.1 | 20.0 | 2844 | 2465 | 1.2 |
| C-6 (PC3 PIP) | 0.05 | — | 2.54 | 6.50 | 49.7 | 42.3 | — | — | — |
| C-7 (PC3 PIP) | 0.14 | — | 1.14 | 3.00 | 31.4 | 48.7 | — | — | — |
| I-2 (PC3 PIP) | 0.75 | 0.6 | 5.0 | 10.1 | 32.4 | 9.8 | 1833 | 604 | 3.0 |
| I-3 (PC3 PIP) | 1.30 | 0.3 | 0.8 | 4.0 | 13.9 | 6.3 | 1231 | 1462 | 0.8 |
| I-4 (PC3 PIP) | 0.95 | 0.1 | 0.2 | 1.2 | 0.79 | 0.3 | 69 | 383 | 0.2 |
| I-7 (PC3 PIP) | 0.54 | 0.7 | 0.9 | 1.4 | 16.7 | 2.6 | 938 | 952 | 0.99 |
| I-11 (PC3 PIP) | 0.04 | 1.4 | 4.6 | 9.2 | 36.3 | 19.0* | 1985* | 487* | 4.1* |
| I-21 (PC3 PIP) | 0.09 | 1.62 | 4.74 | 12.2* | 30.2 | 26.5# | 3208# | 464# | 6.9# |
| I-34 (PC3 PIP) | 0.12 | — | 1.81 | 5.69 | 30.7 | 30.4 | — | — | — |
| I-35 (PC3 PIP) | 0.05 | 0.87 | 4.31 | 9.11* | 23.3 | 21.2# | 2778# | 492# | 5.7# |
| I-36 (PC3 PIP) | 0.02 | — | 1.51 | — | 2.84 | — | — | — | — |
| I-39 (PC3 PIP) | 0.03 | — | 1.30 | — | 5.41 | — | — | — | — |
| I-41 (PC3 PIP) | 0.06 | — | 0.97 | 3.04 | 38.0 | 48.8 | — | — | — |
| I-42 (PC3 PIP) | 0.13 | — | 2.47 | — | 28.7 | — | — | — | — |
| I-18 (PC3-PIP) | 0.07 | — | 1.59 | 3.26 | 27.6 | 16.0 | — | — | — |
| I-43 (PC3-PIP) | 0.28 | — | 1.71 | 5.12 | 35.7 | 44.7 | — | — | — |
| I-49 (PC3-PIP) | 0.09 | — | 3.49 | 13.4 | 35.1 | 26.0 | — | — | — |
| I-52 (PC3-PIP) | 0.05 | — | 3.21 | 9.62 | 38.5 | 35.3 | — | — | — |
| C-1 (LNCap) | 1.00 | 2.52 | 7.04 | 15.5* | 10.0 | 10.1 | 1625^ | 220^ | 7.4^ |
| C-9 (LNCap) | — | — | 1.27 | 0.89 | 45.7 | 52.5 | — | — | — |
| C-10 (LNCap) | 0.92 | — | 0.89 | 3.17 | 46.5 | 34.9 | — | — | — |
| I-21 (LNCap) | 0.09 | 2.22 | 3.93 | 18.9 | 73.8 | 48.0 | 8624^ | 1214^ | 7.1^ |
| I-67 (LNCap) | 0.33 | 1.45 | 3.57 | 12.8 | 33.9 | 11.5 | — | — | — |
| I-18 (LNCap) | 0.04 | — | 1.97 | 2.36 | 54.7 | 32.9 | — | — | — |
| I-69 (LNCap) | — | — | 1.84 | 2.35 | 37.9 | 26.7 | — | — | — |

Abbreviations: T/K: tumor uptake/kidney uptake; T: tumor uptake; AUC T: area under the curve of tumor uptake; AUC K: area under the curve of kidney uptake; AUC T/K: area under the curve of tumor/area under the curve of kidney (*value at 72 h; #value at 120 h; ^0-168 hours)

Human Imaging Data

FIG. 5A, FIG. 5B, FIG. 5C, and FIG. 5D show $^{68}$Ga-PSMA11 (gozetotide) PET/CT imaging (Left panel) and exemplary complex $^{111}$In-I-21 SPECT/CT imaging (48 hours after dosing) (Middle panel: Anterior; Right panel: Posterior) of 4 metastatic castration-resistant prostate cancer (mCRPC) patients. FIGS. 5A to 5D show that, within the same patient relative to the uptake in tumor and other organs, there is less uptake in salivary glands of exemplary complex $^{111}$In-I-21 compared to the approved diagnostic agent $^{68}$Ga-PSMA11 which showed high uptake.

While the present application has been described with reference to examples, it is to be understood that the scope of the claims should not be limited by the embodiments set forth in the examples, but should be given the broadest interpretation consistent with the description as a whole.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the application described and claimed herein.

Full Citations for Documents Referred to in the Specification

A number of publications are cited herein. Full citations for these references are provided below. Each of these references is incorporated herein by reference in its entirety into the present disclosure, to the same extent as if each individual reference was specifically and individually indicated to be incorporated by reference Arano Y, Wakisaka K, Ohmono Y, et al. "Assessment of radiochemical design of antibodies using an ester bond as the metabolizable linkage: evaluation of maleimidoethyl 3-(tri-n-butylstannyl) hippurate as a radioiodination reagent of antibodies for diagnostic and therapeutic applications". *Bioconjug Chem.* 1996 November-December; 7 (6): 628-37.

Choy C J, Ling X, Geruntho J J, et al. "177Lu-labeled phosphoramidate-based PSMA inhibitors: The effect of an albumin binder on biodistribution and therapeutic efficacy in prostate tumor-bearing mice". *Theranostics.* 2017 Apr. 27; 7 (7): 1928-39.

Däpp S, García Garayoa E, Maes V, et al. "PEGylation of (99m) Tc-labeled bombesin analogues improves their pharmacokinetic properties". *Nucl Med Biol.* 2011 October; 38 (7): 997-1009.

Deberle L M, Benešová M, Umbricht C A, et al. "Development of a new class of PSMA radioligands comprising ibuprofen as an albumin-binding entity". *Theranostics.* 2020 Jan. 1; 10 (4): 1678-93.

Dorff T B, Fanti S, Farolfi A, et al. "The evolving role of prostate-specific membrane antigen-based diagnostics and therapeutics in prostate cancer". *Am Soc Clin Oncol Educ Book.* 2019 January; 39:321-30.

Kalli K R, Oberg A L, Keeney G L, et al. "Folate receptor alpha as a tumor target in epithelial ovarian cancer". *Gynecol Oncol.* 2008 March; 108 (3): 619-26.

Körner M, Christ E, Wild D, et al. "Glucagon-like peptide-1 receptor overexpression in cancer and its impact on clinical applications". *Front Endocrinol* (Lausanne). 2012 Dec. 6; 3:158. doi: 10.3389/fendo.2012.00158.

Kramer V, Fernández R, Lehnert W, et al. "Biodistribution and dosimetry of a single dose of albumin-binding ligand [$^{177}$Lu]Lu-PSMA-ALB-56 in patients with mCRPC". *Eur J Nucl Med Mol Imaging.* 2021 March; 48 (3): 893-903.

Kuo H T, Merkens H, Zhang Z, et al. "Enhancing treatment efficacy of $^{177}$Lu-PSMA-617 with the conjugation of an albumin-binding motif: preclinical dosimetry and endo-radiotherapy studies". *Mol Pharm.* 2018 Nov. 5; 15 (11): 5183-91.

Qian Z R, Li T, Ter-Minassian M, et al. "Association between somatostatin receptor expression and clinical outcomes in neuroendocrine tumors". *Pancreas.* 2016 November; 45 (10): 1386-93.

Sgouros G, Bodei Lisa, McDevitt M R, et al. "Radiopharmaceutical therapy in cancer: clinical advances and challenges". *Nat Rev Drug Discov.* 2020 September; 19 (9): 589-608.

Wang Z, Tian R, Niu G, et al., "Single low-dose injection of Evans blue modified PSMA-617 radioligand therapy eliminates prostate-specific membrane antigen positive tumors". *Bioconjug Chem.* 2018 Sep. 19; 29 (9): 3213-21.

The invention claimed is:

1. A compound of Formula I, or a pharmaceutically acceptable salt or solvate thereof, (I)

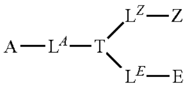

wherein

A is an albumin binding group selected from the group consisting of

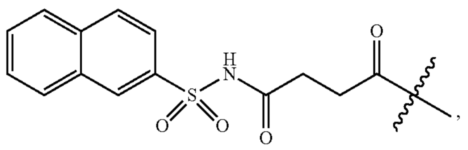

(2-Naph-$SO_2$NH-Suc)

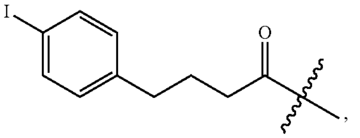

(4-pIBA)

unsubstituted or substituted C(O)$C_{1-26}$alkylene$CO_2$H, unsubstituted or substituted C(O)$C_{2-26}$alkenylene$CO_2$H, unsubstituted or substituted C(O)$C_{1-26}$alkyl, and unsubstituted or substituted C(O)$C_{2-26}$alkenyl;

Z is a tumor binding group, wherein the tumor binding group is a prostate specific membrane antigen (PSMA) binding group, a glucagon-like peptide-1 receptor (GLP-1R) binding group, or a glucose-dependent insulinotropic polypeptide (gastric inhibitory polypeptide; GIP) receptor (GIP-R) binding group;

E is a chelating group;

T is a branching group that is at least trivalent, wherein T is an amino acid residue derived from lysine, ornithine, homo-lysine, 2,3-diaminopropionic acid (DAP), 2,4-diaminobutyric acid (DAB), cysteine, homo-cysteine, glutamine, or trimesic acid (TMA);

$L^A$ and $L^E$ are each independently a direct bond, a cleavable linker or a non-cleavable linker, wherein the non-cleavable linker comprises one or more groups selected from one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, Sec or PCL or the D enantiomers thereof; one or more amino acids residues derived from DAB or DAP; OEG, $R^1$N$C_{1-20}$alkyleneN$R^2$, C(O)$C_{1-20}$alkyleneC(O), $R^1$N$C_{1-20}$alkyleneC(O), and C(O)$C_{1-20}$alkyleneN$R^2$, wherein each $R^1$ and $R^2$ is independently selected from H and $C_{1-2}$alkyl; and $L^Z$ is a direct bond or a non-cleavable linker, wherein the non-cleavable linker comprises one or more of amino acid residues, $R^1$N$C_{1-20}$alkyleneN$R^2$, $R^1$N$C_{1-20}$alkenyleneN$R^2$, C(O)$C_{1-20}$alkyleneC(O), C(O)$C_{1-20}$alkenyleneC(O), $R^1$N$C_{1-20}$alkyleneC(O), $R^1$N$C_{1-20}$alkenyleneC(O), C(O)$C_{1-20}$alkyleneNH$R^2$, C(O)$C_{1-20}$alkenyleneN$R^2$, C(S)$C_{1-20}$alkyleneC(S), C(S)$C_{1-20}$alkenyleneC(S), C(S)$C_{1-20}$alkyleneC(O), C(S)$C_{1-20}$alkenyleneC(O), C(O)$C_{1-20}$alkyleneC(S), C(O)$C_{1-20}$alkenyleneC(S), C(O)$C_{1-20}$alkyleneO, C(O)$C_{1-20}$alkenyleneO, $R^1$N$C_{1-20}$alkenyleneC(S), C(S)$C_{1-20}$alkyleneN$R^2$ and C(S)$C_{1-20}$alkenyleneN$R^2$, the latter 19 groups being optionally interrupted by one or more of S, O, NH, N($C_{1-6}$alkyl), C(O), C(O)NH, NHC(O), C(S)NH, NHC(S), NHC(O)NH, NHC(S)NH, NHC(NH), NHC(N$C_{1-4}$alkyl), C(NH)NH, C(N$C_{1-4}$alkyl)NH, N$C_{4-10}$cycloalkyl, $C_{4-10}$heterocycloalkyl, $C_{6-10}$aryl and $C_{5-10}$heteroaryl, and each alkyl, alkylene and alkenylene is optionally substituted with one or more substituents selected from halo, $CO_2$H, $C_{1-6}$alkyl, OH, O$C_{1-6}$alkyl, SH, S$C_{1-6}$alkyl, N$R^3R^4$, $C_{1-4}$alkyleneOH, $C_{1-4}$alkyleneO$C_{1-4}$alkyl and $C_{1-4}$alkyleneN$R^3R^4$, wherein each $R^1$, $R^2$, $R^3$ and $R^4$ is independently selected from H and $C_{1-4}$alkyl; provided at least one of $L^A$ and $L^E$ is a cleavable linker, wherein the cleavable linker comprises at least one cleavable moiety, and the cleavable moiety is

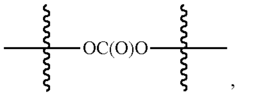, 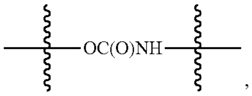,

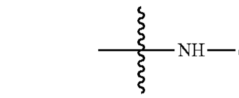, 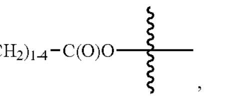, or

, wherein each

is a point of connection as set forth in the compound of Formula I.

2. The compound of claim 1, or a pharmaceutically acceptable salt or solvate thereof, wherein the albumin binding group is unsubstituted or substituted $C(O)C_{6-20}alkyleneCO_2H$.

3. The compound of claim 2, or a pharmaceutically acceptable salt or solvate thereof, wherein the albumin binding group is $C(O)C_{16}alkyleneCO_2H$ or $C(O)C_{18}alkyleneCO_2H$.

4. The compound of claim 1, or a pharmaceutically acceptable salt or solvate thereof, wherein the tumor binding group is a prostate specific membrane antigen (PSMA) binding group (εKuE)

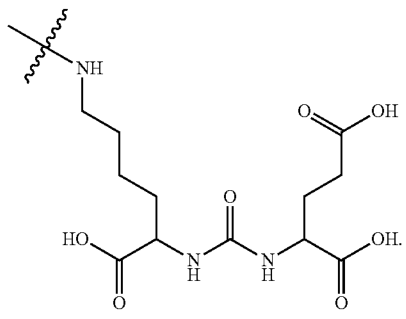

5. The compound of claim 1, or a pharmaceutically acceptable salt or solvate thereof, wherein the chelating group is selected from the group consisting of 1,4,7-Triazacyclononane (TACN); 1,4,7-triazacyclononane-triacetic acid (NOTA); 1,4,7-triazacyclononane-N-succinic acid-N',N"-diacetic acid (NOTASA); 1,4,7-triazacyclononane-N-glutamic acid-N',N"-diacetic acid (NODAGA); 1,4,7-triazacyclononane-N,N',N"-tris (methylenephosphonic) acid (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl) acetate (DO1A); 2,2'-(1,4,7,10-tetraazacyclododecane-1,7-diyl) diacetic acid (DO2A); 2,2',2"-(1,4,7,10-tetraazacyclododecane-1,4,7-triyl) triacetic acid (DO3A); 1,4,7,10-tetraazacyclododecane-1,4,7,10-tetra (methanepnosphonic acid) (DOTP); 1,4,7,10-tetraazacyclododecane-1,7-di(methanephosphoric acid) (DO2P); 1,4,7,10-tetraazacyclododecane-1,4,7-tri(methanephosphonic acid) (DO3P); 1,4,7,10-tetraazacyclo-decane-1-glutamic acid-4,7,10-triacetic acid (DOTAGA); 1,4,7,10-tetraazacyclodecane-1-succinic acid-4,7,10-triacetic acid (DOTASA); 1,4,8,11-tetraazacyclotetradecane ([14]aneN4) (cyclam); 1,4,8,12-tetraazacyclopentadecane ([15]aneN4); 1,5,9,13-tetraazacyclohexadecane ([16]aneN4); 1,4-ethano-1,4,8,11-tetraazacyclo-tetradecane (et-cyclam); 1,4,8,11-tetraazacyclotetradecane-1,4,8,11-tetraacetic acid (TETA); 2-(1,4,8,1-tetraazacyclotetradecane-1-yl) acetic acid (TE1A); 2,2'-(1,4,8,11-tetraazacyclotetradecane-1,8-diyl) diacetic acid (TE2A); 4,11-bis(carboxy methyl)-1,4,8,11-tetraazabicyclo [6.6.2]-hexadecane (CB-TE2A); 3,6,10,13,16,19-hexaazabicyclo [6.6.6]icosane (Sar); 1,4,7,10-tetra-(2-carbamoylmethyl)-cyclododecane (TCMC); N,N'-bis [(6-carboxy-2-pyridil) methyl]-4,13-diaza-18-crown-6 (macropa), phthalocyanines and derivatives thereof; and porphyrins and derivatives thereof.

6. The compound of claim 5, or a pharmaceutically acceptable salt or solvate thereof, wherein the chelating group is selected from the group consisting of DOTA and DOTAGA.

7. The compound of claim 1, or a pharmaceutically acceptable salt or solvate thereof, wherein T is an amino acid residue derived from lysine, ornithine, homo-lysine, 2,3-diaminopropionic acid (DAP), 2,4-diaminobutyric acid (DAB), cysteine, homo-cysteine, or glutamine.

8. The compound of claim 7, or a pharmaceutically acceptable salt or solvate thereof, wherein T is an amino acid residue derived from lysine.

9. The compound of claim 1, or a pharmaceutically acceptable salt or solvate thereof, wherein each non-cleavable linker of $L^Z$ independently comprises one or more groups selected from the group consisting of amino acid residues, $R^1NC_{1-20}alkyleneNR^2$, $C(O)C_{1-20}alkyleneC(O)$, $R^1NC_{1-20}alkyleneC(O)$, and $C(O)C_{1-20}alkyleneNR^2$, wherein the latter 4 groups being optionally interrupted by one or more of S, O, C(O)NH, NHC(O), $NC_4$-6cycloalkyl, $C_{4-6}$heterocycloalkyl, and each alkyl and alkylene is optionally substituted with one or more substituents selected from the group consisting of halo, $CO_2H$, $C_{1-6}$alkyl, OH, $OC_{1-6}$alkyl, SH, $SC_{1-6}$alkyl, $NR^3R^4$, $C_{1-4}$alkyleneOH, $C_{1-4}$alkyleneO$C_{1-4}$alkyl and $C_{1-4}alkyleneNR^3R$, wherein each $R^1$, $R^2$, $R^3$ and $R^4$ is independently H or $C_{1-4}$alkyl.

10. The compound of claim 1, or a pharmaceutically acceptable salt or solvate thereof, wherein each cleavable linker independently comprises at least one cleavable moiety

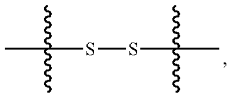, 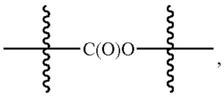, 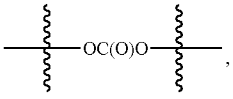, 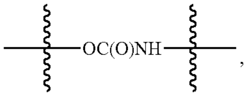, or 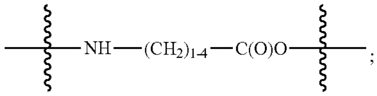;

and one or more groups selected from the group consisting of one or more amino acid residues, $R^5NC_{1-20}alkyleneNR^6$, $C(O)C_{1-20}alkyleneC(O)$, $R^5NC_{1-20}alkyleneC(O)$, $C(O)C_{1-20}alkyleneNR^6$, $R^5NC_{1-20}alkyleneO$, $OC_{1-20}alkyleneNR^6$, $C(O)C_{1-20}alkyleneO$ and $OC_{1-20}alkyleneC$ (O), wherein the latter 8 groups being optionally interrupted by one or more of S, O, C(O)NH, NHC(O), $C_{4-18}$cycloalkyl, and $C_{4-10}$heterocycloalkyl, and each alkyl and alkylene is optionally substituted with one or more substituents selected from the group consisting of halo, $CO_2H$, $NR^7R^7$, and $C_{1-4}alkyleneNR^7R^8$, wherein each $R^5$, $R^6$, $R^7$ and $R^8$ is independently H or $C_{1-4}$alkyl, and wherein the amino acid residue is derived from an naturally occurring amino selected from the group consisting of alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), and valine (Val).

11. The compound of claim 1, or a pharmaceutically acceptable salt or solvate thereof, wherein the cleavable linker comprises at least one group selected from the group consisting of (ESL1)

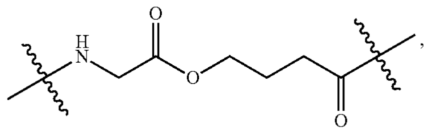
, (SSL1)

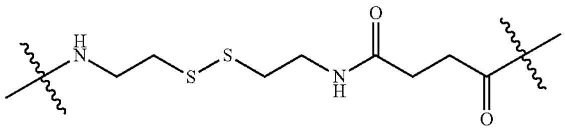
, (ESL2)

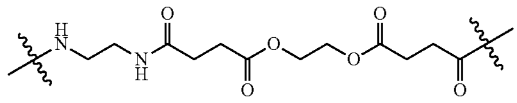
, and (ESL3)

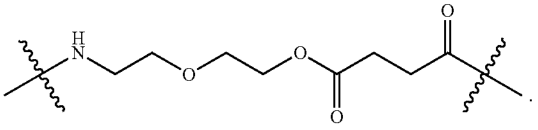
.

12. The compound of claim 1, or a pharmaceutically acceptable salt or solvate thereof, wherein $L^A$ is a cleavable linker, and $L^E$ is a direct bond or a non-cleavable linker, wherein $L^A$ comprises at least one group selected from the group consisting of (ESL1)

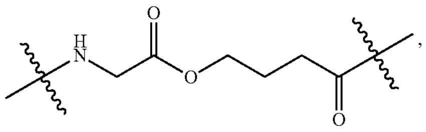
, (SSL1)

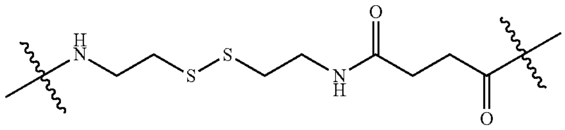
, (ESL2)

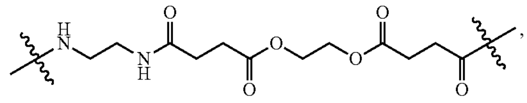
, and (ESL3)

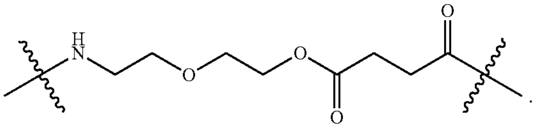
.

13. The compound of claim 12, or a pharmaceutically acceptable salt or solvate thereof, wherein $L^E$ is a direct bond.

14. The compound of claim 1, or a pharmaceutically acceptable salt or solvate thereof, wherein $L^E$ is a cleavable linker, and $L^A$ is a direct bond or a non-cleavable linker, wherein $L^E$ comprises at least one group selected from the group consisting of (ESL1)

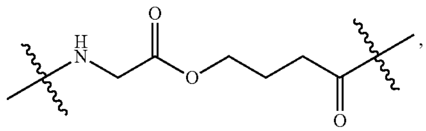
, (SSL1)

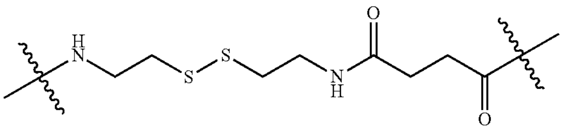
, (ESL2)

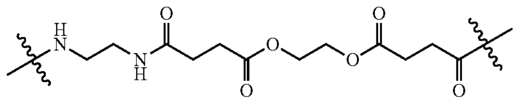
, and (ESL3)

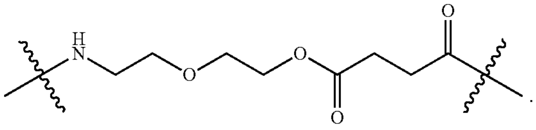
.

15. The compound of claim 14, or a pharmaceutically acceptable salt or solvate thereof, wherein $L^A$ is a non-cleavable linker.

16. The compound of claim 1, or a pharmaceutically acceptable salt or solvate thereof, wherein $L^Z$ further comprises one or more groups selected from the group consisting of one or more amino acids residues derived from Ala, Arg, Asn, Asp, Cys, Gln, Glu, Gly, His, Ile, Leu, Lys, Met, Phe, Pro, Ser, Thr, Trp, Tyr, Val, Pyl, or Sec or the D enantiomers thereof; one or more amino acids residues derived from DAB or DAP;

(OEG)

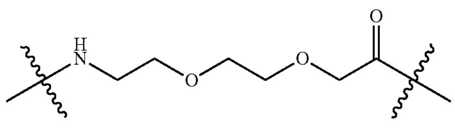
;

$R^1NC_{1-20}$alkyleneNR$^2$, C(O)$C_{1-20}$alkyleneC (O), $R^1NC_{1-20}$alkyleneC (O), and C(O)$C_{1-20}$alkyleneNR$^2$, wherein each $R^1$ and $R^2$ is independently H or $C_{1-2}$alkyl.

17. The compound of claim 1, or a pharmaceutically acceptable salt or solvate thereof, wherein the albumin binding group is selected from the group consisting of 4-pIBA, C(O)$C_{15}$alkyl, C(O)$C_{17}$alkyl, C(O) $C_{15}$alkyleneCO$_2$H, C(O)$C_{16}$alkyleneCO$_2$H, C(O) $C^{17}$alkyleneCO$_2$H, and C(O)$C_{18}$alkyleneCO$_2$H.

18. The compound of claim 1, or a pharmaceutically acceptable salt or solvate thereof, wherein the tumor binding group is a prostate specific membrane antigen (PSMA) binding group.

19. The compound of claim 1, or a pharmaceutically acceptable salt or solvate thereof, wherein the tumor binding group is a PSMA binding group, and wherein the PSMA binding group is a peptide analogue selected from quisqualic acid, aspartate-glutamate (Asp-Glu), Glu-Glu, glycine-glutamate (Gly-Glu), γ-glutamate-glutamate (γ-Glu-Glu) and beta-N-acetyl-L-aspartate-L-glutamate (β-NAAG).

20. A radionuclide complex, or a pharmaceutically acceptable salt or solvate thereof, comprising a compound of claim 1, or a pharmaceutically acceptable salt or solvate thereof, and one or more radionuclides.

21. The radionuclide complex of claim 20, or a pharmaceutically acceptable salt or solvate thereof, wherein the one or more radionuclides are selected from the group consisting of $^{14}C$, $^{15}N$, $^{18}F$, $^{75}Br$, $^{76}Br$, $^{77}Br$, $^{123}I$, $^{124}I$, $^{125}I$, $^{131}I$, $^{35}S$, $^{99}Tc$, $^{99m}Tc$, $^{188}Re$, $^{186}Re$, $^{153}Sm$, $^{67}Ga$, $^{68}Ga$, $^{111}In$, $^{59}Fe$, $^{63}Zn$, $^{52}Fe$, $^{45}Ti$, $^{60}Cu$, $^{61}Cu$, $^{67}Cu$, $^{64}Cu$, $^{62}Cu$, $^{82}Rb$, $^{195m}Pt$, $^{191m}Pt$, $^{193m}Pt$, $^{117m}Sn$, $^{89}Zr$, $^{177}Lu$, $^{66}Ho$, $^{86}Y$, $^{87}Y$, $^{90}Y$, $^{89}Sr$, $^{153}Gd$, $^{225}Ac$, $^{212}Bi$, $^{213}Bi$, $^{211}At$, $^{198}Au$, $^{199}Au$, $^{193m}Pt$, $^{197}Pt$, $^{103}Pd$, $^{109}Pd$, $^{105}Rh$, $^{103m}Rh$, $^{223}Ra$, $^{224}Ra$, $^{97}Ru$, $^{227}Th$, $^{229}Th$, $^{32}P$, $^{161}Tb$, $^{33}P$, $^{149}Tb$, $^{203}Pb$, $^{212}Pb$, $^{201}Tl$, $^{119}Sb$, $^{58m}Co$, $^{55}Co$, $^{47}Sc$, $^{149}Pm$ and $^{161}Ho$.

22. The radionuclide complex of claim 21, or a pharmaceutically acceptable salt or solvate thereof, wherein the one or more radionuclides are selected from the group consisting of $^{111}In$, $^{161}Tb$, $^{64}Cu$, $^{177}Lu$, $^{212}Pb$, and $^{225}Ac$.

* * * * *